(12) United States Patent
Berdini et al.

(10) Patent No.: US 8,796,244 B2
(45) Date of Patent: *Aug. 5, 2014

(54) IMIDAZOPYRIDINE DERIVATIVES AS INHIBITORS OF RECEPTOR TYROSINE KINASES

(75) Inventors: Valerio Berdini, Cambridge (GB); Maria Grazia Carr, Luton (GB); Miles Stuart Congreve, Royston (GB); Martyn Frederickson, Cambridge (GB); Charlotte Mary Griffiths-Jones, Cambridge (GB); Christopher Charles Frederick Hamlett, Cambridge (GB); Andrew Madin, Cambridge (GB); Christopher William Murray, Cambridge (GB); Rajdeep Kaur Benning, Uxbridge (GB); Gordon Saxty, Cambridge (GB); Emma Vickerstaffe, Baldock (GB); Brian John Williams, Great Dunmow (GB); Marian Williams, legal representative, Great Dunmow (GB); Andrew James Woodhead, Cambridge (GB); Steven John Woodhead, San Diego, CA (US); Eddy Jean Edgard Freyne, Rumst (BE); Tom Cornelis Hortense Govaerts, Betekorn (BE); Patrick René Angibaud, Fontaine-Bellenger (FR)

(73) Assignee: Astex Therapeutics Ltd, Cambridge (GB)

( * ) Notice: Subject to any disclaimer, the term of this patent is extended or adjusted under 35 U.S.C. 154(b) by 457 days.

This patent is subject to a terminal disclaimer.

(21) Appl. No.: 12/997,754

(22) PCT Filed: Jun. 12, 2009

(86) PCT No.: PCT/EP2009/057318
§ 371 (c)(1),
(2), (4) Date: Apr. 13, 2012

(87) PCT Pub. No.: WO2009/150240
PCT Pub. Date: Dec. 17, 2009

(65) Prior Publication Data
US 2012/0208791 A1    Aug. 16, 2012

Related U.S. Application Data

(60) Provisional application No. 61/061,184, filed on Jun. 13, 2008.

(30) Foreign Application Priority Data

Jun. 13, 2008 (GB) .................................. 0810902.7

(51) Int. Cl.
*A61K 31/5025* (2006.01)
*C07D 413/02* (2006.01)

(52) U.S. Cl.
USPC .......................... 514/127; 514/300; 544/144

(58) Field of Classification Search
None
See application file for complete search history.

(56) References Cited

U.S. PATENT DOCUMENTS

| 4,666,828 | A | 5/1987 | Gusella |
| 4,683,202 | A | 7/1987 | Mullis |
| 4,801,531 | A | 1/1989 | Frossard |
| 5,192,659 | A | 3/1993 | Simons |
| 5,272,057 | A | 12/1993 | Smulson et al. |
| 5,554,630 | A | 9/1996 | Teuber et al. |
| 5,882,864 | A | 3/1999 | An et al. |
| 5,990,146 | A | 11/1999 | Boschelli et al. |
| 6,218,529 | B1 | 4/2001 | An et al. |
| 6,465,484 | B1 | 10/2002 | Bilodeau et al. |
| 6,498,165 | B1 | 12/2002 | Armstrong et al. |
| 6,855,719 | B1 | 2/2005 | Thomas et al. |
| 7,074,801 | B1 | 7/2006 | Yoshida et al. |
| 8,071,614 | B2 | 12/2011 | Saxty et al. |
| 8,076,354 | B2 | 12/2011 | Saxty et al. |
| 8,131,527 | B1 | 3/2012 | Saxty et al. |
| 8,481,531 | B2 | 7/2013 | Saxty et al. |
| 2002/0041880 | A1 | 4/2002 | DeFeo-Jones et al. |
| 2003/0203897 | A1 | 10/2003 | Love et al. |
| 2004/0019210 | A1 | 1/2004 | Chivikas Connolly et al. |
| 2004/0067948 | A1 | 4/2004 | Hallett |
| 2004/0220189 | A1 | 11/2004 | Sun et al. |
| 2004/0267510 | A1 | 12/2004 | Bemis et al. |
| 2006/0035921 | A1 | 2/2006 | Castelhano et al. |

(Continued)

FOREIGN PATENT DOCUMENTS

| EP | 1382603 A1 | 1/2004 |
| EP | 1724258 A1 | 11/2006 |

(Continued)

OTHER PUBLICATIONS

Morissette et al., High-throughput crystallization: polymorphs, salts, co-crystals and solvates of pharmaceutical solids, Advanced Drug Delivery Reviews 2004, 56, 275-300.*
Hamdi et al., Solvates of indomethacin. Journal of Thermal Analysis and Calorimetry 2004, 76, 985-1001.*
West, Anthony R., Solid state chemistry and its applications, Department of Chemistry, University of Aberdeen, 1988, pp. 358 and 365.
Search Report for GB0625827.1 dated Apr. 25, 2007.
Search Report for GB0719998.7 dated Nov. 12, 2007.

(Continued)

*Primary Examiner* — Brandon Fetterolf
*Assistant Examiner* — Ana Z Muresan
(74) *Attorney, Agent, or Firm* — Heslin Rothenberg Farley & Mesiti P.C.

(57) ABSTRACT

The invention relates to new bicyclic heterocyclic derivative compounds, to pharmaceutical compositions comprising the compounds and to the use of the compounds in the treatment of diseases, e.g. cancer.

21 Claims, No Drawings

(56) References Cited

U.S. PATENT DOCUMENTS

| | | |
|---|---|---|
| 2006/0089362 A1 | 4/2006 | Seno et al. |
| 2006/0116402 A1 | 6/2006 | Crew et al. |
| 2006/0189629 A1 | 8/2006 | Bolger et al. |
| 2007/0185140 A1 | 8/2007 | Bordon-Pallier et al. |
| 2008/0139606 A1 | 6/2008 | Tabart et al. |
| 2008/0167314 A1 | 7/2008 | Uchikawa et al. |

FOREIGN PATENT DOCUMENTS

| | | |
|---|---|---|
| EP | 1748048 A1 | 1/2007 |
| EP | 1790650 A1 | 5/2007 |
| EP | 1882475 A1 | 1/2008 |
| EP | 2116543 A1 | 11/2009 |
| JP | 2001-057292 | 2/2001 |
| JP | 2004-002826 | 1/2004 |
| WO | 95/35296 A1 | 12/1995 |
| WO | 96/34866 A1 | 11/1996 |
| WO | 97/12613 A1 | 4/1997 |
| WO | 98/03510 A1 | 1/1998 |
| WO | 98/54093 A1 | 12/1998 |
| WO | 99/38868 A1 | 8/1999 |
| WO | 00/12089 A1 | 3/2000 |
| WO | 00/53605 A1 | 9/2000 |
| WO | 01/00207 A1 | 1/2001 |
| WO | 01/00213 A1 | 1/2001 |
| WO | 01/00214 A1 | 1/2001 |
| WO | 01/14375 A1 | 3/2001 |
| WO | 01/18000 A1 | 3/2001 |
| WO | 01/21634 A1 | 3/2001 |
| WO | 01/38326 A2 | 5/2001 |
| WO | 01/66098 A1 | 9/2001 |
| WO | 02/12238 A2 | 2/2002 |
| WO | 02/34748 A1 | 5/2002 |
| WO | 02/38569 A1 | 5/2002 |
| WO | 02/46168 A1 | 6/2002 |
| WO | 02/066477 A2 | 8/2002 |
| WO | 02/066478 A1 | 8/2002 |
| WO | 02/066480 A2 | 8/2002 |
| WO | 02/066481 A1 | 8/2002 |
| WO | 02/074773 A1 | 9/2002 |
| WO | 02/080914 A2 | 10/2002 |
| WO | 03/007955 A2 | 1/2003 |
| WO | 03/048132 A1 | 6/2003 |
| WO | 03/050117 A1 | 6/2003 |
| WO | 03/050119 A2 | 6/2003 |
| WO | 03/082208 A2 | 10/2003 |
| WO | 03/092595 A2 | 11/2003 |
| WO | 03/099811 A1 | 12/2003 |
| WO | 03/099817 A1 | 12/2003 |
| WO | 03/101993 A1 | 12/2003 |
| WO | 2004/026867 A2 | 4/2004 |
| WO | 2004/035579 A1 | 4/2004 |
| WO | 2004/052286 A2 | 6/2004 |
| WO | 2004/052315 A2 | 6/2004 |
| WO | 2004/087153 A2 | 10/2004 |
| WO | 2005/021531 A1 | 3/2005 |
| WO | 2005/021544 A2 | 3/2005 |
| WO | 2005/054230 A1 | 6/2005 |
| WO | 2005/075470 A1 | 8/2005 |
| WO | 2006/000420 A1 | 1/2006 |
| WO | 2006/034402 A2 | 3/2006 |
| WO | 2006/038001 A1 | 4/2006 |
| WO | 2006/070198 A1 | 7/2006 |
| WO | 2006/070943 A1 | 7/2006 |
| WO | 2006/091671 A1 | 8/2006 |
| WO | 2006/094235 A1 | 9/2006 |
| WO | 2006/108103 A1 | 10/2006 |
| WO | 2006/135667 A1 | 12/2006 |
| WO | 2007/036732 A1 | 4/2007 |
| WO | 2007/109362 A2 | 9/2007 |
| WO | 2007/112093 A2 | 10/2007 |
| WO | 2008/003511 A1 | 1/2008 |
| WO | 2008/008747 A1 | 1/2008 |
| WO | 2008/075068 A2 | 6/2008 |
| WO | 2008/078091 A1 | 7/2008 |
| WO | 2008/078100 A2 | 7/2008 |
| WO | 2008/081910 A1 | 7/2008 |
| WO | 2008/124323 A1 | 10/2008 |
| WO | 2008/154642 A2 | 12/2008 |
| WO | 2009/002534 A1 | 12/2008 |
| WO | 2009/047506 A1 | 4/2009 |
| WO | 2009/047522 A1 | 4/2009 |
| WO | 2009/150240 A1 | 12/2009 |
| WO | 2010/119284 A1 | 10/2010 |
| WO | 2010/119285 A1 | 10/2010 |

OTHER PUBLICATIONS

Search Report for PCT/GB2007/004960 dated Sep. 22, 2008.
Search Report for GB0625826.3 dated Apr. 25, 2007.
Search Report for GB0720000.9 dated Nov. 12, 2007.
Search Report for PCT/GB2007/004934 dated May 6, 2008.
Search Report for GB0810902.7 dated Sep. 17, 2008.
Search Report for PCT/EP2009/057318 dated Oct. 12, 2009.
Search Report for GB0720038.9 dated Apr. 17, 2008.
Search Report for PCT/GB2008/003439 dated Jan. 29, 2009.
Search Report for GB0720041.3 dated Apr. 17, 2008.
Search Report for PCT/GB2008/003418 dated Jan. 29, 2009.
Search Report for GB0906472.6 dated Jul. 7, 2009.
Search Report for PCT/GB2010/050617 dated Jul. 20, 2010.
Search Report for GB0906470.0 dated Jul. 8, 2009.
Search Report for PCT/GB2010/050618 dated Jul. 23, 2010.
Bilodeau, Mark T. et al., Design and Synthesis of 1,5-Dairylbenzimidazoles as Inhibitors of the VEGF-Receptor KDR, Bioorganic & Medicinal Chemistry Letters 13, 2003, pp. 2485-2488.
Clark, Michael P. et al., Development of new pyrrolopyrimidine-based inhibitors of Janus kinase 3 (JAK3), Bioorganic & Medicinal Chemistry Letters 17 (5), 2007, pp. 1250-1253.
Wermuth, Camille G., Molecular Variations Based on Isosteric Replacements, The Practice of Medicinal Chemistry, 1996, pp. 203-237.
Fraley, Mark E. et al., Synthesis and Initial SAR Studies of 3,6-Disubstituted Pyrazolo[1,5-α]pyrimidines: A New Class of KDR Kinase Inhibitors, Bioorganic & Medicinal Chemistry Letters 12, 2002, pp. 2767-2770.
Wu, Zhicai et al., Design and Synthesis of 3,7-diarylimidazopyridines as inhibitors of the VEGF-receptor KDR, Bioorganic & Medicinal Chemistry Letters 14, 2004, pp. 909-912.
Fraley, Mark E. et al., Optimization of a Pyrazolo[1,5-α]pyrimidine Class of KDR Kinase Inhibitors: Improvements in Physical Properties Enhance Cellular Activity and Pharmacokinetics, Bioorganic & Medicinal Chemistry Letters 12, 2002, pp. 3537-3541.
Skaper, Stephen D. et al., The FGFR1 Inhibitor PD 173074 Selectively and Potently Antagonizes FGF-2 Neurotrophic and Neurotropic Effects, Journal of Neurochemistry, 2000, pp. 1520-1527.
Mohammadi, Moosa et al., Crystal structure of an angiogenesis inhibitor bound to the FGR receptor tyrosine kinase domain, The EMBO Journal, vol. 17, No. 20, 1998, pp. 5896-5904.
Connolly, Cleo J.C. et al., Discovery and Structure-Activity Studies of a Novel Series of Pyrido[2,3-d]Pyrimidine Tyrosine Kinase Inhibitors, Bioorganic & Medicinal Chemistry Letters, vol. 7, No. 18, 1997, pp. 2415-2420.
Hamby, James M. et al., Structure-Activity Relationships for a Novel Series of Pyrido[2,3-d]pyrimidine Tyrosine Kinase Inhibitors, J. Med. Chem, 40, 1997, pp. 2296-2303.
Scribner, Andrew et al., Synthesis and biological activity of imidazopyridine anticoccidial agents: Part I, European Journal of Medicinal Chemistry 42, 2007, pp. 1334-1357.
Anderson, Malcolm et al., Imidazo[1,2-α]pyridines: A Potent and Selective Class of Cyclin-Dependent Kinase Inhibitors Identified Through Structure-Based Hybridisation, Bioorganic & Medicinal Chemistry Letters 13, 2003, pp. 3021-3026.
Mohammadi, Moosa et al., Structures of the Tyrosine Kinase Domain of Fibroblast Growth Factor Receptor in Complex with Inhibitors, Science, 276, 1997, pp. 955-960.
Dorwald, F. Zaragoza, Side Reactions in Organic Synthesis, 2005, Wiley: VCH, Weinheim p. IX of Preface.

(56) References Cited

OTHER PUBLICATIONS

Vippagunta, Sudha R., et al., Crystalline solids, Advanced Drug Delivery Reviews 48, 2001, pp. 3-26.

Ellis, Lee M. et al., "VEGF-Targeted Therapy: Mechanisms of Anti-Tumour Activity" *Nature Reviews/Cancer*, Aug. 2008, vol. 8, pp. 579-591.

Palmer, Brian D., et al."Structure-Activity Relationships for 1-Phenylbenzimidazoles as Selective ATP Site Inhibitors of the Platelet-Derived Growth Factor Receptor" *Journal of Medicinal Chemistry*, 1998, 41 (27), pp. 5457-5465.

Berge, Stephen M. et al. "Pharmaceutical Salts", *Journal of Pharmaceutical Sciences*, vol. 66, No. 1, 1977, pp. 1-19.

Deady, Leslie W. "Ring Nitrogen Oxidation of Amino Substituted Nitrogen Heterocycles with m-Chloroperbenzoic Acid", *Synthetic Communications*, vol. 7(8), 1977, pp. 509-514.

Angerer, Lynne M. et al. "Demonstration of Tissue-Specific Gene Expression by in Situ Hybridization", *Methods in Enzymology*; vol. 152, 1987, pp. 649-661.

Deprimo, Samuel E, et al. "Expression profiling of blood samples from an SU5416 Phase III metastatic colorectal cancer clinical trial: a novel strategy for biomarker identification", *BMC Cancer*, vol. 3, 2003; pp. 1-12.

Orre, Maxine and Rogers, Peter A.W. "VEGF, VEGFR-1, VEGFR-2, Microvessel Density and Endothelial Cell Proliferation in Tumours of the Ovary", *Int. J. Cancer (Prod. Oncol.)*, vol. 84(2), 1999, pp. 101-108.

\* cited by examiner

IMIDAZOPYRIDINE DERIVATIVES AS INHIBITORS OF RECEPTOR TYROSINE KINASES

CROSS REFERENCE TO RELATED APPLICATIONS

This application is a national phase filing under 35 U.S.C. §371 of PCT International Application PCT/EP2009/057318, filed Jun. 12, 2009, and published under PCT Article 21(2) in English as WO 2009/150240 on Dec. 17, 2009. PCT/EP2009/057318 claimed priority from U.S. provisional patent application No. 61/061,184, filed on Jun. 13, 2008, and from GB 0810902.7, filed on Jun. 13, 2008. The entire contents of each of the prior applications are incorporated herein by reference.

FIELD OF THE INVENTION

The invention relates to new bicyclic heterocyclic derivative compounds, to pharmaceutical compositions comprising said compounds and to the use of said compounds in the treatment of diseases, e.g. cancer.

SUMMARY OF THE INVENTION

According to a first aspect of the invention there is provided a compound of formula (I):

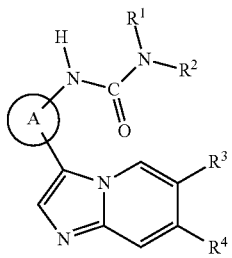

(I)

wherein
(i) when $R^1$ and $R^2$ independently represent hydrogen or $C_{3-8}$ cycloalkyl optionally substituted by one or more (e.g. 1, 2 or 3) $R^a$ groups;
A is a group $A^a$ which represents an aromatic or non-aromatic carbocyclic or heterocyclic group which may be optionally substituted by one or more (e.g. 1, 2 or 3) $R^a$ groups;
$R^3$ represents hydrogen or $C_{1-6}$ alkyl;
$R^4$ is a group $R^{4a}$ which represents an amino, halogen, $C_{1-6}$ alkyl, —X—$R^5$ or an aromatic or non-aromatic carbocyclic or heterocyclic group wherein said carbocyclic or heterocyclic group may be optionally substituted by one or more (e.g. 1, 2 or 3) $R^b$ groups;
(ii) when $R^1$ represents hydrogen and $R^2$ represents $C_{1-6}$ alkyl or halo $C_{1-6}$ alkyl;
A is a group $A^b$ which represents an aromatic 5 membered heterocyclic group which may be optionally substituted by one or more (e.g. 1, 2 or 3) $R^a$ groups;
$R^3$ represents hydrogen or $C_{1-6}$ alkyl;
$R^4$ is a group $R^{4a}$ which represents an amino, halogen, $C_{1-6}$ alkyl, —X—$R^5$ or an aromatic or non-aromatic carbocyclic or heterocyclic group wherein said carbocyclic or heterocyclic group may be optionally substituted by one or more (e.g. 1, 2 or 3) $R^b$ groups;

(iii) when $R^1$ represents hydrogen and $R^2$ represents $C_{1-6}$ alkyl or halo $C_{1-6}$ alkyl;
A is a group $A^c$ which represents an aromatic 6 membered heterocyclic group which may be optionally substituted by one or more (e.g. 1, 2 or 3) $R^a$ groups;
$R^3$ represents hydrogen or $C_{1-6}$ alkyl;
$R^4$ is a group $R^{4b}$ which represents an amino, halogen, $C_{1-6}$ alkyl, —X—$R^5$ or an aromatic or non-aromatic carbocyclic or heterocyclic group wherein said carbocyclic group may be optionally substituted by one or more (e.g. 1, 2 or 3) $R^c$ groups or when said heterocyclic group is other than pyrazolyl, oxadiazolyl or tetrazolyl said heterocyclic group may be optionally substituted by one or more (e.g. 1, 2 or 3) $R^b$ groups or when said heterocyclic group is pyrazolyl, oxadiazolyl or tetrazolyl said heterocyclic group may be optionally substituted by one or more (e.g. 1, 2 or 3) $R^d$ groups or two or more (e.g. 2, 3 or 4) $R^b$ groups;
(iv) when $R^1$ represents hydrogen and $R^2$ represents $C_{1-6}$ alkyl or halo $C_{1-6}$ alkyl;
A is a group $A^d$ which represents a phenyl group which may be optionally substituted by one or more (e.g. 1, 2 or 3) $R^a$ groups;
$R^3$ represents hydrogen or $C_{1-6}$ alkyl;
$R^4$ is a group $R^{4c}$ which is selected from any one of (a)-(h), (j)-(k), (m)-(u) and (w)-(y) which represent:
(a) an amino;
(b) —X—$R^6$;
(c) phenyl substituted by one or more (e.g. 1, 2 or 3) $C_{2-6}$ alkanol groups;
(d) pyridazinyl optionally substituted by one or more (e.g. 1, 2 or 3) $R^e$ groups, or two or more (e.g. 2, 3 or 4) $R^b$ groups;
(e) N-linked imidazolyl optionally substituted on the nitrogen atom or the C-2 or C-5 atoms by one or more (e.g. 1, 2 or 3) $R^b$ groups or at the C-4 atom by one $R^e$ group;
(f) C-linked imidazolyl optionally substituted by one or two $R^m$ groups on either or both of the nitrogen atoms or optionally substituted by one or two $R^e$ groups on one or two carbon atoms;
(g) pyrazinyl optionally substituted by one or more (e.g. 1, 2 or 3) $R^b$ groups;
(h) thiophenyl substituted by one or more (e.g. 1, 2 or 3) $R^e$ groups;
(j) a bicyclic heterocyclic group containing a thiazolyl or thiadiazolyl ring optionally substituted by one or more (e.g. 1, 2 or 3) $R^b$ groups;
(k) triazinyl optionally substituted by one or two $R^b$ groups;
(m) pyrazolyl substituted by one or more (e.g. 1, 2 or 3) $R^f$ groups;
(n) pyrimidin-2-yl optionally substituted by one or more (e.g. 1, 2 or 3) $R^b$ groups;
(o) pyrimidin-4-yl optionally substituted by one or more (e.g. 1, 2 or 3) $R^g$ groups or two or more (e.g. 2, 3 or 4) $R^b$ groups;
(p) pyrimidin-5-yl optionally substituted by one or more (e.g. 1, 2 or 3) $R^p$ groups or two or more (e.g. 2, 3 or 4) $R^b$ groups;
(q) thiadiazolyl substituted by one $R^h$ group;
(r) pyridin-2-yl optionally substituted by one or more (e.g. 1, 2 or 3) $R^b$ groups;
(s) pyridin-3-yl substituted by one or more (e.g. 1, 2 or 3) $R^j$ groups;
(t) pyridin-4-yl substituted by one or more (e.g. 1, 2 or 3) $R^k$ groups or two or more (e.g. 2, 3 or 4) $R^b$ groups;
(u) pyridin-3-yl substituted at the 2-position by —O—$C_{1-6}$ alkyl and optionally substituted by one or more (e.g. 1, 2 or 3) $R^b$ groups;

(w) oxo-dihydro-pyridin-3-yl substituted by one or more (e.g. 1, 2 or 3) $R^j$ groups;

(x) N-methylpyrazolyl optionally substituted by one or more (e.g. 1, 2 or 3) $R^q$ groups;

(y) N-unsubstituted pyridin-3-yl substituted on one of the carbon atoms with a substituent from the group $R^b$ and substituted on another carbon atom with a substituent from the group $R^a$;

(v) when $R^1$ represents hydrogen and $R^2$ represents $C_{1-6}$ alkyl or halo $C_{1-6}$ alkyl and A is $A^d$ which represents a phenyl group which may be optionally substituted by one or more (e.g. 1, 2 or 3) $R^a$ groups;

$R^3$ represents $C_{1-6}$ alkyl;

$R^4$ is a group $R^{4d}$ which represents $C_{1-6}$ alkyl; or (vi) when $R^1$ represents hydrogen and $R^2$ represents halo $C_{1-6}$ alkyl and A is $A^d$ which represents a phenyl group which may be optionally substituted by one or more (e.g. 1, 2 or 3) $R^a$ groups;

$R^3$ represents hydrogen or $C_{1-6}$ alkyl;

$R^4$ is a group $R^{4e}$ which represents unsubstituted pyridin-3-yl, unsubstituted pyridin-4-yl or 3-pyridinyl substituted with unsubstituted piperidine;

X represents $-(CH_2)_q-$, $-CH=CH-$ or $-C\equiv C-$;

$R^5$ represents $-(CH_2)_s-NR^xR^y$, $C_{1-6}$ alkyl, $C_{1-6}$ alkanol, $C_{3-8}$ cycloalkyl or an aromatic or non-aromatic heterocyclic group wherein said heterocyclic group may be optionally substituted by one or more (e.g. 1, 2 or 3) $R^b$ groups;

$R^6$ represents $-(CH_2)_s-NR^xR^y$, $C_{2-6}$ alkyl, $C_{1-6}$ alkanol, $C_{4-8}$ cycloalkyl or an aromatic or non-aromatic heterocyclic group wherein said heterocyclic group may be optionally substituted by one or more (e.g. 1, 2 or 3) $R^b$ groups;

$R^w$, $R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, $-COOC_{1-6}$ alkyl, hydroxy, $C_{1-6}$ alkoxy, halo$C_{1-6}$ alkyl, $-(CH_2)_n-O-C_{1-6}$ alkyl, $-CO-(CH_2)_n-C_{1-6}$ alkoxy, $C_{1-6}$ alkylamino, $-C_{1-6}$ alkyl-$N(C_{1-6}$ alkyl$)_2$, $-C_{1-6}$ alkyl-$NH(C_{1-6}$ alkyl), $C_{3-8}$ cycloalkyl or $C_{3-8}$ cycloalkenyl or when attached to a nitrogen atom, $R^w$, $R^x$, $R^y$ and $R^z$ may form a ring;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, $-OR^x$, $-(CH_2)_n-O-C_{1-6}$ alkyl, $-O-(CH_2)_n-OR^x$, halo$C_{1-6}$ alkyl, halo$C_{1-6}$ alkoxy, $C_{1-6}$ alkanol, $=O$, $=S$, nitro, $Si(R^x)_4$, $-(CH_2)_s-CN$, $-S-R^x$, $-SO-R^x$, $-SO_2-R^x$, $-COR^x$, $-(CR^xR^y)_s-COOR^z$, $-(CR^xR^y)_s-CONR^wR^z$, $-(CH_2)_s-CONR^xR^y$, $-(CH_2)_s-NR^xR^y$, $-(CH_2)_s-NR^xCOR^y$, $-(CH_2)_s-NR^xSO_2-R^y$, $-(CH_2)_s-NH-SO_2-NR^xR^y$, $-OCONR^xR^y$, $-(CH_2)_s-NR^xCO_2R^y$, $-O-(CH_2)_n-NR^xR^y$, $-O-(CH_2)_s-CR^xR^y$, $-(CH_2)_t-OR^z$ or $-(CH_2)_s-SO_2NR^xR^y$ groups;

$R^b$ represents an $R^a$ group or a $-Y$-heterocyclyl group wherein said heterocyclyl group may be optionally substituted by one or more (e.g. 1, 2 or 3) $R^a$ groups;

Y represents a bond, $-CO-(CH_2)_s-$, $-(CR^xR^y)_s-CO-$, $-COO-$, $-(CH_2)_n-(CR^xR^y)_s-$, $-NR^x-(CH_2)_s-$, $-(CH_2)_s-NR^x-$, $-CONR^x-$, $-NR^xCO-$, $-SO_2NR^x-$, $-NR^xSO_2-$, $-NR^xCONR^y-$, $-NR^xCS-NR^y-$, $-O-(CH_2)_s-$, $-(CH_2)_s-O-$, $-S-$, $-SO-$ or $-(CH_2)_s-SO_2-$;

$R^c$ represents chlorine, $C_{1-6}$ alkyl, $C_{2-6}$ alkenyl, $C_{2-6}$ alkynyl, $C_{3-8}$ cycloalkyl, $C_{3-8}$ cycloalkenyl, $-OR^x$, $-(CH_2)_n-O-C_{1-6}$ alkyl, $-O-(CH_2)_n-OR^x$, halo$C_{1-6}$ alkyl, halo$C_{1-6}$ alkoxy, $C_{1-6}$ alkanol, $=O$, $=S$, nitro, $Si(R^x)_4$, $-(CH_2)_s-CN$, $-S-R^x$, $-SO-R^x$, $-SO_2-R^x$, $-COR^x$, $-(CR^xR^y)_s-COOR^z$, $-(CR^xR^y)_s-CONR^wR^z$, $-(CH_2)_s-CONR^xR^y$, $-(CH_2)_s-NR^xR^y$, $-(CH_2)_s-NR^xCOR^y$, $-(CH_2)_s-NR^xSO_2-R^y$, $-(CH_2)_s-NH-SO_2-NR^xR^y$, $-OCONR^xR^y$, $-(CH_2)_s-NR^xCO_2R^y$, $-O-(CH_2)_s-$ $CR^xR^y-(CH_2)_t-OR^z$ or $-(CH_2)_s-SO_2NR^xR^y$ groups, or a $-Y$-heterocyclyl group wherein said heterocyclyl group may be optionally substituted by one or more (e.g. 1, 2 or 3) $R^a$ groups;

$R^d$ represents halogen, $C_{2-6}$ alkenyl, $C_{2-6}$ alkynyl, $C_{3-8}$ cycloalkyl, $C_{3-8}$ cycloalkenyl, $OR^x$, $-(CH_2)_n-O-C_{1-6}$ alkyl, $-O-(CH_2)_n-OR^x$, halo$C_{1-6}$ alkyl, halo$C_{1-6}$ alkoxy, $C_{1-6}$ alkanol, $=O$, $=S$, nitro, $Si(R^x)_4$, $-(CH_2)_s-CN$, $-SO-R^x$, $-SO_2-R^x$, $-COR^x$, $-(CR^xR^y)_s-COOR^z$, $-(CR^xR^y)_s-CONR^wR^z$, $-(CH_2)_s-CONR^xR^y$, $-(CH_2)_s-NR^xR^y$, $-(CH_2)_s-NR^xCOR^y$, $-(CH_2)_s-NR^xSO_2-R^y$, $-(CH_2)_s-NH-SO_2-NR^xR^y$, $-OCONR^xR^y$, $-(CH_2)_s-NR^xCO_2R^y$, $-O-(CH_2)_s-CR^xR^y-(CH_2)_t-OR^z$ or $-(CH_2)_s-SO_2NR^xR^y$ groups, or a $-Y$-heterocyclyl group wherein said heterocyclyl group may be optionally substituted by one or more (e.g. 1, 2 or 3) $R^a$ groups;

$R^e$ represents halogen, $C_{2-6}$ alkyl, $C_{2-6}$ alkenyl, $C_{2-6}$ alkynyl, $C_{3-8}$ cycloalkyl, $C_{3-8}$ cycloalkenyl, $-OR^x$, $-(CH_2)_n-O-C_{1-6}$ alkyl, $-O-(CH_2)_n-OR^x$, halo$C_{1-6}$ alkyl, halo$C_{1-6}$ alkoxy, $C_{1-6}$ alkanol, $=O$, $=S$, nitro, $Si(R^x)_4$, $-(CH_2)_s-CN$, $-S-R^x$, $-SO-R^x$, $-SO_2-R^x$, $-COR^x$, $-(CR^xR^y)_s-COOR^z$, $-(CR^xR^y)_s-CONR^wR^z$, $-(CH_2)_s-CONR^xR^y$, $-(CH_2)_s-NR^xR^y$, $-(CH_2)_s-NR^xCOR^y$, $-(CH_2)_s-NR^xSO_2-R^y$, $-(CH_2)_s-NH-SO_2-NR^xR^y$, $-OCONR^xR^y$, $-(CH_2)_s-NR^xCO_2R^y$, $-O-(CH_2)_s-CR^xR^y-(CH_2)_t-OR^z$ or $-(CH_2)_s-SO_2NR^xR^y$ groups, or a $-Y$-heterocyclyl group wherein said heterocyclyl group may be optionally substituted by one or more (e.g. 1, 2 or 3) $R^a$ groups;

$R^f$ represents halogen, $C_{4-6}$ alkyl, $C_{2-6}$ alkenyl, $C_{2-6}$ alkynyl, $C_{3-8}$ cycloalkyl, $C_{3-8}$ cycloalkenyl, $-OR^x$, $-(CH_2)_n-O-C_{1-6}$ alkyl, $-O-(CH_2)_n-OR^x$, halo$C_{2-6}$ alkyl, monohalomethyl, dihalomethyl, halo$C_{1-6}$ alkoxy, $C_{3-6}$ alkanol, $=O$, $=S$, nitro, $Si(R^x)_4$, $-(CH_2)_s-CN$, $-S-R^x$, $-SO-R^x$, $-SO_2-R^x$, $-COR^x$, $-(CR^xR^y)_s-COOR^z$, $-(CR^xR^y)_s-CONR^wR^z$, $-(CH_2)_s-CONR^xR^y$, $-CH_2-NR^xR^y$, $-(CH_2)_{3-4}-NR^xR^y$, $-(CH_2)_s-NHC_{1-6}$ alkyl, $-(CH_2)_s-N(C_{1-6}$ alkyl$)_2$, $-(CH_2)_s-NR^xCOR^y$, $-(CH_2)_s-NR^xSO_2-R^y$, $-(CH_2)_s-NH-SO_2-NR^xR^y$, $-OCONR^xR^y$, $-(CH_2)_s-NR^xCO_2R^y$, $-O-(CH_2)_s-CR^xR^y-(CH_2)_t-OR^z$, $-(CH_2)_n-SO_2NR^xR^y$ or $-(CH_2)_s-SO_2NHR^y$ groups, or a $-Y$-heterocyclyl group wherein said heterocyclyl group may be optionally substituted by one or more (e.g. 1, 2 or 3) $R^a$ groups;

$R^g$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, $-OR^x$, $-(CH_2)_n-O-C_{1-6}$ alkyl, $-O-(CH_2)_n-OR^x$, halo$C_{1-6}$ alkyl, halo$C_{1-6}$ alkoxy, $C_{1-6}$ alkanol, $=O$, $=S$, nitro, $Si(R^x)_4$, $-(CH_2)_s-CN$, $-S-R^x$, $-SO-R^x$, $-SO_2-R^x$, $-COR^x$, $-(CR^xR^y)_s-COOR^z$, $-(CR^xR^y)_s-CONR^wR^z$, $-(CH_2)_s-CONR^xR^y$, $-(CH_2)_s-NHC_{1-6}$ alkyl, $-(CH_2)_s-N(C_{1-6}$ alkyl$)_2$, $-(CH_2)_n-NR^xR^y$, $-(CH_2)_s-NR^xCOR^y$, $-(CH_2)_s-NR^xSO_2-R^y$, $-(CH_2)_s-NH-SO_2-NR^xR^y$, $-OCONR^xR^y$, $-(CH_2)_s-NR^xCO_2R^y$, $-O-(CH_2)_s-CR^xR^y-(CH_2)_t-OR^z$ or $-(CH_2)_s-SO_2NR^xR^y$ groups, or a $-Y$-heterocyclyl group wherein said heterocyclyl group may be optionally substituted by one or more (e.g. 1, 2 or 3) $R^a$ groups;

$R^h$ represents halogen, $C_{3-6}$ alkyl, $C_{2-6}$ alkenyl, $C_{2-6}$ alkynyl, $C_{4-8}$ cycloalkyl, $C_{3-8}$ cycloalkenyl, $-OR^x$, $-(CH_2)_{2-4}-O-C_{1-6}$ alkyl, $-(CH_2)_n-O-C_{2-6}$ alkyl, $-O-(CH_2)_n-OR^x$, halo$C_{1-6}$ alkyl, halo$C_{1-6}$ alkoxy, $C_{2-6}$ alkanol, $=O$, $=S$, nitro, $Si(R^x)_4$, $-(CH_2)_n-CN$, $-S-R^x$, $-SO-R^x$, $-SO_2-R^x$, $-COR^x$, $-(CR^xR^y)_s-COOR^z$, $-(CR^xR^y)_s-CONR^wR^z$, $-(CH_2)_s-CONR^xR^y$, $-(CH_2)_s-NR^xR^y$, $-(CH_2)_s-NR^xCOR^y$, $-(CH_2)_s-NR^xSO_2-R^y$, —(CH₂)ₛ—NH—SO₂—NRˣRʸ, —OCONRˣRʸ, —(CH₂)ₛ—NRˣCO₂Rʸ, —O—(CH₂)ₛ—CRˣRʸ—(CH₂)ₜ—ORᶻ or —(CH₂)ₛ—SO₂NRˣRʸ groups, or a —Y-heterocyclyl group wherein said heterocyclyl group may be optionally substituted by one or more (e.g. 1, 2 or 3) Rᵃ groups;

Rʲ represents chlorine, ethyl, C₄₋₆ alkyl, C₂₋₆ alkenyl, C₂₋₆ alkynyl, C₃₋₈ cycloalkyl, C₃₋₈ cycloalkenyl, —O—C₂ alkyl, —O—C₄₋₆ alkyl, —(CH₂)ₙ—O—C₁₋₆ alkyl, —O—(CH₂)ₙ—ORˣ, haloC₂₋₆ alkyl, monohalomethyl, dihalomethyl, haloC₁₋₆ alkoxy, C₁₋₂ alkanol, C₄₋₆ alkanol, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COOC₁₋₆ alkyl, —(CRˣRʸ)ₛ—CONRʷRᶻ, —(CH₂)ₛ—CONRˣRʸ, —(CH₂)ₛ—NHC₁₋₆ alkyl, —(CH₂)ₛ—NMe(C₂₋₆ alkyl), —(CH₂)ₛ—N—(C₂₋₆ alkyl)₂, —(CH₂)ₙ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —O—(CH₂)ₙ—NRˣRʸ, —O—(CH₂)ₛ—CRˣRʸ—(CH₂)ₜ—ORᶻ, —(CH₂)ₛ—SO₂NRˣRʸ, piperazine substituted by Rⁿ, or a piperidinyl or a —O-piperidinyl group wherein said piperidinyl groups are substituted by one or more (e.g. 1, 2 or 3) Rᵃ groups;

Rᵏ represents chlorine, C₂₋₆ alkyl, C₂₋₆ alkenyl, C₂₋₆ alkynyl, C₃₋₈ cycloalkyl, C₃₋₈ cycloalkenyl, C₂₋₆ alkoxy, —(CH₂)ₙ—O—C₁₋₆ alkyl, —O—(CH₂)ₙ—ORˣ, haloC₁₋₆ alkyl, haloC₁₋₆ alkoxy, O₁₋₂ alkanol, C₄₋₆ alkanol, =S, nitro, Si(Rˣ)₄, —(CH₂)ₛ—CN, —S—Rˣ, —SO—Rˣ, —SO₂—Rˣ, —CORˣ, —(CRˣRʸ), —COORᶻ, —(CRˣRʸ)ₛ—CONRʷRᶻ, —(CH₂)ₛ—CONRˣRʸ, —(CH₂)ₛ—NHC₁₋₆ alkyl, —(CH₂)ₛ—N(C₁₋₆ alkyl)₂, —(CH₂)ₙ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₛ—CRˣRʸ—(CH₂)ₜ—ORᶻ or —(CH₂)ₛ—SO₂NRˣRʸ groups;

Rᵐ represents halogen, C₃₋₆ alkyl, C₂₋₆ alkenyl, C₂₋₆ alkynyl, C₃₋₈ cycloalkyl, C₃₋₈ cycloalkenyl, —ORˣ, —(CH₂)ₙ—O—C₁₋₆ alkyl, —O—(CH₂)ₙ—ORˣ, haloC₁₋₆ alkyl, haloC₁₋₆ alkoxy, C₁₋₆ alkanol, =O, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COORᶻ, —(CRˣRʸ)ₛ—CONRʷRᶻ, —(CH₂)ₛ—CONRˣRʸ, —(CH₂)ₛ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₛ—CRˣRʸ—(CH₂)ₜ—ORᶻ or —(CH₂)ₛ—SO₂NRˣRʸ groups, or a —Y-heterocyclyl group wherein said heterocyclyl group may be optionally substituted by one or more (e.g. 1, 2 or 3) Rᵃ groups;

Rⁿ represents halogen, C₁₋₆ alkyl, C₂₋₆ alkenyl, C₂₋₆ alkynyl, C₃₋₈ cycloalkyl, C₃₋₈ cycloalkenyl, —ORˣ, —(CH₂)ₙ—O—C₁₋₆ alkyl, —O—(CH₂)ₙ—ORˣ, haloC₁₋₆ alkyl, haloC₁₋₆ alkoxy, C₁₋₆ alkanol, =O, =S, nitro, Si(Rˣ)₄, —(CH₂)ₛ—CN, —S—Rˣ, —SO—Rˣ, —SO₂—Rˣ, —CORˣ, —(CRˣRʸ)ₛ—CONRʷRᶻ, —(CH₂)ₛ—CONRˣRʸ, —(CH₂)ₛ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₛ—CRˣRʸ—(CH₂)ₜ—ORᶻ or —(CH₂)ₛ—SO₂NRˣRʸ groups;

Rᵖ represents halogen, C₁₋₆ alkyl, C₂₋₆ alkenyl, C₂₋₆ alkynyl, C₃₋₈ cycloalkyl, C₃₋₈ cycloalkenyl, —ORˣ, —(CH₂)ₙ—O—C₁₋₆ alkyl, —O—(CH₂)ₙ—ORˣ, haloC₁₋₆ alkyl, haloC₁₋₆ alkoxy, C₁₋₆ alkanol, =O, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COORᶻ, —(CRˣRʸ)ₛ—CONRʷRᶻ, —(CH₂)ₛ—CONRˣRʸ, —(CH₂)ₛ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₛ—CRˣRʸ—(CH₂)ₜ—ORᶻ or —(CH₂)ₛ—SO₂NRˣRʸ groups; a —Y-(4-membered heterocyclyl group) wherein said 4-membered heterocyclyl group is substituted by one or more (e.g. 1, 2 or 3) Rᵃ groups; or a —Y-(5-10 membered heterocyclyl group) wherein said 5-10 membered heterocyclyl group may be optionally substituted by one or more (e.g. 1, 2 or 3) Rᵃ groups;

Rᵠ represents halogen, C₂₋₆ alkyl, C₂₋₆ alkenyl, C₂₋₆ alkynyl, C₃₋₈ cycloalkyl, C₃₋₈ cycloalkenyl, —ORˣ, —(CH₂)ₙ—O—C₁₋₆ alkyl, —O—(CH₂)ₙ—ORˣ, haloC₂₋₆ alkyl, monohalomethyl, dihalomethyl, haloC₁₋₆ alkoxy, C₂₋₆ alkanol, =O, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COORᶻ, —(CRˣRʸ)ₛ—CONRʷRᶻ, —(CH₂)ₛ—CONRˣRʸ, —NH(C₁₋₆alkyl), —N(C₁₋₆alkyl)₂, —(CH₂)ₙ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₙ—NRˣRʸ, —O—(CH₂)ₛ—CRˣRʸ—(CH₂)ₜ—ORᶻ or —(CH₂)ₛ—SO₂NRˣRʸ groups, or a —Y-heterocyclyl group wherein said heterocyclyl group may be optionally substituted by one or more (e.g. 1, 2 or 3) Rᵃ groups;

n and q independently represent an integer from 1-4;

s and t independently represent an integer from 0-4;

or a pharmaceutically acceptable salt, solvate or derivative thereof.

WO2008/078100 (Astex), WO2008/078091 (Astex), WO2009/047522 (Astex), WO2009/047506 (Astex), U.S. Pat. No. 7,074,801 (Eisai), US 2002/0041880 (Merck), WO 98/54093 (Merck), WO 2006/091671 (Eli Lilly), WO 2003/048132 (Merck), WO 2004/052286 (Merck), WO 00/53605 (Merck), WO 03/101993 (Neogenesis), WO 2006/135667 (BMS), WO 2002/46168 (Astra Zeneca), WO 2005/080330 (Chugai), WO 2006/094235 (Sirtris Pharmaceuticals), WO 2006/034402 (Synta Pharmaceuticals), WO 01/18000 (Merck), U.S. Pat. No. 5,990,146 (Warner Lambert) and WO 00/12089 (Merck) each disclose a series of heterocyclic derivatives.

DETAILED DESCRIPTION OF THE INVENTION

According to a first aspect of the invention there is provided a compound of formula (I):

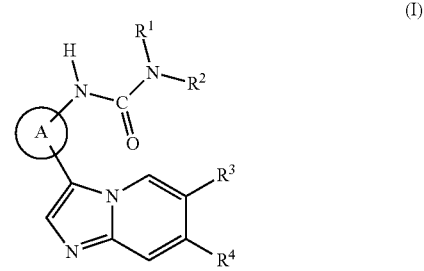

wherein (i) when $R^1$ and $R^2$ independently represent hydrogen or $C_{3-8}$ cycloalkyl optionally substituted by one or more (e.g. 1, 2 or 3) $R^a$ groups;

A is a group $A^a$ which represents an aromatic or non-aromatic carbocyclic or heterocyclic group which may be optionally substituted by one or more (e.g. 1, 2 or 3) $R^a$ groups;

$R^3$ represents hydrogen or $C_{1-6}$ alkyl;

$R^4$ is a group $R^{4a}$ which represents an amino, halogen, $C_{1-6}$ alkyl, —X—$R^5$ or an aromatic or non-aromatic carbocyclic or heterocyclic group wherein said carbocyclic or heterocyclic group may be optionally substituted by one or more (e.g. 1, 2 or 3) $R^b$ groups;

(ii) when $R^1$ represents hydrogen and $R^2$ represents $C_{1-6}$ alkyl or halo $C_{1-6}$ alkyl;

A is a group $A^b$ which represents an aromatic 5 membered heterocyclic group which may be optionally substituted by one or more (e.g. 1, 2 or 3) $R^a$ groups;

$R^3$ represents hydrogen or $C_{1-6}$ alkyl;

$R^4$ is a group $R^{4a}$ which represents an amino, halogen, $C_{1-6}$ alkyl, —X—$R^5$ or an aromatic or non-aromatic carbocyclic or heterocyclic group wherein said carbocyclic or heterocyclic group may be optionally substituted by one or more (e.g. 1, 2 or 3) $R^b$ groups;

(iii) when $R^1$ represents hydrogen and $R^2$ represents $C_{1-6}$ alkyl or halo $C_{1-6}$ alkyl;

A is a group Ac which represents an aromatic 6 membered heterocyclic group which may be optionally substituted by one or more (e.g. 1, 2 or 3) $R^a$ groups;

$R^3$ represents hydrogen or $C_{1-6}$ alkyl;

$R^4$ is a group $R^{4b}$ which represents an amino, halogen, $C_{1-6}$ alkyl, —X—$R^5$ or an aromatic or non-aromatic carbocyclic or heterocyclic group wherein said carbocyclic group may be optionally substituted by one or more (e.g. 1, 2 or 3) $R^c$ groups or when said heterocyclic group is other than pyrazolyl, oxadiazolyl or tetrazolyl said heterocyclic group may be optionally substituted by one or more (e.g. 1, 2 or 3) $R^b$ groups or when said heterocyclic group is pyrazolyl, oxadiazolyl or tetrazolyl said heterocyclic group may be optionally substituted by one or more (e.g. 1, 2 or 3) $R^d$ groups or two or more (e.g. 2, 3 or 4) $R^b$ groups;

(iv) when $R^1$ represents hydrogen and $R^2$ represents $C_{1-6}$ alkyl or halo $C_{1-6}$ alkyl;

A is a group $A^d$ which represents a phenyl group which may be optionally substituted by one or more (e.g. 1, 2 or 3) $R^a$ groups;

$R^3$ represents hydrogen or $C_{1-6}$ alkyl;

$R^4$ is a group $R^{4c}$ which is selected from any one of (a)-(h), (j)-(k), (m)-(u) and (w)-(y) which represent:

(a) an amino;
(b) —X—$R^6$;
(c) phenyl substituted by one or more (e.g. 1, 2 or 3) $C_{2-6}$ alkanol groups;
(d) pyridazinyl optionally substituted by one or more (e.g. 1, 2 or 3) $R^e$ groups, or two or more (e.g. 2, 3 or 4) $R^b$ groups;
(e) N-linked imidazolyl optionally substituted on the nitrogen atom or the C-2 or C-5 atoms by one or more (e.g. 1, 2 or 3) $R^b$ groups or at the C4 atom by one $R^e$ group;
(f) C-linked imidazolyl optionally substituted by one or two $R^m$ groups on either or both of the nitrogen atoms or optionally substituted by one or two $R^e$ groups on one or two carbon atoms;
(g) pyrazinyl optionally substituted by one or more (e.g. 1, 2 or 3) $R^b$ groups;
(h) thiophenyl substituted by one or more (e.g. 1, 2 or 3) $R^e$ groups;
(j) a bicyclic heterocyclic group containing a thiazolyl or thiadiazolyl ring optionally substituted by one or more (e.g. 1, 2 or 3) $R^b$ groups;
(k) triazinyl optionally substituted by one or two $R^b$ groups;
(m) pyrazolyl substituted by one or more (e.g. 1, 2 or 3) $R^f$ groups;
(n) pyrimidin-2-yl optionally substituted by one or more (e.g. 1, 2 or 3) $R^b$ groups;

(o) pyrimidin-4-yl optionally substituted by one or more (e.g. 1, 2 or 3) $R^g$ groups or two or more (e.g. 2, 3 or 4) $R^b$ groups;
(p) pyrimidin-5-yl optionally substituted by one or more (e.g. 1, 2 or 3) $R^p$ groups or two or more (e.g. 2, 3 or 4) $R^b$ groups;
(q) thiadiazolyl substituted by one $R^h$ group;
(r) pyridin-2-yl optionally substituted by one or more (e.g. 1, 2 or 3) $R^b$ groups;
(s) pyridin-3-yl substituted by one or more (e.g. 1, 2 or 3) $R^j$ groups;
(t) pyridin-4-yl substituted by one or more (e.g. 1, 2 or 3) $R^k$ groups or two or more (e.g. 2, 3 or 4) $R^b$ groups;
(u) pyridin-3-yl substituted at the 2-position by —O—$C_{1-6}$ alkyl and optionally substituted by one or more (e.g. 1, 2 or 3) $R^b$ groups;
(w) oxo-dihydro-pyridin-3-yl substituted by one or more (e.g. 1, 2 or 3) $R^j$ groups;
(x) N-methylpyrazolyl optionally substituted by one or more (e.g. 1, 2 or 3) $R^q$ groups;
(y) N-unsubstituted pyridin-3-yl substituted on one of the carbon atoms with a substituent from the group $R^b$ and substituted on another carbon atom with a substituent from the group $R^a$;

(v) when $R^1$ represents hydrogen and $R^2$ represents $C_{1-6}$ alkyl or halo $C_{1-6}$ alkyl and A is $A^d$ which represents a phenyl group which may be optionally substituted by one or more (e.g. 1, 2 or 3) $R^a$ groups;

$R^3$ represents $C_{1-6}$ alkyl;

$R^4$ is a group $R^{4d}$ which represents $C_{1-6}$ alkyl; or (vi) when $R^1$ represents hydrogen and $R^2$ represents halo $C_{1-6}$ alkyl and A is $A^d$ which represents a phenyl group which may be optionally substituted by one or more (e.g. 1, 2 or 3) $R^a$ groups;

$R^3$ represents hydrogen or $C_{1-6}$ alkyl;

$R^4$ is a group $R^{4e}$ which represents unsubstituted pyridin-3-yl, unsubstituted pyridin-4-yl or 3-pyridinyl substituted with unsubstituted piperidine;

X represents —$(CH_2)_q$—, —CH=CH— or —C≡C—;

$R^5$ represents —$(CH_2)_s$—$NR^xR^y$, $C_{1-6}$ alkyl, $C_{1-6}$ alkanol, $C_{3-8}$ cycloalkyl or an aromatic or non-aromatic heterocyclic group wherein said heterocyclic group may be optionally substituted by one or more (e.g. 1, 2 or 3) $R^b$ groups;

$R^6$ represents —$(CH_2)_s$—$NR^xR^y$, $C_{2-6}$ alkyl, $C_{1-6}$ alkanol, $O_{4-8}$ cycloalkyl or an aromatic or non-aromatic heterocyclic group wherein said heterocyclic group may be optionally substituted by one or more (e.g. 1, 2 or 3) $R^b$ groups;

$R^w$, $R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —$COOC_{1-6}$ alkyl, hydroxy, $C_{1-6}$ alkoxy, halo$C_{1-6}$ alkyl, —$(CH_2)_n$—O—$C_{1-6}$ alkyl, —CO—$(CH_2)_n$—$C_{1-6}$ alkoxy, $C_{1-6}$ alkylamino, —$C_{1-6}$ alkyl-N($C_{1-6}$ alkyl)$_2$, —$C_{1-6}$ alkyl-NH($C_{1-6}$ alkyl), $C_{3-8}$ cycloalkyl or $C_{3-8}$ cycloalkenyl or when attached to a nitrogen atom, $R^w$, $R^x$, $R^y$ and $R^z$ may form a ring;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, Si$(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_n$—$NR^xR^y$, —O—$(CH_2)_s$—$CR^xR^y$—$(CH_2)_t$—$OR^z$ or —$(CH_2)_s$—$SO_2NR^xR^y$ groups;

$R^b$ represents an $R^a$ group or a —Y-heterocyclyl group wherein said heterocyclyl group may be optionally substituted by one or more (e.g. 1, 2 or 3) $R^a$ groups;

Y represents a bond, —CO—$(CH_2)_s$—, —$(CR^xR^y)_s$—CO—, —COO—, —$(CH_2)_n$—$(CR^xR^y)_s$—, —$NR^x$—$(CH_2)_s$—, —$(CH_2)_s$—$NR^x$—, —$CONR^x$—, —$NR^xCO$—, —$SO_2NR^x$—, —$NR^xSO_2$—, —$NR^xCONR^y$—, —$NR^xCS$—$NR^y$—, —O—$(CH_2)_s$—, —$(CH_2)_s$—O—, —S—, —SO— or —$(CH_2)_s$—$SO_2$—;

$R^c$ represents chlorine, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^d$ represents halogen, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^e$ represents halogen, $C_{2-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^f$ represents halogen, $C_{4-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{2-6}$ alkyl, monohalomethyl, dihalomethyl, halo$C_{1-6}$ alkoxy, $C_{3-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$CH_2$—$NR^xR^y$, —$(CH_2)_{3-4}$—$NR^xR^y$, —$(CH_2)_s$—$NHC_{1-6}$ alkyl, —$(CH_2)_s$—$N(C_{1-6}$ alkyl$)_2$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$, —$(CH_2)_n$—$SO_2NR^xR^y$ or —$(CH_2)_s$—$SO_2NHR^y$ groups, or a —Y-heterocyclyl group wherein said heterocyclyl group may be optionally substituted by one or more (e.g. 1, 2 or 3) $R^a$ groups;

$R^g$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NHC_{1-6}$ alkyl, —$(CH_2)_s$—$N(C_{1-6}$ alkyl$)_2$, —$(CH_2)_n$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^h$ represents halogen, $C_{3-6}$ alkyl, $C_{2-6}$ alkenyl, $C_{2-6}$ alkynyl, $O_{4-8}$ cycloalkyl, $C_{3-8}$ cycloalkenyl, —$OR^x$, —$(CH_2)_{2-4}$—O—$C_{1-6}$ alkyl, —$(CH_2)_n$—O—$C_{2-6}$ alkyl, —O—$(CH_2)_n$—$OR^x$, halo$C_{1-6}$ alkyl, halo$C_{1-6}$ alkoxy, $C_{2-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^j$ represents chlorine, ethyl, $C_{4-6}$ alkyl, $C_{2-6}$ alkenyl, $C_{2-6}$ alkynyl, $C_{3-8}$ cycloalkyl, $C_{3-8}$ cycloalkenyl, —O—$C_2$ alkyl, —O—$C_{4-6}$ alkyl, —$(CH_2)_n$—O—$C_{1-6}$ alkyl, —O—$(CH_2)_n$—$OR^x$, halo$C_{2-6}$ alkyl, monohalomethyl, dihalomethyl, halo$C_{1-6}$ alkoxy, $O_{1-2}$ alkanol, $C_{4-6}$ alkanol, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOC_{1-6}$ alkyl, —$(CR^xR^y)_s$—$CONR^wR^z$, —$(CH_2)_s$—$CONR^xR^y$, —$(CH_2)_s$—$NHC_{1-6}$ alkyl, —$(CH_2)_n$—$NMe(C_{2-6}$ alkyl), —$(CH_2)_s$—N—$(C_{2-6}$ alkyl$)_2$, —$(CH_2)_n$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —O—$(CH_2)_n$—$NR^xR^y$, —O—$(CH_2)_s$—$CR^xR^y$—$(CH_2)_t$—$OR^z$, —$(CH_2)_s$—$SO_2NR^xR^y$, piperazine substituted by $R^n$, or a piperidinyl or a —O-piperidinyl group wherein said piperidinyl groups are substituted by one or more (e.g. 1, 2 or 3) $R^a$ groups;

$R^k$ represents chlorine, $C_{2-6}$ alkyl, $C_{2-6}$ alkenyl, $C_{2-6}$ alkynyl, $C_{3-8}$ cycloalkyl, $C_{3-8}$ cycloalkenyl, $C_{2-6}$ alkoxy, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-2}$ alkanol, $C_{4-6}$ alkanol, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NHC_{1-6}$ alkyl, —$(CH_2)_s$—$N(C_{1-6}$ alkyl$)_2$, —$(CH_2)_n$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups;

$R^m$ represents halogen, $C_{3-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^n$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups;

$R^p$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups; a —Y-(4-membered heterocyclyl group) wherein said 4-membered heterocyclyl group is substituted by one or more (e.g. 1, 2 or 3) $R^a$ groups; or a —Y-(5-10 membered heterocyclyl group) wherein said 5-10 membered heterocyclyl group may be optionally substituted by one or more (e.g. 1, 2 or 3) $R^a$ groups;

$R^q$ represents halogen, $C_{2-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{2-6}$ alkyl, monohalomethyl, dihalomethyl, halo$C_{1-6}$ alkoxy, $C_{2-6}$ alkanol, =O, =S, nitro, $Si(R^x)_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —NH($C_{1-6}$ alkyl), —N($C_{1-6}$alkyl)$_2$, —$(CH_2)_n$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_n$—$N^xR^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

n and q independently represent an integer from 1-4;
s and t independently represent an integer from 0-4;
or a pharmaceutically acceptable salt, solvate or derivative thereof.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $O_{1-4}$ alkoxy group contains from 1 to 4 carbon atoms, and so on.

In each of the group $(CRR^y)_n$ or $(CR^xR^y)_s$ the $R^x$ and $R^y$ groups can each be independently selected from the definitions of $R^x$ and $R^y$ for each $CR^xR^y$ unit i.e. $(CR^xR^y)_n$ where n is 2, indicates $CR^xR^y$—$CR^xR^y$ and each of $R^x$ and $R^y$ are selected independently from each other and from each of $R^x$ and $R^y$ in the other unit.

The term '$C_{1-6}$ alkyl' as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like. The terms '$C_{1-7}$alkyl', '$C_{2-6}$ alkyl', '$C_{3-6}$ alkyl' or '$C_{4-6}$ alkyl' or $C_2$ alkyl as used herein similarly define a group containing from 1 to 7, from 2 to 6, from 3 to 6, from 4 to 6, or 2 carbon atoms respectively.

The term '$C_{2-6}$ alkenyl' as used herein as a group or a part of the group refers to a linear or branched hydrocarbon group containing from 2 to 6 carbon atoms and containing a C=C bond.

The term '$C_{2-6}$ alkynyl' as used herein as a group or a part of the group refers to a linear or branched hydrocarbon group containing from 2 to 6 carbon atoms and containing a carbon—carbon triple bond.

The term '$C_{1-6}$ alkoxy' as used herein refers to an —O—$C_{1-6}$ alkyl group wherein $C_{1-6}$ alkyl is as defined herein. Examples of such groups include methoxy, ethoxy, propoxy, butoxy, pentoxy or hexoxy and the like. The term '$C_{2-6}$ alkoxy' used herein refer to an —O—$C_{2-6}$ alkyl group wherein $C_{2-6}$ alkyl is as defined herein.

The term '$C_{1-6}$ alkanol' as used herein refers to a $C_{1-6}$ alkyl group substituted by one or more hydroxy groups, wherein $C_{1-6}$ alkyl is as defined herein. The terms '$C_{4-6}$ alkanol', '$C_{1-2}$ alkanol' or '$C_{3-6}$ alkanol' as used herein similarly define a group containing from 4 to 6, from 1 to 2, or from 3 to 6, carbon atoms respectively, substituted by one or more hydroxyl groups. Examples of such groups include hydroxymethyl, hydroxyethyl, hydroxypropyl and the like.

The term '$C_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_{3-6}$ cycloalkyl' as used herein refers to a saturated monocyclic hydrocarbon ring of 3 to 6 carbon atoms. Examples of such groups include cyclopropyl, cyclobutyl, cyclopentyl, cyclohexyl, and the like.

The term '$C_{4-8}$ cycloalkyl' as used herein refers to a saturated monocyclic hydrocarbon ring of 4 to 8 carbon atoms. Examples of such groups include cyclobutyl, cyclopentyl, cyclohexyl, and the like.

The term '$C_{3-8}$ cycloalkenyl' as used herein refers to a non-aromatic monocyclic hydrocarbon ring of 3 to 8 carbon atoms and containing one or more C=C bonds. Examples of such groups include cyclopropene, cyclobutene, cyclopentene, cyclohexene, cycloheptene or cyclooctene and the like.

The term 'halogen' as used herein refers to a fluorine, chlorine, bromine or iodine atom.

The term 'halo$C_{1-6}$ alkyl' as used herein refers to a $C_{1-6}$ alkyl group as defined herein wherein at least one hydrogen atom is replaced with halogen. The term 'halo$C_{2-6}$ alkyl' as used herein similarly defines a group containing from 2 to 6 carbon atoms wherein at least one hydrogen atom is replaced with halogen. Examples of such groups include fluoroethyl, trifluoromethyl or trifluoroethyl and the like.

The term 'halo$C_{1-6}$ alkoxy' as used herein refers to a $C_{1-6}$ alkoxy group as herein defined wherein at least one hydrogen atom is replaced with halogen. Examples of such groups include difluoromethoxy or trifluoromethoxy and the like.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members. Where reference is made herein to carbocyclic and heterocyclic groups, the carbocyclic or heterocyclic ring can, unless the context indicates otherwise, be unsubstituted or substituted by one or more substituents for example molecular fragments, molecular scaffolds or functional groups as discussed herein. It will be appreciated that references to "carbocyclic" and "heterocyclic" groups include reference to carbocyclic and heterocyclic groups which may be optionally substituted by one or more (e.g. 1, 2 or 3) groups as indicated above.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring.

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cyclohexenyl, cycloheptenyl and cyclooctenyl. Saturated heterocyclic groups include piperidine, morpholine, thiomorpholine. Partially saturated heterocyclic groups include pyrazolines, for example 2-pyrazoline and 3-pyrazoline.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to five, e.g. about four, heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. One further example of a five membered heteroaryl group includes thiadiazole.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) an imidazole ring fused to a 5- or 6-membered ring containing 1 or 2 ring heteroatoms;
g) an oxazole ring fused to a 5- or 6-membered ring containing 1 or 2 ring heteroatoms;
h) an isoxazole ring fused to a 5- or 6-membered ring containing 1 or 2 ring heteroatoms;
i) a thiazole ring fused to a 5- or 6-membered ring containing 1 or 2 ring heteroatoms;
j) an isothiazole ring fused to a 5- or 6-membered ring containing 1 or 2 ring heteroatoms;
k) a thiophene ring fused to a 5- or 6-membered ring containing 1, 2 or 3 ring heteroatoms;
l) a furan ring fused to a 5- or 6-membered ring containing 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups. One further example of a bicyclic heteroaryl group containing a six membered ring fused to a five membered ring includes imidazopyridine.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups. One further example of a polycyclic heteroaryl group containing an aromatic ring and a non-aromatic ring includes tetrahydrotriazolopyrazine (e.g. 5,6,7,8-tetrahydro-[1,2,4]triazolo[4,3-a]pyrazine).

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine[6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

Examples of carbocyclic aryl groups include phenyl, naphthyl, indenyl, and tetrahydronaphthyl groups.

Examples of non-aromatic heterocyclic groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclic groups include saturated groups such as piperidine, pyrrolidine, azetidine, morpholine, piperazine and N-alkyl piperazines.

In a nitrogen-containing non-aromatic heterocyclic ring the ring must contain at least one ring nitrogen atom. The heterocyclic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof.

Particular examples of nitrogen-containing non-aromatic heterocyclic groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The carbocyclic and heterocyclic groups can be polycyclic fused ring systems or bridged ring systems such as bicycloalkanes, tricycloalkanes and their oxa- and aza analogues (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

The heterocyclic groups can each be unsubstituted or substituted by one or more substituent groups. For example, heterocyclic groups can be unsubstituted or substituted by 1, 2, 3 or 4 substituents. Where the heterocyclic group is monocyclic or bicyclic, typically it is unsubstituted or has 1, 2 or 3 substituents.

References to "N-linked imidazolyl" refer to an imidazolyl group linked to the carbon atom of the imidazo[1,2-a]pyridin-3-yl ring system by one of the nitrogen atoms of the imidazolyl group. Examples of N-linked imidazolyl groups include imidazol-1-yl.

References to "C-linked imidazolyl" refer to an imidazolyl group linked to the carbon atom of the imidazo[1,2-a]pyridin-3-yl ring system by one of the carbon atoms of the imidazolyl group.

Particular Embodiments of the Invention

Examples of ring systems encompassed by the definition $A^a$ are shown in the following formulae (I)A-(I)O, wherein the nitrogen atom demonstrates the point of attachment with the urea group:

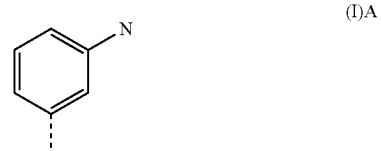

(I)A

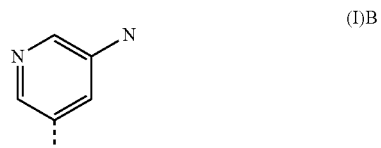

(I)B

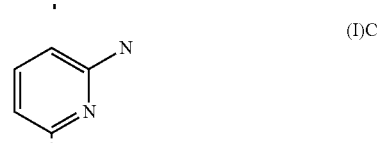

(I)C

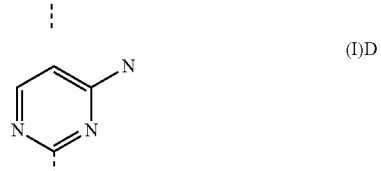

(I)D (I)E 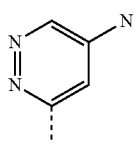

(I)F 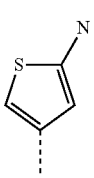

(I)G 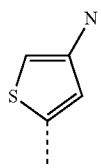

(I)H 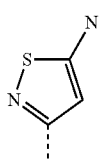

(I)I 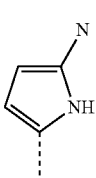

(I)J 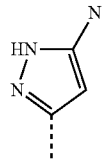

(I)K 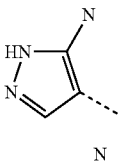

(I)L 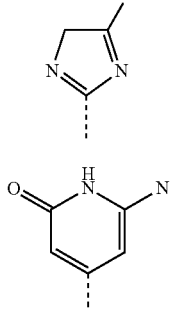

(I)M 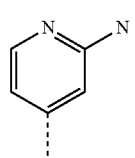

(I)N 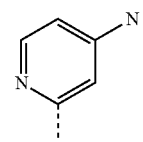

(I)O 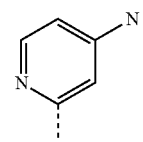

(I)L2 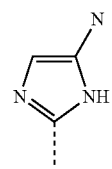

(I)P 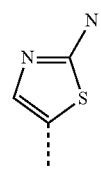

(I)Q 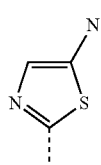

The group (I)L can be any tautomer of imidazole e.g. (I)L2. In one embodiment, $A^a$ or $A^b$ is a group other than pyrazole.

In one embodiment, $A^a$ is selected from (I)A, (I)B, (I)P and (I)Q.

In one embodiment, A is the group (I)A which can be optionally substituted by one or more (e.g. 1, 2 or 3) $R^a$ groups.

In one embodiment, $A^a$ represents a monocyclic aromatic carbocyclic or heterocyclic ring system having for example a 5, 6 or 7 membered ring (e.g. phenyl, pyridyl or thiazolyl).

In a further embodiment, $A^a$ represents a 6 membered carbocyclic ring. In a yet further embodiment, $A^a$ represents a phenyl group (i.e. a ring system of formula (I)A optionally substituted by one or more (e.g. 1, 2 or 3) $R^a$ groups.

In a further embodiment, $A^a$ or $A^c$ represents a pyridyl group (i.e. a ring system of formula (I)B or (I)C) optionally substituted by one or more (e.g. 1, 2 or 3) $R^a$ groups. In a yet further embodiment, $A^a$ or $A^c$ represents a ring system of formula (I)B optionally substituted by one or more (e.g. 1, 2 or 3) $R^a$ groups.

In a one embodiment, $A^a$ or $A^b$ represents a thiazolyl group, isothiazole group or imidazole group optionally substituted by one or more (e.g. 1, 2 or 3) $R^a$ groups.

In a further embodiment, $A^a$ or $A^b$ represents a thiazolyl group (i.e. a ring system of formula (I)H, (I)P or (I)Q) optionally substituted by one or more (e.g. 1, 2 or 3) $R^a$ groups.

In a yet further embodiment, $A^a$ or $A^b$ represents a ring system of formula (I)P or (I)Q optionally substituted by one or more (e.g. 1, 2 or 3) $R^a$ groups e.g. halogen (e.g. chlorine).

In one embodiment, $A^a$ or $A^c$ or $A^d$ represents a 6 membered monocyclic aromatic carbocyclic or heterocyclic ring system (e.g. phenyl or pyridyl), substituted by —NHCONR$^1$R$^2$ at the 3-position or 5-position.

Also disclosed is, $A^a$ or $A^c$ or $A^d$ represents a 6 membered monocyclic aromatic carbocyclic or heterocyclic ring system (e.g. phenyl or pyridyl), substituted by —NHCONR$^1$R$^2$ at the 5-position and further optionally substituted by a single $R^a$ group at the 3-position.

In one embodiment, $A^a$ or $A^c$ represents a 6 membered monocyclic aromatic carbocyclic or heterocyclic ring system (e.g. phenyl or pyridyl), substituted by —NHCONR$^1$R$^2$ at the 5-position and further optionally substituted by a single R$^a$ group at the 3-position, and A$^d$ represents a 6 membered monocyclic aromatic carbocyclic ring system (e.g. phenyl), substituted by —NHCONR$^1$R$^2$ at the 5-position and further optionally substituted by a single R$^a$ group at the 3-position.

In one embodiment, $A^a$ or $A^d$ represents unsubstituted phenyl or phenyl substituted with an —(CH$_2$)$_s$—CONR$^x$R$^y$ (e.g. —CONH$_2$), —(CH$_2$)$_s$—CN (e.g. —CN), halogen (e.g. fluorine), C$_{1-6}$ alkyl (e.g. methyl), C$_{1-6}$ alkanol (e.g. —CH$_2$OH) or —OR$^x$ (e.g. methoxy or —OCH(Me)$_2$) group.

In one embodiment, A$^d$ represents unsubstituted phenyl or phenyl substituted with an —(CH$_2$)$_s$—CONR$^x$R$^y$ (e.g. —CONH$_2$), —(CH$_2$)$_s$—CN (e.g. —CN), halogen (e.g. fluorine, chlorine, bromine), C$_{1-6}$ alkyl (e.g. methyl), C$_{1-6}$ alkanol (e.g. —CH$_2$OH), —O—(CH$_2$)$_n$—OR$^x$ (e.g. —O—CH$_2$—CH$_2$—O—CH$_3$), —(CR$^x$R$^y$)$_s$—COOR$^z$ (e.g. —COOCH$_3$), —(CH$_2$)$_s$—NR$^x$R$^y$ (e.g. —CH$_2$NH$_2$), haloC$_{1-6}$ alkyl (e.g. trifluoromethyl) or —OR$^x$ (e.g. —OH or methoxy or —OCH(Me)$_2$ or —OCH$_5$H$_9$) group.

In a further embodiment, $A^a$ or A$^d$ represents unsubstituted phenyl.

In one embodiment, $A^a$ is as defined in $A^b$. In another embodiment, $A^a$ is as defined in A.

In another embodiment, $A^a$ is as defined in $A^d$.

Also disclosed is, R$^1$ represents hydrogen or C$_{1-6}$ alkyl (e.g. methyl) and R$^2$ represents hydrogen, C$_{1-6}$ alkyl (e.g. methyl, ethyl, butyl, —CH(Me)$_2$, —CH$_2$CH(Me)$_2$ or —C(Me)$_3$), C$_{1-6}$ alkyl substituted by one or more R$^a$ groups (e.g. —CH$_2$—C(Me)$_2$—CH$_2$—NH$_2$, —CH$_2$—CH(Me)-OMe or —CH$_2$—C(F)$_2$—CH$_2$NH$_2$), C$_{3-8}$ cycloalkyl (e.g. cyclopropyl), C$_{1-6}$ alkanol (e.g. —CH$_2$—CH(OH)—CH$_2$OH), —(CH$_2$)$_n$—NR$^x$R$^y$ (e.g. —(CH$_2$)$_2$NHCOOt-Bu, —(CH$_2$)$_2$NH$_2$ or —(CH$_2$)$_3$NH$_2$), —(CH$_2$)$_n$-aryl (e.g. benzyl optionally substituted by a halogen atom, such as a fluorine atom), —(CH$_2$)$_n$-heterocyclyl (e.g. —CH$_2$-dioxaolanyl (optionally substituted by one or more C$_{1-6}$ alkyl (e.g. methyl) groups), —CH$_2$-tetrahydrofuranyl or —CH$_2$-piperidinyl) or haloC$_{1-6}$ alkyl (e.g. —(CH$_2$)$_2$—F, —CH$_2$—CH—F$_2$—CH(Me)-CF$_3$ or —CH$_2$—CF$_3$).

In one embodiment, R$^1$ represents hydrogen or C$_{1-6}$ alkyl (e.g. methyl) and R$^2$ represents hydrogen, C$_{1-6}$ alkyl (e.g. methyl, ethyl, butyl, —CH(Me)$_2$, —CH$_2$CH(Me)$_2$ or —C(Me)$_3$), C$_{3-8}$ cycloalkyl (e.g. cyclopropyl) or haloC$_{1-6}$ alkyl (e.g. —(CH$_2$)$_2$—F, —CH$_2$—CH—F$_2$—CH(Me)-CF$_3$ or —CH$_2$—CF$_3$).

Also disclosed is, when A represents phenyl, R$^1$ and R$^2$ represent a group other than phenyl.

In a further embodiment, R$^1$ represents hydrogen and R$^2$ represents hydrogen, C$_{1-6}$ alkyl (e.g. methyl, ethyl, butyl, —CH(Me)$_2$, —CH$_2$CH(Me)$_2$ or —C(Me)$_3$), C$_{3-8}$ cycloalkyl (e.g. cyclopropyl), or haloC$_{1-6}$ alkyl (e.g. —(CH$_2$)$_2$—F, —CH$_2$—CH—F$_2$—CH(Me)-CF$_3$ or —CH$_2$—CF$_3$). In a yet further embodiment, R$^1$ represents hydrogen and R$^2$ represents C$_{1-6}$ alkyl (e.g. ethyl), C$_{3-8}$ cycloalkyl (e.g. cyclopropyl), or haloC$_{1-6}$ alkyl (e.g.—CH$_2$—CF$_3$). In a yet further embodiment, R$^1$ represents hydrogen and R$^2$ represents —CH$_2$—CF$_3$.

In one embodiment, R$^3$ represents hydrogen or methyl. In a further embodiment, R$^3$ represents hydrogen.

In one embodiment, when R$^1$ and R$^2$ independently represent hydrogen or C$_{3-8}$ cycloalkyl (e.g. R$^1$ represents hydrogen and R$^2$ represents cyclopropyl or R$^1$ and R$^2$ both represent hydrogen), R$^{4a}$ represents halogen (e.g. chlorine) or a monocyclic aromatic carbocyclic group (e.g. phenyl) optionally substituted by one or more (e.g. 1, 2 or 3) R$^b$ groups such as halogen (e.g. fluorine) or R$^{4a}$ represents an aromatic heterocyclic group (e.g. a pyrimidinyl) which may be optionally substituted by one or more (e.g. 1, 2 or 3) R$^a$ groups such as halogen (e.g. fluorine) or —(CH$_2$)$_s$NR$^x$R$^y$ (e.g. —NH$_2$).

In one embodiment, when R$^1$ and R$^2$ independently represent hydrogen or C$_{3-8}$ cycloalkyl (e.g. R$^1$ represents hydrogen and R$^2$ represents cyclopropyl or R$^1$ and R$^2$ both represent hydrogen), R$^{4a}$ represents —X—R$^5$ a further embodiment X represents —C≡C— and R$^5$ represents an aromatic or non-aromatic heterocyclic group wherein said heterocyclic group may be optionally substituted by one or more (e.g. 1, 2 or 3) R$^b$ groups. In a still further embodiment R$^5$ represents an imidazoyl substituted with one methyl group.

In one embodiment, when R$^1$ and R$^2$ independently represent hydrogen or C$_{3-8}$ cycloalkyl (e.g. R$^1$ represents hydrogen and R$^2$ represents cyclopropyl or R$^1$ and R$^2$ both represent hydrogen), R$^{4a}$ represents an aromatic or non-aromatic carbocyclic or heterocyclic group wherein said carbocyclic or heterocyclic group may be optionally substituted by one or more (e.g. 1, 2 or 3) R$^b$ groups. In one embodiment R$^1$ and R$^2$ both represent hydrogen and R$^{4a}$ represents an aromatic or non-aromatic heterocyclic group (e.g. an oxadiazolyl, thiadiazolyl) wherein said heterocyclic group may be optionally substituted by one or more (e.g. 1, 2 or 3) methyl groups.

In one embodiment, when R$^1$ represents hydrogen and R$^2$ represents C$_{1-6}$ alkyl or haloC$_{1-6}$ alkyl (e.g. ethyl or —CH$_2$—CF$_3$), A$^b$ represents pyrrole, furan, thiophene, imidazole, furazan, oxazole, oxadiazole, oxatriazole, isoxazole, thiazole, isothiazole, pyrazole, triazole, thiadiazole or tetrazole optionally substituted by one or more (e.g. 1, 2 or 3) R$^a$ groups. In a further embodiment, A$^b$ represents pyrrole, imidazole, furazan, oxazole, oxadiazole, oxatriazole, isoxazole, thiazole, isothiazole, pyrazole, triazole, thiadiazole or tetrazole optionally substituted by one or more (e.g. 1, 2 or 3) R$^a$ groups. In a yet further embodiment, A$^b$ represents thiazole optionally substituted by one or more (e.g. 1, 2 or 3) R$^a$ groups (e.g. chlorine).

In one embodiment when, R$^1$ represents hydrogen and R$^2$ represents C$_{1-6}$ alkyl or halo C$_{1-6}$ alkyl (e.g. ethyl or —CH$_2$—CF$_3$), A is a group A$^c$ which represents an aromatic 6 membered heterocyclic group which may be optionally substituted by one or more (e.g. 1, 2 or 3) R$^a$ groups and R$^4$ is a group R$^{4b}$ which represents —X—R$^5$. In a further embodiment Ac represents a pyridinyl. In a further embodiment X represents —C≡C— and R$^5$ represents an aromatic or non-aromatic heterocyclic group wherein said heterocyclic group may be optionally substituted by one or more (e.g. 1, 2 or 3) R$^b$ groups (e.g. an imidazolyl substituted by one or methyl groups).

In one embodiment the compound of formula (I) is as defined in (i).

In one embodiment the compound of formula (I) is as defined in (ii).

In one embodiment the compound of formula (I) is as defined in (iii).

In one embodiment the compound of formula (I) is as defined in (iv).

In one embodiment the compound of formula (I) is as defined in (v).

In one embodiment the compound of formula (I) is as defined in (vi).

In one embodiment when R$^4$ is a group R$^{4a}$, R$^{4a}$ is as defined in R$^{4b}$.

In one embodiment when R$^4$ is a group R$^{4a}$, R$^{4a}$ is as defined in R$^{4c}$.

In one embodiment when R$^4$ is a group R$^{4a}$, R$^{4a}$ is as defined in R$^{4d}$.

In one embodiment when $R^4$ is a group $R^{4a}$, $R^{4a}$ is as defined in $R^{4e}$.

In one embodiment when $R^4$ is a group $R^{4b}$, $R^{4b}$ is as defined in $R^{4c}$.

In one embodiment when $R^4$ is a group $R^{4b}$, $R^{4b}$ is as defined in $R^{4d}$.

In one embodiment when $R^4$ is a group $R^{4b}$, $R^{4b}$ is as defined in $R^{4e}$.

In one embodiment when $R^4$ is a group $R^{4c}$, $R^{4c}$ is selected from (b)-(h), (j)-(k), (m)-(u) and (w)-(y).

In one embodiment when $R^4$ is a group $R^{4c}$, $R^{4c}$ is —X—$R^6$.

In one embodiment when $R^4$ is a group $R^{4c}$, $R^{4c}$ is phenyl substituted by one or more (e.g. 1, 2 or 3) $C_{2-6}$ alkanol groups.

In one embodiment when $R^4$ is a group $R^{4c}$, $R^{4c}$ is pyrimidin-2-yl optionally substituted by one or more (e.g. 1, 2 or 3) $R^e$ groups.

In one embodiment when $R^4$ is a group $R^{4c}$, $R^{4c}$ is pyridazinyl (e.g. pyridazin-3-yl or pyridazin-4-yl) optionally substituted by one or more (e.g. 1, 2 or 3) $R^e$ groups.

In one embodiment when $R^4$ is a group $R^{4c}$, $R^{4c}$ is pyrazinyl (e.g. pyrazin-2-yl) optionally substituted by one or more (e.g. 1, 2 or 3) $R^b$ groups.

In one embodiment when $R^4$ is a group $R^{4c}$, $R^{4c}$ is thiophenyl (e.g. thien-3-yl) substituted by one or more (e.g. 1, 2 or 3) $R^e$ groups.

In one embodiment when $R^4$ is a group $R^{4c}$, $R^{4c}$ is pyrazolyl (e.g. pyrazol-4-yl) substituted by one or more (e.g. 1, 2 or 3) $R^f$ groups.

Also disclosed is when $R^4$ is a group $R^{4c}$, $R^{4c}$ is thiadiazolyl (e.g. [1,3,4]thiadiazol-2-yl) substituted by one or more (e.g. 1, 2 or 3) $R^h$ groups.

In one embodiment when $R^4$ is a group $R^{4c}$, $R^{4c}$ is thiadiazolyl (e.g. [1,3,4]thiadiazol-2-yl) substituted by one $R^h$ group.

In one embodiment $R^{4c}$ is thiadiazolyl substituted by one —$(CH_2)_{2-4}$—O—$C_{1-6}$alkyl (e.g. —$CH_2CH_2$—O—$CH_3$). or $C_{2-6}$alkanol (e.g. —$CH_2CH_2OH$).

In one embodiment when $R^4$ is a group $R^{4c}$, $R^{4c}$ is oxo-dihydro-pyridin-3-yl (e.g. 6-oxo-1,6-dihydro-pyridin-3-yl) substituted by one or more (e.g. 1, 2 or 3) $R^j$ groups.

In one embodiment, $R^j$ represents chlorine, ethyl, $C_{4-6}$ alkyl, $C_{2-6}$ alkenyl, $C_{2-6}$ alkynyl, $C_{3-8}$ cycloalkyl, $C_{3-8}$ cycloalkenyl, —O—$C_2$ alkyl, —O—$C_{4-6}$ alkyl, —$(CH_2)_n$—O—$C_{1-6}$ alkyl, —O—$(CH_2)_n$—$OR^x$, halo$C_{2-6}$ alkyl, mono-halomethyl, dihalomethyl, halo$C_{1-6}$ alkoxy, $C_{1-2}$ alkanol, $C_{4-6}$ alkanol, =S, nitro, Si$(R^x)_4$, —$(CH_2)_s$—CN, —S—$R^x$, —SO—$R^x$, —$SO_2$—$R^x$, —$COR^x$, —$(CR^xR^y)_s$—$COOC_{1-6}$ alkyl, —$(CR^xR^y)_s$—$CONR^wR^z$, —$(CH_2)_s$—$CONR^xR^y$, —$(CH_2)_s$—$NHC_{1-6}$ alkyl, —$(CH_2)_s$—NMe$(C_{2-6}$ alkyl), —$(CH_2)_s$—N—$(C_{2-6}$ alkyl$)_2$, —$(CH_2)_n$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —O—$(CH_2)_n$—$NR^xR^y$, —O—$(CH_2)_s$—$CR^xR^y$—$(CH_2)_t$—$OR^z$, —$(CH_2)_s$—$SO_2NR^XR^y$, piperazine substituted by $R''$, or a piperidinyl, or a —O-piperidinyl group wherein said piperidinyl group is substituted by one or more (e.g. 1, 2 or 3) $R^a$ groups;

In one embodiment, when $R^1$ represents hydrogen and $R^2$ represents $C_{1-6}$ alkyl or halo$C_{1-6}$ alkyl (e.g. ethyl or —$CH_2$—$CF_3$), $R^{4a}$ represents halogen (e.g. chlorine).

In one embodiment, when $R^1$ represents hydrogen and $R^2$ represents $C_{1-6}$ alkyl or halo$C_{1-6}$ alkyl (e.g. ethyl or —$CH_2$—$CF_3$), $A^c$ represents pyridinyl (e.g. pyridin-3-yl).

In one embodiment, when $R^1$ and $R^2$ independently represent hydrogen or $C_{3-8}$cycloalkyl, $R^{4a}$ represents oxadiazole, thiadiazole or pyrimidine optionally substituted by one or more (e.g. 1, 2 or 3) $R^a$ groups.

In one embodiment, when $R^1$ represents hydrogen and $R^2$ represents $C_{1-6}$ alkyl or halo$C_{1-6}$ alkyl (e.g. ethyl or —$CH_2$—$CF_3$), $R^{4a}$ represents oxadiazole, thiadiazole or pyrimidine optionally substituted by one or more (e.g. 1, 2 or 3) $R^a$ groups.

In one embodiment when $R^4$ is a group $R^{4a}$, $R^{4a}$ is phenyl substituted by one or more (e.g. 1, 2 or 3) $R^b$ groups.

In one embodiment when $R^4$ is a group $R^{4a}$, $R^{4a}$ is phenyl substituted by one or more (e.g. 1, 2 or 3) $R^a$ groups.

In one embodiment the $R^a$ or $R^b$ group is at the 3- or 4-position of the phenyl ring, in particular at the 4-position of the phenyl ring.

In one embodiment when $R^4$ is a group $R^{4a}$, $R^{4a}$ is phenyl substituted by one or more (e.g. 1, 2 or 3) halogen (e.g. fluorine) groups.

In a further embodiment, $R^{4a}$ represents 4-fluoro-phenyl.

In one embodiment when $R^4$ is a group $R^{4a}$, $R^{4a}$ is pyrimidin-2-yl optionally substituted by one or more (e.g. 1, 2 or 3) $R^b$ groups.

In one embodiment, when $R^1$ represents hydrogen and $R^2$ represents $C_{1-6}$ alkyl or halo$C_{1-6}$ alkyl (e.g. ethyl or —$CH_2$—$CF_3$), $R^{4b}$ represents an aromatic heterocyclic group (e.g. pyrrole, furan, thiophene, imidazole, furazan, oxazole, oxadiazole, oxatriazole, isoxazole, thiazole, isothiazole, pyrazole, triazole, tetrazole, thiadiazole, pyridine, pyrazine, pyridazine, pyrimidine or triazine) optionally substituted by one or more (e.g. 1, 2 or 3) $R^d$ groups. In a further embodiment, when $R^1$ represents hydrogen and $R^2$ represents $C_{1-6}$ alkyl or halo$C_{1-6}$ alkyl (e.g. ethyl or —$CH_2$—$CF_3$), $R^{4b}$ represents an aromatic heterocyclic group (e.g. pyridine, pyrazine, pyridazine, pyrimidine or triazine) optionally substituted by one or more (e.g. 1, 2 or 3) $R^d$ groups.

In one embodiment, when $R^1$ represents hydrogen and $R^2$ represents $C_{1-6}$ alkyl or halo$C_{1-6}$ alkyl (e.g. ethyl or —$CH_2$—$CF_3$), $R^{4b}$ represents an aromatic heterocyclic group (e.g. a pyrimidin-2-yl) optionally substituted by one or more (e.g. 1, 2 or 3) $R^b$ groups (such as fluorine or $NH_2$). In a further embodiment A is a group $A^c$ which represents an aromatic six membered heterocyclic group (e.g. a pyridinyl). In a still further embodiment $R^3$ is hydrogen.

In one embodiment, when $R^1$ represents hydrogen and $R^2$ represents $C_{1-6}$ alkyl or halo$C_{1-6}$ alkyl (e.g. ethyl or —$CH_2$—$CF_3$), $R^{4b}$ represents halogen (e.g. chlorine), —X—$R^5$ (e.g. —C≡C-cyclopropyl) or an aromatic heterocyclic group (e.g. pyridazinyl, thiadiazolyl, pyrimidinyl or pyrazolyl) optionally substituted by one or more (e.g. 1, 2 or 3) $R^d$ groups such as $C_{1-6}$ alkyl (e.g. methyl), —Y-heterocyclyl (e.g. -piperidinyl or -azetidinyl) wherein said —Y-heterocyclyl group may be optionally substituted by one or more (e.g. 1, 2 or 3) $R^a$ groups (such as —COO-t-Bu).

In one embodiment, $R^{4b}$ represents unsubstituted thiadiazole, unsubstituted pyridinyl (e.g. pyridin-2-yl), unsubstituted pyrimidinyl (e.g. pyrimidin-2-yl) or pyridazinyl (e.g. pyridazin-3-yl) optionally substituted with $C_{1-6}$ alkyl (e.g. methyl).

In one embodiment, $R^{4b}$ represents unsubstituted thiadiazole, unsubstituted pyridinyl (e.g. pyridin-2-yl), unsubstituted pyrimidinyl (e.g. pyrimidin-2-yl), pyridazinyl (e.g. pyridazin-3-yl) optionally substituted with $C_{1-6}$alkyl (e.g. methyl) or pyrazolyl substituted with Y-heterocyclyl (e.g. where Y is a bond).

In one embodiment, when $R^1$ represents hydrogen and $R^2$ represents hydrogen or $C_{1-6}$ alkyl (e.g. ethyl), $R^{4b}$ represents a group other than chlorine.

In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents an amino (e.g. —NH$_2$) group. In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents an amino group other than —NH$_2$.

In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents pyrazolyl substituted by one or more (e.g. 1, 2 or 3) $R^f$ groups such as $C_{1-6}$ alkyl (e.g. methyl), $C_{1-6}$ alkanol (e.g. —C(Me)$_2$-CH$_2$—OH), —(CR$^x$R$^y$)$_s$—COOR$^z$ (e.g. —C(Me)$_2$-COOH or —C(Me)$_2$-COO-Et), —(CH$_2$)$_s$—NR$^x$R$^y$ (e.g. —CH$_2$—NH$_2$), —(CR$^x$R$^y$)$_s$—CONR$^w$R$^z$ (e.g. —C(Me)$_2$-CONH$_2$, —C(Me)$_2$-CONHMe, —C(Me)$_2$-CON(Me)$_2$, —C(Me)$_2$-CONH-cyclopropyl, —C(Me)$_2$-CONH—(CH$_2$)$_2$—N(Et)$_2$), Y-heterocyclyl (e.g. pyrrolidinyl, tetrahydrofuranyl, piperidinyl, azetidinyl or —C(Me)$_2$-CO-azetidinyl) wherein said —Y-heterocyclyl group may be optionally substituted by one or more (e.g. 1, 2 or 3) $C_{1-6}$ alkyl (e.g. methyl, ethyl or isopropyl), —COR$^x$ (e.g. —COMe), —(CR$^x$R$^y$)$_s$—COOR$^z$ (e.g. —COO-t-Bu) or —SO$_2$—R$^x$ (e.g. —SO$_2$Me).

Also disclosed is, when $R^1$ represents hydrogen, $R^2$ represents $C_{1-6}$ alkyl or haloC$_{1-6}$ alkyl (e.g. ethyl or —CH$_2$—CF$_3$) and $R^{4c}$ represents pyrazolyl optionally substituted by one or more (e.g. 1, 2 or 3) $R^f$ groups such as $C_{1-6}$ alkyl (e.g. methyl), $C_{1-6}$ alkanol (e.g. —C(Me)$_2$—CH$_2$—OH), —(CR$^x$R$^y$)$_s$—COOR$^z$ (e.g. —C(Me)$_2$-COOH or —C(Me)$_2$-COO-Et), —(CR$^x$R$^y$)$_s$—CONR$^w$R$^z$ (e.g. —C(Me)$_2$-CONH$_2$, —C(Me)$_2$-CONHMe, —C(Me)$_2$-CON(Me)$_2$, —C(Me)$_2$—CONH—(CH$_2$)$_2$—N(Et)$_2$), Y-heterocyclyl (e.g. pyrrolidinyl, tetrahydrofuranyl, piperidinyl, azetidinyl or —C(Me)$_2$-CO-azetidinyl) wherein said —Y-heterocyclyl group may be optionally substituted by one or more (e.g. 1, 2 or 3) $C_{1-6}$ alkyl (e.g. methyl, ethyl or isopropyl), —COR$^x$ (e.g. —COMe) or —SO$_2$—R$^x$ (e.g. —SO$_2$Me).

Also disclosed is, when $R^1$ represents hydrogen, $R^2$ represents $C_{1-6}$ alkyl or haloC$_{1-6}$ alkyl (e.g. ethyl or —CH$_2$—CF$_3$) and $R^{4c}$ represents pyrazolyl substituted by one or more (e.g. 1, 2 or 3) $R^f$ groups such as $C_{1-6}$ alkyl (e.g. methyl), $C_{1-6}$ alkanol (e.g. —C(Me)$_2$-CH$_2$—OH), —(CR$^x$R$^y$)$_s$—COOR$^z$ (e.g. —C(Me)$_2$-COOH or —C(Me)$_2$-COO-Et), —(CR$^x$R$^y$)$_s$—CONR$^w$R$^z$ (e.g. —C(Me)$_2$-CONH$_2$, —C(Me)$_2$-CONHMe, —C(Me)$_2$-CON(Me)$_2$, —C(Me)$_2$-CONH—(CH$_2$)$_2$—N(Et)$_2$), Y-heterocyclyl (e.g. pyrrolidinyl, tetrahydrofuranyl, piperidinyl, azetidinyl or —C(Me)$_2$-CO-azetidinyl) wherein said —Y-heterocyclyl group may be optionally substituted by one or more (e.g. 1, 2 or 3) $C_{1-6}$ alkyl (e.g. methyl, ethyl or isopropyl), —COR$^x$ (e.g. —COMe), —SO$_2$—R$^x$ (e.g. —SO$_2$Me) or $C_{1-6}$alkanol (e.g. —CH$_2$—CH$_2$—OH) groups.

In one embodiment, when $R^1$ represents hydrogen, $R^2$ represents $C_{1-6}$ alkyl or haloC$_{1-6}$ alkyl (e.g. ethyl or —CH$_2$—CF$_3$) and $R^{4c}$ represents pyrazolyl substituted by one or more (e.g. 1, 2 or 3) $R^f$ groups such as $C_{4-6}$ alkyl, $C_{3-6}$ alkanol (e.g. —C(Me)$_2$-CH$_2$—OH), —(CR$^x$R$^y$)$_s$—COOR$^z$ (e.g. —C(Me)$_2$-COOH or —C(Me)$_2$-COO-Et), —(CR$^x$R$^y$)$_s$—CONR$^w$R$^z$ (e.g. —C(Me)$_2$—CONH$_2$, —C(Me)$_2$-CONHMe, —C(Me)$_2$-CON(Me)$_2$, —C(Me)$_2$-CONH—(CH$_2$)$_2$—N(Et)$_2$), Y-heterocyclyl (e.g. pyrrolidinyl, tetrahydrofuranyl, piperidinyl, azetidinyl or —C(Me)$_2$-CO-azetidinyl) wherein said —Y-heterocyclyl group may be optionally substituted by one or more (e.g. 1, 2 or 3) $C_{1-6}$ alkyl (e.g. methyl, ethyl or isopropyl), —COR$^x$ (e.g. —COMe), —SO$_2$—R$^x$ (e.g. —SO$_2$Me) or $C_{1-6}$alkanol (e.g. —CH$_2$—CH$_2$—OH) groups.

Also disclosed is, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents thiadiazolyl substituted by one or more (e.g. 1, 2 or 3) $R^h$ groups such as haloC$_{1-6}$ alkyl (e.g. trifluoromethyl) or —Y-heterocyclyl groups (e.g. tetrahydrofuranyl or —(CH$_2$)$_2$-piperidinyl).

In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents thiadiazolyl substituted by one $R^h$ group such as haloC$_{1-6}$ alkyl (e.g. trifluoromethyl), —(CH$_2$)$_s$—NR$^x$R$^y$ (e.g. diethylaminoethyl, —NH$_2$, —NHCH$_2$CH$_3$, —NH(CH$_2$)$_2$—O—CH$_3$, —NHcyclopropyl) or —Y-heterocyclyl group (e.g. tetrahydrofuranyl or —(CH$_2$)$_2$-piperidinyl). In a further embodiment heterocyclyl represents pyrrolidine and Y represents ethyl. In a still further embodiment —Y-heterocyclyl represents pyrrolidin-1-yl-ethyl. In a further embodiment heterocyclyl represents a pyridinyl and Y represents —NR$^x$—(CH$_2$)$_s$— (e.g. —NH—).

In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents N-linked imidazolyl optionally substituted by one or more (e.g. 1, 2 or 3) $R^b$ groups such as $C_{1-6}$ alkyl (e.g. methyl).

In one embodiment, when $R^1$ represents hydrogen, $R^2$ represents haloC$_{1-6}$ alkyl (e.g. —CH$_2$—CF$_3$) and $R^{4c}$ represents N-linked imidazolyl substituted by a single substituent, said substituent is other than 2-methyl.

In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents —(CH$_2$)$_q$-imidazolyl (e.g. —(CH$_2$)$_2$-imidazolyl) optionally substituted by one or more (e.g. 1, 2 or 3) $R^b$ groups such as $C_{1-6}$ alkyl (e.g. methyl).

In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents pyridazinyl (e.g. pyridazin-3-yl) optionally substituted by one or more (e.g. 1, 2 or 3) $R^e$ groups such as halogen (e.g. chlorine), $C_{1-6}$ alkyl (e.g. methyl), —OR$^x$ (e.g. methoxy), =O, —(CH$_2$)$_s$—NR$^x$R$^y$ (e.g. —N(Me)$_2$, —N—C(Me)$_2$-CH$_2$—OH, —NH—(CH$_2$)$_2$—OH or —NH—(CH$_2$)$_2$—O-Me), —Y-heterocyclyl (e.g. -azetidinyl, -piperidinyl, —NH-piperidinyl, piperazinyl, -morpholinyl, —NH-tetrahydropyranyl) wherein said —Y-heterocyclyl groups may be optionally substituted by one or more (e.g. 1, 2 or 3) $C_{1-6}$ alkyl (e.g. methyl), =O or —(CH$_2$)$_s$—NR$^x$R$^y$ (e.g. —NH$_2$ or —N(Me)$_2$).

In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents pyridazinyl (e.g. pyridazin-3-yl) substituted by one or more (e.g. 1, 2 or 3) $R^e$ groups such as halogen (e.g. chlorine), $C_{1-6}$ alkyl (e.g. methyl), —OR$^x$ (e.g. methoxy), =O, —(CH$_2$)$_s$—CN (e.g. CN), —(CH$_2$)$_s$—NR$^x$R$^y$ (e.g. —N(Me)$_2$, —N—C(Me)$_2$-CH$_2$—OH, —NH—(CH$_2$)$_2$—OH or —NH—(CH$_2$)$_2$—O-Me), —Y-heterocyclyl (e.g. -azetidinyl, -piperidinyl, —NH-piperidinyl, piperazinyl, -morpholinyl, —NH-tetrahydropyranyl) wherein said —Y-heterocyclyl groups may be optionally substituted by one or more (e.g. 1, 2 or 3) $C_{1-6}$ alkyl (e.g. methyl) or —(CH$_2$)$_s$—NR$^x$R$^y$ (e.g. —NH$_2$ or —N(Me)$_2$).

In one embodiment, when $R^1$ represents hydrogen and $R^2$ represents haloC$_{1-6}$ alkyl (e.g. —CH$_2$—CF$_3$), $R^{4c}$ represents pyridazinyl (e.g. pyridazin-3-yl) substituted by one or more (e.g. 1, 2 or 3) $R^e$ groups. In a further embodiment $R^{4c}$ represents pyridazinyl (e.g. pyridazin-3-yl) and is substituted by one $C_{1-6}$alkyl (e.g. methyl) group. In a still further embodiment A is a group $A^d$ and represents a phenyl group and $R^3$ represents hydrogen.

In one embodiment, when $R^1$ represents hydrogen and $R^2$ represents $C_{1-6}$ alkyl or haloC$_{1-6}$ alkyl (e.g. ethyl or —CH$_2$—CF$_3$), $R^{4c}$ represents pyrazinyl (e.g. pyrazin-2-yl) optionally substituted by one or more (e.g. 1, 2 or 3) $R^b$ groups such as $C_{1-6}$ alkyl (e.g. methyl), $—(CH_2)_s—NR^xR^y$ (e.g. $—NH_2$), $—OR^x$ (e.g. hydroxy or methoxy).

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyrazinyl (e.g. pyrazin-2-yl) optionally substituted by one or more (e.g. 1, 2 or 3) $R^b$ groups such as $C_{1-6}$ alkyl (e.g. methyl) or $—OR^x$ (e.g. hydroxy or methoxy).

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyrazinyl (e.g. pyrazin-3-yl) optionally substituted by one or more (e.g. 1, 2 or 3) $R^b$ groups such as haloC$_{1-6}$ alkyl (e.g. trifluoromethyl).

Also disclosed is, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyrimidin-5-yl optionally substituted by one or more (e.g. 1, 2 or 3) $R^g$ groups such as —Y-heterocyclyl (e.g. -azetidinyl, -piperazinyl) wherein said —Y-heterocyclyl groups may be optionally substituted by one or more (e.g. 1, 2 or 3) halogen (e.g. fluorine), $=O$ or $C_{1-6}$ alkyl (e.g. methyl).

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyrimidin-5-yl optionally substituted by one or more (e.g. 1, 2 or 3) $R^p$ groups such as haloC$_{1-6}$ alkyl (e.g. trifluoromethyl), or —Y-heterocyclyl (e.g. -azetidinyl, -piperazinyl) wherein said —Y-heterocyclyl groups is substituted by one or more (e.g. 1, 2 or 3) halogen (e.g. fluorine), $=O$ or $C_{1-6}$ alkyl (e.g. methyl).

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyrimidin-2-yl optionally substituted by one or more (e.g. 1, 2 or 3) $R^b$ groups such as halogen (e.g. fluorine, chlorine), $=O$, $C_{1-6}$ alkyl (e.g. methyl, isopropyl), $C_{1-6}$alkanol (e.g. $—CH_2OH$, $—CHOHCH_3$, $—COH(CH_3)_2$) haloC$_{1-6}$ alkyl (e.g. trifluoromethyl, $—CF_2CH_3$), $—OR^x$ (e.g. methoxy, ethoxy, $—OCH_2CH_2OH$), $—COR^x$ (e.g. $—COCH_3$), $—(CR^xR^y)_s—CONR^wR^z$ (e.g. $CONH_2$), $—(CH_2)_s—NR^xR^y$ (e.g. $—NH_2$ or $—N(Me)_2$, or $—NHMe$, $—NH—CH_2—CH_2—OH$, $NH—CH_2—CH_3$, $—NH$cyclopropyl, $—NH(C_4H_7)$, $—NH—CH_2—CH_2—NH_2$, $—CH_2N(CH_3)_2$, $—N(COOCCH_3)_2$), $—(CH_2)_s—CN$, $—(CH_2)_s—NR^xCO_2R^y$ (e.g. $NHCO_2(CH_2)_3CH_3$, $—NHCO_2CH_2CH_3$, $NHCO_2CH_2CH(CH_3)_2$ or $NHCO_2(CH_2)_4CH_3$), $—(CR^xR^y)_s—COOR^z$ (e.g. $—COOCH_2CH_3$, $—COOCH_3$ or $—COOH$), $—(CH_2)_s—NR^xSO_2—R^y$ (e.g. $NHSO_2—CH_3$), $—(CH_2)_s—NH—SO_2—NR^xR^y$ (e.g. $NHSO_2N(CH_3)_2$ or —Y-heterocyclyl (e.g. -piperidinyl, azetidinyl, imidazolyl, morpholine) wherein said —Y-heterocyclyl groups may be optionally substituted by one or more (e.g. 1, 2 or 3) $—OR^x$ (e.g. hydroxy) or $—(CH_2)_s—NR^xR^y$ (e.g. $—NH_2$) or $C_{1-6}$ alkanol (e.g. $—CH_2CH_2OH$) groups. In a further embodiment Y represents a bond or $—(CR^xR^y)_s—CO—$ (e.g. $—CO—$) or $—(CH_2)_n—(CR^xR^y)_s$ (e.g. $—CH_2$).

Also disclosed is, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyrimidin-4-yl optionally substituted by one or more (e.g. 1, 2 or 3) $R^a$ groups or two or more (e.g. 2, 3 or 4) $R^b$ groups such as $C_{1-6}$ alkyl (e.g. methyl).

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyrimidin-4-yl optionally substituted by one or more (e.g. 1, 2 or 3) $R^g$ groups or two or more (e.g. 2, 3 or 4) $R^b$ groups such as $C_{1-6}$ alkyl (e.g. methyl, isopropyl), haloC$_{1-6}$ alkyl (e.g. trifluoromethyl), $—OR^x$ (e.g. methoxy), $—S—R^x$ (e.g. $—S—CH_3$), $=O$, $—(CH_2)_s—NR^xR^y$ (e.g.$NH_2$, $—NH(C_4H_7)$, $—N(CH_3)_2$)$—(CH_2)_sNHC_{1-6}$alkyl (e.g. $—NH—CH_3$), $—(CH_2)_sN(C_{1-6}$alkyl$)_2$ (e.g. $—N(CH_3)_2$), $—(CH_2)_n—O—C_{1-6}$ alkyl (e.g. $—CH_2—O—CH_3$) or —Y-heterocyclyl (e.g. azetidinyl, piperazinyl, imidazoyl) wherein said —Y-heterocyclyl groups may be optionally substituted by one or more (e.g. 1, 2 or 3) $R^a$ group such as $C_{1-6}$alkanol (e.g.$CH_2—CH_2—OH$), $—(CH_2)_s—NR^xCO_2R^y$ (e.g. $NHCO_2C(CH_3)_3$), $—(CH_2)_s—SO_2NR^xR^y$ (e.g. $SO_2N(CH_3)_2$) groups.

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents thiophenyl substituted by one or more (e.g. 1, 2 or 3) $R^e$ groups such as $—(CH_2)_s—CONR^xR^y$ (e.g. $—CONH_2$).

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyridin-2-yl optionally substituted by one or more (e.g. 1, 2 or 3) $R^b$ groups such as $C_{1-6}$ alkyl (e.g. methyl), $C_{1-6}$ alkanol (e.g. $—CH_2—OH$ or $—(CH_2)_2—OH$), haloC$_{1-6}$alkyl (e.g. trifluoromethyl), halogen (e.g. fluorine), $—OR^x$ (e.g. hydroxy, methoxy or ethoxy), $—(CH_2)_s—CONR^xR^y$ (e.g. $—CONH_2$ or $—CONHCH_3$) or $—(CH_2)_s—NR^xR^y$ (e.g. $—NH_2$) or a —Y-heterocyclyl group (e.g. morpholine) wherein said heterocyclyl group may be substituted by one or more (e.g. 1, 2 or 3) $R^a$ groups. In a further embodiment Y represents a bond or $—CO—(CH_2)_s$ (e.g. $—CO—$) group.

Also disclosed is, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyridin-3-yl substituted by one or more (e.g. 1, 2 or 3) $R^j$ groups such as —Y-heterocyclyl (e.g. -piperidinyl).

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyridin-3-yl substituted by one or more (e.g. 1, 2 or 3) $R^j$ groups such as a piperidinyl.

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyridin-3-yl substituted by one or more (e.g. 1, 2 or 3) $R^j$ groups such as a piperidinyl group substituted by one or more (1, 2 or 3) $R^a$ groups such as $—(CH_2)_s—NR^xCO_2R^y$ (e.g. $—CH_2NH—COOC(CH_3)_3$) or $—(CH_2)_s—NR^xR^y$ (e.g. $—CH_2—NH_2$ or $—NH_2$) or $—(CH_2)_s—NH—SO_2—NR^xR^y$ (e.g. $—NH—SO_2—N(CH_3)_2$.

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents pyridin-4-yl substituted by one or more (e.g. 1, 2 or 3) $R^k$ groups.

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents a bicyclic heterocyclic group (e.g. dihydro-cyclopentathiazolyl, thiadiazolopyrimidinyl or tetrahydrothiazolopyridinyl) containing a thiazolyl or thiadiazolyl ring optionally substituted by one or more (e.g. 1, 2 or 3) $R^b$ groups such as $C_{1-6}$ alkyl (e.g. methyl), $=O$ or $—(CR^xR^y)_s—COOR^z$ (e.g. $—COO$-t-butyl).

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents a bicyclic heterocyclic group (e.g. dihydro-cyclopentathiazolyl, thiadiazolopyrimidinyl or tetrahydrothiazolopyridinyl) containing a thiazolyl or thiadiazolyl ring optionally substituted by one or more (e.g. 1, 2 or 3) $R^b$ groups such as $C_{1-6}$ alkyl (e.g. methyl) or $=O$.

In one embodiment, when $R^1$ represents hydrogen and $R^2$ represents $C_{1-6}$ alkyl or haloC$_{1-6}$ alkyl (e.g. ethyl or $—CH_2—CF_3$), $R^{4c}$ represents a bicyclic heterocyclic group containing a thiazolyl or thiadiazolyl ring optionally substituted by one or more (e.g. 1, 2 or 3) $R^b$ groups such as $C_{1-6}$ alkyl (e.g.

methyl) or =O. In a further embodiment $R^{4c}$ represents imidazothiadiazolyl or benzothiazolyl substituted by a methyl group.

In one embodiment, when $R^1$ represents hydrogen and $R^2$ represents $C_{1-6}$ alkyl or halo$C_{1-6}$ alkyl (e.g. ethyl or —CH$_2$—CF$_3$), $R^{4c}$ represents triazinyl optionally substituted by one or more (e.g. 1, 2 or 3) $R^b$ groups such as $C_{1-6}$ alkyl (e.g. methyl).

In one embodiment, when $R^1$ represents hydrogen and $R^2$ represents $C_{1-6}$ alkyl or halo$C_{1-6}$ alkyl (e.g. ethyl or —CH$_2$—CF$_3$), $R^{4c}$ represents oxo-dihydro-pyridin-3-yl (e.g. 6-oxo-1,6-dihydro-pyridin-3-yl) substituted by one or more (e.g. 1, 2 or 3) $R^j$ groups.

In one embodiment, when $R^1$ represents hydrogen and $R^2$ represents $C_{1-6}$ alkyl or halo$C_{1-6}$ alkyl (e.g. ethyl or —CH$_2$—CF$_3$), $R^{4c}$ represents an N-unsubstituted pyridin-3-yl substituted on one of the carbon atoms with a substituent from the group $R^b$ and on another carbon atom with a substituent from the group $R^a$ such as $C_{1-6}$alkyl (e.g. methyl), —(CH$_2$)$_s$—NR$^x$R$^y$ (e.g. NHCH$_3$) or —OR$^x$ (e.g. methoxy).

In one embodiment, when $R^1$ represents hydrogen and $R^2$ represents $C_{1-6}$ alkyl or halo$C_{1-6}$ alkyl (e.g. ethyl or —CH$_2$—CF$_3$), $R^{4c}$ represents phenyl substituted by one or more (e.g. 1, 2 or 3) $C_{2-6}$ alkanol groups (e.g. —(CH$_2$)$_2$—OH, —COH(CH$_3$)$_2$).

In one embodiment, $R^4$ is a group $R^{4c}$ which is selected from any one of (a)-(h), (j)-(k), (m)-(r), (u), (w), (x) and (y).

In one embodiment, $R^4$ is a group $R^{4c}$ which is selected from any one of (b)-(d), (f), (h), (j)-(k), (m)-(r), (u), (w), (x) and (y).

In one embodiment, $R^4$ is a group $R^{4c}$ which is selected from any one of (b), (c), (f), (h), (n)-(r), (u), (w), (x) and (y).

In one embodiment, $R^4$ is a group $R^{4c}$ which is selected from any one of (b), (c), (h), (n), (o), (p), (q), (r), (u), (w), (x) and (y).

In one embodiment, $R^4$ is a group $R^{4c}$ which is selected from any one of (b), (h), (n), (o), (p), (q), (u), and (w).

In one embodiment, $R^4$ is a group $R^{4c}$ which is selected from any one of (b), (h), (o), (p), (q), (u), and (w).

In one embodiment, $R^{4c}$ is (b).

In one embodiment, $R^{4c}$ is (n).

In one embodiment, $R^{4c}$ is unsubstituted pyrimidin-2-yl.

In one embodiment, when $R^1$ represents hydrogen and $R^2$ represents $C_{1-6}$ alkyl or halo $C_{1-6}$ alkyl and A is $A^d$ which represents a phenyl group which may be optionally substituted by one or more (e.g. 1, 2 or 3) $R^a$ groups (e.g. unsubstituted phenyl), $R^3$ represents $C_{1-6}$ alkyl and $R^{4d}$ represents methyl. In a further embodiment, $R^3$ and $R^{4d}$ both represent methyl.

In one embodiment, when $R^1$ represents hydrogen and $R^2$ represents $C_{1-6}$ alkyl or halo$C_{1-6}$ alkyl (e.g. ethyl or —CH$_2$—CF$_3$), $R^{4c}$ represents a —X—R$^6$ group. In a further embodiment X represents —CH=CH— and $R^6$ represents a $C_{1-6}$alkanol (e.g. —CH(OH) or an aromatic heterocyclic group, such as a pyridinyl or imidazolyl, wherein said heterocyclic group is optionally substituted by one or more (1, 2 or 3) $R^b$ groups such as $C_{1-6}$alkyl (e.g. methyl, isopropyl) or $C_{1-6}$alkanol (e.g. —CH(OH, —CH$_2$CH$_2$OH).

In one embodiment, $R^5$ represents —(CH$_2$)$_s$—NR$^x$R$^y$, $C_{1-6}$ alkanol, $C_{3-8}$ cycloalkyl or an aromatic or non-aromatic heterocyclic group wherein said heterocyclic group may be optionally substituted by one or more (e.g. 1, 2 or 3) $R^b$ groups.

In one embodiment, $R^6$ represents —(CH$_2$)$_s$—NR$^x$R$^y$, $C_{1-6}$ alkanol, $O_{4-8}$ cycloalkyl or an aromatic or non-aromatic heterocyclic group wherein said heterocyclic group may be optionally substituted by one or more (e.g. 1, 2 or 3) $R^b$ groups.

Also disclosed is when X represents a —C≡C— group, $R^6$ represents —(CH$_2$)$_s$—NR$^x$R$^y$ (e.g. —CH$_2$—N(Me)$_2$), $C_{1-6}$ alkanol (e.g. —CH$_2$—OH, —(CH$_2$)$_2$—OH or —CH(OH)-Me), $C_{3-8}$ cycloalkyl (e.g. cyclopropyl) or an aromatic or non-aromatic heterocyclic group (e.g. pyridyl, imidazolyl, pyrazolyl, oxazolyl, oxadiazolyl, triazolyl, thienyl or piperidinyl) wherein said heterocyclic group may be optionally substituted by one or more (e.g. 1, 2 or 3) $R^b$ groups such as $C_{1-6}$ alkyl (e.g. methyl) or —OR$^x$ (e.g. —OH).

When X represents a —C≡C— group, in one embodiment, $R^6$ represents —(CH$_2$)$_s$—NR$^x$R$^y$ (e.g. —CH$_2$—N(Me)$_2$), $C_{1-6}$ alkanol (e.g. —CH$_2$—OH, —(CH$_2$)$_2$—OH or —CH(OH)-Me), $C_{4-8}$ cycloalkyl, or an aromatic or non-aromatic heterocyclic group (e.g. pyridyl, imidazolyl, pyrazolyl, oxazolyl, oxadiazolyl, triazolyl, thienyl or piperidinyl) wherein said heterocyclic group may be optionally substituted by one or more (e.g. 1, 2 or 3) $R^b$ groups such as $C_{1-6}$ alkyl (e.g. methyl) or —OR$^x$ (e.g. —OH).

Also disclosed is when X represents a —C≡C— group, $R^6$ represents —(CH$_2$)$_s$—NR$^x$R$^y$ (e.g. —CH$_2$—N(Me)$_2$), $C_{1-6}$ alkanol (e.g. —CH$_2$—OH, —(CH$_2$)$_2$—OH or —CH(OH)-Me), $C_{3-8}$ cycloalkyl (e.g. cyclopropyl) or an aromatic or non-aromatic heterocyclic group (e.g. pyridyl, imidazolyl, pyrazolyl, oxazolyl, thienyl or piperidinyl) wherein said heterocyclic group may be optionally substituted by one or more (e.g. 1, 2 or 3) $R^b$ groups such as $C_{1-6}$ alkyl (e.g. methyl) or —OR$^x$ (e.g. —OH). In a further embodiment, when X represents a —C≡C— group, $R^6$ represents an aromatic or non-aromatic heterocyclic group (e.g. pyridyl, imidazolyl, pyrazolyl, oxazolyl, thienyl or piperidinyl) wherein said heterocyclic group may be optionally substituted by one or more (e.g. 1, 2 or 3) $R^b$ groups such as $C_{1-6}$ alkyl (e.g. methyl) or —OR$^x$ (e.g. —OH). In a further embodiment, when X represents a —C≡C— group, $R^6$ represents an aromatic or non-aromatic heterocyclic group (e.g. pyridyl, imidazolyl, pyrazolyl, oxazolyl, thienyl or piperidinyl) wherein said heterocyclic group may be optionally substituted by one or more (e.g. 1, 2 or 3) $R^b$ groups such as $C_{1-6}$ alkyl (e.g. methyl).

When X represents a —C≡C— group, in a further embodiment, $R^6$ represents —(CH$_2$)$_s$—NR$^x$R$^y$ (e.g. —CH$_2$—N(Me)$_2$), $C_{1-6}$ alkanol (e.g. —CH$_2$—OH, —(CH$_2$)$_2$—OH or —CH(OH)-Me), $C_{4-8}$ cycloalkyl or an aromatic or non-aromatic heterocyclic group (e.g. pyridyl, imidazolyl, pyrazolyl, oxazolyl, thienyl or piperidinyl) wherein said heterocyclic group may be optionally substituted by one or more (e.g. 1, 2 or 3) $R^b$ groups such as $C_{1-6}$ alkyl (e.g. methyl) or —OR$^x$ (e.g. —OH). In a further embodiment, when X represents a —C≡C— group, $R^6$ represents an aromatic or non-aromatic heterocyclic group (e.g. pyridyl, imidazolyl, pyrazolyl, oxazolyl, thienyl or piperidinyl) wherein said heterocyclic group may be optionally substituted by one or more (e.g. 1, 2 or 3) $R^b$ groups such as $C_{1-6}$ alkyl (e.g. methyl) or —OR$^x$ (e.g. —OH). In a further embodiment, when X represents a —C≡C— group, $R^6$ represents an aromatic or non-aromatic heterocyclic group (e.g. pyridyl, imidazolyl, pyrazolyl, oxazolyl, thienyl or piperidinyl) wherein said heterocyclic group may be optionally substituted by one or more (e.g. 1, 2 or 3) $R^b$ groups such as $C_{1-6}$ alkyl (e.g. methyl).

In a yet further embodiment, when X represents a —C≡C— group, $R^6$ represents an aromatic heterocyclic group (e.g. imidazolyl) optionally substituted by one or more (e.g. 1, 2 or 3) $R^b$ groups such as $C_{1-6}$ alkyl (e.g. methyl).

When X represents a —CH=CH— group, in one embodiment, $R^6$ represents an aromatic heterocyclic group (e.g. imidazolyl) optionally substituted by one or more (e.g. 1, 2 or 3) $R^b$ groups such as $C_{1-6}$ alkyl (e.g. methyl).

When X represents a —(CH$_2$)$_q$— (e.g. —(CH$_2$)$_2$—) group, in one embodiment, R$^6$ represents an aromatic heterocyclic group (e.g. imidazolyl) optionally substituted by one or more (e.g. 1, 2 or 3) R$^b$ groups such as C$_{1-6}$ alkyl (e.g. methyl).

In one embodiment q is two.

In one embodiment, when R$^1$ represents hydrogen and R$^2$ represents cyclopropyl, R$^{4a}$ represents an amino, C$_{1-6}$ alkyl, —X—R$^5$ or an aromatic or non-aromatic carbocyclic or heterocyclic group wherein said carbocyclic or heterocyclic group may be optionally substituted by one or more (e.g. 1, 2 or 3) R$^b$ groups.

In one embodiment R$^5$ or R$^6$ represent imidazole optionally substituted with one or more R$^a$ groups (e.g. methyl).

In one embodiment X represents —(CH$_2$)$_q$—.

In one embodiment X represents —(CH$_2$)$_q$— and R$^5$ or R$^6$ represent aromatic heterocyclic group optionally substituted with one or more R$^a$ groups.

In one embodiment X represents —CH═CH—.

In one embodiment X represents —CH═CH— and R$^5$ or R$^6$ represent aromatic heterocyclic group optionally substituted with one or more R$^a$ groups In one embodiment X represents —C≡C—.

In one embodiment X represents —C≡C— and R$^5$ or R$^6$ represent aromatic heterocyclic group optionally substituted with one or more R$^a$ groups.

In one embodiment Y represents —(CR$^x$R$^y$)$_s$—CO—.

In one embodiment Y represents —NR$^x$—(CH$_2$)$_s$— or —(CH$_2$)$_s$—NR$^x$— wherein s is zero.

In one embodiment R$^a$ is —(CR$^x$R$^y$)$_s$CONR$^w$R$^z$ wherein R$^x$ and R$^y$ are not both hydrogen.

In one embodiment R$^a$, R$^b$, R$^c$, R$^d$, R$^e$, R$^g$, R$^n$, or R$^p$ is C$_{1-6}$ alkanol.

In one embodiment R$^w$, R$^x$, R$^y$ and R$^z$ independently represent hydrogen, —(CH$_2$)$_n$—O—C$_{1-6}$alkyl, C$_{1-6}$ alkyl-N(C$_{1-6}$ alkyl)$_2$, C$_{1-6}$ alkyl-NH(C$_{1-6}$ alkyl), or when attached to a nitrogen atom R$^w$, R$^x$, R$^y$ and R$^z$ may form a ring.

In one embodiment, one of R$^w$, R$^x$, R$^y$ and R$^z$ represents hydrogen and the other represents —(CH$_2$)$_n$—O—C$_{1-6}$alkyl, —C$_{1-6}$ alkyl-N(C$_{1-6}$ alkyl)$_2$, or —C$_{1-6}$ alkyl-NH(C$_{1-6}$ alkyl), or when attached to a nitrogen atom R$^w$, R$^x$, R$^y$ and R$^z$ may form a ring.

In one embodiment, one of R$^w$, R$^x$, R$^y$ and R$^z$ when attached to a nitrogen atom forms a ring.

A particular embodiment is:

(i) when R$^1$ and R$^2$ independently represent hydrogen or C$_{3-8}$ cycloalkyl;

A is a group A$^a$ which represents an aromatic carbocyclic group;

R$^3$ represents hydrogen;

R$^4$ is a group R$^{4a}$ which represents an halogen, —X—R$^5$ or an aromatic or non-aromatic carbocyclic or heterocyclic group wherein said carbocyclic or heterocyclic group may be optionally substituted by one or more (e.g. 1, 2 or 3) R$^b$ groups (e.g. methyl or fluorine, —NH$_2$);

(ii) when R$^1$ represents hydrogen and R$^2$ represents C$_{1-6}$ alkyl or halo C$_{1-6}$ alkyl;

A is a group A$^b$ which represents an aromatic 5 membered heterocyclic;

R$^3$ represents hydrogen;

R$^4$ is a group R$^{4a}$ which represents an halogen;

(iii) when R$^1$ represents hydrogen and R$^2$ represents C$_{1-6}$ alkyl or halo C$_{1-6}$ alkyl;

A is a group A$^c$ which represents an aromatic 6 membered heterocyclic group;

R$^3$ represents hydrogen;

R$^4$ is a group R$^b$ which represents an halogen, —X—R$^5$ or an aromatic heterocyclic group wherein when said heterocyclic group is other than pyrazolyl, oxadiazolyl or tetrazolyl said heterocyclic group may be optionally substituted by one or more (e.g. 1, 2 or 3) R$^b$ groups or when said heterocyclic group is pyrazolyl, oxadiazolyl or tetrazolyl said heterocyclic group may be optionally substituted by one or more (e.g. 1, 2 or 3) R$^d$ groups or two or more (e.g. 2, 3 or 4) R$^b$ groups;

(iv) when R$^1$ represents hydrogen and R$^2$ represents C$_{1-6}$ alkyl or halo C$_{1-6}$ alkyl;

A is a group A$^d$ which represents a phenyl group which may be optionally substituted by one or more (e.g. 1, 2 or 3) R$^a$ groups;

R$^3$ represents hydrogen;

R$^4$ is a group R$^{4c}$ which is selected from any one of (a)-(h), (j)-(k), (m)-(u) and (w)-(y) which represent:

(a) an amino;

(b) —X—R$^6$;

(c) phenyl substituted by one or more (e.g. 1, 2 or 3) C$_{2-6}$ alkanol groups;

(d) pyridazinyl optionally substituted by one or more (e.g. 1, 2 or 3) R$^e$ groups, or two or more (e.g. 2, 3 or 4) R$^b$ groups;

(e) N-linked imidazolyl optionally substituted on the nitrogen atom or the C-2 or C$_{1-5}$ atoms by one or more (e.g. 1, 2 or 3) R$^b$ groups or at the C$_{1-4}$ atom by one R$^e$ group;

(f) C-linked imidazolyl optionally substituted by one or two R$^m$ groups on either or both of the nitrogen atoms or optionally substituted by one or two R$^e$ groups on one or two carbon atoms;

(g) pyrazinyl optionally substituted by one or more (e.g. 1, 2 or 3) R$^b$ groups;

(h) thiophenyl substituted by one or more (e.g. 1, 2 or 3) R$^e$ groups;

(j) a bicyclic heterocyclic group containing a thiazolyl or thiadiazolyl ring optionally substituted by one or more (e.g. 1, 2 or 3) R$^b$ groups;

(k) triazinyl optionally substituted by one or two R$^b$ groups;

(m) pyrazolyl substituted by one or more (e.g. 1, 2 or 3) R$^f$ groups;

(n) pyrimidin-2-yl optionally substituted by one or more (e.g. 1, 2 or 3) R$^b$ groups;

(o) pyrimidin-4-yl optionally substituted by one or more (e.g. 1, 2 or 3) R$^g$ groups or two or more (e.g. 2, 3 or 4) R$^b$ groups;

(p) pyrimidin-5-yl optionally substituted by one or more (e.g. 1, 2 or 3) R$^p$ groups or two or more (e.g. 2, 3 or 4) R$^b$ groups;

(q) thiadiazolyl substituted by one R$^h$ group;

(r) pyridin-2-yl optionally substituted by one or more (e.g. 1, 2 or 3) R$^b$ groups;

(s) pyridin-3-yl substituted by one or more (e.g. 1, 2 or 3) R$^j$ groups;

(t) pyridin-4-yl substituted by one or more (e.g. 1, 2 or 3) R$^k$ groups or two or more (e.g. 2, 3 or 4) R$^b$ groups;

(u) pyridin-3-yl substituted at the 2-position by —O—C$_{1-6}$ alkyl and optionally substituted by one or more (e.g. 1, 2 or 3) R$^b$ groups;

(w) oxo-dihydro-pyridin-3-yl substituted by one or more (e.g. 1, 2 or 3) R$^j$ groups;

(x) N-methylpyrazolyl optionally substituted by one or more (e.g. 1, 2 or 3) R$^q$ groups;

(y) N-unsubstituted pyridin-3-yl substituted on one of the carbon atoms with a substituent from the group R$^b$ and substituted on another carbon atom with a substituent from the group R$^a$;

(v) when $R^1$ represents hydrogen and $R^2$ represents $C_{1-6}$ alkyl or halo $C_{1-6}$ alkyl and A is $A^d$ which represents a phenyl group which may be optionally substituted by one or more (e.g. 1, 2 or 3) $R^a$ groups;

$R^3$ represents $C_{1-6}$ alkyl;

$R^4$ is a group $R^{4d}$ which represents $C_{1-6}$ alkyl; or (vi) when $R^1$ represents hydrogen and $R^2$ represents halo $C_{1-6}$ alkyl and A is $A^d$ which represents a phenyl group which may be optionally substituted by one or more (e.g. 1, 2 or 3) $R^a$ groups;

$R^3$ represents hydrogen or $C_{1-6}$ alkyl;

$R^4$ is a group $R^{4e}$ which represents unsubstituted pyridin-3-yl, unsubstituted pyridin-4-yl or 3-pyridinyl substituted with unsubstituted piperidine;

X represents —$(CH_2)_q$—, —CH=CH— or —C≡C—;

$R^5$ represents —$(CH_2)_s$—$NR^xR^y$, $C_{1-6}$ alkyl, $C_{1-6}$ alkanol, $C_{3-8}$ cycloalkyl or an aromatic or non-aromatic heterocyclic group wherein said heterocyclic group may be optionally substituted by one or more (e.g. 1, 2 or 3) $R^b$ groups;

$R^6$ represents —$(CH_2)_s$—$NR^xR^y$, $C_{2-6}$ alkyl, $C_{1-6}$ alkanol, $C_{4-8}$ cycloalkyl or an aromatic or non-aromatic heterocyclic group wherein said heterocyclic group may be optionally substituted by one or more (e.g. 1, 2 or 3) $R^b$ groups;

$R^w$, $R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —$COOC_{1-6}$ alkyl, hydroxy, $C_{1-6}$ alkoxy, halo$C_{1-6}$ alkyl, —$(CH_2)_n$—O—$C_{1-6}$ alkyl, —CO—$(CH_2)_n$—$C_{1-6}$ alkoxy, $C_{1-6}$ alkylamino, —$C_{1-6}$ alkyl-N($C_{1-6}$ alkyl)$_2$, —$C_{1-6}$ alkyl-NH($C_{1-6}$ alkyl), $C_{3-8}$ cycloalkyl or $C_{3-8}$ cycloalkenyl or when attached to a nitrogen atom, $R^w$, $R^x$, $R^y$ and $R^z$ may form a ring;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, Si($R^x$)$_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_n$—$NR^xR^y$, —O—$(CH_2)_s$—$CR^xR^y$—$(CH_2)_t$—$OR^z$ or —$(CH_2)_s$—$SO_2NR^xR^y$ groups;

$R^b$ represents an $R^a$ group or a —Y-heterocyclyl group wherein said heterocyclyl group may be optionally substituted by one or more (e.g. 1, 2 or 3) $R^a$ groups;

Y represents a bond, —CO—$(CH_2)_s$—, —$(CR^xR^y)_s$—CO—, —COO—, —$(CH_2)_n$—$(CR^xR^y)_s$—, —$NR^x$—$(CH_2)_s$—, —$(CH_2)_s$—$NR^x$—, —$CONR^x$—, —$NR^xCO$—, —$SO_2NR^x$—, —$NR^xSO_2$—, —$NR^xCONR^y$—, —$NR^xCS$—$NR^y$—, —O—$(CH_2)_s$—, —$(CH_2)_s$—O—, —S—, —SO— or —$(CH_2)_s$—$SO_2$—;

$R^c$ represents chlorine, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, Si($R^x$)$_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^d$ represents halogen, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, Si($R^x$)$_4$, —$(CH_2)_s$—CN, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCON$—$R^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^e$ represents halogen, $C_{2-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, Si($R^x$)$_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^f$ represents halogen, $C_{4-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{2-6}$ alkyl, monohalomethyl, dihalomethyl, halo$C_{1-6}$ alkoxy, $C_{3-6}$ alkanol, =O, =S, nitro, Si($R^x$)$_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—, —$CONR^xR^y$, —$CH_2$—$NR^xR^y$, —$(CH_2)_{3-4}$—$NR^xR^y$, —$(CH_2)_s$—$NHC_{1-6}$ alkyl, —$(CH_2)_s$—N($C_{1-6}$ alkyl)$_2$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$, —$(CH_2)_n$—$SO_2NR^xR^y$ or —$(CH_2)_s$—$SO_2NHR^y$ groups, or a —Y-heterocyclyl group wherein said heterocyclyl group may be optionally substituted by one or more (e.g. 1, 2 or 3) $R^a$ groups;

$R^g$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$C_{1-6}$ alkyl, —O—$(CH_2)_n$—$OR^x$, halo$C_{1-6}$ alkyl, halo$C_{1-6}$ alkoxy, $C_{1-6}$ alkanol, =O, =S, nitro, Si($R^x$)$_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—$CON$—$R^xR^y$, —$(CH_2)_s$—$NHC_{1-6}$ alkyl, —$(CH_2)_s$—N($C_{1-6}$ alkyl)$_2$, —$(CH_2)_n$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^h$ represents halogen, $C_{3-6}$ alkyl, $C_{2-6}$ alkenyl, $C_{2-6}$ alkynyl, $O_{4-8}$ cycloalkyl, $C_{3-8}$ cycloalkenyl, —$OR^x$, —$(CH_2)_{2-4}$—O—$C_{1-6}$ alkyl, —$(CH_2)_n$—O—$C_{2-6}$ alkyl, —O—$(CH_2)_n$—$OR^x$, halo$C_{1-6}$ alkyl, halo$C_{1-6}$ alkoxy, $C_{2-6}$ alkanol, =O, =S, nitro, Si($R^x$)$_4$, —$(CH_2)_s$—CN, —S—$R^x$, —SO—$R^x$, —$SO_2$—$R^x$, —$COR^x$, —$(CR^xR^y)_s$—$COOR^z$, —$(CR^xR^y)_s$—$CONR^wR^z$, —$(CH_2)_s$—, —$CONR^xR^y$, —$(CH_2)_s$—$NR^xR^y$, —$(CH_2)_s$—$NR^xCOR^y$, —$(CH_2)_s$—$NR^xSO_2$—$R^y$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$ or —$(CH_2)_s$—$SO_2NR^xR^y$ groups, or a —Y-heterocyclyl group wherein said heterocyclyl group may be optionally substituted by one or more (e.g. 1, 2 or 3) $R^a$ groups;

$R^j$ represents chlorine, ethyl, $C_{4-6}$ alkyl, $C_{2-6}$ alkenyl, $C_{2-6}$ alkynyl, $C_{3-8}$ cycloalkyl, $C_{3-8}$ cycloalkenyl, —O—$C_2$ alkyl, —O—$C_{4-6}$ alkyl, —$(CH_2)_n$—O—$C_{1-6}$ alkyl, —O—

(CH₂)ₙ—ORˣ, haloC₂₋₆ alkyl, monohalomethyl, dihalomethyl, haloC₁₋₆ alkoxy, C₁₋₂ alkanol, C₄₋₆ alkanol, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COOC₁₋₆ alkyl, —(CRˣRʸ)ₛ—CONRʷRᶻ, —(CH₂)ₛ—CONRˣRʸ, —(CH₂)ₛ—NHC₁₋₆ alkyl, —(CH₂)ₛ—NMe(C₂₋₆ alkyl), —(CH₂)ₛ—N—(C₂₋₆ alkyl)₂, —(CH₂)ₙ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —O—(CH₂)ₙ—NRˣRʸ, —O—(CH₂)ₛ—CRˣRʸ—(CH₂)ₜ—ORᶻ, —(CH₂)ₛ—SO₂NRˣRʸ, piperazine substituted by Rⁿ, or a piperidinyl or a —O-piperidinyl group wherein said piperidinyl groups are substituted by one or more (e.g. 1, 2 or 3) Rᵃ groups;

Rᵏ represents chlorine, C₂₋₆ alkyl, C₂₋₆ alkenyl, C₂₋₆ alkynyl, C₃₋₈ cycloalkyl, C₃₋₈ cycloalkenyl, C₂₋₆ alkoxy, —(CH₂)ₙ—O—C₁₋₆ alkyl, —O—(CH₂)ₙ—ORˣ, haloC₁₋₆ alkyl, haloC₁₋₆ alkoxy, C₁₋₂ alkanol, C₄₋₆ alkanol, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COORᶻ, —(CRˣRʸ)ₛ—CONRʷRᶻ, —(CH₂)ₛ—CONRˣRʸ, —(CH₂)ₛ—NHC₁₋₆ alkyl, —(CH₂)ₛ—N(C₁₋₆ alkyl)₂, —(CH₂)ₙ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₛ—CRˣRʸ—(CH₂)ₜ—ORᶻ or —(CH₂)ₛ—SO₂NRˣRʸ groups;

Rᵐ represents halogen, C₃₋₆ alkyl, C₂₋₆ alkenyl, C₂₋₆ alkynyl, C₃₋₈ cycloalkyl, C₃₋₈ cycloalkenyl, —ORˣ, —(CH₂)ₙ—O—C₁₋₆ alkyl, —O—(CH₂)ₙ—ORˣ, haloC₁₋₆ alkyl, haloC₁₋₆ alkoxy, C₁₋₆ alkanol, =O, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COORᶻ, —(CRˣRʸ)ₛ—CONRʷRᶻ, —(CH₂)ₛ—CONRˣRʸ, —(CH₂)ₛ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₛ—CRˣRʸ—(CH₂)ₜ—ORᶻ or —(CH₂)ₛ—SO₂NRˣRʸ groups, or a —Y-heterocyclyl group wherein said heterocyclyl group may be optionally substituted by one or more (e.g. 1, 2 or 3) Rᵃ groups;

Rⁿ represents halogen, C₁₋₆ alkyl, C₂₋₆ alkenyl, C₂₋₆ alkynyl, C₃₋₈ cycloalkyl, C₃₋₈ cycloalkenyl, —ORˣ, —(CH₂)ₙ—O—C₁₋₆ alkyl, —O—(CH₂)ₙ—ORˣ, haloC₁₋₆ alkyl, haloC₁₋₆ alkoxy, C₁₋₆ alkanol, =O, =S, nitro, Si(Rˣ)₄, —(CH₂)ₛ—CN, —S—Rˣ, —SO—Rˣ, —SO₂—Rˣ, —CORˣ, —(CRˣRʸ)ₛ—CONRʷRᶻ, —(CH₂)ₛ—CONRˣRʸ, —(CH₂)ₛ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₛ—CRˣRʸ—(CH₂)ₜ—ORᶻ or —(CH₂)ₛ—SO₂NRˣRʸ groups; Rᵖ represents halogen, C₁₋₆ alkyl, C₂₋₆ alkenyl, C₂₋₆ alkynyl, C₃₋₈ cycloalkyl, C₃₋₈ cycloalkenyl, —ORˣ, —(CH₂)ₙ—O—C₁₋₆ alkyl, —O—(CH₂)ₙ—ORˣ, haloC₁₋₆ alkyl, haloC₁₋₆ alkoxy, C₁₋₆ alkanol, =O, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COORᶻ, —(CRˣRʸ)ₛ—CONRʷRᶻ, —(CH₂)ₛ—CONRˣRʸ, —(CH₂)ₛ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(OH₂)ₛ—CRˣRʸ—(CH₂)ₜ—ORᶻ or —(CH₂)ₛ—SO₂NRˣRʸ groups; a —Y-(4-membered heterocyclyl group) wherein said 4-membered heterocyclyl group is substituted by one or more (e.g. 1, 2 or 3) Rᵃ groups; or a —Y-(5-10 membered heterocyclyl group) wherein said 5-10 membered heterocyclyl group may be optionally substituted by one or more (e.g. 1, 2 or 3) Rᵃ groups;

Rᑫ represents halogen, C₂₋₆ alkyl, C₂₋₆ alkenyl, C₂₋₆ alkynyl, C₃₋₈ cycloalkyl, C₃₋₈ cycloalkenyl, —ORˣ, —(CH₂)ₙ—O—C₁₋₆ alkyl, —O—(CH₂)ₙ—ORˣ, haloC₂₋₆ alkyl, monohalomethyl, dihalomethyl, haloC₁₋₆ alkoxy, C₂₋₆ alkanol, =O, =S, nitro, Si(Rˣ)₄, —(CH₂)ₛ—CN, —S—Rˣ, —SO—Rˣ, —SO₂—Rˣ, —CORˣ, —(CRˣRʸ)ₛ—COORᶻ, —(CRˣRʸ)ₛ—CONRʷRᶻ, —(CH₂)ₛ—CONRˣRʸ, —NH(C₁₋₆alkyl), —N(C₁₋₆alkyl)₂, —(CH₂)ₙ—NRˣRʸ, —(CH₂)ₛ—NRˣCORʸ, —(CH₂)ₛ—NRˣSO₂—Rʸ, —(CH₂)ₛ—NH—SO₂—NRˣRʸ, —OCONRˣRʸ, —(CH₂)ₛ—NRˣCO₂Rʸ, —O—(CH₂)ₙ—NRˣRʸ, —O—(CH₂)ₛ—CRˣRʸ—(CH₂)ₜ—ORᶻ or —(CH₂)ₛ—SO₂NRˣRʸ groups, or a —Y-heterocyclyl group wherein said heterocyclyl group may be optionally substituted by one or more (e.g. 1, 2 or 3) Rᵃ groups;

n and q independently represent an integer from 1-4;

s and t independently represent an integer from 0-4;

or a pharmaceutically acceptable salt, solvate or derivative thereof.

It is to be understood that within the ambit of the present invention is also comprised, the above particular embodiment wherein one or, whenever possible, more of the above-indicated embodiments are incorporated.

In one embodiment the compound of formula (I) is a compound of formula (Ia)

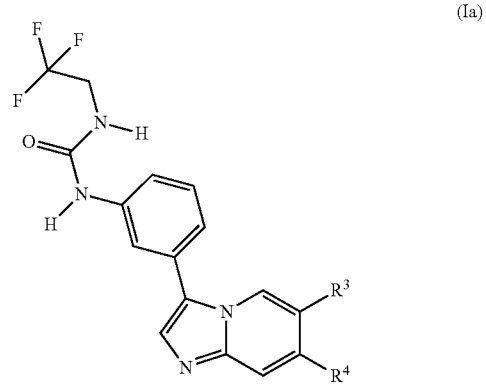

(Ia)

wherein R³ and R⁴ are as defined above for compounds of formula (I).

In one embodiment the compound of formula I is not 1-[5-(7-Chloro-imidazo[1,2-a]pyridin-3-yl)-thiazol-2-yl]-3-ethyl-urea hydrochloride.

In one embodiment the compound of formula I is not

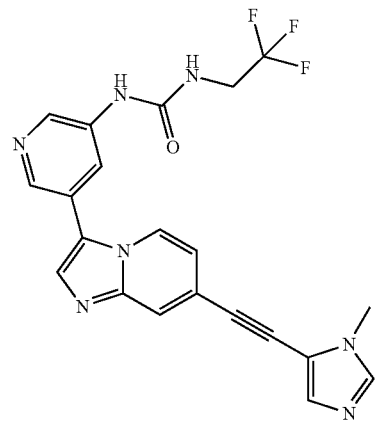 [SMILES: Cn1cncc1C#Cc1ccn2c(-c3cncc(NC(=O)NCC(F)(F)F)c3)cnc2c1]

In one embodiment the compound of formula I is not

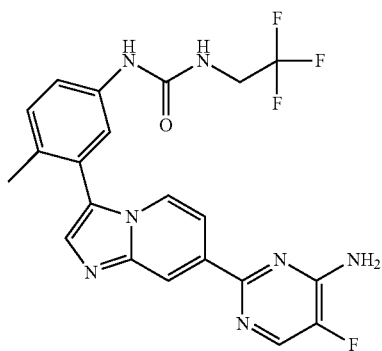 [SMILES: Cc1ccc(NC(=O)NCC(F)(F)F)cc1-c1cnc2cc(-c3ncc(F)c(N)n3)ccn12]

In one embodiment the compound of formula I is not

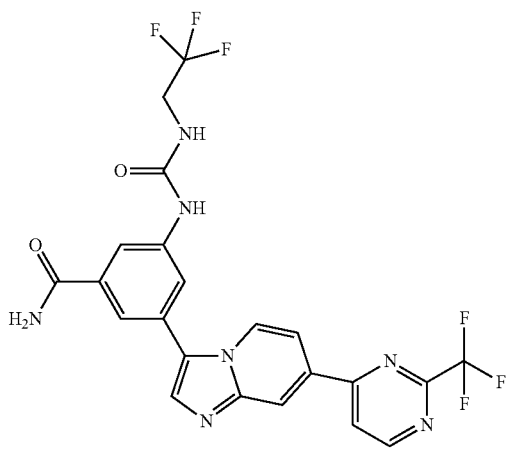 [SMILES: NC(=O)c1cc(NC(=O)NCC(F)(F)F)cc(-c2cnc3cc(-c4ccnc(C(F)(F)F)n4)ccn23)c1]

It will be appreciated that specific embodiments of variables in formula (Ia) above are as outlined hereinbefore for formula (I).

In one embodiment the compound of formula (I) is a compound of formula (Ia) as defined hereinbefore.

In one embodiment, the compound of formula (I) is a compound selected from Examples 1-248 or 250-253, 255-337. In one embodiment, the compound of formula (I) is a compound selected from Examples 1-125, 126A-159A, 126B, 130B-133B, 135B-142B, 144B-146B, 148B-150B, 152B, 154B, 155B, 157B-159B and 160-164, 165A, 165B, 166-248 and 250-253, 255-337. In one embodiment, the compound of formula (I) is a compound selected from Examples 1-125 and 126A-159A. In a further embodiment, the compound of formula (I) is a compound selected from Examples 1-125. In a further embodiment, the compound of formula (I) is a compound selected from Examples 1-116 and 118-125. In a further embodiment, the compound of formula (I) is a compound selected from Examples 1-24, 26-76, 78-83, 85-114, 118 and 120-125. In a further embodiment, the compound of formula (I) is a compound selected from Examples 1-24, 26-38, 40-53, 56, 58-70, 72-76, 78-83, 85-87, 89-102, 114 and 116. In a further embodiment, the compound of formula (I) is a compound selected from Examples 1-19, 21-24, 26-38, 40-53, 56, 58-64, 66-70, 72-76, 78-83, 85-87, 89-94, 96-102 and 114.

Methods for the Preparation of Compounds of Formula (I)

In this section, as in all other sections of this application unless the context indicates otherwise, references to formula (I) also include formulae (Ia), and all other sub-groups and examples thereof as defined herein. References to a group Ar or CYC in the Schemes below relate to optionally substituted groups A and/or $R^4$ as defined in Formula I, as appropriate.

Compounds of the formula (I) can be prepared in accordance with synthetic methods well known to the skilled person. In particular, compounds of formula (I) are readily prepared by palladium mediated coupling chemistries between aromatic chloro, bromo, iodo, or pseudo-halogens such as a trifluoromethanesulphonate (triflate) or tosylate compounds, and aromatic boronic acids or stannane derivatives. In particular, Suzuki coupling chemistry is broadly applicable to synthesis of these compounds. The Suzuki reaction can be carried out under typical conditions in the presence of a palladium catalyst such as bis(tri-t-butylphosphine)palladium, tetrakis(triphenyl-phosphine)-palladium or a palladacycle catalyst (e.g. the palladacycle catalyst described in Bedford, R. B. and Cazin, C. S. J. (2001) *Chem. Commun.*, 1540-1541 and a base (e.g. a carbonate such as potassium carbonate) as discussed in more detail below. The reaction may be carried out in polar solvent for example an aqueous solvent system, including aqueous ethanol, or an ether such as dimethoxyethane or dioxane, and the reaction mixture is typically subjected to heating, for example to a temperature of 80° C. or more, e.g. a temperature in excess of 100° C.

As illustrated in Scheme 1, the imidazo[1,2-a]pyridine core can be synthesised from commercially available starting materials to give a 3,7 disubstituted ring.

4-Chloro-pyridin-2-ylamine or 4-bromo-pyridin-2-ylamine in an appropriate solvent and base can be cyclised under reflux with chloroacetaldehyde to give the imidazopyridine ring. The 7-chloro-imidazo[1,2-a]pyridine in an appropriate solvent can then be iodinated, for example using N-iodosuccinimide at room temperature.

Appropriate functionality can then be added at the halogenated positions, for example using a range of metal-catalysed reactions. In particular, appropriately functionalised boronic acids or their boronate esters may react with the aryl halide. This transformation, commonly known as the Suzuki reaction, has been reviewed by Rossi et al (2004) Synthesis, 15, 2419.

The Suzuki reaction is often carried out in mixtures of water and organic solvents. Examples of suitable organic solvents include toluene, tetrahydrofuran, 1,4-dioxane, 1,2-dimethoxyethane, acetonitrile, N-methylpyrrolidinone, ethanol, methanol and dimethylformamide. The reaction mixture is typically subjected to heating, for example to a temperature in excess of 100° C. The reaction is carried out in the presence of a base. Examples of suitable bases include sodium carbonate, potassium carbonate, cesium carbonate and potassium phosphate. Examples of suitable catalysts include bis(tri-t-butylphosphine)palladium(0), tris(dibenzylideneacetone)dipalladium(0), bis(triphenylphosphine)palladium(II) chloride, palladium(II) acetate, tetrakis(triphenylphosphine) palladium(0), bis(tricyclohexylphosphine) palladium(0), [1,1-bis(diphenylphosphino)ferrocene]-dichloropalladium(II), dichlorobis(tri-o-tolylphosphine)palladium(II), 2'-(dimethylamino)-2-biphenylyl-palladium(II) chloride dinorbornylphosphine complex and 2-(dimethylamino)ferrocen-1-yl-palladium(II) chloride dinorbornylphosphine complex. In some cases additional ligands may be added to facilitate the coupling reaction. Examples of suitable ligands include tri-t-butylphosphine, 2,2-bis(diphenylphosphino)-1,1-binaphthyl, triphenylphosphine, 1,2-bis(diphenylphosphino)ethane, 1,1'-bis(diphenylphosphino)ferrocene, tricyclohexylphosphine, 9,9-dimethyl-4,5-bis(diphenylphosphino)xanthene, 1,3-bis(diphenylphosphino)propane, 2-(di-t-butylphosphino)biphenyl, 2-dicyclohexylphosphino-2'-(n,n-dimethylamino)biphenyl, tri-o-tolylphosphine, 2-(dicyclohexylphosphino)biphenyl, 2-dicyclohexylphosphino-2',4',6'-triisopropylbiphenyl, tri(2-furyl)phosphine, 2-dicyclohexylphosphino-2',6'-dimethoxybiphenyl and 2-di-tert-butylphosphino-2',4',6'-triisopropylbiphenyl.

Scheme 1

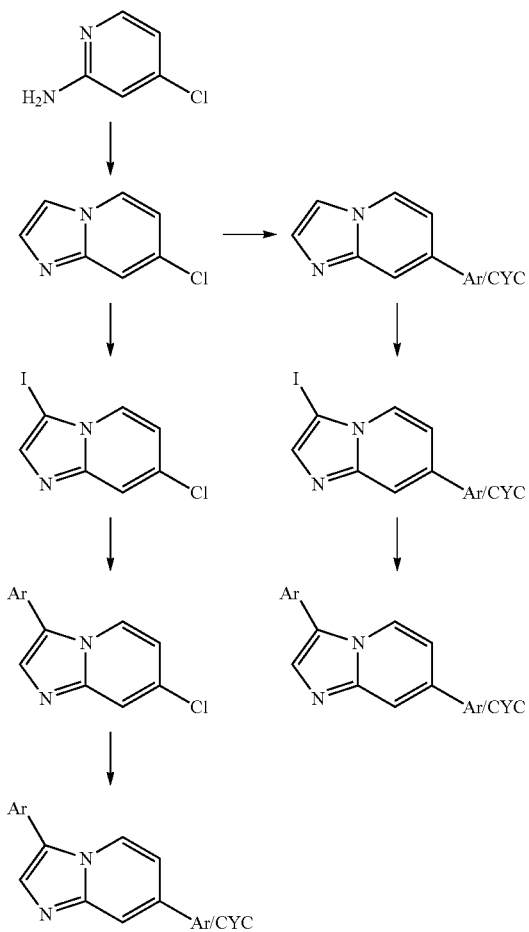

Other examples of possible metal catalysed functionalisations of the halide are reactions with organo-tin reagents (the Stille reaction), with Grignard reagents and reaction with nitrogen nucleophiles. A general overview, and further leading references, of these transformations is presented in 'Palladium Reagents and Catalysts' [Jiro Tsuji, Wiley, ISBN 0-470-85032-9] and Handbook of OrganoPalladium Chemistry for Organic Synthesis [Volume 1, Edited by El-ichi Negishi, Wiley, ISBN 0-471-31506-0].

A further reaction which can be utilised is the Buchwald-Hartwig type reaction (see *Review*: Hartwig, J. F. (1998) *Angew. Chem. Int. Ed.* 37, 2046-2067) which provides a means for palladium-catalyzed synthesis of aryl amines. The starting materials are aryl halides or pseudohalides (for example triflates) and primary or secondary amines, in the presence of a strong base such as sodium tert-butoxide and a palladium catalyst such as tris-(dibenzylideneacetone)-dipalladium ($Pd_2(dba)_3$), or 2,2'-bis(diphenylphosphino)-1'1-binaphthyl (BINAP).

The sequence of reactions outlined in Scheme1 can be alternated as outlined. Alternatively the halogen functionality at the 7-position of the imidazo[1,2-a]pyridine can be converted to a boronic acid or ester and used to synthesise alternative motifs as outlined in Scheme 2. This can then be used directly in any of the metal catalysed reactions outlined herein. For example, for conversion of a halide to a boronate, the halide is reacted with a palladium catalyst and a phosphine ligand in an appropriate solvent e.g. dioxane and base e.g. KOAc, and the appropriate substituted boron compound.

Scheme 2

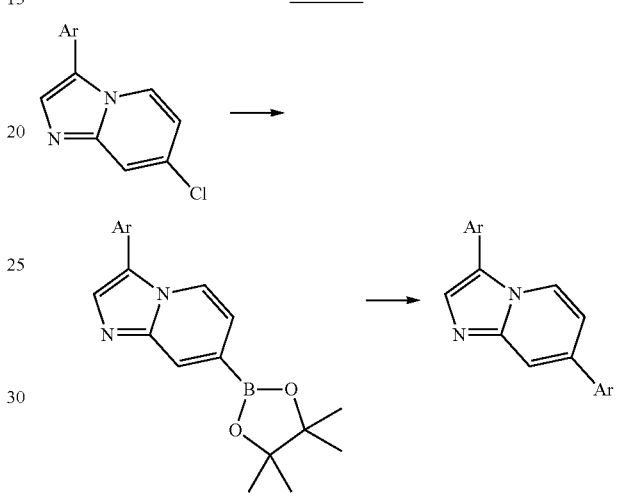

The Sonogashira reaction is a well-known reaction which provides access to internal aryl alkynyl compounds via reaction of an aryl halide (or pseudo halide) and alkyne (see review article: Chinchilla, R., Nájera, C.; (2007) Chem. Rev., 107, 8740). Typical reaction conditions involve a palladium catalyst, a copper (I) cocatalyst and base. Recently, methods have been developed which avoid the use of copper and amine (base) (Liang, Y.; Xie, Y.-X.; Li, J.-H.; (2006) J. Org. Chem., 71, 379).

The Sonogashira reaction efficiently provides access to alkynes. The appropriate chloroimidazopyridine is reacted with the appropriate alkyne e.g. ethynyl compound in the presence of a palladium catalyst and base, in solvent and heating to provide access to aryl-alkynyl or alkyl-alkynyl compounds.

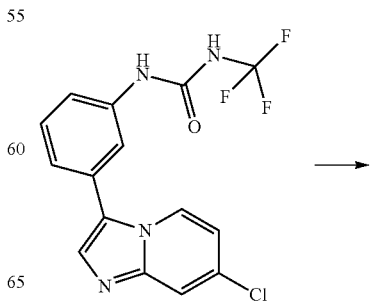

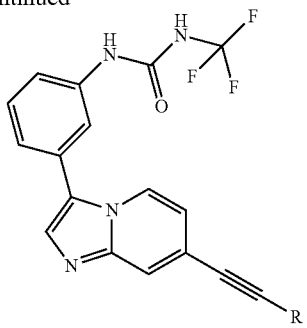

R = Aryl or alkyl (XXI)

Compounds were prepared via a copper-free method utilising PdCl$_2$(PCy$_3$)$_2$ as catalyst, CsCO$_3$ as base and DMSO as solvent (Chenyi, Y. and Hua, R., (2006) J. Org. Chem., 71, 2535).

The alkyne coupling partner for use in the Sonagashira reaction can be prepared from the appropriate iodo-substituted heterocycle and ethynyl-trimethyl-silane by reacting the two together with copper iodide and palladium catalyst in an inert atmosphere in the presence of base (such as triethylamine). The trimethyl silyl group on alkyne coupling partner is then removed for use in the Sonagashira reaction by stirring in methanol at room temperature in the presence of base such as potassium carbonate.

Furthermore, the internal alkyne functionality can also be reduced to form an alkene or an alkane, and thus alkynes of formula XXI could be hydrogenated to compounds of general formula imidazopyridine-CH$_2$CH$_2$R using Pd and H$_2$.

Alkenes can also be prepared by selective partial reduction of the respective alkyne precursor using selective hydrogenation using poisoned palladium or can be prepared using Wittig type chemistry from formyl-imidazopyridine compound and the phosphorous ylide.

Once synthesised, a range of functional group conversions can be employed on di-aryl or alkynynl substituted imidazopyridine compounds to produce further compounds of formula (I) and in particular compounds of formula (II). For example, some of the following reactions can be used hydrogenation e.g. using Raney nickel catalyst, hydrolysis, deprotection, and oxidation.

In particular for synthesis compounds of formula (I), the imidazopyridine halide can be reacted with 3-aminobenzeneboronic acid using an appropriate metal catalyst e.g. bis(triphenylphosphine)palladium(II) chloride, to form the amino precursor for urea bond formations. As outlined Scheme 3, the amine functionality introduced can be used to synthesise ureas.

Scheme 3

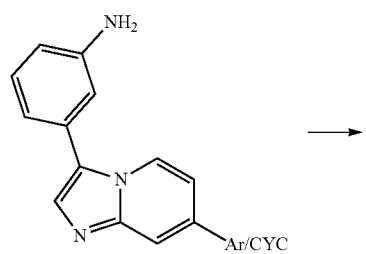

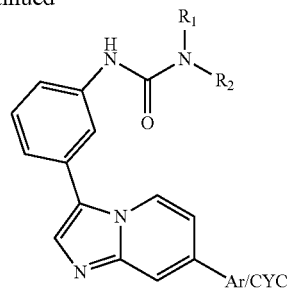

Ureas can be prepared using standard methods. For example, such compounds can be prepared by reacting an amino compound with a suitably substituted isocyanate in a polar solvent such as DMF. The reaction is conveniently carried out at room temperature.

Alternatively, ureas of the formula (I) can be prepared by reacting an amine with an appropriately substituted amine in the presence of carbonyl diimidazole (CDI). The reaction is typically carried out in a polar solvent such as THF with heating (for example using a microwave heater) to a temperature of up to about 150° C. Instead of using CDI, the coupling of the two amines to form the urea can be effected using triphosgene (bis(trichloromethyl) carbonate) in the presence of a non-interfering base such as triethylamine, in a solvent such as dichloromethane at room temperature or below. As a further alternative to CDI, phosgene may be used instead of triphosgene.

A further method for synthesising the urea functionality is by reacting the amine compound with p-nitrophenol chloroformate under conditions well known to the skilled person. The resulting carbamate compound is then reacted with the appropriate amine for example trifluoroethylamine or cyclopropylamine.

In addition the urea compounds can be synthesised by use of the appropriate substituted boronic acid in the Suzuki reaction e.g. 1-methyl-3-[3-(4,4,5,5-tetramethyl-[1,3,2]dioxaborolan-2-yl)-phenyl]-urea or 3-methoxy-5-nitro-phenyl boronic acid pinacol ester. These can be synthesised as described herein.

Ureas can also be synthesised from the amine intermediate using a range of well known functional group interconversions as described in *Advanced Organic Chemistry* by Jerry March, 4$^{th}$ Edition, John Wiley & Sons, 1992.

Appropriate starting material and reagents for these reactions can be obtained commercially or by any of a large number of standard synthetic methods well known those skilled in the art, for example see *Advanced Organic Chemistry* by Jerry March, 4$^{th}$ Edition, John Wiley & Sons, 1992, and *Organic Syntheses*, Volumes 1-8, John Wiley, edited by Jeremiah P. Freeman (ISBN: 0-471-31192-8), 1995, and see also the methods described in the experimental section below. For example, a range of appropriate functionalized aniline and amino pyridine starting materials, and metal catalysts are commercially available.

In particular, heterocyclic halide or pseudo-halide precursors are commercially available or can be prepared from an appropriately functionalised heterocyclic compound. Alternatively the rings can be formed on the imidazopyridine scaffold using intramolecular or radical cyclisation reactions under standard conditions.

Many boronates, for example boronic acids or esters or trifluoroborates, suitable for use in preparing compounds of the invention are commercially available, for example from Boron Molecular Limited of Noble Park, Australia, or from Combi-Blocks Inc. of San Diego, USA. Where the appropriately substituted boronate is not commercially available, they can be prepared by methods known in the art, for example as described in the review article by Miyaura, N. and Suzuki, A. (1995) *Chem. Rev.,* 95, 2457. Thus, boronates can be prepared by reacting the corresponding bromo-compound with an alkyl lithium such as butyl lithium and then reacting with a borate ester e.g. ($^i$PrO)$_3$B. The reaction is typically carried out in a dry polar solvent such as tetrahydrofuran at a reduced temperature (for example −78° C.). Boronate esters (for example a pinacolatoboronate) can also be prepared from a bromo-compound by reaction with a diboronate ester such as bis(pinacolato)diboron in the presence of a phosphine such as tricyclohexyl-phosphine and a palladium (0) reagent such as tris(dibenzylideneacetone)-dipalladium (0). The formation of the boronate ester is typically carried out in a dry polar aprotic solvent such as dioxane or DMSO with heating to a temperature of up to about 100° C., for example around 80° C. The resulting boronate ester derivative can, if desired, be hydrolysed to give the corresponding boronic acid or converted into the trifluoroborate.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(═O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(═O)CH$_3$, —OAc). An aldehyde or ketone group may be protected, for example, as an acetal (R—CH(OR)$_2$) or ketal (R$_2$C(OR)$_2$), respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an C$_{1-7}$ alkyl ester (e.g., a methyl ester; a t-butyl ester); a C$_{1-7}$ haloalkyl ester (e.g., a O$_{1-7}$ trihaloalkyl ester); a triC$_{1-7}$alkylsilyl-C$_{1-7}$alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(═O)CH$_3$).

Key intermediates in the preparation of the compounds of formula (I) are the compounds of formula (XX). Novel chemical intermediates of the formula (XX) form a further aspect of the invention.

A further aspect of the invention is a process for the preparation of a compound of formula (I) as defined herein, which process comprises:

(i) the reaction of a compound of the formula (XX):

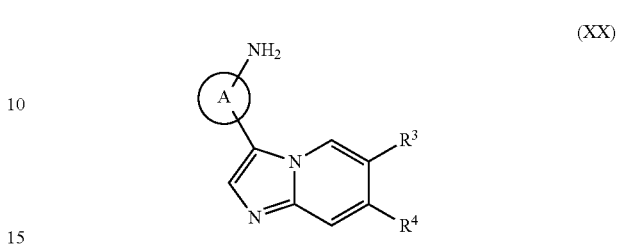

or a protected form thereof, wherein A, R$^3$ and R$^4$ are as defined hereinbefore, with an appropriately substituted isocyanate or an appropriately substituted amine in the presence of carbonyl diimidazole (CDI) and thereafter removing any protecting group present; or (ii) the reaction of a compound of the formula (XX):

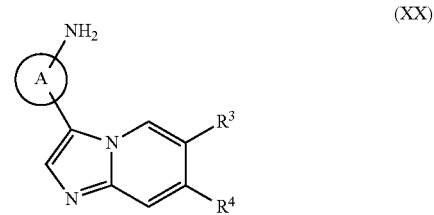

or a protected form thereof, wherein A, R$^3$ and R$^4$ are as defined hereinbefore, with p-nitrophenyl chloroformate and an appropriately substituted amine and thereafter removing any protecting group present; or (iii) the reaction of a compound of the formula (XXX):

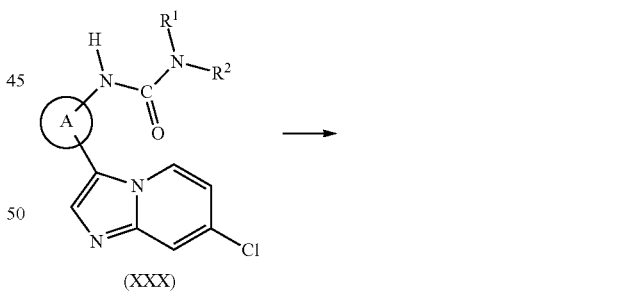

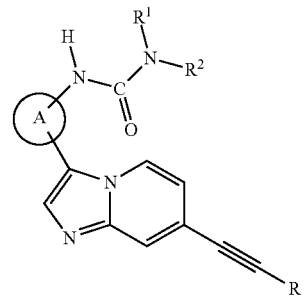

R = R$^5$ or R$^6$ wherein A, $R^1$, $R^2$, $R^5$ and $R^6$ are as defined hereinbefore; or a protected form thereof, with an appropriately substituted alkyne compound and thereafter removing any protecting group present; or (iv) reacting a compound of formula (V) and (VI):

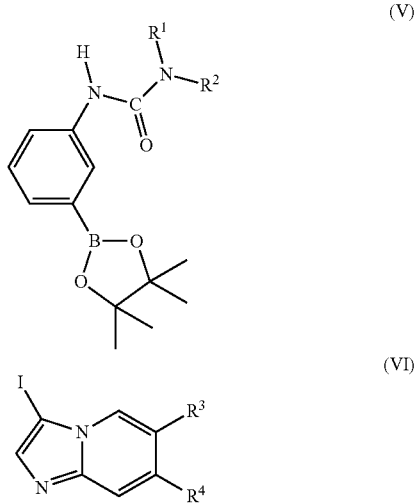

wherein $R^1$, $R^2$, $R^3$ and $R^4$ are as defined above for compounds of formula (I);

and optionally thereafter converting one compound of the formula (I) into another compound of the formula (I).

In one embodiment, $R^1$ represents hydrogen and $R^2$ represents ethyl or $CH_2CF_3$. In an alternative embodiment, $R^1$ represents hydrogen and $R^2$ represents cyclopropyl. In an alternative embodiment, $R^1$ and $R^2$ both represent hydrogen.

According to a further aspect of the invention there is provided a novel intermediate as described herein.

In one embodiment, the novel intermediate is selected from:
N-[5-(7-Chloro-imidazo[1,2-a]pyridin-3-yl)-thiazol-2-yl]-acetamide
1-[3-(7-Chloro-imidazo[1,2-a]pyridin-3-yl)-phenyl]-3-cyclopropyl-urea
Haloaromatic coupling partners e.g. X1-X35, X1-X14, and,
Boronic acid/ester coupling partners e.g. Y1
Pharmaceutically Acceptable Salts, Solvates or Derivatives Thereof.

In this section, as in all other sections of this application, unless the context indicates otherwise, references to formula (I) include references to all other sub-groups, preferences and examples thereof as defined herein. In one embodiment, references to compounds of the formula (I) includes compounds of the formula (I), or a pharmaceutically acceptable salt or solvate thereof.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethane-sulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids.

Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

The compounds of the invention may exist as mono- or di-salts depending upon the pKa of the acid from which the salt is formed.

If the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry, by Jerry March,* 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane. Particular examples of N-oxides include morpholine N-oxides and pyridine N-oxides.

Also encompassed by formula (I) are any polymorphic forms of the compounds, and solvates such as hydrates.

The compound of the invention and its salts and tautomers may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR(SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described above, can be used to establish whether solvates had formed.

Furthermore, the compounds of the present invention may have one or more polymorph (crystalline) forms or may be amorphous and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

Other examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

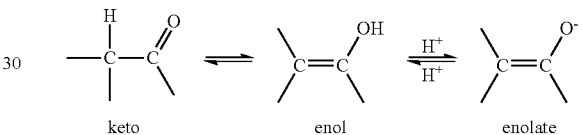

keto          enol          enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.,* 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Where compounds of the formula (I) contain one or more double bonds, and can exist in the form of two geometric isomers, references to compounds of the formula (I) include both stereoisomeric forms thereof (i.e. cis-trans isomerism or (E) and (Z) isomerism), either as individual isomers, or mixtures of two isomers, unless the context requires otherwise.

The term "geometric isomer" means isomers that differ in the orientation of substituent atoms in relationship to a carbon-carbon double bond, to a carbon-nitrogen double bond, to a cycloalkyl ring, or to a bridged bicyclic system. Substituent atoms (other than hydrogen) on each side of a carbon-carbon or carbon-nitrogen double bond may be in an E or Z configuration. Whether a molecular configuration is designated E or Z is determined by the Cahn-lngold-Prelog priority rules (higher atomic numbers are given higher priority). For each of the two atoms in the double bond, it is necessary to determine which of the two substituents is of a higher priority. In the "E" configuration, both of the substituents of higher priority are on opposite sides in relationship to the double bond. In the "Z" configuration, both of the substituents of higher priority are on the same side in relationship to the double bond.

The isomeric descriptors ("R," "S," "E," and "Z") indicate atom configurations and are intended to be used as defined in the literature. Where a compound is drawn or indicated as a specific isomer, the alternative isomer and mixtures of the isomers are also within the scope of the application.

Synthetic processes can result in a mixture of geometric isomers and then chirally stable isomers can be separated by a number of techniques including chromatography and such techniques well known to the person skilled in the art. Alternatively various synthetic processes can be used to influence whether the E or Z geometric isomer was produced.

In cases where the compounds of the invention exist as the E and Z isomers, the invention includes individual isomers as well as mixtures thereof. Where compounds of the formula (I) exist as two or more stereoisomeric forms, one stereoisomer in a pair may exhibit advantages over the other, for example, in terms of biological activity. Thus, in certain circumstances, it may be desirable to use as a therapeutic agent only one of a pair of stereoisomers. Accordingly, the invention provides compositions containing a compound of the formula (I) having one or more double bonds, wherein at least 55% (e.g. at least 60%, 65%, 70%, 75%, 80%, 85%, 90% or 95%) of the compound of the formula (I) is present as a single isomer (e.g. (E) or (Z) isomer). In one general embodiment, 99% or more (e.g. substantially all) of the total amount of the compound of the formula (I) may be present as a single stereoisomer.

The compounds of the invention include compounds with one or more isotopic substitutions, and a reference to a particular element includes within its scope all isotopes of the element. For example, a reference to hydrogen includes within its scope $^1H$, $^2H$ (D), and $^3H$(T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-7}$ alkyl group, a $C_{3-20}$ heterocyclyl group (a heterocyclic groups as defined above but having from 3 to 20 ring members), or a $C_{5-20}$ aryl group (an aryl group as defined above but having from 5 to 20 ring members), preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and prodrugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);

$C_{1-7}$-aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl;

1-acetoxyethyl; 1-(1-methoxy-1-methyl)ethyl-carbonyloxyethyl; 1-(benzoyloxy)ethyl; isopropoxy-carbonyloxymethyl;

1-isopropoxy-carbonyloxyethyl; cyclohexyl-carbonyloxymethyl; 1-cyclohexyl-carbonyloxyethyl; cyclohexyloxy-carbonyloxymethyl;

1-cyclohexyloxy-carbonyloxyethyl; (4-tetrahydropyranyloxy) carbonyloxymethyl; 1-(4-tetrahydropyranyloxy)carbonyloxyethyl;

(4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.).

For example, the prodrug may be a sugar derivative or other glycoside conjugate, or may be an amino acid ester derivative.

It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof.

According to a further aspect of the invention there is provided a compound as defined herein or a salt or solvate thereof.

References to compounds of the formula (I) and (Ia) and sub-groups thereof as defined herein include within their scope the salts or solvates or tautomers or N-oxides of the compounds.

Protein Tyrosine Kinases (PTK)

The compounds of the invention described herein inhibit or modulate the activity of certain tyrosine kinases, and thus the compounds will be useful in the treatment or prophylaxis of disease states or conditions mediated by those tyrosine kinases in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state (Powers, et al. (2000) Endocr. Relat. Cancer, 7, 165-197).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Ozawa, et al. (2001), Teratog. Carcinog. Mutagen., 21, 27-44).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4). Upon ligand binding, the receptors dimerize and auto- or trans-phosphorylate specific cytoplasmic tyrosine residues to transmit an intracellular signal that ultimately regulates nuclear transcription factor effectors.

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2 (Lemonnier, et al. (2001), J. Bone Miner. Res., 16, 832-845). In addition, mutation screening in patients with syndromic craniosynostoses indicates that a number of recurrent FGFR2 mutations accounts for severe forms of Pfeiffer syndrome (Lajeunie et al, *European Journal of Human Genetics* (2006) 14, 289-298). Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene (Meyers, et al. (1996) Am. J. Hum. Genet., 58, 491-498; Plomp, et al. (1998) Am. J. Med. Genet., 75, 245-251), and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2 (Yu, et al. (2000), Proc. Natl. Acad. Sci. U.S.A., 97, 14536-14541).

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas (Powers, C. J. (2000), et al., Endocr. Rel. Cancer, 7, 165; Qiu, W. et. al. (2005), World Journal Gastroenterol, 11(34)). Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC) (Journal of Pathology (2007), 213 (1), 91-98). Increased expression was associated with mutation (85% of mutant tumors showed high-level expression) but also 42% of tumors with no detectable mutation showed over-expression, including many muscle-invasive tumors.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Over expression of FGFR4 has been linked to poor prognosis in both prostate and thyroid carcinomas (Ezzat, S., et al. (2002) The Journal of Clinical Investigation, 109, 1; Wang et al. (2004) Clinical Cancer Research, 10). In addition a germ-line polymorphism (Gly388Arg) is associated with increased incidence of lung, breast, colon and prostate cancers (Wang et al. (2004) Clinical Cancer Research, 10). In addition, a truncated form of FGFR4 (including the kinase domain) has also been found to present in 40% of pituitary tumours but not present in normal tissue. FGFR4 overexpression has been observed in liver, colon and lung tumours (Desnoyers et al. (2008) Oncogene, 27; Ho et al. (2009) Journal of Hepatology, 50). These studies described targetting of either FGFR4 kinase activity or its ligand FGF 19 with an antibody antagonist inhibited proliferation and induced apoptosis in cell line models. Ho et al showed that one third of patients with a common polymorphism in the FGFR4 gene expressed high levels of mRNA and these tumours were associated with high secreted levels of the hepatocellular carcinoma marker alpha-fetoprotein.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. (2006) Clin Cancer Res. 12(22): 6652-6662.

Rhabdomyosarcoma (RMS), the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes (Genes, Chromosomes & Cancer (2007), 46(11), 1028-1038).

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis (Inoue, et al. (1997 & 2002); Barrios, et al. (1997)). TGFβ1 and PDGF have been reported to be involved in the fibrogenic process (reviewed by Atamas & White, 2003) and further published work suggests the elevation of FGF's and consequent increase in fibroblast proliferation, may be in response to elevated TGFβ1 (Khalil, et al., 2005). The potential therapeutic relevance of this pathway in fibrotic conditions is suggested by the reported clinical effect of Pirfenidone (Arata, et al., 2005) in idiopathic pulmonary fibrosis (IPF).

Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels. (Folkman (1997), 79, 1-81; Folkman (1995), *Nature Medicine*, 1, 27-31; Folkman and Shing (1992) J. Biol. Chem., 267, 10931).

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott (1992), *Ann. Rhum. Dis.*, 51, 919). In diabetes (and in many different eye diseases), new vessels invade the macula or retina or other ocular structures, and may cause blindness (Brooks, et al. (1994) *Cell*, 79, 1157). The process of atherosclerosis has been linked to angiogenesis (Kahlon, et al. (1992) *Can. J. Cardiol.*, 8, 60). Tumor growth and metastasis have been found to be angiogenesis-dependent (Folkman (1992), *Cancer Biol*, 3, 65; Denekamp, (1993) *Br. J. Rad.*, 66,181; Fidler and Ellis (1994), *Cell*, 79,185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly, et al. (1994) *Cell*, 79, 315; Ingber, et al. (1990) *Nature*, 348, 555), ocular diseases (Friedlander, et al. (1995) *Science*, 270,1500), arthritis (Peacock, et al. (1992), *J. Exp. Med.*, 175, 1135; Peacock et al. (1995), *Cell. Immun.*, 160,178) and hemangioma (Taraboletti, et al. (1995) *J. Natl. Cancer Inst.*, 87, 293).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al. (2000), *The Oncologist*, 5(90001), 1-2). VEGFR(s) are protein tyrosine kinases (PTKs). PTKs catalyze the phosphorylation of specific tyrosine residues in proteins involved in cell function thus regulating cell growth, survival and differentiation. (Wilks, A. F. (1990), *Progress in Growth Factor Research*, 2, 97-111; Courtneidge, S. A. (1993) *Dev. Supp.1*, 57-64; Cooper, J. A. (1994), *Semin. Cell Biol.*, 5(6), 377-387; Paulson, R. F. (1995), *Semin. Immunol.*, 7(4), 267-277; Chan, A. C. (1996), *Curr. Opin. Immunol.*, 8(3), 394-401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. (1995), et al., *J. Cell Biol.*, 129, 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G. (2000), *The Oncologist*, 5(90001), 3-10).

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition. Inhibition of VEGFR2 but not VEGFR1 markedly disrupted angiogenic switching, persistent angiogenesis, and initial tumor growth. In late-stage tumours, phenotypic resistance to VEGFR2 blockade emerged, as tumours regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

A FGF-trap adenovirus has been previously reported to bind and block various ligands of the FGF family, including FGF1, FGF3, FGF7, and FGF10, thereby effectively inhibiting angiogenesis in vitro and in vivo. Indeed, adding the FGF-trap treatment in the regrowth phase of a mouse model produced a significant decrease in tumor growth compared to anti-VEGFR2 alone. This decrease in tumor burden was accompanied by a decrease in angiogenesis that was observed as decreased intratumoral vessel density.

Batchelor et al. (Batchelor et al., 2007, *Cancer Cell*, 11(1), 83-95) provide evidence for normalization of glioblastoma blood vessels in patients treated with a pan-VEGF receptor tyrosine kinase inhibitor, AZD2171, in a phase 2 study. The rationale for using AZD2171 was based partially on results showing a decrease in perfusion and vessel density in an in vivo breast cancer model (Miller et al., 2006, *Clin. Cancer Res.* 12, 281-288). Furthermore, using an orthotopic glioma model, it had previously been identified that the optimal window of time to deliver anti-VEGFR2 antibody to achieve a synergistic effect with radiation. During the window of normalization, there was improved oxygenation, increased pericyte coverage, and upregulation of angiopoietin-1 leading to a decrease in interstitial pressure and permeability within the tumour (Winkler et al., 2004, Cancer Cell 6, 553-563). The window of normalization can be quantified using magnetic resonance imaging (MRI) using MRI gradient echo, spin echo, and contrast enhancement to measure blood volume, relative vessel size, and vascular permeability.

The authors showed that progression on treatment with AZD2171 was associated with an increase in CECs, SDF1, and FGF2, while progression after drug interruptions correlated with increases in circulating progenitor cells (CPCs) and plasma FGF2 levels. The increase in plasma levels of SDF1 and FGF2 correlated with MRI measurements, demonstrated an increase in the relative vessel density and size. Thus, MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment of chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. In addition, sorafenib (BAY 43-9006) which has the chemical name 4-(4-(3-(4-chloro-3 (trifluoromethyl)phenyl)ureido)phenoxy)-N-2-methylpyridine-2-carboxamide, targets both the Raf signalling pathway to inhibit cell proliferation and the VEGFR/PDGFR signalling cascades to inhibit tumour angiogenesis. Sorafenib is being investigated for the treatment of a number of cancers including liver and kidney cancer.

There are conditions which are dependent on activation of PDGFR such as hypereosinophilic syndrome. PDGFR activation is also associated with other malignancies, which include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Imatinib has which is a known inhibitor of PDGFR has activity against all three of these diseases.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, it is envisaged that the compounds of the invention will be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3.

Preferred compounds are compounds that inhibit one or more FGFR selected from FGFR1, FGFR2 and FGFR3, and also FGFR4. Preferred compounds of the invention are those having $IC_{50}$ values of less than 0.1 μM.

Compounds of the invention also have activity against VEGFR.

Compounds of the invention also have activity against PDGFR kinases. In particular, the compounds are inhibitors of PDGFR and, for example, inhibit PDGFR A and/or PDGFR B.

In addition many of the compounds of the invention exhibit selectivity for the FGFR1, 2, and/or 3 kinase, and/or FGFR4 compared to VEGFR (in particular VEGFR2) and/or PDGFR and such compounds represent one preferred embodiment of the invention. In particular, the compounds exhibit selectivity for VEGFR2. For example, many compounds of the invention have $IC_{50}$ values against FGFR1, 2 and/or 3 and/or FGFR4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, VEGFR and/or PDGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukemia, acute lymphocytic leukemia, chronic lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, myeloproliferative syndrome, myelodysplastic syndrome, or promyelocytic leukemia; multiple myeloma; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis.

Thus, in the pharmaceutical compositions, uses or methods of this invention for treating a disease or condition comprising abnormal cell growth, the disease or condition comprising abnormal cell growth in one embodiment is a cancer.

Further T-cell lymphoproliferative diseases include those derived from natural Killer cells. The term B-cell lymphoma includes diffuse large B-cell lymphoma.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

A further example of a tumour of mesenchymal origin is Ewing's sarcoma.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

It is further envisaged that the compound of the invention having FGFR such as FGFR1 inhibitory activity, will be particularly useful in the treatment or prevention of breast cancer in particular Classic Lobular Carcinomas (CLC).

As the compounds of the invention have FGFR4 activity they will also be useful in the treatment of prostate or pituitary cancers.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are in the treatment of multiple myeloma (in particular multiple myeloma with t(4;14) translocation or overexpressing FGFR3), prostate cancer (hormone refractory prostate carcinomas), endometrial cancer (in particular endometrial tumours with activating mutations in FGFR2) and breast cancer (in particular lobular breast cancer).

In particular the compounds are useful for the treatment of lobular carcinomas such as CLC (Classic lobular carcinoma).

As the compounds have activity against FGFR3 they will be useful in the treatment of multiple myeloma and bladder.

In particular the compounds are useful for the treatment of t(4;14) translocation positive multiple myeloma.

As the compounds have activity against FGFR2 they will be useful in the treatment of endometrial, ovarian, gastric and colorectal cancers. FGFR2 is also overexpressed in epithelial ovarian cancer, therefore the compounds of the invention may be specifically useful in treating ovarian cancer such as epithelial ovarian cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR, VEGFR or PDGFR signalling may be determined by means of a cell growth assay as set out below or by a method as set out in the section headed "Methods of Diagnosis".

It is further envisaged that the compounds of the invention, and in particular those compounds having FGFR, VEGFR or PDGFR inhibitory activity, will be particularly useful in the treatment or prevention of cancers of a type associated with or characterised by the presence of elevated levels of FGFR, VEGFR or PDGFR, for example the cancers referred to in this context in the introductory section of this application.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

It is also envisaged that the compounds of the invention will be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions where it is envisaged that the compounds of the invention will be useful consists of inflammatory diseases, cardiovascular diseases and wound healing.

FGFR, VEGFR and PDGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

It is further envisaged that the compound of the invention having FGFR such as FGFR2 or FGFR3 inhibitory activity, will be particularly useful in the treatment or prevention of the skeletal diseases. Particular skeletal diseases are achondroplasia or thanatophoric dwarfism (also known as thanatophoric dysplasia).

It is further envisaged that the compound of the invention having FGFR such as FGFR1, FGFR2 or FGFR3 inhibitory activity, will be particularly useful in the treatment or prevention in pathologies in which progressive fibrosis is a symptom. Fibrotic conditions in which the compounds of the inventions may be useful in the treatment of in include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

Since compounds of the invention inhibit PDGFR they may also be useful in the treatment of a number of tumour and leukemia types including glioblastomas such as glioblastoma multiforme, prostate carcinomas, gastrointestinal stromal tumours, liver cancer, kidney cancer, chronic myeloid leukemia, chronic myelomonocytic leukemia (CMML) as well as hypereosinophilic syndrome, a rare proliferative hematological disorder and dermatofibrosarcoma protuberans, an infiltrative skin tumour.

The activity of the compounds of the invention as inhibitors of FGFR1-4, VEGFR and/or PDGFR NB can be measured using the assays set forth in the examples below and the level of activity exhibited by a given compound can be defined in terms of the $IC_{50}$ value. Preferred compounds of the present invention are compounds having an $IC_{50}$ value of less than 1 μM, more preferably less than 0.1 μM.

The invention provides compounds that have FGFR inhibiting or modulating activity, and which it is envisaged will be useful in preventing or treating disease states or conditions mediated by FGFR kinases.

In one embodiment, there is provided a compound as defined herein for use in therapy. In a further embodiment, there is provided a compound as defined herein for use in the prophylaxis or treatment of a disease state or condition mediated by a FGFR kinase.

Thus, for example, it is envisaged that the compounds of the invention will be useful in alleviating or reducing the incidence of cancer. Therefore, in a further embodiment, there is provided a compound as defined herein for use in the prophylaxis or treatment of cancer.

Accordingly, in one aspect, the invention provides the use of a compound for the manufacture of a medicament for the prophylaxis or treatment of a disease state or condition mediated by a FGFR kinase, the compound having the formula (I) as defined herein.

In one embodiment, there is provided the use of a compound as defined herein for the manufacture of a medicament for the prophylaxis or treatment of a disease state or condition as described herein.

In a further embodiment, there is provided the use of a compound as defined herein for the manufacture of a medicament for the prophylaxis or treatment of cancer.

Accordingly, the invention provides inter alia:

A method for the prophylaxis or treatment of a disease state or condition mediated by a FGFR kinase, which method comprises administering to a subject in need thereof a compound of the formula (I) as defined herein.

In one embodiment, there is provided a method for the prophylaxis or treatment of a disease state or condition as described herein, which method comprises administering to a subject in need thereof a compound of the formula (I) as defined herein.

In a further embodiment, there is provided a method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use as a modulator (e.g. inhibitor) of FGFR.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of FGFR kinase, thereafter administering to the patient a compound of the formula (I) as defined herein having FGFR kinase inhibiting activity.

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme (Carter et al (2005), PNAS, 102(31), 11011-110116).

A study in gastric cancer patient samples showed the presence of two mutations in FGFR2, Ser167Pro in exon 111a and a splice site mutation 940-2A-G in exon 111c. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group (Jang et. al. (2001) Cancer Research 61 3541-3543.

There are mutations that have been observed in PDGFR in imatinib-treated patients, in particular the T6741 mutation. The clinical importance of these mutations may grow considerably, as to date it appears to represent the primary mechanism of resistance to src/Abl inhibitors in patients.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR or PDGFR including PDGFR-beta and PDGFR-alpha in particular the T6741 mutation of PDGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561 M showed that this mutation conferred resistance to a tyrosine kinase inhibitor compared to that of the wild type.

Advantages of the Compositions of the Invention

The compounds of the formula (I) have a number of advantages over prior art compounds.

For example, the compounds of formula (I) have advantageous ADMET and physiochemical properties over prior art compounds. In particular, many of the compounds of formula (I) have exhibit reduced HERG binding, better P450 profile, better metabolic stability (for example as determined with mouse liver microsomes) and/or better solubility. The compounds of the invention also have advantageous biological and pharmacokinetic properties such as improved cell potency, increased selectivity in vitro or in cells over related kinases, display oral bioavailability (oral exposure or AUC), and/or beneficial clearance (e.g. low clearance). The compounds of formula (I) are potentially less toxic than prior art compounds. Many of the compounds of formula (I) have a reduced toxicity and therefore a greater therapeutic window.

Potentially the compositions of the invention have physiochemical properties suitable for oral exposure.

The composition as defined herein should exhibit improved oral bioavailability relative to prior art compounds. Oral bioavailability can be defined as the ratio (F) of the plasma exposure of a compound when dosed by the oral route to the plasma exposure of the compound when dosed by the intravenous (i.v.) route, expressed as a percentage.

Compositions having an oral bioavailability (F value) of greater than 30%, more preferably greater than 40%, are particularly advantageous in that they may be administered orally rather than, or as well as, by parenteral administration.

Furthermore, the compounds of formula (I) are both more potent and more selective in their activities against different kinases, and demonstrate enhanced selectivity for and potency against FGFR kinases (e.g. FGFR1, FGFR2, FGFR3 and/or FGFR4). The compounds of formula (I) are in particular potent at inhibiting FGFR in vitro and in cells. The $IC_{50}$ for the compound of formula (I) against the isolated FGFR enzymes in an in vitro radiometric assay and in cells can be determined using the assays described herein. The compounds demonstrate improved cell activity in proliferation and clonogenic assays and/or potency in cell-based mechanistic assays for example one which measures FGF-induced ERK1/2 phosphorylation, a downstream substrate of FGFR. This indicates improved anti-cancer activity against a wide range of solid tumour and leukemic (e.g. multiple myeloma) cell lines.

In addition the compounds exhibit selectivity against the closely related kinases VEGFR2 and/or PDGFR. Therefore the compounds have decreased activity against VEGFR2 and/or PDGFR. In particular the compounds show an approximate >10-fold difference in potency against VEGFR2.

Many of the compounds of formula (I) are advantageous over prior art compounds in that they have different susceptibilities to P450 enzymes. For example, the preferred compounds of formula (I) have $IC_{50}$ values of greater than 10 μM against each of the cytochrome P450 enzymes 1A2, 2C9, 2C19, 3A4 and 2D6.

In addition, many compounds of the invention are also advantageous over prior art compounds in that they exhibit improvements with regard to drug metabolism and pharmacokinetic properties. In particular many of the compounds of the invention have reduced plasma protein binding and/or better metabolic stability in mouse liver microsomes. In addition many of the compounds of the inventions have improved solubility in aqueous solution and better physicochemical properties, e.g. a lower logD. These features could confer the advantage of having more free drug available in the systemic circulation to reach the appropriate site of action to exert its therapeutic effect. Increased free fraction to exert pharmacological action in tumours potentially leads to improved efficacy which thereby allows reduced dosages to be administered. Thus, the compounds of formula (I) should exhibit reduced dosage requirements and should be more readily formulated and administered.

hERG

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. *Nature,* 345(6277): 672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. *Cell,* 81:299-307, and Trudeau, M. C., Warmke, J. W., Ganetzky, B., and Robertson, G. A. (1995). HERG, a Human Inward Rectifier in the Voltage-Gated Potassium Channel Family. *Science,* 269:92-95.

The elimination of hERG blocking activity remains an important consideration in the development of any new drug. It has been found that many compounds of the formula (I) have low hERG activity and a good separation between FGFR inhibitory activity and hERG activity.

One method for measurement of hERG activity is the patch clamp electrophysiology method. Alternative methods for measurement of functional hERG activity include hERG binding assays, which can use commercially available membranes isolated from cells stably expressing the hERG channel or commercially available cell lines expressing the hERG channel.

The preferred compounds of formula (I) have low hERG ion channel blocking activity. Preferred compounds of the formula (I) have mean $IC_{50}$ values against hERG that are greater than 30 times, or greater than 40 times, or greater than 50 times the $IC_{50}$ values of the compounds in cellular proliferation assays. Preferred compounds of the formula (I) have mean $IC_{50}$ values against hERG that are greater than 5 µM, more particularly greater than 10 µM, and more preferably greater than 15 µM. Some compounds of the invention have mean $IC_{50}$ values against hERG that are greater than 30 µM or display % inhibition representative of such an $IC_{50}$ at concentrations of 1, 3, 10 or 30 µM.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly (2004), Solubilizing Excipients in oral and injectable formulations, Pharmaceutical Research, Vol 21(2), p 201-230).

Liposomes are closed spherical vesicles composed of outer lipid bilayer membranes and an inner aqueous core and with an overall diameter of <100 µm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman (1971), J. Pharm. Sci., 60, 1281-1300) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavours.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

The skilled person will have the expertise to select the appropriate amounts of ingredients for use in the formulations. For example tablets and capsules typically contain 0-20% disintegrants, 0-5% lubricants, 0-5% flow aids and/or 0-100% fillers/or bulking agents (depending on drug dose). They may also contain 0-10% polymer binders, 0-5% antioxidants, 0-5% Pigments. Slow release tablets would in addition contain 0-100% polymers (depending on dose). The film coats of the tablet or capsule typically contain 0-10% polymers, 0-3% pigments, and/or 0-2% plasticizers.

Parenteral formulations typically contain 0-20% buffers, 0-50% cosolvents, and/or 0-100% Water for Injection (WFI) (depending on dose and if freeze dried). Formulations for intramuscular depots may also contain 0-100% oils.

Examples of Pharmaceutical Formulations (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

Methods of Treatment

It is envisaged that the compounds of the formula (I) and sub-groups thereof as defined herein will be useful in the prophylaxis or treatment of a range of disease states or conditions mediated by FGFR. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic.

However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:
Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

Each of the compounds present in the combinations of the invention may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against FGFR, VEGFR and for PDGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, VEGFR and for PDGFR or to sensitisation of a pathway to normal FGFR, VEGFR and for PDGFR activity, or to upregulation of these growth factor signalling pathways such as growth factor ligand levels or growth factor ligand activity or to upregulation of a biochemical pathway downstream of FGFR, VEGFR and for PDGFR activation.

Examples of such abnormalities that result in activation or sensitisation of the FGFR, VEGFR and/or PDGFR signal include loss of, or inhibition of apoptotic pathways, up-regulation of the receptors or ligands, or presence of mutant variants of the receptors or ligands e.g. PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions (Lemonnier, et al. (2001), J. Bone Miner. Res., 16, 832-845). In particular activating mutations in FGFR2 have been identified in 10% of endometrial tumours (Pollock et al, Oncogene, 2007, 26, 7158-7162).

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas (Powers, C. J., et al. (2000), Endocr. Rel. Cancer, 7, 165). A particular mutation T6741 of the PDGF receptor has been identified in imatinib-treated patients.

In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. (2006), Clin Cancer Res. 12(22), 6652-6662).

Alternatively, a biological sample taken from a patient may be analysed for loss of a negative regulator or suppressor of FGFR, VEGFR or PDGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, VEGFR and for PDGFR. The term diagnosis includes screening. By marker we include genetic markers including, for example, the measurement of DNA composition to identify mutations of FGFR, VEGFR and for PDGFR. The term marker also includes markers which are characteristic of up regulation of FGFR, VEGFR and for PDGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, VEGFR and for PDGFR may mean that the patient would be particularly suitable for treatment with a FGFR, VEGFR and for PDGFR inhibitor. Tumours may preferentially be screened for presence of a FGFR, VEGFR and for PDGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, VEGFR and/or PDGFR, or detection of FGFR, VEGFR and/or PDGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105 (Mineo et al. (2004) J Clin Pathol. 57(6), 591-7).

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung and breast cancer.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect of the inventions includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

EXPERIMENTAL

The following examples illustrate the present invention but are examples only and are not intended to limit the scope of the claims in any way.

Analytical LC-MS System and Method Description

In the examples, the compounds prepared were characterised by liquid chromatography and mass spectroscopy using commercially available systems (Waters Platform LC-MS system, Waters Fractionlynx LC-MS system), standard operating conditions and commercially available columns (Phenomenex, Waters etc) but a person skilled in the art will appreciate that alternative systems and methods could be used. Where atoms with different isotopes are present and a single mass quoted, the mass quoted for the compound is the monoisotopic mass (i.e. 35Cl; 79Br etc.).

Mass Directed Purification LC-MS System

Preparative LC-MS (or HPLC) is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; J Comb Chem.; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; J Comb Chem.; 2003; 5(3); 322-9.

Two such systems for purifying compounds via preparative LC-MS are the Waters Fractionlynx system or the Agilent 1100 LC-MS preparative system although a person skilled in the art will appreciate that alternative systems and methods could be used. In particular, reverse phase methods were used for preparative HPLC for the compounds described herein, but normal phase preparative LC based methods might be used in place of the reverse phase methods. Most preparative LC-MS systems utilise reverse phase LC and volatile acidic modifiers, since the approach is very effective for the purification of small molecules and because the eluents are compatible with positive ion electrospray mass spectrometry. According to the analytical trace obtained the most appropriate preparative chromatography type is chosen. A typical routine is to run an analytical LC-MS using the type of chromatography (low or high pH) most suited for compound structure. Once the analytical trace showed good chromatography a suitable preparative method of the same type is chosen. A range of chromatographic solutions e.g. normal or reverse phase LC; acidic, basic, polar, or lipophilic buffered mobile phase; basic modifiers could be used to purify the compounds. From the information provided someone skilled in the art could purify the compounds described herein by preparative LC-MS.

All compounds were usually dissolved in 100% MeOH or 100% DMSO.

General Synthetic Routes

General Route A

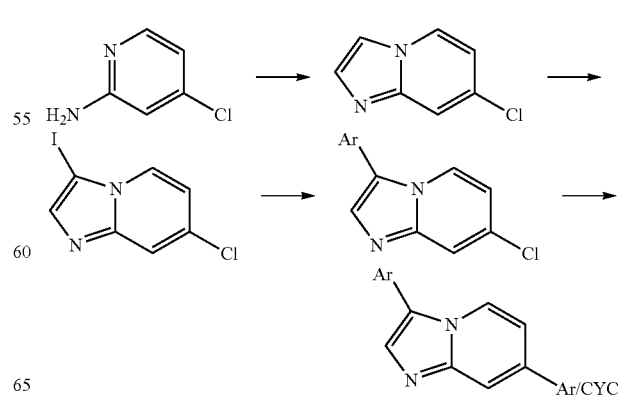

Procedure A1

7-Chloro-imidazol[1,2-a]pyridine

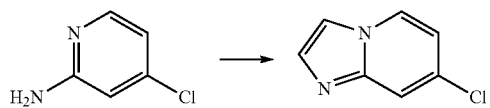 [SMILES: Nc1cc(Cl)ccn1 ; Clc1ccn2ccnc2c1]

To a solution of 4-Chloro-pyridin-2-ylamine (12.8 g, 100 mmol, 1.0 equiv) in EtOH (170 ml) was added NaHCO$_3$ (16.8 g, 200 mmol, 2.0 equiv) followed by chloroacetaldehyde (19.0 ml, 150 mmol, 1.5 equiv). The mixture was refluxed for 6 h. Solvents removed under reduced pressure and the crude mixture was partitioned between water and EtOAc. The organic layer was washed with brine, dried (MgSO$_4$), filtered and concentrated under reduced pressure. The product was purified by column chromatography (SiO$_2$, eluted with 50% EtOAC-petrol) to afford 13.2 g of product. MS: [M+H]$^+$=153.

Procedure A2

7-Chloro-3-iodoimidazo[1,2-a]pyridine

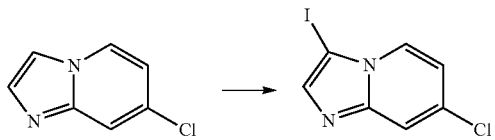 [SMILES: Clc1ccn2ccnc2c1 ; Clc1ccn2c(I)cnc2c1]

To a solution of 7-Chloro-imidazo[1,2-a]pyridine (30.9 g, 186 mmol, 1.0 equiv) in DMF (280 ml) was added N-iodosuccinimide (43.6 g, 194 mmol, 1.05 equiv) and the resulting mixture was stirred overnight at RT. The thin brown slurry was diluted with water (840 ml), brine (280 ml) and extracted with EtOAc (560 ml). The aqueous layer was further extracted with EtOAc (3×280 ml). The combined organic phases were washed with water (2×280 ml), 10% w/v sodium thiosulfate (280 ml), brine (280 ml), dried (MgSO$_4$), filtered and concentrated in vacuo to give a brown residue. The residue was triturated with ether (200 ml), filtered and the solid was washed with ether (2×50 ml) and dried on the filter to give 39 g of product. MS: [M+H]$^+$=279.

Procedure A3

1-[3-(4,4,5,5-Tetramethyl-[1,3,2]dioxaborolan-2-yl)-phenyl]-3-(2,2,2-trifluoro-ethyl)-urea

Step 1: 1-(3-Bromo-phenyl)-3-(2,2,2-trifluoro-ethyl)urea

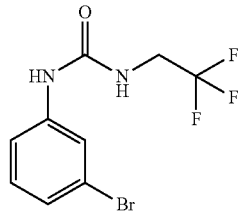 [SMILES: O=C(NCC(F)(F)F)Nc1cccc(Br)c1]

3-Bromophenyl isocyanate (1.0 ml, 8.1 mmol) was added slowly to a stirred solution of 2,2,2-trifluoroethyl amine (3.2 ml, 40 mmol) in THF (10 ml) at 0° C. under N$_2$. After 1 hour the reaction was allowed to warm to RT and kept at this temperature for 16 hours. The volatiles were removed in vacuo to give the title compound (2.5 g, solid). $^1$H NMR (400 MHz, DMSO-d6): 9.00 (1H, s), 7.86 (1H, t), 7.33 (1H, ddd), 7.26 (1H, t), 7.18 (1H, ddd), 6.89 (1H, t), 4.03-3.92 (2H, m).

Step 2: 1-[3-(4,4,5,5-Tetramethyl-[1,3,2]dioxaborolan-2-yl)-phenyl]-3-(2,2,2-trifluoro-ethyl)-urea

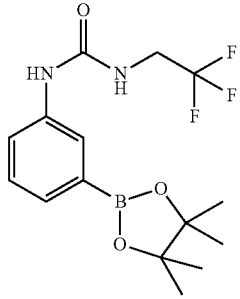 [SMILES: CC1(C)OB(c2cccc(NC(=O)NCC(F)(F)F)c2)OC1(C)C]

A mixture of 1-(3-bromo-phenyl)-3-(2,2,2-trifluoro-ethyl)-urea (2.1 g, 7.1 mmol), bis(pinacolato)diboron (3.6 g, 14 mmol) and KOAc (2.1 g, 21 mmol) in dry DMSO (7 ml) was deoxygenated by evacuation/refill with N$_2$ (×3). PdCl$_2$ddpf (512 mg, 0.7 mmol) was added and the mixture was deoxygenated again (×2) then stirred and heated at 100° C. under N$_2$ for 3 hours. The reaction was allowed to cool to RT and then left to stand at this temperature for 18 hours. The mixture was partitioned between EtOAc/H$_2$O then filtered through Celite®. The layers were separated and the aqueous layer was extracted with EtOAc (×1). The combined organic extracts were washed with water (×1), brine (×1), then dried (MgSO$_4$), filtered and evaporated. The residue was triturated with petrol to give the title compound (2.6 g, solid). $^1$H NMR (400 MHz, CDCl$_3$): 7.65 (1H, s), 7.60 (1H, d), 7.49 (1H, d), 7.37 (1H, t), 6.64 (1H, brs), 5.20 (1H, brs), 3.99-3.86 (2H, m), 1.35 (12H, s).

Procedure A4

1-[3-(7-Chloroimidazo[1,2-a]pyridin-3-yl)phenyl]-3-(2,2,2-trifluoroethyl)urea:

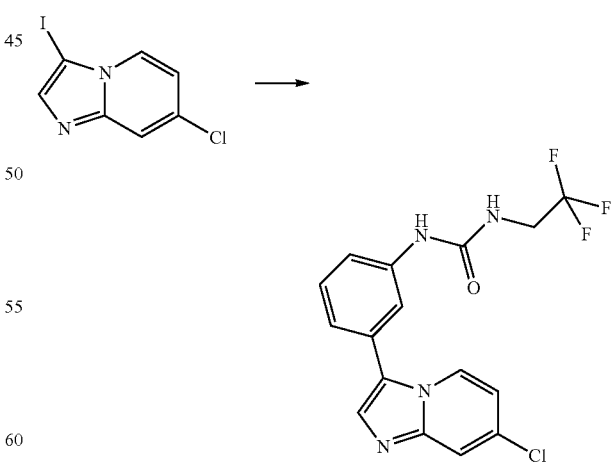

To a solution of 7-Chloro-3-iodo-imidazo[1,2-a]pyridine (15.17 g, 54.5 mmol) in 1,4-dioxane (260 ml) was added 1-[3-(4,4,5,5-Tetramethyl-[1,3,2]dioxaborolan-2-yl)-phenyl]-3-(2,2,2-trifluoro-ethyl)-urea (22.5 g, 65.4 mmol) and aqueous K$_3$PO$_4$ (23.1 g in 65 ml H$_2$O, 109 mmol) [reaction degassed by bubbling N₂ through] followed by 1,1'-bis (diphenylphosphino)ferrocene palladium (II) chloride (1.99 g, 2.72 mmol). The mixture was heated at 80° C. overnight, then diluted with water and extracted with EtOAc. The organic layer was washed with brine, dried (MgSO₄), filtered and concentrated under reduced pressure. The residue was triturated with DCM (100 ml), filtered and the filtercake washed with 1:1 DCM:Petroleum ether to give the product (13.2 g) as a beige solid. MS: [M+H]⁺=369.

Procedure A5a

General Suzuki Coupling at the 7-Position

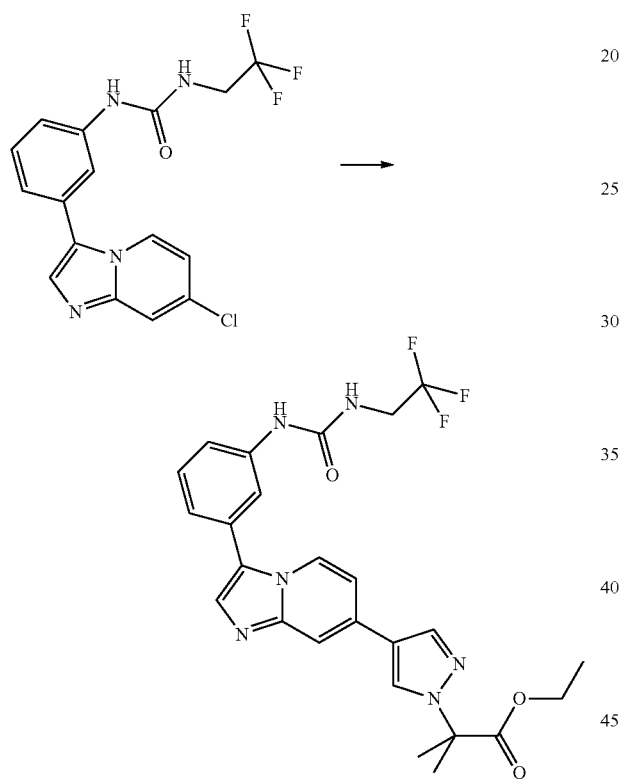

To a solution of 1-[3-(7-Chloroimidazo[1,2-a]pyridin-3-yl)phenyl]-3-(2,2,2-trifluoroethyl)urea (565 mg, 1.5 mmol) and 2-Methyl-2-[4-(4,4,5,5-tetramethyl-[1,3,2]dioxaborolan-2-yl)pyrazol-1-yl]propionic acid ethyl ester (Y1) (714 mg, 2.3 mmol) in 1,4-dioxane (9 ml) was added tris(dibenzylideneacetone)dipalladium (35 mg, 0.38 mmol), 2-dicyclohexylphosphino-2',6'-dimethoxybiphenyl (31 mg, 0.075 mmol) and 1M K₃PO₄ (4.5 ml, 4.5 mmol) [reaction degassed by bubbling N₂ through]. The mixture was heated using microwave radiation in a CEM discover microwave synthesizer (50W) at 120° C. for 30 min. The reaction was diluted with water and extracted with EtOAc. The organic layer was dried (MgSO₄), filtered and concentrated under reduced pressure and purified by column chromatography (0-3% 2M NH₃-MeOH/DCM), then triturated with MeOH to give the product as a colourless solid (40 mg). MS: [M+H]⁺=515.

Procedure A5b

General Suzuki Coupling at the 7-Position

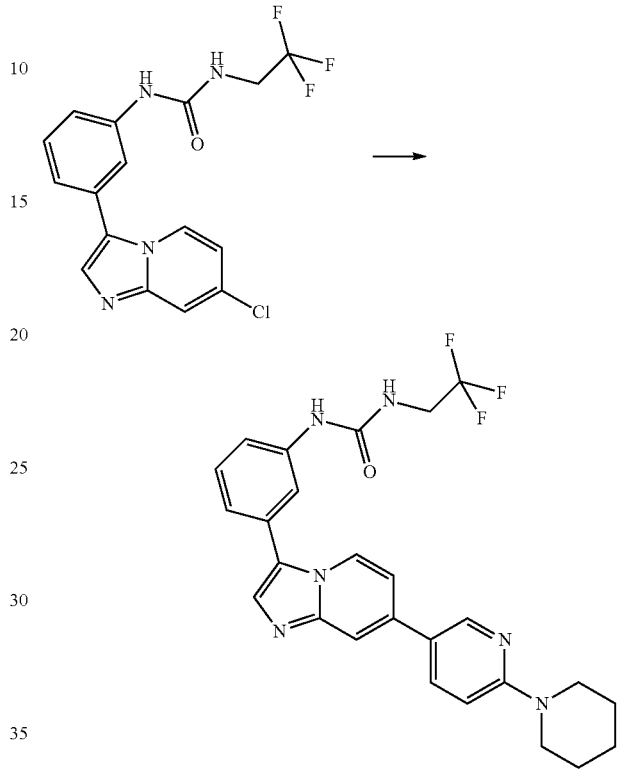

1-[3-(7-Chloroimidazo[1,2-a]pyridin-3-yl)phenyl]-3-(2,2,2-trifluoroethyl)urea and 5'-(4,4,5,5-Tetramethyl-[1,3,2]dioxaborolan-2-yl)-3,4,5,6-tetrahydro-2H-[1,2']bipyridinyl were coupled using the method described in Procedure B3b.

Procedure A5c

General Suzuki Coupling at the 7-Position

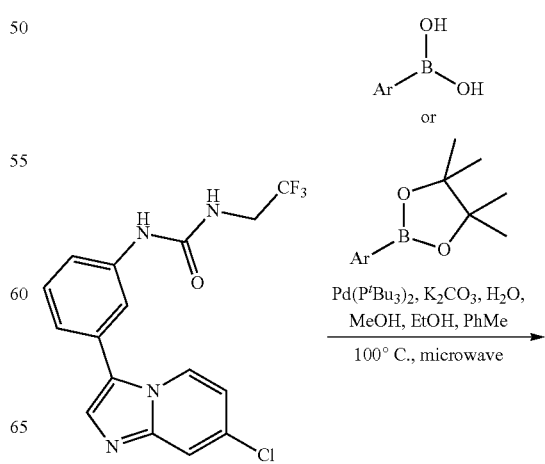

81
-continued

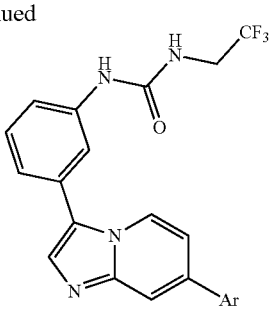

Bis(tri-tert-butylphosphine)palladium (0) (8 mg) was added to a mixture of 1-[3-(7-chloro-imidazo[1,2-a]pyridin-3-yl)-phenyl]-3-(2,2,2-trifluoroethyl)-urea (184 mg, 0.5 mmol), aryl boronic acid or arylboronate pinocol ester (0.6 mmol) and anhydrous potassium carbonate (345 mg, 2.5 mmol) in methanol (1 ml), ethanol (1 ml), toluene (1 ml) and water (1 ml) and the mixture was stirred and held at 100° C. for 30 minutes under the influence of microwave irradiation. Upon cooling to room temperature the mixture was filtered and the organic solvent was removed in vacuo. The residue was partitioned between ethyl acetate and water, the organic layer was separated and the solvent removed in vacuo. The residue was dissolved in methanol and applied to a Strata SCX cartridge. Elution with 2M ammonia in methanol afforded a brown oil which was triturated with dichloromethane. The solid material was collected by filtration, sucked dry under reduced pressure and recrystallized from ethyl acetate to afford the corresponding 1-[3-(7-aryl-imidazo[1,2-a]pyridin-3-yl)-phenyl]-3-(2,2,2-trifluoroethyl)-urea.

General Route B

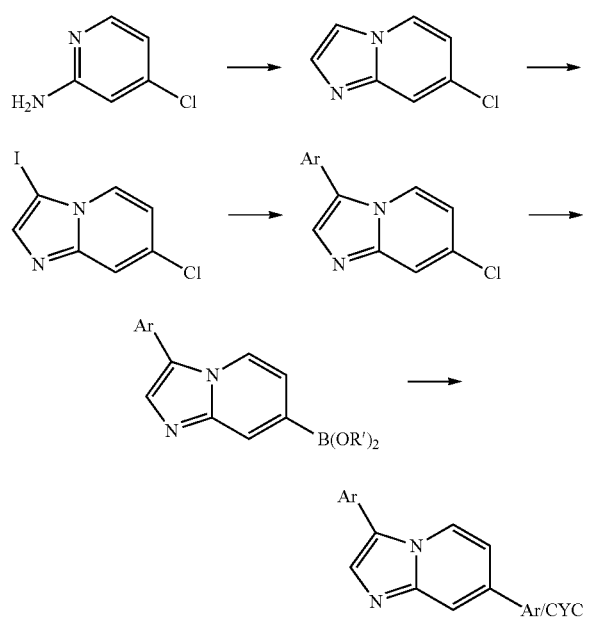

82

Procedure B1

1-[3-(7-Chloro-imidazo[1,2-a]pyridin-3-yl)-phenyl]-3-(2,2,2-trifluoro-ethyl)-urea was prepared using the methods outlined in procedure A1 to A4.

Procedure B2

Conversion of Halide to Boronate

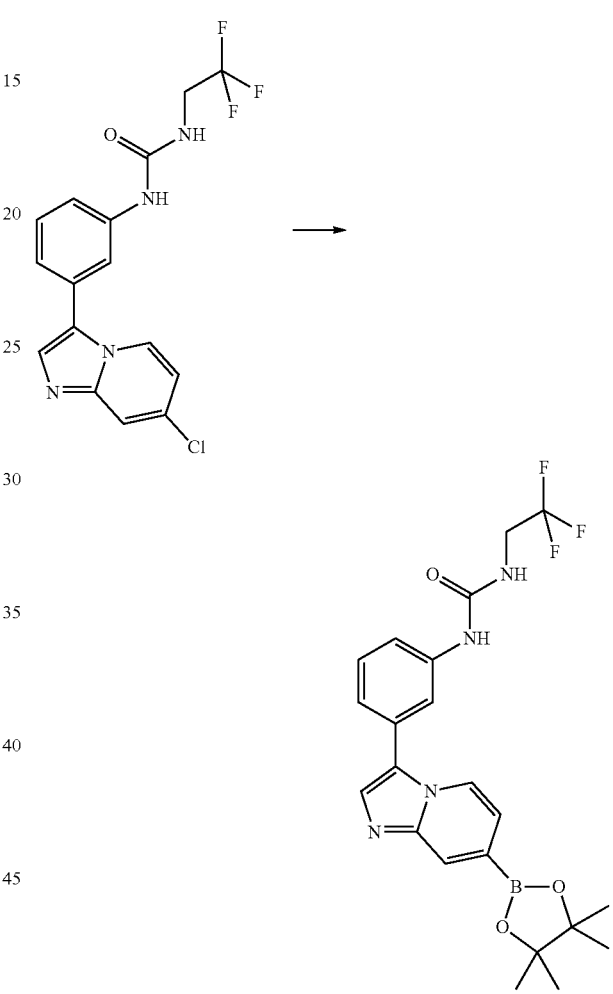

To a solution of 1-[3-(7-Chloro-imidazo[1,2-a]pyridin-3-yl)-phenyl]-3-(2,2,2-trifluoro-ethyl)-urea (10 g, 27.2 mmol) in dioxane (160 ml) was added bis(pinacolato)boron (22.8 g, 89.6 mmol), tris(dibenzylideneacetone)dipalladiumO) (3.8 g, 4.2 mmol), tricyclohexylphosphine (3.8 g, 13 mmol) and KOAc (12 g, 122.2 mmol). The reaction mixture was heated at 126° C. for 18 h before being allowed to cool and filtered through a glass microfibre filter. The filtrate was partitioned between EtOAc and H$_2$O, the organic layer separated, dried (Na$_2$SO$_4$), filtered and the solvent removed in vacuo. The residue was dissolved in a mixture EtOAc (150 ml) and petrol/ether (500 ml) and stirred at room temperature for 1 h. The resulting suspension was filtered and the resulting solid triturate with a petrol/ether and a mixture of EtOAc/petrol (8:2). This afford 1-{3-[7-(4,4,5,5-Tetramethyl-[1,3,2]dioxaborolan-2-yl)-imidazo[1,2-a]pyridin-3-yl]-phenyl}-3-(2,2, 2-trifluoro-ethyl)-urea (13.93 g) as the crude material (80% pure), which was used directly in the next step.

Procedure B3

Suzuki Coupling in the 7-Position

Procedure B3a

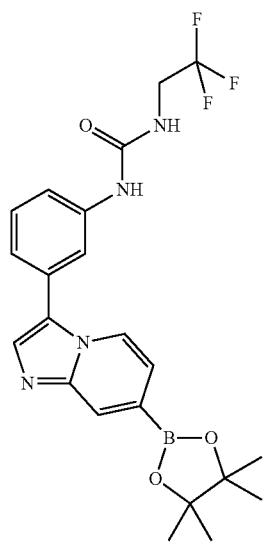

To a solution of 1-{3-[7-(4,4,5,5-Tetramethyl-[1,3,2]diox-aborolan-2-yl)imidazo[1,2-a]pyridin-3-yl]phenyl}-3-(2,2,2-trifluoroethy)urea (100 mg, 0.21 mmol) and 2-bromopyridine (31 mg, 0.21 mmol) in 1,4-dioxane (1.5 ml) and water (0.6 ml) was added $K_3PO_4$ (138 mg, 0.63 mmol), tris(dibenzylideneacetone)dipalladium (4 mg, 0.04 mmol) and 2-dicyclohexylphosphino-2',6'-dimethoxybiphenyl (4 mg, 0.01 mmol) [reaction degassed by bubbling $N_2$ through]. The mixture was heated to 80° C. for 3 h, then partitioned between water and EtOAc. The organic fraction was dried (MgSO$_4$), filtered and concentrated in vacuo and the residue purified by preparative HPLC to give the product (17 mg). MS: [M+H]$^+$=412.

Procedure B3b

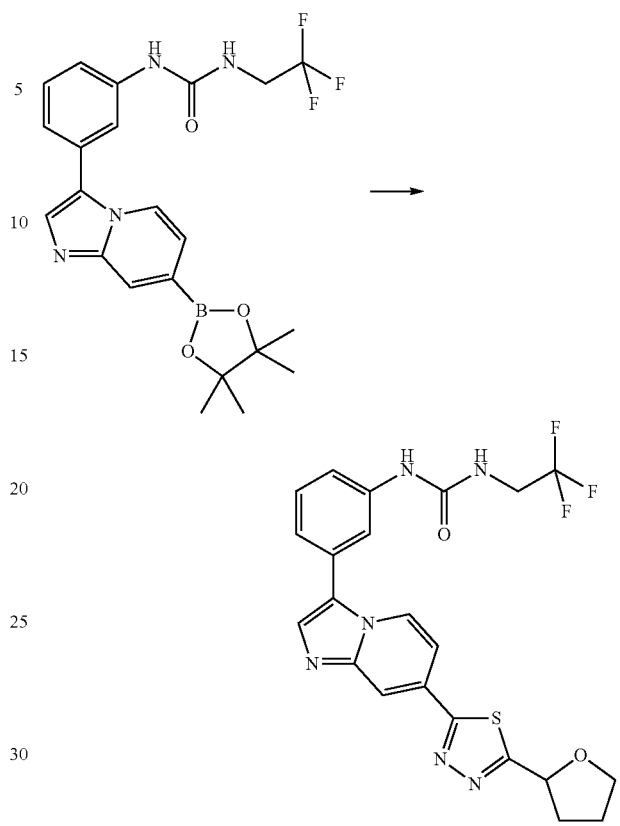

To a solution of 1-{3-[7-(4,4,5,5-tetramethyl-[1,3,2]diox-aborolan-2-yl)-imidazo[1,2-a]pyridin-3-yl]-phenyl}-3-(2,2,2-trifluoro-ethyl)-urea (200 mg, 0.43 mmol) in a mixture of toluene (3.6 ml), "butanol (3.6 ml), water (0.9 ml), cesium carbonate (424 mg, 1.3 mmol), was added 2-Bromo-5-(tetrahydro-furan-2-yl)-[1,3,4]thiadiazole (×1) (250 mg, 1.08 mmol). The reaction mixture was deoxygenated and tetrakis(triphenylphosphine)palladium (0) (70 mg, 60 µmol) added. The reaction mixture was again degassed and heated at 80° C. for 2.5 h. The mixture was cooled, partitioned between EtOAc and H$_2$O, the organic layer separated, dried (MgSO$_4$), filtered and the solvent remove in vacuo. The crude product was purified by preparative HPLC to give the mg of product. MS: [M+H]$^+$489.

Procedure B3c

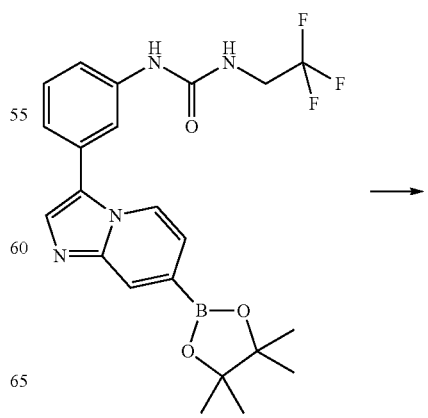

85
-continued

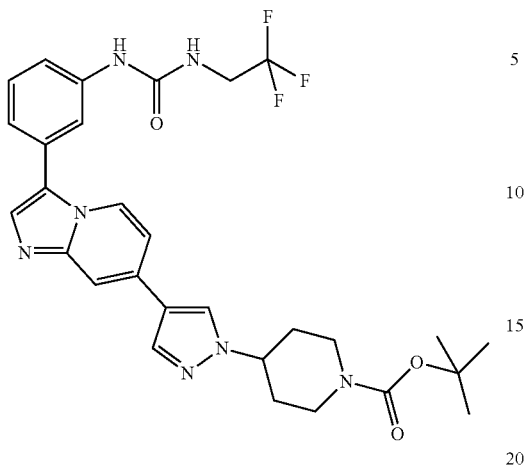

To a mixture of 1-{3-[7-(4,4,5,5-tetramethyl-[1,3,2]diox-aborolan-2-yl)-imidazo[1,2-a]pyridin-3-yl]-phenyl}-3-(2,2,2-trifluoro-ethyl)-urea (460 mg, 1.00 mmol), in a MW tube was added 4-(4-Bromo-pyrazol-1-yl)-piperidine-1-carboxylic acid tert-butyl ester (500 mg, 1.5 mmol), SPHOS (41 mg, 0.1 mmol) and $Pd_2(dba)_3$ (45 mg, 0.05 mmol) in dioxane (6 ml) followed by a 1M $K_3PO_4$ (3 ml) in water. The reaction mixture was heated in a CEM discover microwave synthesizer (300W) at 120° C. for 30 min. The mixture was allowed to cool, then partitioned between EtOAc /$H_2O$, the organic layer was separated, extracted with EtOAc (×2), dried ($Na_2SO_4$), filtered and the solvent removed in vacuo. The residue was purified by silica column chromatography running a 0-3% 2M methanolic $NH_3$/$CH_2Cl_2$ gradient. This afforded the crude product as a yellow gum (210 mg), which was used directly in the next step.

Procedure B3d

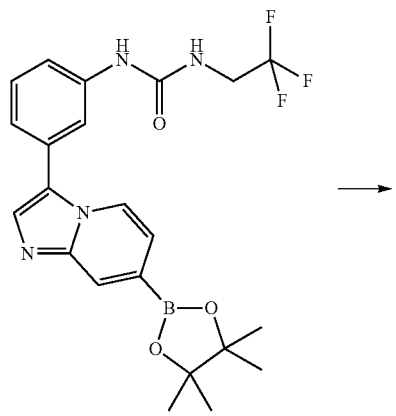

86
-continued

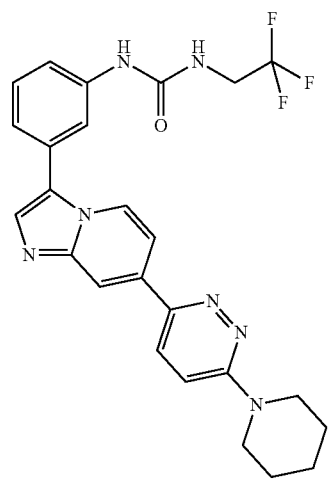

3-Chloro-6-piperidin-1-ylpyridazine (112 mg, 0.56 mmol) and 2M $Na_2CO_3$ (2.2 ml, 4.4 mmol) were added to a solution of 1-{3-[7-(4,4,5,5-tetramethyl-[1,3,2]dioxaborolan-2-yl)-imidazo[1,2-a]pyridin-3-yl]-phenyl}-3-(2,2,2-trifluoro-ethyl)-urea (200 mg, 0.43 mmol) in DME (2.5 ml) [reaction degassed by bubbling through nitrogen], followed by tetrakis (triphenylphosphine)palladium (0) (50 mg, 0.04 mmol). The reaction was heated to 90° C. for 4 h, before being partitioned between water and EtOAc. The organic fraction was dried ($MgSO_4$), filtered and concentrated in vacuo and the residue was purified by preparative HPLC to generate the product (50 mg). MS: $[M+H]^+=496$.

Procedure B3e

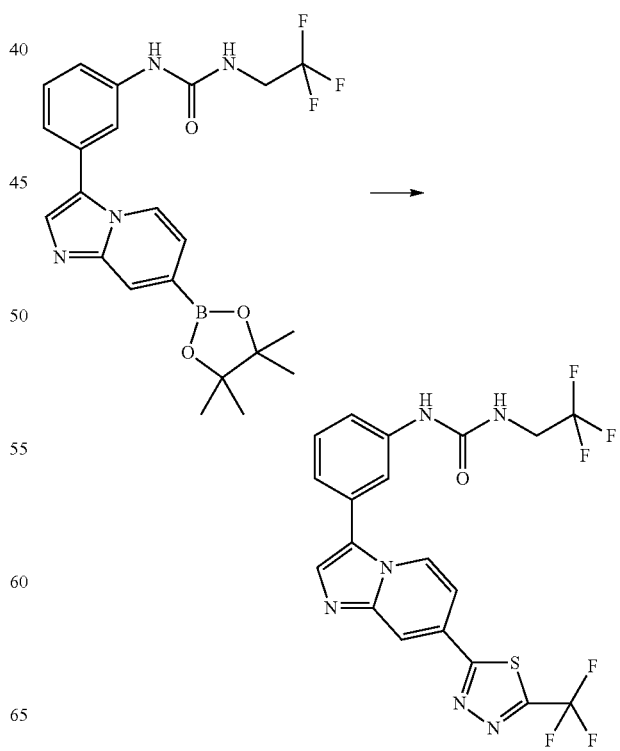

2-Chloro-5-trifluoromethyl-[1,3,4]thiadiazole (56 mg, 0.30 mmol) and 2M Na$_2$CO$_3$ (2.1 ml, 4.2 mmol) were added to a solution of 1-{3-[7-(4,4,5,5-tetramethyl-[1,3,2]dioxaborolan-2-yl)-imidazo[1,2-a]pyridin-3-yl]-phenyl}-3-(2,2,2-trifluoro-ethyl)-urea (139 mg, 0.30 mmol) in DME (5 ml) [reaction degassed by bubbling through nitrogen], 2-(Dimethylamino)ferrocen-1-yl-palladium(II) chloride dinorbornylphosphine complex (17 mg, 0.03 mmol) was added and the resulting solution was heated to 80° C. overnight. The reaction was partitioned between water and EtOAc. The organic fraction was washed with water, dried (MgSO$_4$), filtered and concentrated in vacuo. The residue was purified by preparative HPLC to give the product (12 mg). MS: [M+H]$^+$= 487.

General Route C

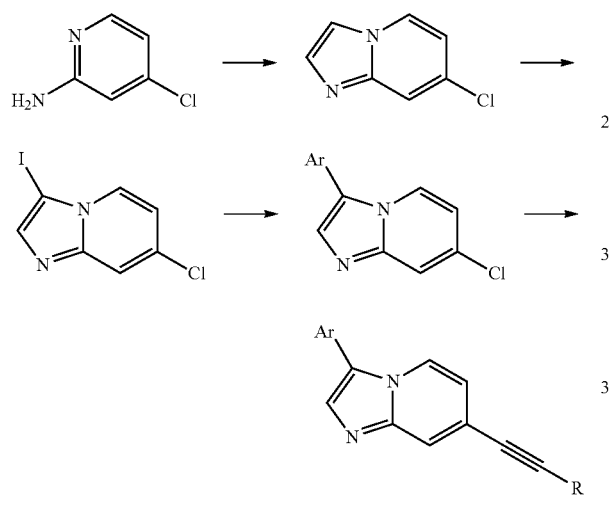

Procedure C1

1-[3-(7-Chloro-imidazo[1,2-a]pyridin-3-yl)-phenyl]-3-(2,2,2-trifluoro-ethyl)urea was prepared using the methods outlined in procedure A1 to A4.

Procedure C2

Sonagashira Reaction

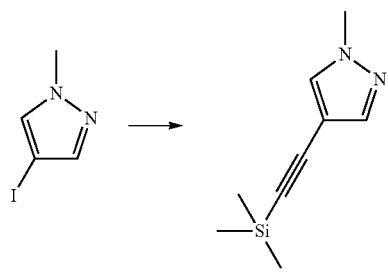

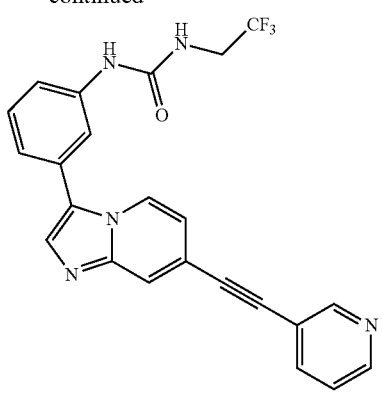

A solution of 1-[3-(7-Chloro-imidazo[1,2-a]pyridin-3-yl)-phenyl]-3-(2,2,2-trifluoro-ethyl)-urea (107 mg, 0.3 mmol) in DMSO (3 ml) was added to 3-ethynylpyridine (103 mg, 0.3 mmol), Cs$_2$CO$_3$ (104 mg, 0.3 mmol) and bis(tricyclohexylphosphino)palladium (II) chloride (6 mg, 0.009 mmol) and the resulting mixture was heated to 120° C. for 17 h. The reaction was filtered and partitioned between water and EtOAc. The organic fraction was washed with water, dried (MgSO$_4$), filtered and concentrated under reduced pressure. The residue was purified by preparative HPLC to give the product (8.5 mg). MS: [M+H]$^+$=436.

Procedure C3

Preparation of Alkyne Coupling Partner for Sonagashira Reaction

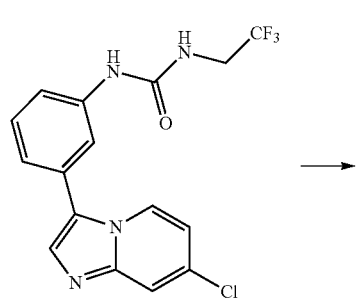

To 4-iodo-1-methyl-1H-pyrazole (1.0346 g, 4.97 mmol) in THF (20 ml) was added CuI (0.36 g, 1.89 mmol), and PdCl$_2$(PPh$_3$)$_2$. The reaction flask was purged with N$_2$ and NEt$_3$ (10.4 mL, 75 mmol) and ethynyl-trimethyl-silane (5.27 ml, 37 mmol) was added. The reaction mixture was heated at 80° C. overnight for 21 hours. After cooling to room temperature, the reaction was diluted with EtOAc and filtered. The filtrate was washed successively with 1M HCl, 1M NaOH and H$_2$O. The organic phase was dried over MgSO$_4$, filtered and concentrated in vacuo. The crude product was purified by column chromatography (20:8 v/v petroleum ether:EtOAc to give the product as a brown oil (676 mg).

Procedure C4

Removal of Trimethyl Silyl Group on Alkyne Coupling Partner

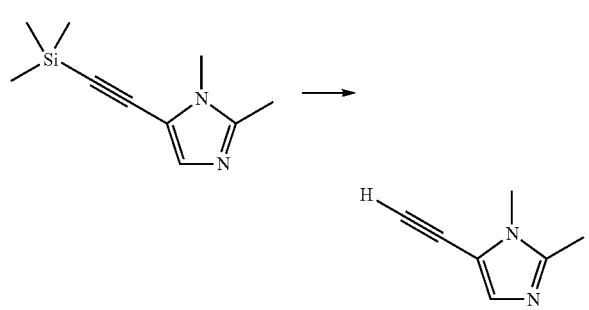

To 1,2-dimethyl-5-trimethylsilanylethynyl-1H-imidazole (137 mg, 0.71 mmol) in MeOH was added K$_2$CO$_3$ (0.049 g, 0.36 mmol) and the reaction stirred at room temperature for 3.5 hours. The mixture was cocenentrated in vacuo and EtOAc and brine added. The phases were separated and the aqueous phase re-extracted with EtOAc (×2). The combined organic phase was dried over MgSO$_4$, filtered and concentrated in vacuo to give yellow solids (87.3 mg). The product was used crude in the subsequent Sonagashira step.

General Route D

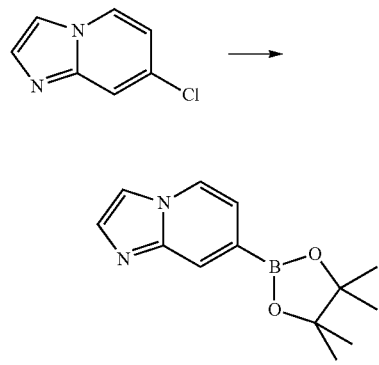

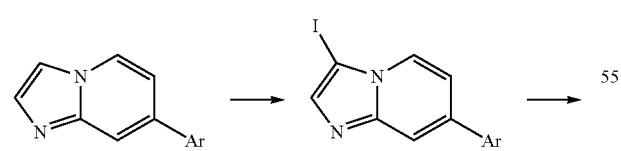

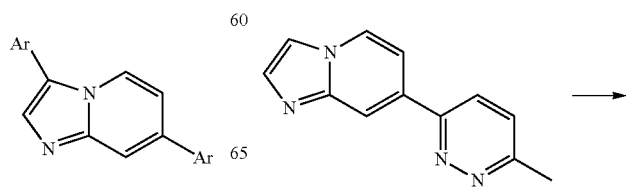

Procedure D1

Boronate Formation

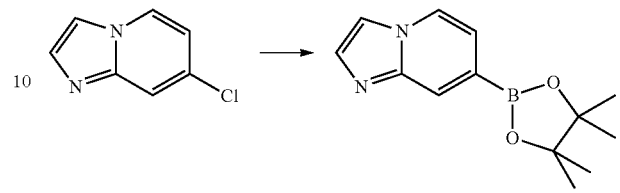

To a solution of 7-chloroimidazo-[1,2,a]pyridine (10 g, 65.5 mmol) and bis(pinocolato)diboron (20 g, 78.7 mmol) in diglyme (100 ml) were added K$_2$CO$_3$ (13.5 g, 97.7 mmol), palladium (II) acetate (730 mg, 3.25 mmol), tricyclohexylphosphine (1.8 g, 6.42 mmol) and water (0.14 ml). The resulting mixture was heated at 100° C. overnight under an inert atmosphere, diluted with water (50 ml) and stirred for 1 h at room temperature. The precipitate was separated by filtration, washed with diglyme/water (2/1, ml) and water (20 ml) then dried to generate the product (7.58 g) as a grey powder.

MS: [M+H]$^+$=246.

Procedure D2

Suzuki Coupling

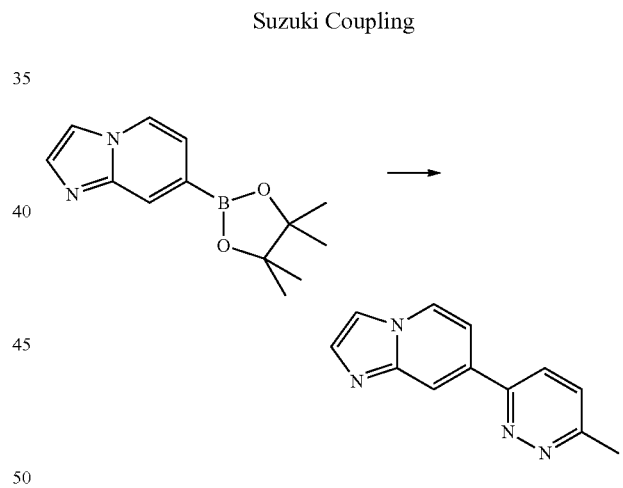

Method as described in General Route B Procedure B3b

Procedure D3

Iodination

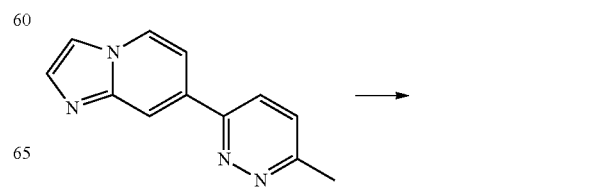

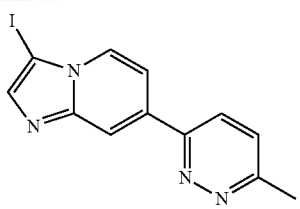

Method as described in General Route A Procedure A2.

Procedure D4

1-[5-(4,4,5,5-Tetramethyl-[1,3,2]dioxaborolan-2-yl)-pyridin-3-yl]-3-(2,2,2-trifluoro-ethyl)-urea

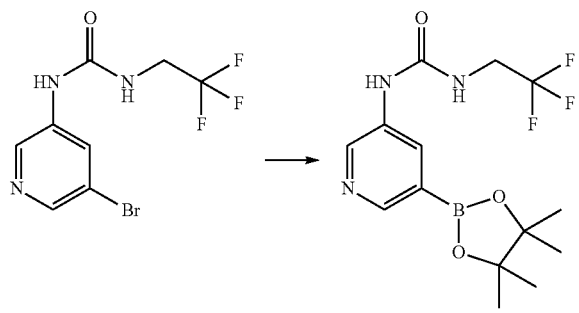 [SMILES: O=C(NCC(F)(F)F)Nc1cncc(Br)c1 ; CC1(C)OB(c2cncc(NC(=O)NCC(F)(F)F)c2)OC1(C)C]

To 1-(5-bromo-pyridin-3-yl)-3-(2,2,2-trifluoro-ethyl)urea (0.51 g, 1.72 mmol) in anhydrous DMSO (3 mL) was added bis(pinacolato)diboron (0.88 g, 3.45 mmol). The reaction flask was purged with $N_2$ and $PdCl_2dppf$ (40 mg, 0.05 mmol) added. The flask was further purged with $N_2$ and the reaction then heated at 100° C. for 22 hours. After cooling to room temperature, $H_2O$ (30 mL) and EtOAc (30 mL) were added and the two phases separated. The organic phase was further washed with $H_2O$ (2×35 mL). The organic phase was dried over $MgSO_4$, filtered and concentrated in vacuo and used crude in the subsequent reaction.

Procedure D5

Suzuki Coupling

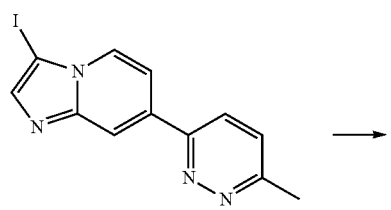

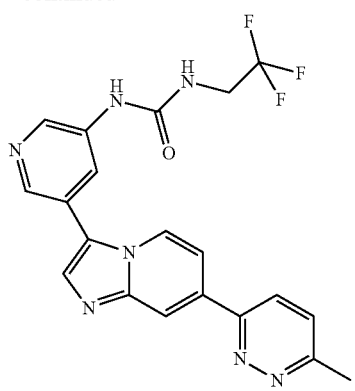

3-Iodo-7-(6-methylpyridazine-3-yl)imidazo-[1,2,a]pyridine (70 mg, 0.21 mmol), 1-[5-(4,4,5,5-Tetramethyl-[1,3,2]dioxaborolan-2-yl)-pyridin-3-yl]-3-(2,2,2-trifluoro-ethyl)-urea (73 mg, 0.25 mmol), $K_3PO_4$ (140 mg, 0.66 mmol) and tetrakis(triphenylphosphine)palladium (0) (12 mg, 0.01 mmol) were dissolved in DME (2 ml) and water (2 ml) [reaction degassed by bubbling $N_2$ through]. The resulting mixture was heated to 80° C. overnight, then allowed to cool. DCM and MeOH were added and the resulting suspension was filtered. The liquor was concentrated under reduced pressure and the residue purified by column chromatography (0-25% MeOH/DCM) to give the product (35 mg) as a yellow solid. MS:

[M+H]$^+$=428.

General Route E

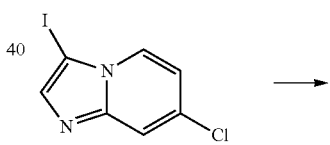

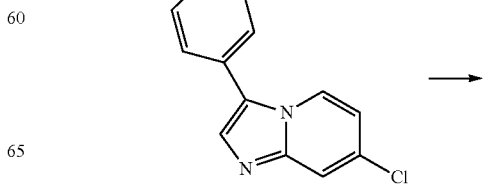

-continued

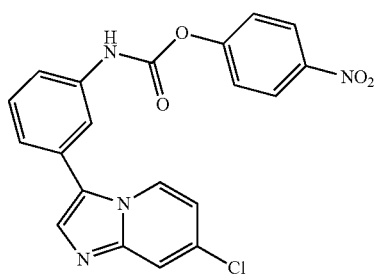

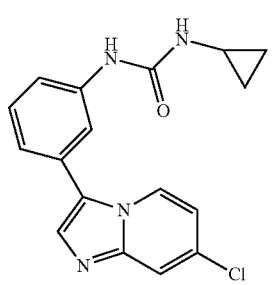

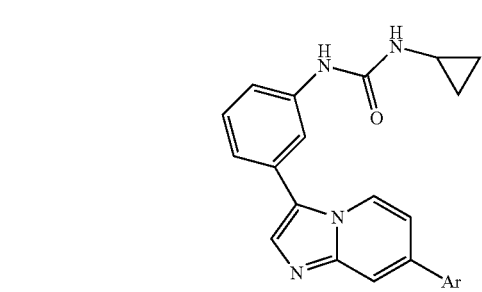

Procedure E1—Suzuki Coupling

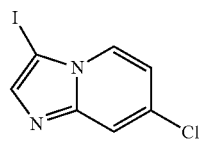 → 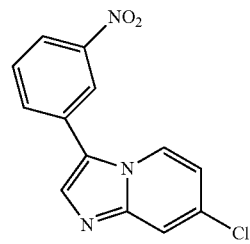

7-Chloro-3-iodoimidazo-[1,2,a]pyridine was coupled with 3-nitrophenyl boronic acid using the method described in Procedure B3b to synthesise 7-Chloro-3-(3-nitro-phenyl)-1,7-imidazo[1,2-a]pyridine. MS: [M+H]$^+$=274.

1H NMR (400 MHz, DMSO-d6): 8.68 (1H, d), 8.47 (1H, t), 8.28 (1H, dd), 8.15 (1H, d), 7.99 (1H, s), 7.89 (1H, d), 7.84 (1H, t), 7.09 (1H, dd)

Procedure E2

Nitro Reduction

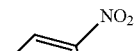 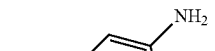

To a solution of 7-chloro-3-(3-nitrophenyl)imidazo-[1,2,a]pyridine (0.5 g, 1.83 mmol) in dioxane (10 ml) and water (2 ml) was added iron powder (0.97 g, 18.3 mmol) and iron sulphate heptahydrate (2.05 g, 7.31 mmol). The resulting solution was heated to reflux for 3 h, cooled, filtered through celite and concentrated under reduced pressure. The residue was partitioned between DCM and brine and the organic fraction was dried (Na$_2$SO$_4$), filtered and concentrated in vacuo to give the product (400 mg), which was used without further purification. MS: [M+H]$^+$=244.

Procedure E3

Carbamate Formation

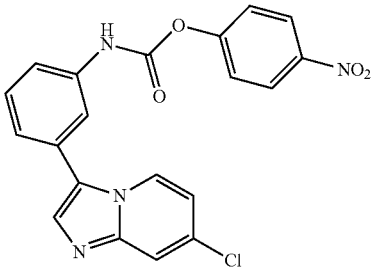

A solution of 7-chloro-3-(3-aminophenyl)imidazo-[1,2,a]pyridine (400 mg, 1.64 mmol) and 4-nitrophenyl chloroformate (330 mg, 1.64 mg) in THF (20 ml) was heated to 60° C. for 2 h, then stirred at room temperature overnight. The resulting precipitate was separated by filtration, washed with THF and dried to give the product (585 mg), which was used without further purification. MS: [M+H]$^+$=409.

Procedure E4

Urea Formation

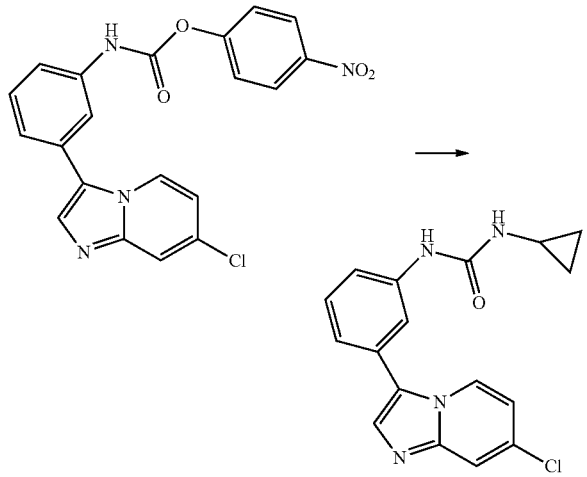

To a solution of [3-(7-Chloro-imidazo[1,2-a]pyridin-3-yl)-phenyl]-carbamic acid 4-nitro-phenyl ester (200 mg, 0.49 ml) in THF (10 ml) was added cyclopropylamine (0.04 ml, 0.54 mmol) and triethylamine ((0.08 ml, 0.54 ml) and the resulting mixture was stirred at room temperature overnight. The reaction was diluted with DCM and 2M NaOH and the layers separated. The organic fraction was dried (Na$_2$SO$_4$), filtered and concentrated under reduced pressure. The residue was purified by column chromatography (0-100% EtOAc/Petrol) to give the product (115 mg). MS: [M+H]$^+$=327.

Procedure E5

Suzuki Coupling

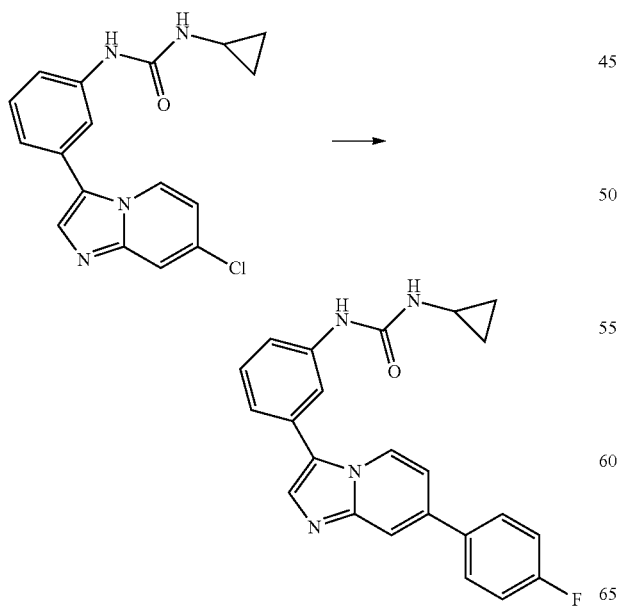

1-[3-(7-Chloroimidazo[1,2-a]pyridin-3-yl)-phenyl]-3-cyclopropylurea was reacted with 4-fluorophenyl boronic acid using the method described in Procedure B3c. MS: [M+H]$^+$= 387.

General Route F

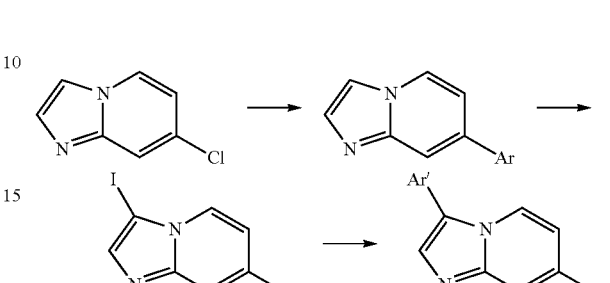

Procedure F1

Suzuki Coupling

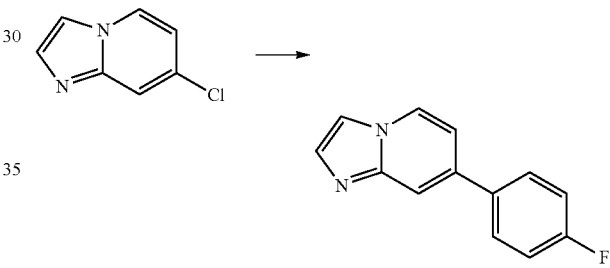

7-Chloroimidazo-[1,2,a]pyridine was coupled with 4-fluorophenylboronic acid according to the method in Procedure B3d.

Procedure F2

Iodination

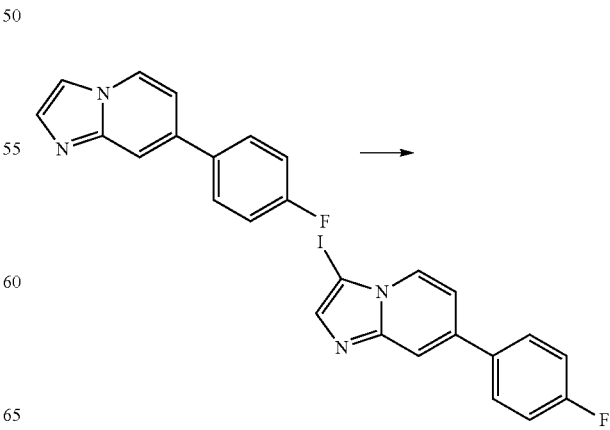

Iodination was performed according to the method in Procedure A2

Procedure G

Reduction of Alkynes to Alkanes 1-(3-{7-[2-(3-Methyl-3H-imidazol-4-yl)-ethyl]-imidazol[1,2-a]pyridin-3-yl}-phenyl)-3-(2,2,2-trifluoro-ethyl)-urea

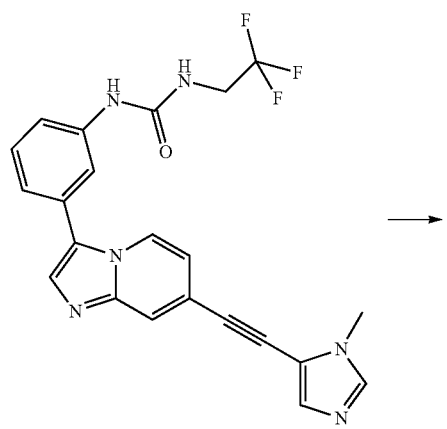

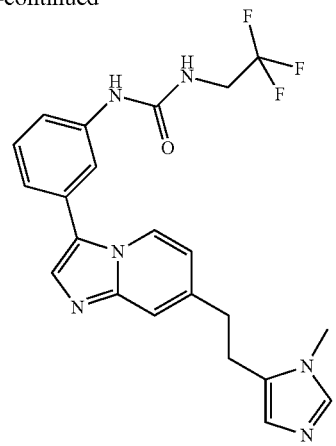

To an evacuated flask back-filled with $N_2$ containing 1-{3-[7-(3-methyl-3H-imidazol-4-ylethynyl)-imidazo[1,2-a]pyridin-3-yl]-phenyl}-3-(2,2,2-trifluoro-ethyl)-urea (65.7 mg, 0.15 mmol) in MeOH was added Pd (10 wt % on activated carbon) (25.5 mg). The flask was filled with $H_2$ and the reaction stirred for a total of 7.5 hours. The reaction was filtered and the filtrate concentrated in vacuo. The crude product was purified by preparative HPLC to give pure product (6.1 mg). MS: [M+H]$^+$443.

General Route H

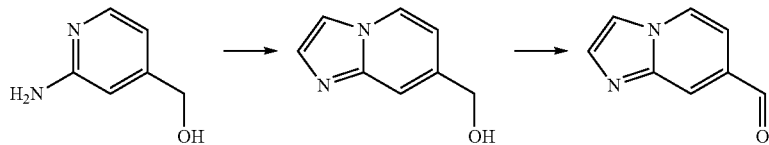

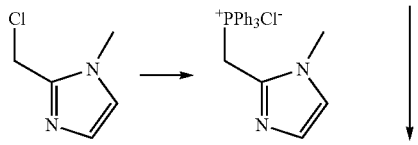

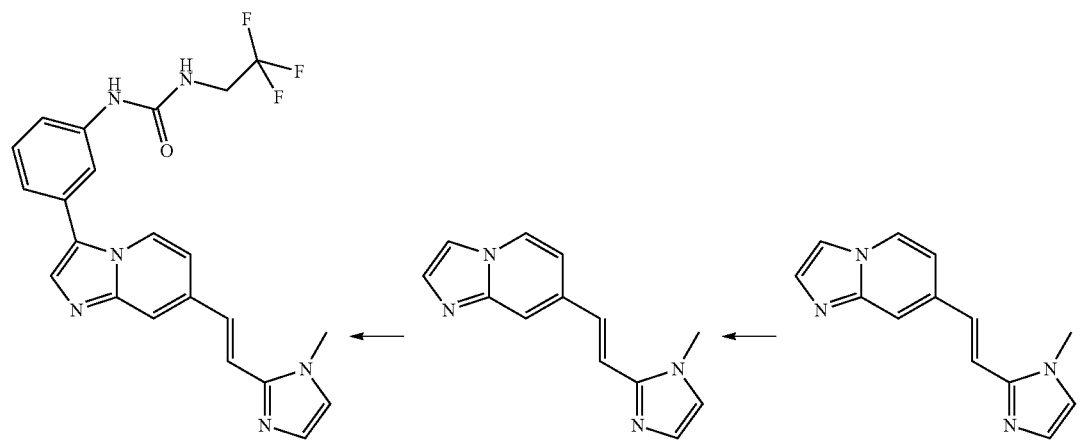

Procedure H1

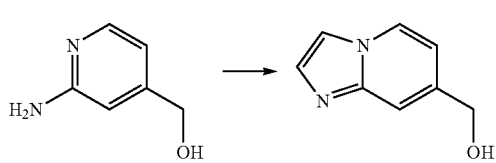 [SMILES: Nc1cc(CO)ccn1 ; OCc1ccn2ccnc2c1]

Imidazo[1,2-a]pyridin-7-yl-methanol was prepared as Procedure A1 using (2-Amino-pyridin-4-yl)-methanol. MS: [M+H]+419

Procedure H2

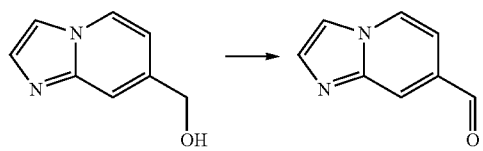 [SMILES: OCc1ccn2ccnc2c1 ; O=Cc1ccn2ccnc2c1]

To imidazo[1,2-a]pyridin-7-yl-methanol (100 mg, 0.7 mmol) suspended in chloroform (5 ml) at room temperature was added 1,1,1-tris(acetyloxy)-1,1-dihydro-1,2-benziodoxol-3-(1H)-one (Dess-Martin periodinane, 0.373 g, 0.9 mmol, 1.3 equiv). This mixture was stirred at room temperature overnight and then dilute sodium hydroxide solution was added and the mixture was stirred for 60 minutes. The mixture was then extracted with dichloromethane and the organic liquors were concentrated in vacuo to furnish imidazo[1,2-a]pyridine-7-carbaldehyde (90 mg) as a white solid. $^1$H NMR (400 MHz, DMSO-d6): 10.00 (1H, s), 8.67 (1H, d), 8.33 (1H, s), 8.20 (1H, s), 7.86 (1H, d), 7.25 (1H, dd).

Procedure H3

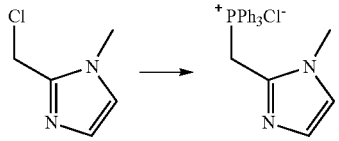

A mixture of 2-chloromethyl-1-methyl-1H-imidazole (200 mg, 1.5 mmol) and triphenylphosphine (402 mg, 1.0 mmol, 1 equiv) in acetonitrile (5 ml) was heated to 80 deg C. overnight. The reaction was then allowed to cool to room temperature and the solid was isolated by vacuum filtration to afford 2-triphenylphosphonium-1-methyl-1H-imidazole chloride (458 mg) as a white solid. MS: [M+H]+357

Procedure H4

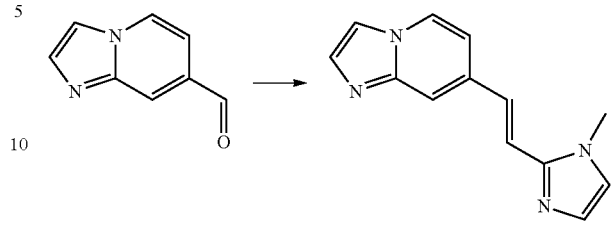

To a stirred solution of 2-triphenylphosphonium-1-methyl-1H-imidazole chloride (656 mg, 1.6 mmol, 1 equiv) in tetrahydrofuran (5 ml) at room temperature was added dropwise a solution of potassium tert-butoxide in tetrahydrofuran (1M, 3.3 ml, 3.3 mmol, 2 equiv). This brightly orange mixture was stirred thus for 2 hours and then a solution of imidazo[1,2-a] pyridine-7-carbaldehyde (245 mg, 1.7 mmol, 1 equiv) in tetrahydrofuran (8 ml) was added and the lightly coloured mixture was stirred at room temperature overnight. To the reaction was added water and the mixture was extracted with ethyl acetate. The organic liquors were washed with water and brine and then dried (MgSO$_4$) and concentrated in vacuo. The residue was purified by column chromatography (0-20% methanol/ethyl acetate) furnishing 7-[(E)-2-(1-methyl-1H-imidazol-2-yl)-vinyl]-imidazo[1,2-a]pyridine (87 mg). MS: [M+H]+225

Procedure H5

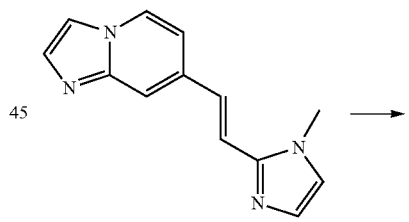

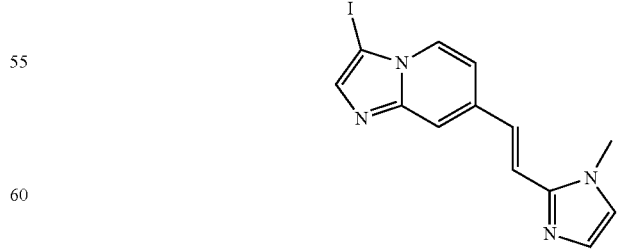

7-[(E)-2-(1-methyl-1H-imidazol-2-yl)-vinyl]imidazo[1,2-a]pyridine was iodinated as Procedure A2 to furnish the desired iodide as a yellow solid. MS: [M+H]+351

Procedure H6

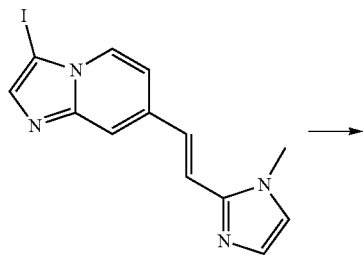

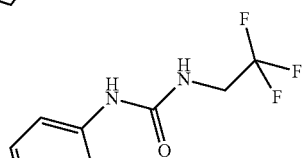

1-(3-{7-[(E)-2-(1-Methyl-1H-imidazol-2-yl)-vinyl]imidazo[1,2-a]pyridin-3-yl}-phenyl)-3-(2,2,2-trifluoro-ethyl)-urea (86 mg) was prepared according to Procedure B3d using 3-Iodo-7-[(E)-2-(1-methyl-1H-imidazol-2-yl)-vinyl]imidazo[1,2-a]pyridine (170 mg, 0.49 mmol) and 1-[3-(4,4,5,5-tetramethyl-[1,3,2]dioxaborolan-2-yl)-phenyl]-3-(2,2,2-trifluoro-ethyl)-urea. $^1$H NMR (400 MHz, Me-d$_3$-OD): 8.74 (1H, d), 8.01 (3H, d), 7.77-7.66 (2H, m), 7.64-7.50 (4H, m), 7.45-7.32 (2H, m), 4.04 (3H, s), 4.01-3.89 (2H, m). MS: [M+H]$^+$441

Procedure G

Synthesis of Additional Monomers

Synthesis of (E)-3-Imidazo[1,2-a]pyridin-7-yl-prop-2-en-1-ol

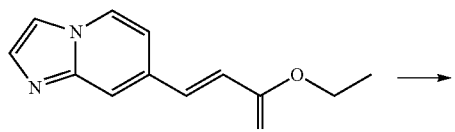

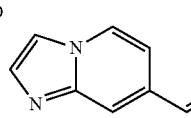

(E)-3-Imidazo[1,2-a]pyridin-7-yl-acrylic acid ethyl ester (prepared according to Procedure H1 to H4 using triethylphosphono acetate, 519 mg, 2.4 mmol) was dissolved in a mixture of toluene/dichloromethane (1:1, 12 ml) and cooled on a dry ice/acetone bath. Diisobutylaluminium hydride (1 M in toluene, 3 ml) was added dropwise. After 45 minutes the reaction was transferred to a salt/ice bath and further portions of DIBAL were added until the reaction was complete. The reaction was quenched by the cautious addition of methanol and was allowed to warm to room temperature. The reaction was concentrated in vacuo and 2N sodium hydroxide solution was added. This was extracted twice with dichloromethane and the combined liquors were dried and concentrated to furnish the desired monomer (327 mg) as a yellow solid MS: [M+H]$^+$=175

Section X

Preparation of Haloaromatic Coupling Partners

X1

Preparation of 2-Bromo-5-(tetrahydro-furan-2-yl)-[1,3,4]thiadiazole

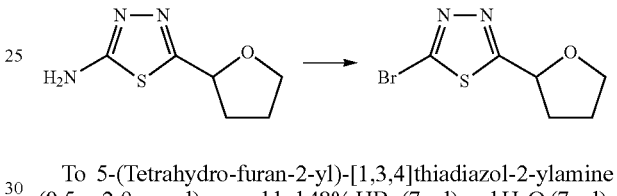

To 5-(Tetrahydro-furan-2-yl)-[1,3,4]thiadiazol-2-ylamine (0.5 g, 2.9 mmol) was added 48% HBr (7 ml) and H$_2$O (7 ml). The reaction mixture was cooled to 0° C. using an icebath. Cu(I)Br (0.42 g, 2.9 mmol) was added, followed by a the dropwise addition of solution of NaNO$_2$ (0.48 g, 10 mmol) in H$_2$O (18 ml). The reaction mixture was stirred for a further 10 mins at 0° C. then allowed to warm up to room temperature over a 35 min period. A solution of saturated bicarbonated was added to the reaction mixture until the pH=6, then extracted with EtOAc, dried (MgSO$_4$), filtered and the solvent removed in vacuo to afford the product (0.5 g, 2.1 mmol). MS: [M+H]$^+$235, 237.

X2

Preparation of 4-(4-Bromo-pyrazol-1-yl)-piperidine-1-carboxylic acid tert-butyl ester

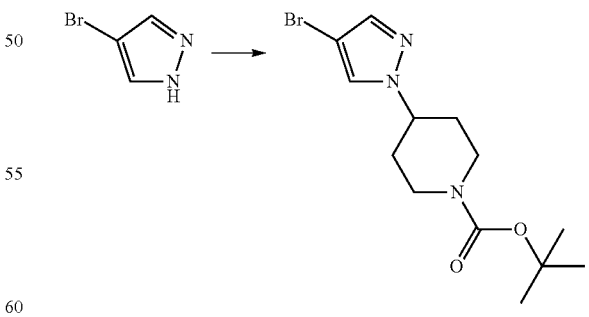

Sodium hydride (400 mg, 60% dispersion, 10 mmol) was added to a stirred solution of the bromopyrazole (1.47 g, 10 mmol) and 4-Methanesulfonyloxy-piperidine-1-carboxylic acid tert-butyl ester (2.4 g, 8.6 mmol) in dry DMF (10 ml) at room temperature. After gas evolution had ceased, the reaction was stirred and heated at 110° C. under N$_2$ for 4 h. The reaction mixture was allowed to cool to room temperature and stand at for 18 h before being partitioned between EtOAc and H₂O. The organic layer was separated, washed with water H₂O (×2), brine (×1), then dried (Na₂SO₄), filtered and the solvent removed in vacuo. The residue was purified using silica column chromatography running a 10-25% EtOAc/petrol gradient to give a colourless oil (1.7 g, 5.15 mmol). 1H NMR (400 MHz, CDCl3): 7.48 (1H, s), 7.45 (1H, s), 4.45-4.07 (3H, m), 2.90 (2H, t), 2.12 (2H, d), 1.97-1.79 (2H, m), 1.50 (9H, s).

X3

Preparation of 4-(4-Bromo-pyrazol-1-yl)-1-methyl-piperidine

Step 1:

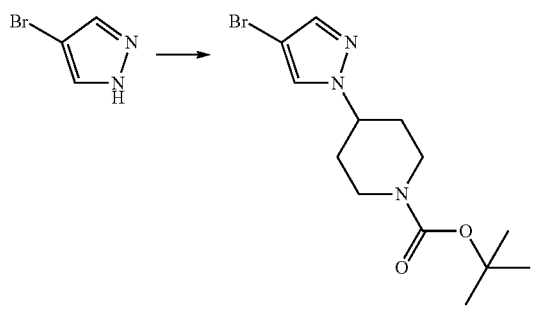 [SMILES: Brc1cn[nH]c1 ; CC(C)(C)OC(=O)N1CCC(n2cc(Br)cn2)CC1]

Prepared using procedure X2.
Step 2:

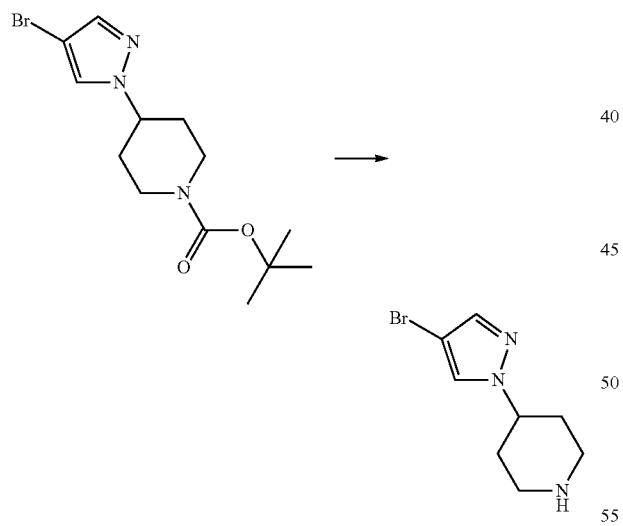

To a stirred solution of 4-(4-Bromo-pyrazol-1-yl)-piperidine-1-carboxylic acid tert-butyl ester (1.2 g, 3.6 mmol) in CH₂Cl₂ (4 ml) was added TFA (2 ml) and the reaction mixture stirred at room temperature for 2 h. The volatiles were removed in vacuo and the residue partitioned between CH₂Cl₂/NaHCO₃(aq). The aqueous layer was extracted with CH₂Cl₂ (×3), and the organic fractions combined, dried (using a phase separating cartridge) and the solvent removed in vacuo to give a solid. (0.49 g). ¹H NMR (400 MHz, CDCl3): 7.48 (1H, s), 7.46 (1H, s), 4.29-4.15 (1H, m), 3.27 (2H, d), 2.99-2.75 (2H, m), 2.16 (2H, d), 2.05-1.81 (2H, m).

Step 3:

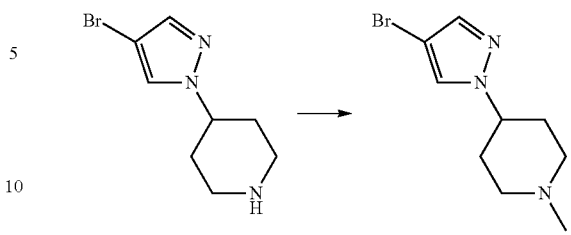

To a solution of 4-(4-bromopyrazol-1-yl)piperidine (480 mg, 2.09 mmol) and triethylamine (0.295 ml, 2.1 mmol) in DMF (4 ml) was added methyl iodide (2.1 ml of a 1.0M solution in DMF, 2.1 mmol) under an inert atmosphere. The reaction was stirred at room temperature overnight, then partitioned between water and EtOAc. The organic layer was washed with brine, dried over MgSO₄, filtered and concentrated under reduced pressure to give the product (260 mg), which was used without further purification. ¹H NMR (400 MHz, CDCl₃): 7.47 (1H, s), 7.45 (1H, s), 4.16-4.04 (1H, m), 3.09-2.92 (2H, m), 2.34 (3H, s), 2.30-2.10 (4H, m), 2.10-1.96 (2H, m).

X4

Preparation of 2-Chloro-5,6-dihydro-4H-cyclopentathiazole

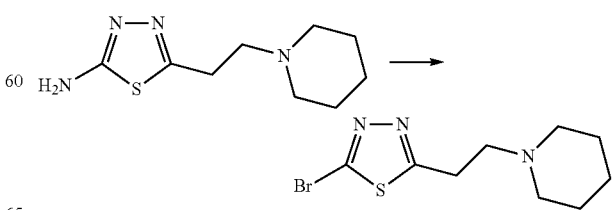

2-Amino-5,6-dihydro-4H-cyclopentathiazole (230 mg, 1.64 mmol) was added to a solution of cupric chloride (260 mg, 1.97 mmol) and tert-butylnitrite (0.3 ml, 2.46 mmol) in MeCN (0.5 ml) and the resulting mixture was stirred for 2 h at room temperature, then at 65° C. for 1 h. The reaction was filtered and the filtrate partitioned between water and EtOAc. The organic fraction was dried (MgSO₄), filtered and concentrated under reduced pressure to give the chloride (140 mg), which was used without further purification. MS: [M+H]⁺=160.

X5

Preparation of 1-[2-(5-Bromo-[1,3,4]thiadiazol-2-yl)ethyl]piperidine

Prepared using the method described in procedure X1

X6

Preparation of 4-Bromo-1-(1-methylpiperidin-3-yl)-1H-pyrazole

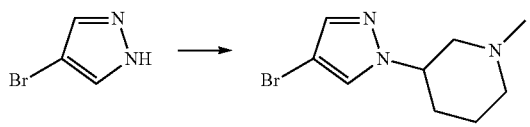

DIAD (3.21 ml, 16.3 ml) was added dropwise to a solution of 4-bromopyrazole (2.0 g, 13.6 mmol), 3-hydroxy-1-methylpiperidine (1.57 ml, 13.6 ml) and triphenylphosphine (4.3 g, 16.3 mmol) in THF (50 ml) at 0° C. The mixture was allowed to warm to room temperature and stirred overnight. The reaction was partitioned between water and ethyl acetate and the organic layers were extracted into 2N HCl. The aqueous fraction was basified with sodium bicarbonate and extracted into ethyl acetate. The organic fractions were dried (MgSO$_4$), filtered and concentrated under reduced pressure to give the product (1.64 g), which was used without purification. MS: [M+H]$^+$=244.

X7

Preparation of 4-Bromo-1-(1-tert-butoxycarbonylpiperidin-3-yl)-1H-pyrazole

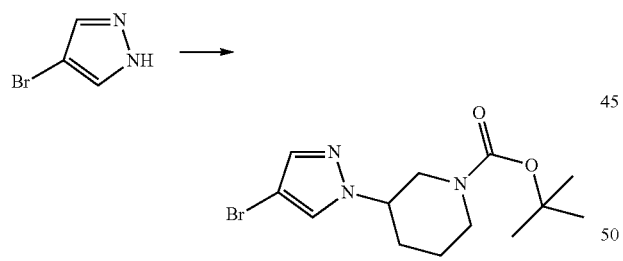

DIAD (1.18 ml, 6.0 ml) was added dropwise to a solution of 4-bromopyrazole (0.74 g, 5.0 mmol), 3-hydroxy-1-tert-butoxycarbonylpiperidine (1.00 g, 5.0 mmol) and triphenylphosphine (1.57 g, 6.0 mmol) in THF (50 ml) at 0° C. The mixture was allowed to warm to room temperature and stirred overnight. The reaction was partitioned between water and ethyl acetate. The organic fractions were washed with water and brine, dried (MgSO$_4$), filtered and concentrated under reduced pressure. The residue was purified by column chromatography (50% EtOAc/Petrol) to give the product (1.46 g). MS: [M+H]$^+$=332.

X8

Preparation of 4-Bromo-1-(1-ethylpyrrolidin-3-yl)-1H-pyrazole

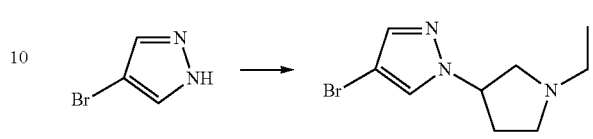

Prepared as described in X3, using N-tert-butoxycarbonylpyrrolidine-3-methanesulfonate in step 1 and ethyl iodide in step 3.

X9

Preparation of 4-Bromo-1-(1-tert-butoxycarbonylpyrrolidin-3-yl)-1H-pyrazole

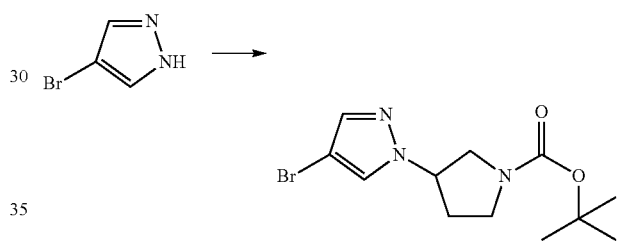

Prepared as described in X3, using N-tert-butoxycarbonylpyrrolidine-3-methanesulfonate in step 1 and missing out step 3.

X10

Preparation of 4-Bromo-1-(tetrahydrofuran-3-yl)-1H-pyrazole

Step 1:

To a solution of 3-hydroxytetrahydrofuran (1.83 ml, 23 mmol) in DCM (35 ml) at 0° C. was added triethylamine (5.06 ml, 36 mmol) followed by methanesulfonyl chloride (2.64 ml, 34 mmol). The reaction was allowed to warm to room temperature and stirred for 3 h. DCM (30 ml) and water (30 ml) were added. The layers were separated and the aqueous fraction was further extracted with DCM. The combined organic fractions were dried (MgSO$_4$), filtered and concentrated in vacuo to give the product (4.54 g) as a pale yellow oil, which was used without further purification.

Step 2:

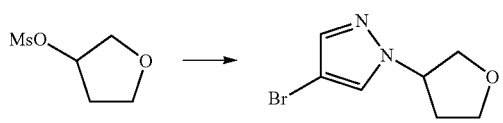 [SMILES: CS(=O)(=O)OC1CCOC1 ; Brc1cnn(C2CCOC2)c1]

Prepared using the method described in X3 Step 1.

X11

Preparation of
4-Bromo-1-(1-isopropylpiperidin-4-yl)-1H-pyrazole

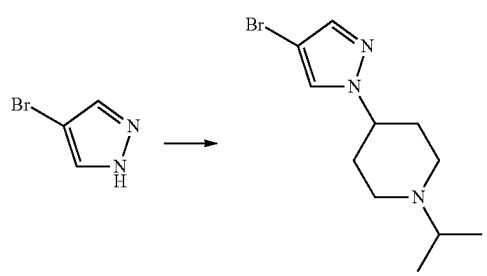

Prepared as described in X3, using 2-iodopropane in Step 3.

X12

Preparation of 1-[4-(4-Bromo-pyrazol-1-yl)-piperidin-1-yl]-ethanone

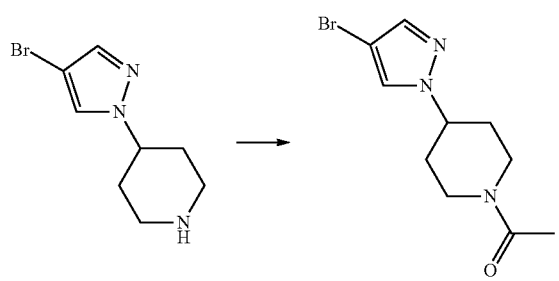

To a solution of 4-(4-bromopyrazol-1-yl)piperidine hydrochloride (300 mg, 1.13 mmol) in pyridine (3 ml) was added acetic anhydride (0.107 ml, 1.13 mmol) under an inert atmosphere. The reaction was stirred at 40° C., until reaction complete then evaporated under reduced pressure and re-evaporated with toluene twice, then partitioned between water and EtOAc. The organic layer was washed with brine, dried over MgSO₄, filtered and concentrated under reduced pressure to give the product (250 mg), which was used without further purification MS: [M+H]⁺=272

X13

Preparation of 4-(4-Bromo-pyrazol-1-yl)-1-methane-sulfonyl-piperidine

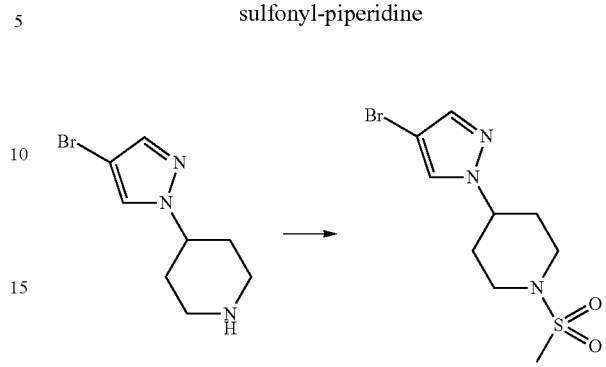

To a solution of 4-(4-bromopyrazol-1-yl)piperidine hydrochloride (380 mg, 1.43 mmol) in CH3CN (10 ml) at 0° C. was added DIPEA (0.75 mlml, 4.3 mmol) followed by methane-sulphonyl chloride (0.11 ml, 1.43 mmol), stirred at 0° C. for 1 hour then allowed to warm up to RT over 1 hour. The reaction then partitioned between water and EtOAc. The organic layer was washed with brine, dried over MgSO₄, filtered and concentrated under reduced pressure to give the product (380 mg), which was used without further purification 1H NMR (400 MHz, Me-d3-OD): 7.84 (1H, s), 7.50 (1H, s), 4.40-4.27 (1H, m), 3.86 (2H, d), 3.05-2.93 (2H, m), 2.90 (3H, s), 2.25-2.01 (4H, m).

X14

2-(6-chloro-pyridin-3-yl)-ethanol

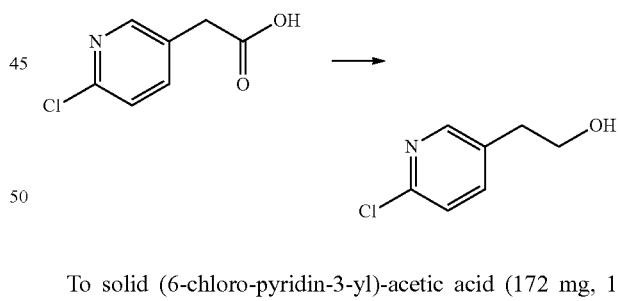

To solid (6-chloro-pyridin-3-yl)-acetic acid (172 mg, 1 mmol) was added borane in THF (1M, 5 ml) and the reaction was stirred at room temperature. After 2 hours, the reaction was heated to 50 degC for 90 minutes. Aqueous hydrochloric acid (2N, 8 ml) was added to the reaction and it was allowed to cool to room temperature. After 10 minutes the reaction was basified with saturated aqueous sodium bicarbonate and extracted into ethyl acetate. The organic liquors were washed with water (×2) and brine, dried (MgSO₄) and concentrated to furnish the crude product as a yellow oil (126 mg). This material was used as such in the coupling reaction. MS: [M+H]⁺158.

X15

Synthesis of (2-Chloro-5-fluoro-pyrimidin-4-yl)-cyclopropyl-amine

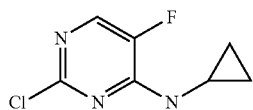 [SMILES: Fc1cnc(Cl)nc1NC1CC1]

To 2,4 dichloro-5-fluoropyridine (1 g, 6 mmol) dissolved in CH$_3$CN (8 ml) cooled in an ice bath was added Et$_3$N (1.16 ml, 8.4 mmol) and cyclopropylamine (0.29 ml, 8.4 mmol) in CH$_3$CN (2 ml). Reaction stirred 0° C. for 2 hours, evaporated water added and reaction extracted with EtOAc (×3). The organic fractions were combined washed with brine, dried over MgSO$_4$, filtered and concentrated under reduced pressure to give the product (0.92 g).

MS: [M+H]$^+$=188

X16

Synthesis of (2-Chloro-5-fluoro-pyrimidin-4-yl)-ethyl-amine

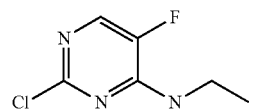

Same procedure as X15 using ethylamine

X17

Synthesis of 2-(2-Chloro-5-fluoro-pyrimidin-4-ylamino)-ethyl-carbamic acid tert-butyl ester

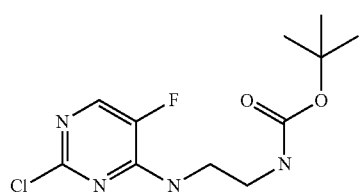 [SMILES: CC(C)(C)OC(=O)NCCNc1nc(Cl)ncc1F]

Same procedure as X15 using tert-butyl N-(2-aminoethyl) carbamate

X18

Synthesis of 4-Chloro-2-methyl-6-{4-[2-(tetrahydro-pyran-2-yloxy)-ethyl]-piperazin-1-yl}-pyrimidine

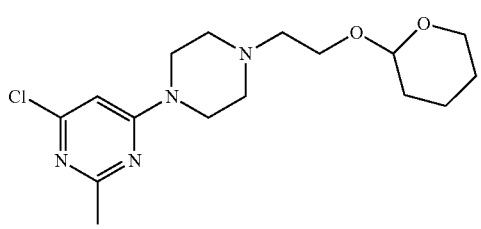 [SMILES: Cc1nc(Cl)cc(N2CCN(CCOC3CCCCO3)CC2)n1]

To tert-butyl 4-(6-chloro-2-methyl-4-pyrimidinyl)tetrohydro-1(2H)-pyrazinecarboxylate (0.5 g, 1.6 mmol) was added saturated HCl in EtOAc, reaction stirred RT for 3 hours then evaporated, re-evaporated with toluene (2×) to give the product (0.34 g). To crude product in a mix of acetone/DMF (20 ml) was added 2-(2-bromoethoxy)tetrahydro-2H-pyran (0.4 g, 1.9 mmol) and K$_2$CO$_3$ (0.4 g, 2.9 mmol) and heated at 60° C. for 1 hour, little reaction therefore further pyran (0.3 g) and K$_2$CO$_3$ (0.4 g) added heated O/N. The mixture was partitioned between EtOAc and H$_2$O, the organic layer separated and washed with H$_2$O and brine. The residue was purified by column chromatography to give the product (340 mg).

MS: [M+H]$^+$=341.

X19

Synthesis of 2-(2-Chloro-pyrimidin-4-yl)-imidazole-1-sulfonic acid dimethylamide

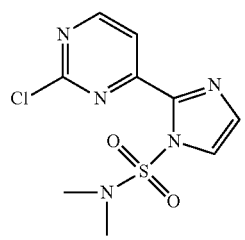 [SMILES: CN(C)S(=O)(=O)n1ccnc1-c1ccnc(Cl)n1]

N-BuLi [2.5M in hexane] (4 ml, 10 mmol) added at −78° C. to a solution of N,N-dimethyl imidazole-1-sulphonamide (1.75 g, 10 mmol) in dry ether (60 ml), stirred 1 hour, anion transferred to a suspension of 2-chloropyrimidine (1.48 g, 10 mmol) in ether (80 ml) keeping the temperature -30° C., temperature brought to 0° C. and held for 30 min. Reaction quenched with AcOH (0.64 ml) and water (0.1 ml), to the reaction was added THF (2 ml) then DDQ (2.27 g) in THF (10 ml) and stirred O/N. Reaction diluted with EtOAc, solid filtered off and filtrate washed with water (3×) then ice cold 0.5% NaOH, organic layer dried over MgSO$_4$, filtered and concentrated under reduced pressure, residue was purified by column chromatography to give the product (130 mg).

MS: [M+H]$^+$=228.

111

X20

Synthesis of 1-[3-(4-Bromo-pyrazol-1-yl)-azetidin-1-yl]-ethanone

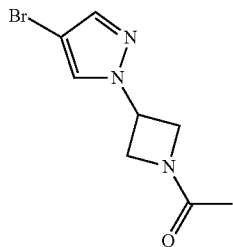

Prepared using procedure X10 step 2 using 1-boc-3-(hydroxy)azetidine followed by procedure X3.

To 1-Azetidin-3-yl-4-bromo-1H-pyrazole hydrochloride (0.3 g, 1.26 mmol) in CH$_2$Cl$_2$ (15 ml) added ET$_3$N (0.47 ml) and acetyl chloride (0.107 ml, 1.5 mmol) stirred at RT for 2 hours then partitioned between EtOAc and H$_2$O. The organic layer was separated, washed with water H$_2$O, dried over MgSO$_4$, filtered and concentrated under reduced pressure to give the product (276 mg).

MS: [M+H]$^+$=246.

X21

Synthesis of 4-Bromo-1-{1-[2-(tetrahydro-pyran-2-yloxy)-ethyl]-azetidin-3-yl}-1H-Pyrazole

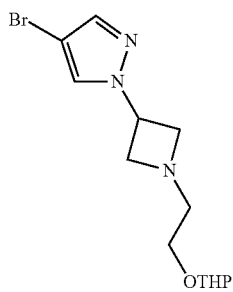

Prepared using procedure X10 step 2 using 1-boc-3-(hydroxy)azetidine followed by procedure X3.

To 1-Azetidin-3-yl-4-bromo-1H-pyrazole hydrochloride (0.3 g, 1.26 mmol) in CH$_3$CN (15 ml) added K$_2$CO$_3$ (0.78 g, 5.6 mmol) followed by 2-(2-bromoethoxy)tetrahydro-2H-pyran (0.205 ml, 1.5 mmol) reaction heated at reflux O/N. Reaction mixture filtered, solid washed with EtOAc, filtrate concentrated under reduced pressure, residue partitioned between CH$_2$Cl$_2$ and H$_2$O. The organic layer was separated, dried over MgSO$_4$, filtered and concentrated under reduced pressure to give the product (380 mg).

MS: [M+H]$^+$=331

112

X22

Synthesis of [2-(6-chloro-pyrimidin-4-ylamino)-ethyl]-carbamic acid tert-butyl ester

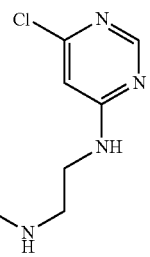

To 4,6-dichloropyrimidine (0.533 g, 35.8 mmol) in MeOH (15 ml) was added tert-butyl N-(2-aminoethyl)carbamate and the reaction stirred at room temperature for 6.5 hours. Reaction concentrated in vacuo, solids triturated with EtOAc/petrol. Filtrate which contains the desired product was concentrated and EtOAc and sat. NaHCO$_3$ added.

Phases separated and organics dried over MgSO$_4$, filtered and concentrated in vacuo. Crude purified by column chromatography to give desired product as a white solid (414 mg). MS: [M+H]$^+$=273

X23

Synthesis of 2-Chloro-5-methoxy-pyrimidin-4-ylamine

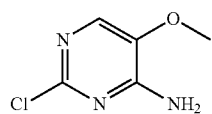

A mixture of 2,4 dichloro-5-methoxypyrimidine (0.45 g, 2.5 mmol) and ammonia in methanol (2N, 20 ml) was stirred at room temperature overnight. The mixture was then concentrated in vacuo and washed with water. The residue was purified by column chromatography (20-60% ethyl acetate/petroleum ether) to furnish the title compound as a white solid (211 mg). MS: [M+H]$^+$=160

X24

Synthesis of 2-Chloro-5-trifluoromethyl-pyrimidin-4-ylamine and 4-Chloro-5-trifluoromethyl-pyrimidin-2-ylamine

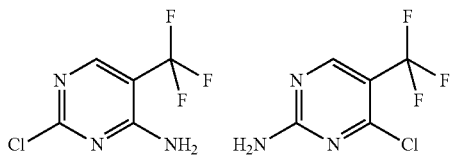 [SMILES: Nc1nc(Cl)ncc1C(F)(F)F ; Nc1ncc(C(F)(F)F)c(Cl)n1]

Synthesised as 2-chloro-5-methoxy-pyrimidin-4-ylamine using 2,4-dichloro-5-trifluoromethylpyrimidine. Both regioisomers isolated. 2-chloro-5-trifluoromethyl-pyrimidin-4-ylamine 1H NMR (400 MHz, Me-d3-OD): 8.32 (1H, s); 4-chloro-5-trifluoromethyl-pyrimidin-2-ylamine 1H NMR (400 MHz, Me-d3-OD): 8.46 (1H, s).

X25

Synthesis of (2-Chloro-5-trifluoromethyl-pyrimidin-4-yl)-cyclobutyl-amine and (4-Chloro-5-trifluoromethyl-pyrimidin-2-yl)-cyclobutyl-amine

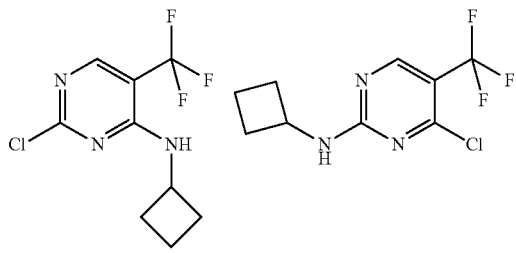

A mixture of 2,4-dichloro-5-trifluoromethylpyrimidine (0.3 ml, 2.3 mmol) and cyclobutylamine (0.2 ml, 2.3 mmol) was stirred at room temperature overnight in methanol (5 ml). After the addition of further amine (0.4 ml) and 4 hours, the reaction was concentrated in vacuo. Ethyl acetate was added to the residue and the mixture was washed with water (×2) and brine then dried (MgSO$_4$) and concentrated again. Purified by column chromatography (0-20% ethyl acetate/petroleum ether) furnishing 2 regioisomers as a mixture (635 mg). MS: [M+H]$^+$=252

X26

Synthesis of [1-(2-Chloro-pyrimidin-4-yl)-azetidin-3-yl]-carbamic acid tert-butyl ester

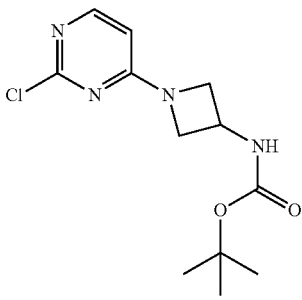 [SMILES: CC(C)(C)OC(=O)NC1CN(c2ccnc(Cl)n2)C1]

A mixture of azetidin-3-yl-carbamic acid tert-butyl ester (635 mg, 3.4 mmol), 2,4-dichloropyrimidine (500 mg, 3.4 mmol) and triethylamine (0.5 ml, 3.6 mmol) in methanol (10 ml) was stirred at room temperature overnight. The mixture was concentrated and purified by column chromatography (0-40% ethyl acetate/petroleum ether) furnishing 561 mg title compound. MS: [M+H]$^+$=283/285

X27

Synthesis of 4-Azetidin-1-yl-2-chloro-pyrimidine

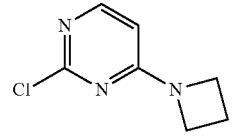 [SMILES: Clc1nccc(N2CCC2)n1]

Prepared as [1-(2-chloro-pyrimidin-4-yl)-azetidin-3-yl]-carbamic acid tert-butyl ester using azetidine hydrochloride. MS: [M+H]$^+$=170

X28

Synthesis of 1-(2-Chloro-pyrimidin-4-yl)-azetidin-3-ol

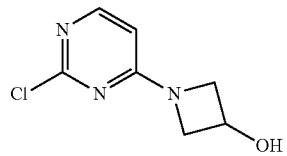 [SMILES: OC1CN(c2ccnc(Cl)n2)C1]

Prepared as [1-(2-chloro-pyrimidin-4-yl)-azetidin-3-yl]-carbamic acid tert-butyl ester using azetidin-3-ol hydrochloride. MS: [M+H]$^+$=186

X29

Synthesis of 2-Chloro-pyrimidine-4-carboxylic acid methylamide

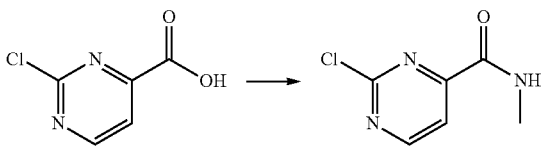

To a solution of 2-chloro-pyrimidine-4-carboxylic acid (200 mg, 1.3 mmol) in dichloromethane (10 ml) cooled in an ice/water bath was added oxalyl chloride (0.7 ml) and dimethylformamide (3 drops). The reaction was incomplete after 45 minutes so a further portion of oxalyl chloride was added (0.7 ml) and the reaction allowed to proceed at room temperature for a further hour. The reaction was then concentrated and to the crude acid chloride was added pyridine (0.1 ml) and methylamine hydrochloride (0.16 g, 1.9 mmol). After stirring for 3 hours a further portion of both reagents were added and the reaction left to stir overnight. To the reaction was added dilute bicarbonate solution and the mixture was extracted with dichloromethane. The organic liquors were concentrated to furnish the title compound as a yellow solid (150 mg). 1H NMR (400 MHz, DMSO-d6): 9.01 (1H, d), 8.99-8.88 (1H, m), 8.01 (1H, d), 2.83 (3H, d).

X30

Synthesis of (2-Chloro-pyrimidin-4-yl)-morpholin-4-yl-methanone

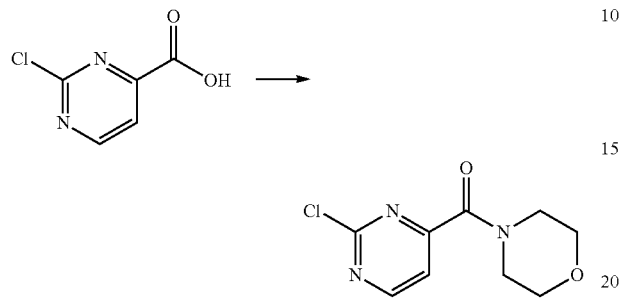

Prepared as 2-chloro-pyrimidine-4-carboxylic acid methylamide. Produced as a 50% pure mixture

X31

Synthesis of (2-Chloro-pyrimidin-4-yl)-morpholin-4-yl-methanone

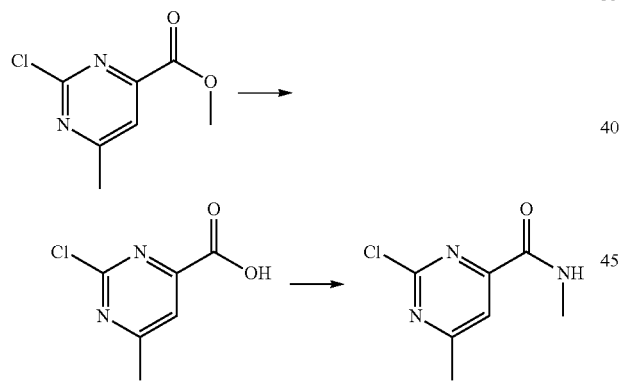

A mixture of 2-chloro-6-methyl-pyrimidine-4-carboxylic acid methyl ester (2.0 g, 10.7 mmol), sodium hydroxide pellets (600 mg) and water (60 ml) was stirred at room temperature for 3 hours. The reaction was then acidified with 5N hydrochloric acid and left to stand over the weekend. The reaction was cooled on ice and a brown material removed by vacuum filtration. The liquors were extracted with ethyl acetate and the combined organic liquors were concentrated to furnish the acid intermediate as a brown solid (1.59 g). 1H NMR (400 MHz, DMSO-d6): 14.13 (1H, s), 7.95 (1H, s), 2.59 (3H, s). The amide was produced according to the method for preparation of 2-chloro-pyrimidine-4-carboxylic acid methylamide. MS: [M+H]$^+$=186

X32

Synthesis of 6-Chloro-5-trifluoromethyl-pyridin-2-ylamine and 6-Chloro-3-trifluoromethyl-pyridin-2-ylamine A mixture of 2,6-dichloro-3-trifluoromethyl-pyridine (1.0 g, 4.6 mmol) and ammonia (saturated aqueous solution '0.880', 0.6 ml) in 1,4-dioxane (4 ml) was heated in a sealed tube in a microwave. More ammonia was added and the temperature slowly increased to 120 deg C. until ca. 90% conversion achieved (after about 2 hours). The reaction was allowed to stand overnight and the resultant solid was isolated by vacuum filtration and was washed with water. The resultant solid was purified by column chromatography (0-30% ethyl acetate/petroleum ether) to furnish the 2 regioisomers. 6-Chloro-5-trifluoromethyl-pyridin-2-ylamine 1H NMR (400 MHz, CDCl3): 7.70 (1H, d), 6.43 (1H, d), 5.47-4.30 (2H, m). -6-Chloro-3-trifluoromethyl-pyridin-2-ylamine-1H NMR (400 MHz, CDCl3): 7.66 (1H, d), 6.75 (1H, d), 5.17 (2H, s).

X33

Synthesis of 4-Chloro-5-isopropyl-pyrimidin-2-ylamine and 2-Chloro-5-isopropyl-pyrimidin-4-ylamine Prepared as 6-chloro-5-trifluoromethyl-pyridin-2-ylamine and 6-chloro-3-trifluoromethyl-pyridin-2-ylamine using 2,4-dichloro-5-isopropyl-pyrimidine as starting material. 4-Chloro-5-isopropyl-pyrimidin-2-ylamine 1H NMR (400 MHz, Me-d3-OD): 7.86 (1H, s), 2.92-2.78 (1H, m), 1.26 (6H, d). 2-Chloro-5-isopropyl-pyrimidin-4-ylamine 1H NMR (400 MHz, Me-d3-OD): 8.15 (1H, s), 3.21-3.08 (1H, m), 1.27 (6H, d).

X34

Synthesis of 2-Chloro-5-trifluoromethyl-pyrimidine

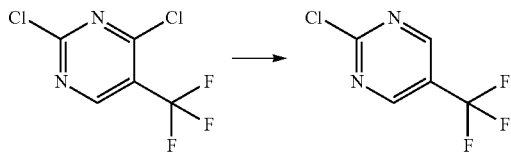 [SMILES: FC(F)(F)c1cnc(Cl)nc1Cl ; FC(F)(F)c1cnc(Cl)nc1]

2,4-Dichloro-5-trifluoromethyl-pyrimidine (300 mg, 1.4 mmol), zinc dust (90 mg, 1.4 mmol) and tetrahydrofuran (3 ml) heated to reflux. Acetic acid (0.16 ml, 2.8 mmol) in tetrahydrofuran (3 ml) added dropwise to the mixture over 30 minutes. The resultant mixture was heated for a further 3 hours and then allowed to cool to room temperature and filtered through GF-A paper. The liquors were concentrated and wet with dichloromethane. The mixture was washed with dilute bicarbonate solution and then concentrated in vacuo furnishing a crude material from which the desired target molecule was produced.

X35

Synthesis of 2,5-dichloro-pyrimidin-4-ylamine

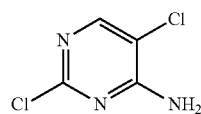

A solution of 2,4,5-trichloropyrimidine (2.2 ml) in 2M ammonia in methanol (50 ml) was stirred at room temperature overnight. The reaction was then concentrated in vacuo and the resultant solid was washed with water. The residue was triturated with methanol and the solid was isolated by vacuum filtration to furnish the title compound as a white solid (487 mg). 1H NMR (400 MHz, DMSO-d6): 8.18 (1H, s).

Section Y

Preparation of Boronic Acid/Ester Coupling Partners

Y1

Preparation of 2-Methyl-2-[4-(4,4,5,5-tetramethyl-[1,3,2]dioxaborolan-2-yl)pyrazol-1-yl]propionic acid ethyl ester

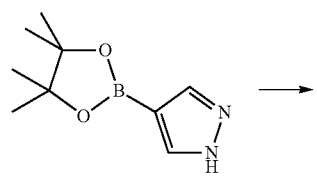

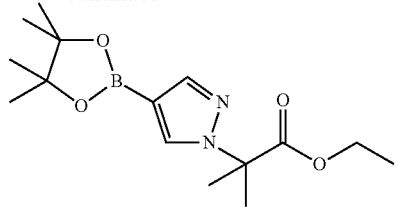

To a stirred mixture of 4-(4,4,5,5-Tetramethyl-[1,3,2]dioxaborolan-2-yl)-1H-pyrazole (5.0 g, 25.8 mmol) and Cesium carbonate (12.6 g, 38.7 mmol) in dry DMF (50 ml) was added 2-Bromo-2-methyl-propionic acid ethyl ester (5.5 g, 28.2 mmol). The reaction mixture was heated at 90° C. under $N_2$ for 18 h, before being allowed to cool to room temperature. The mixture was partitioned between EtOAc and $H_2O$, the organic layer separated and washed with $H_2O$ (×2) and brine (×1), dried ($Na_2SO_4$), filtered and the solvent removed in vacuo. This afforded the crude product as a yellow oil, which was used directly in the next step (4.7 g, 15.3 mmol).

Section Z

General Modifications

Procedure Z1a

Boc group removal

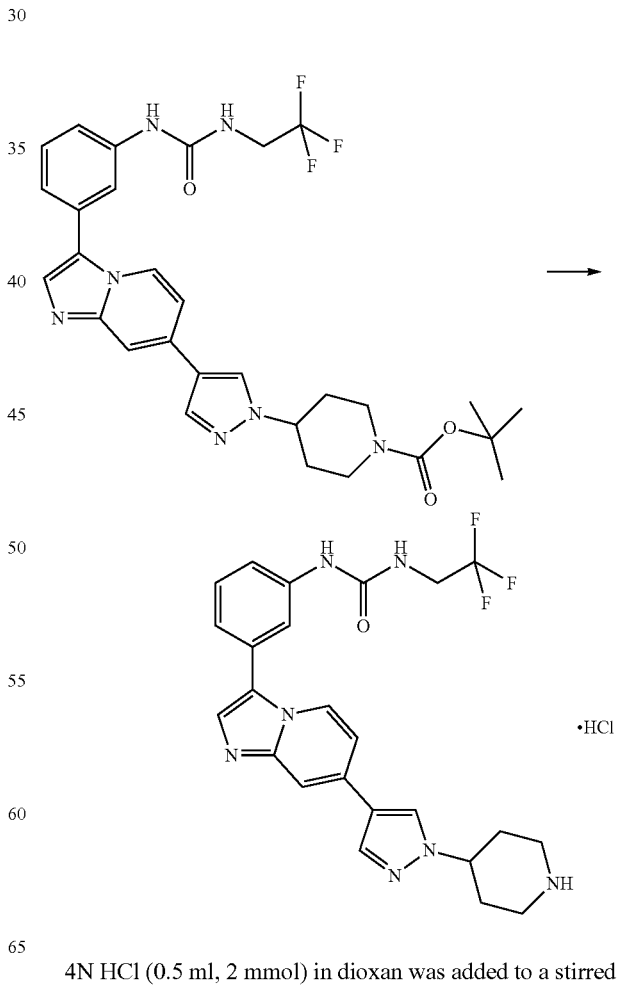

4N HCl (0.5 ml, 2 mmol) in dioxan was added to a stirred suspension of 4-[4-(3-{3-[3-(2,2,2-Trifluoro-ethyl)-ureido]- phenyl}-imidazo[1,2-a]pyridin-7-yl)-pyrazol-1-yl]-piperidine-1-carboxylic acid tert-butyl ester (210 mg, 0.36 mmol) in CH$_2$Cl$_2$ (2 ml). The suspension was stirred at room temperature for 3 h and the solvent removed in vacuo. The residue was partitioned between EtOAc and NaHCO$_3$ solution and the aqueous layer was extracted with EtOAc (×2). The organic extracts were combined, dried (Na$_2$SO$_4$), filtered and the solvent removed in vacuo. The residue was purified by preparative HPLC to give a colourless solid. The solid was dissolved in a solution of HCl in MeOH (1 equiv), the solvent removed and the residue triturated with Et$_2$O to give a cream solid (110 mg, 0.23 mmol). MS: [M+H]$^+$484.

Procedure Z1b

Alternative Boc Group Removal

The Boc protected compound may be dissolved in DCM and treated with trifluoroacetic acid. The reaction is stirred at room temperature until complete, then all volatiles are removed in vacuo to leave the unprotected amino compound, which may be purified as necessary.

Procedure Z2

Ester Hydrolysis

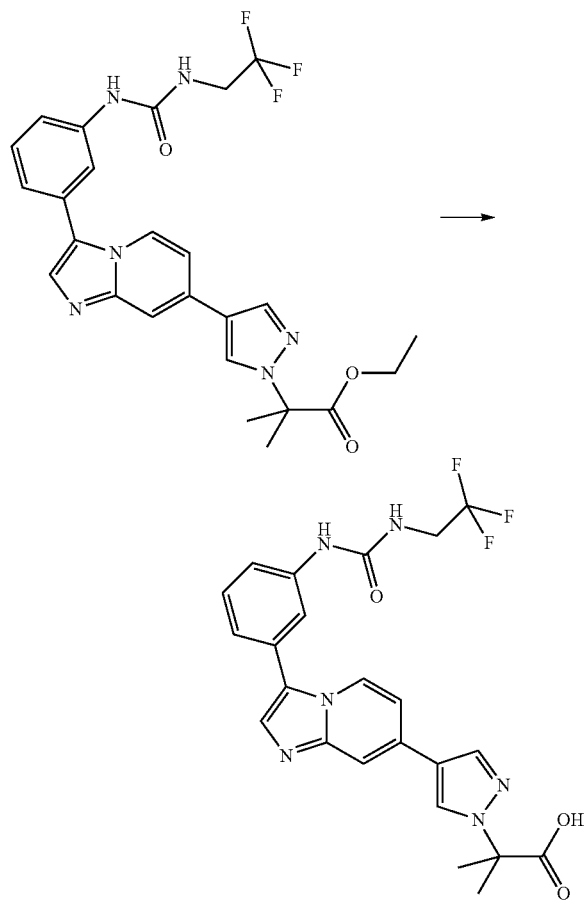

To a stirred suspension of 2-Methyl-2-[4-(3-{3-[3-(2,2,2-trifluoroethypureido]phenyl}imidazo[1,2-a]pyridin-7-yl) pyrazol-1-yl]propionic acid ethyl ester (300 mg, 0.58 mmol) in dioxane (4 ml) was added a solution of LiOH (70 mg, 2.9 mmol) in H$_2$O (1 ml). MeOH (1 ml) was added to give a homogeneous solution, which was stirred at room temperature for 3 days. 2N HCl (1.5 ml) was added and the volatiles removed in vacuo. The aqueous residue was partitioned between EtOAc and H$_2$O. The layers were separated and the aqueous layer further extracted with EtOAc, resulting in the formation of a solid. The liquid fraction was decanted off and the solid dissolved in MeOH. The aqueous layer was further extracted with EtOAc (×1) and CH$_2$Cl$_2$ (×1). The organic fractions were combined, the solvent removed in vacuo and the residue azeotroped with EtOH to give a beige foam. A portion of this foam (70 mg) was purified by preparative HPLC to give a colourless solid (33 mg). MS: [M+H]$^+$487.

Procedure Z3

Reduction

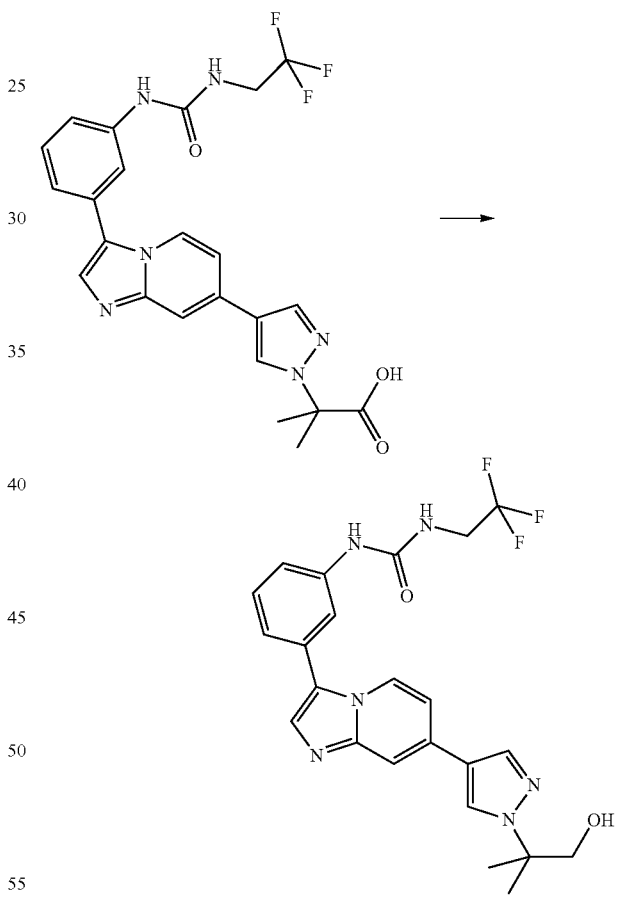

Borane-THF (1 M in THF, 3 ml, 3 mmol) was added to a suspension of 2-Methyl-2-[4-(3-{3-[3-(2,2,2-trifluoroethypureido]phenyl}imidazo[1,2-a]pyridin-7-yl)pyrazol-1-yl] propionic acid (250 mg, 1.9 mmol) in THF (3 ml) at 0° C. under a nitrogen atmosphere. The reaction was stirred at room temperature for 3 h, then at 65° C. overnight. After cooling to room temperature, water (1 ml), 5N HCl (1 ml) and MeOH (5 ml) were added and the resulting solution was stirred at room temperature for 18 h. The mixture was concentrated in vacuo and diluted with 1N NaOH and EtOAc. The mixture was filtered and the solid purified by preparative HPLC to give the product (28 mg) as an off-white solid. MS: [M+H]⁺=473.

Procedure Z4

Alkylation

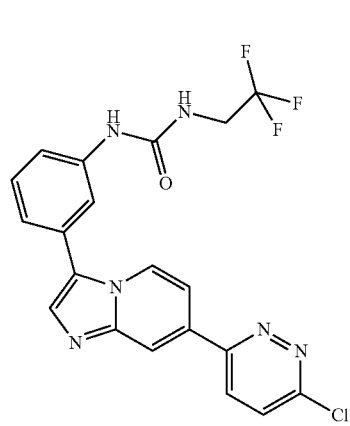

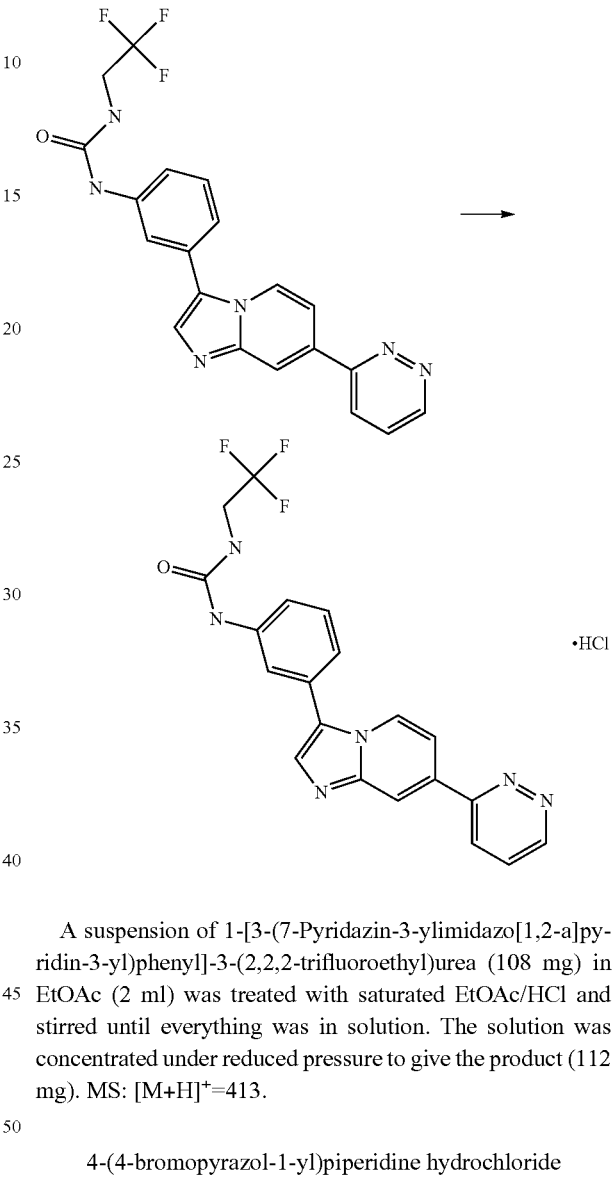

Procedure Z5

Hydrochloride Salt Formation

A suspension of 1-[3-(7-Pyridazin-3-ylimidazo[1,2-a]pyridin-3-yl)phenyl]-3-(2,2,2-trifluoroethyl)urea (108 mg) in EtOAc (2 ml) was treated with saturated EtOAc/HCl and stirred until everything was in solution. The solution was concentrated under reduced pressure to give the product (112 mg). MS: [M+H]⁺=413.

4-(4-bromopyrazol-1-yl)piperidine hydrochloride

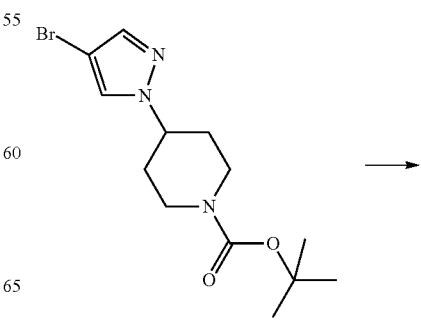

1-{3-[7-(6-Chloropyridazin-3-yl)-imidazo[1,2-a]pyridin-3-yl]phenyl}-3-(2,2,2-trifluoroethyl)urea (20 mg, 0.04 mmol) and 4-(dimethylamino)piperidine (8 mg, 0.05 mmol) were dissolved in NMP (0.25 ml) and heated in a CEM Discover microwave for 10 mins at 120° C., 30 mins at 130° C. and 60 mins at 150° C. After cooling, the reaction mixture was diluted with brine and filtered. The solid was redissolved in MeOH/DCM, dried (Na₂SO₄), filtered and concentrated in vacuo. The residue was purified by preparative HPLC to give the product (10 mg). MS: [M+H]⁺=539.

-continued

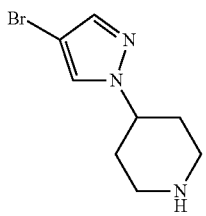

To 4-(4-Bromo-pyrazol-1-yl)-piperidine-1-carboxylic acid tert-butyl ester (1 g, 3. mmol) in ETOAc (4 ml) was added sat. ETOAc in HCl (5 ml) and the reaction mixture stirred at room temperature for 2 h. The solvent removed in vacuo and re-evaporated with toluene to give the product (0.68 g), which was used without further purification MS: [M+H]$^+$=230

Procedure Z6

Amide Formation

Preparation of N-(2-Diethylamino-ethyl)-2-[4-(3-{3-[3-(2,2,2-trifluoro-ethyl)-ureido]-phenyl}-imidazo[1,2-a]pyridin-7-yl)-pyrazol-1-yl]-isobutyramide

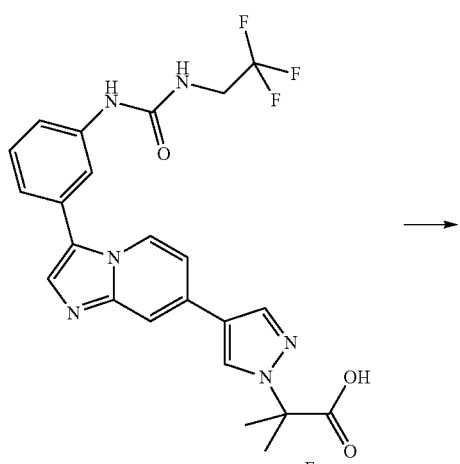

To a solution of 2-Methyl-2-[4-(3-{3-[3-(2,2,2-trifluoroethypureido]phenyl}imidazo[1,2-a]pyridin-7-yl)pyrazol-1-yl] propionic acid (0.1 g, 0.2 mmol) in DMF (3 ml) added EDAC (0.043 g, 0.22 mmol), HOAt (0.031 g, 0.22 mmol) followed by N,N-diethylethylenediamine (0.029 ml, 0.2 mmol), Reaction stirred at RT until complete then partitioned between water and EtOAc. The aqueous layer was washed with further EtOAc, oranics combined, dried over MgSO$_4$, filtered and concentrated under reduced pressure. The residue was purified by preparative HPLC to give the product (0.027 g) MS: [M+H]$^+$=585

Procedure Z6a

SNAr Reaction

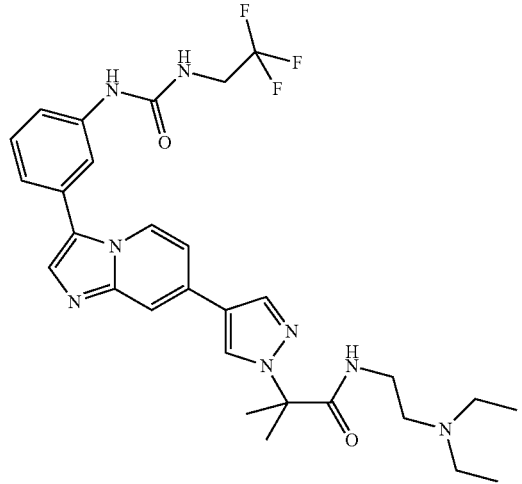

A mixture of 3,6-dichloropyridazine (500 mg; 3.35 mmol) and ethanolamine (250 □l; 1.25 equivalents) in 1 ml of NMP was heated at 120° C. for 20 minutes in a CEM Discover microwave synthesizer. The reaction mixture was diluted with brine then extracted with DCM (×2). The combined DCM extracts were dried (Na$_2$SO$_4$), filtered and evaporated. The crude material was triturated with Et$_2$O, the solid was collected by filtration, washed with further Et$_2$O and sucked dry to give 80 mg of the product as a fawn solid. $^1$H NMR (400 MHz, DMSO-d6): 7.34 (1H, d), 7.10 (1H, s), 6.95 (1H, d), 4.75 (1H, s), 3.58 (2H, d), 3.40 (2H, d).

Procedure Z7

O-dealkylation

125

-continued

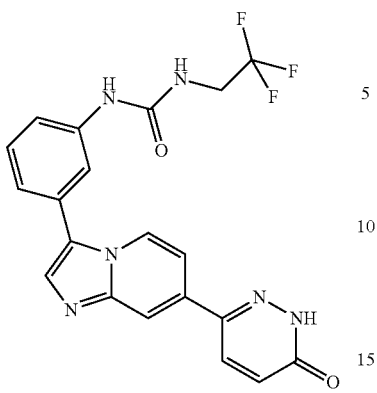

A solution of 1-{3-[7-(6-Methoxy-pyridazin-3-yl)-imidazo[1,2-a]pyridin-3-yl]-phenyl}-3-(2,2,2-trifluoro-ethyl)-urea (40 mg; 0.09 mmol) in acetonitrile (5 ml) was treated with potassium iodide (50 mg; 3.3 equivalents), followed by trimethylchlorosilane (38 μl; 3.3 equivalents) then heated at 60° C. for 2 hours. The reaction was cooled, treated with 2M HCl, stirred for 30 minutes then evaporated. The residue was partitioned between DCM and sat NaHCO$_3$, the undissolved solid was collected by filtration, washed with water then DCM and sucked dry. The product was isolated as a pale yellow solid (35 mg). 1H NMR (400 MHz, DMSO-d6): 9.50 (1H, s), 8.56 (1H, d), 8.24-8.12 (2H, m), 7.80 (2H, s), 7.58 (1H, d), 7.53-7.35 (3H, m), 7.25 (1H, d), 6.91 (1H, d), 4.02-3.88 (2H, m).

Z8

Deprotection of Sulphonamide 1-(3-{7-[4-(1H-Imidazol-2-yl)-pyrimidin-2-yl]-imidazo[1,2-a]pyridin-3-yl}-phenyl)-3-(2,2,2-trifluoro-ethyl)-urea

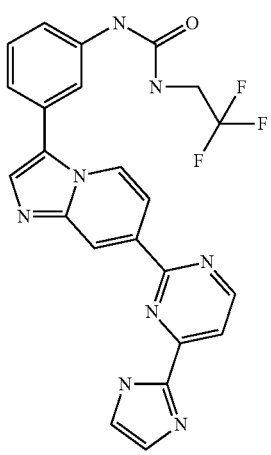 [SMILES: O=C(NCC(F)(F)F)Nc1cccc(-c2cnc3cc(-c4nccc(-c5ncc[nH]5)n4)ccn23)c1]

126

2-[2-(3-{3-[3-(2,2,2-Trifluoro-ethyl)-ureido]-phenyl}-imidazo[1,2-a]pyridin-7-yl)-pyrimidin-4-yl]-imidazole-1-sulfonic acid dimethylamide (140 mg, 0.23 mmol) dissolved in EtOH (5 ml) and MeOH(1 ml) treated with 2M HCl (1 ml) heated at 60° C. for 2 hours. Reaction mixture concentrated under reduced pressure and was purified by preparative HPLC to give product (20 mg).

MS: [M+H]+ 479

Z9

Deprotection of THP

1-[3-(7-{6-[4-(2-Hydroxy-ethyl)-piperazin-1-yl]-2-methyl-pyrimidin-4-yl}-imidazo[1,2-a]pyridin-3-yl)-phenyl]-3-(2,2,2-trifluoro-ethyl)-urea

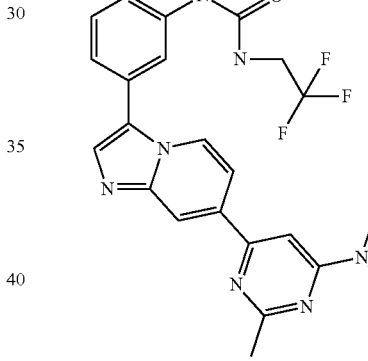

To 1-{3-[7-(2-Methyl-6-{4-[2-(tetrahydro-pyran-2-yloxy)-ethyl]-piperazin-1-yl}-pyrimidin-4-yl)-imidazo[1,2-a]pyridin-3-yl]-phenyl}-3-(2,2,2-trifluoro-ethyl)-urea (150 mg) treated with saturated HCl in EtOAc, reaction stirred RT for 1 hour, precipitated solid filtered and washed with EtOAc. The crude product was purified by preparative HPLC twice to give product (30 mg).

MS: [M+H]+ 555

Examples 1 to 13

By following the methods described above, the compounds set out in the Table below were prepared.

All MS Data is [M+H]$^+$

| Eg. | Compound and Name | N.M.R. Data | M.S | Procedure |
|---|---|---|---|---|
| 1 | 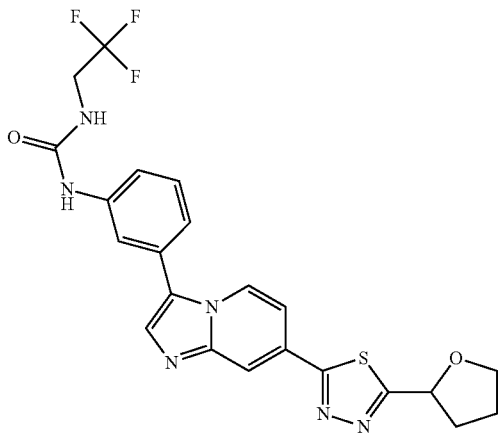 [SMILES: O=C(NCC(F)(F)F)Nc1cccc(-c2cnc3cc(-c4nnc(C5CCCO5)s4)ccn23)c1]<br>1-(3-{7-[5-(Tetrahydrofuran-2-yl)-[1,3,4]thiadiazol-2-yl]imidazo[1,2-a]pyridin-3-yl}-phenyl)-3-(2,2,2-trifluoroethyl)urea | 1H NMR (400 MHz, DMSO-d6): 9.00 (1H, s), 8.68 (1H, d), 8.28 (1H, s), 7.92 (1H, s), 7.77 (1H, s), 7.61 (1H, dd), 7.55-7.44 (2H, m), 7.30 (1H, d), 6.89 (1H, t), 5.39 (1H, dd), 4.06-3.86 (4H, m), 2.49-2.41 (1H, m), 2.21-2.11 (1H, m), 2.08-1.96 (2H, m). | 489 | General route B, procedure B3b using 2-Bromo-5-(tetrahydro-furan-2-yl)-[1,3,4]thiadiazole (X1) |
| 2 | 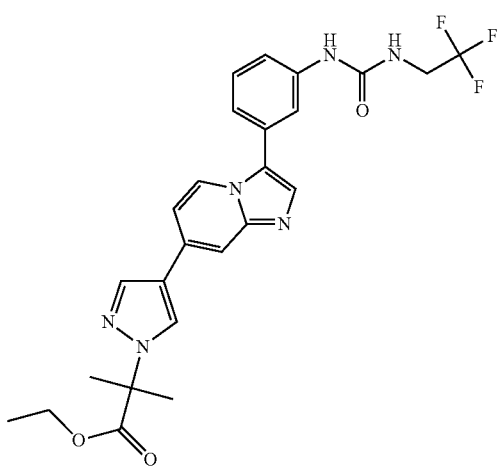 [SMILES: CCOC(=O)C(C)(C)n1cc(-c2ccn3c(-c4cccc(NC(=O)NCC(F)(F)F)c4)cnc3c2)cn1]<br>2-Methyl-2-[4-(3-{3-[3-(2,2,2-trifluoroethyl)ureido]phenyl}imidazo[1,2-a]pyridin-7-yl)pyrazol-1-yl] propionic acid ethyl ester | 1H NMR (400 MHz, DMSO-d6): 8.95 (1H, s), 8.64 (1H, s), 8.55 (1H, d), 8.16 (1H, s), 7.99-7.93 (1H, m), 7.80-7.78 (1H, m), 7.71 (1H, s), 7.48-7.39 (2H, m), 7.35 (1H, dd), 7.25 (1H, dt), 6.85 (1H, t), 4.12 (2H, q), 4.01-3.89 (2H, m), 1.82 (6H, s), 1.15 (3H, t). | 515 | General route A, procedure A5a using 2-Methyl-2-[4-(4,4,5,5-tetramethyl-[1,3,2]dioxaborolan-2-yl) pyrazol-1-yl] prop-ionic acid ethyl ester (Y1) |

| Eg. | Compound and Name | N.M.R. Data | M.S | Procedure |
|---|---|---|---|---|
| 3 | 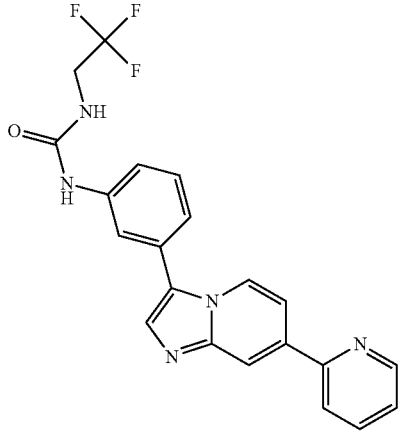 [SMILES: O=C(NCC(F)(F)F)Nc1cccc(-c2cnc3cc(-c4ccccn4)ccn23)c1]<br>1-[3-(7-Pyridin-2-ylimidazo[1,2-a]pyridinyl)phenyl]-3-(2,2,2-trifluoroethyl)urea | 1H NMR (400 MHz, Me-d3-OD): 8.71 (1H, d), 8.68 (1H, d), 8.33-8.24 (1H, m), 8.05 (1H, d), 8.01-7.91 (1H, m), 7.84 (1H, d), 7.79 (1H, s), 7.73 (1H, dd), 7.50 (1H, t), 7.47-7.38 (2H, m), 7.34 (1H, d), 3.96 (2H, q). | 412 | General route B, procedure B3a using 2-bromopyridine |
| 4 | 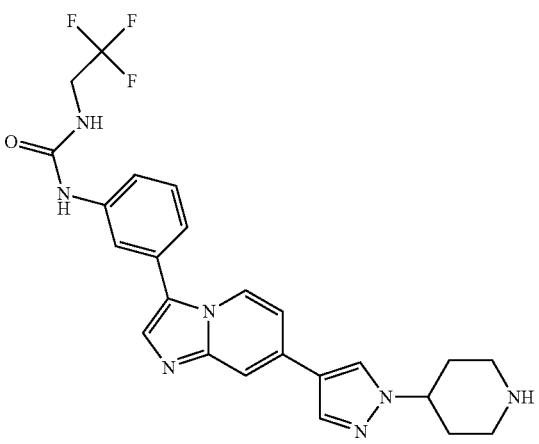 [SMILES: O=C(NCC(F)(F)F)Nc1cccc(-c2cnc3cc(-c4cnn(C5CCNCC5)c4)ccn23)c1]<br>1-{3-[7-(1-Piperidin-4-yl-1H-pyrazol-4-yl)-imidazo[1,2-a]pyridin-3-yl]phenyl}-3-(2,2,2-trifluoroethyl)urea hydrochloride | 1H NMR (400 MHz, DMSO-d6): 9.42 (1H, s), 9.12 (1H, br s), 8.93 (1H, br s), 8.74-8.65 (2H, m), 8.32 (1H, s), 8.20 (1H, s), 8.08 (1H, s), 7.89 (1H, s), 7.70 (1H, dd), 7.51 (2H, d), 7.34-7.25 (1H, m), 7.11 (1H, t), 4.62-4.52 (1H, m), 4.01-3.89 (2H, m), 3.53-3.20 (2H, m), 3.17-3.06 (2H, m), 2.35-2.14 (4H, m). | 484 | General route B, procedure B3c using 4-(4-Bromo-pyrazol-1-yl)-piperidine-1-carboxylic acid tert-butyl ester (X2). Modification Z1a |

| Eg. | Compound and Name | N.M.R. Data | M.S | Procedure |
|---|---|---|---|---|
| 5 | 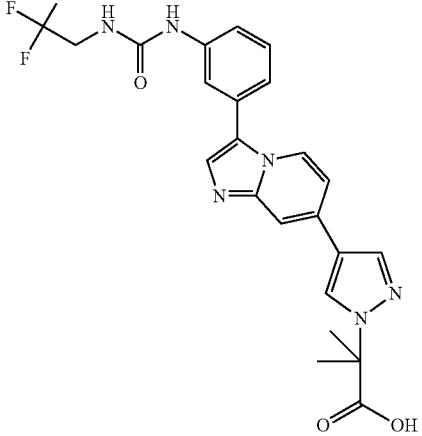<br>2-Methyl-2-[4-(3-{3-[3-(2,2,2-trifluoroethyl)ureido]phenyl}imidazo[1,2-a]pyridin-7-yl)pyrazol-1-yl]propionic acid | 1H NMR (400 MHz, DMSO-d6): 9.49 (1H, s), 8.56-8.47 (2H, m), 8.05 (1H, s), 7.87 (1H, s), 7.74 (1H, s), 7.68 (1H, s), 7.55-7.47 (1H, m), 7.47-7.36 (2H, m), 7.27 (1H, dd), 7.25-7.18 (1H, m), 4.00-3.87 (2H, m), 1.75 (6H, s). | 487 | General route A, procedure A5a using 2-Methyl-2-[4-(4,4,5,5-tetramethyl-[1,3,2]dioxaborolan-2-yl)pyrazol-1-yl]propionic acid ethyl ester (Y1). Modification Z2 |
| 6 | 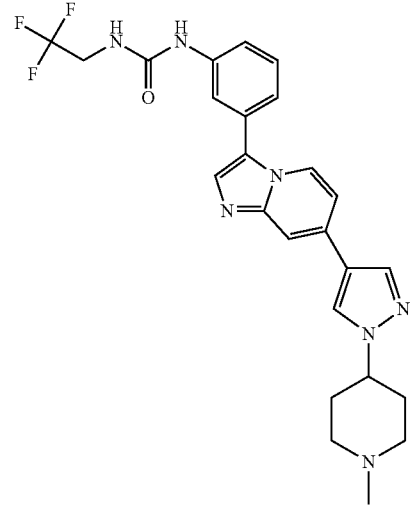 [SMILES: CN1CCC(n2cc(-c3ccn4c(-c5cccc(NC(=O)NCC(F)(F)F)c5)cnc4c3)cn2)CC1]<br>1-(3-{7-[1-(1-Methyl-piperidin-4-yl)-1H-pyrazol-4-yl]imidazo[1,2-a]pyridin-3-yl}phenyl)-3-(2,2,2-trifluoroethyl)urea | 1H NMR (400 MHz, DMSO-d6): 8.94 (1H, s), 8.53 (1H, dd), 8.48 (1H, s), 8.10 (1H, s), 7.92-7.85 (1H, m), 7.81-7.73 (1H, m), 7.70 (1H, s), 7.47-7.38 (2H, m), 7.28 (1H, dd), 7.25 (1H, dt), 6.84 (1H, t), 4.20-4.09 (1H, m), 4.02-3.89 (2H, m), 2.95-2.84 (2H, m), 2.24 (3H, s), 2.17-1.94 (6H, m). | 498 | General route B, procedure B3c using 4-(4-Bromo-pyrazol-1-yl)-1-methyl-piperidine (X3) |

| Eg. | Compound and Name | N.M.R. Data | M.S | Procedure |
|---|---|---|---|---|
| 7 | 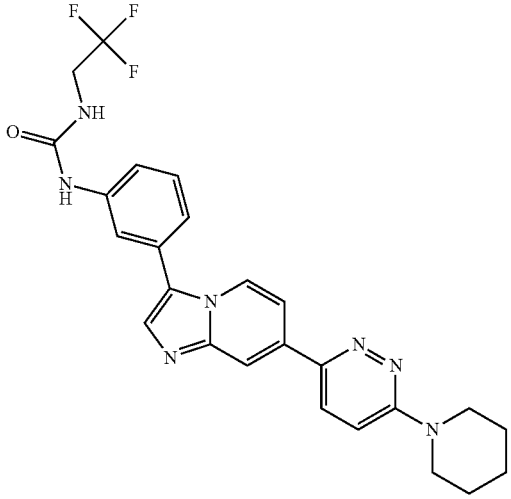 [SMILES: O=C(NCC(F)(F)F)Nc1cccc(-c2cnc3cc(-c4ccc(N5CCCCC5)nn4)ccn23)c1]<br>1-{3-[7-(6-Piperidin-1-yl-pyridazin-3-yl)-imidazo[1,2-a]pyridin-3-yl]phenyl}-3-(2,2,2-trifluoroethyl)urea | 1H NMR (400 MHz, Me-d3-OD): 8.91 (1H, d), 8.59 (1H, s), 8.41 (1H, d), 8.25 (1H, s), 8.16 (1H, dd), 8.03 (1H, s), 7.90 (1H, d), 7.58 (1H, t), 7.49 (1H, d), 7.40 (1H, d), 3.95 (2H, q), 3.87 (4H, s), 1.83 (6H, s). | 496 | General route B, procedure B3d using 3-chloro-6-piperidin-1-ylpyridazine. |
| 8 | 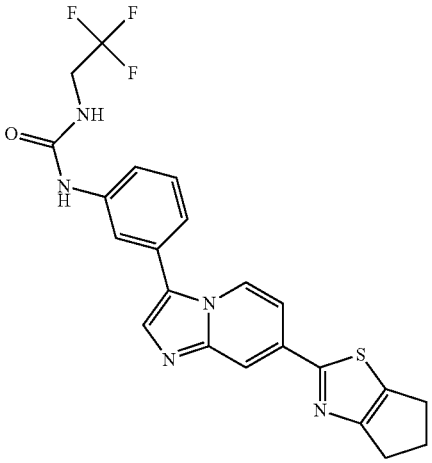 [SMILES: O=C(NCC(F)(F)F)Nc1cccc(-c2cnc3cc(-c4nc5c(s4)CCC5)ccn23)c1]<br>1-{3-[7-(5,6-Dihydro-4H-cyclopentathiazol-2-yl)imidazo[1,2-a]pyridin-3-yl]-phenyl}-3-(2,2,2-trifluoroethyl)urea | 1H NMR (400 MHz, Me-d3-OD): 8.64 (1H, d), 8.11 (1H, s), 7.83 (1H, t), 7.79 (1H, s), 7.59-7.53 (1H, m), 7.50 (1H, t), 7.45-7.39 (1H, m), 7.38-7.31 (1H, m), 3.96 (2H, q), 3.04 (2H, t), 2.93 (2H, t), 2.64-2.56 (2H, m). | 458 | General route B, procedure B3a using 2-Chloro-5,6-dihydro-4H-cyclopenta-thiazole (X4) |

| Eg. | Compound and Name | N.M.R. Data | M.S | Procedure |
|---|---|---|---|---|
| 9 | 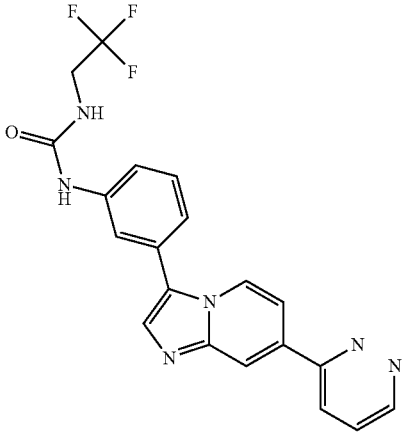 [SMILES: N/C=C\C=C(/N)c1ccn2c(-c3cccc(NC(=O)NCC(F)(F)F)c3)cnc2c1]<br>1-[3-(7-Pyridazin-3-ylimidazo[1,2-a]pyridin-3-yl)phenyl]-3-(2,2,2-trifluoroethyl)urea hydrochloride | 1H NMR (400 MHz, Me-d3-OD): 9.41 (1H, dd), 9.01 (1H, d), 8.81 (1H, s), 8.63 (1H, dd), 8.38-8.29 (2H, m), 8.13-8.03 (2H, m), 7.61 (1H, t), 7.53-7.47 (1H, m), 7.44 (1H, d), 3.96 (2H, q). | 413 | General route B, procedure B3d using 3-chloro-pyridazine. General Modification Z5. |
| 10 | 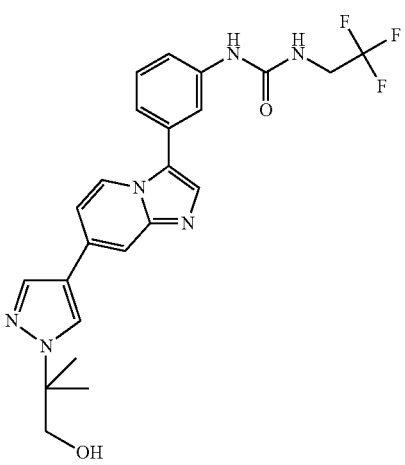 [SMILES: CC(C)(CO)n1cc(-c2ccn3c(-c4cccc(NC(=O)NCC(F)(F)F)c4)cnc3c2)cn1]<br>1-(3-{7-[1-(2-Hydroxy-1,1-dimethylethyl)-1H-pyrazol-4-yl]-imidazo[1,2-a]pyridin-3-yl}phenyl)-3-(2,2,2-trifluoroethyl)urea | 1H NMR (400 MHz, DMSO-d6): 8.98 (1H, s), 8.53 (1H, dd), 8.46 (1H, s), 8.10 (1H, s), 7.92-7.90 (1H, m), 7.78 (1H, s), 7.69 (1H, s), 7.48-7.38 (2H, m), 7.32 (1H, dd), 7.24 (1H, dt), 6.89 (1H, t), 4.99 (1H, t), 4.01-3.89 (2H, m), 3.62 (2H, d), 1.52 (6H, s). | 473 | General route A, procedure A5a using 2-Methyl-2-[4-(4,4,5,5-tetramethyl-[1,3,2]dioxaborolan-2-yl) pyrazol-1-yl]propionic acid ethyl ester (Y1). Modification Z2. Modification Z3 |

| Eg. | Compound and Name | N.M.R. Data | M.S | Procedure |
|---|---|---|---|---|
| 11 | 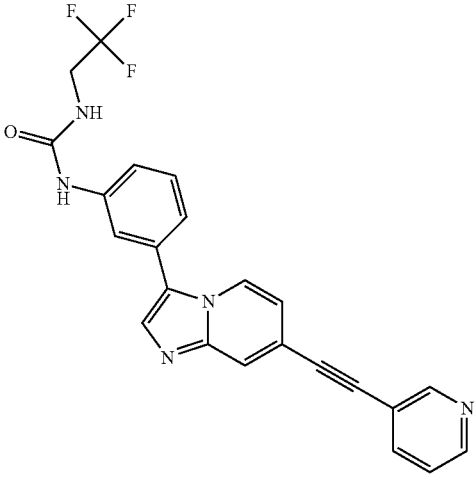 [SMILES: O=C(NCC(F)(F)F)Nc1cccc(-c2cnc3cc(C#Cc4cccnc4)ccn23)c1]<br>1-[3-(7-Pyridin-3-ylethynylimidazo[1,2-a]pyridin-3-yl)phenyl]-3-(2,2,2-trifluoroethyl)urea | 1H NMR (400 MHz, Me-d3-OD): 8.85 (1H, d), 8.81 (1H, d), 8.61 (1H, d), 8.22 (1H, s), 8.19-8.06 (2H, m), 7.99 (1H, s), 7.73-7.52 (3H, m), 7.48 (1H, d), 7.43-7.28 (1H, m), 4.02-3.89 (2H, m). | 436 | General Route C. Procedure C2 using 2-ethynylpyridine |
| 12 | 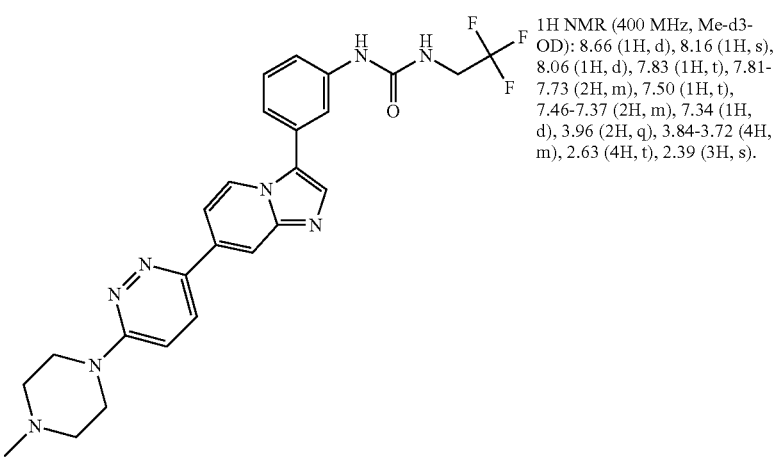<br>1-(3-{7-[6-(4-Methylpiperazin-1-yl)pyridazin-3-yl]imidazo[1,2-a]pyridin-3-yl}phenyl)-3-(2,2,2-trifluoroethyl)urea | 1H NMR (400 MHz, Me-d3-OD): 8.66 (1H, d), 8.16 (1H, s), 8.06 (1H, d), 7.83 (1H, t), 7.81-7.73 (2H, m), 7.50 (1H, t), 7.46-7.37 (2H, m), 7.34 (1H, d), 3.96 (2H, q), 3.84-3.72 (4H, m), 2.63 (4H, t), 2.39 (3H, s). | 511 | General route B, procedure B3d using 3-chloro-6-(4-methyl-piperidin-1-yl)pyridazine. |

| Eg. | Compound and Name | N.M.R. Data | M.S | Procedure |
|---|---|---|---|---|
| 13 | 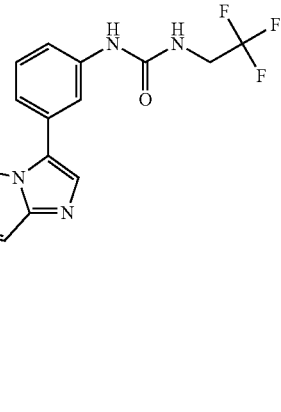

1-{3-[7-(3-Methyl-3H-imidazol-4-ylethynyl)imidazo[1,2-a]pyridin-3-yl]phenyl}-3-(2,2,2-trifluoroethyl)urea formate | 1H NMR (400 MHz, Me-d3-OD): 8.58 (1H, d), 8.13 (1H, s), 7.83-7.73 (3H, m), 7.49 (1H, t), 7.44-7.35 (2H, m), 7.31 (1H, d), 7.10 (1H, dd), 3.95 (2H, q), 3.84 (3H, s). | 439 | General Route C. Procedure C2 using 1-methyl-5-ethynyl-imidazole |

Example 13B

1-{3-[7-(3-Methyl-3H-imidazol-4-ylethynyl)-imidazo[1,2-a]pyridin-3-yl]-phenyl}-3-(2,2,2-trifluoro-ethyl)-urea dihydrochloride

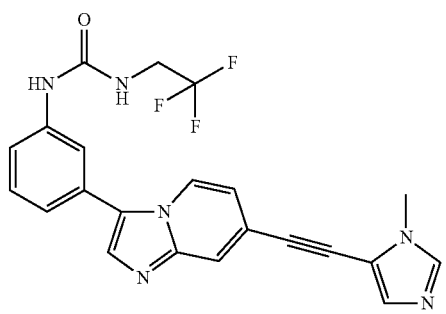 [SMILES: Cn1cncc1C#Cc1ccn2c(-c3cccc(NC(=O)NCC(F)(F)F)c3)cnc2c1]

A mixture of 1-[3-(7-Chloro-imidazo[1,2-a]pyridin-3-yl)-phenyl]-3-(2,2,2-trifluoro-ethyl)-urea (3.08 g, 8.3 mmol), 5-Ethynyl-1-methyl-1H-imidazole (1.78 g, 10 mmol) and cesium carbonate (5.43 g, 16.7 mmol) in dry DMSO (31 ml) was deoxygenated by evacuation /refill with $N_2$ (×3). $PdCl_2(PCy_3)_2$ (185 mg, 0.25 mmol) was added and the mixture was deoxygenated again (×3) then stirred and heated at 100° C. under $N_2$ for 16 hours. The reaction was allowed to cool to RT, diluted with water (65 ml) and the mixture was extracted with EtOAc (3×50 ml). The combined organic extracts were washed with brine (40 ml) then dried ($MgSO_4$), filtered and evaporated. The residue was mixed with dichloromethane (20 ml), cooled in ice and filtered to give the title compound (1.34 g, yellow solid). 1H NMR (400 MHz, Me-d3-OD): 8.59 (1H, d), 7.87-7.74 (4H, m), 7.50 (1H, t), 7.42 (1H, d), 7.37 (1H, s), 7.32 (1H, d), 7.10 (1H, dd), 3.95 (2H, q), 3.85 (3H, s). A solution of the title compound in methanol (10 ml) was cooled in ice and was treated with a solution of saturated hydrogen chloride in ethyl acetate (15 ml). The mixture was evaporated to give the bis-HCl salt (1.59 g, yellow foam). $^1$H NMR (400 MHz, Me-d3-OD): 9.06 (1H, s), 8.88 (1H, d), 8.34-8.27 (2H, m), 8.08 (2H, d), 7.65 (1H, d), 7.59 (1H, t), 7.47-7.35 (2H, m), 4.09 (3H, s), 3.96 (2H, q).

Examples 14 to 114

By following the methods described above, the compounds set out in the Table below were prepared.

All MS Data is [M+H]$^+$

| Eg. | Compound and Name | N.M.R. Data | M.S | Procedure |
|---|---|---|---|---|
| 14 | 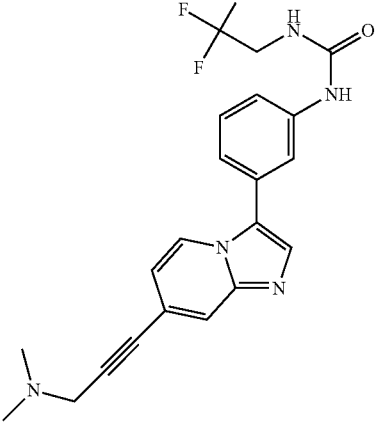<br>1-{3-[7-(3-Dimethylaminoprop-1-ynyl)imidazo[1,2-a]pyridin-3-yl]phenyl}-3-(2,2,2-trifluoroethyl)urea | 1H NMR (400 MHz, Me-d3-OD): 8.54 (1H, d), 7.80 (1H, t), 7.76 (1H, s), 7.71 (1H, s), 7.49 (1H, t), 7.45-7.38 (1H, m), 7.38-7.25 (1H, m), 7.00 (1H, dd), 3.95 (2H, q), 3.60 (2H, s), 2.43 (6H, s). | 416 | General Route C. Procedure C2 using 1-dimethylamino-2-propyne |
| 15 | 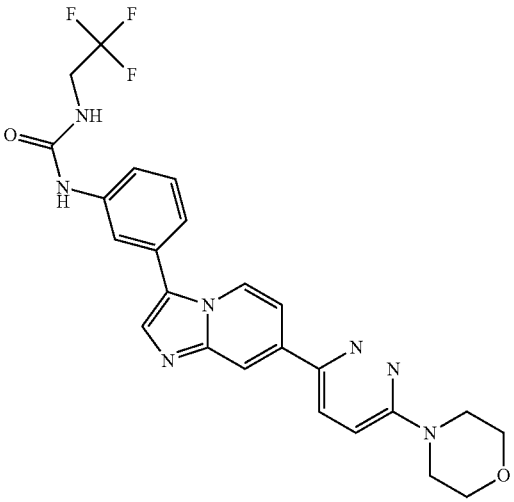 [SMILES: N/C(=C\C=C(/N)N1CCOCC1)c1ccn2c(-c3cccc(NC(=O)NCC(F)(F)F)c3)cnc2c1]<br>1-{3-[7-(6-Morpholin-4-y-pyridazin-3-yl)imidazo[1,2-a]pyridin-3-yl]phenyl}-3-(2,2,2-trifluoroethyl)urea hydrochloride | 1H NMR (400 MHz, Me-d3-OD): 8.97 (1H, d), 8.64 (1H, s), 8.58 (1H, d), 8.31 (1H, s), 8.20 (1H, dd), 8.10 (1H, t), 8.03 (1H, d), 7.60 (1H, t), 7.49-7.38 (2H, m), 4.03-3.92 (6H, m), 3.88 (4H, t). | 498 | General route B, procedure B3d using 3-chloro-6-morpholin-1-ylpyridazine. |

| Eg. | Compound and Name | N.M.R. Data | M.S | Procedure |
|---|---|---|---|---|
| 16 | 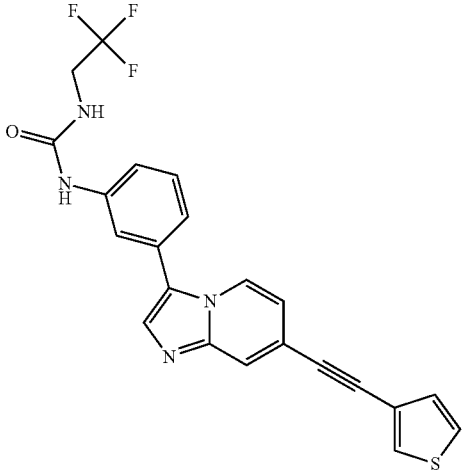 [SMILES: O=C(NCC(F)(F)F)Nc1cccc(-c2cnc3cc(C#Cc4ccsc4)ccn23)c1]<br>1-[3-(7-Thiophen-3-ylethynylimidazo[1,2-a]pyridinyl)phenyl]-3-(2,2,2-trifluoroethyl)urea | 1H NMR (400 MHz, Me-d3-OD): 8.55 (1H, d), 7.81 (1H, t), 7.77 (1H, s), 7.77-7.72 (2H, m), 7.55-7.45 (2H, m), 7.45-7.37 (1H, m), 7.31 (1H, d), 7.27 (1H, dd), 7.06 (1H, dd), 3.95 (2H, q). | 441 | General Route C. Procedure C2 using 3-ethynylthiophene |
| 17 | 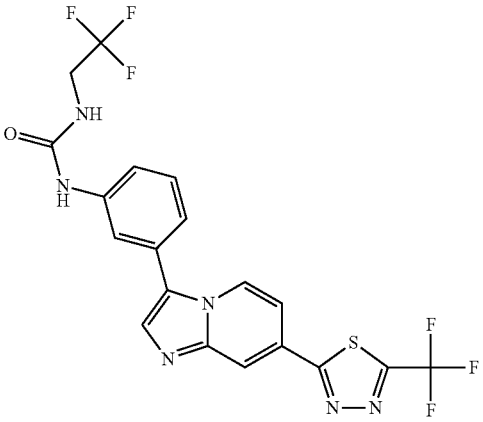 [SMILES: O=C(NCC(F)(F)F)Nc1cccc(-c2cnc3cc(-c4nnc(C(F)(F)F)s4)ccn23)c1]<br>1-(2,2,2-Trifluoroethyl)-3-{3-[7-(5-trifluoromethyl[1,3,4]thiadiazol-2-yl)-imidazo[1,2-a]pyridin-3-yl]phenyl}urea | 1H NMR (400 MHz, Me-d3-OD): 8.76 (1H, d), 8.40 (1H, s), 7.93 (1H, s), 7.89 (1H, t), 7.74 (1H, dd), 7.53 (1H, t), 7.44 (1H, d), 7.36 (1H, d), 3.96 (2H, q). | 487 | General route B, procedure B3e using 2-chloro-5-trifluoromethyl-[1,3,4]thiadiazole |

-continued

| Eg. | Compound and Name | N.M.R. Data | M.S | Procedure |
|---|---|---|---|---|
| 18 | 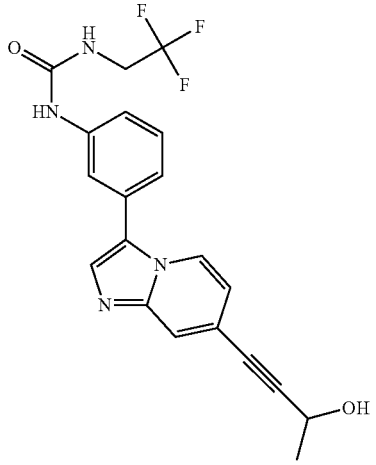 [SMILES: CC(O)C#Cc1ccn2c(-c3cccc(NC(=O)NCC(F)(F)F)c3)cnc2c1]<br>1-{3-[7-(3-Hydroxybut-1-ynyl)imidazo[1,2-a]pyridin-3-yl]phenyl}-3-(2,2,2-trifluoroethyl)urea formate | 1H NMR (400 MHz, Me-d3-OD): 8.52 (1H, d), 8.16 (1H, s), 7.78 (2H, d), 7.68 (1H, s), 7.54-7.44 (1H, m), 7.40 (1H, d), 7.33-7.23 (1H, m), 6.98 (1H, dd), 4.81-4.68 (1H, m), 3.95 (2H, q), 1.51 (3H, d). | 403 | General Route C. Procedure C2 using 3-hydroxy-but-1-yne |
| 19 | 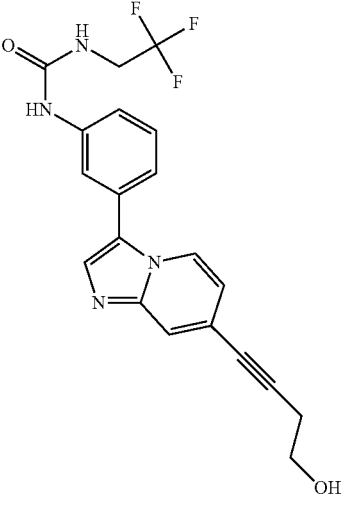 [SMILES: O=C(NCC(F)(F)F)Nc1cccc(-c2cnc3cc(C#CCCO)ccn23)c1]<br>1-{3-[7-(4-Hydroxybut-1-ynyl)imidazo[1,2-a]pyridin-3-yl]phenyl}-3-(2,2,2-trifluoroethyl)urea | 1H NMR (400 MHz, Me-d3-OD): 8.49 (1H, d), 7.78 (1H, s), 7.72 (1H, s), 7.67-7.59 (1H, m), 7.47 (1H, t), 7.41 (1H, d), 7.29 (1H, d), 7.01-6.90 (1H, m), 3.95 (2H, q), 3.78 (2H, t), 2.70 (2H, t). | 403 | General Route C. Procedure C2 using 4-hydroxy-but-1-yne |

| Eg. | Compound and Name | N.M.R. Data | M.S | Procedure |
|---|---|---|---|---|
| 20 | 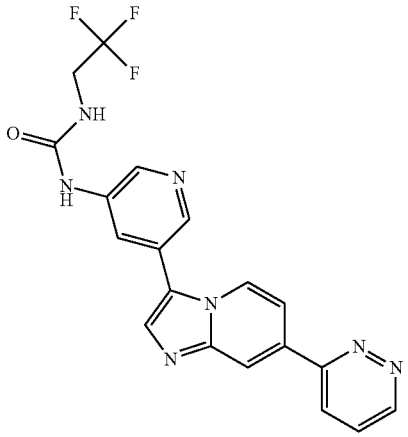 [SMILES: O=C(NCC(F)(F)F)Nc1cncc(-c2cnc3cc(-c4cccnn4)ccn23)c1]<br>1-[5-(7-Pyridazin-3-ylimidazo[1,2-a]pyridin-3-yl)pyridin-3-yl]-3-(2,2,2-trifluoroethyl)urea | 1H NMR (400 MHz, DMSO-d6): 10.26 (1H, s), 9.41 (1H, dd), 9.04 (1H, d), 8.94 (1H, d), 8.81 (1H, s), 8.69 (1H, d), 8.67-8.59 (2H, m), 8.50 (1H, d), 8.34-8.25 (1H, m), 8.04-7.94 (1H, m), 7.54 (1H, t), 4.06-3.92 (2H, m). | 414 | General Route D. Procedure D2 using 3-Chloro-pyridazine. |
| 21 | 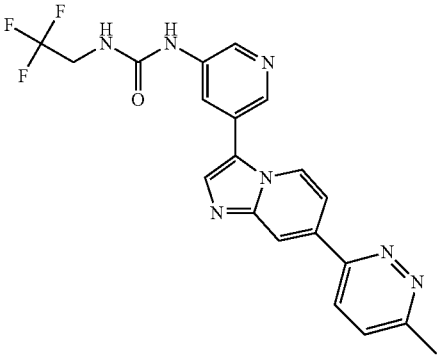 [SMILES: Cc1ccc(-c2ccn3c(-c4cncc(NC(=O)NCC(F)(F)F)c4)cnc3c2)nn1]<br>1-{5-[7-(6-Methylpyridazin-yl)imidazo[1,2-a]pyridin-3-yl]pyridin-3-yl}-3-(2,2,2-trifluoroethyl)urea | 1H NMR (400 MHz, DMSO-d6): 10.15 (1H, s), 9.00 (1H, d), 8.90 (1H, d), 8.79-8.74 (1H, m), 8.65 (1H, d), 8.63-8.58 (1H, m), 8.56 (1H, d), 8.47 (1H, t), 8.31-8.21 (1H, m), 7.94-7.85 (1H, m), 7.55-7.44 (1H, m), 4.05-3.92 (2H, m), 2.76 (3H, s). | 428 | General Route D. Procedure D2 using 3-Chloro-6-methyl-pyridazine |
| 22 | 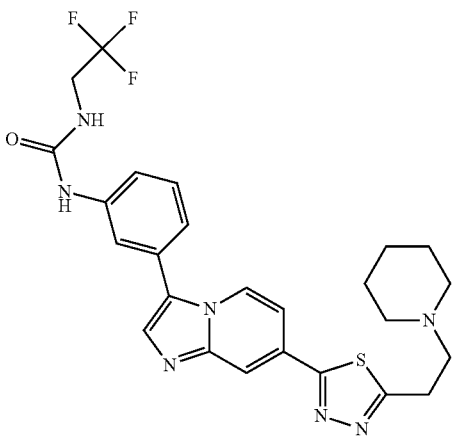 [SMILES: O=C(NCC(F)(F)F)Nc1cccc(-c2cnc3cc(-c4nnc(CCN5CCCCC5)s4)ccn23)c1]<br>1-(3-{7-[5-(2-Piperidin-1-ylethyl)-[1,3,4]thiadiazol-2-yl]imidazo[1,2-a] pyridin-3-yl}phenyl)-3-(2,2,2-trifluoroethyl)urea hydrochloride | 1H NMR (400 MHz, Me-d3-OD): 8.71 (1H, d), 8.19 (1H, s), 7.87 (2H, s), 7.66 (1H, dd), 7.51 (1H, t), 7.43 (1H, d), 7.35 (1H, d), 3.96 (2H, q), 3.54-3.45 (2H, m), 3.12-2.96 (2H, m), 2.96-2.68 (4H, m), 1.83-1.70 (4H, m), 1.67-1.54 (2H, m). | 530 | General Route B. Procedure B3b using 1-[2-(5-Bromo-[1,3,4]thiadiazol-2-yl)ethyl]piperidine (X5) |

| Eg. | Compound and Name | N.M.R. Data | M.S | Procedure |
|---|---|---|---|---|
| 23 | 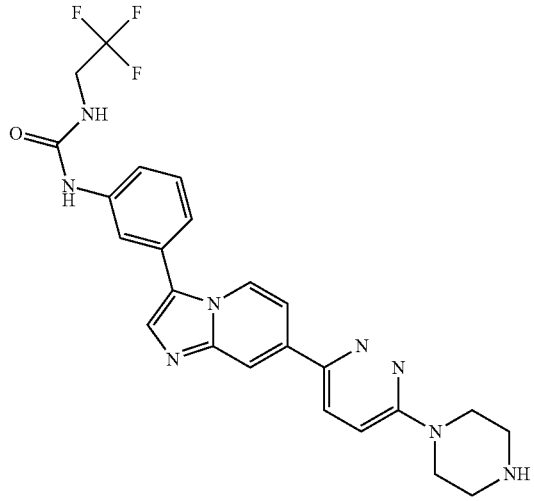 [SMILES: N/C(=C\C=C(/N)N1CCNCC1)c1ccn2c(-c3cccc(NC(=O)NCC(F)(F)F)c3)cnc2c1]<br>1-{3-[7-(6-Piperazin-1-ylpyridazin-3-yl)-imidazo[1,2-a]pyridin-3-yl]phenyl}-3-(2,2,2-trifluoroethyl)urea trifluoroacetate | 1H NMR (400 MHz, Me-d3-OD): 8.91 (1H, d), 8.59 (1H, s), 8.32-8.18 (3H, m), 8.04 (1H, s), 7.64-7.52 (2H, m), 7.48 (1H, d), 7.41 (1H, d), 4.10 (4H, t), 3.96 (2H, q), 3.44 (4H, t). | 497 | General Route B. Procedure B3b using 3-Chloro-6-piperidin-1-yl pyridazine |
| 24 | 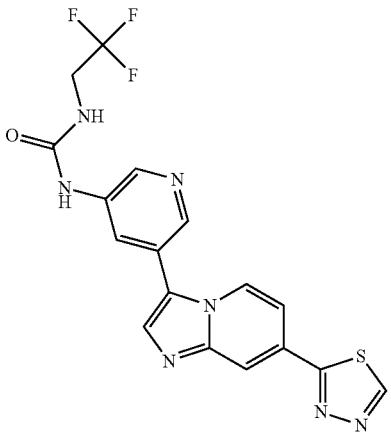 [SMILES: O=C(NCC(F)(F)F)Nc1cncc(-c2cnc3cc(-c4nncs4)ccn23)c1]<br>1-[5-(7-[1,3,4]Thiadiazol-2-ylimidazo[1,2-a]pyridin-3-yl)pyridin-3-yl]-3-(2,2,2-trifluoroethyl)urea hydrochloride | 1H NMR (400 MHz, DMSO-d6): 9.71 (1H, s), 9.24 (1H, s), 6.73 (1H, d), 8.69 (1H, d), 8.53 (1H, d), 3.33 (1H, s), 8.23 (1H, t), 8.04 (1H, s), 7.67 (1H, dd), 7.13 (1H, t), 4.04-3.90 (2H, m). | 420 | General Route D. Procedure D2 using 2-Bromo-[1,3,4]thiadiazole. |
| 25 | 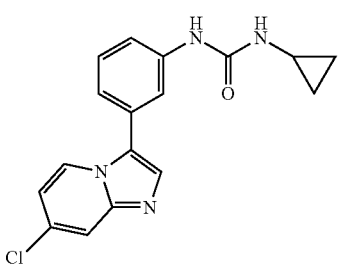 [SMILES: O=C(Nc1cccc(-c2cnc3cc(Cl)ccn23)c1)NC1CC1]<br>1-[3-(7-Chloroimidazo[1,2-a]pyridin-3-yl)-phenyl]-3-cyclopropylurea | 1H NMR (400 MHz, DMSO-d6): 8.55 (1H, d), 8.49 (1H, s), 7.84 (1H, d), 7.76 (1H, s), 7.75 (1H, s), 7.49-7.36 (2H, m), 7.19 (1H, dd), 7.05 (1H, dd), 6.49 (1H, s), 2.61-2.53 (1H, m), 0.70-0.59 (2H, m), 0.47-0.38 (2H, m). | 327 | General Route E. Steps E1-E4. |

| Eg. | Compound and Name | N.M.R. Data | M.S | Procedure |
|---|---|---|---|---|
| 26 | 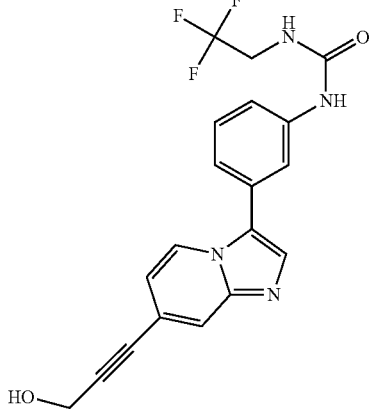<br>1-{3-[7-(3-Hydroxyprop-1-ynyl)imidazo[1,2-a]pyridin-3-yl]phenyl}-3-(2,2,2-trifluoroethyl)urea | 1H NMR (400 MHz, Me-d3-OD): 8.53 (1H, d), 7.85-7.78 (1H, m), 7.76 (1H, s), 7.70 (1H, s), 7.49 (1H, t), 7.41 (1H, d), 7.30 (1H, d), 6.99 (1H, dd), 4.47 (2H, s), 3.95 (2H, q). | 389 | General Route C. Procedure C2 using propargyl alcohol |
| 27 | 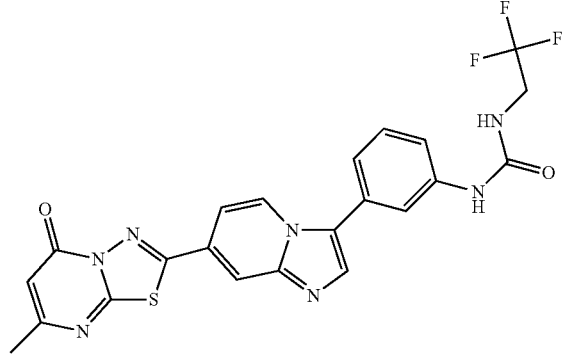 [SMILES: Cc1cc(=O)n2nc(-c3ccn4c(-c5cccc(NC(=O)NCC(F)(F)F)c5)cnc4c3)sc2n1]<br>1-{3-[7-(7-Methyl-5-oxo-5H-[1,3,4]thiadiazolo[3,2-a]pyrimidin-2-yl)imidazo[1,2-a]pyridin-3-yl]phenyl}-3-(2,2,2-trifluoroethyl)urea | 1H NMR (400 MHz, DMSO-d6): 9.05 (1H, s), 8.75 (1H, d), 8.39 (1H, s), 8.00 (1H, s), 7.78 (1H, s), 7.61-7.52 (2H, m), 7.52-7.46 (1H, m), 7.31 (1H, d), 6.96-6.90 (1H, m), 6.39-6.33 (1H, m), 4.00-3.90 (2H, m), 2.33 (3H, s). | 500 | General Route B. Procedure B3b using 2-Bromo-7-methyl-[1,3,4]thiadiazolo[3,2-a]pyrimidin-5-one |
| 28 | 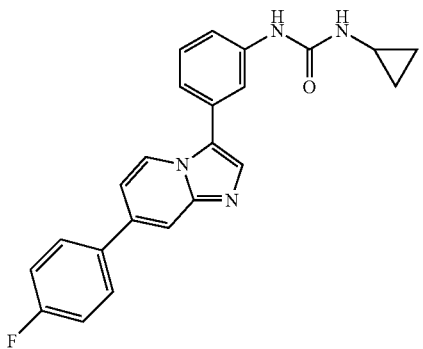 [SMILES: O=C(Nc1cccc(-c2cnc3cc(-c4ccc(F)cc4)ccn23)c1)NC1CC1]<br>1-Cyclopropyl-3-{3-[7-(4-fluorophenyl)imidazo[1,2-a]pyridin-3-yl]phenyl}urea | 1H NMR (400 MHz, DMSO-d6): 8.62 (1H, d), 8.50 (1H, s), 7.99 (1H, s), 7.97-7.87 (2H, m), 7.82 (1H, s), 7.78 (1H, s), 7.42 (2H, d), 7.40-7.29 (3H, m), 7.27-7.18 (1H, m), 6.48 (1H, s), 2.62-2.53 (1H, m), 0.71-0.60 (2H, m), 0.48-0.39 (2H, m). | 387 | General Route E. |

-continued

| Eg. | Compound and Name | N.M.R. Data | M.S | Procedure |
|---|---|---|---|---|
| 29 | 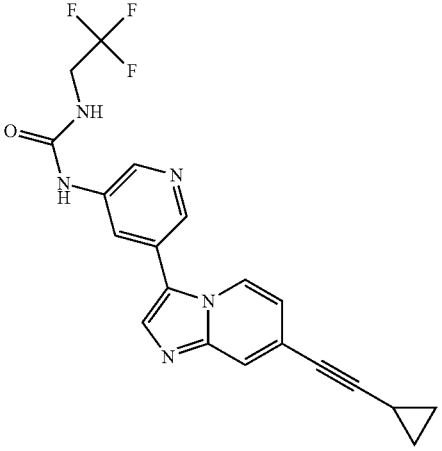 [SMILES: O=C(NCC(F)(F)F)Nc1cncc(-c2cnc3cc(C#CC4CC4)ccn23)c1]<br>1-[5-(7-Cyclopropylethynyl imidazo[1,2-a]pyridin-3-yl)pyridin-3-yl]-3-(2,2,2-trifluoroethyl)urea | 1H NMR (400 MHz, DMSO-d6): 9.16 (1H, s), 8.64 (1H, d), 8.50 (1H, dd), 8.46 (1H, d), 8.19-8.12 (1H, m), 7.90 (1H, s), 7.68 (1H, s), 7.07 (1H, t), 6.90 (1H, dd), 4.02-3.90 (2H, m), 1.66-1.57 (1H, m), 1.00-0.89 (2H, m), 0.86-0.76 (2H, m) | 400 | General Route C. Procedure C1 using 1-[5-(4,4,5,5-Tetramethyl-[1,3,2]dioxaborolan-2-yl)pyridin-3-yl]-3-(2,2,2-trifluoroethyl)urea (as described in Procedure D4). Procedure C2 using cyclopropyl ethyne. |
| 30 | 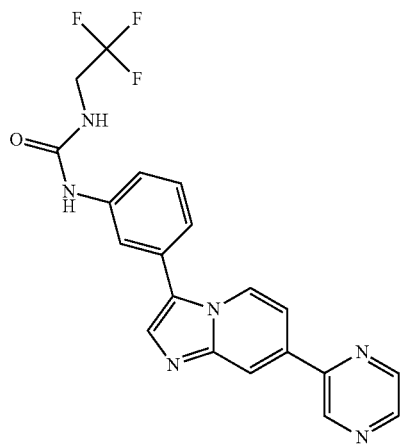 [SMILES: O=C(NCC(F)(F)F)Nc1cccc(-c2cnc3cc(-c4cnccn4)ccn23)c1]<br>1-[3-(7-Pyrazin-2-ylimidazo[1,2-a]pyridin-3-yl)phenyl]-3-(2,2,2-trifluoroethyl)urea | 1H NMR (400 MHz, Me-d3-OD): 9.28 (1H, s), 8.74 (1H, s), 8.69 (1H, d), 8.60 (1H, d), 8.41 (1H, s), 7.84 (1H, s), 7.82-7.74 (2H, m), 7.49 (1H, t), 7.42 (1H, d), 7.33 (1H, d), 3.96 (2H, q). | 413 | General Route B. Procedure B3a using 2-bromopyrazine. |
| 31 | 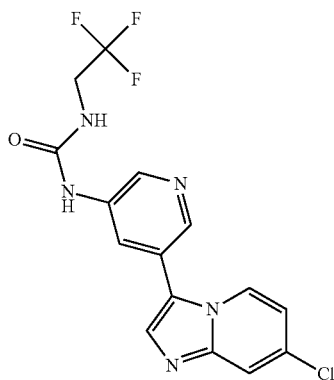 [SMILES: O=C(NCC(F)(F)F)Nc1cncc(-c2cnc3cc(Cl)ccn23)c1]<br>1-[5-(7-Chloroimidazo[1,2-a]pyridin-3-yl)pyridin-3-yl]-3-(2,2,2-trifluoroethyl)urea | 1H NMR (400 MHz, DMSO-d6): 9.18-9.11 (1H, m), 8.65 (1H, d), 8.58 (1H, d), 8.47 (1H, d), 8.17 (1H, t), 7.89 (1H, s), 7.87 (1H, d), 7.12-7.00 (2H, m), 4.02-3.90 (2H, m). | 370 | General Route A. Procedure A1, A2. Procedure A3 using 1-[5-(4,4,5,5-Tetramethyl-[1,3,2]dioxaborolan-2-yl) pyridin-3-yl]-3-(2,2,2-trifluoroethyl)urea (as described in Procedure D4). |

| Eg. | Compound and Name | N.M.R. Data | M.S | Procedure |
|---|---|---|---|---|
| 32 | 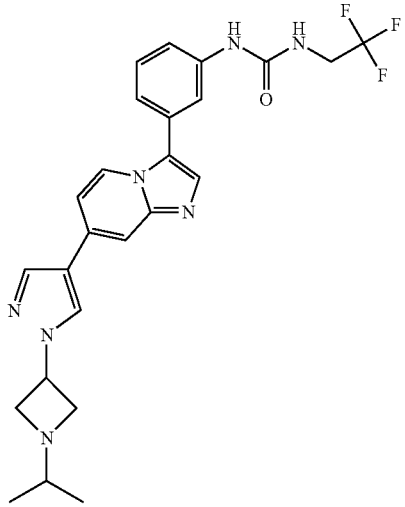 [SMILES: CC(C)N1CC(N/C=C(\C=N)c2ccn3c(-c4cccc(NC(=O)NCC(F)(F)F)c4)cnc3c2)C1]<br>1-(3-{7-[1-(1-Isopropylazetidin-3-yl)-1H-pyrazol-4-yl]imidazo[1,2-a]pyridin-3-yl}phenyl)-3-(2,2,2-trifluoroethyl)-urea | 1H NMR (400 MHz, Me-d3-OD): 8.56 (1H, dd), 8.36 (1H, s), 8.08 (1H, s), 7.82 (1H, t), 7.78 (1H, dd), 7.67 (1H, s), 7.48 (1H, t), 7.39 (1H, ddd), 7.31 (1H, dt), 7.28 (1H, dd), 5.06 (1H, quintet), 3.95 (2H, q), 3.91-3.83 (2H, m), 3.68-3.58 (2H, m), 2.71-2.61 (1H, m), 1.05 (6H, d). | 498 | General Route B. Procedure B3a using 4-Bromo-1-(1-isopropyl-azetidin-3-yl)-1H-pyrazole hydrochloride (synthesised by procedure X3 using 1-(tert-butoxycarbonyl)-3-(methane-sulfonyloxy) azetidine in step 1 and 2-iodopropane in step 3) |
| 33 | 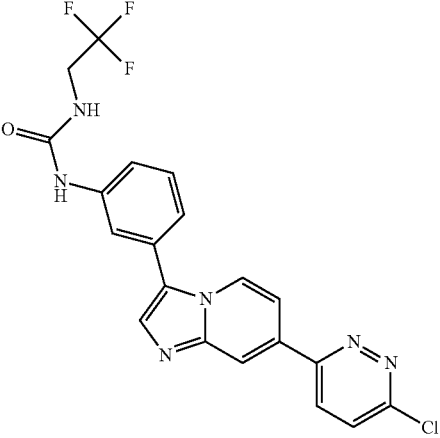 [SMILES: O=C(NCC(F)(F)F)Nc1cccc(-c2cnc3cc(-c4ccc(Cl)nn4)ccn23)c1]<br>1-{3-[7-(6-Chloropyridazin-3-yl)-imidazo[1,2-a]pyridin-3-yl]phenyl}-3-(2,2,2-trifluoroethyl)urea | 1H NMR (400 MHz, DMSO-d6): 9.06 (1H, s), 8.72 (1H, d), 8.61 (1H, d), 8.55 (1H, s), 8.08 (1H, d), 7.91 (1H, s), 7.88 (1H, dd), 7.80 (1H, s), 7.55-7.42 (2H, m), 7.31 (1H, d), 6.96 (1H, t), 4.03-3.88 (2H, m). | 447 | General Route B. Procedure B3d using 3,6-dichloro-pyridazine. |

| Eg. | Compound and Name | N.M.R. Data | M.S | Procedure |
|---|---|---|---|---|
| 34 | 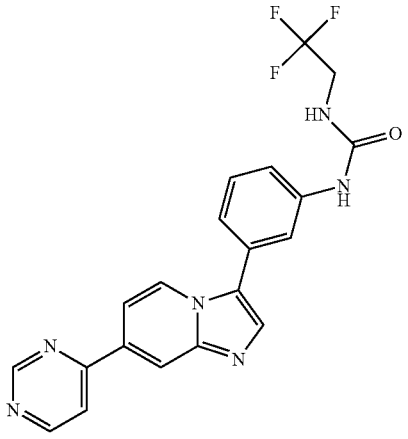 [SMILES: O=C(NCC(F)(F)F)Nc1cccc(-c2cnc3cc(-c4ccncn4)ccn23)c1]<br>1-[3-(7-Pyrimidin-4-ylimidazo[1,2-a]pyridin-3-yl)phenyl]-3-(2,2,2-trifluoroethyl)urea hydrochloride | 1H NMR (400 MHz, Me-d3-OD): 9.41 (1H, d), 9.05 (1H, d), 8.98 (1H, d), 8.86 (1H, s), 8.36-8.33 (1H, m), 8.33-8.27 (2H, m), 8.08 (1H, t), 7.60 (1H, t), 7.51-7.45 (1H, m), 7.43 (1H, dd), 3.96 (2H, q). | 413 | General Route B. Procedure B3d using 4-chloropyrimidine. General modification Z5. |
| 35 | 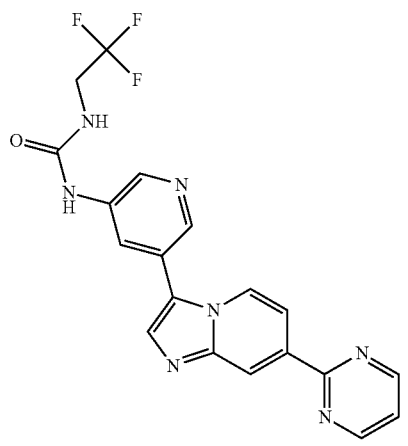 [SMILES: O=C(NCC(F)(F)F)Nc1cncc(-c2cnc3cc(-c4ncccn4)ccn23)c1]<br>1-[5-(7-Pyrimidin-2-yl-imidazo[1,2-a]pyridine-3-yl)pyridin-3-yl]-3-(2,2,2-trifluoroethyl)urea hydrochloride | 1H NMR (400 MHz, Me-d3-OD): 9.32 (1H, d), 9.12-9.00 (4H, m), 8.93 (1H, s), 8.89 (1H, d), 8.65 (1H, dd), 8.59 (1H, s), 7.61 (1H, t), 4.01 (2H, q). | 414 | General Route D. Procedure D2 using 2-chloropyrimidine. General modification Z5. |

| Eg. | Compound and Name | N.M.R. Data | M.S | Procedure |
|---|---|---|---|---|
| 36 | 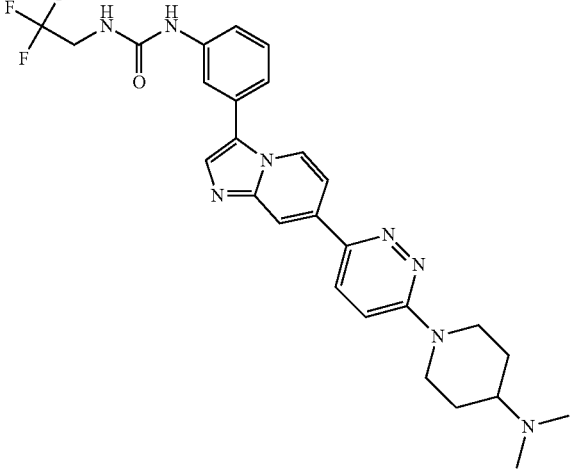<br>1-(3-{7-[6-(4-Dimethylaminopiperidin-1-yl)pyridazin-3-yl]imidazo[1,2-a]pyridin-3-yl}-phenyl)-3-(2,2,2-trifluoroethyl)urea hydrochloride. | 1H NMR (400 MHz, DMSO-d6): 7.83 (1H, d), 7.63 (1H, s), 7.32 (1H, s), 7.22 (1H, d), 7.04 (1H, s), 6.99-6.89 (2H, m), 6.68 (1H, t), 6.64-6.55 (2H, m), 6.51 (1H, d), 4.05 (6H, s), 3.94-3.79 (2H, m), 3.15 (2H, q), 2.76-2.63 (1H, m), 2.28 (2H, t), 1.48-1.34 (2H, m), 1.05-0.83 (2H, m). | 539 | General Route B. Procedure B3d using 3,6-dichloro-pyridazine. General modification Z4. General modification Z5. |
| 37 | 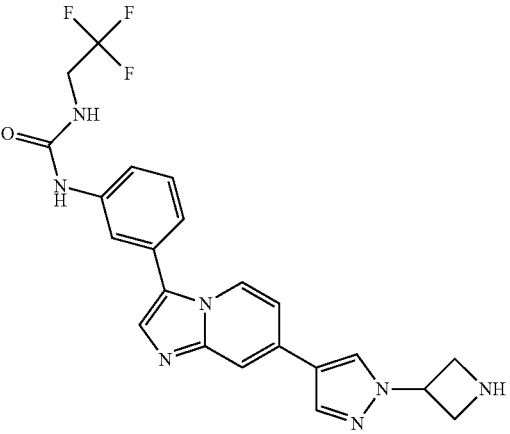 [SMILES: O=C(NCC(F)(F)F)Nc1cccc(-c2cnc3cc(-c4cnn(C5CNC5)c4)ccn23)c1]<br>1-{3-[7-(1-Azetidin-3-yl-1H-pyrazol-4-yl)-imidazo[1,2-a]pyridin-3-yl]phenyl}-3-(2,2,2-trifluoroethyl)urea | 1H NMR (400 MHz, Me-d3-OD): 8.54 (1H, d), 8.33 (1H, s), 8.09 (1H, s), 7.81 (1H, s), 7.76 (1H, s), 7.66 (1H, s), 7.47 (1H, t), 7.38 (1H, d), 7.29 (1H, d), 7.26 (1H, dd), 5.39-5.29 (1H, m), 4.18 (2H, t), 4.06-3.98 (2H, m), 3.98-3.89 (2H, m). | 456 | General Route B. Procedure B3a using 4-Bromo-1-(azetidin-3-yl)-1H-pyrazole trifluoroacetate. |

-continued

| Eg. | Compound and Name | N.M.R. Data | M.S | Procedure |
|---|---|---|---|---|
| 38 | 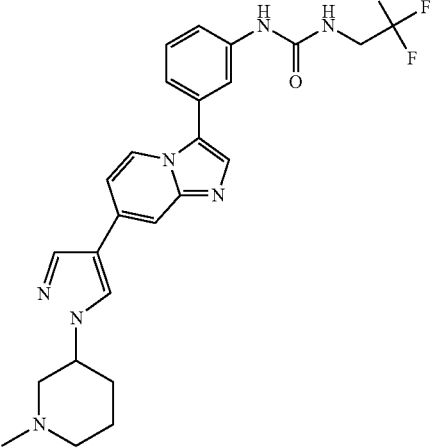<br>1-(3-{7-[1-(1-Methylpiperidin-3-yl)-1H-pyrazol-4-yl]imidazo[1,2-a]pyridin-3-yl}phenyl)-3-(2,2,2-trifluoroethyl)urea hydrochloride | 1H NMR (400 MHz, DMSO-d6): 10.94 (1H, d), 9.44-9.37 (1H, m), 8.85 (1H, s), 8.76 (1H, d), 8.46-8.39 (1H, m), 8.35 (1H, s), 8.11 (1H, d), 7.91 (1H, s), 7.80-7.72 (1H, m), 7.57-7.49 (2H, m), 7.35-7.27 (1H, m), 7.10 (1H, t), 4.87-4.77 (1H, m), 4.61 (1H, dd), 4.02-3.87 (3H, m), 3.81-3.81 (3H, m), 3.16-3.06 (1H, m), 2.87-2.79 (1H, m), 2.68 (2H, d), 2.56-2.46 (20H, m), 2.09-1.90 (2H, m). | 498 | General Route B. Procedure B3a using 4-bromo-1-(1-methylpiperidin-3-yl)-1H-pyrazole (X6). General modification Z5. |
| 39 | 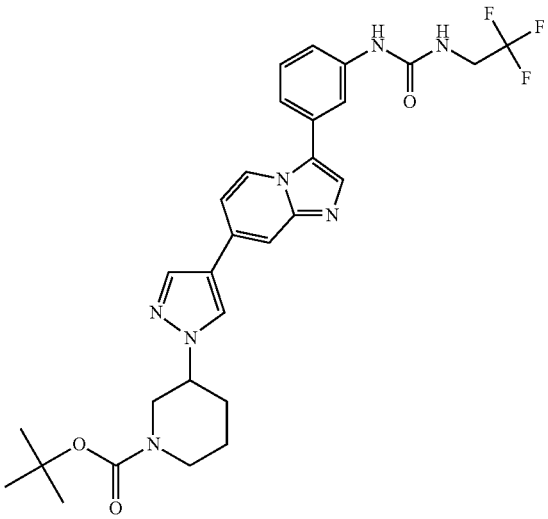 [SMILES: CC(C)(C)OC(=O)N1CCCC(n2cc(-c3ccn4c(-c5cccc(NC(=O)NCC(F)(F)F)c5)cnc4c3)cn2)C1]<br>3-[4-(3-{3-[3-(2,2,2-Trifluoroethyl)ureido]phenyl}imidazo[1,2-a]pyridin-7-yl)pyrazol-1-yl]piperidine-1-carboxylic acid tert-butyl ester formate | 1H NMR (400 MHz, Me-d3-OD): 8.57 (1H, d), 8.33 (1H, s), 8.22 (1H, s), 8.10-8.01 (1H, m), 7.85 (1H, s), 7.80 (1H, s), 7.73 (1H, s), 7.49 (1H, t), 7.39 (1H, d), 7.37-7.33 (1H, m), 7.31 (1H, d), 4.38-4.21 (2H, m), 4.04-3.89 (3H, m), 3.43-3.34 (1H, m), 3.03 (1H, t), 2.32-2.10 (2H, m), 1.90 (1H, s), 1.74-1.57 (1H, m), 1.49 (9H, s). | 584 | General Route B. Procedure B3a using 4-bromo-1-(1-tert-butoxycarbonyl-piperidin-3-yl)-1H-pyrazole (X7). |

| Eg. | Compound and Name | N.M.R. Data | M.S | Procedure |
|---|---|---|---|---|
| 40 | 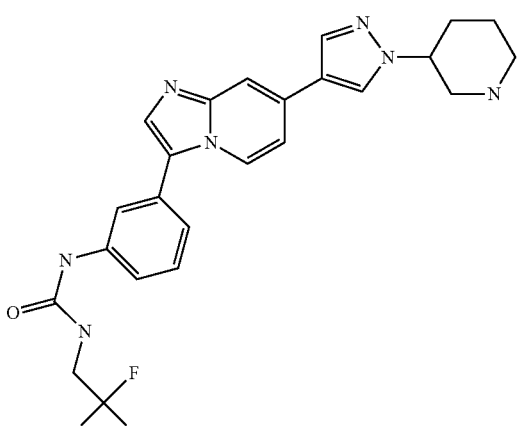<br>1-{3-[7-(1-Piperidin-3-yl-1H-pyrazol-4-yl)-imidazo[1,2-a]pyridin-3-yl]-phenyl}-3-(2,2,2-trifluoro-ethyl)-urea formate | 1H NMR (400 MHz, DMSO-d6): 9.57 (1H, s), 8.57-8.47 (2H, m), 8.30 (3H, s), 8.15-8.09 (1H, m), 7.93-7.86 (1H, m), 7.81 (1H, s), 7.69 (1H, d), 7.52 (1H, s), 7.48-7.39 (2H, m), 7.28 (1H, s), 7.22 (1H, d), 4.32-4.24 (1H, m), 3.93 (2H, s), 3.31 (1H, d), 2.98 (1H, d), 2.91 (1H, s), 2.61-2.54 (1H, m), 2.17 (1H, d), 1.95 (1H, d), 1.79 (1H, d), 1.60 (1H, d). | 484 | General Route B. Procedure B3a using 4-bromo-1-(1-tert-butoxycarbonyl-piperidin-3-yl)-1H-pyrazole (X7). Modification Z1a. |
| 41 | 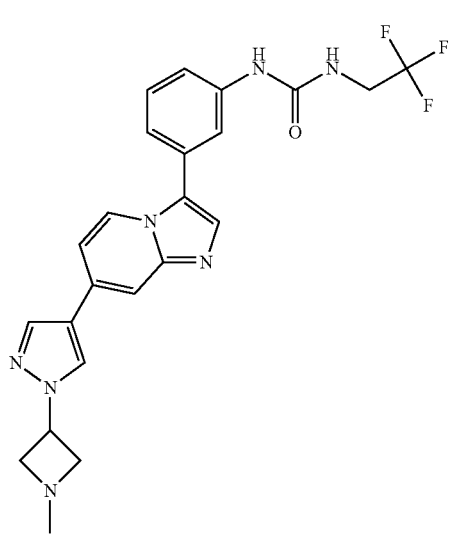 [SMILES: CN1CC(n2cc(-c3ccn4c(-c5cccc(NC(=O)NCC(F)(F)F)c5)cnc4c3)cn2)C1]<br>1-(3-{7-[1-(1-Methyl-azetidin-3-yl)-1H-pyrazol-4-yl]-imidazo[1,2-a]pyridin-3-yl}-phenyl)-3-(2,2,2-trifluoro-ethyl)-urea formate | 1H NMR (400 MHz, Me-d3-OD): 8.70 (1H, d), 8.44 (1H, s), 8.34 (1H, s), 8.03-7.90 (3H, m), 7.61-7.50 (2H, m), 7.40 (1H, d), 7.35 (1H, d), 5.49 (1H, quintet), 4.82-4.70 (2H, m), 4.70-4.56 (2H, m), 3.96 (2H, q), 3.15 (3H, s). | 470 | General Route B. Procedure B3a using 4-Bromo-1-(1-methylazetidin-3-yl)-1H-pyrazole hydrochloride. |

| Eg. | Compound and Name | N.M.R. Data | M.S | Procedure |
|---|---|---|---|---|
| 42 | 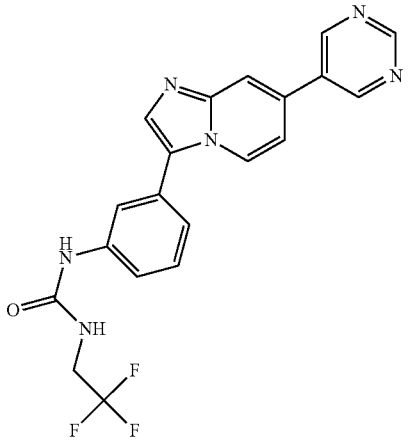 [SMILES: O=C(NCC(F)(F)F)Nc1cccc(-c2cnc3cc(-c4cncnc4)ccn23)c1]<br>1-[3-(7-Pyrimidin-5-yl-imidazo[1,2-a]pyridin-3-yl)-phenyl]-3-(2,2,2-trifluoro-ethyl)-urea hydrochloride | 1H NMR (400 MHz, Me-d3-OD): 9.25 (2H, s), 9.22 (1H, s), 8.73 (1H, d), 8.07 (1H, s), 7.87 (1H, d), 7.82 (1H, s), 7.51 (1H, t), 7.47-7.38 (2H, m), 7.34 (1H, d), 3.96 (2H, q). | 413 | General Route B. Procedure B3d using 5-bromopyrimidine; procedure Z5 |
| 43 | 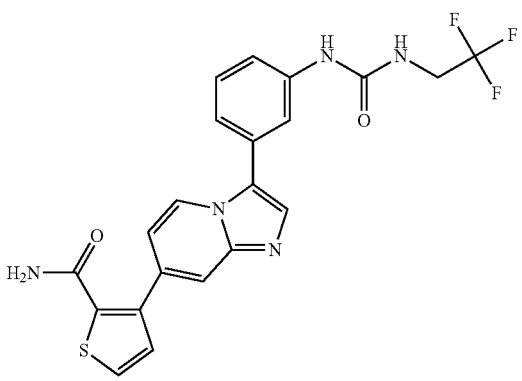 [SMILES: NC(=O)c1sccc1-c1ccn2c(-c3cccc(NC(=O)NCC(F)(F)F)c3)cnc2c1]<br>3-(3-{3-[3-(2,2,2-Trifluoroethyl)-ureido]-phenyl}-imidazo[1,2-a]pyridin-7-yl)-thiophene-2-carboxylic acid amide hydrochloride | 1H NMR (400 MHz, Me-d3-OD): 8.85-8.77 (1H, m), 8.22-8.16 (1H, m), 8.10-7.99 (2H, m), 7.79 (1H, d), 7.63 (1H, dd), 7.61-7.53 (1H, m), 7.46 (1H, dd), 7.43-7.35 (2H, m), 4.02-3.89 (2H, m). | 460 | General Route B. Procedure B3c using 3-bromothiophene-2-carboxamide; procedure Z5 |

| Eg. | Compound and Name | N.M.R. Data | M.S | Procedure |
|---|---|---|---|---|
| 44 | 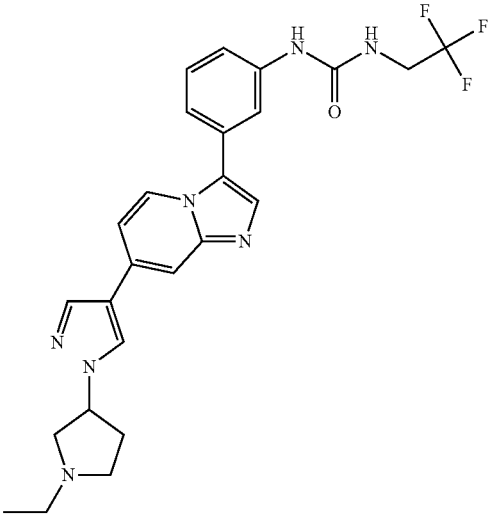 [SMILES: CCN1CCC(N/C=C(\C=N)c2ccn3c(-c4cccc(NC(=O)NCC(F)(F)F)c4)cnc3c2)C1]<br>1-(3-{7-[1-(1-Ethyl-pyrrolidin-3-yl)-1H-pyrazol-4-yl)-imidazo[1,2-a]pyridin-3-yl}-phenyl)-3-(2,2,2-trifluoro-ethyl)-urea | 1H NMR (400 MHz, Me-d3-OD): 8.54 (1H, d), 8.31 (1H, s), 8.02 (1H, s), 7.81 (1H, s), 7.75 (1H, s), 7.71-7.59 (1H, m), 7.55-7.41 (1H, m), 7.38 (1H, d), 7.29 (1H, d), 7.25 (1H, dd), 5.12-4.99 (1H, m), 3.95 (2H, q), 3.25 (1H, dd), 3.18-2.98 (2H, m), 2.98-2.84 (1H, m), 2.84-2.64 (2H, m), 2.62-2.46 (1H, m), 2.43-2.23 (1H, m), 1.23 (3H, t). | 498 | General Route B. Procedure B3a using 4-Bromo-1-(1-ethylpyrrolidin-3-yl)-1H-pyrazole (X8). |
| 45 | 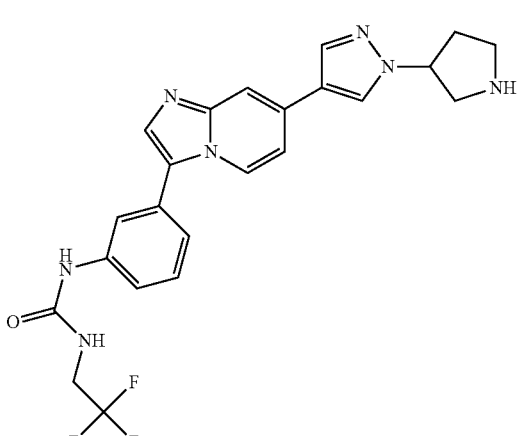<br>1-{3-[7-(1-Pyrrolidin-3-yl-1H-pyrazol-4-yl)-imidazo[1,2-a]pyridin-3-yl]-phenyl}-3-(2,2,2-trifluoro-ethyl)-urea | 1H NMR (400 MHz, Me-d3-OD): 8.51 (1H, d), 8.25 (1H, s), 8.00 (1H, s), 7.81 (1H, s), 7.73 (1H, s), 7.64 (1H, s), 7.59-7.43 (1H, m), 7.43-7.33 (1H, m), 7.28 (1H, d), 7.23 (1H, dd), 5.09-4.97 (1H, m), 4.86 (7H, s), 4.04-3.78 (2H, m), 3.65-3.57 (1H, m), 3.57-3.33 (3H, m), 3.17-3.03 (1H, m), 2.67 (1H, s), 2.51-2.19 (2H, m), 1.99-1.68 (1H, m). | 470 | General Route B. Procedure B3a using 4-Bromo-1-(1-tert-butoxycarbonyl-pyrrolidin-3-yl)-1H-pyrazole (X9). General Modification Z1a. |

-continued

| Eg. | Compound and Name | N.M.R. Data | M.S | Procedure |
|---|---|---|---|---|
| 46 | 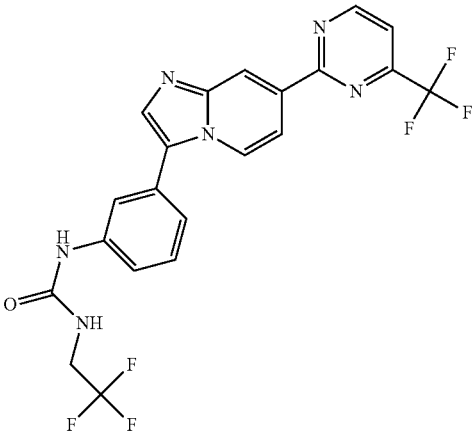 [SMILES: O=C(NCC(F)(F)F)Nc1cccc(-c2cnc3cc(-c4nccc(C(F)(F)F)n4)ccn23)c1]<br>1-(2,2,2-Trifluoro-ethyl)-3-{3-[7-(4-trifluoromethyl-pyrimidin-2-yl)-imidazo[1,2-a]pyridin-3-yl]-phenyl}-urea hydrochloride | 1H NMR (400 MHz, Me-d3-OD): 9.35 (1H, d), 9.04 (1H, s), 8.98 (1H, d), 8.54 (1H, dd), 8.31 (1H, s), 8.09-7.96 (2H, m), 7.60 (1H, t), 7.53-7.38 (2H, m), 3.96 (2H, q). | 481 | General Route B. Procedure B3d using 2-bromo-4-trifluoromethyl-pyrimidine; procedure Z5 |
| 47 | 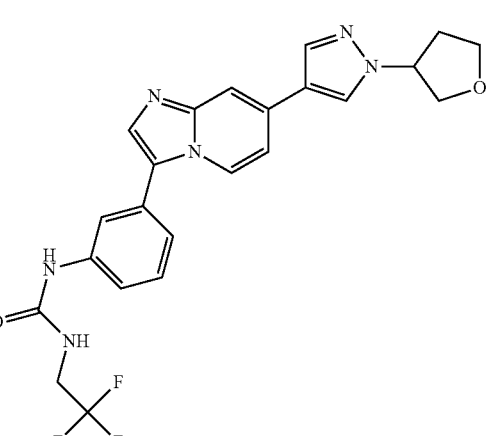<br>1-(3-{7-[1-(Tetrahydro-furan-3-yl)-1H-pyrazol-4-yl]-imidazo[1,2-a]pyridin-3-yl}-phenyl)-3-(2,2,2-trifluoro-ethyl)-urea hydrochloride | 1H NMR (400 MHz, Me-d3-OD): 8.74 (1H, d), 8.50 (1H, s), 8.20 (1H, s), 8.09 (1H, s), 8.08 (1H, s), 8.02 (1H, s), 7.79 (1H, dd), 7.57 (1H, t), 7.49-7.41 (1H, m), 7.38 (1H, d), 5.20-5.11 (1H, m), 4.19 (1H, q), 4.15-4.05 (2H, m), 4.03-3.89 (3H, m), 2.63-2.52 (1H, m), 2.48-2.36 (1H, m), 0.95-0.87 (1H, m). | 471 | General Route B. Procedure B3c using 4-bromo-1-(tetrahydrofuran-3-yl)-1H-pyrazole (X10); procedure Z5 |

| Eg. | Compound and Name | N.M.R. Data | M.S | Procedure |
|---|---|---|---|---|
| 48 | 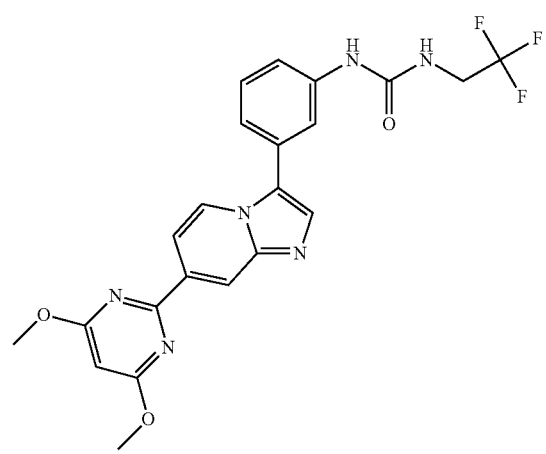 [SMILES: COc1cc(OC)nc(-c2ccn3c(-c4cccc(NC(=O)NCC(F)(F)F)c4)cnc3c2)n1]<br>1-{3-[7-(4,6-Dimethoxy-pyrimidin-2-yl)-imidazo[1,2-a]pyridin-3-yl]-phenyl}-3-(2,2,2-trifluoro-ethyl)-urea hydrochloride | 1H NMR (400 MHz, Me-d3-OD): 8.97-8.87 (2H, m), 8.49 (1H, dd), 8.26 (1H, s), 8.06 (1H, t), 7.59 (1H, t), 7.46 (1H, dd), 7.42 (1H, d), 6.27 (1H, s), 4.14 (6H, s), 3.96 (2H, q). | 473 | General Route B. Procedure B3d using 2-chloro-4,6-dimethoxy-pyrimidine. |
| 49 | 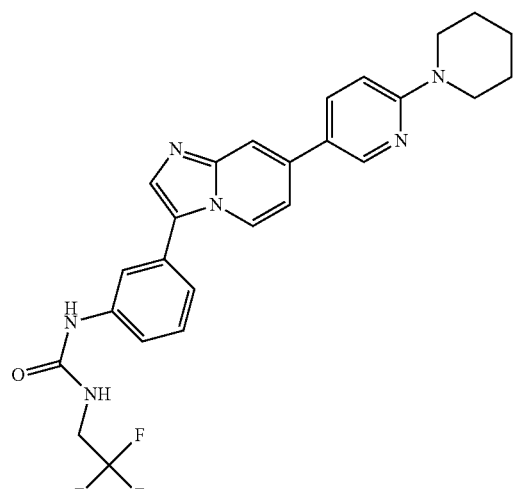<br>1-{3-[7-(3,4,5,6-Tetrahydro-2H-[1,2']bipyridinyl-5'-yl)-imidazo[1,2-a]pyridin-3-yl]-phenyl}-3-(2,2,2-trifluoro-ethyl)-urea hydrochloride | 1H NMR (400 MHz, Me-d3-OD): 8.61 (1H, d), 8.52 (1H, d), 7.97 (1H, dd), 7.83 (1H, t), 7.77 (1H, s), 7.70 (1H, s), 7.49 (1H, t), 7.45-7.37 (1H, m), 7.32 (2H, dd), 6.94 (1H, d), 3.96 (2H, q), 3.70-3.61 (4H, m), 1.79-1.64 (6H, m). | 495 | General route A, procedure A5b using 5-(4,4,5,5-Tetramethyl-[1,3,2]dioxaborolan-2-yl)-3,4,5,6-tetrahydro-2H-[1,2']bipyridinyl; procedure Z5 |

| Eg. | Compound and Name | N.M.R. Data | M.S | Procedure |
|---|---|---|---|---|
| 50 | 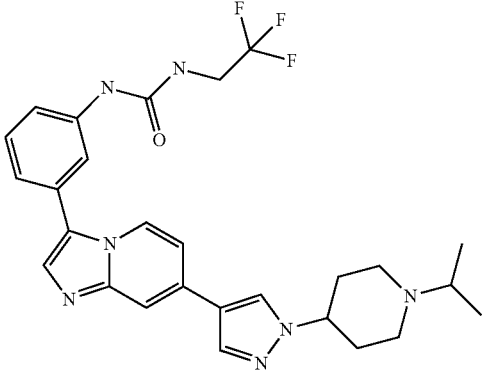 [SMILES: CC(C)N1CCC(n2cc(-c3ccn4c(-c5cccc(NC(=O)NCC(F)(F)F)c5)cnc4c3)cn2)CC1]<br>1-(3-{7-[1-(1-Isopropylpiperidin-4-yl)-1H-pyrazol-4-yl]imidazo[1,2-a]pyridin-3-yl}-phenyl)-3-(2,2,2-trifluoroethyl)urea hydrochloride | 1H NMR (400 MHz, Me-d3-OD): 8.65 (1H, d), 8.43 (1H, s), 8.15 (1H, s), 7.96-7.89 (2H, m), 7.86 (1H, s), 7.57-7.45 (2H, m), 7.42-7.37 (1H, m), 7.33 (1H, d), 4.77-4.60 (1H, m), 3.96 (2H, q), 3.74-3.58 (3H, m), 3.41-3.34 (2H, m), 2.56-2.37 (4H, m), 1.45 (6H, d). | 526 | General Route B. Procedure B3a using 4-Bromo-1-(1-isopropyl-piperidin-4-yl)-1H-pyrazole (X11). General Modification Z5. |
| 51 | 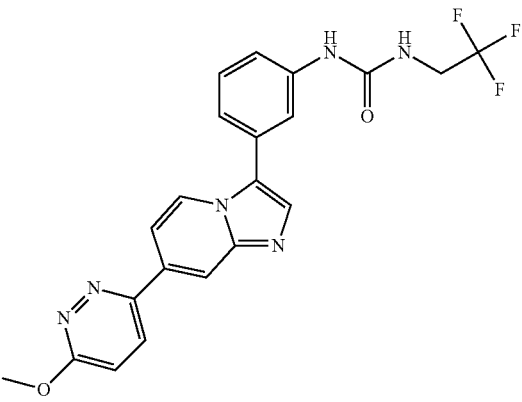 [SMILES: COc1ccc(-c2ccn3c(-c4cccc(NC(=O)NCC(F)(F)F)c4)cnc3c2)nn1]<br>1-{3-[7-(6-Methoxy-pyridazin-3-yl)-1,7-imidazo[1,2-a]pyridin-3-yl]-phenyl}-3-(2,2,2-trifluoro-ethyl)-urea | 1H NMR (400 MHz, DMSO-d6): 8.97 (1H, s), 8.69 (1H, d), 8.46 (1H, d), 8.41 (1H, s), 7.90-7.82 (2H, m), 7.78 (1H, s), 7.54-7.42 (2H, m), 7.38 (1H, d), 7.30 (1H, d), 6.86 (1H, t), 4.11 (3H, s), 4.03-3.89 (2H, m) | 443 | General route B, procedure B3d using 3-chloro-6-methoxy-pyridazine |
| 52 | 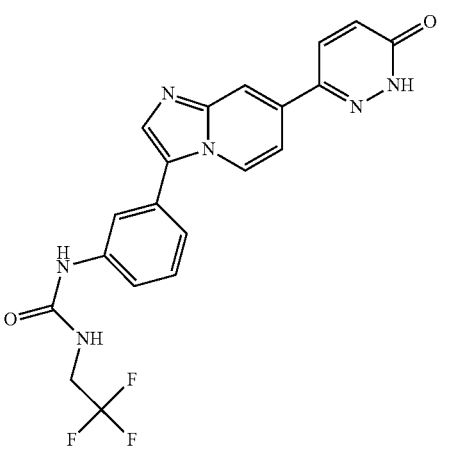 [SMILES: O=C(NCC(F)(F)F)Nc1cccc(-c2cnc3cc(-c4ccc(=O)[nH]n4)ccn23)c1]<br>1-{3-[7-(6-Oxo-1,6-dihydro pyridazin-3-yl)-imidazo[1,2-a]pyridin-3-yl]-phenyl}-3-(2,2,2-trifluoro-ethyl)-urea | 1H NMR (400 MHz, DMSO-d6): 9.50 (1H, s), 8.56 (1H, d), 8.24-8.12 (2H, m), 7.80 (2H, s), 7.58 (1H, d), 7.53-7.35 (3H, m), 7.25 (1H, d), 6.91 (1H, d), 4.02-3.88 (2H, m) | 429 | General route B, procedure B3d using 3-chloro-6-methoxy-pyridazine; procedure Z7. |

-continued

| Eg. | Compound and Name | N.M.R. Data | M.S | Procedure |
|---|---|---|---|---|
| 53 | 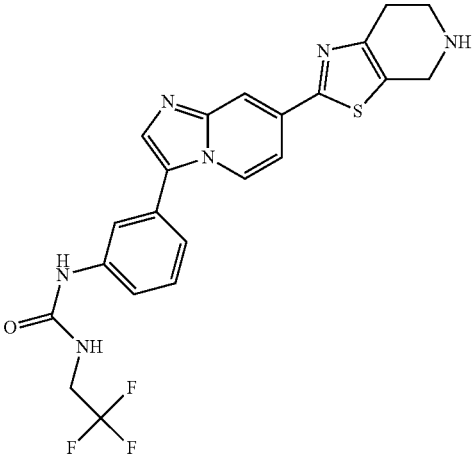 [SMILES: O=C(NCC(F)(F)F)Nc1cccc(-c2cnc3cc(-c4nc5c(s4)CNCC5)ccn23)c1]<br>1-{3-[7-(4,5,6,7-Tetrahydro-thiazolo[5,4-c]pyridin-2-yl)-imidazo[1,2-a]pyridin-3-yl]-phenyl}-3-(2,2,2-trifluoroethyl)-urea formate | 1H NMR (400 MHz, Me-d3-OD): 8.67 (1H, d), 8.34 (1H, s), 8.17 (1H, s), 7.92-7.80 (2H, m), 7.58 (1H, dd), 7.51 (1H, t), 7.44-7.37 (1H, m), 7.37-7.29 (1H, m), 4.48 (2H, s), 4.02-3.89 (2H, m), 3.62-3.47 (2H, m), 3.22-3.12 (2H, m). | 473 | General route B, procedure B3a using t-butyl 2-bromo-6,7-dihydro[1,3]thiazolo[5,4-C]pyridine-5(4H)-carboxylate followed by procedure Z1a |
| 54 | 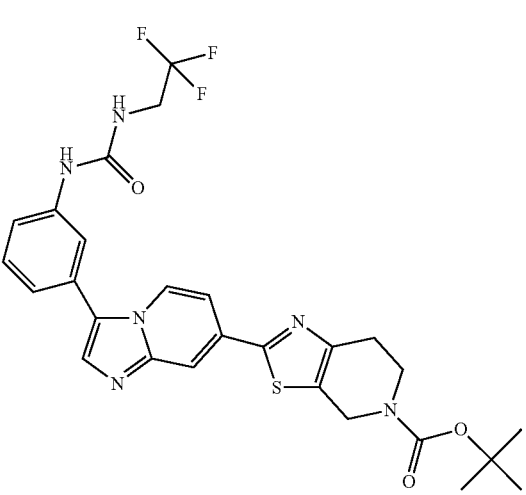 [SMILES: CC(C)(C)OC(=O)N1CCc2nc(-c3ccn4c(-c5cccc(NC(=O)NCC(F)(F)F)c5)cnc4c3)sc2C1]<br>2-(3-{3-[3-(2,2,2-Trifluoro-ethyl)-ureido]-phenyl}-imidazo[1,2-a]pyridin-7-yl)-1,4,6,7-tetrahydro-3lambda*4*-thiazolo[5,4-c]pyridine-5-carboxylic acid tert-butyl ester | 1H NMR (400 MHz, Me-d3-OD): 8.63 (1H, d), 8.12 (1H, s), 7.81 (2H, d), 7.59-7.38 (3H, m), 7.32 (1H, d), 4.75 (2H, s), 3.96 (2H, q), 3.89-3.72 (2H, m), 2.94 (2H, t), 1.53 (9H, s). | 573 | General route B, procedure B3d using 1-butyl 2-bromo-6,7-dihydro[1,3]thiazolo[5,4-C]pyridine-5(4H)-carboxylate |

| Eg. | Compound and Name | N.M.R. Data | M.S | Procedure |
|---|---|---|---|---|
| 55 | 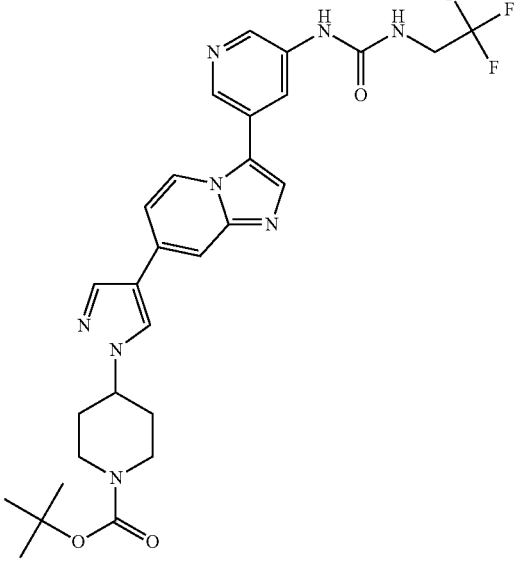<br>4-[4-(3-{5-[3-(2,2,2-Trifluoro-ethyl)-ureido]-pyridin-3-yl}-imidazo[1,2-a]pyridin-7-yl)-pyrazol-1-yl]-piperidine-1-carboxylic acid tert-butyl ester | 1H NMR (400 MHz, DMSO-d6): 9.20 (1H, s), 8.61 (1H, d), 8.56 (1H, d), 8.52 (1H, s), 8.48 (1H, d), 8.21 (1H, t), 8.13 (1H, s), 7.92 (1H, s), 7.82 (1H, s), 7.31 (1H, dd), 7.11 (1H, t), 4.44-4.35 (1H, m), 4.12-4.02 (2H, m), 4.02-3.91 (2H, m), 3.03-2.88 (2H, m), 2.13-2.02 (2H, m), 1.89-1.75 (2H, m), 1.44 (9H, s). | 585 | General route A: procedure A1; A2; & A4 using 1M Na$_2$CO$_3$, PdCl$_2$(PPh$_3$)$_3$, DME and 1-[5-(4,4,5,5-tetramethyl-[1,3,2]dioxaborolan-2-yl)-pyridin-3-yl]-3-(2,2,2-trifluoro-ethyl)-urea from procedure D4; B2, procedure B3c using 4-(4-bromo-pyrazol-1-yl)-pipe-ridine-1-carboxylic acid tert-butyl ester |
| 56 | 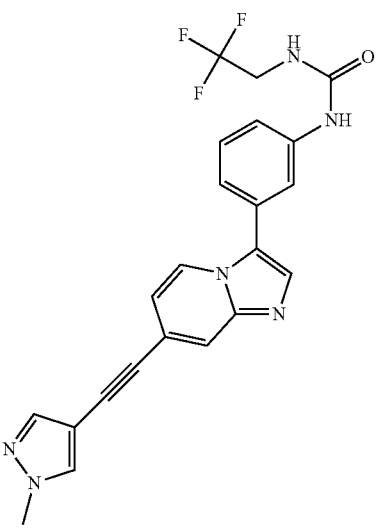 [SMILES: Cn1cc(C#Cc2ccn3c(-c4cccc(NC(=O)NCC(F)(F)F)c4)cnc3c2)cn1]<br>1-{3-[7-(1-Methyl-1H-pyrazol-4-ylethynyl)-imidazo[1,2-a]pyridin-3-yl]-phenyl}-3-(2,2,2-trifluoro-ethyl)-urea formate | 1H NMR (400 MHz, Me-d3-OD): 8.54 (1H, d), 8.14 (1H, s), 7.92 (1H, s), 7.89-7.79 (1H, m), 7.78 (1H, s), 7.71 (1H, s), 7.70 (1H, s), 7.49 (1H, t), 7.45-7.36 (1H, m), 7.35-7.25 (1H, m), 7.04 (1H, dd), 4.02-3.86 (5H, m). | 439 | General Route C. Procedure C3, procedure C2 using 1-methyl-4-trimethylsilanyl-ethynyl-1H-pyrazole (reaction time 3 hrs) |

| Eg. | Compound and Name | N.M.R. Data | M.S | Procedure |
|---|---|---|---|---|
| 57 | 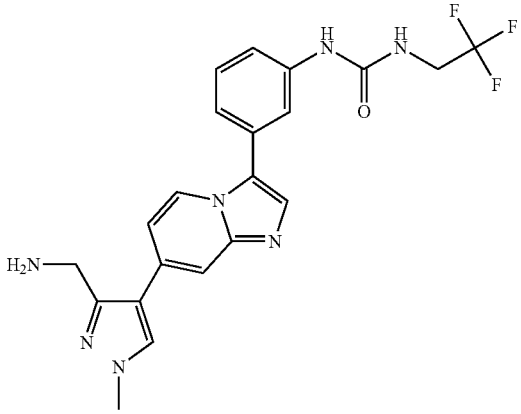 [SMILES: CN/C=C(\C(=N)CN)c1ccn2c(-c3cccc(NC(=O)NCC(F)(F)F)c3)cnc2c1]<br>1-{3-[7-(3-Aminomethyl-1-methyl-1H-pyrazol-4-yl)-imidazo[1,2-a]pyridin-3-yl]-phenyl}-3-(2,2,2-trifluoro-ethyl)-urea | 1H NMR (400 MHz, Me-d3-OD): 8.61 (1H, d), 8.05 (1H, s), 7.90 (1H, s), 7.72 (1H, s), 7.59 (1H, s), 7.49 (1H, t), 7.36-7.29 (2H, m), 7.13 (1H, dd), 4.30 (2H, s), 4.02-3.91 (5H, m). | 444 | General route B, procedure B3a using (4-bromo-1-methyl-1H-pyrazol-3-yl)methylamine |
| 58 | 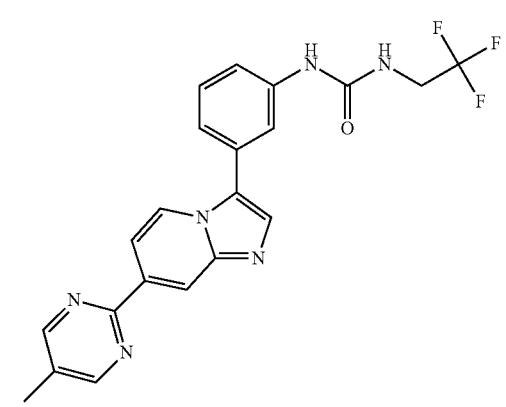<br>1-{3-[7-(5-Methyl-pyrimidin-2-yl)-imidazo[1,2-a]pyridin-3-yl]-phenyl}-3-(2,2,2-trifluoro-ethyl)-urea hydrochloride | 1H NMR (400 MHz, Me-d3-OD): 8.77 (2H, s), 8.73-8.63 (2H, m), 8.04 (1H, dd), 7.84 (1H, t), 7.81 (1H, s), 7.51 (1H, t), 7.48-7.40 (1H, m), 7.40-7.31 (1H, m), 3.96 (2H, q), 2.41 (3H, s). | 427 | General route B, procedure B3d 2-chloro-5-methyl-pyrimidine; procedure Z5 |
| 59 | 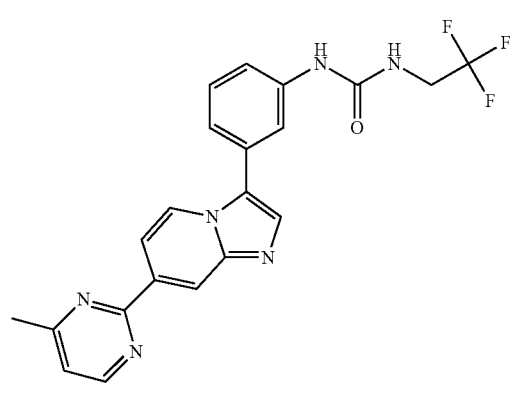 [SMILES: Cc1ccnc(-c2ccn3c(-c4cccc(NC(=O)NCC(F)(F)F)c4)cnc3c2)n1]<br>1-{3-[7-(4-Methyl-pyrimidin-2-yl)-imidazo[1,2-a]pyridin-3-yl]-phenyl}-3-(2,2,2-trifluoro-ethyl)-urea hydrochloride | 1H NMR (400 MHz, Me-d3-OD): 8.99 (1H, s), 8.93 (1H, d), 8.84 (1H, d), 8.55 (1H, dd), 8.29 (1H, s), 8.02 (1H, s), 7.59 (1H, t), 7.52 (1H, d), 7.46 (1H, d), 7.42 (1H, d), 3.96 (2H, q), 2.69 (3H, s). | [Adduct] + 427 | General route B, procedure B3a using 2-Chloro-4-Methyl-pyrimidine; procedure Z5 |

| Eg. | Compound and Name | N.M.R. Data | M.S | Procedure |
|---|---|---|---|---|
| 60 | 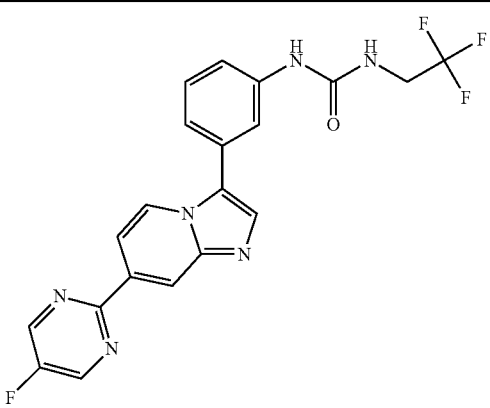<br>1-{3-[7-(5-Fluoro-pyrimidin-2-yl)-imidazo[1,2-a]pyridin-3-yl]-phenyl}-3-(2,2,2-trifluoro-ethyl)-urea hydrochloride | 1H NMR (400 MHz, DMSO-d6): 9.34-9.28 (1H, m), 9.17 (2H, s), 8.89 (1H, d), 8.76 (1H, s), 8.43 (1H, s), 8.23 (1H, dd), 7.89 (1H, s), 7.62-7.50 (2H, m), 7.38-7.30 (1H, m), 7.09-7.00 (1H, m), 3.99-3.92 (2H, m). | [Adduct] + 431 | General route B, procedure B3a using 2-Chloro-5-Fluoro-pyrimidine; procedure 25 |
| 61 | 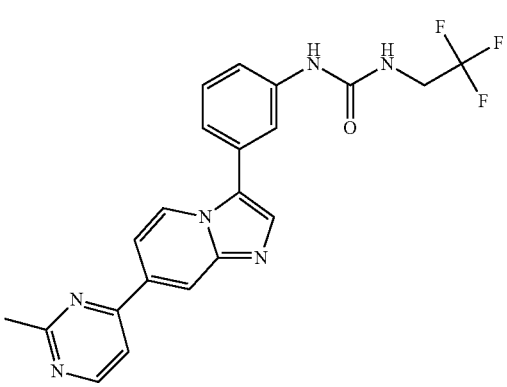 [SMILES: Cc1nccc(-c2ccn3c(-c4cccc(NC(=O)NCC(F)(F)F)c4)cnc3c2)n1]<br>1-{3-[7-(2-Methyl-pyrimidin-4-yl)-imidazo[1,2-a]pyridin-3-yl]-phenyl}-3-(2,2,2-trifluoro-ethyl)-urea hydrochloride | 1H NMR (400 MHz, DMSO-d6): 9.46 (1H, s), 8.97 (1H, d), 8.91 (1H, d), 8.79 (1H, s), 8.51 (1H, s), 8.27-8.16 (2H, m), 7.93 (1H, s), 7.60-7.52 (2H, m), 7.38-7.30 (1H, m), 7.18-7.08 (1H, m), 4.00-3.91 (2H, m), 2.78 (3H, s). | [Adduct] + 427 | General route B, procedure B3a using 4-Chloro-2-Methyl-pyrimidine; procedure Z5 |
| 62 | 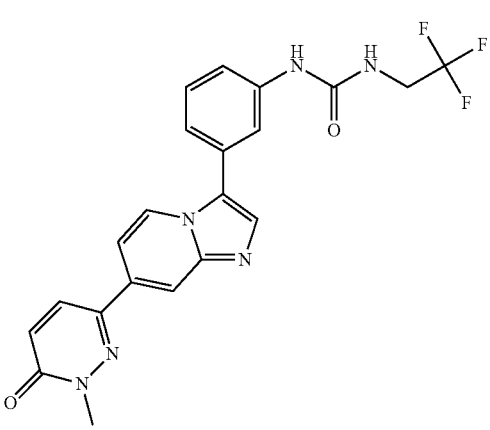 [SMILES: Cn1nc(-c2ccn3c(-c4cccc(NC(=O)NCC(F)(F)F)c4)cnc3c2)ccc1=O]<br>1-{3-[7-(1-Methyl-6-oxo-1,6-dihydro-pyridazin-3-yl)-imidazo[1,2-a]pyridin-3-yl]-phenyl}-3-(2,2,2-trifluoro-ethyl)-urea hydrochloride | 1H NMR (400 MHz, Me-d3-OD): 8.93-8.83 (1H, m), 8.43 (1H, s), 8.31-8.21 (2H, m), 8.12 (1H, dd), 8.06 (1H, s), 7.64-7.54 (1H, m), 7.46 (1H, d), 7.41 (1H, d), 7.20 (1H, d), 4.03-3.89 (5H, m) | 443 | General route B, procedure B3d using 6-chloro-2-methyl-2H-pyridazin-3-one; procedure Z5 |

-continued

| Eg. | Compound and Name | N.M.R. Data | M.S | Procedure |
|---|---|---|---|---|
| 63 | 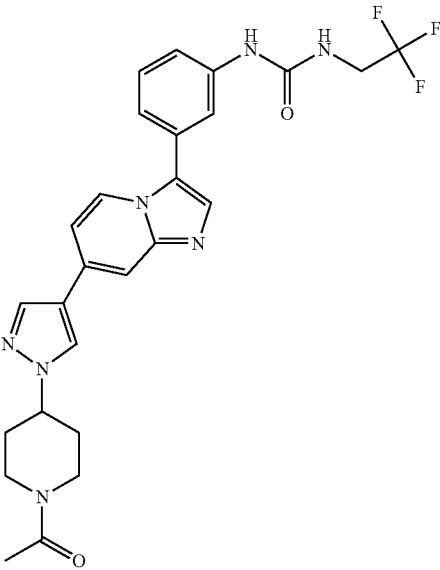 [SMILES: CC(=O)N1CCC(n2cc(-c3ccn4c(-c5cccc(NC(=O)NCC(F)(F)F)c5)cnc4c3)cn2)CC1]<br>1-(3-{7-[1-(1-Acetyl-piperidin-4-yl)-1H-pyrazol-4-yl]-imidazo[1,2-a]pyridin-3-yl}-phenyl)-3-(2,2,2-trifluoro-ethyl)-urea formate | 1H NMR (400 MHz, Me-d3-OD): 8.59 (1H, d), 8.34 (1H, s), 8.20 (2H, s), 8.06 (1H, s), 7.84 (2H, d), 7.75 (1H, s), 7.50 (1H, t), 7.44-7.34 (2H, m), 7.31 (1H, d), 4.69 (1H, d), 4.60-4.47 (1H, m), 4.11 (1H, d), 3.95 (2H, q), 3.40-3.35 (1H, m), 2.94-2.81 (1H, m), 2.20 (5H, d), 2.14-1.91 (2H, m). | 526 | General route B, procedure B3a using X12 |
| 64 | 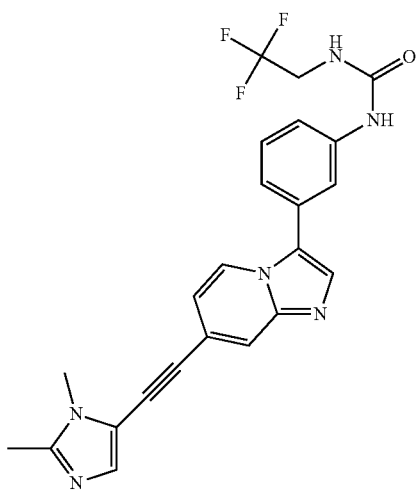 [SMILES: Cc1ncc(C#Cc2ccn3c(-c4cccc(NC(=O)NCC(F)(F)F)c4)cnc3c2)n1C]<br>1-{3-[7-(2,3-Dimethyl-3H-imidazol-4-ylethynyl)-imidazo[1,2-a]pyridin-3-yl]-phenyl}-3-(2,2,2-trifluoro-ethyl)-urea | 1H NMR (400 MHz, Me-d3-OD): 8.63-8.55 (1H, m), 7.82 (3H, d), 7.50 (1H, t), 7.47-7.37 (1H, m), 7.36-7.27 (2H, m), 7.10 (1H, dd), 3.95 (2H, q), 3.75 (3H, s), 2.46 (3H, s). | 453 | General Route C. Procedure C3 using 5-bromo-1,2-dimethyl-1H-imidazole (microwave 110° C. for 1 hr; solvent dioxane), procedure C4, procedure C2 using 5-ethynyl-1,2-dimethyl-1H-imidazole (reaction time 4 hrs) |

| Eg. | Compound and Name | N.M.R. Data | M.S | Procedure |
|---|---|---|---|---|
| 65 | 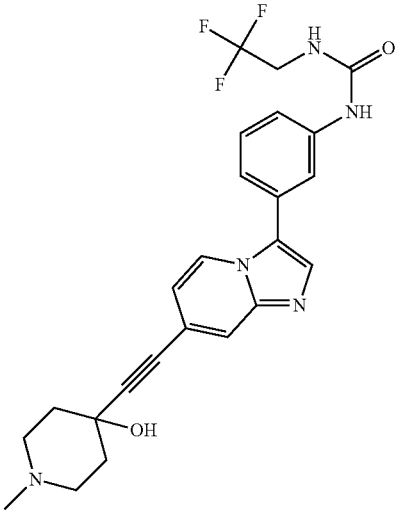 [SMILES: CN1CCC(O)(C#Cc2ccn3c(-c4cccc(NC(=O)NCC(F)(F)F)c4)cnc3c2)CC1]<br>1-{3-[7-(4-Hydroxy-1-methyl-piperidin-4-ylethynyl)-imidazo[1,2-a]pyridin-3-yl]-phenyl}-3-(2,2,2-trifluoro-ethyl)-urea formate | 1H NMR (400 MHz, Me-d3-OD): 8.55 (1H, d), 8.29 (2H, s), 7.85 (1H, s), 7.79 (1H, s), 7.74 (1H, s), 7.48 (1H, t), 7.38 (1H, d), 7.29 (1H, d), 7.01 (1H, d), 3.95 (2H, q), 3.59-3.35 (4H, m), 2.92 (3H, s), 2.38-2.25 (2H, m), 2.25-2.11 (2H, m). | 472 | General Route C. Procedure C2 using 4-ethynyl-1-methyl-piperidin-4-ol (reaction time 2 hrs) |
| 66 | 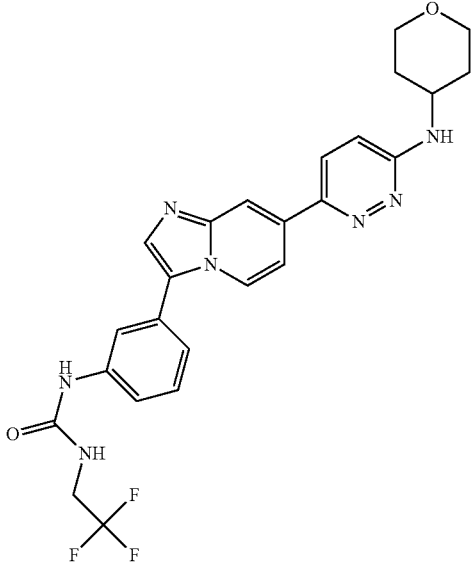 [SMILES: O=C(NCC(F)(F)F)Nc1cccc(-c2cnc3cc(-c4ccc(NC5CCOCC5)nn4)ccn23)c1]<br>1-(3-{7-[6-(Tetrahydro-pyran-4-ylamino)-pyridazin-3-yl]-imidazo[1,2-a]pyridin-3-yl}-phenyl)-3-(2,2,2-trifluoro-ethyl)-urea bis-hydrochloride | 1H NMR (400 MHz, Me-d3-OD): 8.98 (1H, d), 8.63 (1H, s), 8.57 (1H, d), 8.37-8.30 (1H, m), 8.17 (1H, dd), 8.10 (1H, s), 7.74 (1H, d), 7.60 (1H, t), 7.49-7.38 (2H, m), 4.06 (3H, d), 3.96 (2H, q), 3.62 (2H, t), 2.10 (2H, d), 1.84-1.70 (2H, m). | 512 | General Route B, Procedure Z4 using tetrahydro-pyran-4-ylamine and 3,6-dichloro-pyridazine - heated at 120° C. for 4 hours, Procedure B3d using boronate from Procedure B2—heated in microwave at 85° C. for 45 min, Procedure Z5 |

| Eg. | Compound and Name | N.M.R. Data | M.S | Procedure |
|---|---|---|---|---|
| 67 | 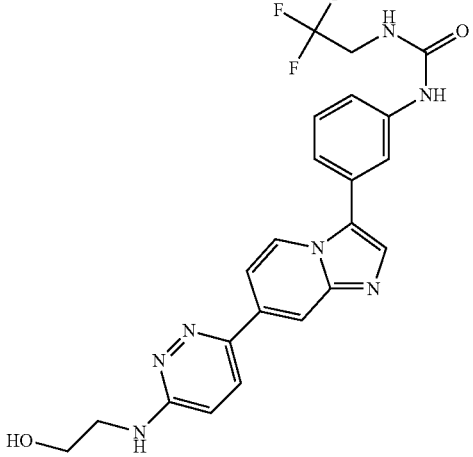<br>1-(3-{7-[6-(2-Hydroxy-ethylamino)-pyridazin-3-yl]-imidazo[1,2-a]pyridin-3-yl}-phenyl)-3-(2,2,2-trifluoro-ethyl)-urea | 1H NMR (400 MHz, DMSO-d6): 7.83 (1H, d), 7.30 (1H, s), 7.15 (1H, d), 7.06-6.90 (3H, m), 6.69 (1H, t), 6.62 (1H, d), 6.52 (1H, d), 6.26 (1H, d), 3.15 (2H, q), 3.01 (2H, t), 2.83 (2H, t) | 472 | General route B, procedure B3d using 2-(6-Chloro-pyridazin-3-ylamino)-ethanol (prepared using procedure Z6a) |
| 68 | 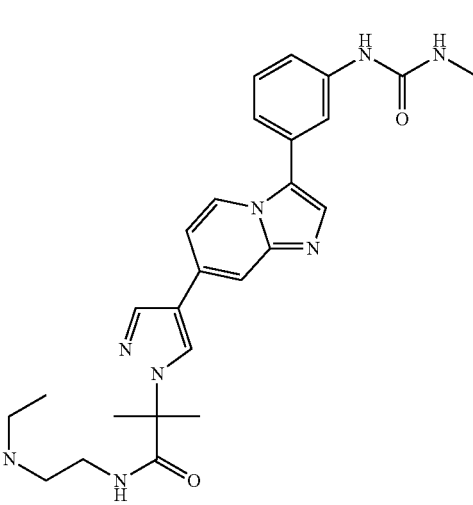<br>N-(2-Diethylamino-ethyl)-2-[4-(3 {3-[3-(2,2,2-trifluoro-ethyl)-ureido]-phenyl}-imidazo[1,2-a]pyridin-7-yl)-pyrazol-1-yl]-isobutyramide | 1H NMR (400 MHz, DMSO-d6): 8.95 (1H, s), 8.61 (1H, s), 8.55 (1H, d), 8.21 (1H, s), 7.97 (1H, s), 7.79 (1H, s), 7.71 (1H, s), 7.48-7.31 (3H, m), 7.25 (1H, d), 7.03 (1H, s), 6.84 (1H, t), 4.01-3.90 (2H, m), 3.08 (2H, q), 2.38 (6H, q), 1.77 (6H, s), 0.88 (6H, t). | 585 | General route A, procedure A5a, procedureZ2 followed by procedure Z6 |

| Eg. | Compound and Name | N.M.R. Data | M.S | Procedure |
|---|---|---|---|---|
| 69 | 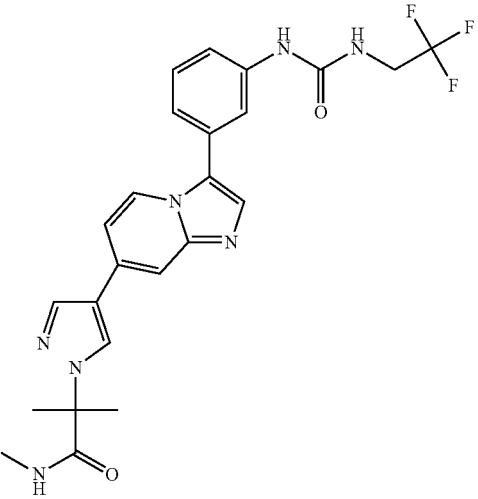 [SMILES: CNC(=O)C(C)(C)N/C=C(\C=N)c1ccn2c(-c3cccc(NC(=O)NCC(F)(F)F)c3)cnc2c1]<br>N-Methyl-2-[4-(3-{3-[3-(2,2,2-trifluoro-ethyl)-ureido]-phenyl}-imidazo[1,2-a]pyridin-7-yl)-pyrazol-1-yl]-isobutyramide | 1H NMR (400 MHz, Me-d3-OD): 8.60-8.52 (1H, m), 8.42 (1H, s), 8.14-8.07 (1H, m), 7.82 (2H, s), 7.70-7.64 (1H, m), 7.53-7.36 (2H, m), 7.36-7.27 (2H, m), 3.96 (2H, q), 2.78-2.71 (3H, m), 1.88 (6H, s). | 500 | General route A, procedure A5a, procedureZ2 followed by procedure Z6 using methylamine |
| 70 | 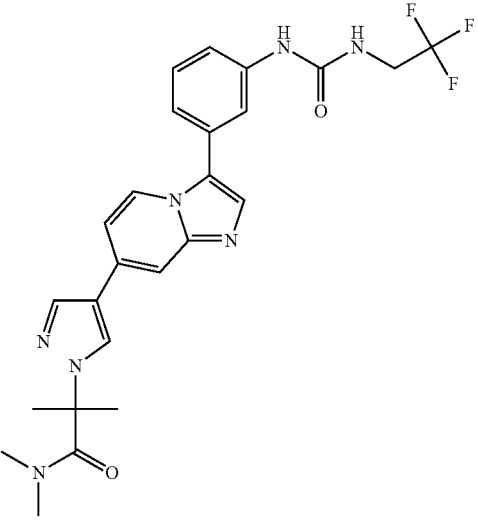 [SMILES: CN(C)C(=O)C(C)(C)N/C=C(\C=N)c1ccn2c(-c3cccc(NC(=O)NCC(F)(F)F)c3)cnc2c1]<br>N,N-Dimethyl-2-[4-(3-{3-[3-(2,2,2-trifluoro-ethyl)-ureido]-phenyl}-imidazo[1,2-a]pyridin-yl)-pyrazol-1-yl]-isobutyramide | 1H NMR (400 MHz, Me-d3-OD): 8.56 (1H, d), 8.42 (1H, s), 8.10 (1H, s), 7.82 (2H, s), 7.71-7.63 (1H, m), 7.48 (1H, t), 7.44-7.26 (3H, m), 3.96 (2H, q), 2.97 (3H, s), 2.55 (3H, s), 1.87 (6H, s). | 514 | General route A, procedure A5a, procedureZ2 followed by procedure Z6 using dimethylamine |

| Eg. | Compound and Name | N.M.R. Data | M.S | Procedure |
|---|---|---|---|---|
| 71 | 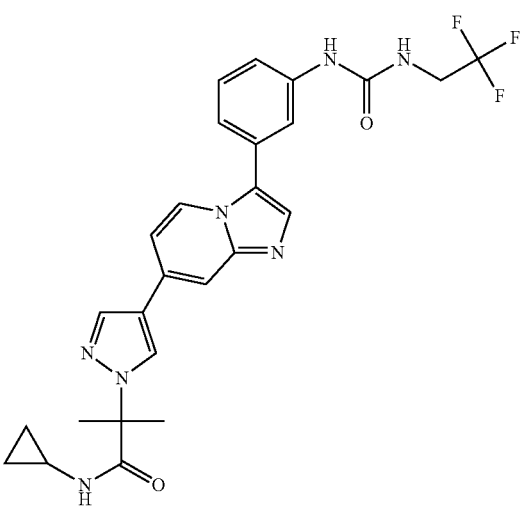 [SMILES: CC(C)(C(=O)NC1CC1)n1cc(-c2ccn3c(-c4cccc(NC(=O)NCC(F)(F)F)c4)cnc3c2)cn1]<br>N-Cyclopropyl-2-[4-(3-{3-[3-(2,2,2-trifluoro-ethyl)-ureido]-phenyl}-imidazo[1,2-a]pyridin-yl)-pyrazol-1-yl)-isobutyramide | 1H NMR (400 MHz, Me-d3-OD): 8.56 (1H, d), 8.39 (1H, s), 8.09 (1H, s), 7.81 (2H, d), 7.67 (1H, s), 7.54-7.36 (2H, m), 7.31 (2H, d), 3.96 (2H, q), 2.70-2.60 (1H, m), 1.86 (6H, s), 0.77-0.66 (2H, m), 0.55-0.45 (2H, m). | 526 | General route A, procedure A5a, procedureZ2 followed by procedure Z6 using cyclopropylamine |
| 72 | 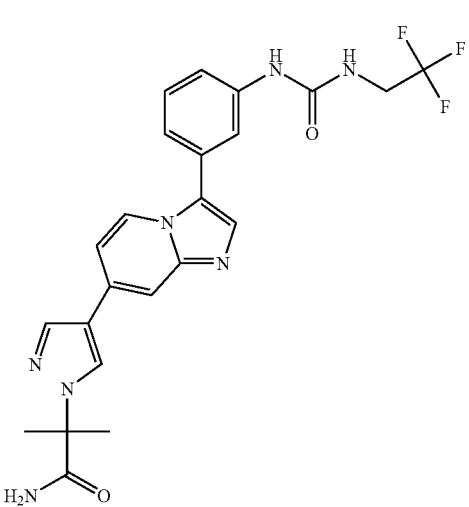 [SMILES: CC(C)(N/C=C(\C=N)c1ccn2c(-c3cccc(NC(=O)NCC(F)(F)F)c3)cnc2c1)C(N)=O]<br>2-[4-(3-{3-[3-(2,2,2-Trifluoro-ethyl)-ureido]-phenyl}-imidazo[1,2-a]pyridin-7-yl)-pyrazol-1-yl]-isobutyramide | 1H NMR (400 MHz, Me-d3-OD): 8.57 (1H, d), 8.47-8.40 (1H, m), 8.12 (1H, s), 7.82 (2H, s), 7.67 (1H, s), 7.49 (1H, t), 7.42-7.36 (1H, m), 7.35-7.29 (2H, m), 3.96 (2H, q), 1.91 (6H, s). | 486 | General route A, procedure A5a, procedureZ2 followed by procedure Z6 using ammonia |

-continued

| Eg. | Compound and Name | N.M.R. Data | M.S | Procedure |
|---|---|---|---|---|
| 73 | 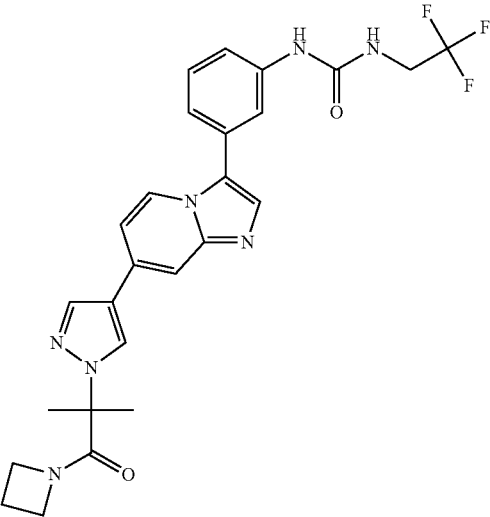 [SMILES: CC(C)(C(=O)N1CCC1)n1cc(-c2ccn3c(-c4cccc(NC(=O)NCC(F)(F)F)c4)cnc3c2)cn1]<br>1-(3-{7-[1-(2-Azetidin-1-yl-1,1-dimethyl-2-oxo-ethyl)-1H-pyrazol-4-yl]-imidazo[1,2-a]pyridin-3-yl}-phenyl)-3-(2,2,2-trifluoro-ethyl)-urea | 1H NMR (400 MHz, Me-d3-OD): 8.59-8.55 (1H, m), 8.45 (1H, s), 8.15 (1H, s), 7.83 (2H, s), 7.70-7.66 (1H, m), 7.49 (1H, t), 7.41-7.35 (1H, m), 7.35-7.29 (2H, m), 4.08-4.00 (2H, m), 3.96 (2H, q), 3.48-3.42 (2H, m), 2.14 (2H, t), 1.84 (6H, s). | 526 | General route A, procedure A5a, procedureZ2 followed by procedure Z6 using azetidine |
| 74 | 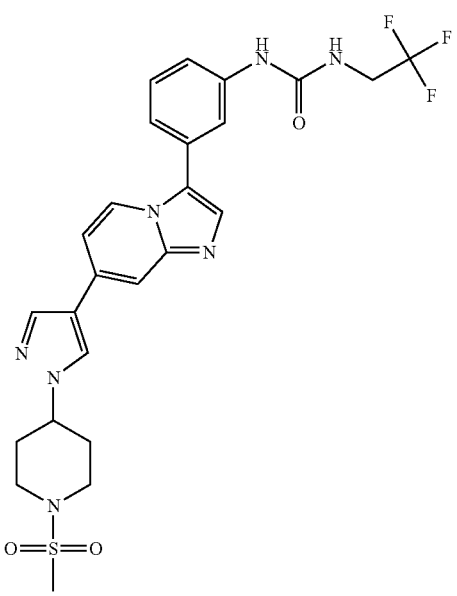 [SMILES: CS(=O)(=O)N1CCC(N/C=C(\C=N)c2ccn3c(-c4cccc(NC(=O)NCC(F)(F)F)c4)cnc3c2)CC1]<br>1-(3-{7-[1-(1-Methanesulfonyl-piperidin-4-yl)-1H-pyrazol-4-yl]-imidazo[1,2-a]pyridin-3-yl}-phenyl)-3-(2,2,2-trifluoro-ethyl)-urea | 1H NMR (400 MHz, Me-d3-OD): 8.55 (1H, d), 8.32 (1H, s), 8.04 (1H, s), 7.82 (1H, d), 7.77 (1H, s), 7.70-7.63 (1H, m), 7.53-7.43 (1H, m), 7.39 (1H, d), 7.35-7.23 (2H, m), 4.48-4.36 (1H, m), 4.02-3.85 (4H, m), 3.10-2.97 (2H, m), 2.97-2.88 (3H, m), 2.34-2.12 (4H, m). | 562 | General route B, procedure B3a using X13 |

| Eg. | Compound and Name | N.M.R. Data | M.S | Procedure |
|---|---|---|---|---|
| 75 | 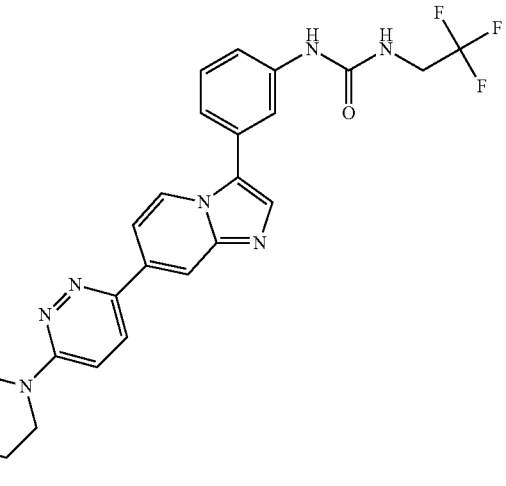<br>1-(3-{7-[6-(4-Amino-piperidin-1-yl)-pyridazin-3-yl]-imidazo[1,2-a]pyridin-3-yl}-phenyl)-3-(2,2,2-trifluoro-ethyl)-urea tris-trifluoroacetate | 1H NMR (400 MHz, Me-d3-OD): 8.90 (1H, d), 8.59 (1H, s), 8.35 (1H, d), 8.23 (1H, s), 8.20 (1H, d), 8.01 (1H, s), 7.76 (1H, d), 7.57 (1H, t), 7.50 (1H, d), 7.40 (1H, d), 4.62 (2H, d), 3.95 (2H, q), 3.64-3.49 (1H, m), 3.35 (2H, m, obscured) 2.24 (2H, d), 1.87-1.70 (2H, m). | 511 | General Route B, Procedure Z4 using 3,6-dichloro-pyridazine and piperidin-4-yl-carbamic acid tert-butyl ester— heated at 120° C. overnight, Procedure B3d using boronate from Procedure B2, heated in microwave at 120° C. for 20 min, Procedure Z1b |
| 76 | 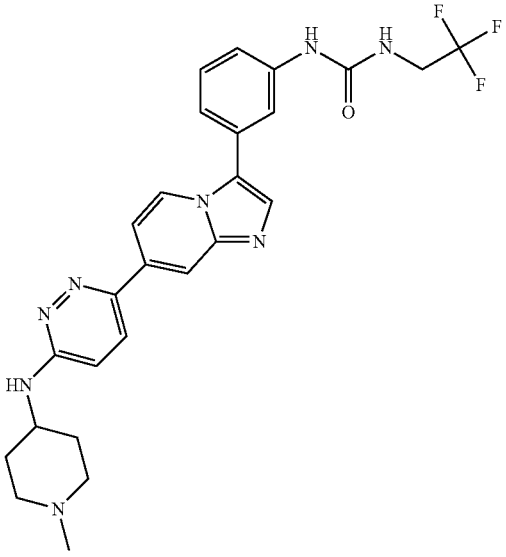 [SMILES: CN1CCC(Nc2ccc(-c3ccn4c(-c5cccc(NC(=O)NCC(F)(F)F)c5)cnc4c3)nn2)CC1]<br>1-(3-{7-[6-(1-Methyl-piperidin-4-ylamino)-pyridazin-3-yl]-imidazo[1,2-a]pyridin-3-yl}-phenyl)-3-(2,2,2-trifluoro-ethyl)-urea tri-hydrochloride | 1H NMR (400 MHz, Me-d3-OD): 8.97 (1H, d), 8.67 (1H, s), 8.62 (1H, d), 8.33 (1H, s), 8.19 (1H, d), 8.07 (1H, s), 7.80 (1H, d), 7.60 (1H, t), 7.49 (1H, d), 7.42 (1H, d), 4.25 (1H, t), 3.96 (2H, q), 3.71 (2H, d), 3.35 (obscured 2H, m), 3.04-2.93 (3H, m), 2.44 (2H, d), 2.08 (2H, q). | 525 | General Route B, Procedure Z4 using 3,6-dichloro-pyridazine and 1-methyl-piperidin-4-ylamine, heated at 120° C. for 2 h, Procedure B3d using boronate from Procedure B2, heated in microwave at 120° C. for 20 min, Procedure Z5 |

| Eg. | Compound and Name | N.M.R. Data | M.S | Procedure |
|---|---|---|---|---|
| 77 | 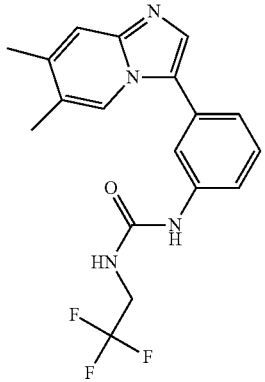 [SMILES: Cc1cc2ncc(-c3cccc(NC(=O)NCC(F)(F)F)c3)n2cc1C]<br>1-[3-(6,7-Dimethyl-imidazo[1,2-a]pyridin-3-yl)-phenyl]-3-(2,2,2-trifluoro-ethyl)-urea formate | 1H NMR (400 MHz, Me-d3-OD): 8.39 (1H, s), 8.25 (1H, s), 7.82 (1H, s), 7.71 (1H, s), 7.55-7.45 (2H, m), 7.41 (1H, d), 7.30 (1H, d), 3.95 (2H, q), 2.46 (3H, s), 2.35 (3H, s). | 363 | General route A, procedure A1 using 2-amino-4,5-dimethylpyridine followed by procedure A2, A3 and A4 using product from Procedure A2 |
| 78 | 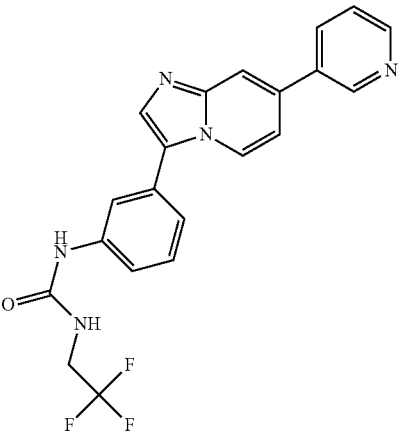 [SMILES: O=C(NCC(F)(F)F)Nc1cccc(-c2cnc3cc(-c4cccnc4)ccn23)c1]<br>1-[3-(7-Pyridin-3-yl-imidazo[1,2-a]pyridin-3-yl)-phenyl]-3-(2,2,2-trifluoro-ethyl)-urea | 1H NMR (DMSO-d6) 9.10 (1H, s), 8.98 (1H, s), 8.67 (1H, d), 8.64 (1H, d), 8.28 (1H, d), 8.14 (1H, s), 7.84 (1H, s), 7.81 (1H, s), 7.53 (1H, dd), 7.44 (3H, m), 7.29 (1H, m), 6.83 (1H, t), 3.96 (2H, m) | 410 | General route A, procedure A5c using pyridine 3-boronic acid |
| 79 | 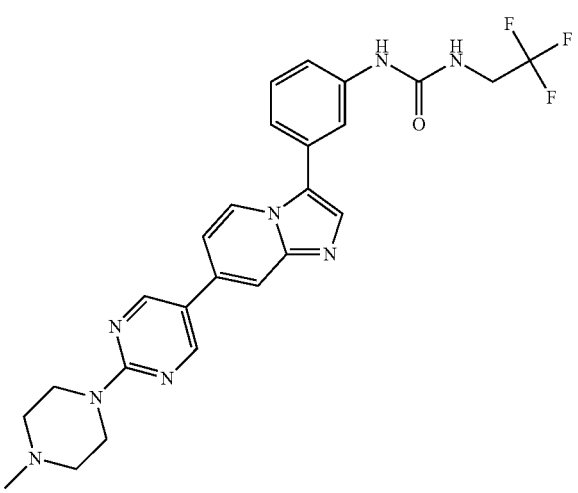 [SMILES: CN1CCN(c2ncc(-c3ccn4c(-c5cccc(NC(=O)NCC(F)(F)F)c5)cnc4c3)cn2)CC1]<br>1-(3-{7-[2-(4-Methyl-piperazin-1-yl)-pyrimidin-5-yl]-imidazo[1,2-a]pyridin-3-yl}-phenyl)-3-(2,2,2-trifluoro-ethyl)-urea bis-formate | 1H NMR (400 MHz, Me-d3-OD): 8.79 (2H, s), 8.60 (1H, d), 8.30 (2H, s), 7.84 (1H, s), 7.80 (1H, s), 7.77-7.66 (1H, m), 7.47 (1H, t), 7.36 (1H, d), 7.28 (2H, t), 4.14 (4H, s), 4.03-3.88 (2H, m), 3.22 (4H, s), 2.86 (3H, s). | 511 | General Route B, Procedure Z4 using 5-bromo-2-chloro-pyrimidine and 1-methyl piperazine heated at 120° C. for 3 hours, Procedure B3d using boronate from Procedure B2, heated in microwave at 120° C. for 20 min |

| Eg. | Compound and Name | N.M.R. Data | M.S | Procedure |
|---|---|---|---|---|
| 80 | 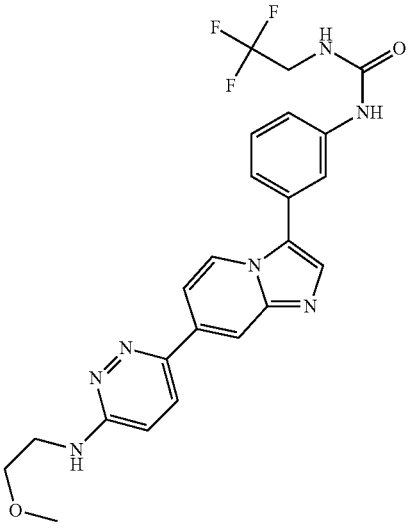 [SMILES: COCCNc1ccc(-c2ccn3c(-c4cccc(NC(=O)NCC(F)(F)F)c4)cnc3c2)nn1]<br>1-(3-{7-[6-(2-Methoxy-ethylamino)-pyridazin-3-yl]-imidazo[1,2-a]pyridin-3-yl}-phenyl)-3-(2,2,2-trifluoro-ethyl)-urea hydrochloride | 1H NMR (400 MHz, Me-d3-OD): 8.61 (1H, d), 8.10 (1H, s), 7.91 (1H, d), 7.86-7.78 (2H, m), 7.74 (1H, s), 7.48 (1H, t), 7.40 (1H, d), 7.30 (1H, d), 7.05 (1H, d), 3.93 (2H, q), 3.75-3.63 (4H, m), 3.42 (3H, s) | 486 | General route B, procedure B3d using (6-chloropyridazin-3-yl)-(2-methoxy-ethyl)-amine (prepared using a procedure analogous to Z6a) |
| 81 | 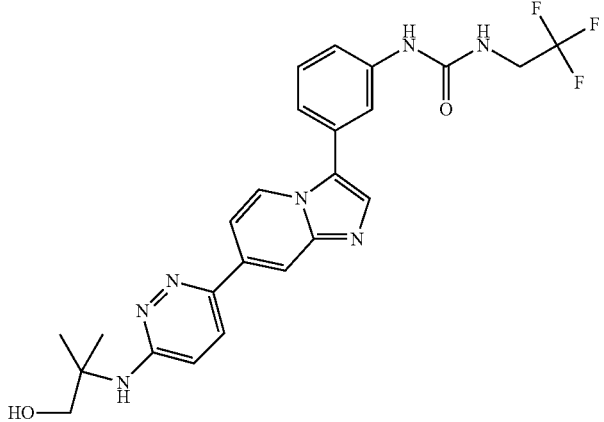 [SMILES: CC(C)(CO)Nc1ccc(-c2ccn3c(-c4cccc(NC(=O)NCC(F)(F)F)c4)cnc3c2)nn1]<br>1-(3-{7-[6-(2-Hydroxy-1,1-dimethyl-ethylamino)-pyridazin-3-yl]-1,7-dihydro-imidazo[1,2-a]pyridin-3-yl}-phenyl)-3-(2,2,2-trifluoro-ethyl)-urea hydrochloride | 1H NMR (400 MHz, Me-d3-OD): 8.51 (1H, d), 7.98 (1H, s), 7.87-7.70 (2H, m), 7.70-7.54 (2H, m), 7.48-7.31 (2H, m), 7.24 (1H, d), 6.99 (1H, d), 3.95 (2H, q), 3.77 (2H, s), 1.45 (6H, s) | 500 | General route B, procedure B3d using 2-(6-chloropyridazin-3-ylamino)-2-methyl-propan-1-ol (prepared using a procedure analogous to Z6a) |

| Eg. | Compound and Name | N.M.R. Data | M.S | Procedure |
|---|---|---|---|---|
| 82 | 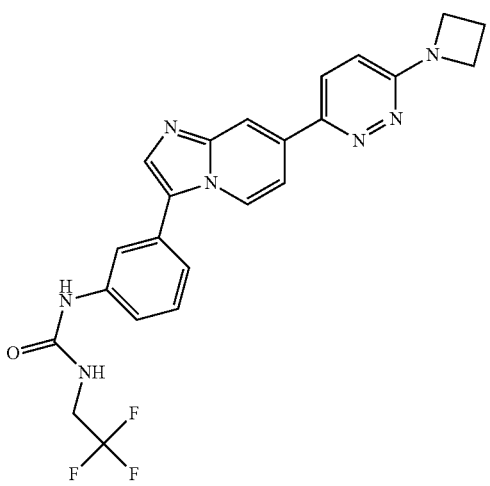 [SMILES: O=C(NCC(F)(F)F)Nc1cccc(-c2cnc3cc(-c4ccc(N5CCC5)nn4)ccn23)c1]<br>1-{3-[7-(6-Azetidin-1-yl-pyridazin-3-yl)-imidazo[1,2-a]pyridin-3-yl]-phenyl}-3-(2,2,2-trifluoro-ethyl)-urea hydrochloride | 1H NMR (400 MHz, Me-d3-OD): 8.95 (1H, d), 8.62 (1H, s), 8.56 (1H, d), 8.31 (1H, s), 8.15 (1H, d), 8.07 (1H, s), 7.70-7.53 (2H, m), 7.47 (1H, d), 7.41 (1H, d), 4.56 (4H, t), 3.96 (2H, q), 2.70 (2H, pent) | 468 | Procedure Z4 using azetidine |
| 83 | 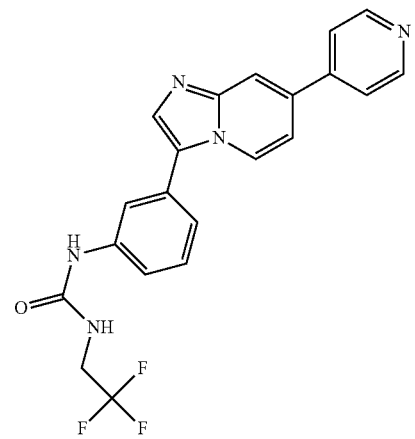 [SMILES: O=C(NCC(F)(F)F)Nc1cccc(-c2cnc3cc(-c4ccncc4)ccn23)c1]<br>1-[3-(7-Pyridin-4-yl-imidazo[1,2-a]pyridin-3-yl)-phenyl]-3-(2,2,2-trifluoro-ethyl)-urea | 1H NMR (DMSO-d6) 8.98 (1H, s), 8.67 (3H, m), 8.26 (1H, s), 7.92 (2H, d), 7.88 (1H, s), 7.82 (1H, s), 7.48 (4H, m), 6.87 (1H, t), 3.96 (2H, m) | 412 | General route A, procedure A5c using 4-(4,4,5,5-tetramethyl-[1,3,2]dioxaborolan-2-yl)-pyridine |
| 84 | 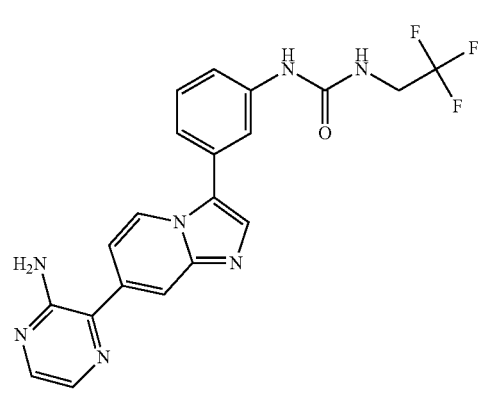 [SMILES: Nc1nccnc1-c1ccn2c(-c3cccc(NC(=O)NCC(F)(F)F)c3)cnc2c1]<br>1-{3-[7-(3-Amino-pyrazin-2-yl)-imidazo[1,2-a]pyridin-3-yl]-phenyl}-3-(2,2,2-trifluoro-ethyl)-urea | 1H NMR (400 MHz, Me-d3-OD): 8.69 (1H, d), 8.08-7.94 (3H, m), 7.86 (1H, s), 7.84-7.76 (1H, m), 7.54-7.45 (1H, m), 7.45-7.30 (3H, m), 3.95 (2H, q). | 428 | General route B, procedure B3a using 2-Amino-3-Chloropyrazine |

| Eg. | Compound and Name | N.M.R. Data | M.S | Procedure |
|---|---|---|---|---|
| 85 | 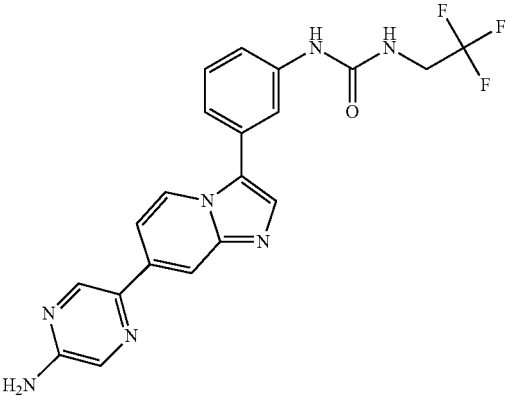 [SMILES: Nc1cnc(-c2ccn3c(-c4cccc(NC(=O)NCC(F)(F)F)c4)cnc3c2)cn1]<br>1-{3-[7-(5-Amino-pyrazin-2-yl)-imidazo[1,2-a]pyridin-3-yl]-phenyl}-3-(2,2,2-trifluoro-ethyl)-urea formate | 1H NMR (400 MHz, Me-d3-OD): 8.67-8.53 (2H, m), 8.19 (2H, d), 8.09 (1H, s), 7.84 (1H, s), 7.80-7.63 (2H, m), 7.49 (1H, t), 7.45-7.27 (2H, m), 3.95 (2H, q). | 428 | General route B, procedure B3a using 2-Amino-5-Bromo-Pyrazine |
| 86 | 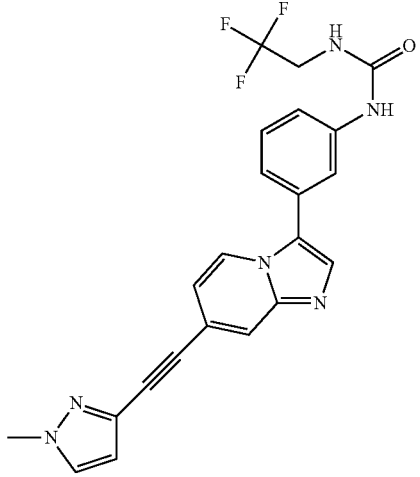 [SMILES: Cn1ccc(C#Cc2ccn3c(-c4cccc(NC(=O)NCC(F)(F)F)c4)cnc3c2)n1]<br>1-{3-[7-(1-Methyl-1H-pyrazol-3-ylethynyl)-imidazo[1,2-a]pyridin-3-yl]-phenyl}-3-(2,2,2-trifluoro-ethyl)-urea formate | 1H NMR (400 MHz, Me-d3-OD): 8.58 (1H, d), 8.15 (1H, s), 7.90-7.71 (3H, m), 7.67 (1H, d), 7.49 (1H, t), 7.42 (1H, d), 7.31 (1H, d), 7.09 (1H, d), 6.56 (1H, d), 4.02-3.88 (5H, m). | 439 | General Route C. Procedure C3 using 3-iodo-1-methyl-1H-pyrazole, Procedure C2 using 1-methyl-3-trimethylsilanyl-ethynyl-1H-pyrazole (reaction time 4.5 hrs) |

| Eg. | Compound and Name | N.M.R. Data | M.S | Procedure |
|---|---|---|---|---|
| 87 | 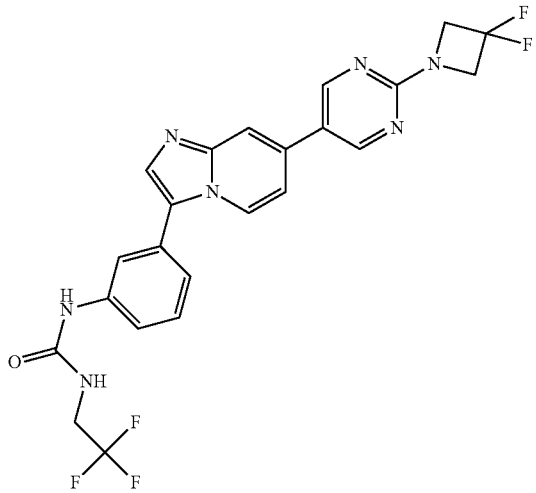 [SMILES: O=C(NCC(F)(F)F)Nc1cccc(-c2cnc3cc(-c4cnc(N5CC(F)(F)C5)nc4)ccn23)c1]<br>1-(3-{7-[2-(3,3-Difluoro-azetidin-1-yl)-pyrimidin-5-yl]-imidazo[1,2-a]pyridin-3-yl}-phenyl)-3-(2,2,2-trifluoro-ethyl)-urea bis-trifluoroacetate | 1H NMR (400 MHz, Me-d3-OD): 8.98 (2H, s), 8.85 (1H, d), 8.21 (1H, s), 8.17 (1H, s), 8.03 (1H, s), 7.85 (1H, d), 7.58 (1H, t), 7.46 (1H, d), 7.39 (1H, d), 4.60 (4H, t), 3.95 (2H, q). | 504 | General Route B, Procedure Z4 using 5-bromo-2-chloro-pyrimidine and 3,3-difluoro-azetidine hydrochloride heated at 120° C. for 3 hours, Procedure B3d using boronate from Procedure B2, heated in microwave at 120° C. for 40 min |
| 88 | 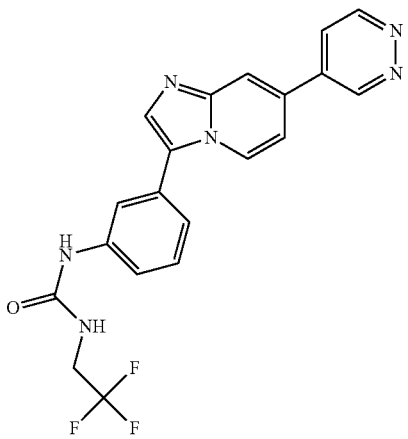 [SMILES: O=C(NCC(F)(F)F)Nc1cccc(-c2cnc3cc(-c4ccnnc4)ccn23)c1]<br>1-[3-(7-Pyridazin-4-yl-imidazo[1,2-a]pyridin-3-yl)-phenyl]-3-(2,2,2-trifluoro-ethyl)-urea formate | 1H NMR (400 MHz, DMSO-d6): 9.84 (1H, s), 9.33 (1H, d), 8.99 (1H, s), 8.71 (1H, d), 8.46 (1H, s), 8.24-8.12 (2H, m), 7.92 (1H, s), 7.83 (1H, s), 7.62-7.57 (1H, m), 7.51-7.43 (2H, m), 7.30 (1H, d), 6.87 (1H, t), 4.00-3.91 (2H, m). | 413 | General route B, procedure B3a using 4-Bromopyridazine |

| Eg. | Compound and Name | N.M.R. Data | M.S | Procedure |
|---|---|---|---|---|
| 89 | 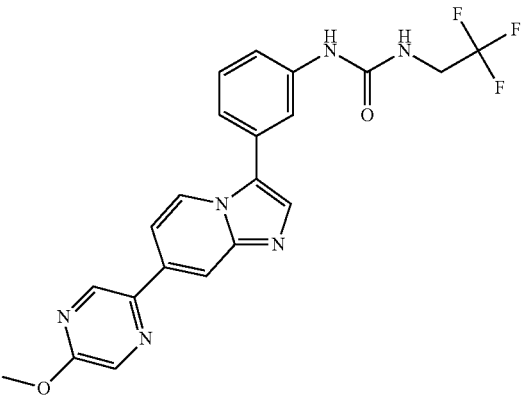 [SMILES: COc1cnc(-c2ccn3c(-c4cccc(NC(=O)NCC(F)(F)F)c4)cnc3c2)cn1]<br>1-{3-[7-(5-Methoxy-pyrazin-2-yl)-imidazo[1,2-a]pyridin-3-yl]-phenyl}-3-(2,2,2-trifluoro-ethyl)-urea | 1H NMR (400 MHz, DMSO-d6): 9.05 (1H, s), 8.96 (1H, s), 8.70-8.62 (1H, m), 8.45 (1H, s), 8.38 (1H, s), 7.87-7.80 (1H, m), 7.80-7.66 (2H, m), 7.47 (2H, d), 7.29 (1H, d), 6.85 (1H, t), 4.05-3.91 (5H, m). | 443 | General route B, procedure B3a using 2-bromo-5-methoxypyrazine |
| 90 | 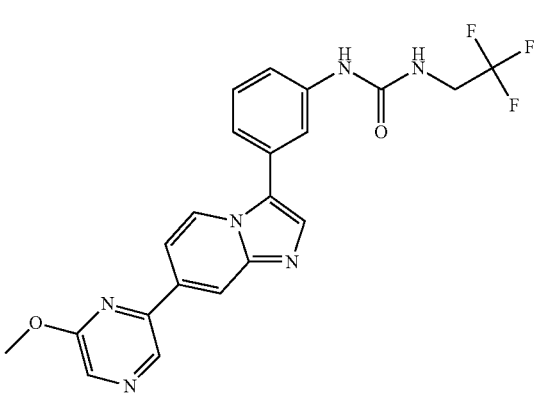 [SMILES: COc1cncc(-c2ccn3c(-c4cccc(NC(=O)NCC(F)(F)F)c4)cnc3c2)n1]<br>1-{3-[7-(6-Methoxy-pyrazin-2-yl)-imidazo[1,2-a]pyridin-3-yl]-phenyl}-3-(2,2,2-trifluoro-ethyl)-urea formate | 1H NMR (400 MHz, DMSO-d6): 9.08-9.02 (1H, m), 8.99 (1H, s), 8.73-8.65 (1H, m), 8.54 (1H, s), 8.33 (1H, s), 8.19-8.12 (1H, m), 7.89 (1H, s), 7.86-7.76 (2H, m), 7.51-7.42 (2H, m), 7.31 (1H, d), 6.89 (1H, t), 4.08 (3H, s), 4.02-3.89 (2H, m). | 443 | General route B, procedure B3a using 2-iodo-6-methoxypyrazine |
| 91 | 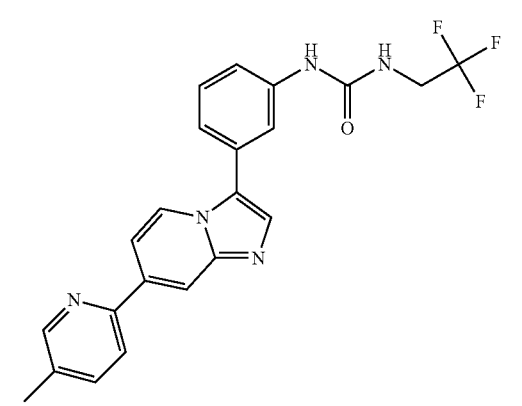 [SMILES: Cc1ccc(-c2ccn3c(-c4cccc(NC(=O)NCC(F)(F)F)c4)cnc3c2)nc1]<br>1-{3-[7-(5-Methyl-pyridin-2-yl)-imidazo[1,2-a]pyridin-3-yl]-phenyl}-3-(2,2,2-trifluoro-ethyl)-urea formate | 1H NMR (400 MHz, Me-d3-OD): 8.67 (1H, d), 8.54 (1H, s), 8.26 (1H, s), 7.94 (1H, d), 7.89-7.75 (3H, m), 7.72 (1H, d), 7.50 (1H, t), 7.42 (1H, d), 7.33 (1H, d), 3.96 (2H, q), 2.43 (3H, s). | 426 | General Route B. Procedure B3c using 2-bromo-5-methyl-pyridine |

| Eg. | Compound and Name | N.M.R. Data | M.S | Procedure |
|---|---|---|---|---|
| 92 | 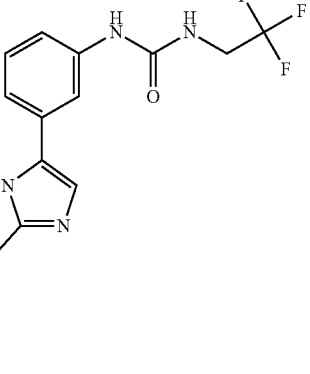<br>1-{3-[7-(5-Hydroxymethyl-pyridin-2-yl)-imidazo[1,2-a]pyridin-3-yl]-phenyl}-3-(2,2,2-trifluoro-ethyl)-urea formate | 1H NMR (400 MHz, Me-d3-OD): 8.68 (2H, d), 8.30 (1H, s), 8.20 (1H, s), 8.04 (1H, d), 7.95 (1H, d), 7.84 (1H, s), 7.81 (1H, s), 7.76 (1H, d), 7.50 (1H, t), 7.43 (1H, d), 7.34 (1H, d), 4.74 (2H, s), 3.96 (2H, q). | 442 | General Route B. Procedure B3c using (6-chloro-pyridin-3-yl)-methanol |
| 93 | 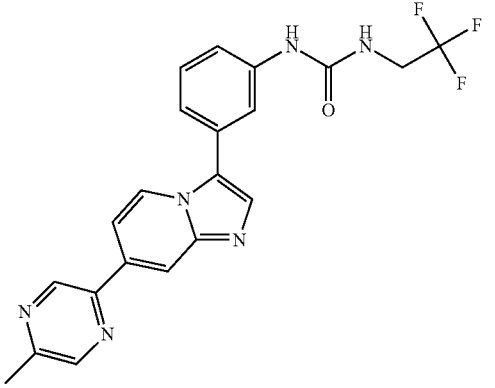 [SMILES: Cc1cnc(-c2ccn3c(-c4cccc(NC(=O)NCC(F)(F)F)c4)cnc3c2)cn1]<br>1-{3-[7-(5-Methyl-pyrazin-2-yl)-imidazo[1,2-a]pyridin-3-yl]-phenyl}-3-(2,2,2-trifluoro-ethyl)-urea | 1H NMR (400 MHz, Me-d3-OD): 9.12 (1H, s), 8.72-8.59 (2H, m), 8.37 (1H, s), 8.15 (1H, s), 7.89-7.72 (3H, m), 7.49 (1H, t), 7.41 (1H, d), 7.32 (1H, d), 3.96 (2H, q), 2.62 (3H, s) | 427 | General route B, procedure B3a using 2-Bromo-5-Methylpyrazine |
| 94 | 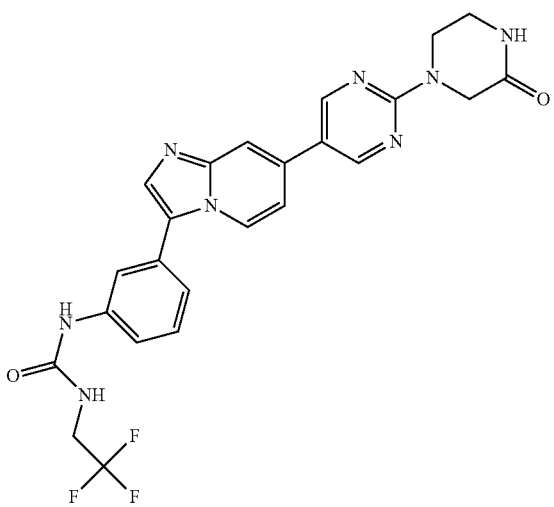 [SMILES: O=C1CN(c2ncc(-c3ccn4c(-c5cccc(NC(=O)NCC(F)(F)F)c5)cnc4c3)cn2)CCN1]<br>1-(3-{7-[2-(3-Oxo-piperazin-1-yl)-pyrimidin-5-yl]-imidazo[1,2-a]pyridin-3-yl}-phenyl)-3-(2,2,2-trifluoro-ethyl)-urea hydrochloride | 1H NMR (400 MHz, Me-d3-OD): 8.99 (2H, s), 8.89-8.80 (1H, m), 8.18 (2H, d), 8.05 (1H, s), 7.86 (1H, d), 7.58 (1H, t), 7.46 (1H, d), 7.39 (1H, d), 4.50 (2H, s), 4.18 (2H, t), 3.96 (2H, q), 3.49 (2H, t). | 511 | General Route B, Procedure Z4 using 5-bromo-2-chloropyrimidine and piperazin-2-one heated at 120° C. for 3 hours, Procedure B3d using boronate from Procedure B2, heated in microwave at 120° C. for 30 min, Procedure Z5 |

-continued

| Eg. | Compound and Name | N.M.R. Data | M.S | Procedure |
| --- | --- | --- | --- | --- |
| 95 | 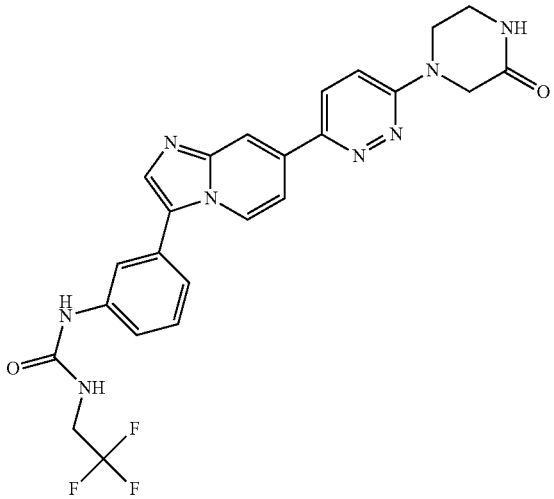 [SMILES: O=C1CN(c2ccc(-c3ccn4c(-c5cccc(NC(=O)NCC(F)(F)F)c5)cnc4c3)nn2)CCN1]<br>1-(3-{7-[6-(3-Oxo-piperazin-1-yl)-pyridazin-3-yl]-imidazo[1,2-a]pyridin-3-yl}-phenyl)-3-(2,2,2-trifluoro-ethyl)-urea bis-hydrochloride | 1H NMR (400 MHz, Me-d3-OD): 8.97 (1H, d), 8.66 (1H, s), 8.65-8.57 (1H, m), 8.31 (1H, s), 8.28-8.17 (1H, m), 8.08 (1H, s), 8.02 (1H, d), 7.60 (1H, t), 7.46 (1H, d), 7.42 (1H, d), 4.44 (2H, s), 4.15-4.02 (2H, m), 3.96 (2H, q), 3.63 (2H, t). | 511 | General Route B, Procedure Z4 using 3,6-dichloro-pyridazine and piperazin-2-one, heated at 120° C. for 3 hours, Procedure B3d using boronate from Procedure B2, heated in microwave at 120° C. for 30 min, Procedure Z5 |
| 96 | 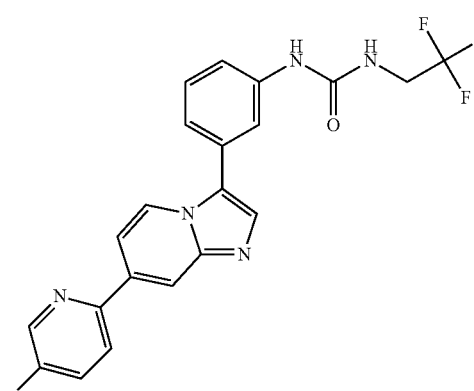<br>1-{3-[7-(5-Fluoro-pyridin-2-yl)-imidazo[1,2-a]pyridin-3-yl]-phenyl}-3-(2,2,2-trifluoro-ethyl)-urea bis-hydrochloride | 1H NMR (400 MHz, Me-d3-OD): 8.90 (1H, d), 8.72 (1H, d), 8.63 (1H, s), 8.30 (1H, dd), 8.23 (2H, d), 8.05 (1H, s), 7.90-7.79 (1H, m), 7.59 (1H, t), 7.47 (1H, d), 7.41 (1H, d), 3.96 (2H, q). | 430 | General Route B, Procedure B3d using boronate from Procedure B2 and 2-chloro-5-fluoro pyridine, heated in microwave at 120° C. for 30 min, Procedure Z5 |

| Eg. | Compound and Name | N.M.R. Data | M.S | Procedure |
|---|---|---|---|---|
| 97 | 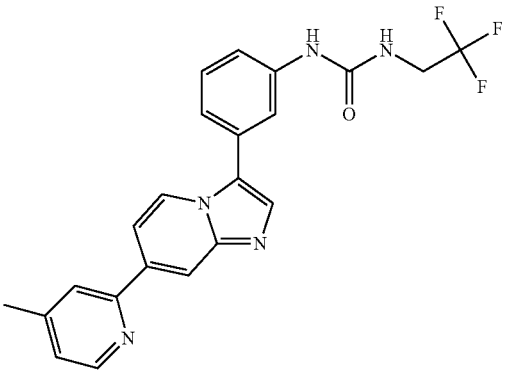<br>1-{3-[7-(4-Methyl-pyridin-2-yl)-imidazo[1,2-a]pyridin-3-yl]-phenyl}-3-(2,2,2-trifluoro-ethyl)-urea bis-hydrochloride | 1H NMR (400 MHz, Me-d3-OD): 8.97 (1H, d), 8.73 (1H, d), 8.66 (1H, s), 8.31 (1H, s), 8.23 (1H, s), 8.16 (1H, dd), 8.07 (1H, s), 7.64 (1H, t), 7.59 (1H, d), 7.48 (1H, d), 7.43 (1H, d), 3.96 (2H, q), 2.65 (3H, s). | 426 | General Route B, Procedure B3d using boronate from Procedure B2 and 2-chloro-5-methylpyridine, heated in microwave at 120° C. for 30 min, Procedure Z5 |
| 98 | 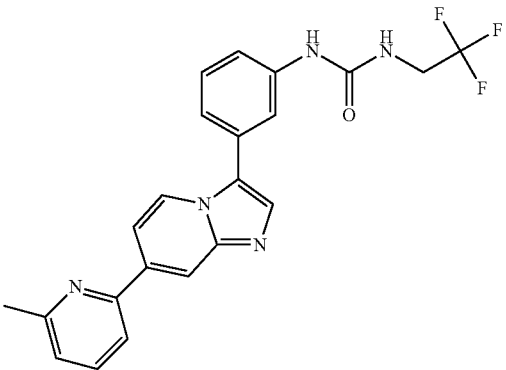 [SMILES: Cc1cccc(-c2ccn3c(-c4cccc(NC(=O)NCC(F)(F)F)c4)cnc3c2)n1]<br>1-{3-[7-(6-Methyl-pyridin-2-yl)-imidazo[1,2-a]pyridin-3-yl]-phenyl}-3-(2,2,2-trifluoro-ethyl)-urea bis-hydrochloride | 1H NMR (400 MHz, Me-d3-OD): 8.99 (1H, d), 8.67 (1H, s), 8.33 (1H, s), 8.27 (1H, t), 8.18 (1H, d), 8.16-8.11 (1H, m), 8.08 (1H, s), 7.74 (1H, d), 7.60 (1H, t), 7.48 (1H, d), 7.43 (1H, d), 3.96 (2H, q), 2.83 (3H, s). | 426 | General Route B, Procedure B3d using boronate from Procedure B2 and 2-chloro-6-methyl pyridine, heated in microwave at 120° C. for 30 min, Procedure Z5 |
| 99 | 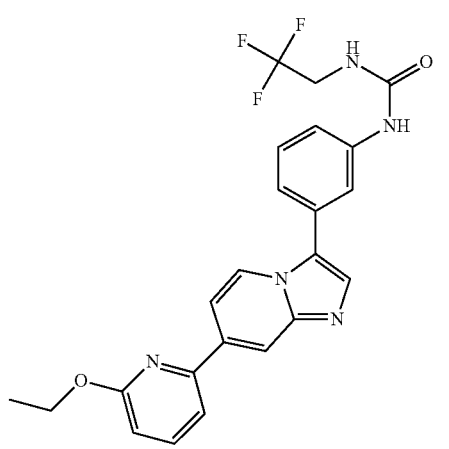 [SMILES: CCOc1cccc(-c2ccn3c(-c4cccc(NC(=O)NCC(F)(F)F)c4)cnc3c2)n1]<br>1-{3-[7-(6-Ethoxy-pyridin-2-yl)-imidazo[1,2-a]pyridin-3-yl]-phenyl}-3-(2,2,2-trifluoro-ethyl)-urea bis-hydrochloride | 1H NMR (400 MHz, Me-d3-OD): 8.88 (1H, d), 8.67 (1H, s), 8.29-8.18 (2H, m), 8.06 (1H, s), 7.89 (1H, t), 7.80 (1H, d), 7.59 (1H, t), 7.46 (1H, d), 7.41 (1H, d), 6.95 (1H, d), 4.56 (2H, q), 3.96 (2H, q), 1.49 (3H, t). | 456 | General Route B, Procedure B3d using boronate from Procedure B2 and 2-chloro-6-ethoxy pyridine, heated in microwave at 120° C. for 30 min, Procedure Z5 |

-continued

| Eg. | Compound and Name | N.M.R. Data | M.S | Procedure |
|---|---|---|---|---|
| 100 | 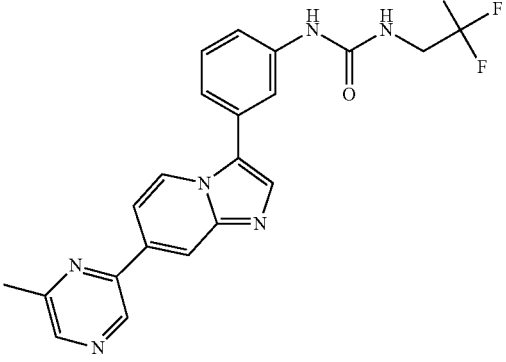<br>1-{3-[7-(6-Methyl-pyrazin-2-yl)-imidazo[1,2-a]pyridin-3-yl]-phenyl}-3-(2,2,2-trifluoro-ethyl)-urea | 1H NMR (400 MHz, Me-d3-OD): 9.07 (1H, s), 8.70 (1H, d), 8.50 (1H, s), 8.42 (1H, s), 7.89-7.75 (3H, m), 7.51 (1H, t), 7.43 (1H, d), 7.35 (1H, d), 3.96 (2H, q), 2.67 (3H, s). | 427 | General route B, procedure B3a using 2-Bromo-6-Methylpyrazine |
| 101 | 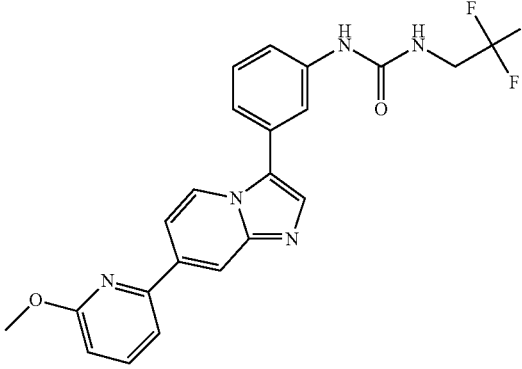<br>1-{3-[7-(6-Methoxy-pyridin-2-yl)-imidazo[1,2-a]pyridin-3-yl]-phenyl}-3-(2,2,2-trifluoro-ethyl)-urea | 1H NMR (400 MHz, Me-d3-OD): 8.66 (1H, d), 8.39 (1H, s), 7.90-7.84 (1H, m), 7.84-7.74 (3H, m), 7.63 (1H, d), 7.50 (1H, t), 7.46-7.38 (1H, m), 7.38-7.30 (1H, m), 6.82 (1H, d), 4.07 (3H, s), 4.04-3.89 (2H, m). | 442 | General Route B. Procedure B3c using 2-bromo-6-methoxy-pyridine |
| 102 | 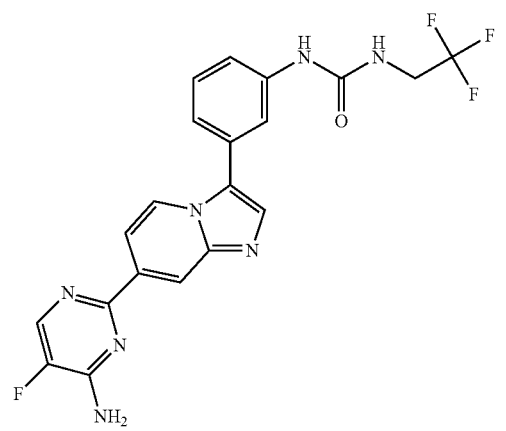 [SMILES: Nc1nc(-c2ccn3c(-c4cccc(NC(=O)NCC(F)(F)F)c4)cnc3c2)ncc1F]<br>1-{3-[7-(4-Amino-5-fluoro-pyrimidin-2-yl)-imidazo[1,2-a]pyridin-3-yl]-phenyl}-3-(2,2,2-trifluoro-ethyl)-urea bis-hydrochloride | 1H NMR (400 MHz, Me-d3-OD): 8.91 (1H, d), 8.80 (1H, s), 8.41-8.33 (2H, m), 8.29 (1H, s), 8.05 (1H, s), 7.59 (1H, t), 7.47 (1H, d), 7.41 (1H, d), 3.96 (2H, q). | 446 | General Route B, Procedure B3d using boronate from Procedure B2 and 2-chloro-5-fluoro-pyrimidin-4-ylamine, heated in microwave at 120° C. for 30 min, Procedure Z5 |

| Eg. | Compound and Name | N.M.R. Data | M.S | Procedure |
|---|---|---|---|---|
| 103 | 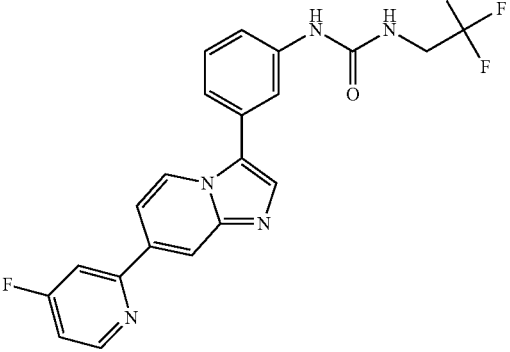<br>1-{3-[7-(4-Fluoro-pyridin-2-yl)-imidazo[1,2-a]pyridin-3-yl]-phenyl}-3-(2,2,2-trifluoro-ethyl)-urea | 1H NMR (400 MHz, Me-d3-OD): 8.76-8.62 (2H, m), 8.34 (1H, s), 7.89 (1H, dd), 7.83 (1H, s), 7.82-7.77 (1H, m), 7.74 (1H, dd), 7.55-7.46 (1H, m), 7.42 (1H, d), 7.33 (1H, d), 7.28-7.18 (1H, m), 3.96 (2H, q). | 430 | General Route B, Procedure B3d using boronate from Procedure B2 and 2-chloro-4-fluoro pyridine, heated in microwave at 120° C. for 30 min |
| 104 | 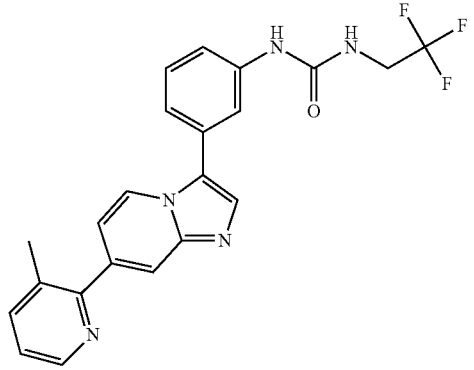 [SMILES: Cc1cccnc1-c1ccn2c(-c3cccc(NC(=O)NCC(F)(F)F)c3)cnc2c1]<br>1-{3-[7-(3-Methyl-pyridin-2-yl)-imidazo[1,2-a]pyridin-3-yl]-phenyl}-3-(2,2,2-trifluoro-ethyl)-urea formate | 1H NMR (400 MHz, Me-d3-OD): 8.69 (1H, d), 8.51 (1H, d), 8.20 (1H, s), 7.90-7.73 (4H, m), 7.50 (1H, t), 7.47-7.37 (2H, m), 7.35 (1H, d), 7.24 (1H, d), 3.95 (2H, q), 2.48 (3H, s). | 426 | General Route B. Procedure B3c using 2-chloro-3-methyl-pyridine |
| 105 | 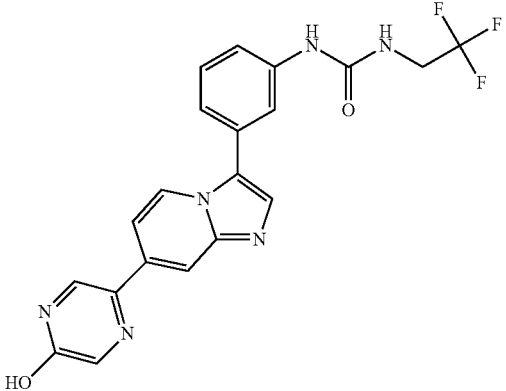 [SMILES: O=C(NCC(F)(F)F)Nc1cccc(-c2cnc3cc(-c4cnc(O)cn4)ccn23)c1]<br>1-{3-[7-(5-Hydroxy-pyrazin-2-yl)-imidazo[1,2-a]pyridin-3-yl]-phenyl}-3-(2,2,2-trifluoro-ethyl)-urea hydrochloride | 1H NMR (400 MHz, Me-d3-OD): 8.62 (1H, d), 8.25 (1H, s), 8.13 (2H, d), 7.83 (1H, s), 7.73 (1H, s), 7.56-7.47 (3H, m), 7.41 (1H, d), 7.33 (1H, d), 4.00-3.91 (3H, m), 3.44-3.23 (197H, m). | 429 | General route B, procedure B3a using 2-bromo-5-hydroxy-pyrazine |

| Eg. | Compound and Name | N.M.R. Data | M.S | Procedure |
|---|---|---|---|---|
| 106 | 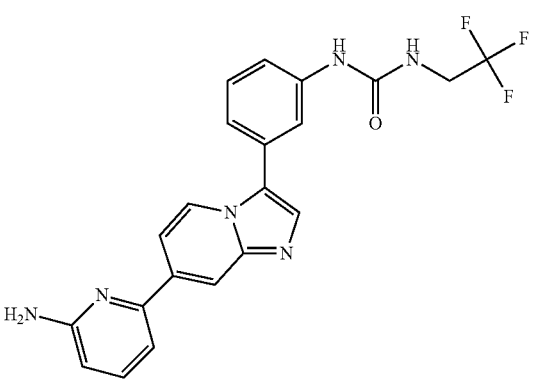 [SMILES: Nc1cccc(-c2ccn3c(-c4cccc(NC(=O)NCC(F)(F)F)c4)cnc3c2)n1]<br>1-{3-[7-(6-Amino-pyridin-2-yl)-imidazo[1,2-a]pyridin-3-yl]-phenyl}-3-(2,2,2-trifluoro-ethyl)-urea hydrochloride | 1H NMR (400 MHz, Me-d3-OD): 8.99 (1H, d), 8.56 (1H, s), 8.35 (1H, s), 8.13-8.01 (2H, m), 7.93 (1H, d), 7.60 (1H, t), 7.52-7.37 (3H, m), 7.15 (1H, d), 3.96 (2H, q). | 427 | General Route B. Procedure B3c using 6-bromo-pyridin-2-ylamine. Procedure Z5 |
| 107 | 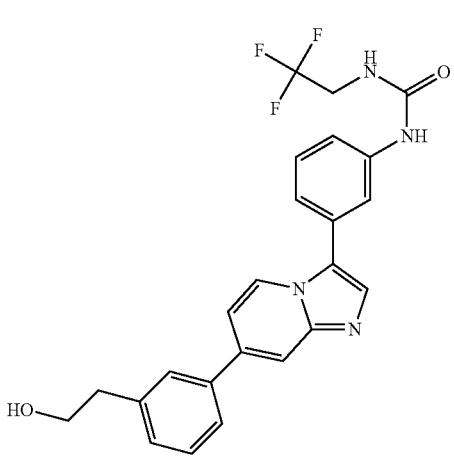 [SMILES: O=C(NCC(F)(F)F)Nc1cccc(-c2cnc3cc(-c4cccc(CCO)c4)ccn23)c1]<br>1-(3-{7-[3-(2-Hydroxy-ethyl)-phenyl]-imidazo[1,2-a]pyridin-yl}-phenyl)-3-(2,2,2-trifluoro-ethyl)-urea formate | 1H NMR (400 MHz, Me-d3-OD): 8.60 (1H, d), 8.29 (1H, s), 7.85 (2H, d), 7.80-7.68 (1H, m), 7.64 (1H, s), 7.62-7.53 (1H, m), 7.53-7.42 (2H, m), 7.39 (2H, d), 7.33 (1H, d), 7.28 (1H, d), 3.95 (2H, q), 3.84 (2H, t), 2.93 (2H, t). | 455 | General Route B, Procedure B3d using boronate from Procedure B2 and 2-(3-bromo-phenyl)-ethanol |
| 108 | 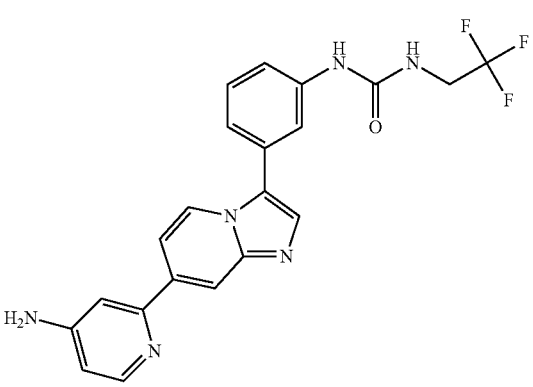 [SMILES: Nc1ccnc(-c2ccn3c(-c4cccc(NC(=O)NCC(F)(F)F)c4)cnc3c2)c1]<br>1-{3-[7-(4-Amino-pyridin-2-yl)-imidazo[1,2-a]pyridin-3-yl]-phenyl}-3-(2,2,2-trifluoro-ethyl)-urea diformate | 1H NMR (400 MHz, Me-d3-OD): 8.73 (1H, d), 8.39 (2H, s), 8.16-8.04 (2H, m), 7.91 (1H, s), 7.87 (1H, s), 7.50 (1H, t), 7.44-7.36 (2H, m), 7.33 (1H, d), 7.19 (1H, s), 6.86-6.77 (1H, m), 3.95 (2H, q). | 427 | General Route B. Procedure B3c using 2-chloro-pyridin-4-ylamine |

| Eg. | Compound and Name | N.M.R. Data | M.S | Procedure |
|---|---|---|---|---|
| 109 | 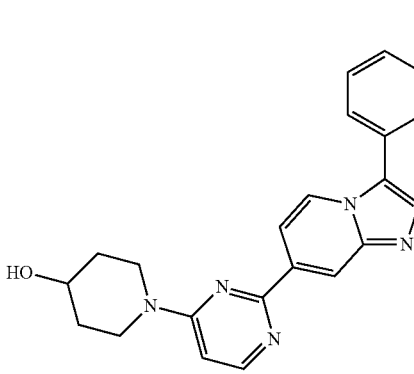<br>1-(3-{7-[4-(4-Hydroxy-piperidin-1-yl)-pyrimidin-2-yl]-imidazo[1,2-a]pyridin-3-yl}-phenyl)-3-(2,2,2-trifluoro-ethyl)-urea | 1H NMR (400 MHz, Me-d3-OD): 8.68-8.55 (2H, m), 8.28 (1H, d), 7.94 (1H, d), 7.81 (2H, d), 7.55-7.38 (2H, m), 7.34 (1H, d), 6.76 (1H, d), 4.33 (2H, s), 4.03-3.89 (3H, m), 3.52-3.39 (2H, m), 2.00 (2H, s), 1.65-1.50 (2H, m). | 512 | General route B, procedure B3a 1-(2-Chloropyrimidin-4-yl)Piperidin-4-ol |
| 110 | 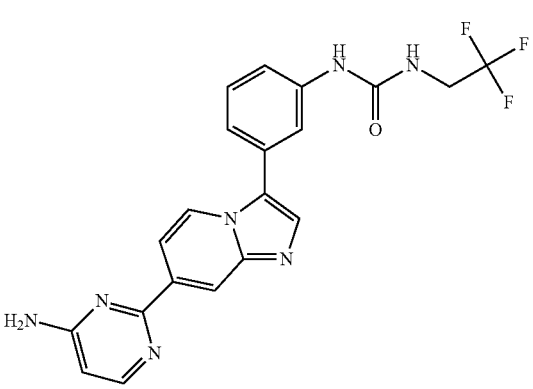 [SMILES: Nc1ccnc(-c2ccn3c(-c4cccc(NC(=O)NCC(F)(F)F)c4)cnc3c2)n1]<br>1-{3-[7-(4-Amino-pyrimidin-2-yl)-imidazo[1,2-a]pyridin-3-yl]-phenyl}-3-(2,2,2-trifluoro-ethyl)-urea | 1H NMR (400 MHz, DMSO-d6): 9.00-8.94 (1H, m), 8.63 (1H, d), 8.49 (1H, s), 8.27-8.20 (1H, m), 7.84 (2H, d), 7.75 (1H, s), 7.54-7.43 (2H, m), 7.29 (1H, d), 7.06-6.98 (2H, m), 6.86 (1H, t), 6.42 (1H, d), 4.00-3.90 (2H, m) | 428 | General route B, procedure B3a using 2-Chloro-4-Aminopyrimidine |
| 111 | 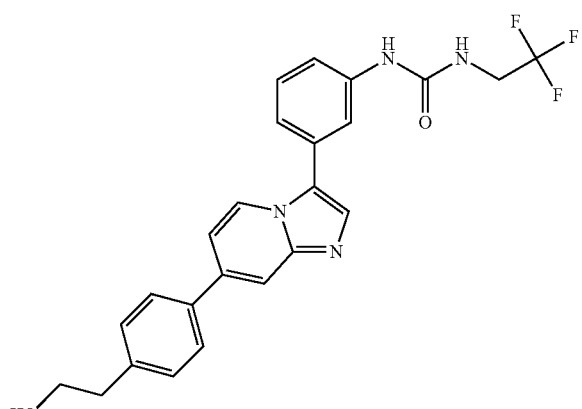<br>1-(3-{7-[4-(2-Hydroxy-ethyl)-phenyl]-imidazo[1,2-a]pyridin-yl}-phenyl)-3-(2,2,2-trifluoro-ethyl)-urea formate | 1H NMR (400 MHz, Me-d3-OD): 8.65 (1H, d), 8.22 (1H, s), 7.86 (2H, s), 7.83-7.62 (3H, m), 7.56-7.47 (1H, m), 7.41 (4H, d), 7.33 (1H, d), 4.02-3.89 (2H, m), 3.83 (2H, t), 2.91 (2H, t). | 455 | General Route B, Procedure B3c using boronate from Procedure B2 and 2-(4-chloro-phenyl)-ethanol |

-continued

| Eg. | Compound and Name | N.M.R. Data | M.S | Procedure |
|---|---|---|---|---|
| 112 | 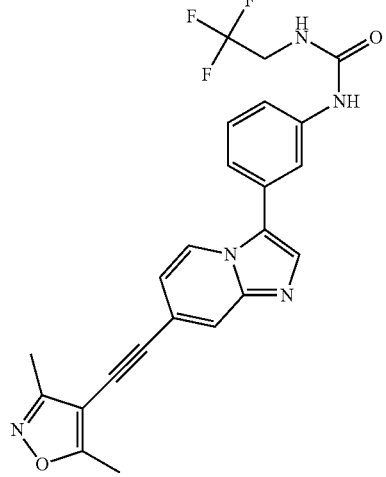<br>1-{3-[7-(3,5-Dimethyl-isoxazol-4-ylethynyl)-imidazo[1,2-a]pyridin-3-yl]-phenyl}-3-(2,2,2-trifluoro-ethyl)-urea trifluoroacetate | 1H NMR (400 MHz, Me-d3-OD): 8.69 (1H, d), 8.02 (1H, s), 7.96 (1H, s), 7.92 (1H, s), 7.54 (1H, t), 7.46-7.41 (1H, m), 7.37-7.30 (2H, m), 3.99-3.92 (2H, m), 2.59 (3H, s), 2.39 (3H, s). | 454 | General Route C. Procedure C3 using 4-iodo-3,5-dimethyl-isoxazole, Procedure C2 using 3,5-dimethyl-4-trimethylsilanyl-ethynyl-isoxazole (reaction time 4 hrs) |
| 113 | 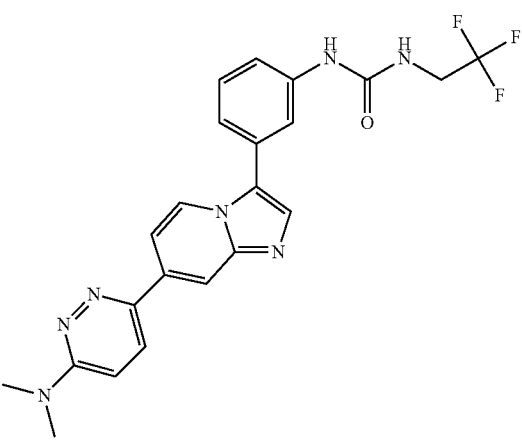 [SMILES: CN(C)c1ccc(-c2ccn3c(-c4cccc(NC(=O)NCC(F)(F)F)c4)cnc3c2)nn1]<br>1-{3-[7-(6-Dimethylamino-pyridazin-3-yl)-imidazo[1,2-a]pyridin-3-yl]-phenyl}-3-(2,2,2-trifluoro-ethyl)-urea formate | 1H NMR (400 MHz, Me-d3-OD): 8.66 (1H, d), 8.22 (1H, s), 8.15 (1H, s), 8.03 (1H, d), 7.88-7.80 (2H, m), 7.78 (1H, s), 7.50 (1H, t), 7.43 (1H, d), 7.34 (1H, d), 7.25 (1H, d), 3.96 (2H, q), 3.25 (6H, s). | 456 | General Route B. Procedure B3c using (6-chloro-pyridazin-3-yl)-dimethyl-amine |

| Eg. | Compound and Name | N.M.R. Data | M.S | Procedure |
|---|---|---|---|---|
| 114 | 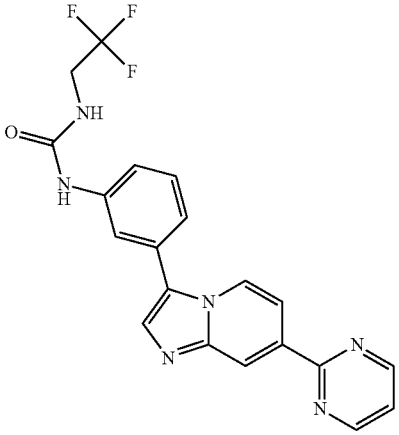 [SMILES: O=C(NCC(F)(F)F)Nc1cccc(-c2cnc3cc(-c4ncccn4)ccn23)c1]<br>1-{3-[7-(Pyrimidin-2-yl)-imidazo[1,2-a]pyridin-3-yl]-phenyl}-3-(2,2,2-trifluoro-ethyl)-urea hydrochloride | 1H NMR (400 MHz, DMSO-d6): 9.29 (1H, s), 9.08 (2H, d), 8.90 (1H, d), 8.83 (1H, s), 8.47-8.40 (1H, m), 8.29 (1H, dd), 7.89 (1H, s), 7.66 (1H, t), 7.62-7.52 (2H, m), 7.35 (1H, d), 7.03 (1H, t), 4.00-3.91 (2H, m). | 413 | General Route B. Procedure B3d using 2-chloropyrimidine. General modification Z5. |

Example 114B

1-[3-(7-Pyrimidin-2-yl-imidazo[1,2-a]pyridin-3-yl)-phenyl]-3-(2,2,2-trifluoro-ethyl)-urea dimesylate

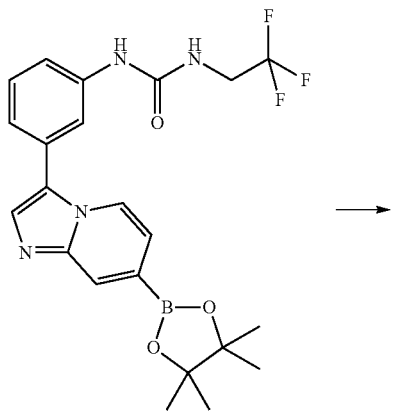

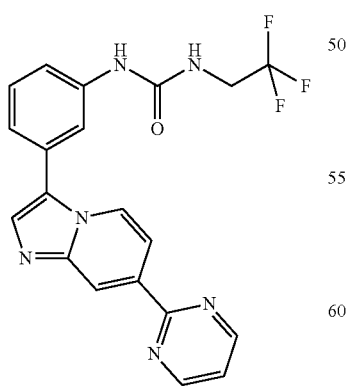

2-chlororpyrimidine (2.24 g, 19.64 mmol) and 2M Na₂CO₃ (66 ml, 13.2 mmol) were added to a solution of 1-{3-[7-(4,4,5,5-tetramethyl-[1,3,2]dioxaborolan-2-yl)-imidazo[1,2-a]pyridin-3-yl]-phenyl}-3-(2,2,2-trifluoro-ethyl)-urea [from procedure B2] (6 g, 13.04 mmol) in DME (66 ml) [reaction degassed by bubbling through nitrogen], followed by tetrakis(triphenylphosphine)palladium (0) (1.5 g, 1.2 mmol). The reaction was heated to 80° C. for 3 h, before being partitioned between water and EtOAc. The organic fraction was dried (MgSO₄), filtered and concentrated in vacuo and the residue was purified by preparative HPLC to generate the product as TFA salt (1.8 g).

Product (1.1 g) taken up in CH₂Cl₂ (700 ml) then washed with 2M NH₄OH (300 ml) some solid formed between the layers filtered off (170 mgs). Aqueous re-extracted with CH₂Cl₂ (250 ml), all organics combined and washed with water (100 ml) dried (MgSO₄), filtered and concentrated in vacuo to generate the product as free base (0.548 g), both samples added together suspended in methanol (100 ml) treated with methane sulphonic acid (0.226 2 eq) and evaporated down, re-evaporated with CH₂Cl₂/MeOH to give a foam (1.45 g) MS:

[M+H]⁺=413.

Example 115

1-[3-(7-Aminoimidazol[1,2-a]pyridin-3-yl)phenyl]-3-(2,2,2-trifluoroethyl)urea

Step 1:

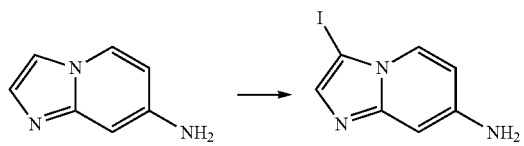 [SMILES: Nc1ccn2ccnc2c1 ; Nc1ccn2c(I)cnc2c1]

Prepared using the method described in General Route A Procedure A2. MS: [M+H]⁺=259.

Step 2:

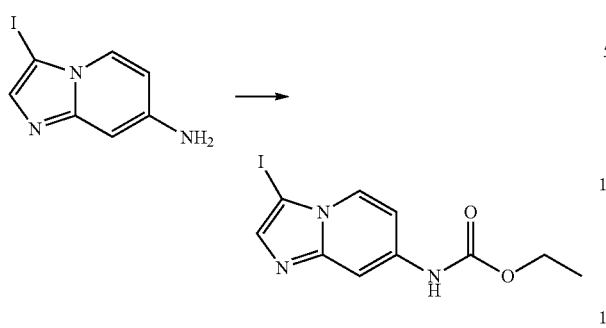

To a solution of 7-amino-3-iodoimidazo-[1,2,a]pyridine (840 mg, 3.2 mmol) in THF (80 ml) was added diisopropyl-ethylamine (1.4 ml, 8.5 mmol) and ethyl chloroformate (0.36 ml, 3.8 mmol). The reaction was stirred at room temperature for 2 h and the resulting solid separated by filtration and washed with THF to give the product (468 mg) which was used without purification. MS: [M+H]$^+$=331.

Step 3:

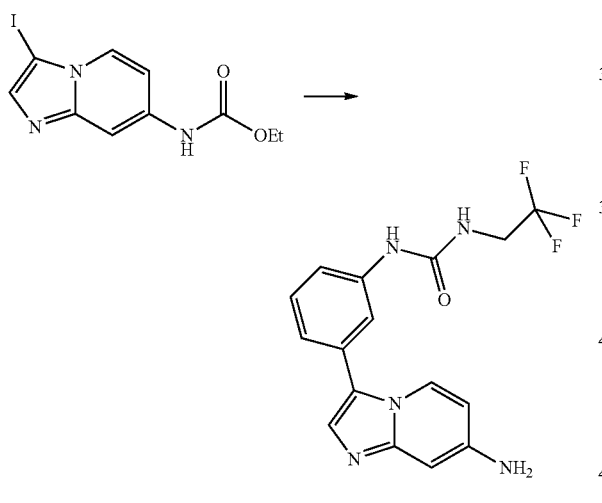

To a solution of (3-Iodo-imidazo[1,2-a]pyridin-7-yl)car-bamic acid ethyl ester (100 mg, 0.30 mmol) in toluene (0.5 ml) was added 1-[3-(4,4,5,5-Tetramethyl-[1,3,2]dioxaboro-lan-2-yl)-phenyl]-3-(2,2,2-trifluoro-ethyl)-urea (described in procedure A4) (126 mg, 0.36 mmol), K$_2$CO$_3$ (250 mg, 1.80 mmol), MeOH (0.5 ml), EtOH (0.5 ml) and water (0.7 ml) [reaction degassed by bubbling N$_2$ through]. Bis(tri-tert-bu-tylphosphine)palladium (0) (1.5 mg, 0.003 mmol) was added and the reaction was heated in a CEM discover microwave synthesizer (300W) at 135° C. for 30 min. The mixture was partitioned between water and EtOAc and the organic fraction was dried (MgSO$_4$), filtered and concentrated in vacuo. The residue was purified by preparative HPLC to give the product (12 mg). MS: [M+H]$^+$=350.

1H NMR (400 MHz, DMSO-d6): 8.97 (1H, s), 8.24 (1H, d), 7.61 (1H, s), 7.40-7.37 (2H, m), 7.33 (1H, s), 7.17-7.09 (1H, m), 6.92 (1H, t), 6.47 (1H, dd), 6.43 (1H, d), 5.71 (2H, s), 4.01-3.88 (2H, m).

Example 116

1-{3-[7-(2-Methylimidazol-1-yl)-1,7-dihydroimida-zol[1,2-a]pyridin-3-yl]-phenyl}-3-(2,2,2-trifluoroet-hyl)urea Step 1:

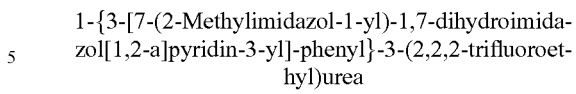

7-Bromoimidazo-[1,2,a]pyridine was prepared according to the method described in General Route A procedure A1.

Step 2:

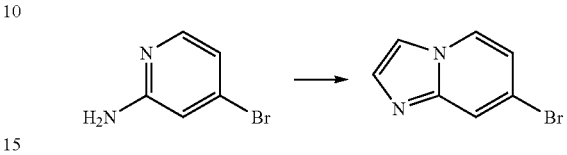

7-Bromoimidazo-[1,2,a]pyridine (500 mg, 2.5 mmol), 2-methylimidazole (208 mg, 2.5 mmol), copper (I) iodide (24 mg, 0.13 mmol), trans-N,N'-Dimethyl-cyclohexane-1,2-di-amine (360 mg, 0.5 mmol) and cesium carbonate (650 mg, 5 mmol) were dissolved in DMF (5 ml) and heated to 110° C. overnight under an inert atmosphere. The reaction was filtered, concentrated under reduced pressure and the residue purified by column chromatography (5-10% MeOH/DCM) to generate the product (120 mg). MS: [M+H]$^+$=199.

Step 3:

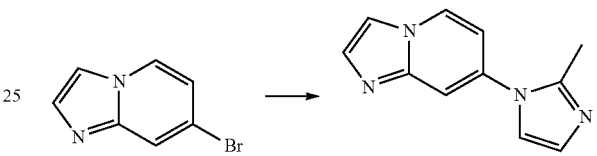

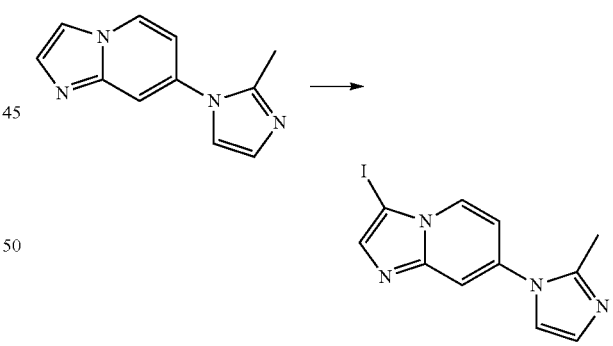

Prepared according to the method described in General Route A Procedure A2.

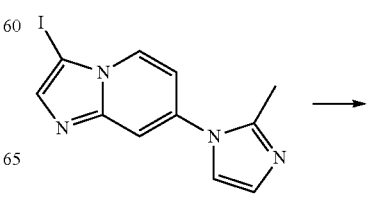

-continued

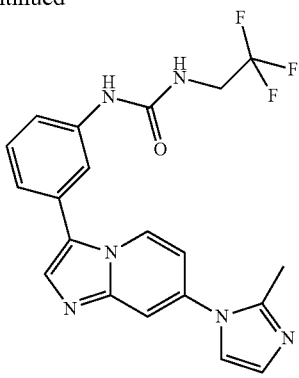

Step 4:
Prepared according to the method described in General Route B Procedure B3a using the boronate described in General Route A Procedure A4. [M+H]⁺=415

1H NMR (400 MHz, Me-d3-OD): 8.72 (1H, d), 7.88 (1H, t), 7.82 (1H, s), 7.71 (1H, d), 7.51 (1H, t), 7.45-7.38 (1H, m), 7.38-7.31 (2H, m), 7.12 (1H, dd), 7.05 (1H, d), 4.02-3.88 (2H, m), 2.49 (3H, s).

Example 117

1-[5-(7-Chloro-imidazo[1,2-a]pyridin-3-yl)-thiazol-2-yl]-3-ethyl-urea hydrochloride Step 1:

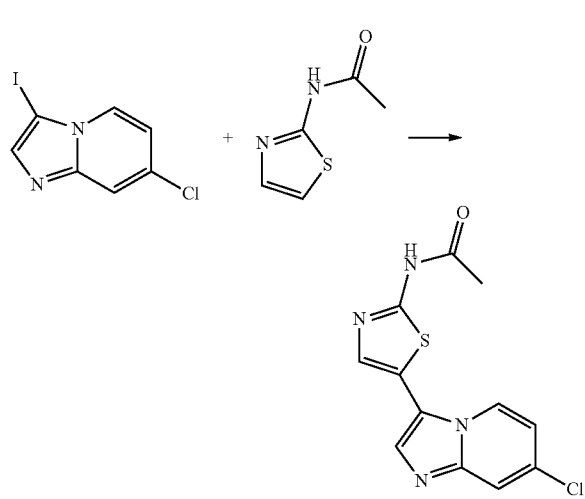

A mixture of the iodide (From Procedure A2, 1.06 g, 3.81 mmol), palladium acetate (catalytic amount), DavePhos (catalytic amount), cesium carbonate (1.86 g, 5.71 mmol), pivalic acid (583 mg, 5.71 mmol), dimethylacetamide (20 ml) and 2-acetamidothiazole (1.56 g, 9.52 mmol) was heated to 110° C. under nitrogen overnight. The reaction was then allowed to cool. The reaction was filtered under suction washing with ethyl acetate and water. These solids were discarded and the liquors were re-filtered to furnish some crude product. The liquors were taken; the ethyl acetate layer separated and was washed with 10% aqueous lithium chloride and brine. This solution was dried (MgSO₄) and concentrated in vacuo. The residue was triturated with dichloromethane to furnish the desired product (500 mg). MS: [M+H]⁺=293.

1H NMR (400 MHz, DMSO-d6): 12.35 (1H, s), 8.56 (1H, d), 7.91-7.81 (3H, m), 7.08 (1H, dd), 2.20 (3H, s).

Step 2:

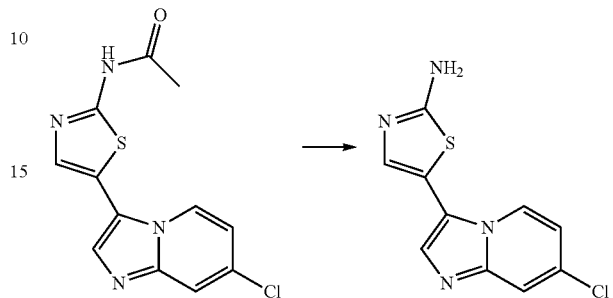

A mixture of the acetamide (200 mg, 0.685 mmol), methanol (3 ml) and concentrated hydrochloric acid (1 ml) was heated in a sealed tube in a microwave to 100° C. for 10 minutes. The solution was concentrated to dryness to furnish the crude amine as a tan solid (210 mg). MS: [M+H]⁺=251.

Step 3:

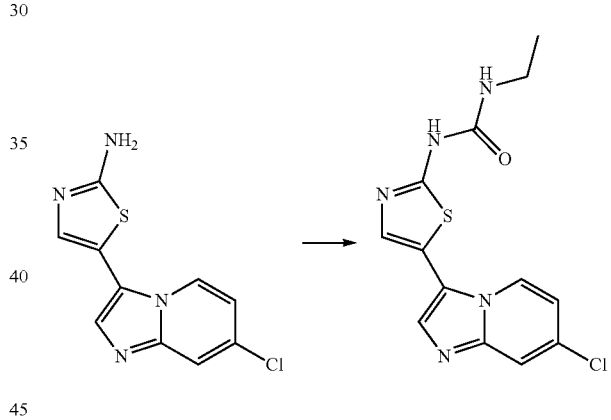

A mixture of the amine (75 mg crude), ethyl isocyanate (200u1) and 1,4-dioxane (2 ml) was stirred at room temperature for 2 hours before the temperature was raised to 40° C. After 2 hours at this temperature, a further portion of ethyl isocyanate (100u1) was added and the reaction was left at this temperature overnight. The reaction was allowed to cool before addition of water (5 ml). The reaction was heated to 40° C. for 1 hour then the reaction was allowed to cool and dichloromethane was added. The organic layer was separated, washed with water and brine, dried (MgSO₄) and concentrated. The residue was purified on silica Biotage column eluting 0-10% methanol/dichloromethane and purified further by preparative HPLC. The hydrochloride salt was formed using the method described in Procedure Z5. Yield=2 mg. MS: [M+H]⁺=322

1H NMR (400 MHz, Me-d3-OD): 8.76 (1H, d), 8.31 (1H, s), 8.16 (1H, d), 7.90 (1H, s), 7.63 (1H, dd), 3.35 (obscured, 2H), 1.22 (3H, t).

Example 118

1-{3-[7-(5,6-Dimethyl-[1,2,4]triazin-3-yl)-imidazo[1,2-a]pyridin-3-yl]-phenyl}-3-(2,2,2-trifluoro-ethyl)-urea hydrochloride Step 1:

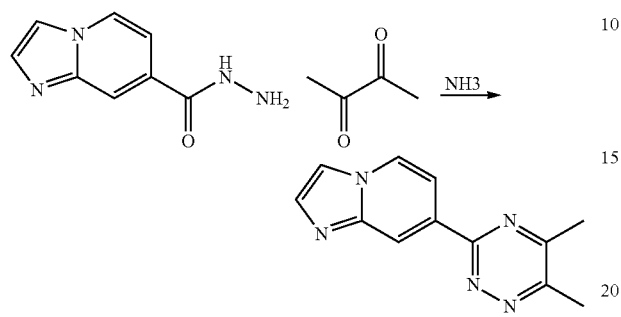

A mixture of the hydrazide (Chezal J M et. al. Tetrahedron 2002, 58(2), 295-308, 705 mg, 4.0 mmol), diacetyl (379 mg, 4.4 mmol) and ethanol (10 ml) was stirred at room temperature overnight. Ammonia in methanol (2M, 10 ml) was then added and after stirring for 30 minutes was heated to 110° C. in a seal tube in a microwave for 70 minutes. The reaction was then filtered to remove a while solid. The liquors were concentrated and purified on a silica Biotage column eluting with 0-10% methanol/dichloromethane. The product was further purified by trituration with diethyl ether to furnish the product as an off-white solid (277 mg). MS: [M+H]$^+$=226.

Step 2:

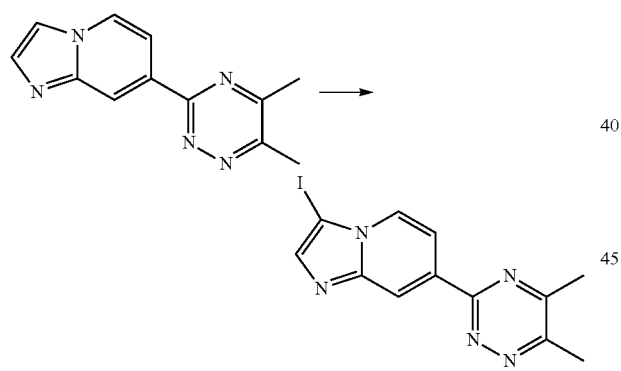

Prepared using the method described in General Route A Procedure A2. MS: [M+H]$^+$=338.

Step 3:

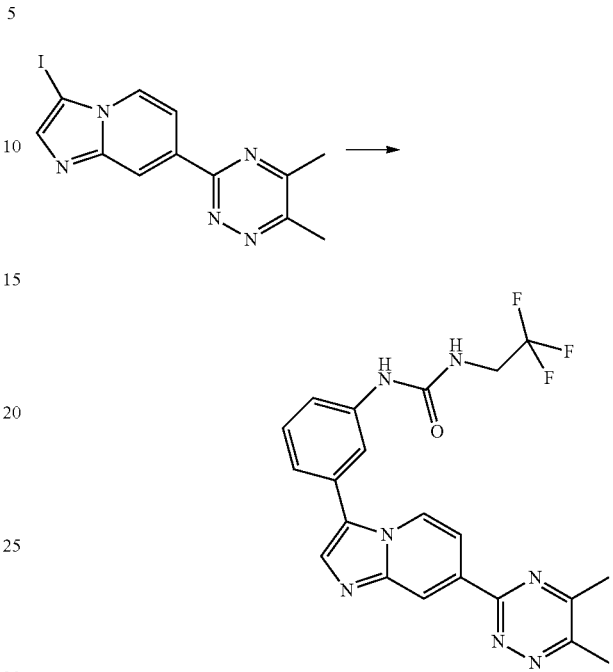

Prepared using the method described in General Route A Procedure A4 under conventional heating at 80° C. overnight. The product was purified by silica Biotage column eluting 0-15% ethyl acetate/petroleum ether. The product was salted using the method described in Procedure Z5. MS: [M+H]$^+$= 442.

1H NMR (400 MHz, Me-d3-OD): 9.02 (1H, s), 8.99 (1H, d), 8.57 (1H, d), 8.32 (1H, s), 8.06 (1H, s), 7.60 (1H, t), 7.49 (1H, d), 7.43 (1H, d), 3.96 (2H, q), 2.81 (3H, s), 2.74 (3H, s).

Examples 119 to 125

By following the methods described above, the compounds set out in the Table below were prepared.

All MS Data is [M+H]$^+$

| Eg. | Compound and Name | N.M.R. Data | M.S | Procedure |
|---|---|---|---|---|
| 119 | ![structure] <br> [3-(7-Chloro-imidazo[1,2-a]pyridin-3-yl)-phenyl]-urea | 1H NMR (400 MHz, DMSO-d6): 8.71 (1H, s), 8.54 (1H, d), 7.83 (1H, s), 7.75 (1H, s), 7.71 (1H, s), 7.49-7.35 (2H, m), 7.18 (1H, d), 7.03 (1H, dd), 5.92 (2H, s). | 287 | Procedure E4 using 2N NH3 in MeOH |

| Eg. | Compound and Name | N.M.R. Data | M.S | Procedure |
|---|---|---|---|---|
| 120 | 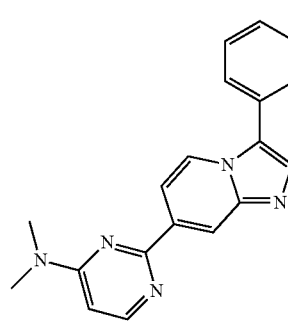<br>1-{3-[7-(4-Dimethylamino-pyrimidin-2-yl)-imidazo[1,2-a]pyridin-3-yl]-phenyl}-3-(2,2,2-trifluoro-ethyl)-urea hydrochloride | 1H NMR (400 MHz, Me-d3-OD): 9.05 (1H, d), 8.87 (1H, s), 8.42 (1H, s), 8.34 (1H, d), 8.29-8.20 (1H, m), 8.11 (1H, s), 7.60 (1H, t), 7.51-7.38 (2H, m), 7.12 (1H, d), 3.96 (2H, q), 3.65-3.39 (6H, m). | 456 | General Route B. Procedure B3c using (2-chloro-pyrimidin-4-yl)-dimethyl-amine |
| 121 | 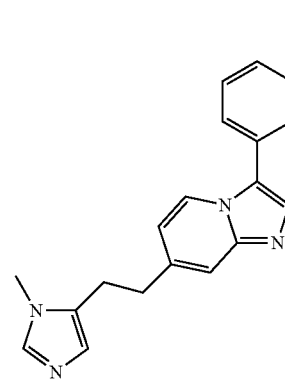<br>1-(3-{7-[2-(3-Methyl-3H-imidazol-4-yl)-ethyl]-imidazo[1,2-a]pyridin-3-yl}-phenyl)-3-(2,2,2-trifluoro-ethyl)-urea | 1H NMR (400 MHz, Me-d3-OD): 8.50 (1H, d), 7.79 (1H, s), 7.63 (1H, s), 7.55 (1H, s), 7.51-7.34 (3H, m), 7.28 (1H, d), 6.94 (1H, d), 6.75 (1H, s), 3.95 (2H, q), 3.65 (3H, s), 3.15-2.98 (4H, m). | 443 | General Route C. Procedure C2 using 5-ethynyl-1-methyl-1H-imidazoleol (reaction time 5 hrs), procedure G |
| 122 | 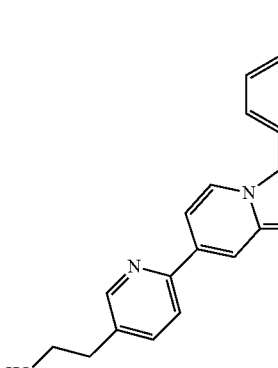<br>1-(3-{7-[5-(2-Hydroxy-ethyl)-pyridin-2-yl]-imidazo[1,2-a]pyridin-3-yl}-phenyl)-3-(2,2,2-trifluoro-ethyl)-urea | 1H NMR (400 MHz, Me-d3-OD): 8.61 (1H, d), 8.56 (1H, s), 8.24 (1H, s), 8.17 (1H, s), 7.92 (1H, d), 7.81 (3H, d), 7.76-7.66 (1H, m), 7.46 (1H, t), 7.39 (1H, d), 7.28 (1H, d), 3.95 (2H, q), 3.84 (2H, t), 2.90 (2H, t). | 456 | General Route B, Procedure B3c using boronate from Procedure B2 and X14 |

| Eg. | Compound and Name | N.M.R. Data | M.S | Procedure |
|---|---|---|---|---|
| 123 | 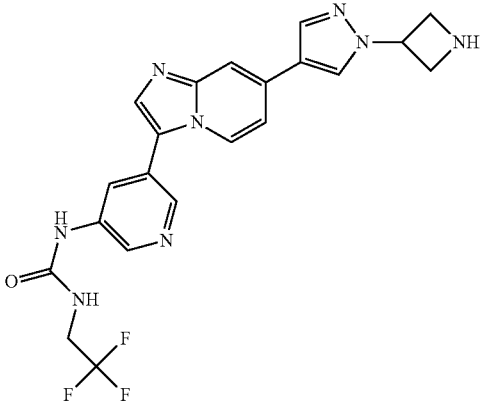 [SMILES: O=C(NCC(F)(F)F)Nc1cncc(-c2cnc3cc(-c4cnn(C5CNC5)c4)ccn23)c1]<br>1-{5-[7-(1-Azetidin-3-yl-1H-pyrazol-4-yl)-imidazo[1,2-a]pyridin-3-yl]-pyridin-3-yl}-3-(2,2,2-trifluoro-ethyl)-urea formate | 1H NMR (400 MHz, Me-d3-OD): 8.63-8.51 (2H, m), 8.51-8.43 (1H, m), 8.43-8.36 (1H, m), 8.33 (2H, s), 8.29 (1H, s), 8.23 (1H, s), 7.82 (2H, s), 7.32 (1H, dd), 5.57-5.44 (1H, m), 4.60 (4H, d), 3.97 (2H, q). | 457 | General route B: procedure A1; A2; A4 using conditions in procedure B3d (substitutingPdCI$_2$(PPh$_3$)$_2$ for Pd(PPh$_3$)$_4$ and 1-[5-(4,4,5,5-tetramethyl-[1,3,2]dioxaborolan-2-yl)-pyridin-3-yl]-3-(2,2,2-trifluoro-ethyl)-urea from procedure D4; B2, procedure B3c using 1-azetidin-3-yl-4-bromo-1H-pyrazole prepared using conditions in procedure X3 (step 1 & 2) |
| 124 | 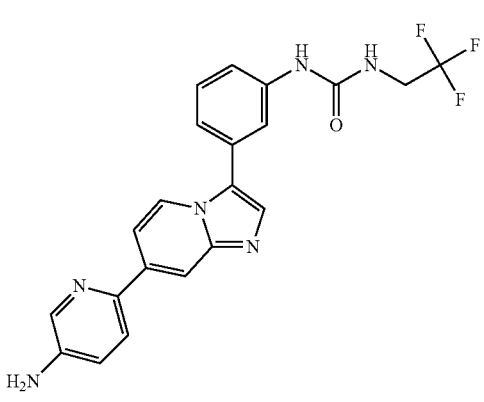 [SMILES: Nc1ccc(-c2ccn3c(-c4cccc(NC(=O)NCC(F)(F)F)c4)cnc3c2)nc1]<br>1-{3-[7-(5-Amino-pyridin-2-yl)-imidazo[1,2-a]pyridin-3-yl]-phenyl}-3-(2,2,2-trifluoro-ethyl)-urea hydrochloride | 1H NMR (400 MHz, Me-d3-OD): 8.98 (1H, d), 8.50 (1H, s), 8.33 (1H, s), 8.30-8.19 (2H, m), 8.10-8.06 (1H, m), 8.00-7.91 (1H, m), 7.81 (1H, dd), 7.60 (1H, t), 7.51-7.37 (2H, m), 3.95 (2H, q). | 427 | General Route B. Procedure B3c using 6-chloro-pyridin-3-ylamine |
| 125 | 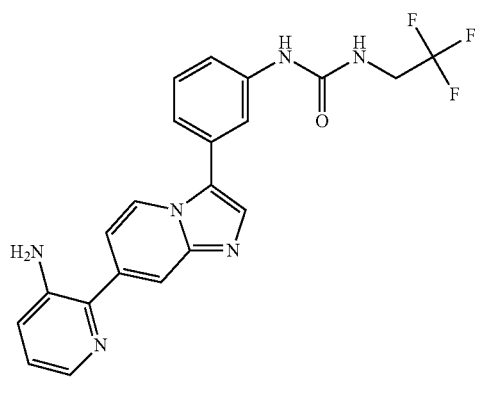 [SMILES: Nc1cccnc1-c1ccn2c(-c3cccc(NC(=O)NCC(F)(F)F)c3)cnc2c1]<br>1-{3-[7-(3-Amino-pyridin-2-yl)-imidazo[1,2-a]pyridin-3-yl]-phenyl}-3-(2,2,2-trifluoro-ethyl)-urea hydrochloride | 1H NMR (400 MHz, Me-d3-OD): 9.05 (1H, d), 8.45 (1H, s), 8.39 (1H, s), 8.18 (1H, dd), 8.14-8.07 (1H, m), 7.93 (1H, dd), 7.86-7.75 (2H, m), 7.61 (1H, t), 7.51-7.38 (2H, m), 3.96 (2H, q). | 427 | General Route B. Procedure B3c using 2-chloro-pyridin-3-ylamine |

Examples 126A-159B

The following compounds can be prepared using the methods described herein. In particular the appropriate coupling partner such as the required aromatic halide or aromatic boronic acid will be used in the cross-coupling reaction with 1-[3-(7-chloro-imidazo[1,2-a]pyridin-3-yl)-phenyl]-3-(2,2,2-trifluoro-ethyl)-urea or 1-[3-(7-boronate-imidazo[1,2-a]pyridin-3-yl)-phenyl]-3-(2,2,2-trifluoro-ethyl)-urea. The required coupling partners are commercially available or can be synthesised using the methods described herein.

Example 126A 1-(3-{7-[1-(2-Hydroxy-ethyl)-6-oxo-1,6-dihydro-pyridazin-3-yl]-imidazol[1,2-a]pyridin-3-yl}-phenyl)-3-(2,2,2-trifluoro-ethyl)-urea

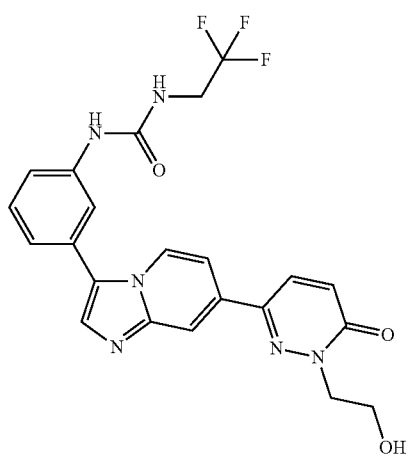 [SMILES: O=C(NCC(F)(F)F)Nc1cccc(-c2cnc3cc(-c4ccc(=O)n(CCO)n4)ccn23)c1]

Example 127A 1-(3-{7-[1-(2-Amino-ethyl)-6-oxo-1,6-dihydro-pyridazin-3-yl]-imidazo[1,2-a]pyridin-3-yl}-phenyl)-3-(2,2,2-trifluoro-ethyl)-urea

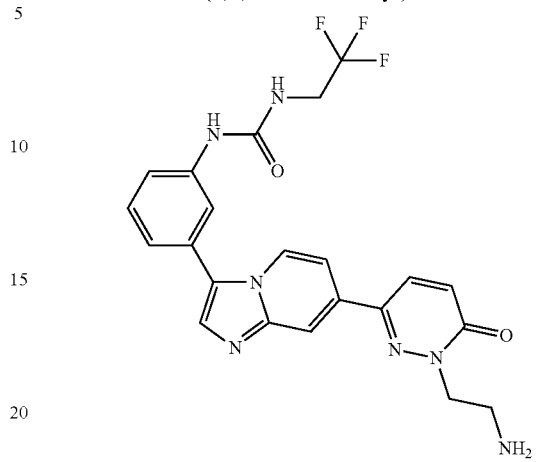

Example 128A 1-(3-{7-[1-(2-Methoxy-ethyl)-6-oxo-1,6-dihydro-pyridazin-3-yl]-imidazo[1,2-a]pyridin-3-yl}-phenyl)-3-(2,2,2-trifluoro-ethyl)-urea

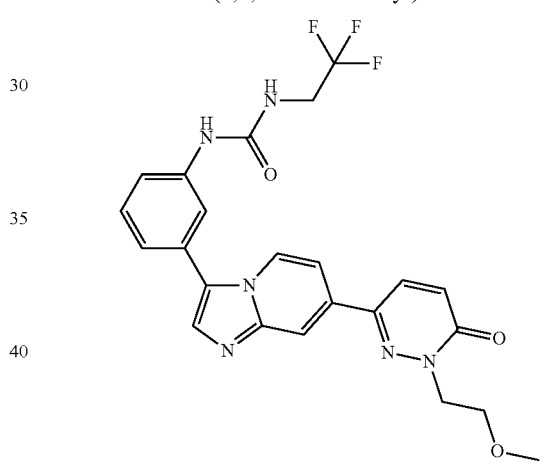

Example 126B

Example 126B was prepared in accordance with the procedure set out in the Table below.

| Eg. | Structure | Chemical name | Route/Method | NMR Data (solvent) | MS Data |
|---|---|---|---|---|---|
| 126B | (structure shown) | 1-(3-{7-[1-(2-Hydroxy-ethyl)-6-oxo-1,6-dihydro-pyridazin-3-yl]-imidazo-[1,2-a]pyridin-3-yl}-phenyl)-3-(2,2,2-trifluoroethyl)-urea hydrochloride | General Route B followed by procedure B3d using 6-chloro-2-(2-chloro-ethyl)-2H-pyridazin-3-one | (Me-d3-OD): 8.88 (1H, d), 8.47 (1H, s), 8.33-8.19 (2H, m), 8.14 (1H, d), 8.01 (1H, s), 7.57 (1H, t), 7.49 (1H, d), 7.39 (1H, d), 7.19 (1H, d), 4.46 (2H, t), 4.05 (2H, t), 3.95 (2H, q) | 473 |

Example 129A 1-(3-{7-[1-(2-Methylamino-ethyl)-6-oxo-1,6-dihydro-pyridazin-3-yl]-imidazo[1,2-a]pyridin-3-yl}-phenyl)-3-(2,2,2-trifluoro-ethyl)-urea

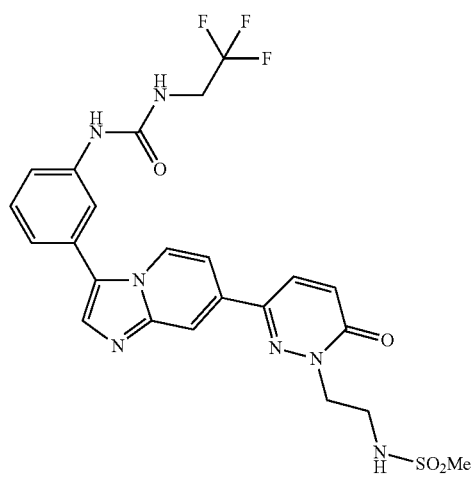 [SMILES: CS(=O)(=O)NCCn1nc(-c2ccn3c(-c4cccc(NC(=O)NCC(F)(F)F)c4)cnc3c2)ccc1=O]

Example 130A 1-(3-{7-[6-(Piperidin-4-yloxy)-pyridazin-3-yl]-imidazo[1,2-a]pyridin-3-yl}-phenyl)-3-(2,2,2-trifluoro-ethyl)-urea

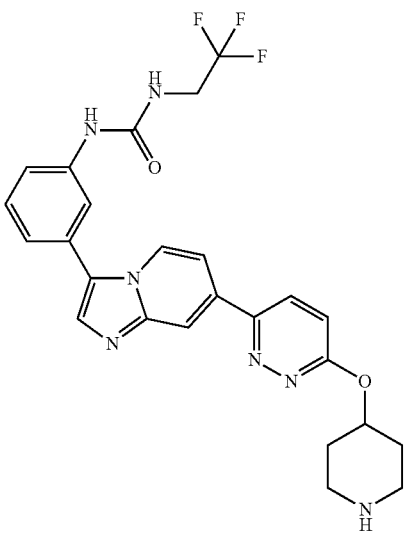 [SMILES: O=C(NCC(F)(F)F)Nc1cccc(-c2cnc3cc(-c4ccc(OC5CCNCC5)nn4)ccn23)c1]

Example 130B

Example 130B was prepared in accordance with the procedure set out in the Table below.

| Eg. | Structure | Chemical name | Route/Method | NMR Data (solvent) | MS Data |
|---|---|---|---|---|---|
| 130B | 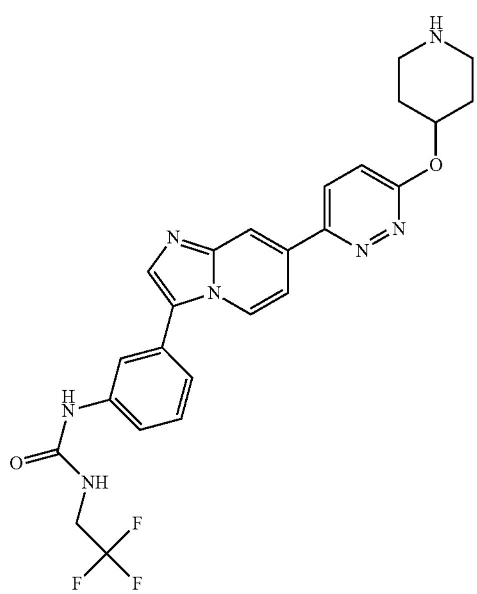 | 1-(3-{7-[6-(Piperidin-4-yloxy)-pyridazin-3-yl]-imidazo[1,2-a]pyridin-3-yl}-phenyl)-3-(2,2,2-trifluoroethyl)-urea hydrochloride | General route B: procedure B1, procedure B2, procedure B3c using 3-chloro-6-(piperidin-4-yloxy)-pyridazine, procedure Z5 | (Me-d3-OD): 8.96 (1H, d), 8.65 (1H, s), 8.43 (1H, d), 8.33-8.23 (2H, m), 8.08 (1H, s), 7.60 (1H, t), 7.51-7.37 (3H, m), 5.74-5.65 (1H, m), 3.96 (2H, q), 3.55-3.46 (2H, m), 2.46-2.33 (2H, m), 2.30-2.17 (2H, m), 2.06-1.98 (1H, m), 1.29-1.18 (1H, m). | 512 |

Example 131A 1-(3-{7-[6-(Piperidin-3-yloxy)-pyridazin-3-yl]-imidazo[1,2-a]pyridin-3-yl}-phenyl)-3-(2,2,2-trifluoroethyl)-urea

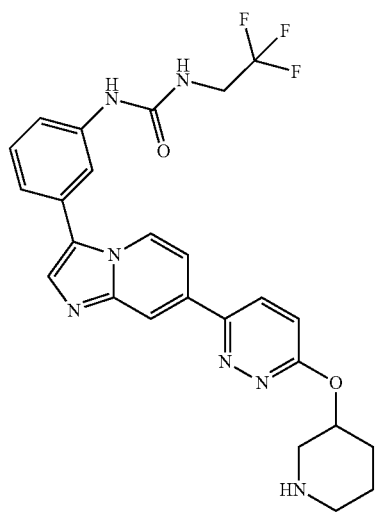 [SMILES: O=C(NCC(F)(F)F)Nc1cccc(-c2cnc3cc(-c4ccc(OC5CCCNC5)nn4)ccn23)c1]

Example 132A

1-{3-[7-(6-Methylamino-pyridazin-3-yl)-imidazo[1,2-a]pyridin-3-yl]-phenyl}-3-(2,2,2-trifluoro-ethyl)-urea

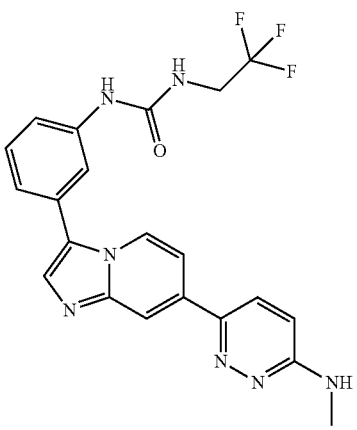 [SMILES: CNc1ccc(-c2ccn3c(-c4cccc(NC(=O)NCC(F)(F)F)c4)cnc3c2)nn1]

Example 131B

Example 131B was prepared in accordance with the procedure set out in the Table below.

Example 132B

Example 132B was prepared in accordance with the procedure set out in the Table below.

| Eg. | Structure | Chemical name | Route/ Method | NMR Data (solvent) | MS Data |
|---|---|---|---|---|---|
| 131B | 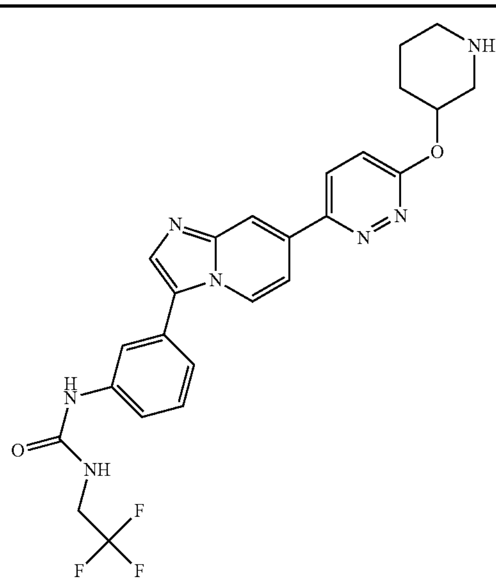 | 1-(3-{7-[6-(Piperidin-3-yloxy)-pyridazin-3-yl]-imidazo[1,2-a]pyridin-3-yl}-phenyl)-3-(2,2,2-trifluoro-ethyl)-urea hydrochloride | General route B: procedure B1, procedure B2, procedure B3c using 3-chloro-6-(piperidin-3-yloxy)-pyridazine, procedure Z5 | (Me-d3-OD): 8.96 (1H, d), 8.67 (1H, s), 8.47 (1H, d), 8.34-8.23 (2H, m), 8.12-8.03 (1H, m), 7.60 (1H, t), 7.55-7.45 (2H, m), 7.42 (1H, d), 5.80 (1H, s), 3.96 (2H, q), 3.74-3.60 (1H, m), 3.60-3.47 (1H, m), 3.47-3.35 (2H, m), 3.28-3.16 (1H, m), 2.32-2.07 (3H, m), 1.99-1.87 (1H, m). | 512 |

| Eg. | Structure | Chemical name | Route/Method | NMR Data (solvent) | MS Data |
|---|---|---|---|---|---|
| 132B | 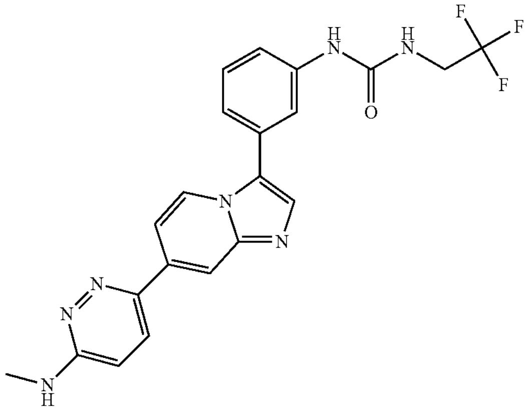 [SMILES: CNc1ccc(-c2ccn3c(-c4cccc(NC(=O)NCC(F)(F)F)c4)cnc3c2)nn1] | 1-{3-[7-(6-Methylamino-pyridazin-3-yl)-imidazo[1,2-a]pyridin-3-yl]-phenyl}-3-(2,2,2-trifluoroethyl)-urea formate | General route B: B1, B2, B3c using (6-chloro-pyridazin-3-yl)-methyl-amine | (Me-d3-OD): 8.98 (1H, d), 8.63 (1H, s), 8.56 (1H, d), 8.34 (1H, s), 8.17 (1H, dd), 8.10 (1H, s), 7.79-7.71 (1H, m), 7.60 (1H, t), 7.49-7.38 (2H, m), 3.96 (2H, q), 3.21 (3H, s). | 442 |

Example 133A 1-(3-{7-[6-(3-Hydroxy-piperidin-1-yl)-pyridazin-3-yl]-imidazo[1,2-a]pyridin-3-yl}-phenyl)-3-(2,2,2-trifluoro-ethyl)-urea

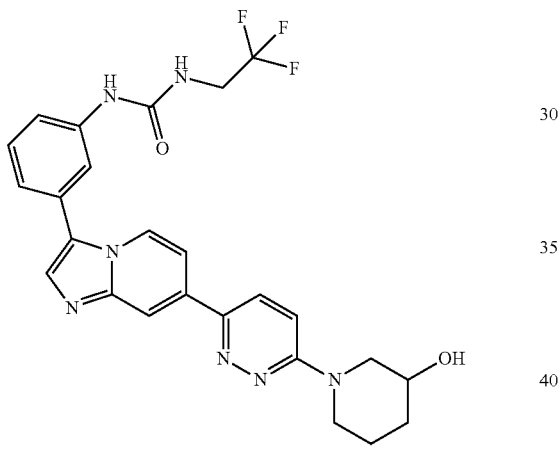

Example 133B

Example 133B was prepared in accordance with the procedure set out in the Table below.

| Eg. | Structure | Chemical name | Route/Method | NMR Data (solvent) | MS Data |
|---|---|---|---|---|---|
| 133B | 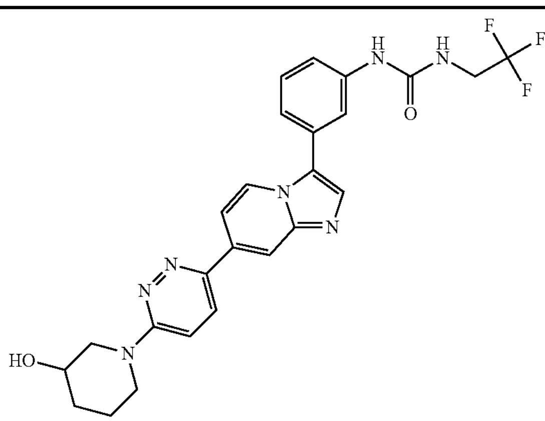 | 1-(3-{7-[6-(3-Hydroxy-piperidin-1-yl)-pyridazin-3-yl]-imidazo[1,2-a]pyridin-3-yl}-phenyl)-3-(2,2,2-trifluoro-ethyl)-urea hydrochloride | General route B: B1, B2, procedure B3c using 1-(6-bromo-pyridazin-3-yl)-piperidin-3-ol, procedure Z5 | (Me-d3-OD): 8.95 (1H, d), 8.63 (1H, s), 8.55 (1H, d), 8.30 (1H, s), 8.18 (1H, d), 8.07 (2H, d), 7.59 (1H, t), 7.44 (2H, dd), 4.06 (1H, s), 4.02-3.87 (5H, m), 3.86-3.74 (1H, m), 2.16-1.98 (2H, m), 1.90-1.72 (2H, m). | 512 |

Example 134A

1-{3-[7-(4-Methyl-pyridazin-3-yl)-imidazol[1,2-a]pyridin-3-yl]-phenyl}-3-(2,2,2-trifluoro-ethyl)-urea

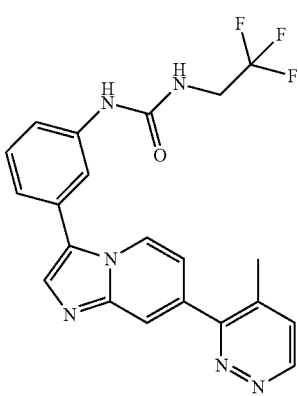 [SMILES: Cc1ccnnc1-c1ccn2c(-c3cccc(NC(=O)NCC(F)(F)F)c3)cnc2c1]

Example 135A

1-{3-[7-(6-Chloro-5-methyl-pyridazin-3-yl)-imidazo[1,2-a]pyridin-3-yl]-phenyl}-3-(2,2,2-trifluoro-ethyl)-urea

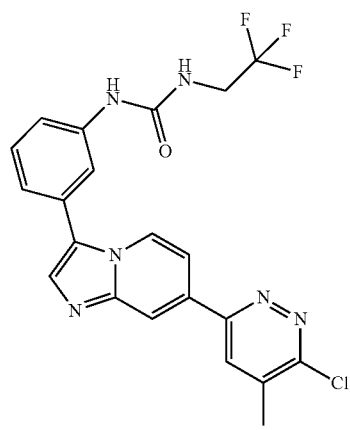 [SMILES: Cc1cc(-c2ccn3c(-c4cccc(NC(=O)NCC(F)(F)F)c4)cnc3c2)nnc1Cl]

Example 135B

Example 135B was prepared in accordance with the procedures set out in the Table below.

| Eg. | Structure | Chemical name | Route/Method | NMR Data (solvent) | MS Data |
|---|---|---|---|---|---|
| 135B | 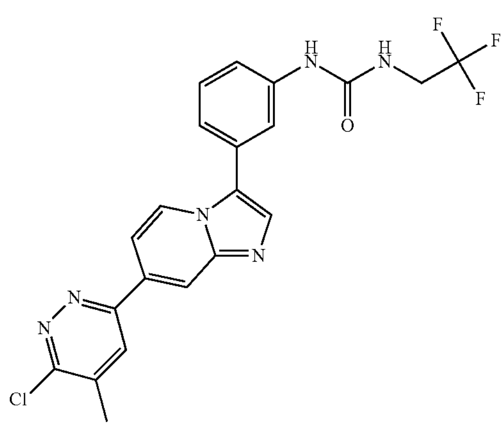 [SMILES: Cc1cc(-c2ccn3c(-c4cccc(NC(=O)NCC(F)(F)F)c4)cnc3c2)nnc1Cl] | 1-{3-[7-(6-Chloro-5-methyl-pyridazin-3-yl)-imidazo-[1,2-a]pyridin-3-yl]-phenyl}-3-(2,2,2-trifluoroethyl)-urea trifluoroacetate | General Route B in step B3d used 3,6-dichloro-4-methyl-pyridazine | (Me-d3-OD): 8.96 (1H, d), 8.74 (1H, s), 8.45 (1H, s), 8.28 (2H, d), 8.04 (1H, s), 7.58 (1H, t), 7.48 (1H, d), 7.41 (1H, d), 3.95 (2H, q), 2.60 (3H, s). | 461 |

Example 136A

1-{3-[7-(6-Chloro-4-methyl-pyridazin-3-yl)-imidazol[1,2-a]pyridin-3-yl]-phenyl}-3-(2,2,2-trifluoro-ethyl)-urea

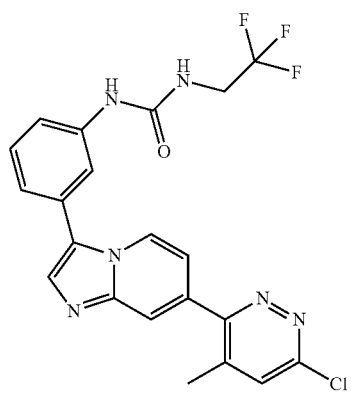 [SMILES: Cc1cc(Cl)nnc1-c1ccn2c(-c3cccc(NC(=O)NCC(F)(F)F)c3)cnc2c1]

Example 137A

1-{3-[7-(5-Methyl-pyridazin-3-yl)-imidazo[1,2-a]pyridin-3-yl]-phenyl}-3-(2,2,2-trifluoro-ethyl)-urea

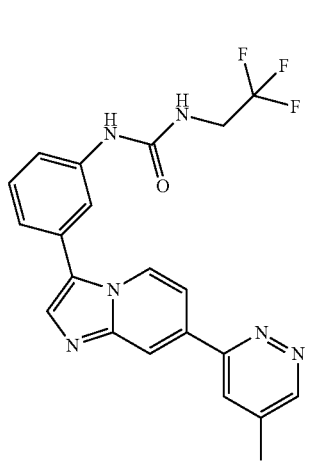 [SMILES: Cc1cnnc(-c2ccn3c(-c4cccc(NC(=O)NCC(F)(F)F)c4)cnc3c2)c1]

Example 136B

Example 136B was prepared in accordance with the procedures set out in the Table below.

Example 137B

Example 137B was prepared in accordance with the procedure set out in the Table below.

| Eg. | Structure | Chemical name | Route/Method | NMR Data (solvent) | MS Data |
|---|---|---|---|---|---|
| 136B | 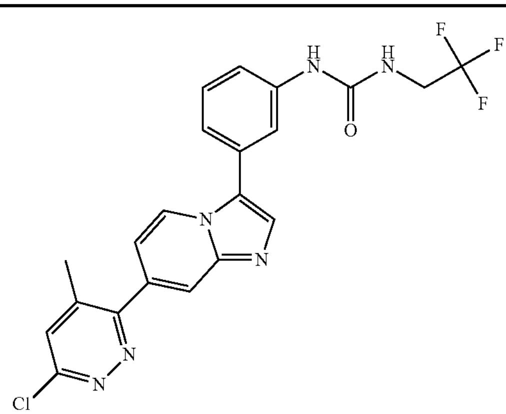 | 1-{3-[7-(6-Chloro-4-methyl-pyridazin-3-yl)-imidazo-[1,2-a]pyridin-3-yl]-phenyl}-3-(2,2,2-trifluoroethyl)-urea trifluoroacetate | General Route B in step B3d used 3,6-dichloro-4-methyl-pyridazine | (Me-d3-OD): 8.97 (1H, d), 8.30 (2H, s), 8.06 (1H, s), 7.94 (1H, s), 7.81 (1H, d), 7.59 (1H, t), 7.48 (1H, d), 7.43 (1H, d), 3.95 (2H, q), 2.54 (3H, s). | 461 |

| Eg. | Structure | Chemical name | Route/ Method | NMR Data (solvent) | MS Data |
|---|---|---|---|---|---|
| 137B | 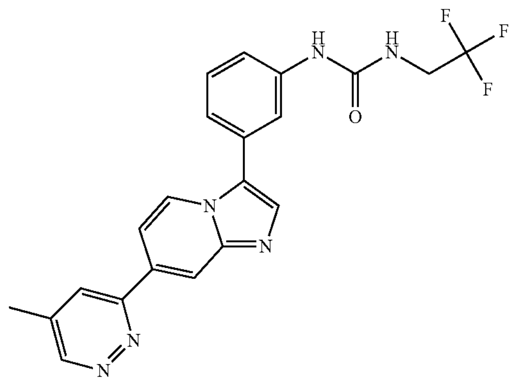 [SMILES: Cc1cnnc(-c2ccn3c(-c4cccc(NC(=O)NCC(F)(F)F)c4)cnc3c2)c1] | 1-{3-[7-(5-Methyl-pyridazin-3-yl)-imidazo[1,2-a]pyridin-3-yl]-phenyl}-3-(2,2,2-trifluoro-ethyl)-urea hydrochloride | General Route B in step B3c used 3-chloro-5-methylpyridazine | (Me-d3-OD): 9.48 (1H, s), 9.03 (1H, d), 8.83 (1H, s), 8.81 (1H, s), 8.36 (1H, s), 8.31 (1H, dd), 8.09 (1H, s), 7.61 (1H, t), 7.53-7.46 (1H, m), 7.44 (1H, d), 3.96 (2H, q), 2.71 (3H, s). | 427 |

Example 138A

1-{3-[7-(5-Methoxy-pyrimidin-2-yl)-imidazo[1,2-a]pyridin-3-yl]-phenyl}-3-(2,2,2-trifluoro-ethyl)-urea

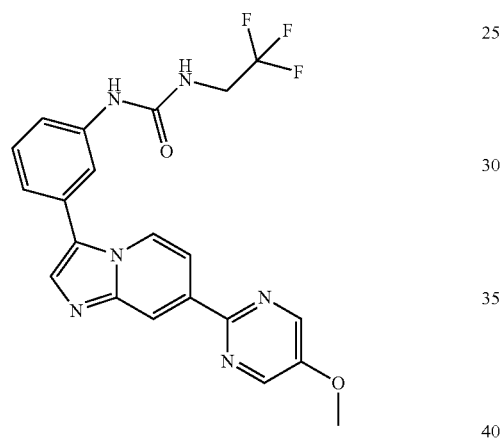

Example 138B

Example 138B was prepared in accordance with the procedure set out in the Table below.

| Eg. | Structure | Chemical name | Route/ Method | NMR Data (solvent) | MS Data |
|---|---|---|---|---|---|
| 138B | 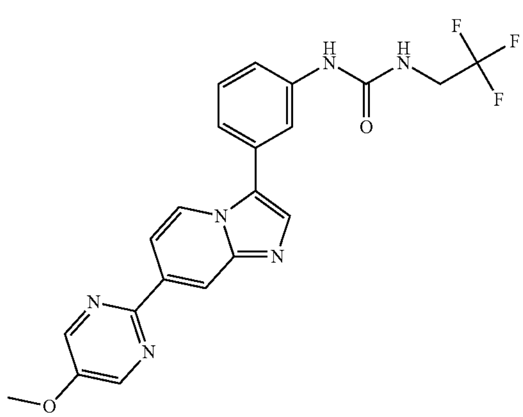 [SMILES: COc1cnc(-c2ccn3c(-c4cccc(NC(=O)NCC(F)(F)F)c4)cnc3c2)nc1] | 1-{3-[7-(5-Methoxy-pyrimidin-2-yl)-imidazo[1,2-a]pyridin-3-yl]-phenyl}-3-(2,2,2-trifluoro-ethyl)-urea | General route B: B1, B2, procedure B3d using 2-chloro-5-methoxy-pyrimidine (MW irradiation) | (Me-d3-OD): 8.66 (1H, d), 8.62 (3H, s), 8.04 (1H, dd), 7.88-7.83 (1H, m), 7.82 (1H, s), 7.51 (1H, t), 7.47-7.40 (1H, m), 7.34 (1H, d), 4.04 (3H, s), 3.96 (2H, q). | 443 |

Example 139A

1-{3-[7-(2-Chloro-5-methoxy-pyrimidin-4-yl)-imidazo[1,2-a]pyridin-3-yl]-phenyl}-3-(2,2,2-trifluoro-ethyl)-urea

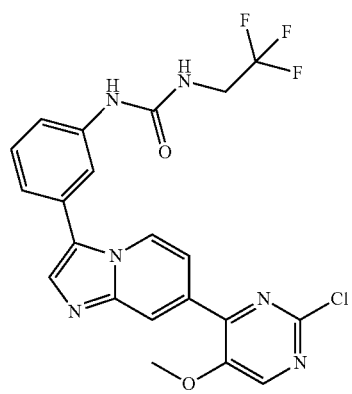 [SMILES: COc1cnc(Cl)nc1-c1ccn2c(-c3cccc(NC(=O)NCC(F)(F)F)c3)cnc2c1]

Example 140A

1-{3-[7-(5-Methoxy-pyrimidin-4-yl)-imidazo[1,2-a]pyridin-3-yl]-phenyl}-3-(2,2,2-trifluoro-ethyl)-urea

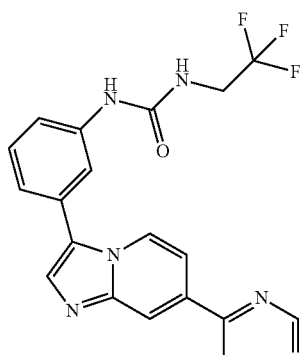

Example 139B

Example 139B was prepared in accordance with the procedure set out in the Table below.

Example 140B

Example 140B was prepared in accordance with the procedure set out in the Table below.

| Eg. | Structure | Chemical name | Route/Method | NMR Data (solvent) | MS Data |
|---|---|---|---|---|---|
| 139B | 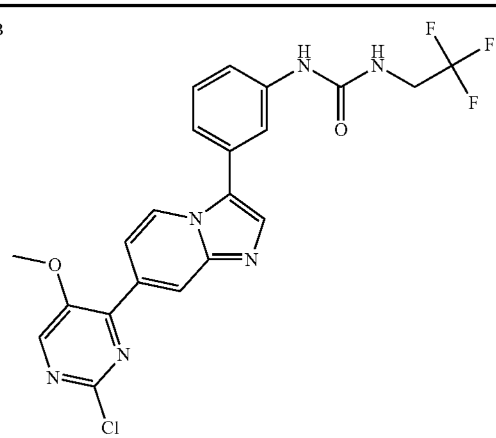 | 1-{3-[7-(2-Chloro-5-methoxy-pyrimidin-4-yl)-imidazo-[1,2-a]pyridin-3-yl]-phenyl}-3-(2,2,2-trifluoroethyl)-urea | General Route B followed by procedure B3d using 2,4-dichloro-5-methoxypyrimidine. | (Me-d3-OD): 8.56 (3H, d), 7.78 (3H, s), 7.46 (1H, t), 7.42-7.32 (1H, m), 7.28 (1H, d), 4.13 (3H, s), 3.96 (3H, q). | 477 |

| Eg. | Structure | Chemical name | Route/ Method | NMR Data (solvent) | MS Data |
|---|---|---|---|---|---|
| 140B | 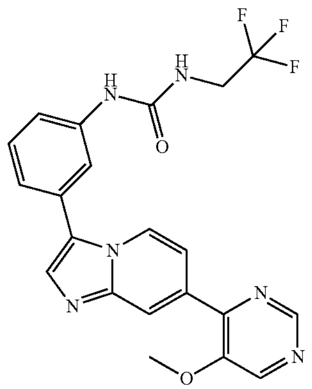 [SMILES: COc1cncnc1-c1ccn2c(-c3cccc(NC(=O)NCC(F)(F)F)c3)cnc2c1] | 1-{3-[7-(5-Methoxy-pyrimidin-4-yl)-imidazo-[1,2-a]pyridin-3-yl]-phenyl}-3-(2,2,2-trifluoroethyl)-urea hydrochloride | General Route B followed by B3d using 2,4-dichloro-5-methoxy-pyrimidine, then procedure G. | (Me-d3-OD): 9.02 (1H, s), 8.97-8.85 (3H, m), 8.42 (1H, d), 8.30 (1H, s), 8.07 (1H, s), 7.60 (1H, t), 7.47 (1H, d), 7.42 (1H, d), 4.22 (3H, s), 3.96 (2H, q). | 443 |

Example 141A

1-[3-(7-[1,2,4]-Triazin-3-yl-imidazo[1,2-a]pyridin-3-yl)-phenyl]-3-(2,2,2-trifluoro-ethyl)-urea

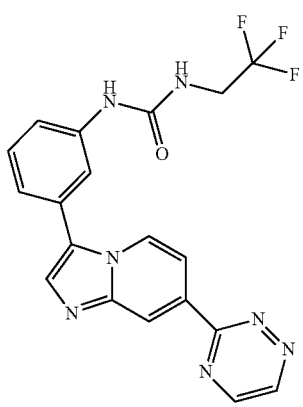 [SMILES: O=C(NCC(F)(F)F)Nc1cccc(-c2cnc3cc(-c4nccnn4)ccn23)c1]

The title compound could be prepared by routes described herein or using the reagents laid out below:

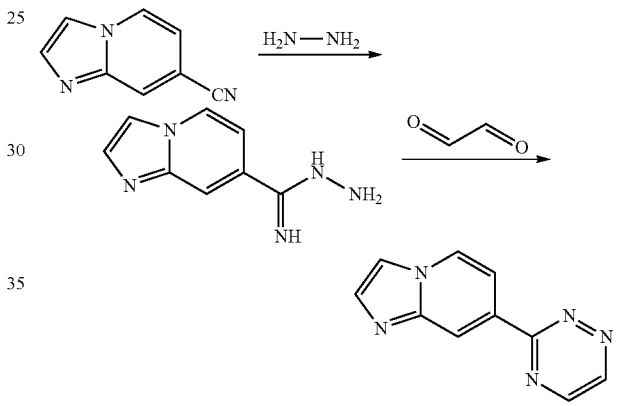

Example 141B

Example 141B was prepared in accordance with the procedure set out below.

| Eg. | Structure | Chemical name | Route/ Method | NMR Data (solvent) | MS Data |
|---|---|---|---|---|---|
| 141B | 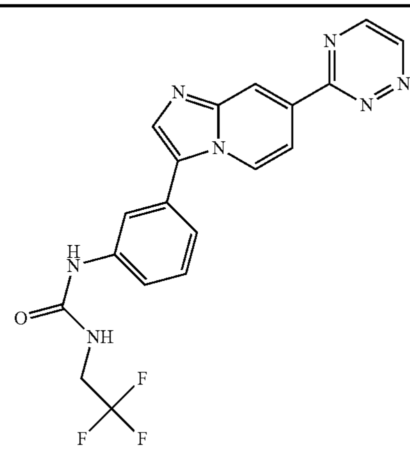 | 1-[3-(7-[1,2,4]Triazin-3-yl-imidazo[1,2-a]pyridin-3-yl)-phenyl]-3-(2,2,2-trifluoro-ethyl)-urea | Set out below | (Me-d3-OD & CDCl3): 9.26 (1H, d), 8.91-8.80 (2H, m), 8.67 (1H, d), 8.16-8.04 (2H, m), 7.85 (2H, d), 7.48 (1H, t), 7.39 (1H, d), 7.30 (1H, d), 3.91 (2H, q). | 414 |

Example 141B

Process for preparing 1-[3-(7-[1,2,4]-Triazin-3-yl-imidazo[1,2-a]pyridin-3-yl-Phenyl]-3-(2,2,2-trifluoro-ethyl)-urea

Step (a) Imidazo[1,2-a]pyridine-7-carboxylic acid amide

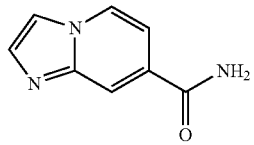 [SMILES: NC(=O)c1ccn2ccnc2c1]

Prepared as described in procedure A1 using 2-aminoisonicotinamide MS: [M+H]$^+$162.

Step (b) Imidazo[1,2-a]pyridine-7-carbonitrile

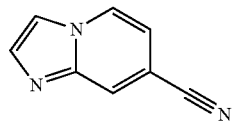 [SMILES: N#Cc1ccn2ccnc2c1]

To a solution of Imidazo[1,2-a]pyridine-7-carboxylic acid amide (38 mg, 0.24 mmol) and triethylamine (0.066 ml, 0.47 mmol) in CH$_2$Cl$_2$ (5 ml) was added trifluoroacetic anhydride (0.39, 2.83 mmol) dropwise. The reaction mixture was stirred at room temperature for 2 h before the crude mixture was loaded onto a SCX SPE cartridge, washing with MeOH and eluting with the product with 2M NH$_3$/MeOH. Removal of solvent in vacuo afforded the title compounds (32 mg). MS: [M+H]$^+$143.

Step (c) Imidazo[1,2-a]pyridine-7-carboximidic Acid Methyl Ester Hydrochloride

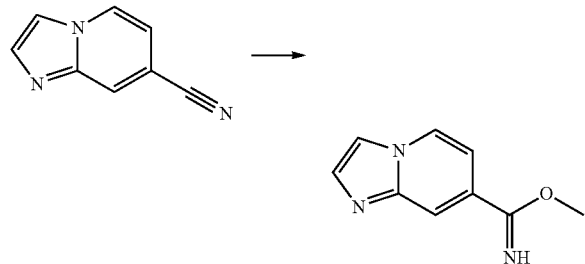

Hydrogen chloride gas was bubbled through a mixture of imidazo[1,2-a]pyridine-7-carbonitrile (1.0 g, 7.0 mmol), methanol (10 ml) and ether (25 ml) at room temperature for 3 minutes. The resultant mixture was stirred for 3 hours. The solid material was isolated by filtration and was washed with diethyl ether to furnish a 80% pure tan solid (1.7 g). MS: [M+H]$^+$176

Step (d) Imidazo[1,2-a]pyridine-7-carboximidic Acid, Hydrazide

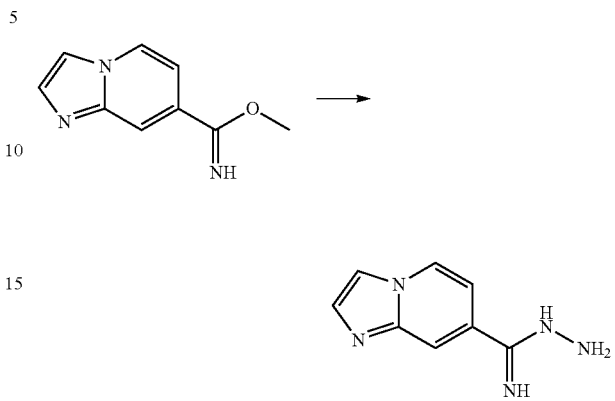

Hydrazine hydrate (80% in water, 0.25 ml, 2 equiv) was added to a mixture of imidazo[1,2-a]pyridine-7-carboximidic acid methyl ester hydrochloride (1.0 g, 4.7 mmol, 1 equiv) in methanol (30 ml). The mixture was heated to 70 deg C. for 1 hour then allowed to cool to room temperature. After leaving to stand overnight, any solid was removed by vacuum filtration and the solution was concentrated in vacuo and re-concentrated from methanol and was used crude without further purification in the cyclisation step

Step (e) 7-[1,2,4]Triazin-3-yl-imidazo[1,2-a]pyridine

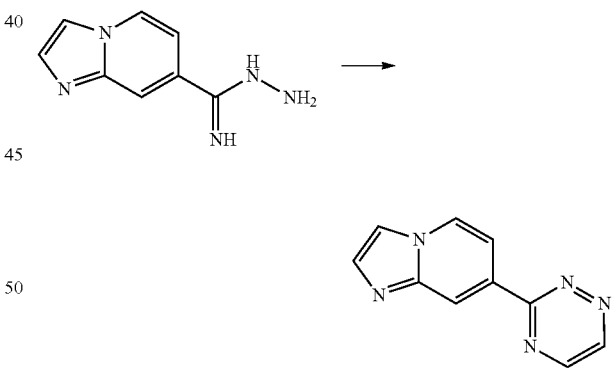

To half the material from step d (ca. 2.3 mmol) was added glyoxal (40% in water, 1 ml) and ethanol (15 ml) and the mixture heated to 100 deg C. After 1 hour the reaction was allowed to cool and was concentrated in vacuo. Water and dichloromethane was added and the mixture filtered under suction. The organic liquors were discarded and the aqueous layer was basified with 2N sodium hydroxide solution. To this was added dichloromethane and the mixture was again filtered under suction. The dichloromethane layer was separated and concentrated to furnish 289 mg of a yellow solid (80% clean). MS: [M+H]$^+$198

Step (f) 3-Iodo-7-[1,2,4]triazin-3-yl-imidazo[1,2-a]pyridine

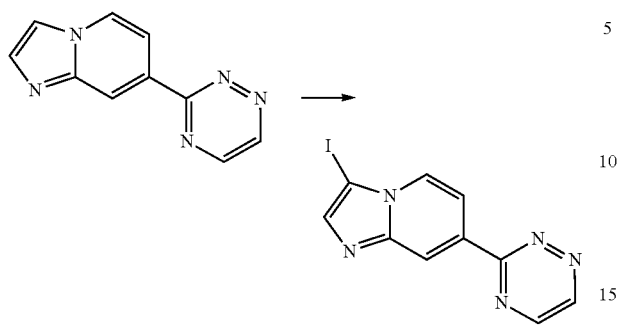

7-[1,2,4]Triazin-3-yl-imidazo[1,2-a]pyridine (280 mg) was iodinated according to Procedure A2 to furnish the title compound (96 mg). MS: [M+H]$^+$324

Step (g) 1-[3-(7-[1,2,4]Triazin-3-yl-imidazo[1,2-a]pyridin-3-yl)-phenyl]-3-(2,2,2-trifluoro-ethyl)-urea

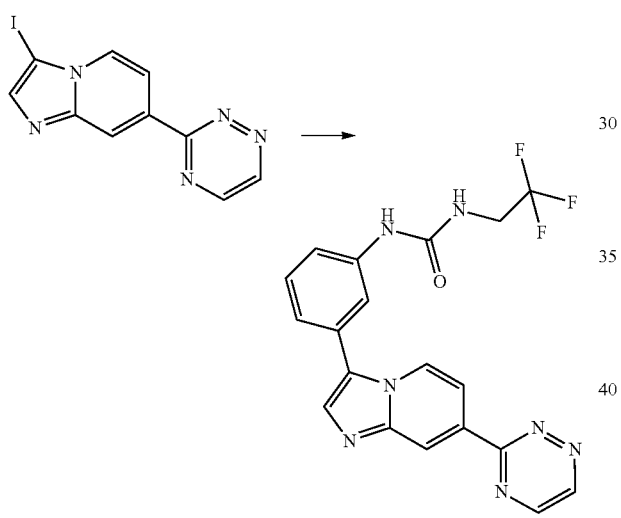

3-Iodo-7-[1,2,4]triazin-3-yl-imidazo[1,2-a]pyridine (96 mg, 0.3 mmol) and 1-[3-(4,4,5,5-tetramethyl-[1,3,2]dioxaborolan-2-yl)-phenyl]-3-(2,2,2-trifluoro-ethyl)-urea were coupled according to procedure D4 to furnish the title compound as a yellow solid (39 mg). $^1$H NMR (400 MHz, Me-d$_3$-OD & CDCl$_3$): 9.26 (1H, d), 8.91-8.80 (2H, m), 8.67 (1H, d), 8.16-8.04 (2H, m), 7.85 (2H, d), 7.48 (1H, t), 7.39 (1H, d), 7.30 (1H, d), 3.91 (2H, q). MS: [M+H]$^+$414

Example 142A

1-{3-[7-(5-Methyl-[1,2,4]triazin-3-yl)-imidazo[1,2-a]pyridin-3-yl]-phenyl}-3-(2,2,2-trifluoro-ethyl)-urea

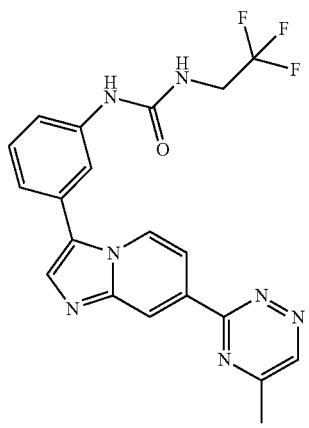 [SMILES: Cc1cnnc(-c2ccn3c(-c4cccc(NC(=O)NCC(F)(F)F)c4)cnc3c2)n1]

The title compound could be prepared by routes described herein or using the reagents laid out above but using pyruvic aldehyde in place of glyoxal.

Example 142B

Example 142B was prepared in accordance with the procedure set out below.

| Eg. | Structure | Chemical name | Route/Method | NMR Data (solvent) | MS Data |
|---|---|---|---|---|---|
| 142B | 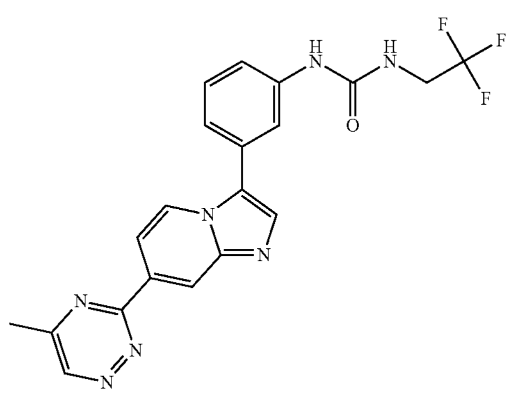 [SMILES: Cc1cnnc(-c2ccn3c(-c4cccc(NC(=O)NCC(F)(F)F)c4)cnc3c2)n1] | 1-{3-[7-(5-Methyl-[1,2,4]triazin-3-yl)-imidazo[1,2-a]pyridin-3-yl]-phenyl}-3-(2,2,2-trifluoro-ethyl)-urea | Set out below | (DMSO-d6): 9.34 (1H, s), 8.99 (1H, s), 8.74 (1H, d), 8.67 (1H, s), 7.98 (1H, d), 7.93 (1H, s), 7.79 (1H, s), 7.55-7.43 (2H, m), 7.31 (1H, d), 6.87 (1H, t), 3.99-3.88 (2H, m), 2.65 (3H, s). | 428 |

Example 142B

Process for preparing 1-{3-[7-(5-Methyl-[1,2,4]triazin-3-yl)-imidazo[1,2-a]pyridin-3-yl]-phenyl}-3-(2,2,2-trifluoro-ethyl)-urea

Step (a): Methyl imidazo[1,2-a]pyridine-7-carboxylate

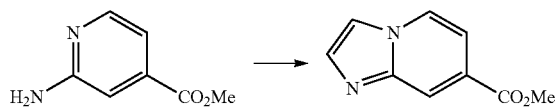

To a solution of Methyl 2-aminopyridine-4-carboxylate (10.0 g, 66 mmol, 1.0 equiv) in EtOH (150 ml) was added NaHCO$_3$ (11.1 g, 132 mmol, 2.0 equiv) followed by chloroacetaldehyde (13.0 ml, 99 mmol, 1.5 equiv). The mixture was refluxed for 2 h. Solvents were removed under reduced pressure and the crude mixture was partitioned between water and EtOAc. The resulting precipitate was washed with Et$_2$O and recrystallised from MeOH/Et$_2$O to afford 8.4 g of product. $^1$H NMR (400 MHz, DMSO-d$^6$): 8.66 (1H, d), 8.16 (2H, s), 7.80 (1H, s), 7.33 (1H, d), 3.90 (3H, s). MS: [M+H]$^+$177.

Step (b) Imidazo[1,2-a]pyridine-7-carboxylic Acid Hydrazide

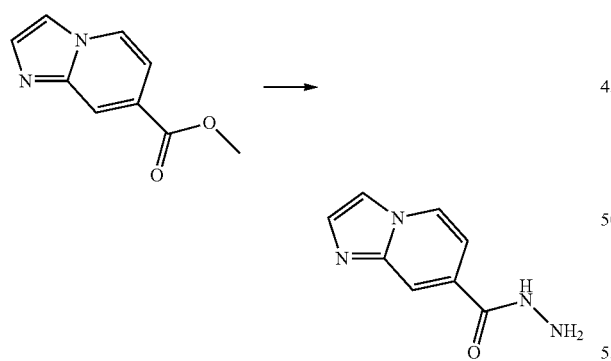

To a suspension of methyl-3-Iodo-imidazo[1,2-a]pyridine-7-carboxylate (0.3 g, 1.7 mmol, 1.0 equiv) in ethanol (3 ml) was added hydrazine hydrate (0.414 ml, 8.52 mmol). The mixture was heated to 70 deg C. for 1 h then allowed to cool. The solid was filtered off and washed with ethyl acetate and ether then dried to afford 0.209 g of product. 1H NMR (400 MHz, DMSO-d6): 9.95 (1H, s), 8.60 (1H, d), 8.05 (2H, d), 7.70 (1H, d), 7.30 (1H, dd), 4.58 (2H, s).

Step (c) 7-(5-Methyl-[1,2,4]triazin-3-yl)-imidazo[1,2-a]pyridine

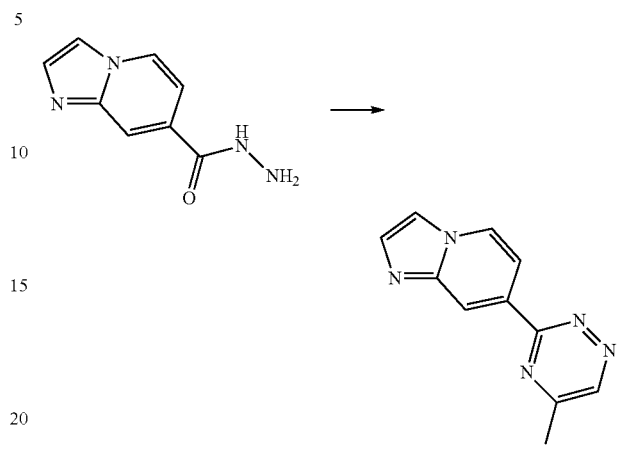

A suspension of imidazo[1,2-a]pyridine-7-carboxylic acid hydrazide (705 mg, 4.0 mmol, 1.0 equiv) and pyruvic aldehyde (40 wt % in water, 0.8 ml) in ethanol (10 ml) was stirred at room temperature for 2.5 hours. Ammonia (2M in methanol, 10 ml) was added and stirred at room temperature for 15 minutes before heating to 100 deg C. in a microwave for 60 minutes. The reaction mixture was concentrated in vacuo and dichloromethane was added. After stirring at room temperature for 15 minutes the solid (recovered starting material) was filtered off and the liquors were purified by column chromatography (0-10% methanol/dichloromethane) furnishing 200 mg of a yellow solid. MS: [M+H]$^+$212

Step (d) 3-Iodo-7-(5-methyl-[1,2,4]triazin-3-yl)-imidazo[1,2-a]pyridine

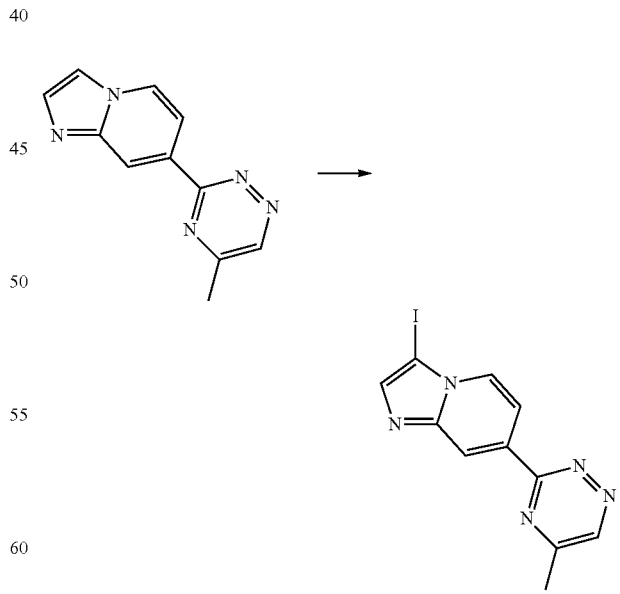

7-(5-Methyl-[1,2,4]triazin-3-yl)-imidazo[1,2-a]pyridine (200 mg, 0.9 mmol, 1 equiv) and N-iodosuccinamide (300 mg, 1.3 mmol, 1.4 equiv) in dimethylformamide (5 ml) was stirred at room temperature. After 3 hours diethyl ether was Step (e) 1-{3-[7-(5-Methyl-[1,2,4]triazin-3-yl)-imidazo[1,2-a]pyridin-3-yl]-phenyl}-3-(2,2,2-trifluoro-ethyl)-urea

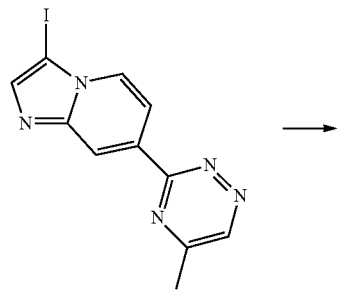

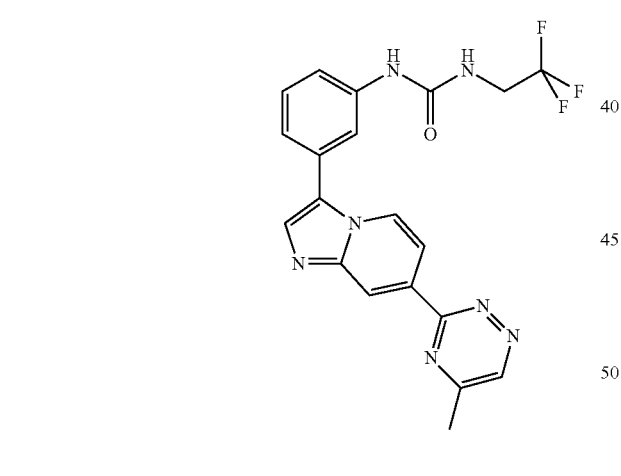

3-Iodo-7-(5-methyl-[1,2,4]triazin-3-yl)-imidazo[1,2-a]pyridine (120 mg, 0.4 mmol, 1 equiv) and 1-[3-(4,4,5,5-Tetramethyl-[1,3,2]dioxaborolan-2-yl)-phenyl]-3-(2,2,2-trifluoro-ethyl)-urea were coupled according to procedure D4 to furnish the title compound as a yellow solid (85 mg). 1H NMR (400 MHz, DMSO-d6): 9.34 (1H, s), 8.99 (1H, s), 8.74 (1H, d), 8.67 (1H, s), 7.98 (1H, d), 7.93 (1H, s), 7.79 (1H, s), 7.55-7.43 (2H, m), 7.31 (1H, d), 6.87 (1H, t), 3.99-3.88 (2H, m), 2.65 (3H, s). MS: [M+H]+428

Example 143A 1-(3-{7-[6-(Piperidin-4-yloxy)-Pyridin-3-yl]-imidazo[1,2-a]pyridin-3-yl}-phenyl)-3-(2,2,2-trifluoro-ethyl)-urea

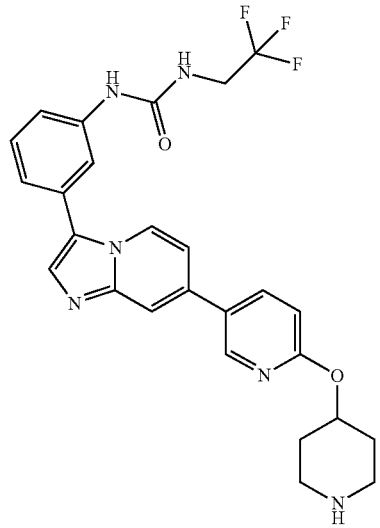 [SMILES: O=C(NCC(F)(F)F)Nc1cccc(-c2cnc3cc(-c4ccc(OC5CCNCC5)nc4)ccn23)c1]

Example 144A 1-(3-{7-[6-(3-Dimethylamino-propoxy)-pyridin-3-yl]-imidazo[1,2-a]pyridin-3-yl}-phenyl)-3-(2,2,2-trifluoro-ethyl)-urea

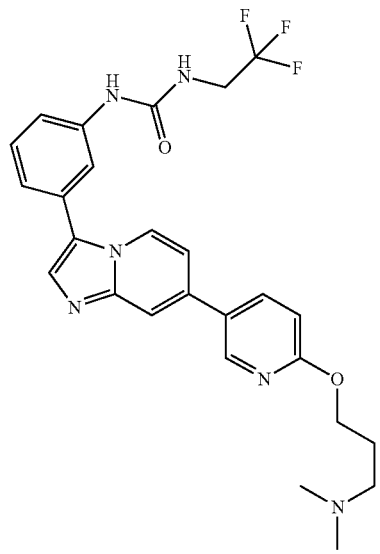 [SMILES: CN(C)CCCOc1ccc(-c2ccn3c(-c4cccc(NC(=O)NCC(F)(F)F)c4)cnc3c2)cn1]

Example 144B

Example 144B was prepared in accordance with the procedure set out in the table below.

| Eg. | Structure | Chemical name | Route/ Method | NMR Data (solvent) | MS Data |
|---|---|---|---|---|---|
| 144B | 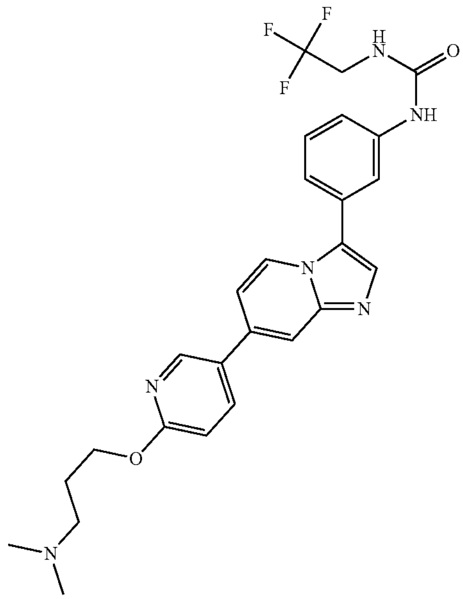 [SMILES: CN(C)CCCOc1ccc(-c2ccn3c(-c4cccc(NC(=O)NCC(F)(F)F)c4)cnc3c2)cn1] | 1-(3-{7-[6-(3-Dimethylamino-propoxy)-pyridin-3-yl]-imidazo[1,2-a]pyridin-3-yl}-phenyl)-3-(2,2,2-trifluoro-ethyl)-urea hydrochloride | General route A: A1, A2, A3, A4, A5a using dimethyl-{3-[5-(4,4,5,5-tetramethyl-[1,3,2]-dioxaborolan-2-yl)-pyridin-2-yloxy]-propyl}-amine, procedure Z5 | (DMSO-d6): 9.66 (1H, s), 8.86-8.77 (2H, m), 8.43 (1H, s), 8.35 (1H, dd), 8.29 (1H, s), 7.92 (2H, s), 7.60-7.49 (2H, m), 7.36-7.21 (2H, m), 7.05 (1H, d), 4.03-3.87 (2H, m), 3.28-3.13 (2H, m), 2.78 (7H, d), 2.20 (2H, s). | 513 |

Example 145A 1-(3-{7-[6-(4-Acetyl-piperazin-1-yl)-pyridin-3-yl]-imidazo[1,2-a]pyridin-3-yl}-phenyl)-3-(2,2,2-trifluoro-ethyl)-urea

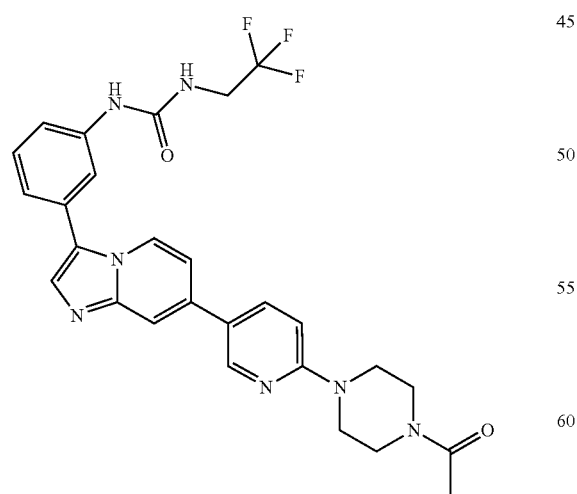

Example 145B

Example 145B was prepared in accordance with the procedure set out in the Table below.

| Eg. | Structure | Chemical name | Route/ Method | NMR Data (solvent) | MS Data |
|---|---|---|---|---|---|
| 145B | 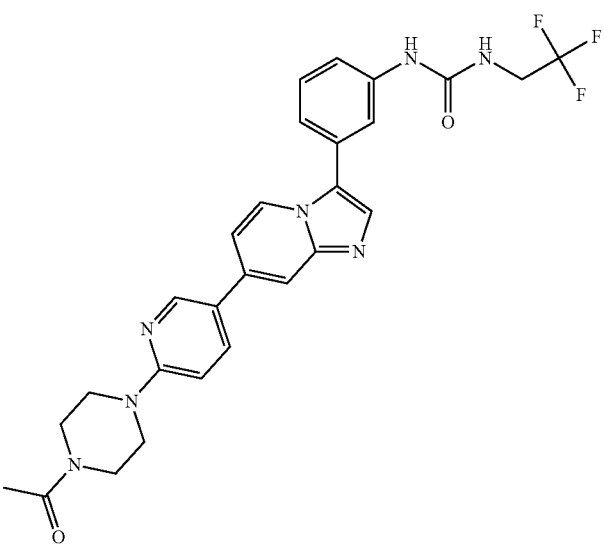 [SMILES: CC(=O)N1CCN(c2ccc(-c3ccn4c(-c5cccc(NC(=O)NCC(F)(F)F)c5)cnc4c3)cn2)CC1] | 1-(3-{7-[6-(4-Acetyl-piperazin-1-yl)-pyridin-3-yl]-imidazo[1,2-a]pyridin-3-yl}-phenyl)-3-(2,2,2-trifluoro-ethyl)-urea hydrochloride | General route A: A1, A2, A3, A4, and A5a using 1-{4-[5-(4,4,5,5-tetramethyl-[1,3,2]-dioxaborolan-2-yl)-pyridin-2-yl]-pipera-zin-1-yl}-ethanone, procedure Z5 | (Me-d3-OD): 8.92 (1H, d), 8.67-8.56 (2H, m), 8.36 (1H, s), 8.25 (1H, s), 8.06 (1H, s), 7.95-7.85 (1H, m), 7.67-7.53 (2H, m), 7.47 (1H, d), 7.40 (1H, d), 4.02-3.87 (10H, m), 2.21 (3H, s). | 538 |

Example 146A

1-{3-[7-(3-Amino-5-chloro-pyridin-2-yl)-imidazo[1,2-a]pyridin-3-yl]-phenyl}-3-(2,2,2-trifluoro-ethyl)-urea

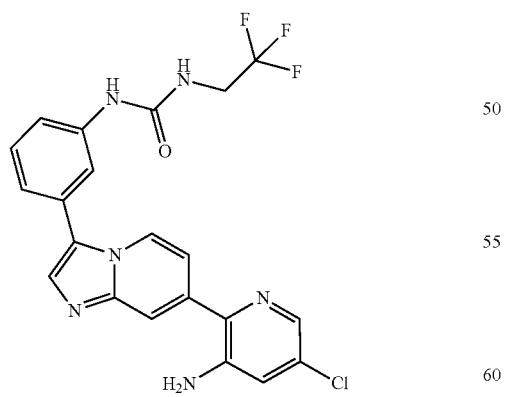

Example 146B

Example 146B was prepared in accordance with the procedure set out in the table below.

| Eg. | Structure | Chemical name | Route/ Method | NMR Data (solvent) | MS Data |
|---|---|---|---|---|---|
| 146B | 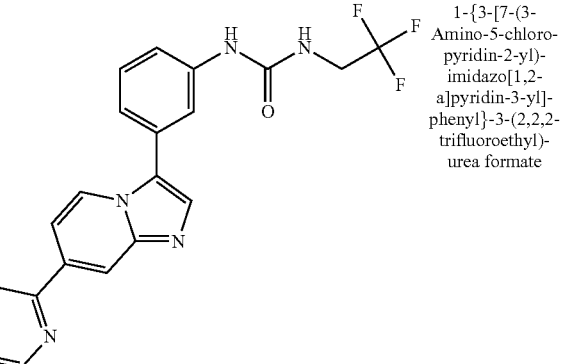 | 1-{3-[7-(3-Amino-5-chloro-pyridin-2-yl)-imidazo[1,2-a]pyridin-3-yl]-phenyl}-3-(2,2,2-trifluoroethyl)-urea formate | General Route B in step B3d used 2,5-dichloro-pyridin-3-ylamine | (Me-d3-OD): 8.66 (1H, d), 8.17 (1H, s), 7.98 (1H, s), 7.92 (1H, d), 7.85 (1H, s), 7.80 (1H, s), 7.54-7.44 (1H, m), 7.43-7.34 (2H, m), 7.34-7.24 (2H, m), 3.95 (2H, q). | 461 |

Example 147A

1-{3-[7-(4-piperazin-1-yl-pyridin-2-yl)-imidazo[1,2-a]pyridin-3-yl]-phenyl}-3-(2,2,2-trifluoro-ethyl)-urea

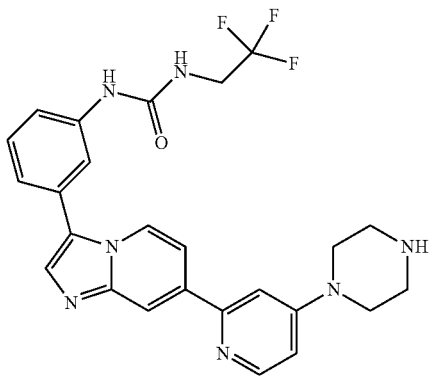 [SMILES: O=C(NCC(F)(F)F)Nc1cccc(-c2cnc3cc(-c4cc(N5CCNCC5)ccn4)ccn23)c1]

Example 148A

1-{3-[7-(4,6-Dimethyl-pyridin-2-yl)-imidazo[1,2-a]pyridin-3-yl]-phenyl}-3-(2,2,2-trifluoro-ethyl)-urea

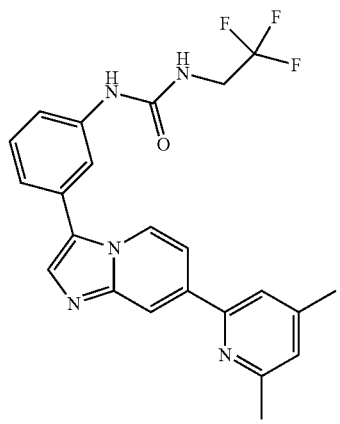 [SMILES: Cc1cc(C)nc(-c2ccn3c(-c4cccc(NC(=O)NCC(F)(F)F)c4)cnc3c2)c1]

Example 148B

Example 148B was prepared in accordance with the procedure set out in the Table below.

| Eg. | Structure | Chemical name | Route/Method | NMR Data (solvent) | MS Data |
|---|---|---|---|---|---|
| 148B | 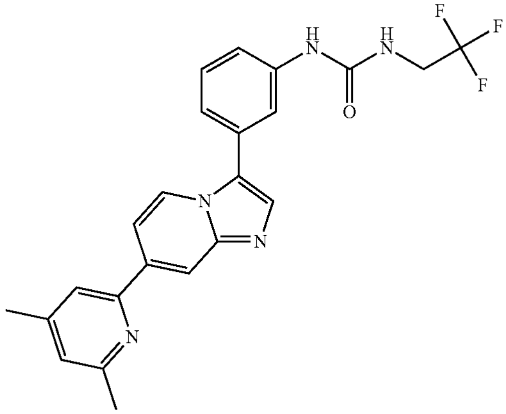 [SMILES: Cc1cc(C)nc(-c2ccn3c(-c4cccc(NC(=O)NCC(F)(F)F)c4)cnc3c2)c1] | 1-{3-[7-(4,6-Dimethyl-pyridin-2-yl)-imidazo[1,2-a]pyridin-3-yl]-phenyl}-3-(2,2,2-trifluoro-ethyl)-urea formate | General route B: B1, procedure B2, procedure B3d using 2-chloro-4,6-dimethyl-pyridine | (Me-d3-OD): 8.67 (1H, d), 8.27 (1H, s), 8.18 (1H, s), 7.90-7.84 (1H, m), 7.82 (1H, s), 7.75(1H, dd), 7.67 (1H, s), 7.51 (1H, t), 7.43 (1H, d), 7.34 (1H, d), 7.16 (1H, s), 3.96 (2H, q), 2.59 (3H, s), 2.45 (3H, s). | 440 |

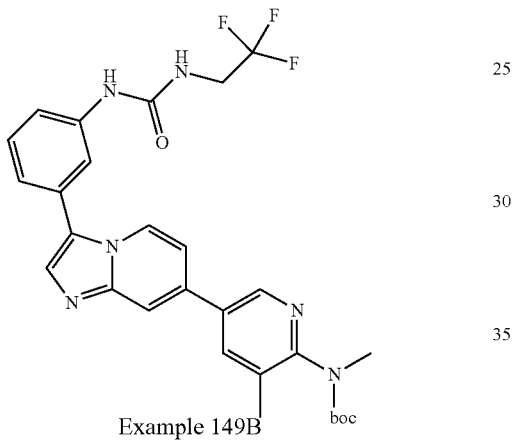

Example 149A

Example 149B

Example 149B was prepared in accordance with the procedure set out in the Table below.

| Eg. | Structure | Chemical name | Route/Method | NMR Data (solvent) | MS Data |
|---|---|---|---|---|---|
| 149B | 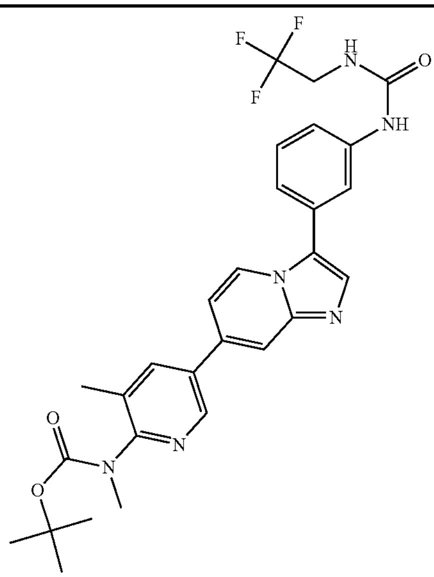 | Methyl-[3-methyl-5-(3-{3-[3-(2,2,2-trifluoro-ethyl)-ureido]-phenyl}-imidazo[1,2-a]pyridin-7-yl)-pyridin-2-yl]-carbamic acid tert-butyl ester | General route A: A1, A2, A3, A4, A5a using methyl-[3-methyl-5-(4,4,5,5-tetramethyl-[1,3,2]-dioxaborolan-2-yl)-pyridin-2-yl]-carbamic acid tert-butyl ester | (Me-d3-OD): 8.76-8.64 (2H, m), 8.19 (1H, s), 7.97 (1H, s), 7.85 (1H, s), 7.77 (1H, s), 7.50 (1H, t), 7.40 (2H, d), 7.33 (1H, d), 3.96 (2H, q), 3.25 (3H, s), 2.38 (3H, s), 1.47 (9H, s). | 555 |

Example 150A

1-{3-[7-(2-Methoxy-pyridin-3-yl)-imidazo[1,2-a]pyridin-3-yl]-phenyl}-3-(2,2,2-trifluoro-ethyl)-urea

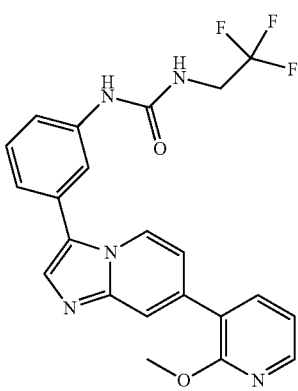 [SMILES: COc1ncccc1-c1ccn2c(-c3cccc(NC(=O)NCC(F)(F)F)c3)cnc2c1]

Example 150B

Example 150B was prepared in accordance with the procedures set out in the Table below.

| Eg. | Structure | Chemical name | Route/Method | NMR Data (solvent) | MS Data |
|---|---|---|---|---|---|
| 150B | 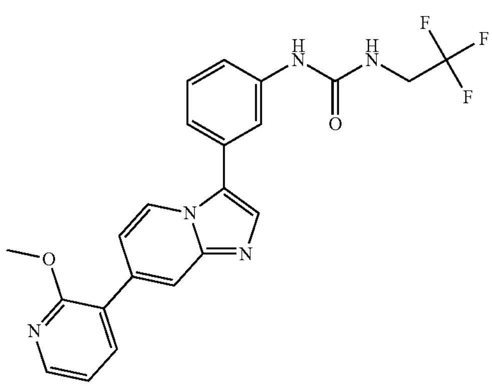 [SMILES: COc1ncccc1-c1ccn2c(-c3cccc(NC(=O)NCC(F)(F)F)c3)cnc2c1] | 1-{3-[7-(2-Methoxy-pyridin-3-yl)-imidazo[1,2-a]pyridin-3-yl]-phenyl}-3-(2,2,2-trifluoro-ethyl)-urea formate | General Route B in step B3c used 2-methoxy-3-(4,4,5,5-tetramethyl-[1,3,2]-dioxaborolan-2-yl pyridine | (Me-d3-OD): 8.60 (1H, d), 8.26-8.19 (1H, m), 8.16 (1H, s), 7.96-7.88 (2H, m), 7.86 (1H, s), 7.80 (1H, s), 7.48 (1H, t), 7.43-7.34 (2H, m), 7.31 (1H, d), 7.17-7.06 (1H, m), 4.02 (3H, s), 3.99-3.88 (2H, m). | 442 |

Example 151A 1-(3-{7-[5-(4-Acetyl-piperazin-1-yl)-pyridin-2-yl]-imidazo[1,2-a]pyridin-3-yl}-phenyl)-3-(2,2,2-trifluoro-ethyl)-urea

Example 152A

1-{5-[7-(1-Piperidin-4-yl-1H-pyrazol-4-yl)-imidazo[1,2-a]pyridin-3-yl]-pyridin-3-yl}-3-(2,2,2-trifluoro-ethyl)-urea

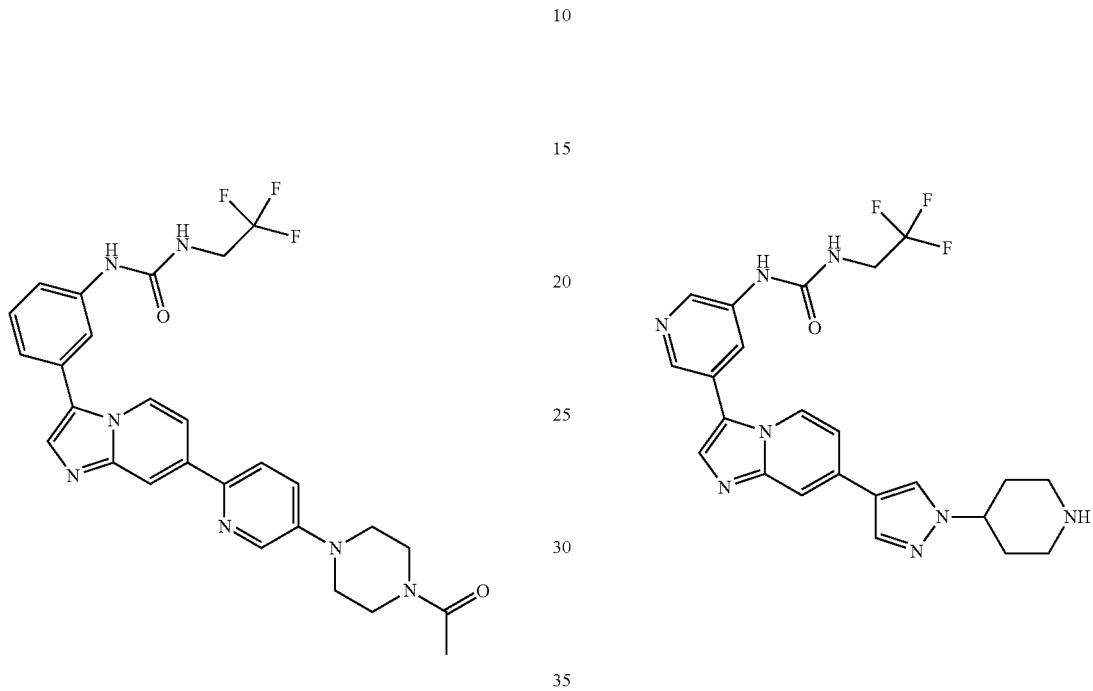

Example 152B

Example 152B was prepared in accordance with the procedure set out in the Table below.

| Eg. | Compound | Name | Route/Method | NMR Data (solvent) | MS Data |
|---|---|---|---|---|---|
| 152B | 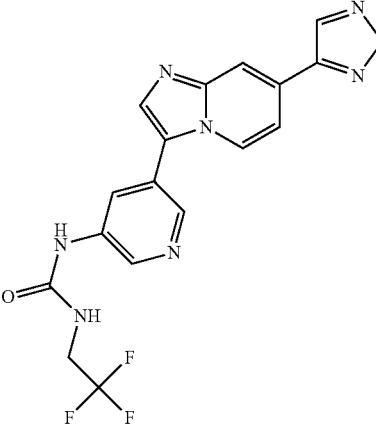 | 1-{5-[7-(1-Piperidin-4-yl-1H-pyrazol-4-yl)-imidazo[1,2-a]pyridin-3-yl]-pyridin-3-yl}-3-(2,2,2-trifluoroethyl)-urea formate | General route B: B1 using monomer from procedure D4, B2, B3c using monomer from procedure X2, then Z1 | (Me-d3-OD): 8.62-8.51 (2H, m), 8.47 (1H, s), 8.43-8.24 (4H, m), 8.08 (1H, s), 7.80 (2H, s), 7.32 (1H, d), 4.71-4.55 (1H, m), 3.97 (2H, q), 3.61 (2H, d), 3.30-3.12 (2H, m), 2.47-2.24 (4H, m). | 485 |

Example 153A

1-{5-[7-(1-Piperidin-3-yl-1H-pyrazol-4-yl)-imidazo[1,2-a]pyridin-3-yl]-pyridin-3-yl}-3-(2,2,2-trifluoro-ethyl)-urea

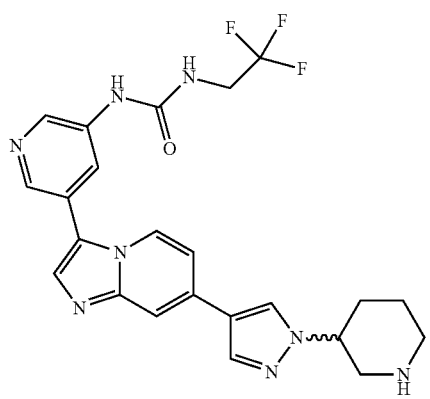 [SMILES: O=C(NCC(F)(F)F)Nc1cncc(-c2cnc3cc(-c4cnn(C5CCCNC5)c4)ccn23)c1]

Example 154A

{3-[7-(4-Fluoro-phenyl)-imidazo[1,2-a]pyridin-3-yl]-phenyl}-urea

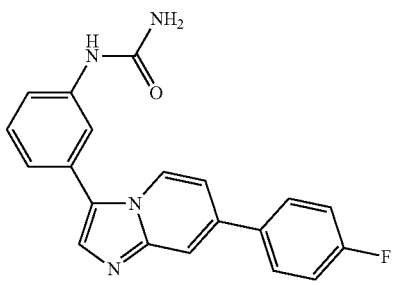 [SMILES: NC(=O)Nc1cccc(-c2cnc3cc(-c4ccc(F)cc4)ccn23)c1]

Example 154B

Example 154B was prepared in accordance with the procedure set out in the Table below

| Eg. | Compound | Name | Route/Method | NMR Data (solvent) | MS Data |
|---|---|---|---|---|---|
| 154B |  | {3-[7-(4-Fluoro-phenyl)-imidazo[1,2-a]pyridin-3-yl]-phenyl}-urea hydrochloride | General route D: D1, D2 using 4-fluorophenyl-boronic acid and A5c but heating thermally, procedure D3, D5 (substituting Na₂CO₃ for K₃PO₄) using [3-(4,4,5,5-Tetramethyl-[1,3,2]-dioxaborolan-2-yl)-phenyl]-urea, Z5 | (DMSO-d6): 8.99 (1H, s), 8.79 (1H, d), 8.36 (1H, s), 8.22 (1H, s), 8.07-7.98 (2H, m), 7.91 (1H, s), 7.83 (1H, dd), 7.56-7.40 (4H, m), 7.31-7.23 (1H, m), 6.03 (1H, s). | 347 |

Example 155A 1-(3-{7-[(E)-2-(3-Methyl-3H-imidazol-4-yl)-vinyl]-imidazo[1,2-a]pyridin-3-yl}-phenyl)-3-(2,2,2-trifluoro-ethyl)-urea

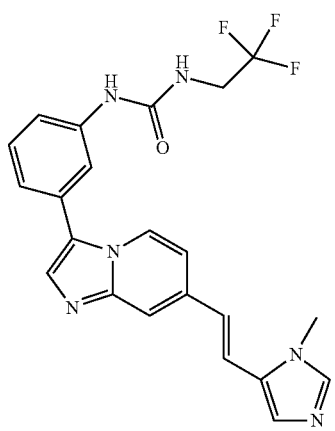 [SMILES: Cn1cncc1/C=C/c1ccn2c(-c3cccc(NC(=O)NCC(F)(F)F)c3)cnc2c1]

The E-isomer of the title compound could be prepared by routes described herein or via selective hydrogenation, using poisoned palladium on the alkyne precursor.

Example 155B

Example 155B was prepared in accordance with the procedure set out in the Table below

Example 156A 1-(3-{7-[(Z)-2-(3-Methyl-3H-imidazol-4-yl)-vinyl]-imidazo[1,2-a]pyridin-3-yl}-phenyl)-3-(2,2,2-trifluoro-ethyl)-urea

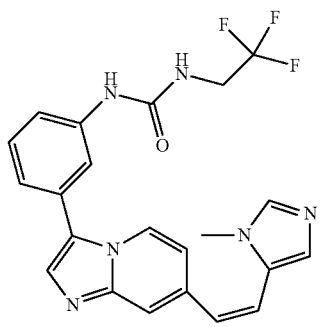 [SMILES: Cn1cncc1/C=C\c1ccn2c(-c3cccc(NC(=O)NCC(F)(F)F)c3)cnc2c1]

The Z-isomer of the title compound could be prepared by routes described herein or using Wittig type chemistry from 1-[3-(7-formyl-imidazo[1,2-a]pyridin-3-yl)-phenyl]-3-(2,2,2-trifluoro-ethyl)-urea and the phosphorous ylide derived from 2-(chloromethyl-1-methyl-1H-imidazole.

Example 157A

1-Cyclopropyl-3-{3-[7-(5-methyl-[1,3,4]oxadiazol-2-yl)-imidazo[1,2-a]pyridin-3-yl]-phenyl}-urea

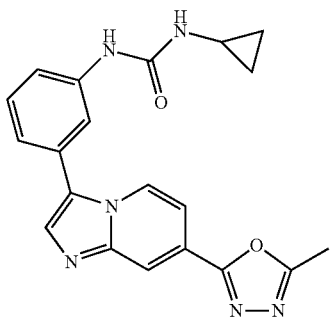 [SMILES: Cc1nnc(-c2ccn3c(-c4cccc(NC(=O)NC5CC5)c4)cnc3c2)o1]

| Eg. | Compound | Name | Route/Method | NMR Data (solvent) | MS Data |
|---|---|---|---|---|---|
| 155B | (structure) | 1-(3-{7-[(E)-2-(3-Methyl-3H-imidazol-4-yl)-vinyl]-imidazo[1,2-a]pyridin-3-yl}-phenyl)-3-(2,2,2-trifluoro-ethyl)-urea hydrochloride | General Route H using 5-(chloromethyl)-1H-imidazole hydrochloride in stepH3 | (Me-d3-OD): 9.00 (1H, s), 8.82 (1H, d), 8.21 (1H, s), 8.12 (1H, s), 8.09 (1H, d), 8.06 (1H, t), 7.94 (1H, dd), 7.68-7.60 (2H, m), 7.60-7.54 (1H, m), 7.45 (1H, dd), 7.39 (1H, d), 4.09 (3H, s), 3.96 (2H, q). | 441 |

Example 157B

Example 157B was prepared in accordance with the procedure set out below

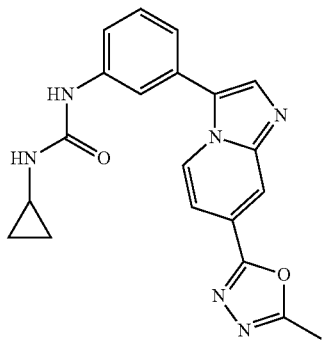 [SMILES: Cc1nnc(-c2ccn3c(-c4cccc(NC(=O)NC5CC5)c4)cnc3c2)o1]

To a solution of intermediate 39 (490 mg, 1.68 mmol) (from the Preparation of Intermediate section below) in triethylamine (0.47 ml) and DMF (20 ml), 4-nitrophenyl-N-cyclopropylcarbamic acid ester [(187 mg, 0.84 mmol) was added and the mixture was stirred at RT for 12 hours. Over a period of 36 hours, 3 additional amount of 4-nitrophenyl-N-cyclopropylcarbamic acid ester (187 mg, 0.84 mmol) had to be added to complete the conversion. The mixture was poured onto NH$_4$OH 30% and water, stirred for 30 minutes and the precipitate was filtered off. It was washed with ACN and purified by Normal phase on Spherical SiOH 10 µm 60 g PharmPrep MERCK, Mobile phase (97% DCM, 3% MeOH). The pure fractions were collected and the solvent was evaporated. The residue was taken up into Et$_2$O, filtered and dried, yielding 371 mg (59%) of compound 157B. MP=229.6° C. (DSC)

Example 158A

1-Cyclopropyl-3-[3-(7-[1,3,4]thiadiazol-2-yl-imidazo[1,2-a]pyridin-3-yl)-phenyl]-urea

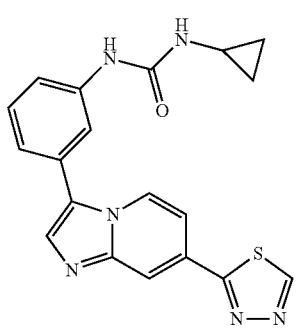 [SMILES: O=C(Nc1cccc(-c2cnc3cc(-c4nncs4)ccn23)c1)NC1CC1]

Example 158B

Example 158B was prepared in accordance with the procedure set out below

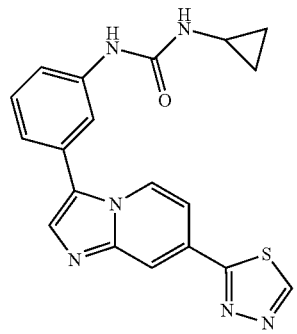 [SMILES: O=C(Nc1cccc(-c2cnc3cc(-c4nncs4)ccn23)c1)NC1CC1]

A mixture of intermediate 44 (0.52 g, 1.77 mmol) (from the Preparation of Intermediate section below) and 4-nitrophenyl chloroformate (0.39 g, 1.95 mmol) in THF (10 ml) was heated at 60° C. for 2 hours. The mixture was cooled to RT, N-ethyl-N-(1-methylethyl)-2-propanamine (0.59 ml, 3.54 mmol) was added dropwise at RT followed by cyclopropanamine (0.135 ml, 1.95 mmol). The mixture was stirred at RT for 2 hours. The mixture was poured onto ice water and EtOAc was added. The organic layer was separated, washed with brine, dried (MgSO$_4$), filtered and the solvent was evaporated. The residue was purified by Normal phase on Irregular SiOH 15-40 µm 300 g MERCK, Mobile phase (92% DCM, 8% MeOH). The pure fractions were collected and the solvent was evaporated. The residue was crystallized from DIPE/ACN (90/10), the precipitate was filtered, dried under vacuum, yielding 589 mg (88%) of compound 158B. MP=205° C. (kofler).

Example 159A

1-Cyclopropyl-3-[3-(7-pyrimidin-2-yl-imidazo[1,2-a]pyridin-3-yl)-phenyl]-urea

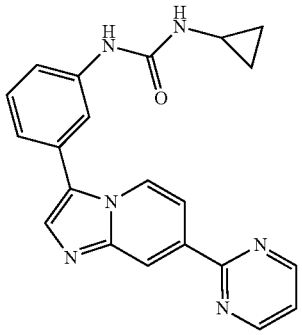 [SMILES: O=C(Nc1cccc(-c2cnc3cc(-c4ncccn4)ccn23)c1)NC1CC1]

Example 159B

Preparation of the Intermediate Compounds for Example 159B

Example 1

Preparation of Intermediate A

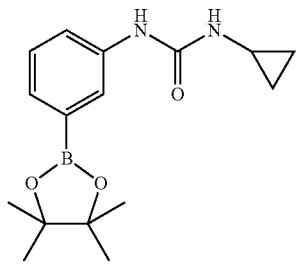 [SMILES: CC1(C)OB(c2cccc(NC(=O)NC3CC3)c2)OC1(C)C]

A mixture of

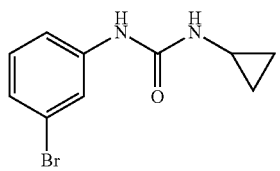 [SMILES: O=C(Nc1cccc(Br)c1)NC1CC1]

prepared according to the procedure of Example 1.2 (1.34 g; 5.2 mmol), 4,4,4',4',5,5,5',5'-octamethyl-2,2'-bi-1,3,2-dioxaborolane (2.7 g; 10.5 mmol), potassium acetate (1.54 g; 15.5 mmol) in dioxane (54 ml) was stirred at RT under a $N_2$ flow. After 10 minutes, palladium(11)acetate 47% Pd (0.35 g; 1.57 mmol) and 2-dicyclohexylphosphino-2',6' dimethoxybiphenyl (1.08 g, 2.62 mmol) were added portionwise. Then the mixture was heated at 80° C. overnight. The solution was poured onto cooled water. EtOAc was added. The RM was filtered through a pad of celite. The product was extracted with EtOAc. The organic layer was dried over $MgSO_4$, filtered and evaporated to dryness, yielding 3.1 g (>100%) of intermediate A. The product was used without further purification.

Example 2 a) Preparation of Intermediate B

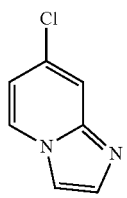

2-amino-4-chloropyridine (20 g, 156 mmol) and $NaHCO_3$ (26.14 g, 311 mmol) in EtOH (200 ml) were heated to 60° C. Chloroacetaldehyde, 50% weight solution in water (30.1 ml, 233 mmol) was added dropwise and the RM was heated to 80° C. for 1 hour. The RM was cooled to room temperature and evaporated to dryness. The residue was poured onto water and then, extracted with EtOAc. The organic layer was dried over $MgSO_4$, filtered and evaporated to dryness. The residue was poured onto a mixture of water and HCl 3N. The aqueous layer was washed with EtOAc to remove organic impurities. Then, the aqueous leyer was basified with $K_2CO_3$ and extracted with EtOAc. The organic layer was dried over $MgSO_4$, filtered and evaporated to dryness to give 23.5 g (99%) of intermediate B.

b) Preparation of Intermediate C

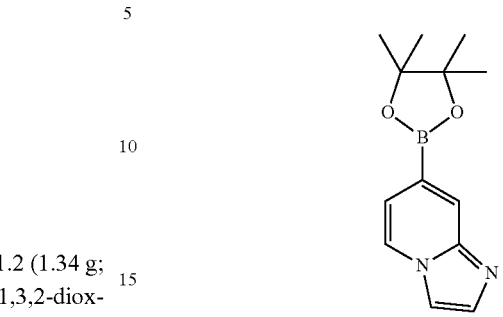

Intermediate B (10 g; 65.5 mmol), 4,4,4',4',5,5,5',5'-octamethyl-2,2'-bi-1,3,2-dioxaborolane (20 g, 78.65 mmol), $K_2CO_3$ (13.6 g, 98.3 mmol), tricyclohexylphosphine (1.84 g, 6.55 mmol), palladium(11)acetate 47% Pd (736 mg, 3.3 mmol) in 2-methoxyethyl ether (100 ml) and water (133 µl) were heated to 100° C. for 15 hours under $N_2$. The RM was cooled to RT and then cooled to 5° C. The RM was filtered and the precipitate was washed with 2-methoxyethyl ether (2*10 ml). The residue was poured onto water (50 ml), then filtered. The precipitate was washed with water (2*20 ml) and dried to give 11.25 g (70%) of intermediate C.

c) Preparation of Intermediate D

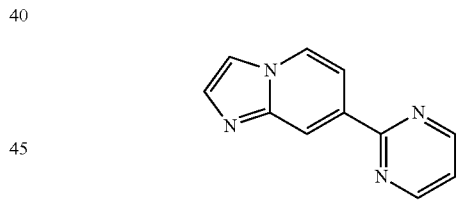

The reaction was performed 2 times on 5.6 g of intermediate C.

A solution of intermediate C (5.6 g, 22.9 mmol) and 2-bromopyrimidine (5.47 g, 34.4 mmol) in dioxane (220 ml) was degassed under $N_2$ for 30 minutes at RT. Aqueous 2M $Na_2CO_3$ (115 ml, 229.5 mol) and Pddppf (1.68 g, 2.3 mmol) were added and the solution was heated at 100° C. overnight. The RM was poured onto cooled water and filtered over a pad of celite. The filtrate was extracted with DCM. The organic layer was dried over $MgSO_4$ and evaporated to dryness. The residue coming from each reaction were mixed (15.05 g) and purified by Normal phase on Irregular SiOH 15-40 µm 300 g MERCK, Mobile phase (0.5% $NH_4OH$, 97% DCM, 3% MeOH) to give 8.6 g (95%) of intermediate D.

d) Preparation of Intermediate E

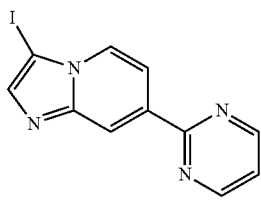 [SMILES: Ic1cnc2cc(-c3ncccn3)ccn12]

N-iodosuccinimide (6.88 g, 30.6 mmol) was added in one portion to a solution of intermediate D (5 g, 25.5 mmol) in ACN (250 ml). The mixture was stirred at RT for 2 hours. The precipitate was filtered off, washed with ACN and dried, yielding 7.48 g (91%) of intermediate D.

Preparation of Example 159B

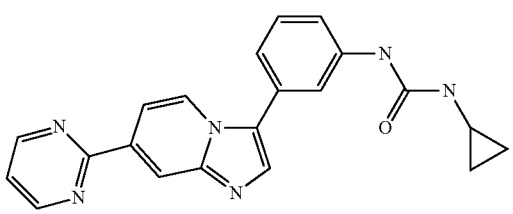 [SMILES: O=C(Nc1cccc(-c2cnc3cc(-c4ncccn4)ccn23)c1)NC1CC1]

A solution of intermediate D (1.3 g; 4.05 mmol), intermediate A (1.59 g; 5.2 mmol) in dioxane (50 ml) was degassed by bubbling $N_2$ through. $K_3PO_4$ (1.72 g; 8.1 mmol), Pddppf (661 mg; 0.81 mmol) and water (1 ml) were added under $N_2$ flow. The solution was heated at 80° C. overnight. The RM was poured onto cooled water. EtOAc was added. The mixture was filtered through a pad of celite. The filtrate was extracted with EtOAc. The organic layer was dried over $MgSO_4$, filtered and evaporated to dryness to afford a crude residue (3.59 g). This reaction was performed 2 other times respectively on 1.3 g and 0.105 g of intermediate D.

After work-up, the residue coming from the different reactions were mixed and purified by Normal phase on Irregular SiOH 20-45 μm 450 g MATREX, Mobile phase (0.5% NH4OH, 94% DCM, 6% MeOH. The desired fraction was collected and the solvent was evaporated. The residue was crystallized from a mixture of acetone/$Et_2O$ yielding 531 mg (15%) of compound 159B

MP=229.5 (DSC)

LC/MS data

Rt: 2.75

$MH^+$: 371-Method: 1

The abbreviations used in the above protocol for 159B are as defined after example 248. Also method 1 (see above) refers to the method 1 described after example 337.

Examples 160 to 250

By following the methods described above, or by individual routes described following the below Table, the compounds set out in the Table below were prepared.

MS Data is [Molecular ion]$^+$ unless indicated

NMR Data: 1H NMR (400 MHz) unless indicated

| Eg. | Structure and Chemical name | Route/ Method | NMR Data (solvent) | MS Data |
|---|---|---|---|---|
| 160 | 1-{3-[7-(4,6-Dimethyl-pyrimidin-2-yl)-imidazo[1,2-a]pyridin-3-yl]-phenyl}-3-(2,2,2-trifluoro-ethyl)-urea hydrochloride | General route B: B1, B2, procedure B3c using 2-chloro-4,6-dimethyl-pyrimidine, procedure Z5 | (Me-d3-OD): 8.98 (1H, s), 8.92 (1H, d), 8.57 (1H, d), 8.28 (1H, s), 8.05 (1H, s), 7.60 (1H, t), 7.48 (1H, d), 7.42 (1H, d), 7.34 (1H, s), 3.96 (2H, q), 2.63 (6H, s). | 441 |

| Eg. | Structure and Chemical name | Route/Method | NMR Data (solvent) | MS Data |
|---|---|---|---|---|
| 161 | 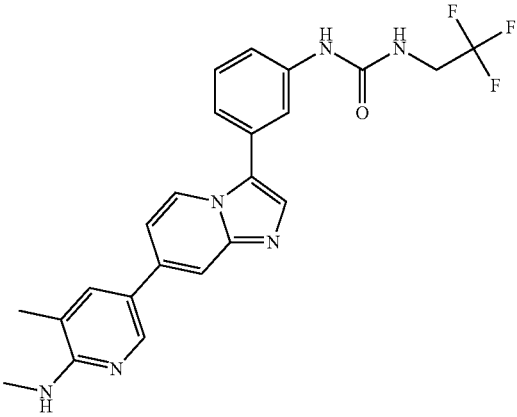<br>1-{3-[7-(5-Methyl-6-methylamino-pyridin-3-yl)-imidazo[1,2-a]pyridin-3-yl]-phenyl}-3-(2,2,2-trifluoro-ethyl)-urea formate | General route A: A1, A2, A3, A4, A5a using methyl-[3-methyl-5-(4,4,5,5-tetramethyl-[1,3,2]-dioxaborolan-2-yl)-pyridin-2-yl]-carbamic acid tert-butyl ester, method Z1 | (Me-d3-OD): 8.63 (1H, d), 8.31 (1H, s), 7.87 (1H, s), 7.82 (2H, s), 7.77 (1H, s), 7.50 (1H, t), 7.45-7.35 (2H, br m), 7.32 (1H, d), 3.96 (2H, q), 3.05 (3H, s), 2.24 (3H, s). | 455 |
| 162 | 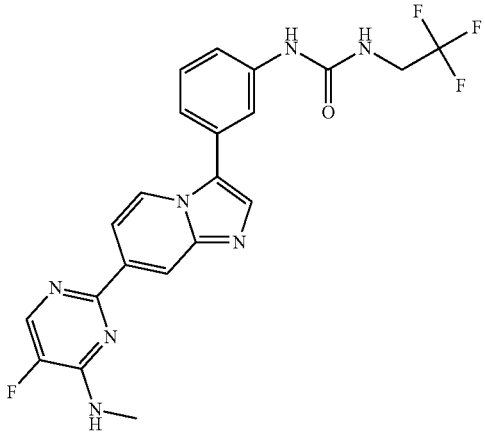<br>1-{3-[7-(5-Fluoro-4-methylamino-pyrimidin-2-yl)-imidazo-[1,2-a]pyridin-3-yl]-phenyl}-3-(2,2,2-trifluoro-ethyl)-urea trifluoroacetate | General Route B in step B3d used 2-chloro-5-fluoro-N-methyl-4-pyrimidinamine | (Me-d3-OD): 8.84 (1H, s), 8.78 (1H, s), 8.37 (1H, d), 8.21 (1H, s), 8.16 (1H, d), 7.97 (1H, s), 7.55 (1H, t), 7.48 (1H, d), 7.40-7.25 (1H, m), 3.95 (2H, q), 3.13 (3H, s). | 460 |

| Eg. | Structure and Chemical name | Route/Method | NMR Data (solvent) | MS Data |
|---|---|---|---|---|
| 163 | 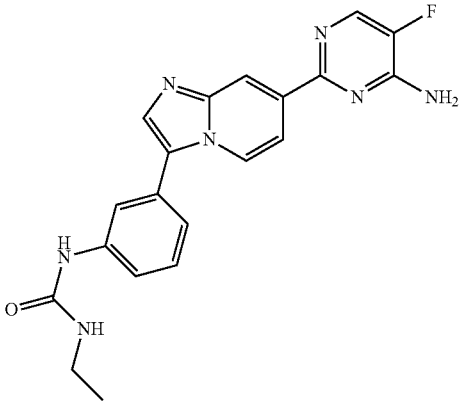<br>1-{3-[7-(4-Amino-5-fluoro-pyrimidin-2-yl)-imidazo[1,2-a]pyridin-3-yl]-phenyl}-3-ethyl-urea hydrochloride | General route D: D1, D2 using 2-chloro-5-fluoro-pyrimidin-4-ylamine and A5c but heating thermally, procedure D3, A3 using ethylamine, D5 (using $Na_2CO_3$ for $K_3PO_4$) using 1-ethyl-3-[3-(4,4,5,5-tetramethyl-[1,3,2]-dioxaborolan-2-yl)-phenyl]-urea, Z5 | (DMSO-d6): 9.14 (1H, s), 8.87 (1H, d), 8.66 (1H, s), 8.49 (1H, s), 8.42 (1H, d), 8.21 (1H, dd), 7.87 (1H, s), 7.72 (2H, s), 7.60-7.54 (1H, m), 7.50 (1H, t), 7.26 (1H, d), 3.12 (2H, q), 1.06 (3H, t). | 392 |
| 164 | 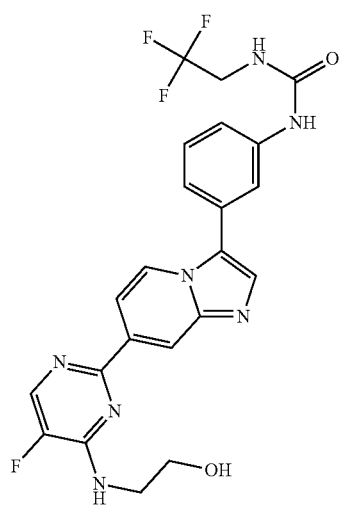<br>1-(3-{7-[5-Fluoro-4-(2-hydroxy-ethylamino)-pyrimidin-2-yl]-imidazo-[1,2-a]pyridin-3-yl}-phenyl)-3-(2,2,2-trifluoroethyl)-urea formate | General route B: B1, B2, procedure B3c using 2-(2-chloro-5-fluoro-pyrimidin-4-ylamino)-ethanol | (Me-d3-OD): 8.54 (1H, d), 8.47 (1H, s), 8.17 (1H, s), 8.06 (1H, d), 7.89 (1H, d), 7.78 (2H, d), 7.50-7.33 (2H, m), 7.25 (1H, d), 3.96 (2H, q), 3.83 (2H, t), 3.74 (2H, t). | 490 |

| Eg. | Structure and Chemical name | Route/Method | NMR Data (solvent) | MS Data |
|---|---|---|---|---|
| 165A | 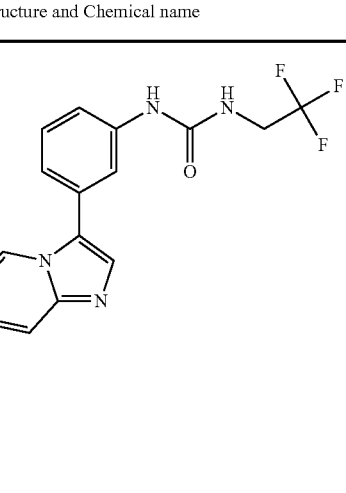<br>1-{3-[7-(4-Amino-5-cyano-pyrimidin-2-yl)-imidazo-[1,2-a]pyridin-3-yl]-phenyl}-3-(2,2,2-trifluoroethyl)-urea formate | General Route B followed by procedure B3c using 4-amino-2-chloropyrimidine-5-carbonitrile | (DMSO-d6): 8.97 (1H, s), 8.78 (1H, s), 8.68 (1H, d), 8.56 (1H, s), 8.08 (2H, s), 7.91 (1H, s), 7.87-7.80 (1H, m), 7.76 (1H, s), 7.55-7.43 (2H, m), 7.30 (1H, d), 6.87 (1H, t), 4.01-3.90 (2H, m). | 453 |
| 165B | 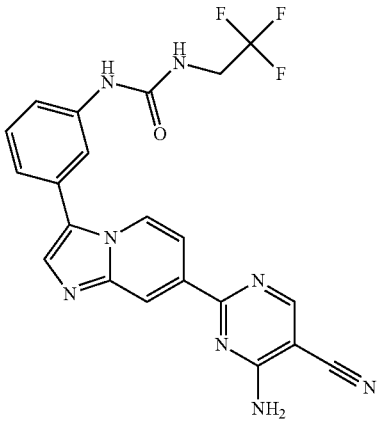 [SMILES: N#Cc1cnc(-c2ccn3c(-c4cccc(NC(=O)NCC(F)(F)F)c4)cnc3c2)nc1N] | See Below Example 2.2b) | | |
| 166 | 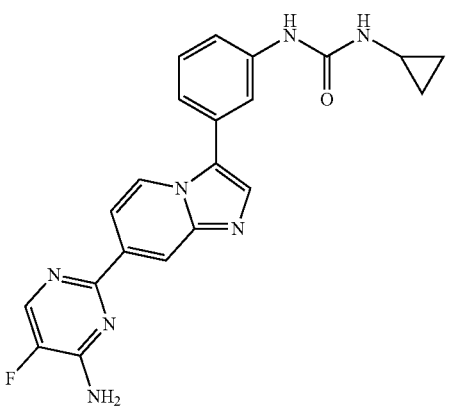<br>1-{3-[7-(4-Amino-5-fluoro-pyrimidin-2-yl)-imidazo[1,2-a]pyridin-3-yl]-phenyl}-3-cyclopropyl-urea hydrochloride | General route D: D1, D2 using 2-chloro-5-fluoro-pyrimidin-4-ylamine and A5c but heating thermally, D3, A3 using cyclopropylamine, D5 (using Na$_2$CO$_3$ for K$_3$PO$_4$) using 1-cyclopropyl-3-[3-(4,4,5,5-tetramethyl-[1,3,2]-dioxaborolan-2-yl)-phenyl]-urea, Z5 | (DMSO-d6): 8.95 (1H, s), 8.91-8.83 (1H, m), 8.66 (1H, s), 8.49 (1H, s), 8.42 (1H, d), 8.21 (1H, dd), 7.88 (1H, s), 7.72 (2H, br s), 7.58 (1H, d), 7.52 (1H, t), 7.28 (1H, d), 6.74 (1H, s), 2.60-2.53 (1H, m), 0.69-0.60 (2H, m), 0.46-0.37 (2H, m). | 404 |

| Eg. | Structure and Chemical name | Route/ Method | NMR Data (solvent) | MS Data |
|---|---|---|---|---|
| 167 | {3-[7-(4-Amino-5-fluoro-pyrimidin-2-yl)-imidazo[1,2-a]pyridin-3-yl]-phenyl}-urea formate | General route D: D1, D2 using 2-chloro-5-fluoro-pyrimidin-4-ylamine and method described in A5c but heating thermally, D3, A3 using NH₃(g), procedure D5 (using Na₂CO₃ for K₃PO₄) | (DMSO-d6): 8.73 (1H, s), 8.62 (1H, d), 8.42 (1H, s), 8.32 (1H, d), 7.82 (1H, s), 7.79 (1H, dd), 7.76-7.70 (1H, m), 7.53-7.37 (4H, m), 7.22 (1H, d), 5.93 (2H, s). | 364 |
| 168 | 1-{5-[7-(4-Amino-5-fluoro-pyrimidin-2-yl)-imidazo[1,2-a]pyridin-3-yl]-pyridin-3-yl}-3-(2,2,2-trifluoro-ethyl)-urea | General route D: D1, D2 using 2-chloro-5-fluoro-pyrimidin-4-ylamine and method described in A5c but heating thermally, D3, D4, D5 (using Na₂CO₃ for K₃PO₄), Z5 | (Me-d3-OD): 9.37 (1H, s), 9.04 (1H, d), 8.94 (1H, s), 8.89 (2H, d), 8.61 (1H, s), 8.47-8.35 (2H, m), 4.01 (2H, q). | 447 |
| 169 | 1-{3-[7-(4-Dimethylamino-5-fluoro-pyrimidin-2-yl)-imidazo-[1,2-a]pyridin-3-yl]-phenyl}-3-(2,2,2-trifluoroethyl)-urea hydrochloride | General Route B in step B3d used 2-chloro-5-fluoro-4-dimethylaminopyrimidine | (DMSO-d6): 9.34 (1H, s), 8.85 (1H, d), 8.71 (1H, s), 8.47 (1H, s), 8.43 (1H, d), 8.25 (1H, dd), 7.91 (1H, s), 7.60-7.51 (2H, m), 7.38-7.29 (1H, m), 7.06 (1H, t), 4.03-3.90 (2H, m), 3.32 (6H, d). | [Adduct] + 474 |

| Eg. | Structure and Chemical name | Route/Method | NMR Data (solvent) | MS Data |
|---|---|---|---|---|
| 170 | 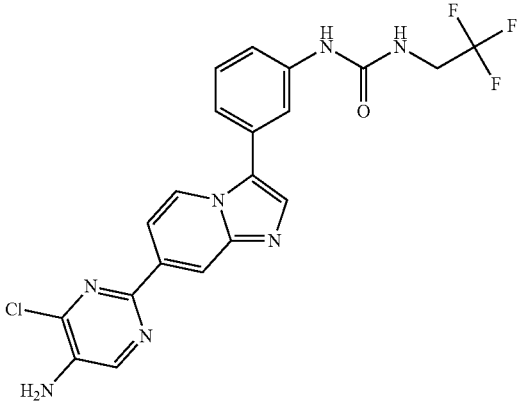<br>1-{3-[7-(5-Amino-4-chloro-pyrimidin-2-yl)-imidazo-[1,2-a]pyridin-3-yl]-phenyl}-3-(2,2,2-trifluoroethyl)-urea hydrochloride | General Route B in step B3c used 5-amino-2,4-dichloropyrimidine | (DMSO-d6): 9.39 (1H, s), 8.87 (1H, d), 8.47 (1H, s), 8.37 (2H, d), 7.92 (1H, s), 7.74 (1H, dd), 7.56 (2H, d), 7.36-7.28 (1H, m), 7.09 (1H, t), 3.43-3.35 (2H, m). | 462 |
| 171 | 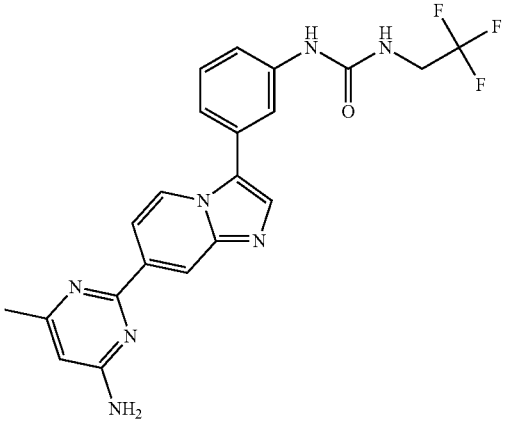<br>1-{3-[7-(4-Amino-6-methyl-pyrimidin-2-yl)-imidazo[1,2-a]pyridin-3-yl]-phenyl}-3-(2,2,2-trifluoro-ethyl)-urea | General Route B followed by procedure B3d using 2-chloro-6-methylpyrimidin-4-ylamine | (DMSO-d6): 8.96 (1H, s), 8.62 (1H, d), 8.49 (1H, s), 7.89-7.80 (2H, m), 7.75 (1H, s), 7.52-7.43 (2H, m), 7.32-7.25 (1H, m), 6.91-6.82 (3H, m), 6.27 (1H, s), 4.01-3.90 (2H, m), 2.33 (3H, s). | 442 |

| Eg. | Structure and Chemical name | Route/Method | NMR Data (solvent) | MS Data |
|---|---|---|---|---|
| 172 | 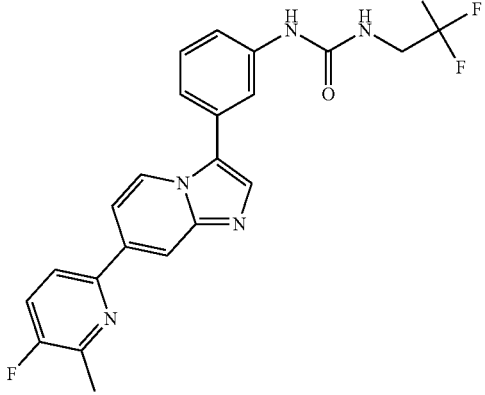<br>1-{3-[7-(5-Fluoro-6-methyl-pyridin-2-yl)-imidazo[1,2-a]pyridin-3-yl]-phenyl}-3-(2,2,2-trifluo-roethyl)-urea | General Route B followed by procedure B3d using 6-chloro-3-fluoro-2-methylpyridine | (Me-d3-OD): 8.66 (1H, d), 8.26 (1H, s), 7.92 (1H, dd), 7.84 (1H, s), 7.83-7.71 (2H, m), 7.62 (1H, t), 7.50 (1H, t), 7.42 (1H, d), 7.34 (1H, d), 3.96 (2H, q), 2.61 (3H, d). | 444 |
| 173 | 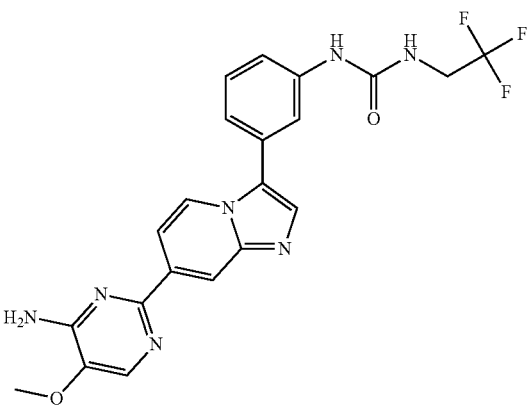<br>1-{3-[7-(4-Amino-5-methoxy-pyrimidin-2-yl)-imidazo-[1,2-a]pyridin-3-yl]-phenyl}-3-(2,2,2-trifluoroethyl)-urea hydrochloride | General Route B in step B3c used 2-chloro-5-methoxy-pyrimidin-4-ylamine | (Me-d3-OD): 9.03 (1H, d), 8.80 (1H, s), 8.40 (1H, s), 8.20 (1H, dd), 8.09 (1H, s), 8.03 (1H, s), 7.60 (1H, t), 7.51-7.45 (1H, m), 7.42 (1H, d), 4.12 (3H, s), 3.96 (2H, q). | 458 |
| 174 | 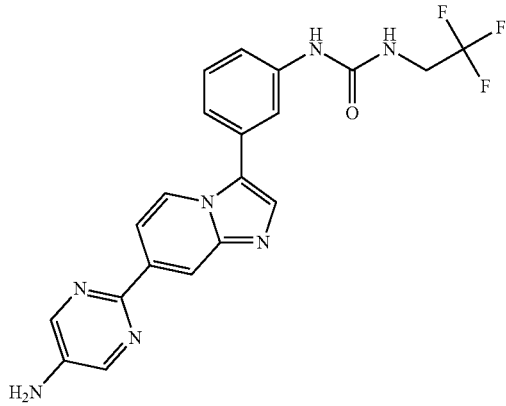<br>1-{3-[7-(5-Amino-pyrimidin-2-yl)-imidazo[1,2-a]pyridin-3-yl]-phenyl}-3-(2,2,2-trifluoro-ethyl)-urea | General Route B followed by procedure B3d using 5-amino-2-chloropyrimidine | (DMSO-d6): 9.00 (1H, s), 8.60 (1H, d), 8.33 (1H, s), 8.27 (2H, s), 7.84-7.70 (3H, m), 7.54-7.41 (2H, m), 7.27 (1H, d), 6.90 (1H, s), 5.87 (2H, s), 4.01-3.89 (2H, m). | 428 |

| Eg. | Structure and Chemical name | Route/Method | NMR Data (solvent) | MS Data |
|---|---|---|---|---|
| 175 | 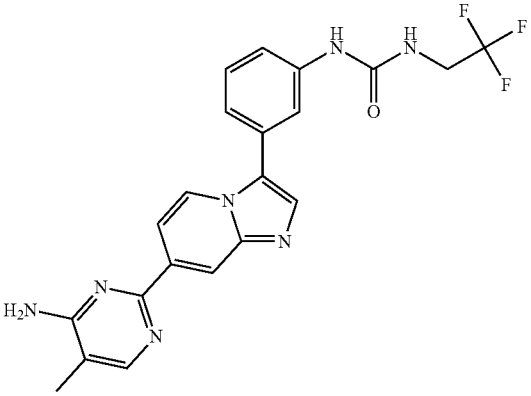<br>1-{3-[7-(4-Amino-5-methyl-pyrimidin-2-yl)-imidazo-[1,2-a]pyridin-3-yl]-phenyl}-3-(2,2,2-trifluoroethyl)-urea | General Route B followed by B3d using 4-amino-2-chloro-5-methylpyrimidine | (DMSO-d6): 8.96 (1H, s), 8.62 (1H, d), 8.47 (1H, s), 8.11 (1H, s), 7.88-7.79 (2H, m), 7.75 (1H, s), 7.52-7.43 (2H, m), 7.29 (1H, d), 6.86 (3H, t), 4.00-3.91 (2H, m), 2.06 (3H, s). | 442 |
| 176 | 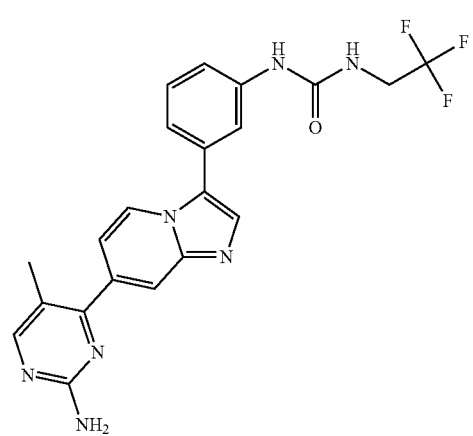<br>1-{3-[7-(2-Amino-5-methyl-pyrimidin-4-yl)-imidazo[1,2-a]pyridin-3-yl]-phenyl}-3-(2,2,2-trifluoro-ethyl)-urea | General Route B followed by procedure B3d using 4-amino-2-chloro-5-methylpyrimidine (minor product) | (DMSO-d6): 8.98 (1H, s), 8.64 (1H, d), 8.23 (1H, s), 7.87 (2H, d), 7.82-7.75 (1H, m), 7.51-7.43 (2H, m), 7.32-7.24 (2H, m), 6.87 (1H, t), 6.53 (2H, s), 4.00-3.90 (2H, m), 2.26 (3H, s). | 442 |

| Eg. | Structure and Chemical name | Route/Method | NMR Data (solvent) | MS Data |
|---|---|---|---|---|
| 177 | 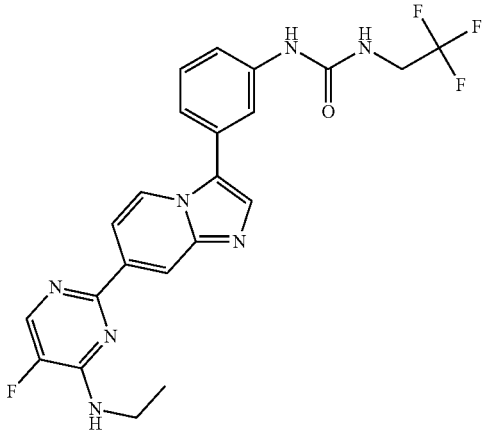<br>1-{3-[7-(4-Ethylamino-5-fluoro-pyrimidin-2-yl)-imidazo[1,2-a]pyridin-3-yl]-phenyl}-3-(2,2,2-trifluoro-ethyl)-urea | General Route B followed by procedure B3d using X16 | (DMSO-d6): 8.97 (1H, s), 8.63 (1H, d), 8.46 (1H, s), 8.27 (1H, d), 7.89-7.80 (3H, m), 7.77 (1H, s), 7.52-7.43 (2H, m), 7.32-7.25 (1H, m), 6.86 (1H, t), 4.00-3.90 (2H, m), 3.63-3.54 (2H, m), 3.18 (1H, d), 1.27 (3H, t). | 474 |
| 178 | 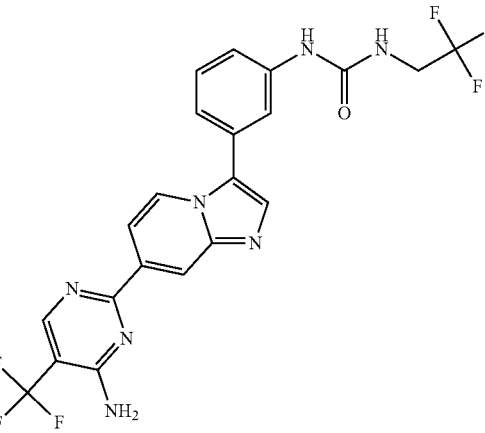<br>1-{3-[7-(4-Amino-5-trifluoromethyl-pyrimidin-2-yl)-imidazo-[1,2-a]pyridin-3-yl]-phenyl}-3-(2,2,2-trifluoroethyl)-urea hydrochloride | General Route B in step B3d used 2-chloro-5-trifluoromethyl-pyrimidin-4-ylamine | (Me-d3-OD): 8.93 (2H, d), 8.68 (1H, s), 8.48 (1H, dd), 8.30 (1H, s), 8.05 (1H, t), 7.60 (1H, t), 7.48 (1H, dd), 7.42 (1H, d), 3.96 (2H, q). | 496 |

-continued

| Eg. | Structure and Chemical name | Route/Method | NMR Data (solvent) | MS Data |
|---|---|---|---|---|
| 179 | 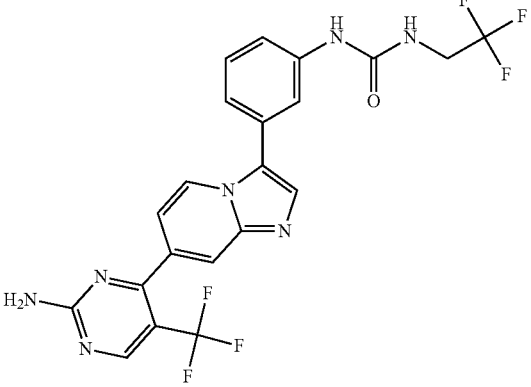<br>1-{3-[7-(2-Amino-5-trifluoromethyl-pyrimidin-4-yl)-imidazo-[1,2-a]pyridin-3-yl]-phenyl}-3-(2,2,2-trifluoroethyl)-urea hydrochloride | General Route B in step B3d used 4-chloro-5-trifluoromethyl-pyrimidin-2-ylamine | (Me-d3-OD): 8.94 (1H, d), 8.73 (1H, s), 8.30 (1H, s), 8.19 (1H, s), 8.05 (1H, t), 7.71 (1H, dd), 7.60 (1H, t), 7.53-7.46 (1H, m), 7.42 (1H, d), 3.96 (2H, q). | 496 |
| 180 | 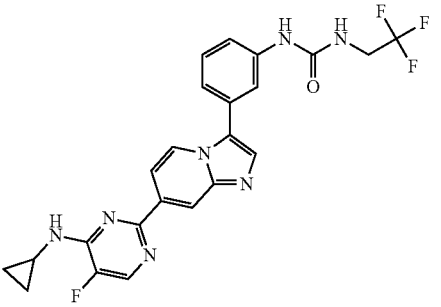<br>1-{3-[7-(4-Cyclopropylamino-5-fluoro-pyrimidin-2-yl)-1,7-dihydro-imidazo[1,2-a]pyridin-3-yl]-phenyl}-3-(2,2,2-trifluoro-ethyl)-urea | General Route B followed by procedure B3d using X15 | (DMSO-d6): 8.99 (1H, s), 8.64 (1H, d), 8.52 (1H, s), 8.29 (1H, d), 7.98 (1H, d), 7.92-7.82 (2H, m), 7.81-7.74 (1H, m), 7.52-7.42 (2H, m), 7.33-7.25 (1H, m), 6.89 (1H, t), 4.01-3.89 (2H, m), 3.10-3.02 (1H, m), 0.89-0.80 (2H, m), 0.71-0.63 (2H, m). | 486 |
| 181 | 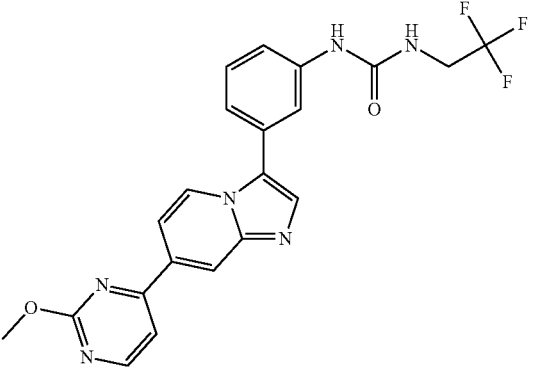<br>1-{3-[7-(2-Methoxy-pyrimidin-4-yl)-imidazo[1,2-a]pyridin-3-yl]-phenyl}-3-(2,2,2-trifluoro-ethyl)-urea | General route B: B1, B2, B3d using 2-chloro-5-methoxy-pyrimidine (MW irradiation 120° C., 1 hr) | (DMSO-d6): 9.00 (1H, s), 8.73-8.66 (2H, m), 8.66-8.60 (1H, m), 7.94 (1H, dd), 7.90 (1H, s), 7.80 (1H, s), 7.53-7.42 (2H, m), 7.35-7.26 (1H, m), 6.94 (1H, d), 6.89 (1H, t), 4.11 (3H, s), 4.04-3.89 (2H, m). | 443 |

| Eg. | Structure and Chemical name | Route/Method | NMR Data (solvent) | MS Data |
|---|---|---|---|---|
| 182 | 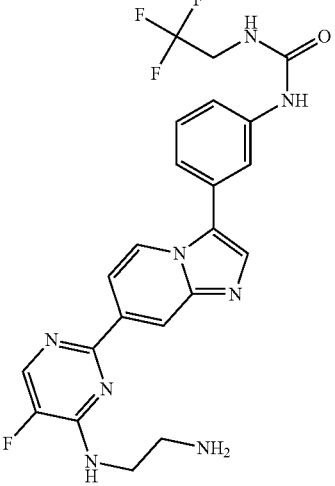<br>1-(3-{7-[4-(2-Amino-ethylamino)-5-fluoro-pyrimidin-2-yl]-imidazo-[1,2-a]pyridin-3-yl}-phenyl)-3-(2,2,2-trifluoroethyl)-urea formate | General Route B, procedure B3d using X17 followed by procedure Z1a | (Me-d3-OD): 8.70-8.61 (1H, m), 8.59 (1H, s), 8.39 (2H, s), 8.25 (1H, d), 8.02-7.90 (2H, m), 7.86-7.80 (1H, m), 7.55-7.46 (1H, m), 7.41-7.30 (2H, m), 4.02-3.91 (4H, m). | 489 |
| 183 | 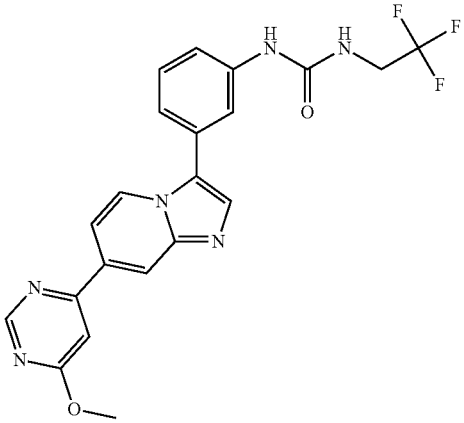<br>1-{3-[7-(6-Methoxy-pyrimidin-4-yl)-imidazo[1,2-a]pyridin-3-yl]-phenyl}-3-(2,2,2-trifluoro-ethyl)-urea formate | General route B: B1, B2, B3d (MW irradiation 120° C., 1 hr) using 4-iodo-6-methoxy-pyrimidine | (DMSO-d6): 9.01 (1H, s), 8.91 (1H, d), 8.67 (1H, d), 8.59 (1H, s), 7.90 (1H, s), 7.85-7.77 (2H, m), 7.73 (1H, s), 7.53-7.43 (2H, m), 7.34-7.25 (1H, m), 6.90 (1H, t), 4.01 (3H, s), 3.99-3.88 (2H, m). | 443 |

| Eg. | Structure and Chemical name | Route/Method | NMR Data (solvent) | MS Data |
|---|---|---|---|---|
| 184 | 1-{3-[7-(6-Oxo-1,6-dihydro-pyrimidin-4-yl)-imidazo[1,2-a]pyridin-3-yl]-phenyl}-3-(2,2,2-trifluoro-ethyl)-urea formate | General route B: B1, procedure B2, B3d (MW irradiation 120° C., 1 hr) using 4-iodo-6-methoxy-pyrimidine, procedure Z5 | (Me-d3-OD): 8.66 (1H, d), 8.46 (1H, s), 8.31 (1H, s), 8.20 (1H, s), 7.88-7.80 (2H, m), 7.61 (1H, dd), 7.51 (1H, t), 7.47-7.39 (1H, m), 7.34 (1H, d), 7.05 (1H, s), 3.96 (2H, q). | 429 |
| 185 | 2-(3-{3-[3-(2,2,2-Trifluoroethyl)-ureido]-phenyl}-imidazo[1,2-a]pyridin-7-yl)-pyrimidine-4-carboxylic acid amide hydrochloride | General Route B in step B3d used 2-chloro-pyrimidine-4-carboxylic acid amide | (Me-d3-OD): 9.27 (1H, d), 9.15 (1H, s), 8.97 (1H, d), 8.72 (1H, dd), 8.33 (1H, s), 8.17 (1H, d), 8.08 (1H, s), 7.61 (1H, t), 7.54-7.47 (1H, m), 7.44 (1H, d), 3.96 (2H, q). | 456 |
| 186 | 1-{3-[7-((E)-2-Pyridin-2-yl-vinyl)-imidazo[1,2-a]pyridin-3-yl]-phenyl}-3-(2,2,2-trifluoro-ethyl)-urea hydrochloride | General RouteH using commercially available triphenyl(2-pyridylmethyl)phosphonium chloride hydrochloride in stepH4 | (Me-d3-OD): 8.88 (1H, d), 8.84 (1H, d), 8.57 (1H, t), 8.42 (1H, d), 8.26 (2H, d), 8.13 (1H, d), 8.07 (1H, s), 8.01-7.88 (2H, m), 7.78 (1H, d), 7.59 (1H, t), 7.51-7.43 (1H, m), 7.41 (1H, d), 3.96 (2H, q). | 438 |

| Eg. | Structure and Chemical name | Route/Method | NMR Data (solvent) | MS Data |
|---|---|---|---|---|
| 187 | 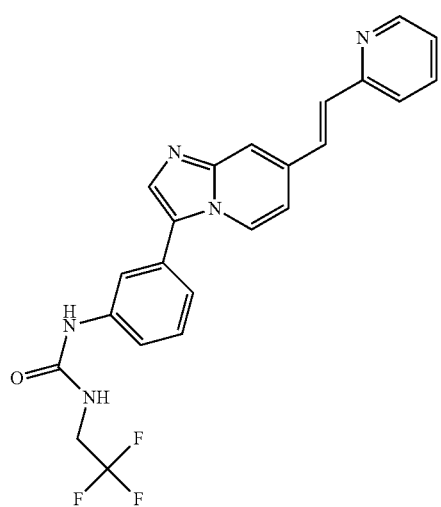<br>1-{3-[7-(6-Fluoro-5-methyl-pyridin-3-yl)-imidazo[1,2-a]pyridin-3-yl]-phenyl}-3-(2,2,2-trifluoro-ethyl)-urea | General route B: B1, B2, B3d (MW irradiation 120° C., 1 hr) using 5-chloro-2-fluoro-3-methyl-pyridine | (DMSO-d6): 8.96 (1H, s), 8.65 (1H, d), 8.57 (1H, s), 8.39 (1H, dd), 8.15-8.08 (1H, m), 7.83 (1H, s), 7.81 (1H, s), 7.51-7.39 (3H, m), 7.32-7.24 (1H, m), 6.85 (1H, t), 4.03-3.88 (2H, m), 2.35 (3H, s). | 444 |
| 188 | 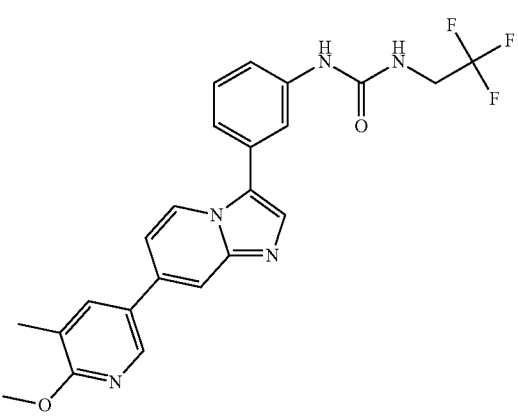<br>1-{3-[7-(6-Methoxy-5-methyl-pyridin-3-yl)-imidazo[1,2-a]pyridin-3-yl]-phenyl}-3-(2,2,2-trifluoro-ethyl)-urea | General route B: B1, B2, B3d (MW irradiation 120° C., 1 hr) using 5-chloro-2-fluoro-3-methyl-pyridine, procedure Z5 (using MeOH to solubilise) | (DMSO-d6): 8.96 (1H, s), 8.62 (1H, d), 8.53 (1H, d), 8.11 (1H, d), 8.02 (1H, s), 7.80 (2H, s), 7.49-7.43 (2H, m), 7.43-7.37 (1H, m), 7.31-7.24 (1H, m), 6.85 (1H, t), 4.02-3.90 (5H, m), 2.25 (3H, s). | 456 |

| Eg. | Structure and Chemical name | Route/Method | NMR Data (solvent) | MS Data |
|---|---|---|---|---|
| 189 | 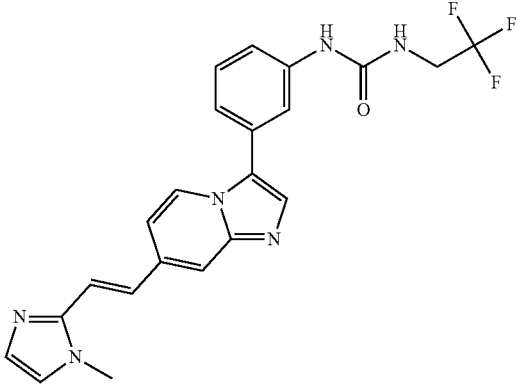<br>1-(3-{7-[(E)-2-(1-Methyl-1H-imidazol-2-yl)-vinyl]-imidazo[1,2-a]pyridin-3-yl}-phenyl)-3-(2,2,2-trifluoro-ethyl)-urea hydrochloride | General Route H | (Me-d3-OD): 8.74 (1H, d), 8.01 (3H, d), 7.77-7.66 (2H, m), 7.64-7.50 (4H, m), 7.45-7.32 (2H, m), 4.04 (3H, s), 4.01-3.89 (2H, m). | 441 |
| 190 | 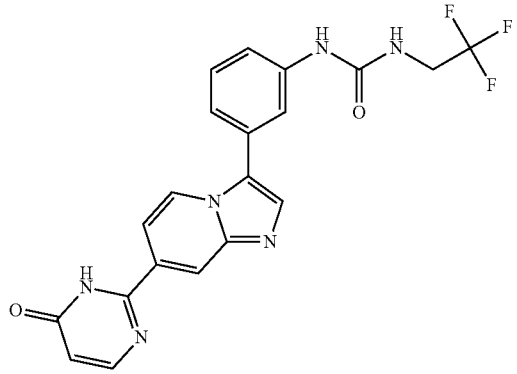<br>1-{3-[7-(6-Oxo-1,6-dihydro-pyrimidin-2-yl)-imidazo-[1,2-a]pyridin-3-yl]-phenyl}-3-(2,2,2-trifluoroethyl)-urea trifluoro-acetate | General Route B followed by procedure B3d using 2-chloro-4-methoxypyrimidine then procedure Z7 | (Me-d3-OD): 8.92 (1H, d), 8.82 (1H, s), 8.49 (1H, d), 8.39-8.25 (2H, m), 8.04 (1H, s), 7.59 (1H, t), 7.52-7.37 (2H, m), 6.73 (1H, d), 3.96 (2H, q). | 429 |

| Eg. | Structure and Chemical name | Route/Method | NMR Data (solvent) | MS Data |
|---|---|---|---|---|
| 191 | 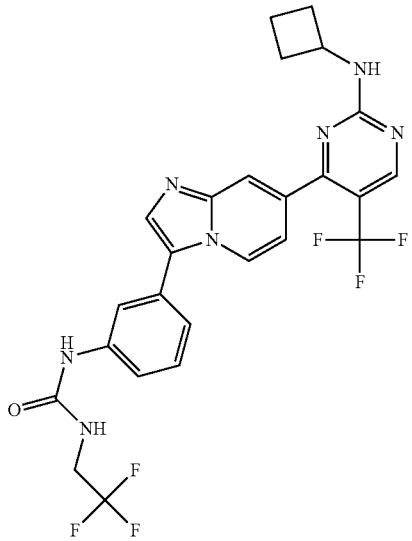<br>1-{3-[7-[(2-Cyclobutylamino-5-trifluoromethyl-pyrimidin-4-yl)-imidazo[1,2-a]pyridin-3-yl]-phenyl}-3-(2,2,2-trifluoro-ethyl)-urea hydrochloride | General Route B in step B3d used (4-chloro-5-trifluoromethyl-pyrimid-in-2-yl)-cyclobutyl-amine (as mixture with regioisomer) | (Me-d3-OD): 8.94 (1H, d), 8.71 (1H, s), 8.30 (1H, s), 8.18 (1H, s), 8.04 (1H, s), 7.71 (1H, d), 7.59 (1H, t), 7.49 (1H, d), 7.42 (1H, d), 4.54 (1H, d), 4.03-3.89 (3H, m), 2.38 (2H, s), 2.16-2.01 (2H, m), 1.87-1.69 (2H, m). | 550 |
| 192 | 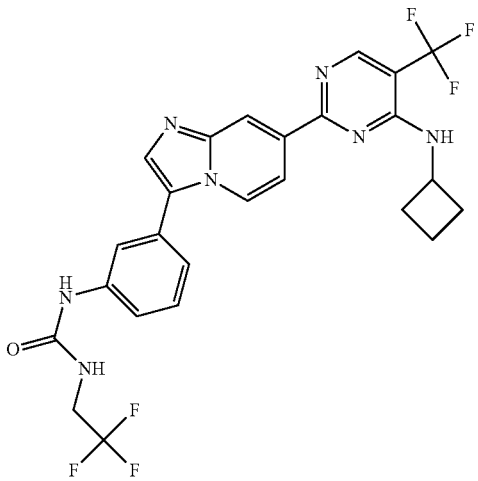<br>1-{3-[7-(4-Cyclobutylamino-5-trifluoromethyl-pyrimidin-2-yl)-imidazo[1,2-a]pyridin-3-yl]-phenyl}-3-(2,2,2-trifluoro-ethyl)-urea hydrochloride | General Route B in step B3d used (2-chloro-5-trifluoromethyl-pyrimid-in-4-yl)-cyclobutyl-amine (as mixture with regioisomer) | (Me-d3-OD): 8.95 (2H, d), 8.65 (1H, s), 8.48 (1H, d), 8.31 (1H, s), 8.07 (1H, s), 7.60 (1H, t), 7.48 (1H, d), 7.43 (1H, d), 4.99-4.88 (2H, m), 4.03-3.90 (2H, m), 2.59-2.46 (2H, m), 2.35-2.19 (2H, m), 1.97-1.84 (2H, m). | 550 |

-continued

| Eg. | Structure and Chemical name | Route/ Method | NMR Data (solvent) | MS Data |
|---|---|---|---|---|
| 193 | 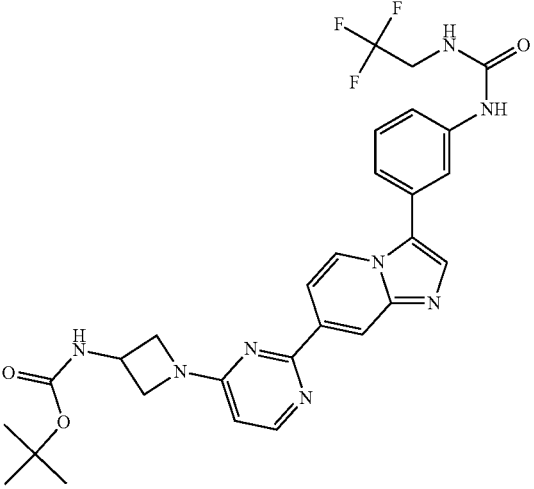<br>{1-[2-(3-{3-[3-(2,2,2-Trifluoroethyl)-ureido]-phenyl}-imidazo[1,2-a]pyridin-7-yl)-pyrimidin-4-yl]-azetidin-3-yl}-carbamic acid tert-butyl ester | General Route B in step B3d used [1-(2-chloro-pyrimidin-4-yl)-azetidin-3-yl]-carbamic acid tert-butyl ester | (DMSO-d6): 8.96 (1H, s), 8.64 (1H, d), 8.53 (1H, s), 8.34 (1H, d), 7.92-7.83 (2H, m), 7.77 (1H, s), 7.65 (1H, d), 7.52-7.43 (2H, m), 7.29 (1H, dd), 6.85 (1H, t), 6.41 (1H, d), 4.50 (1H, s), 4.38 (2H, d), 4.03-3.89 (4H, m), 1.41 (9H, s). | 583 |
| 194 | 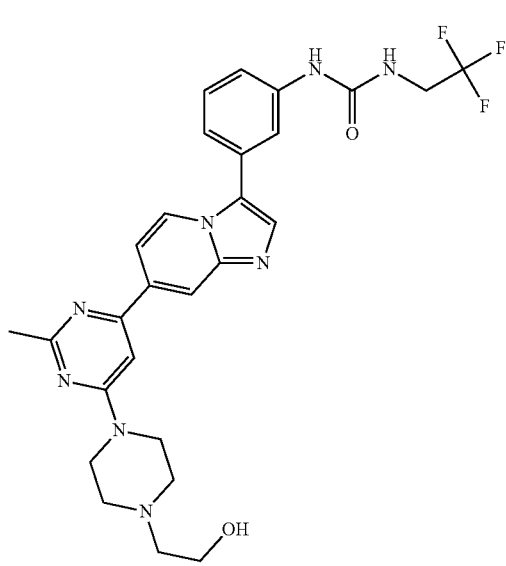<br>1-[3-(7-{6-[4-(2-Hydroxy-ethyl)-piperazin-1-yl]-2-methyl-pyrimidin-4-yl}-imidazo-[1,2-a]pyridin-3-yl)-phenyl]-3-(2,2,2-trifluoro-ethyl)-urea | General Route B followed by procedure B3d using X18 then Z9 | (Me-d3-OD): 8.66 (1H, d), 8.31 (1H, s), 7.88-7.78 (2H, m), 7.65 (1H, dd), 7.50 (1H, t), 7.47-7.40 (1H, m), 7.34 (1H, d), 7.12 (1H, s), 3.95 (2H, q), 3.85 (4H, d), 3.76 (2H, t), 2.67 (4H, t), 2.62 (2H, t), 2.56 (3H, s). | 555 |

| Eg. | Structure and Chemical name | Route/Method | NMR Data (solvent) | MS Data |
|---|---|---|---|---|
| 195 | 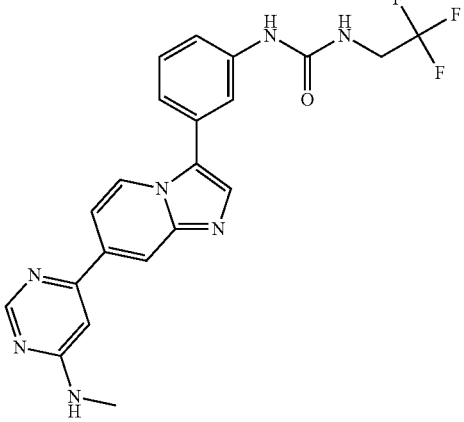<br>1-{3-[7-(6-Methylamino-pyrimidin-4-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using (6-chloro-pyrimidin-4-yl)-methyl-amine, method Z5 | (Me-d3-OD): 9.03 (1H, d), 8.82 (1H, s), 8.60 (1H, s), 8.39 (1H, s), 8.11 (1H, s), 7.95-7.86 (1H, m), 7.60 (1H, t), 7.50-7.37 (2H, m), 7.30 (1H, s), 3.96 (2H, q), 3.20 (3H, s). | 442 |
| 196 | 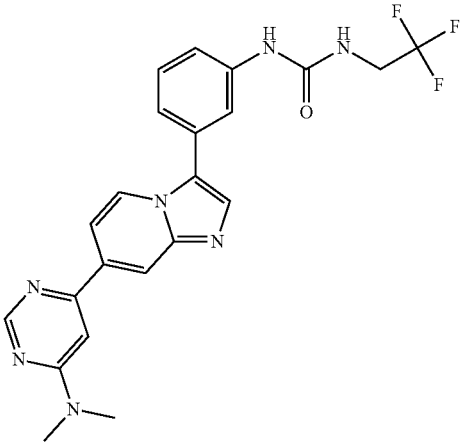<br>1-{3-[7-(6-Dimethylamino-pyrimidin-4-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using (6-chloro-pyrimidin-4-yl)-dimethyl-amine, method Z5 | (Me-d3-OD): 9.04 (1H, d), 8.81 (1H, s), 8.64 (1H, s), 8.40 (1H, s), 8.11 (1H, s), 7.98 (1H, dd), 7.61 (1H, t), 7.54 (1H, s), 7.50-7.38 (2H, m), 3.96 (2H, q), 3.48 (6H, s). | 456 |
| 197 | 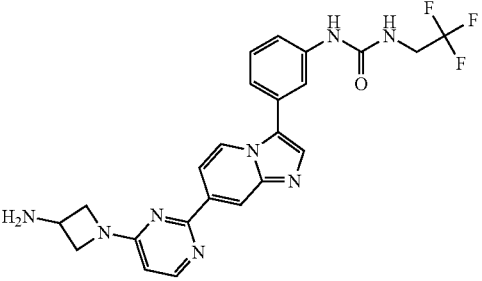<br>1-(3-{7-[4-(3-Amino-azetidin-1-yl)-pyrimidin-2-yl]-imidazo[1,2-a]pyridin-3-yl}-phenyl)-3-(2,2,2-trifluoro-ethyl)-urea hydrochloride | Prepared from {1-[2-(3-{3-[3-(2,2,2-trifluoroethyl)-ureido]-phenyl}-imidazo[1,2-a]-pyridin-7-yl)-pyrimi-din-4-yl]-azetidin-3-yl}-carbamic acid tert-butyl ester by depro-tection X3 | (Me-d3-OD): 9.01 (1H, d), 8.90 (1H, s), 8.44 (1H, d), 8.38 (1H, s), 8.32 (1H, dd), 8.10 (1H, t), 7.60 (1H, t), 7.47 (1H, dd), 7.43 (1H, d), 6.81 (1H, d), 4.82-4.74 (2H, m), 4.53-4.38 (3H, m), 3.96 (2H, q). | 483 |

| Eg. | Structure and Chemical name | Route/Method | NMR Data (solvent) | MS Data |
|---|---|---|---|---|
| 198 | 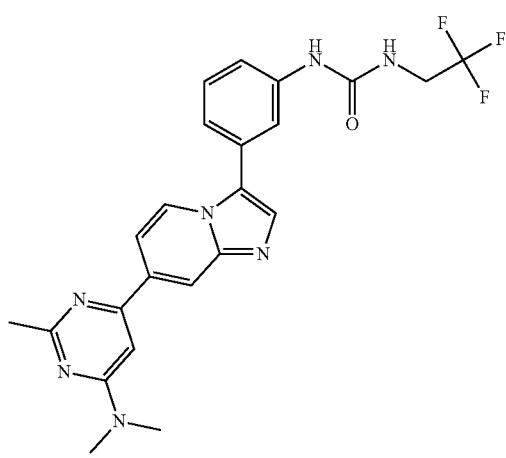<br>1-{3-[7-(6-Dimethylamino-2-methyl-pyrimidin-4-yl)-imidazo[1,2-a]pyridin-3-yl]-phenyl}-3-(2,2,2-trifluoro-ethyl)-urea | General Route B followed by procedure B3d using (6-chloro-2-methyl-pyrimidin-4-yl)-dimethyl-amine | (DMSO-d6): 9.08 (1H, s), 8.63 (1H, d), 8.54 (1H, s), 7.89-7.75 (3H, m), 7.46 (2H, d), 7.33-7.24 (1H, m), 7.19 (1H, s), 6.99 (1H, d), 4.03-3.89 (2H, m), 3.21-3.11 (6H, m), 2.48 (3H, s). | 470 |
| 199 | 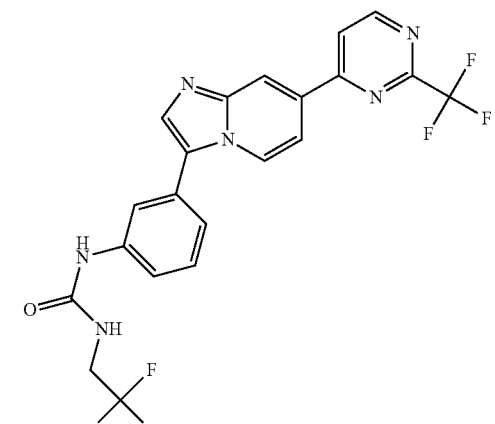<br>1-(2,2,2-Trifluoro-ethyl)-3-{3-[7-(2-trifluoromethyl-pyrimidin-4-yl)-imidazo[1,2-a]pyridin-3-yl]-phenyl}-urea hydrochloride | General route B: B1, B2, B3d (MW irradiation 120° C., 1 hr) using 4-chloro-2-trifluoromethyl-pyrimidine, method Z5 | (Me-d3-OD): 9.24 (1H, d), 9.01 (1H, d), 8.90 (1H, s), 8.51 (1H, d), 8.35 (1H, s), 8.33 (1H, dd), 8.12-8.04 (1H, m), 7.60 (1H, t), 7.52-7.38 (2H, m), 3.96 (2H, q). | 481 |

| Eg. | Structure and Chemical name | Route/ Method | NMR Data (solvent) | MS Data |
|---|---|---|---|---|
| 200 | 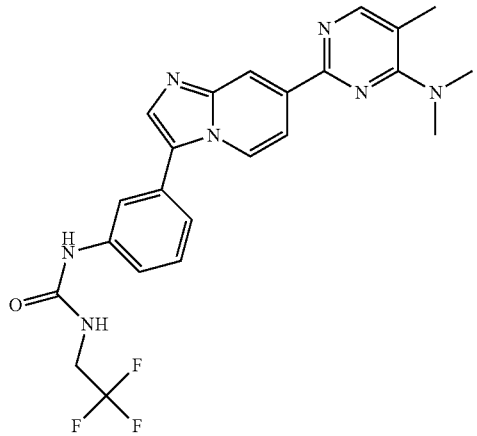<br>1-{3-[7-(4-Dimethylamino-5-methyl-pyrimidin-2-yl)-imidazo-[1,2-a]pyridin-3-yl]-phenyl}-3-(2,2,2-trifluoroethyl)-urea trifluoro-acetate | General Route B followed by procedure B3d using (2-Chloro-5-methyl-pyrimidin-4-yl)-dimethyl-amine | (Me-d3-OD): 8.93-8.85 (1H, m), 8.78 (1H, s), 8.30 (1H, dd), 8.21 (2H, d), 8.05 (1H, s), 7.58 (1H, t), 7.48-7.37 (2H, m), 3.96 (2H, q), 3.40 (6H, s), 2.50 (3H, s). | [Fragment] + 470 |
| 201 | 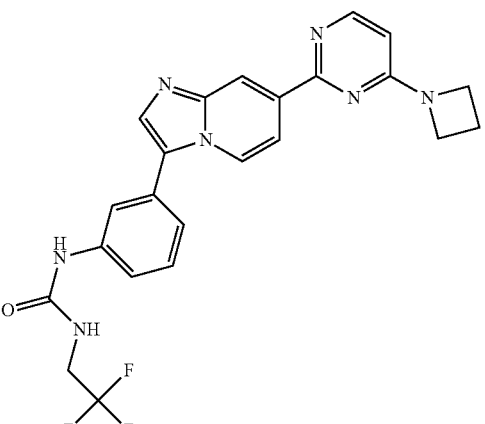<br>1-{3-[7-(4-Azetidin-1-yl-pyrimidin-2-yl)-imidazo[1,2-a]pyridin-3-yl]-phenyl}-3-(2,2,2-trifluoro-ethyl)-urea hydrochloride | General Route B in step B3d used 4-azetidin-1-yl-2-chloro-pyrimidine | (Me-d3-OD): 9.04 (1H, d), 8.83 (1H, s), 8.42 (1H, s), 8.27 (1H, d), 8.19 (1H, dd), 8.11 (1H, t), 7.61 (1H, t), 7.49-7.38 (2H, m), 6.74 (1H, d), 4.51 (4H, s), 3.96 (2H, q), 2.69-2.58 (2H, m). | 468 |

| Eg. | Structure and Chemical name | Route/Method | NMR Data (solvent) | MS Data |
|---|---|---|---|---|
| 202 | 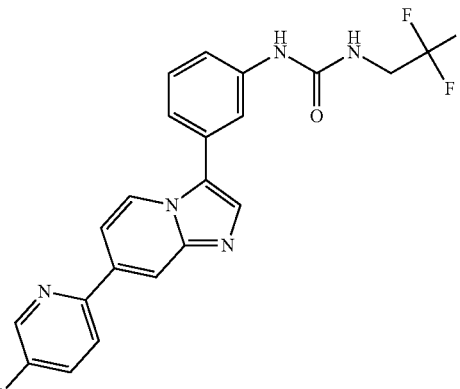<br>1-{3-[7-(5-Hydroxy-pyridin-2-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using 6-chloro-pyridin-3-ol, procedure Z5 | (Me-d3-OD): 8.91 (1H, d), 8.53 (1H, s), 8.41 (1H, d), 8.24 (1H, s), 8.21 (1H, d), 8.12 (1H, d), 8.05 (1H, s), 7.68-7.54 (2H, m), 7.52-7.44 (1H, m), 7.41 (1H, d), 3.96 (2H, q). | 428 |
| 203 | 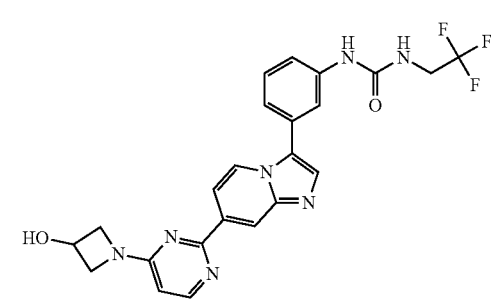<br>1-(3-{7-[4-(3-Hydroxy-azetidin-1-yl)-pyrimidin-2-yl]-imidazo-[1,2-a]pyridin-3-yl}-phenyl)-3-(2,2,2-trifluoro-ethyl)-urea hydrochloride | General Route B in step B3d used 1-(2-chloro-pyrimidin-4-yl)-azetidin-3-ol | (Me-d3-OD): 9.06 (1H, d), 8.85 (1H, s), 8.44 (1H, s), 8.30 (1H, d), 8.20 (1H, d), 8.11 (1H, s), 7.61 (1H, t), 7.51-7.38 (2H, m), 6.82 (1H, d), 4.72 (2H, s), 4.26 (2H, d), 3.96 (2H, q). | 484 |
| 204 | 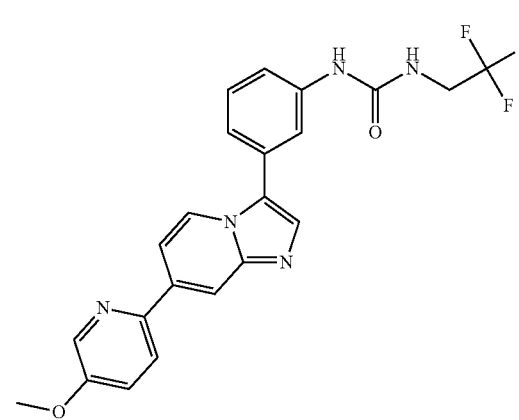<br>1-{3-[7-(5-Methoxy-pyridin-2-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using 2-chloro-5-methoxy-pyridine, method Z5 | (Me-d3-OD): 8.90 (1H, d), 8.58 (1H, s), 8.55 (1H, d), 8.26 (1H, d), 8.23 (1H, s), 8.17 (1H, dd), 8.08-8.00 (1H, m), 7.74 (1H, dd), 7.59 (1H, t), 7.53-7.45 (1H, m), 7.41 (1H, d), 4.03 (3H, s), 3.96 (2H, q). | 442 |

| Eg. | Structure and Chemical name | Route/Method | NMR Data (solvent) | MS Data |
|---|---|---|---|---|
| 205 | 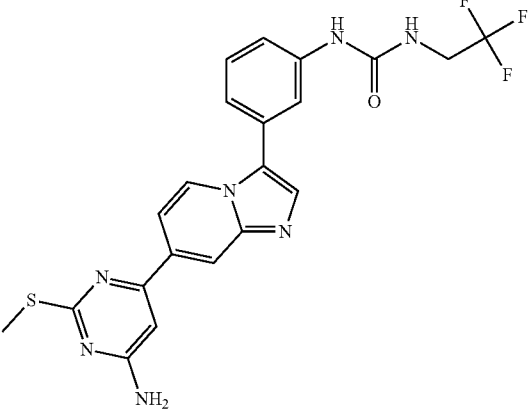<br>1-{3-[7-(6-Amino-2-methylsulfanyl-pyrimidin-4-yl)-imidazo[1,2-a]pyridin-3-yl]-phenyl}-3-(2,2,2-trifluoro-ethyl)-urea | General route B: B1, B2, B3d (MW irradiation 120° C., 1 hr) using 3-chloro-5-methylsulfanylphenyl-amine, method Z5 | (Me-d3-OD): 8.99 (1H, d), 8.62 (1H, s), 8.37 (1H, s), 8.09 (1H, s), 7.96 (1H, dd), 7.60 (1H, t), 7.51-7.37 (2H, m), 7.02 (1H, s), 3.96 (2H, q), 2.75 (3H, s). | 474 |
| 206 | 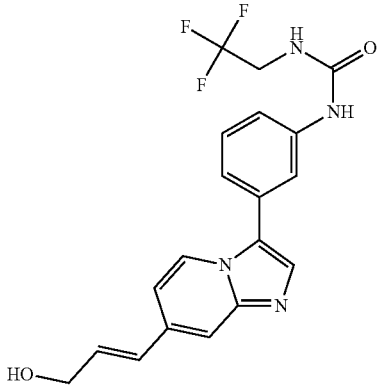<br>1-{3-[7-((E)-3-Hydroxy-propenyl)-imidazo[1,2-a]pyridin-3-yl]-phenyl}-3-(2,2,2-trifluoro-ethyl)-urea hydrochloride | General Route H using (E)-3-imidazo-[1,2-a]pyridin-7-yl-prop-2-en-1-ol | (Me-d3-OD): 8.71 (1H, d), 8.15-8.07 (1H, m), 7.99 (1H, s), 7.88-7.80 (1H, m), 7.69 (1H, d), 7.56 (1H, t), 7.46 (1H, d), 7.36 (1H, d), 6.97-6.85 (2H, m), 4.38 (2H, d), 3.95 (2H, q). | 391 |

| Eg. | Structure and Chemical name | Route/Method | NMR Data (solvent) | MS Data |
|---|---|---|---|---|
| 207 | 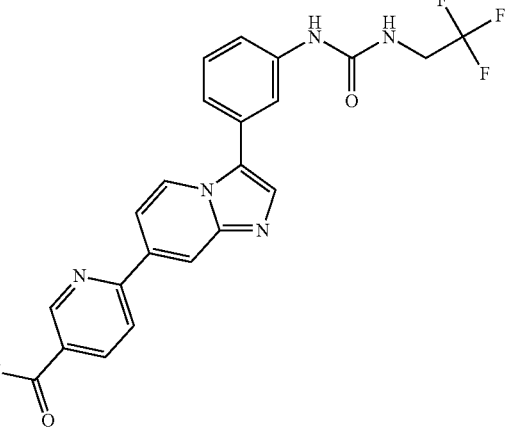<br>6-(3-{3-[3-(2,2,2-Trifluoro-ethyl)-ureido]-phenyl}-imidazo[1,2-a]pyridin-7-yl)-nicotinamide | General Route B in step B3d used 6-chloronicotinamide | (DMSO-d6): 9.16 (1H, s), 8.97 (1H, s), 8.69 (1H, d), 8.51 (1H, s), 8.38-8.30 (2H, m), 8.22 (1H, s), 7.90 (1H, s), 7.86 (1H, dd), 7.80 (1H, s), 7.64 (1H, s), 7.52-7.44 (2H, m), 7.34-7.26 (1H, m), 6.86 (1H, t), 4.01-3.90 (2H, m). | 455 |
| 208 | 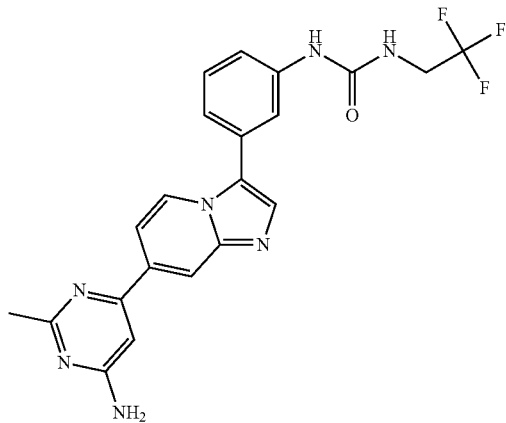<br>1-{3-[7-(6-Amino-2-methyl-pyrimidin-4-yl)-imidazo-[1,2-a]pyridin-3-yl]-phenyl}-3-(2,2,2-trifluoroethyl)-urea hydrochloride | General route B: B1, B2, B3d (MW irradiation 120° C., 1 hr) using 3-chloro-5-methylphenylamine, method Z5 | (Me-d3-OD): 9.02 (1H, d), 8.64 (1H, s), 8.39 (1H, s), 8.09 (1H, s), 7.93 (1H, d), 7.60 (1H, t), 7.52-7.37 (2H, m), 7.21 (1H, s), 3.96 (2H, q), 2.73 (3H, s). | 442 |
| 209 | 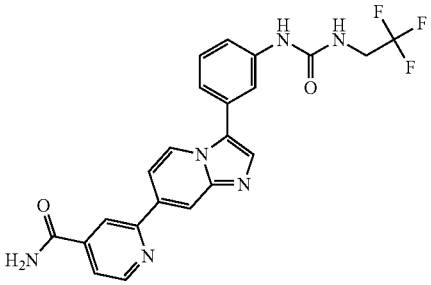<br>2-(3-{3-[3-(2,2,2-Trifluoro-ethyl)-ureido]-phenyl}-imidazo[1,2-a]pyridin-7-yl)-isonicotinamide | General Route B in B3d used 2-chloroisonicotinamide | (DMSO-d6): 8.98 (1H, s), 8.85 (1H, d), 8.69 (1H, d), 8.57 (1H, s), 8.50 (1H, s), 8.39 (1H, s), 7.87 (1H, s), 7.86-7.80 (2H, m), 7.80-7.75 (2H, m), 7.52-7.44 (2H, m), 7.34-7.26 (1H, m), 6.86 (1H, t), 4.02-3.90 (2H, m). | 455 |

| Eg. | Structure and Chemical name | Route/ Method | NMR Data (solvent) | MS Data |
|---|---|---|---|---|
| 210 | 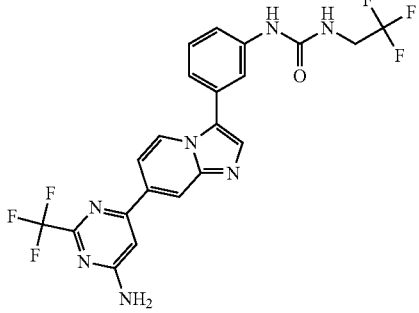<br>1-{3-[7-(6-Amino-2-trifluoromethyl-pyrimidin-4-yl)-imidazo[1,2-a]pyridin-3-yl]-phenyl}-3-(2,2,2-trifluoro-ethyl)-urea | General route B: B1, B2, B3d (MW irradiation 120° C., 1 hr) using 6-chloro-2-trifluoromethyl-pyrimid-in-4-ylamine | (Me-d3-OD): 8.68 (1H, d), 8.40 (1H, s), 7.89-7.84 (1H, m), 7.83 (1H, s), 7.69 (1H, dd), 7.50 (1H, t), 7.42 (1H, d), 7.34 (1H, d), 7.19 (1H, s), 3.96 (2H, q). | 496 |
| 211 | 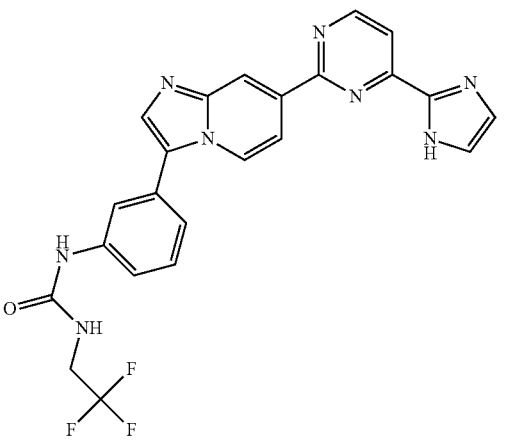<br>1-(3-{7-[4-(1H-Imidazol-2-yl)-pyrimid-in-2-yl]-imidazo[1,2-a]pyridin-3-yl}-phenyl)-3-(2,2,2-trifluoroethyl)-urea trifluoro-acetate | General Route B followed by procedure B3d using X19 sulphonamide deprotection Z8 | (DMSO-d6): 9.46-9.39 (1H, m), 9.12 (1H, s), 8.96 (1H, d), 8.70 (1H, d), 8.32 (1H, s), 8.13 (1H, dd), 7.96-7.82 (3H, m), 7.57-7.42 (3H, m), 7.40-7.23 (3H, m), 4.01-3.88 (2H, m). | 479 |

-continued

| Eg. | Structure and Chemical name | Route/Method | NMR Data (solvent) | MS Data |
|---|---|---|---|---|
| 212 | 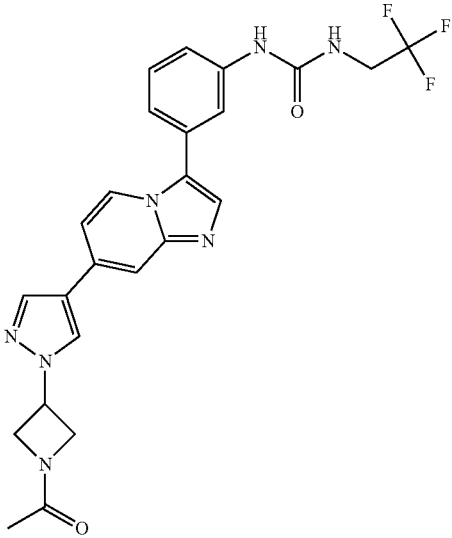<br>1-(3-{7-[1-(1-Acetyl-azetidin-3-yl)-1H-pyrazol-4-yl]-imidazo[1,2-a]pyridin-3-yl}-phenyl)-3-(2,2,2-trifluoro-ethyl)-urea | General Route B followed by procedure B3c using X20 | (DMSO-d6): 8.95 (1H, s), 8.62 (1H, s), 8.55 (1H, d), 8.25 (1H, s), 7.96-7.89 (1H, m), 7.77 (1H, s), 7.71 (1H, s), 7.47-7.39 (2H, m), 7.33-7.21 (2H, m), 6.85 (1H, t), 5.32-5.23 (1H, m), 4.62 (1H, t), 4.45 (1H, dd), 4.34 (1H, t), 4.17 (1H, dd), 4.01-3.90 (2H, m), 1.84 (3H, s) | 498 |
| 213 | 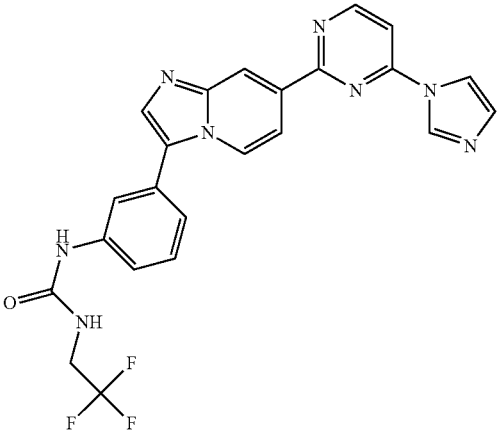<br>1-{3-[7-(4-Imidazol-1-yl-pyrimidin-2-yl)-imidazo[1,2-a]pyridin-3-yl]-phenyl}-3-(2,2,2-trifluoro-ethyl)-urea | General Route B followed by procedure B3d using 2-chloro-4-(1h-imidazol-1-yl)pyrimidine | (DMSO-d6): 9.07 (1H, d), 8.97 (2H, d), 8.82 (1H, s), 8.70 (1H, d), 8.30 (1H, s), 8.05 (1H, dd), 7.97-7.87 (2H, m), 7.82 (1H, s), 7.53-7.45 (2H, m), 7.36-7.28 (1H, m), 7.25 (1H, s), 6.87 (1H, t), 4.02-3.90 (2H, m). | 479 |

| Eg. | Structure and Chemical name | Route/ Method | NMR Data (solvent) | MS Data |
|---|---|---|---|---|
| 214 | 1-{3-[7-(6-Dimethyl-amino-2-trifluoromethyl-pyrimidin-4-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using (3-chloro-5-trifluoro methyl-phenyl)-dimethyl-amine, method Z5 | (Me-d3-OD): 8.93 (1H, d), 8.81 (1H, s), 8.32-8.23 (2H, m), 8.06 (1H, s), 7.59 (1H, t), 7.51 (1H, s), 7.47 (1H, d), 7.42 (1H, d), 3.96 (2H, q). | 524 |
| 215 | 1-{3-[7-(2-Imidazol-1-yl-pyrimidin-4-yl)-imidazo-[1,2-a]pyridin-3-yl]-phenyl}-3-(2,2,2-trifluoroethyl)-urea trifluoroacetate | General Route B followed by procedure B3d using 2-(imidazol-1-yl)-4-chloropyrimidine | (Me-d3-OD): 9.91 (1H, s), 9.17 (1H, d), 9.03-8.91 (2H, m), 8.60 (1H, t), 8.44-8.28 (3H, m), 8.12 (1H, t), 7.76 (1H, t), 7.60 (1H, t), 7.43 (2H, dd), 3.96 (2H, q). | 479 |
| 216 | 2-[2-(3-{3-[3-(2,2,2-Trifluoroethyl)-ureido]-phenyl}-imidazo[1,2-a]pyridin-7-yl)-pyrimidin-4-yl]-imidazole-1-sulfonic acid dimethylamide | General Route B followed by procedure B3d using X19 | (DMSO-d6): 9.10 (1H, d), 8.97 (1H, s), 8.80-8.67 (2H, m), 8.02 (1H, dd), 7.96-7.85 (3H, m), 7.77 (1H, s), 7.58-7.42 (2H, m), 7.40-7.27 (2H, m), 6.86 (1H, t), 4.03-3.89 (2H, m), 3.00 (6H, s) | 586 |

| Eg. | Structure and Chemical name | Route/Method | NMR Data (solvent) | MS Data |
|---|---|---|---|---|
| 217 | 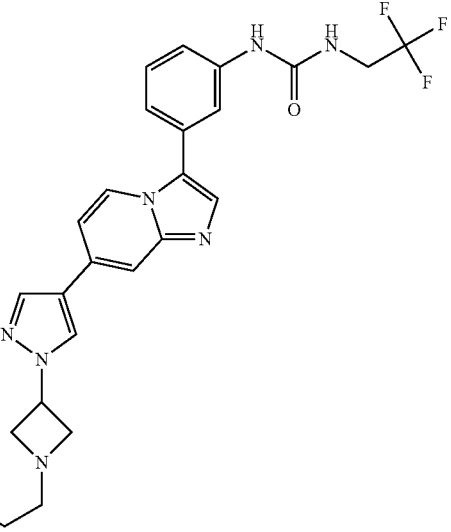<br>1-[3-(7-{1-[1-(2-Hydroxy-ethyl)-azetidin-3-yl]-1H-pyrazol-4-yl}-imidazo[1,2-a]pyridin-3-yl)-phenyl]-3-(2,2,2-trifluoro-ethyl)-urea | General Route B followed by procedure B3c using X21 loss of THP occurred | (Me-d3-OD): 8.57 (1H, d), 8.48 (1H, s), 8.34 (1H, s), 8.14 (1H, s), 7.87-7.80 (1H, m), 7.78 (1H, s), 7.71-7.64 (1H, m), 7.48 (1H, t), 7.38 (1H, d), 7.29 (2H, t), 5.31-5.21 (1H, m), 4.25 (2H, t), 4.14-4.03 (2H, m), 3.95 (2H, q), 3.77-3.63 (2H, m), 3.09 (2H, t). | 500 |
| 218 | 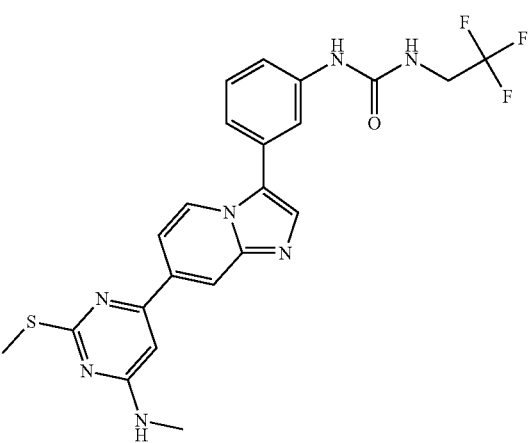<br>1-{3-[7-(6-Methylamino-2-methyl-sulfanyl-pyrimidin-4-yl)-imidazo[1,2-a]pyridin-3-yl]-phenyl}-3-(2,2,2-trifluoro-ethyl)-urea hydrochloride | General route B: B1, B2, B3c using (3-chloro-5-methyl-sulfanyl-phenyl)-methyl-amine, procedure Z5 | (Me-d3-OD): 8.98 (1H, d), 8.57 (1H, br s), 8.36 (1H, s), 8.09 (1H, s), 7.91 (1H, br s), 7.60 (1H, t), 7.50-7.37 (2H, m), 6.94 (1H, br s), 3.96 (2H, q), 3.17 (3H, s), 2.75 (3H, s). | 488 |

| Eg. | Structure and Chemical name | Route/Method | NMR Data (solvent) | MS Data |
|---|---|---|---|---|
| 219 | 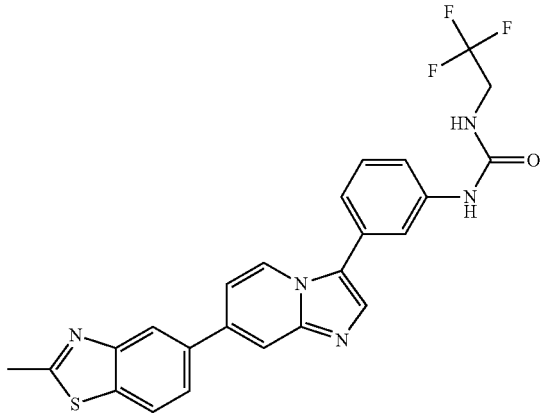<br>1-{3-[7-(2-Methyl-benzothiazol-5-yl)-imidazo[1,2-a]pyridin-3-yl]-phenyl}-3-(2,2,2-trifluoro-ethyl)-urea | General Route B in step B3a used 5-bromo-2-methylbenzothiazole | (DMSO-d6): 9.00 (1H, s), 8.65 (1H, d), 8.38 (1H, d), 8.17 (1H, d), 8.11 (1H, s), 7.91 (1H, dd), 7.81 (2H, d), 7.50 (1H, dd), 7.48-7.43 (2H, m), 7.33-7.25 (1H, m), 6.89 (1H, t), 4.02-3.90 (2H, m), 2.85 (3H, s). | 482 |
| 220 | 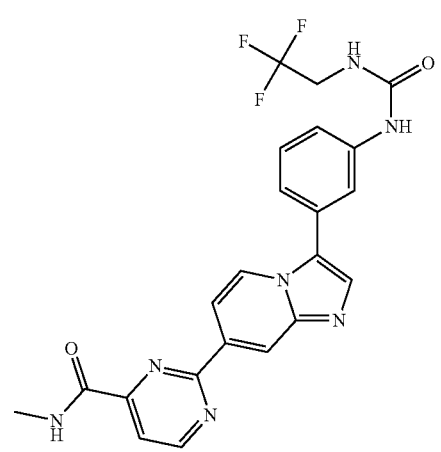<br>2-(3-{3-[3-(2,2,2-Trifluoroethyl)-ureido]-phenyl}-imidazo[1,2-a]pyridin-7-yl)-pyrimidine-4-carboxylic acid methylamide | General Route B in step B3d used 2-chloro-pyrimidine-4-carboxylic acid methylamide | (DMSO-d6): 9.46-9.39 (1H, m), 9.17 (1H, d), 9.14 (1H, s), 8.98 (1H, s), 8.70 (1H, d), 8.12 (1H, dd), 7.95 (2H, d), 7.84 (1H, s), 7.52-7.44 (2H, m), 7.36-7.28 (1H, m), 6.87 (1H, t), 4.01-3.91 (2H, m), 2.93 (3H, d). | 470 |

| Eg. | Structure and Chemical name | Route/Method | NMR Data (solvent) | MS Data |
|---|---|---|---|---|
| 221 | 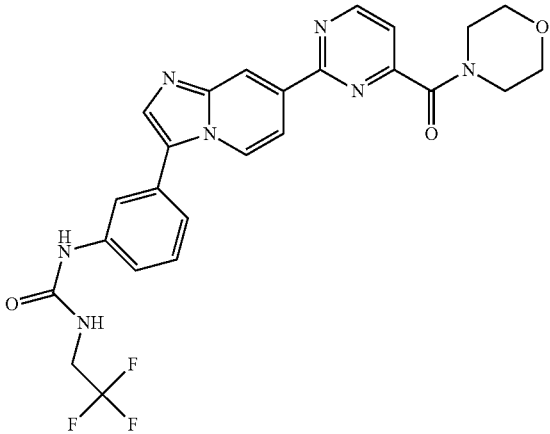<br>1-(3-{7-[4-(Morpholine-4-carbonyl)-pyrimidin-2-yl]-imidazo-[1,2-a]pyridin-3-yl}-phenyl)-3-(2,2,2-trifluoroethyl)-urea hydrochloride | General Route B in step B3d used (2-chloro-pyrimidin-4-yl)-morpholin-4-yl-methanone | (Me-d3-OD): 9.19 (1H, d), 9.03-8.93 (2H, m), 8.53 (1H, dd), 8.32 (1H, s), 8.07 (1H, s), 7.77 (1H, d), 7.60 (1H, t), 7.53-7.46 (1H, m), 7.43 (1H, d), 3.96 (2H, q), 3.86 (4H, s), 3.76 (2H, t), 3.66 (2H, t). | 526 |
| 222 | 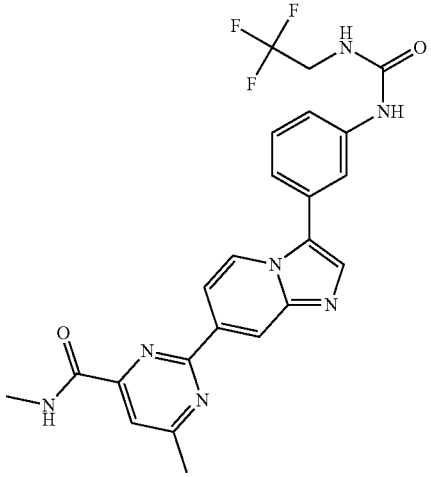<br>6-Methyl-2-(3-{3-[3-(2,2,2-trifluoroethyl)-ureido]-phenyl}-imidazo[1,2-a]pyridin-7-yl)-pyrimidine-4-carboxylic acid methylamide hydrochloride | General Route B in step B3d used (2-chloro-pyrimidin-4-yl)-morpholin-4-yl-methanone | (Me-d3-OD): 9.16 (1H, s), 8.95 (1H, d), 8.75 (1H, dd), 8.33 (1H, s), 8.09 (1H, s), 8.04 (1H, s), 7.61 (1H, t), 7.48 (1H, d), 7.44 (1H, d), 3.96 (2H, q), 3.07 (3H, s), 2.79 (3H, s). | 484 |

| Eg. | Structure and Chemical name | Route/Method | NMR Data (solvent) | MS Data |
|---|---|---|---|---|
| 223 | 1-(3-{7-[5-(Morpholine-4-carbonyl)-pyridin-2-yl]-imidazo[1,2-a]pyridin-3-yl}-phenyl)-3-(2,2,2-trifluoro-ethyl)-urea hydrochloride | General Route B in step B3d used (6-chloro-pyridin-3-yl)-morpholin-4-yl-methanone | (Me-d3-OD): 8.94 (1H, d), 8.89 (1H, s), 8.74 (1H, s), 8.35 (1H, d), 8.28 (2H, d), 8.14 (1H, d), 8.04 (1H, s), 7.59 (1H, t), 7.50 (1H, d), 7.42 (1H, d), 3.96 (2H, q), 3.78 (6H, d), 3.67-3.54 (2H, m), 1.19 (1H, t). | 525 |
| 224 | N-Methyl-6-(3-{3-[3-(2,2,2-trifluoroethyl)-ureido]-phenyl}-imidazo[1,2-a]pyridin-7-yl)-nicotinamide hydrochloride | General Route B in step B3d used 6-chloro-N-methyl-nicotinamide | (Me-d3-OD): 9.21 (1H, d), 8.94 (1H, d), 8.75 (1H, s), 8.42 (1H, dd), 8.36-8.24 (3H, m), 8.06 (1H, s), 7.60 (1H, t), 7.48 (1H, d), 7.42 (1H, d), 3.96 (2H, q), 3.00 (3H, s). | 469 |
| 225 | 1-{3-[7-(6-Methyl-imidazo[2,1-b][1,3,4]thiadiazol-2-yl)-imidazo[1,2-a]pyridin-3-yl]-phenyl}-3-(2,2,2-trifluoro-ethyl)-urea | General Route B in step B3d used 2-bromo-6-methylimidazo[2,1-B][1,3,4]thiadiazole | (Me-d3-OD): 8.75-8.67 (1H, m), 8.16 (1H, s), 7.87 (2H, d), 7.80 (1H, s), 7.59 (1H, d), 7.56-7.46 (1H, m), 7.43 (1H, d), 7.35 (1H, d), 3.96 (2H, q), 2.38 (3H, s). | 472 |

-continued

| Eg. | Structure and Chemical name | Route/Method | NMR Data (solvent) | MS Data |
|---|---|---|---|---|
| 226 | 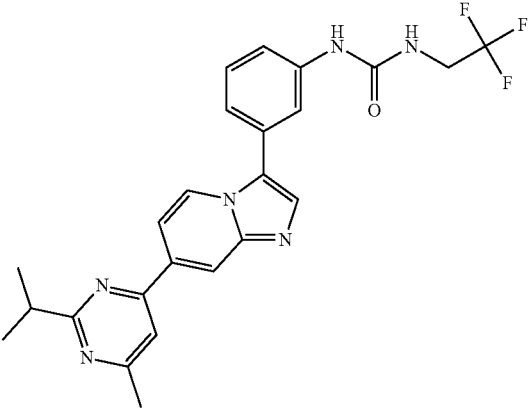<br>1-{3-[7-(2-Isopropyl-6-methyl-pyrimidin-4-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using 1-chloro-3-isopropyl-5-methyl-benzene, procedure Z5 | (DMSO-d6): 9.35 (1H, s), 8.92 (1H, d), 8.79 (1H, s), 8.48 (1H, s), 8.20 (1H, d), 8.14 (1H, s), 7.94 (1H, s), 7.56 (2H, d), 7.35 (1H, s), 7.07 (1H, t), 4.01-3.91 (2H, m), 3.28-3.18 (1H, m), 2.60 (3H, s), 1.37 (6H, d). | 469 |
| 227 | 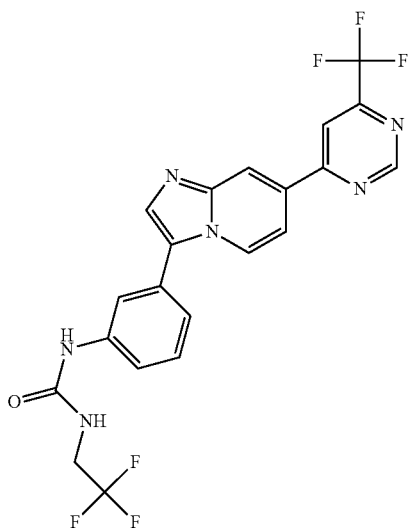<br>1-(2,2,2-Trifluoro-ethyl)-3-{3-[7-(6-trifluoromethyl-pyrimidin-4-yl)-imidazo[1,2-a]pyridin-3-yl]-phenyl}-urea hydrochloride | General route B: B1, B2, B3d (MW irradiation 120° C., 1 hr) using 4-chloro-6-trifluoromethyl-pyrimidine, procedure Z5 | (Me-d3-OD): 9.59 (1H, s), 9.00 (1H, d), 8.96 (1H, s), 8.73 (1H, s), 8.44-8.33 (2H, m), 8.09 (1H, s), 7.61 (1H, t), 7.52-7.39 (2H, m), 3.96 (2H, q). | 481 |

| Eg. | Structure and Chemical name | Route/Method | NMR Data (solvent) | MS Data |
|---|---|---|---|---|
| 228 | 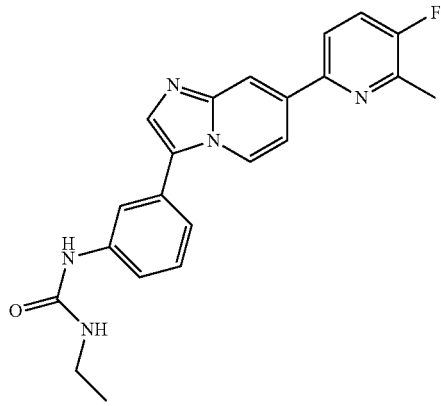<br>1-Ethyl-3-{3-[7-(5-fluoro-6-methyl-pyridin-2-yl)-imidazo[1,2-a]pyridin-3-yl]-phenyl}-urea | General Route B. In A3 ethylamine was used and step B3d used 2-chloro-5-fluoro-6-picoline | (DMSO-d6): 8.63 (2H, d), 8.36 (1H, s), 8.11 (1H, dd), 7.81 (2H, d), 7.78-7.71 (2H, m), 7.42 (2H, d), 7.26-7.18 (1H, m), 6.20 (1H, t), 3.20-3.08 (2H, m), 2.57 (3H, d), 1.15-1.02 (3H, m). | 390 |
| 229 | 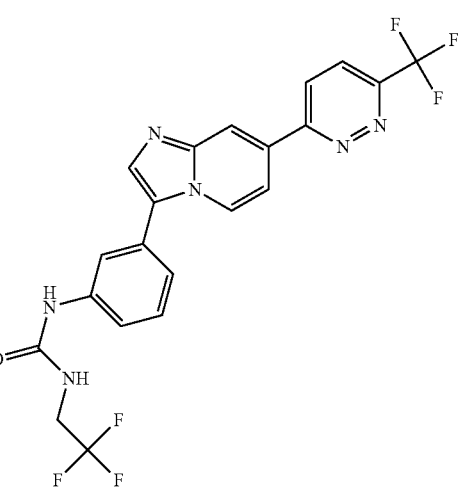<br>1-(2,2,2-Trifluoro-ethyl)-3-{3-[7-(6-trifluoromethyl-pyridazin-3-yl)-imidazo[1,2-a]pyridin-3-yl]-phenyl}-urea hydrochloride | General route B: B1, B2, B3d (MW irradiation 120° C., 1 hr) using 3-chloro-6-trifluoromethyl-pyridazine, method Z5 | (Me-d3-OD): 9.03 (1H, d), 8.88 (1H, s), 8.73 (1H, d), 8.42-8.31 (3H, m), 8.09 (1H, s), 7.61 (1H, t), 7.53-7.39 (2H, m), 3.96 (2H, q). | 481 |

| Eg. | Structure and Chemical name | Route/Method | NMR Data (solvent) | MS Data |
|---|---|---|---|---|
| 230 | 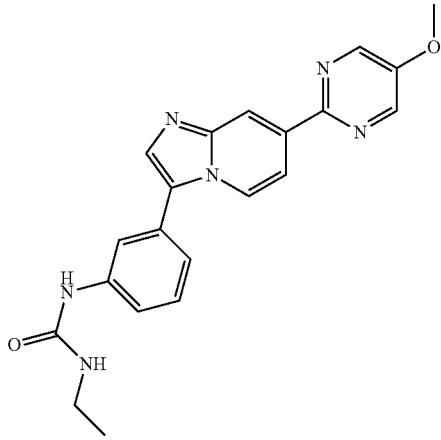<br>1-Ethyl-3-{3-[7-(5-methoxy-pyrimidin-2-yl)-imidazo[1,2-a]pyridin-3-yl]-phenyl}-urea | General Route B. In A3 using ethylamine and step B3d used 2-chloro-5-methoxypyrimidine | (DMSO-d6): 8.72 (2H, s), 8.66 (1H, d), 8.62 (1H, s), 8.48 (1H, s), 7.87 (1H, dd), 7.83 (1H, s), 7.77 (1H, s), 7.49-7.39 (2H, m), 7.27-7.19 (1H, m), 6.20 (1H, t), 4.00 (3H, s), 3.18-3.08 (2H, m), 1.07 (3H, t). | 389 |
| 231 | 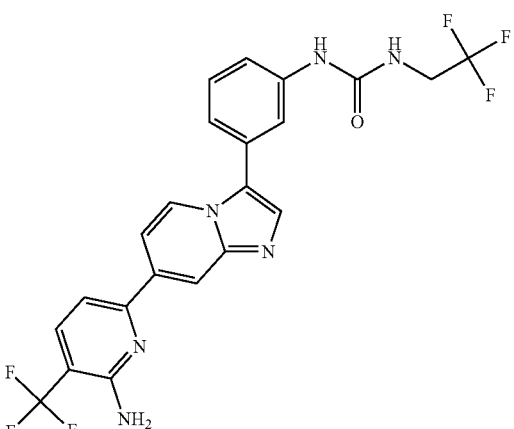<br>1-{3-[7-(6-Amino-5-trifluoromethyl-pyrimidin-2-yl)-imidazo[1,2-a]pyridin-3-yl]-phenyl}-3-(2,2,2-trifluoroethyl)-urea hydrochloride | General Route B in step B3d used 6-chloro-3-trifluoromethyl-pyridin-2-ylamine | (DMSO-d6): 9.66 (1H, s), 8.88 (1H, d), 8.60 (1H, s), 8.51 (1H, s), 8.13 (1H, dd), 8.01 (1H, d), 7.92 (1H, s), 7.64-7.49 (3H, m), 7.33 (1H, d), 7.25 (1H, t), 4.03-3.88 (2H, m) | 495 |

-continued

| Eg. | Structure and Chemical name | Route/Method | NMR Data (solvent) | MS Data |
|---|---|---|---|---|
| 232 | 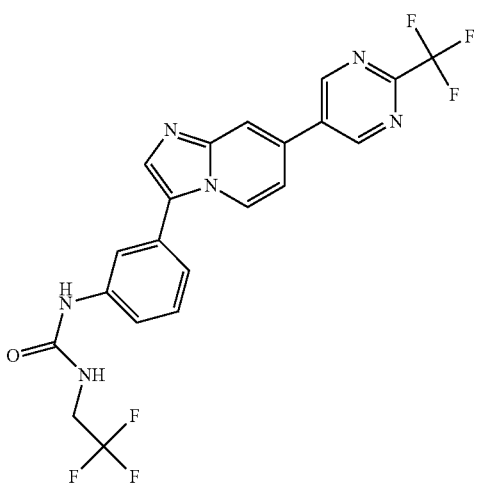<br>1-(2,2,2-Trifluoro-ethyl)-3-{3-[7-(2-trifluoromethyl-pyrimidin-5-yl)-imidazo[1,2-a]pyridin-3-yl]-phenyl}-urea hydrochloride | General route B: B1, B2, B3d (MW irradiation 120° C., 1 hr) using 5-bromo-2-trifluoro-methyl-pyrimidine, method Z5 | (DMSO-d6): 9.64 (2H, s), 9.29 (1H, s), 8.92 (1H, d), 8.54 (1H, s), 8.37 (1H, s), 7.93 (2H, s), 7.53 (2H, s), 7.34 (1H, s), 7.04 (1H, t), 3.99-3.92 (2H, m). | 481 |
| 233 | 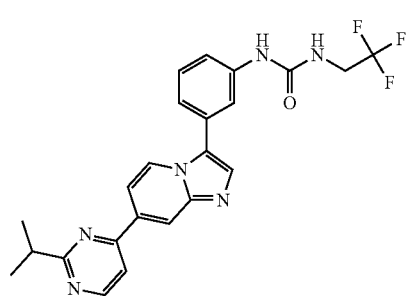<br>1-{3-[7-(2-Isopropyl-pyrimidin-4-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using 4-chloro-2-isopropyl-pyrimidine, procedure Z5 | (DMSO-d6): 9.53 (1H, s), 9.02 (1H, d), 8.92 (1H, d), 8.82 (1H, s), 8.52 (1H, s), 8.29-8.19 (2H, m), 7.94 (1H, s), 7.62-7.51 (2H, m), 7.34 (1H, d), 7.17 (1H, t), 4.03-3.88 (2H, m), 3.35-3.24 (1H, m), 1.39 (6H, d). | 455 |
| 234 | 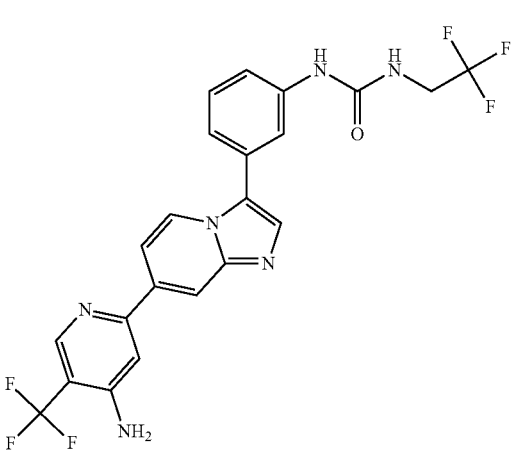<br>1-{3-[7-(4-Amino-5-trifluoromethyl-pyrimidin-2-yl)-imidazo[1,2-a]pyridin-3-yl]-phenyl}-3-(2,2,2-trifluoroethyl)-urea hydrochloride | General Route B in step B3d used 6-chloro-5-trifluoromethyl-pyridin-2-ylamine | (Me-d3-OD): 9.07 (1H, d), 8.72 (1H, s), 8.57 (1H, s), 8.42 (1H, s), 8.10 (1H, s), 7.88 (1H, dd), 7.61 (1H, t), 7.55 (1H, s), 7.48 (1H, d), 7.43 (1H, d), 3.96 (2H, q). | 495 |

| Eg. | Structure and Chemical name | Route/Method | NMR Data (solvent) | MS Data |
|---|---|---|---|---|
| 235 | 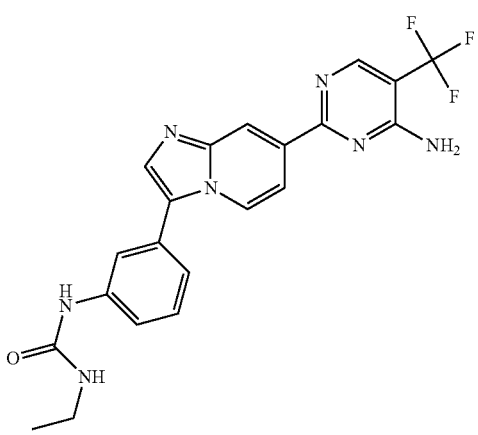<br>1-{3-[7-(4-Amino-5-trifluoromethyl-pyrimidin-2-yl)-imidazo[1,2-a]pyridin-3-yl]-phenyl}-3-ethyl-urea formate | General Route B. In A3 used ethylamine and step B3d used 2-chloro-4-amino-5-triflouromethylpyrimidine which was prepared using the method described for Example 178 | (Me-d3-OD): 8.93 (1H, d), 8.72 (1H, s), 8.27 (1H, s), 8.17 (1H, s), 8.03 (1H, t), 7.68 (1H, dd), 7.56 (1H, t), 7.42 (1H, d), 7.37 (1H, d), 3.31-3.24 (2H, m), 1.24-1.14 (3H, m). | 442 |
| 236 | 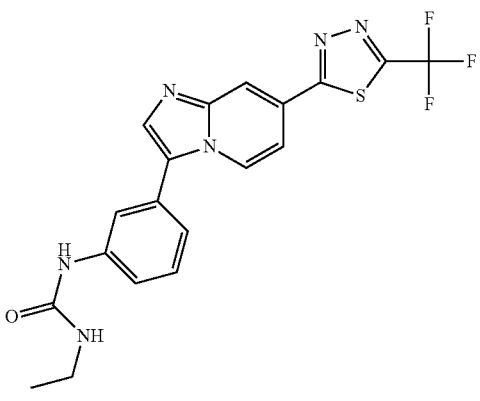<br>1-Ethyl-3-{3-[7-(5-trifluoromethyl-[1,3,4]thiadiazol-2-yl)-imidazo[1,2-a]pyridin-3-yl]-phenyl}-urea | General Route B. In A3 ethylamine and step B3d used 2-chloro-5-trifluoromethyl-(1,3,4)-thiadiazole | (Me-d3-OD): 8.76 (1H, d), 8.39 (1H, s), 7.91 (1H, s), 7.88 (1H, s), 7.73 (1H, dd), 7.50 (1H, t), 7.39 (1H, d), 7.32 (1H, d), 3.31-3.22 (2H, m), 1.19 (3H, t). | 433 |

| Eg. | Structure and Chemical name | Route/ Method | NMR Data (solvent) | MS Data |
|---|---|---|---|---|
| 237 | 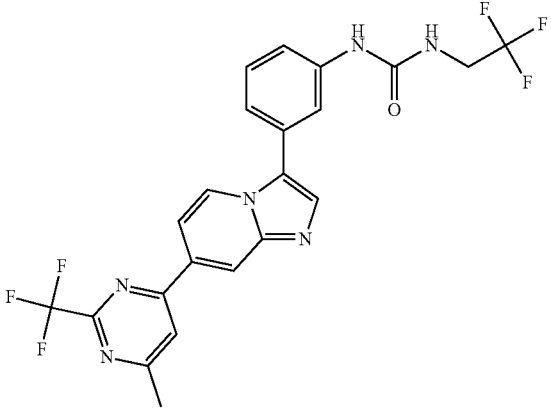<br>1-{3-[7-(6-Methyl-2-trifluoromethyl-pyrimidin-4-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using 4-chloro-6-methyl-2-trifluoromethyl-pyrimidine, method Z5 | (DMSO-d6): 9.43 (1H, s), 8.93 (1H, d), 8.81 (1H, s), 8.66 (1H, s), 8.44 (1H, s), 8.14 (1H, dd), 7.92 (1H, s), 7.60-7.49 (2H, m), 7.38-7.29 (1H, m), 7.11 (1H, t), 4.03-3.88 (2H, m), 2.73 (3H, s). | 495 |
| 238 | 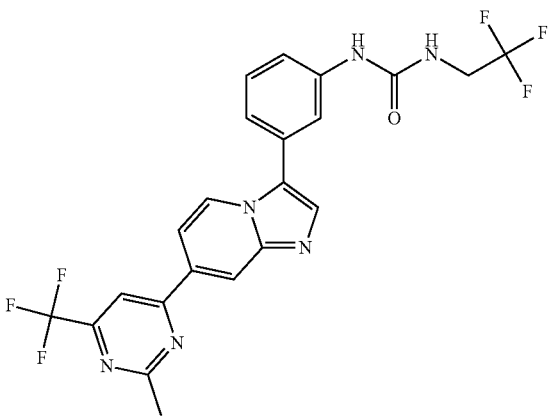<br>1-{3-[7-(2-Methyl-6-trifluoromethyl-pyrimidin-4-yl)-imidazo[1,2-a]pyridin-3-yl]-phenyl}-3-(2,2,2-trifluoro-ethyl)-urea hydrochloride | General route B: B1, B2, B3d (MW irradiation 120° C., 1 hr) using 4-chloro-2-methyl-6-trifluoromethyl-pyrimidine, method Z5 | (DMSO-d6): 9.44 (1H, s), 8.95 (1H, s), 8.90 (1H, d), 8.75 (1H, s), 8.45 (1H, s), 8.26 (1H, d), 7.93 (1H, s), 7.61-7.49 (2H, br m), 7.34 (1H, s), 7.12 (1H, t), 4.00-3.91 (2H, m), 2.87 (3H, s). | 495 |

| Eg. | Structure and Chemical name | Route/Method | NMR Data (solvent) | MS Data |
|---|---|---|---|---|
| 239 | 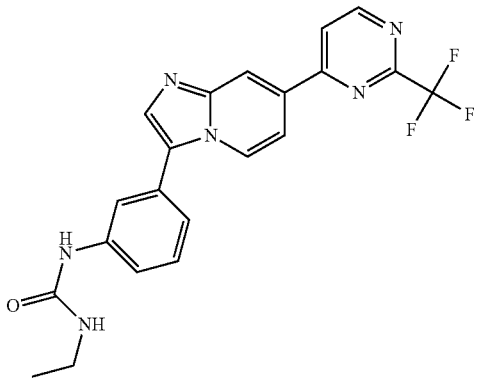<br>1-Ethyl-3-{3-[7-(2-trifluoromethyl-pyrimidin-4-yl)-imidazo[1,2-a]pyridin-3-yl]-phenyl}-urea hydrochloride | General route B: B1, B2, B3d (MW irradiation 120° C., 1 hr) using 4-chloro-2-trifluoromethyl-pyrimi-dine, method Z5 | (DMSO-d6): 9.29 (1H, d), 9.00 (1H, s), 8.92 (1H, d), 8.84 (1H, s), 8.73 (1H, d), 8.42 (1H, s), 8.16 (1H, d), 7.94 (1H, s), 7.50 (2H, s), 7.28 (1H, s), 6.41 (1H, br s), 3.20-3.07 (2H, m), 1.07 (3H, t). | 427 |
| 240 | 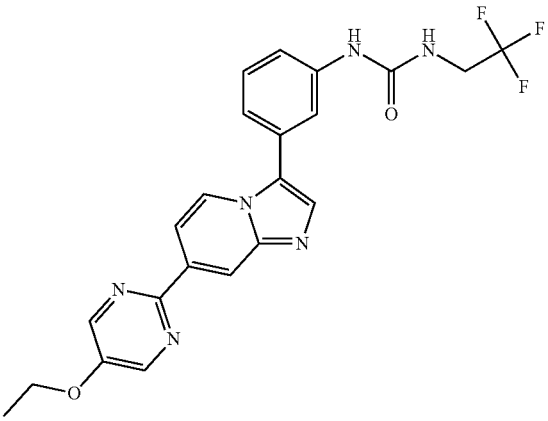<br>1-{3-[7-(5-Ethoxy-pyrimidin-2-yl)-imidazo[1,2-a]pyridin-3-yl]-phenyl}-3-(2,2,2-trifluoro-ethyl)-urea | General route B: B1, B2, B3d (MW irradiation 120° C., 1 hr) using 2-chloro-5-ethoxy-pyrimidine | (DMSO-d6): 8.99 (1H, s), 8.70 (2H, s), 8.67 (1H, d), 8.48 (1H, s), 7.87 (1H, dd), 7.85 (1H, s), 7.76 (1H, s), 7.55-7.43 (2H, m), 7.29 (1H, dt), 6.88 (1H, t), 4.29 (2H, q), 4.01-3.89 (2H, m), 1.41 (3H, t). | 457 |

| Eg. | Structure and Chemical name | Route/Method | NMR Data (solvent) | MS Data |
|---|---|---|---|---|
| 241 | 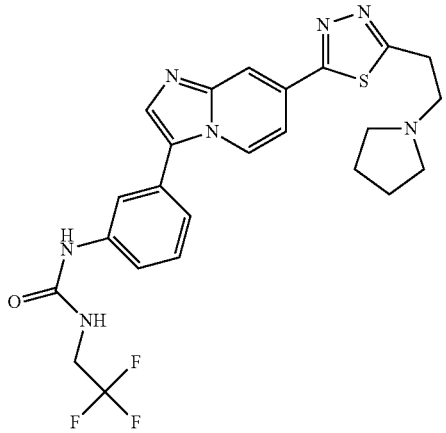<br>1-(3-{7-[5-(2-Pyrrolidin-1-yl-ethyl)-[1,3,4]thiadiazol-2-yl]-imidazo[1,2-a]pyridin-3-yl}-phenyl)-3-(2,2,2-trifluoro-ethyl)-urea | General Route B in step B3d used 2-bromo-5-(2-pyrroli-din-1-yl-ethyl)-[1,3,4]thiadiazole, which was prepared using method X1 from 5-(2-pyrrolidin-1-yl-ethyl)-[1,3,4] thiadiazol-2-ylamine | (DMSO-d6): 9.01-8.94 (1H, m), 8.71-8.63 (1H, m), 8.22 (1H, s), 7.94-7.87 (1H, m), 7.77 (1H, s), 7.64-7.54 (1H, m), 7.54-7.42 (2H, m), 7.34-7.25 (1H, m), 6.90-6.81 (1H, m), 4.01-3.89 (2H, m), 2.88-2.73 (2H, m), 2.59 (4H, s), 1.77 (4H, s). | 516 |
| 242 | 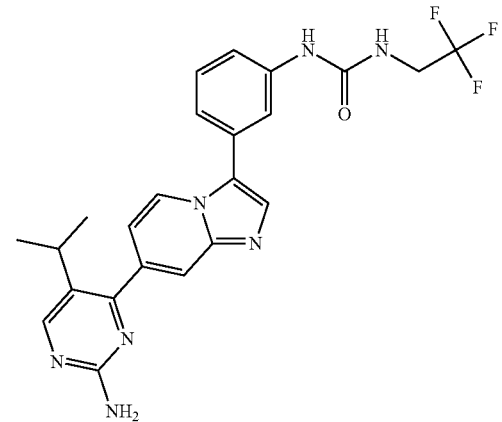<br>1-{3-[7-(2-Amino-5-isopropyl-pyrimidin-4-yl)-imidazo[1,2-a]pyridin-3-yl]-phenyl}-3-(2,2,2-trifluoro-ethyl)-urea hydrochloride | General Route B in step B3d used 4-chloro-5-isopropyl-pyrimidin-2-ylamine | (Me-d3-OD): 9.00 (1H, d), 8.55 (1H, s), 8.36 (1H, s), 8.30 (1H, s), 8.09 (1H, s), 7.72 (1H, dd), 7.70-7.62 (1H, m), 7.52-7.45 (1H, m), 7.43 (1H, d), 3.96 (2H, q), 3.22-3.09 (1H, m), 1.30 (6H, d). | 470 |

| Eg. | Structure and Chemical name | Route/ Method | NMR Data (solvent) | MS Data |
|---|---|---|---|---|
| 243 | 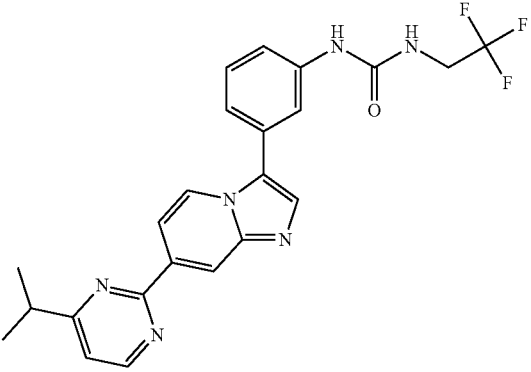<br>1-{3-[7-(4-Isopropyl-pyrimidin-2-yl)-imidazo[1,2-a]pyridin-3-yl]-phenyl}-3-(2,2,2-trifluoro-ethyl)-urea hydrochloride | General Route B in step B3d used 2-chloro-4-isopropyl-pyrimidine | (Me-d3-OD): 9.02 (1H, s), 8.94 (1H, d), 8.89 (1H, d), 8.59 (1H, dd), 8.29 (1H, s), 8.05 (1H, s), 7.60 (1H, t), 7.54-7.46 (2H, m), 7.43 (1H, d), 3.96 (2H, q), 3.28-3.14 (1H, m), 1.43 (6H, d). | 455 |
| 244 | 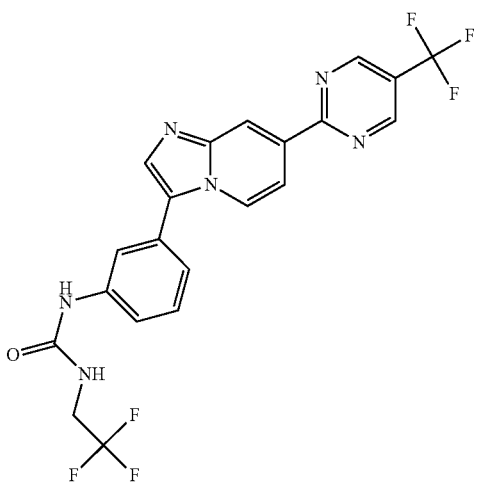<br>1-(2,2,2-Trifluoroethyl)-3-{3-[7-(5-trifluoro-methyl-pyrimidin-2-yl)-imidazo-[1,2-a]pyridin-3-yl]-phenyl}-urea hydrochloride | General Route B in step B3d used 2-chloro-5-trifluoromethyl-pyrimidine | (Me-d3-OD): 9.38 (2H, s), 9.09 (1H, s), 8.99 (1H, d), 8.59 (1H, dd), 8.34 (1H, s), 8.07 (1H, t), 7.60 (1H, t), 7.48 (1H, dd), 7.43 (1H, d), 3.96 (2H, q). | 481 |

| Eg. | Structure and Chemical name | Route/Method | NMR Data (solvent) | MS Data |
|---|---|---|---|---|
| 245 | 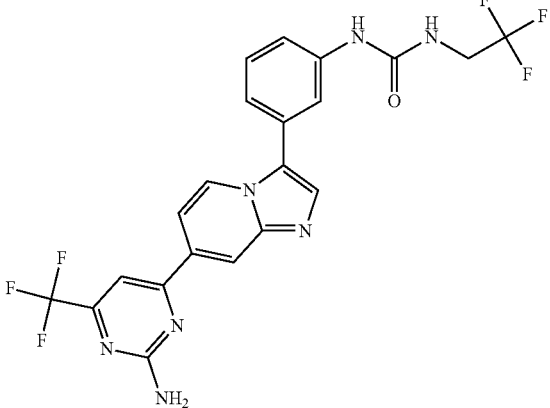<br>1-{3-[7-(2-Amino-6-trifluoromethyl-pyrimidin-4-yl)-imidazo[1,2-a]pyridin-3-yl]-phenyl}-3-(2,2,2-trifluoro-ethyl)-urea | General Route B in step B3d used 2-amino-4-chloro-6-trifluoromethylpyrimidine | (DMSO-d6): 8.99 (1H, s), 8.69 (1H, d), 8.65 (1H, s), 7.93 (1H, s), 7.84-7.75 (3H, m), 7.53-7.45 (2H, m), 7.45-7.39 (2H, m), 7.35-7.26 (1H, m), 6.87 (1H, t), 4.01-3.89 (2H, m). | 496 |
| 246 | 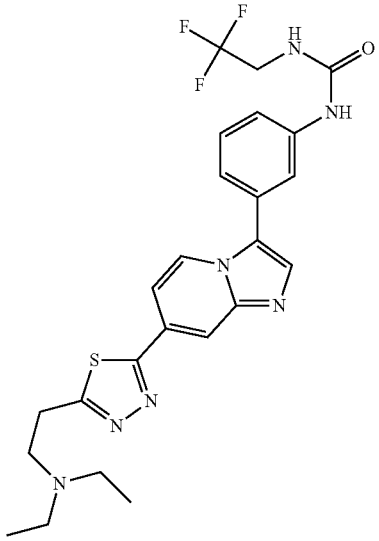<br>1-(3-{7-[5-(2-Diethylamino-ethyl)-[1,3,4]thiadiazol-2-yl]-imidazo[1,2-a]pyridin-3-yl}-phenyl)-3-(2,2,2-trifluoro-ethyl)-urea | General Route B in step B3d used [2-(5-Bromo-[1,3,4]thiadiazol-2-yl)-ethyl]-diethyl-amine, which was prepared using method X1 from 5-(2-diethyl-amino-ethyl)-[1,3,4]thiadiazol-2-ylamine | (Me-d3-OD): 8.71 (1H, d), 8.19 (1H, s), 7.86 (2H, d), 7.66 (1H, dd), 7.51 (1H, t), 7.44 (1H, d), 7.35 (1H, d), 3.96 (2H, q), 4.41-3.36 (2H, m), 2.98 (2H, t), 2.79-2.68 (4H, m), 1.14 (6H, t). | 518 |

| Eg. | Structure and Chemical name | Route/Method | NMR Data (solvent) | MS Data |
|---|---|---|---|---|
| 247 | 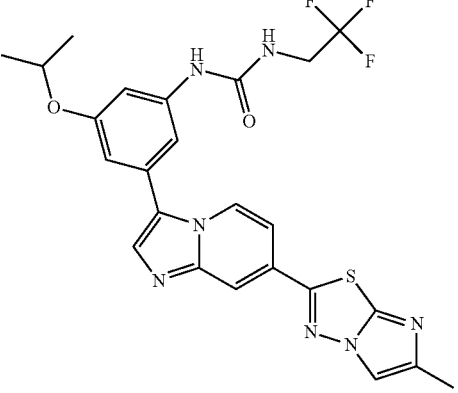<br>1-{3-Isopropoxy-5-[7-(6-methyl-imidazo[2,1-b][1,3,4]thiadiazol-2-yl)-imidazo[1,2-a]pyridin-3-yl]-phenyl}-3-(2,2,2-trifluoro-ethyl)-urea | 3-Iodo-7-(6-methyl-imidazo[2,1-b]-[1,3,4]-thiadiazol-2-yl)-imidazo[1,2-a] pyridine prepared from 2-bromo-6-methyl-imidazo[2,1-b]-[1,3,4]thiadiazole using A1, A2 and A3. Then B3d | (DMSO-d$_6$) 8.98 (1H, br s), 8.74 (1H, d), 8.22 (1H, s), 8.14 (1H, s), 7.78 (1H, s), 7.49 (1H, d), 7.43 (1H, m), 7.16 (1H, m), 6.94 (1H, m), 6.86 (1H, t), 4.64 (1H, m), 3.95 (2H, m), 2.48 (3H, s), 1.35 (6H, d) | 530 |
| 248 | 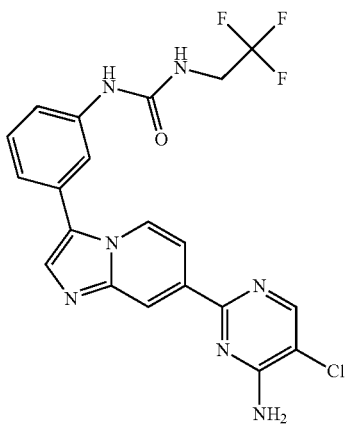<br>1-{3-[7-(4-Amino-5-chloro-pyrimidin-2-yl)-imidazo[1,2-a]pyridin-3-yl]-phenyl}-3-(2,2,2-trifluoro-ethyl)-urea hydrochloride | General Route B in step B3d used 2,5-dichloro-pyrimidin-4-ylamine | (Me-d$_3$-OD): 8.95 (1H, d), 8.85 (1H, s), 8.54 (1H, s), 8.38-8.29 (2H, m), 8.05 (1H, s), 7.60 (1H, t), 7.49 (1H, d), 7.42 (1H, d), 3.96 (2H, q). | 462 |

The following examples further illustrate the present invention:

Hereinafter, "MeOH" is defined as methanol, "EtOH" is defined as ethanol, "EtOAc" is defined as ethyl acetate, "DCM" is defined as dichloromethane, "DME" is defined as 1,2-dimethoxyethane, "THF" is defined as tetrahydrofuran, "RM" is defined as reaction mixture, "RT" is defined as room temperature, "DMF" is defined as N,N-dimethylformamide, DMSO is defined as dimethylsulfoxide, "Et$_2$O" is defined as diethyl ether, "ACN" is defined as acetonitrile, "DIPE" is defined as diisopropyl ether, "TFA" is defined as trifluoroacetic acid, "NH$_4$OH" is defined as ammonium hydroxide, "Pddppf" is defined as 1,1'-bis(diphenylphosphino)ferrocenedichloropalladium, "MP" is defined as melting point.

Preparation of the Intermediate Compounds

Example 1.1 a) Preparation of Intermediate 1

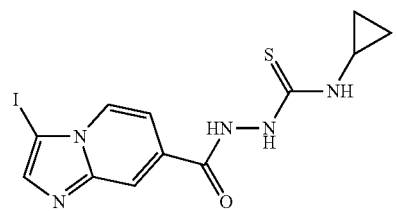 [SMILES: O=C(NNC(=S)NC1CC1)c1ccn2c(I)cnc2c1]

3-Iodo-imidazo[1,2-a]pyridine-7-carboxylic acid hydrazide (1 g, 3.31 mmol) was diluted in EtOH (20 ml). Then, isothiocyanatocyclopropane (0.92 ml, 9.93 mmol) was added and the mixture was heated to 90° C. during 18 hours. The reaction mixture was filtered and washed with EtOH, then Et₂O and dried under vacuum, yielding 1.4 g (>100%) of intermediate 1, used as it is in the next step.

b) Preparation of Intermediate 2

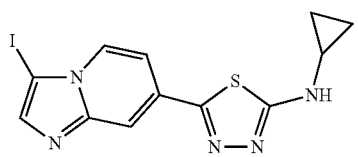 [SMILES: Ic1cnc2cc(-c3nnc(NC4CC4)s3)ccn12]

A mixture of intermediate 1 (1.33 g, 3.31 mmol) in concentrated H₂SO₄ (6 ml) was stirred for 30 minutes at RT. The reaction mixture was basified with NaOH (3N) at 0° C. The precipitate was filtered off, washed with acetone, then Et₂O and dried, yielding 1.1 g (86%) of intermediate 2, used as it is in the next step.

Example 1.2 a) Preparation of Intermediate 3

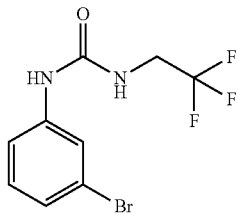 [SMILES: O=C(NCC(F)(F)F)Nc1cccc(Br)c1]

1-Bromo-3-isocyanatobenzene (25 ml, 200 mmol) was added dropwise at 5° C. to a solution of 2,2,2-trifluoroethanamine (24.05 ml, 300 mmol) in THF (160 ml). The mixture was stirred at 5° C. then RT for 4 hours. The mixture was evaporated till dryness, yielding 58.8 g (100%) of intermediate 3.

b) Preparation of Intermediate 4

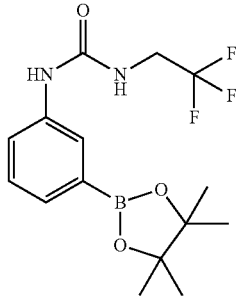 [SMILES: CC1(C)OB(c2cccc(NC(=O)NCC(F)(F)F)c2)OC1(C)C]

Intermediate 3 (20 g, 67.3 mmol), 4,4,4',4',5,5,5',5'-octamethyl-2,2'-bi-1,3,2-dioxaborolane (18.8 g, 74.1 mmol) and potassium acetate (19.8 g, 202 mmol) in DMSO (149 ml) was stirred and degassed with N₂ for 15 minutes, Pddppf (1.48 g, 2.02 mmol) was added. The mixture was heated at 100° C. for 20 hours. The mixture was poured onto water, EtOAc was added. The mixture was filtered through a pad of celite, the organic layer was separated, washed with water then brine, dried over MgSO₄, filtered and evaporated till dryness. The crude product was taken-up by petroleum ether (200 ml) and EtOAc (5 ml), stirred at RT for 45 minutes. The precipitate was filtered, washed with petroleum ether (51 ml) and EtOAc (3 ml) and dried, yielding 20.19 g (87%) of intermediate 4.

Example 1.3 a) Preparation of Intermediate 5

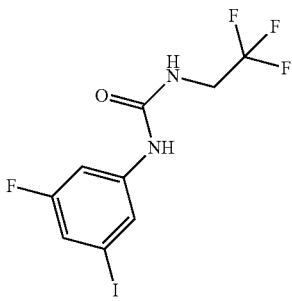 [SMILES: O=C(NCC(F)(F)F)Nc1cc(F)cc(I)c1]

A mixture of 3-fluoro-5-iodobenzenamine (2.7 g, 11.4 mmol) and 4-nitrophenyl chloroformate (2.3 g, 11.34 mmol) in THF (30 ml) was heated at 60° C. for 1 hour, then allowed to cool down to RT. N,N-diisopropylethylamine (1.9 ml, 11.4 mmol) then 2,2,2-trifluoroethanamine (1 ml, 12.53 mmol) were added dropwise at RT. The mixture was heated at 60° C. for 2 hours. The mixture was poured onto ice water and EtOAc was added. The organic layer was washed successively with 10% K₂CO₃ aqueous solution, 3N HCl aqueous solution and water. The organic layer was separated, dried (MgSO₄), filtered and the solvent was evaporated. The crude product was crystallized from DIPE. The precipitate was filtered and dried under vacuum, yielding 3.2 g (78%) of intermediate 5.

b) Preparation of Intermediate 6

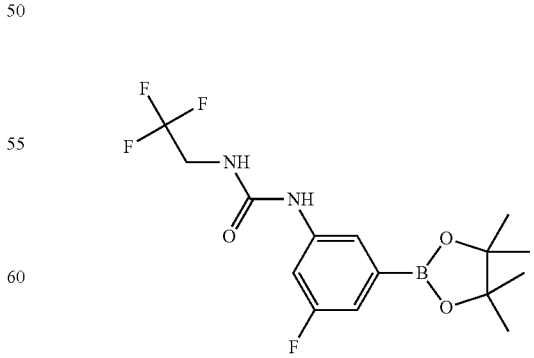

Intermediate 5 (3.2 g, 8.84 mmol), 4,4,4',4',5,5,5',5'-octamethyl-2,2'-bi-1,3,2-dioxaborolane (2.47 g, 9.72 mmol) and potassium acetate (2.6 g, 26.52 mmol) in DMSO (40 ml)

was stirred and degassed with N₂ for 15 minutes. Pddppf (194 mg, 0.26 mmol) was added. The mixture was heated at 100° C. for 3 hours. The mixture was poured onto water. EtOAc was added and the mixture was filtered through of pad of celite. The organic layer was separated, washed with water, then brine, dried over MgSO₄, filtered and evaporated to dryness. The crude product was taken-up with petrol ether, stirred at RT for 45 minutes, the precipitate was filtered and dried under vacuum, yielding 2.6 g (81%) of intermediate 6.

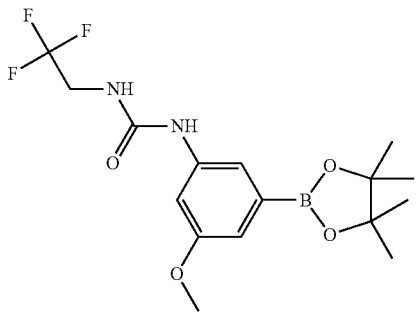 [SMILES: COc1cc(NC(=O)NCC(F)(F)F)cc(B2OC(C)(C)C(C)(C)O2)c1]

Intermediate 7 used in preparation Example B1b was made according to preparation Example 1.3.

Example 1.4 a) Preparation of Intermediate 8

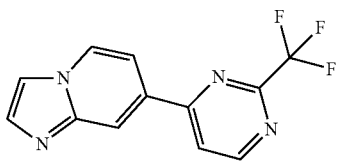 [SMILES: FC(F)(F)c1nccc(-c2ccn3ccnc3c2)n1]

A solution of 7-(4,4,5,5-tetramethyl-1,3,2-dioxaborolan-2-yl)imidazo[1,2-a]pyridine (12.1 g, 49.6 mmol), 4-chloro-2-(trifluoromethyl)pyrimidine (8.24 g, 45.1 mmol), Cs₂CO₃ (44.1 g, 135.4 mmol) in toluene (190 ml), 1-butanol (190 ml) and H₂O (50 ml) was degassed with N₂ for 20 minutes. Tetrakis(triphenylphosphine)palladium (7.8 g, 6.7 mmol) was added and the mixture was heated at 80° C. (bath at 85° C.) for 2 hours under N₂. The mixture was poured onto ice-water and filtered over a pad of celite which was rinced with EtOAc. The filtrate was extracted with EtOAc. The organic layer was washed with water (twice), dried over MgSO₄, filtered and evaporated to dryness. The crude product was taken up into Et₂O. The precipitate was filtered and dried, yielding 15.7 g (88%) of intermediate 8. MP=212° C. (kofler).

b) Preparation of Intermediate 9

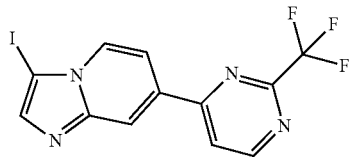 [SMILES: FC(F)(F)c1nccc(-c2ccn3c(I)cnc3c2)n1]

1-Iodo-2,5-pyrrolidinedione (6.06 g, 26.9 mmol) was added portionwise to a solution of intermediate 8 (5.93 g, 22.44 mmol) in DMF (60 ml) at RT. The reaction mixture was stirred at RT for 2 hours. The reaction mixture was poured onto ice water. The precipitate was filtered, washed with water, then Et₂O, and dried under vacuum, yielding 8.75 g (100%) of intermediate 9.

Example 1.5 a) Preparation of Intermediate 10

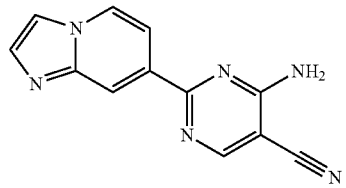 [SMILES: N#Cc1cnc(-c2ccn3ccnc3c2)nc1N]

4-Amino-2-chloro-5-pyrimidinecarbonitrile (5 g, 32.35 mmol) and 7-(4,4,5,5-tetramethyl-1,3,2-dioxaborolan-2-yl)imidazo[1,2-a]pyridine (9.48 g, 38.82 mmol) in dioxane (250 ml) were stirred under nitrogen. A solution of K₃PO₄ (13.73 g, 64.70 mmol) in H₂O was added and the mixture was degassed with vacuum /nitrogen (×3). Pddppf (1.18 g, 1.62 mmol) was added and then the mixture was degassed with vacuum/nitrogen (×3). The RM was heated for 2 hours at 80° C. The RM was cooled to RT and concentrated under vacuum. Acetone was added and the precipitate was filtered, washed with water, acetone, then Et₂O and dried yielding 6.8 g (89%) of intermediate 10.

b) Preparation of Intermediate 11

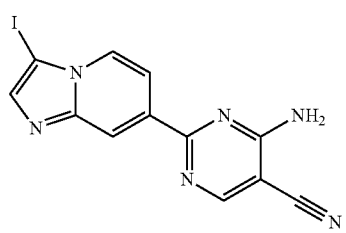 [SMILES: N#Cc1cnc(-c2ccn3c(I)cnc3c2)nc1N]

1-Iodo-2,5-pyrrolidinedione (2.86 g, 12.7 mmol) was added portionwise to a solution of intermediate 10 in CH₃CN at RT. The RM was stirred at RT for 2 hours and then refluxed overnight. The RM was filtered hot and the precipitate was washed with ACN, then Et₂O and dried under vacuum, yielding 3 g (98%) of intermediate 11.

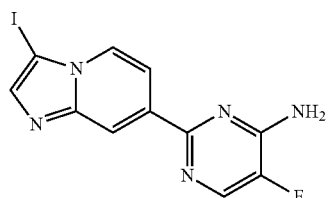

Intermediate 12 used in preparation Example B1b was made according to preparation Example 1.5.

Example 1.6 a) Preparation of Intermediate 13

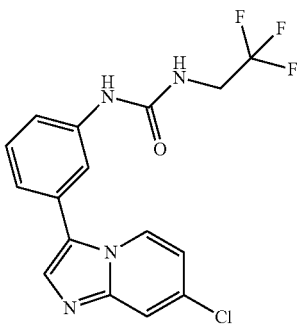 [SMILES: O=C(NCC(F)(F)F)Nc1cccc(-c2cnc3cc(Cl)ccn23)c1]

a-1) using a Heck Coupling

A mixture of 7-chloro imidazopyridine (5 g, 32.77 mmol), intermediate 3 (10.22 g, 34.41 mmol;), triphenylphosphine (1.72 g, 6.55 mmol;), cesium carbonate (21.35 g, 65.54 mmol), Palladium(II) acetate (0.74 g; 3.28 mmol) in DMF (70 ml) was stirred at RT under $N_2$ flow. After 10 minutes, the mixture was heated at 100° C. for 2 hours. The RM was cooled to RT and poured onto ice water. EtOAc was added and the mixture was filtered through a pad of celite which was washed with EtOAc. The filtrate was extracted with EtOAc, washed with brine, dried ($MgSO_4$), filtered and the solvent was evaporated.

The residue (15 g) was purified by silica gel chromatography on Irregular SiOH 20-45 µm 1000 g MATREX, Mobile phase (DCM/MeOH/$NH_4OH$: 97/3/0.1). The pure fractions were collected, and the solvent evaporated under reduced pressure.

The residue was triturated in $Et_2O$, filtered and dried under vacuum at 40° C., yielding 6.80 g (56%) of intermediate 13. MP=188° C., DSC.

a-2) using a Suzuki Coupling

A mixture of 3-iodo-7-chloro imidazopyridine (10 g; 35.9 mmol;), intermediate 4 (14.8 g, 43.1 mmol), potassium phosphate (15.2 g; 71.8 mmol) in water (51 ml) and dioxane (192 ml) was stirred at RT and degassed with a $N_2$ flow. After 30 minutes, Pddppf (1.31 g, 1.8 mmol) was added portionwise at RT under $N_2$ flow. The RM was heated at 80° C. overnight. The reaction was cooled to RT and poured onto ice-water. The aqueous layer was extracted with EtOAc, dried over $MgSO_4$, filtered and concentrated. The residue was purified by silica gel chromatography on Irregular SiOH 20-45 µm 1000 g MATREX, Mobile phase (DCM/MeOH/$NH_4OH$: 95/5/0.5). The pure fractions were collected, concentrated to afford, after drying, 13.3 g (100%) of intermediate 13.

b) Preparation of intermediate 14

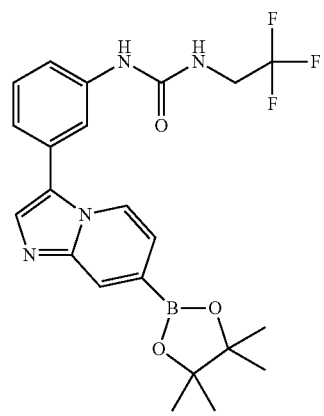 [SMILES: CC1(C)OB(c2ccn3c(-c4cccc(NC(=O)NCC(F)(F)F)c4)cnc3c2)OC1(C)C]

A mixture of intermediate 13 (3 g, 8.14 mmol), 4,4,4',4',5,5,5',5'-octamethyl-2,2'-bi-1,3,2-dioxaborolane [73183-34-3] (6.2 g, 24.41 mmol), tricyclohexylphosphine (0.91 g, 3.25 mmol), potassium acetate (3.19 g, 32.54 mmol) in dioxane (40 ml) was stirred at RT under a $N_2$ flow. After 10 minutes, tris(dibenzylideneacetone)-dipalladium (1.12 g, 1.22 mmol) was added portionwise at RT. The RM was heated at 90° C. overnight and then cooled to RT and poured onto ice water. EtOAc was added and the mixture was filtered through a pad of celite. The celite was washed with EtOAc, then the filtrate was extracted with EtOAc. The organic layer was washed with brine, dried ($MgSO_4$), filtered and the solvent was evaporated. The residue was taken up with DIPE, stirred overnight. The precipitate was filtered, dried under vacuum, yielding 3 g (80%) of intermediate 14.

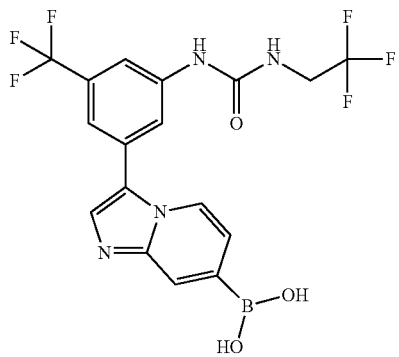 [SMILES: O=C(NCC(F)(F)F)Nc1cc(-c2cnc3cc(B(O)O)ccn23)cc(C(F)(F)F)c1]

Intermediate 15 used in preparation Example B5 was obtained in a reaction procedure similar to preparation Example 1.6.

Example 1.7 a) Preparation of Intermediate 16

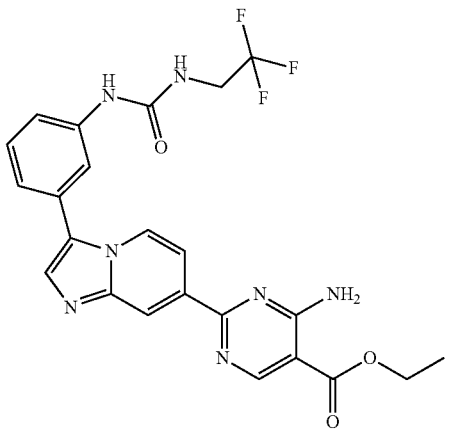 [SMILES: CCOC(=O)c1cnc(-c2ccn3c(-c4cccc(NC(=O)NCC(F)(F)F)c4)cnc3c2)nc1N]

Ethyl 4-amino-2-chloropyrimidinecarboxylic acid, ester (1.10 g, 5.43 mmol) and intermediate 14 (3 g, 6.52 mmol) in dioxane (125 ml) were stirred under nitrogen. A solution of $K_3PO_4$ (2.31 g, 10.86 mmol) in $H_2O$ (30 ml) was added and the mixture was degassed with vacuum/nitrogen (×3). Pddppf (198.72 mg, 0.27 mmol) was added and then the mixture was degassed with vacuum/nitrogen (×3). The RM was heated for 3 hours at 80° C., then cooled to RT, diluted with EtOAc and a 10% solution of $K_2CO_3$ was added. The organic layer was decanted, washed with brine, dried over $MgSO_4$, filtered and evaporated to dryness. The residue (5.4 g) was crystallized from $CH_2Cl_2$/MeOH. The precipitate was filtered off, washed with $CH_3CN$ and dried, yielding 1.9 g (70%) of intermediate 16.

b) Preparation of Intermediate 17

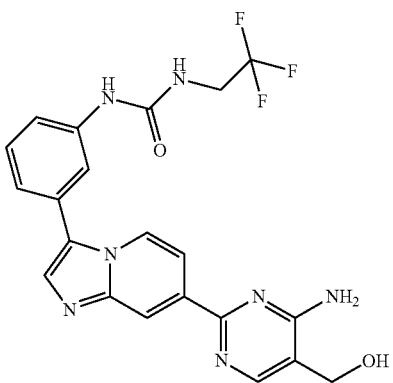 [SMILES: Nc1nc(-c2ccn3c(-c4cccc(NC(=O)NCC(F)(F)F)c4)cnc3c2)ncc1CO]

Lithium aluminium hydride solution 1M in THF (3.0 ml, 3.00 mmol) was added dropwise at RT to a suspension of intermediate 16 (500 mg, 1.00 mmol) in THF. The RM was stirred at RT for 3 hours. 0.25 ml of iced water was added with caution, followed by 0.25 ml of NaOH 3N and 0.75 ml of water. The salts were removed by filtration over a büchner and washed with EtOAc. The filtrate was evaporated to dryness. The residue was taken up with DCM/MeOH 90/10 and the precipitate was filtered off and dried, yielding 300 mg (65%) of intermediate 17.
MP=235° C.

c) Preparation of Intermediate 18

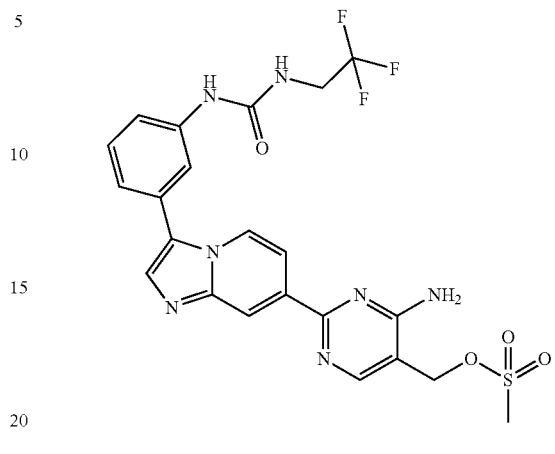

Methanesulfonyl chloride (166 µl, 2.15 mmol) was added dropwise at RT to a suspension of intermediate 17 (490 mg, 1.07 mmol) and N,N-diethylethanamine (312 µl, 2.25 mmol) in a 50/50 mixture of DCM/THF (20 ml). The RM was stirred at RT for 1 hour, and directly used in the next step without further work-up.

Example 1.8 a) Preparation of Intermediate 19

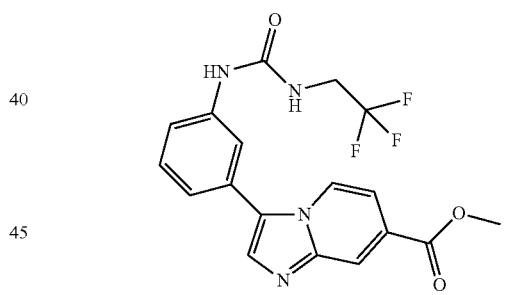

Methyl 3-iodo-imidazo[1,2-a]pyridine-7-carboxylic acid, ester and intermediate 4 (5.47 g, 15.89 mmol) in dioxane (136 ml) were stirred under nitrogen. A solution of $K_3PO_4$ (5.62 g, 26.48 mmol) in $H_2O$ (30 ml) was added and the mixture was degassed with vacuum/nitrogen (×3). Pddppf (484.47 mg, 0.66 mmol) was added and then the mixture was degassed with vacuum/nitrogen (×3). The RM was heated overnight at 80° C. under nitrogen. The RM was cooled to RT, diluted with DCM/MeOH and quenched with water. The organic layer was decanted, washed with brine, dried over $MgSO_4$, filtered and evaporated to dryness. The residue was purified by silica gel chromatography (90 g $SiO_2$ 15/40 µm, eluent: DCM/MeOH/$NH_4OH$ 100/0/0 to 96/4/0.1). The pure fractions were collected and the solvent was evaporated to dryness, yielding 4.17 g (80%) of intermediate 19.

b) Preparation of Intermediate 20

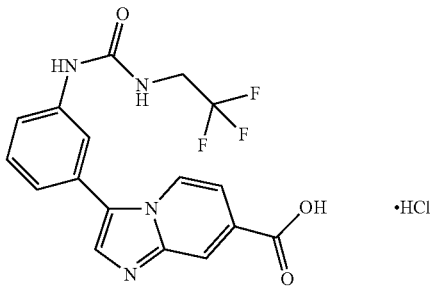 [SMILES: O=C(NCC(F)(F)F)Nc1cccc(-c2cnc3cc(C(=O)O)ccn23)c1 ; Cl]

Lithium hydroxide monohydrate (0.65 g, 15.52 mmol) was added to a solution of intermediate 19 (4.06 g, 10.35 mmol) in THF (83 ml) and H$_2$O (9 ml). The RM was stirred at RT overnight. HCl 3N was added and the RM was evaporated to dryness. The solid residue was taken up with water. The precipitate was filtered off, washed with Et$_2$O and dried under vacuum, yielding 3.91 g (100%) of intermediate 20. MP=222° C.

c) Preparation of Intermediate 21

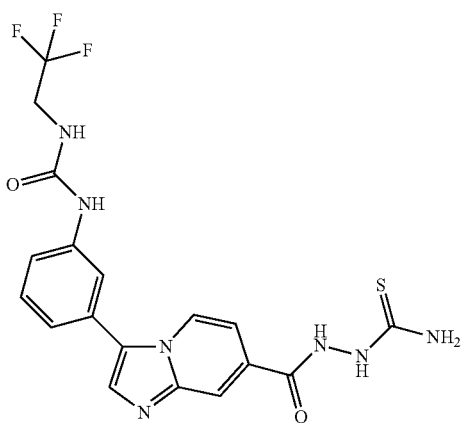 [SMILES: NC(=S)NNC(=O)c1ccn2c(-c3cccc(NC(=O)NCC(F)(F)F)c3)cnc2c1]

Intermediate 20 (0.5 g, 1.3 mmol), N,N-diethylethanamine (378 μl, 02.6 mmol), 1-[bis(dimethylamino)methylene]-1H-benzotriazoliumhexafluorophosphate(1-) 3-oxide (0.75 g, 1.98 mmol) and a 10/1 mixture of THF/DMF (20 ml) were mixed at RT. Then, thiosemicarbazide (0.24 g, 2.64 mmol) was added and the mixture was stirred for 4 hours. The reaction mixture was partitioned between DCM (50 ml) and water (30 ml). The organic layer was dried over MgSO$_4$, filtered and concentrated, yielding 0.8 g (>100%) of intermediate 21.

Example 1.9 a) Preparation of Intermediate 22

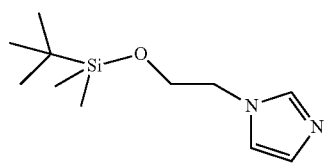

1H-Imidazole (1 g, 14.7 mmol) was dissolved in DMF (20 ml). Then, the solution was cooled down to 0° C. and sodium hydride (646 mg, 16.1 mmol) was added. After 30 minutes stirring, (2-bromoethoxy)(tert-butyl)dimethyl silane (4.2 g, 17.6 mmol) was added and the reaction was stirred overnight allowing the temperature to raise to RT. The RM was partitioned between water (100 ml) and EtOAc (200 ml). Then the organic layer was washed twice with a saturated NaCl solution (100 ml), dried over MgSO$_4$, filtered and concentrated. The residue was purified by silica gel chromatography (DCM/MeOH/NH$_4$OH: 100/0/0 to 95/5/0.5). The pure fractions were collected and the solvent was evaporated, yielding 3.03 g (86%) of intermediate 22.

b) Preparation of Intermediate 23

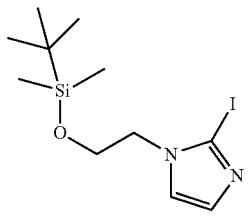 [SMILES: CC(C)(C)[Si](C)(C)OCCn1ccnc1I]

Intermediate 22 (1 g, 4.41 mmol), N,N,N',N'-tetramethylethylenediamine (1.68 ml, 11.02 mmol) were dissolved in THF (10 ml). The solution was cooled down to −78° C. and butyllithium 1.6M in hexane (6.9 ml, 11.0 mmol) was added dropwise. The RM was stirred for 1.5 hour allowing the temperature to raise to −30° C. Then, iodine (2.94 g, 11.5 mmol) in THF (10 ml) was added keeping the temperature below −30° C. The reaction was quenched with a 10% Na$_2$S$_2$O$_5$ aqueous solution and diluted with EtOAc (150 ml). The organic layer was washed with 10% Na$_2$S$_2$O$_5$ aqueous solution (100 ml) and water (100 ml), then dried over MgSO$_4$, filtered and concentrated. The residue was purified by silica gel chromatograpy (Cyclohexane/EtOAc:5/5). The pure fractions were collected and the solvent was evaporated, yielding 0.8 g (51%) of intermediate 23.

c) Preparation of Intermediate 24

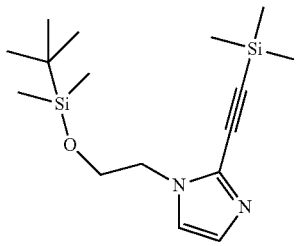 [SMILES: CC(C)(C)[Si](C)(C)OCCn1ccnc1C#C[Si](C)(C)C]

To a mixture of intermediate 23 (0.8 g, 2.27 mmol) N,N-diethylethanamine (6.3 ml, 45.4 mmol), CuI (44 mg, 0.23 mmol), dichlorobis(triphenylphosphine)palladium (160 mg, 0.23 mmol) and THF (4 ml) previously degassed under vacuum and refilled with $N_2$, was added trimethylsilylacetylene (1.65 ml, 11.3 mmol). The RM was stirred at RT overnight, filtered over a pad of celite and the filtrate was diluted with EtOAc (200 ml). The organic layer was washed several times with a saturated aqueous $NH_4Cl$ solution (5×50 ml until pH=7), dried over $MgSO_4$, filtered and concentrated. The residue was purified by silica gel chromatography (EtOAc/cyclohexane:2/8 to 4/6). The pure fractions were collected and the solvent was evaporated, yielding 0.138 g (23%) of intermediate 24.

d) Preparation of Intermediate 25

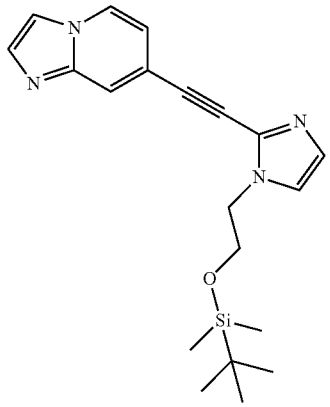 [SMILES: CC(C)(C)[Si](C)(C)OCCn1ccnc1C#Cc1ccn2ccnc2c1]

7-Chloro-imidazo[1,2-a]pyridine (63 mg, 0.41 mmol), intermediate 24 (146 mg, 0.4 mmol), $Cs_2CO_3$ (134 mg, 0.41 mmol), 1,8-diazabicyclo[5.4.0]undec-7-ene (7 µl, 0.07 mmol) in DMF (1.1 ml) were introduced in a tube. The mixture was degassed with $N_2$ and dichlorobis(triphenylphosphine)palladium (6 mg, 0.008 mmol) and tri-tert-butylphosphine (5 µl, 0.016 mmol) were quickly introduced. The mixture was degassed again with $N_2$. Then, it was heated at 150° C. in a microwave for 12 minutes. The RM was partitioned between EtOAc (50 ml) and water (25 ml). The organic layer was washed with brine (25 ml), dried over $MgSO_4$, filtered and concentrated, yielding 0.16 g (>100%) of intermediate 25, used in the next without further purification.

e) Preparation of Intermediate 26

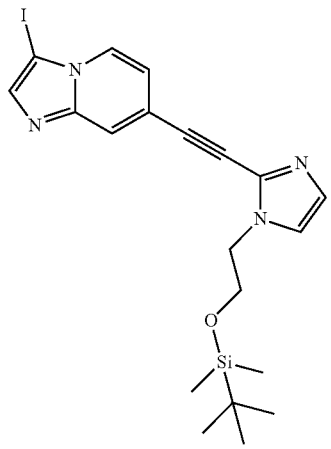 [SMILES: CC(C)(C)[Si](C)(C)OCCn1ccnc1C#Cc1ccn2c(I)cnc2c1]

N-iodosuccinimide (0.1 g, 0.45 mmol) was added portionwise to intermediate 25 (0.15 g, 0.41 mmol) in DMF (2 ml) at RT. The RM was stirred for 5 hours at RT. Then, additional N-iodosuccinimide (48 mg, 0.21 mmol) was added and the RM was stirred overnight at RT. Water (50 ml) and EtOAc (100 ml) were added to the mixture. After decantation, the organic layer was washed with brine (50 ml), then dried over $MgSO_4$, filtered and concentrated, yielding 0.23 g (>100%) of intermediate 26, used in the next step without further purification.

f) Preparation of Intermediate 27

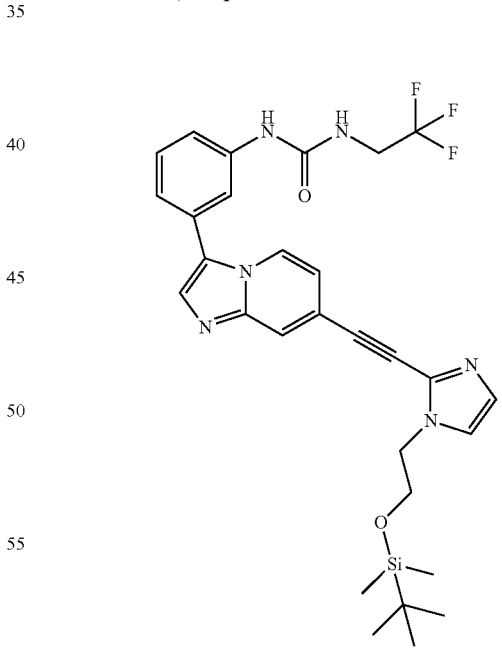

A solution of intermediate 26 (210 mg, 0.43 mmol), intermediate 4 (176.11 mg, 0.51 mmol) and $K_3PO_4$ (181.05 mg, 0.85 mmol) in dioxane (11.7 ml) and $H_2O$ (3 ml) was degassed for few minutes with nitrogen. Then Pddppf (34.81 mg, 0.043 mmol) was added. The RM was heated to 80° C. for 5 hours. Then the RM was partitioned between water (50 ml) and EtOAc (100 ml). The organic layer was dried over MgSO₄, filtered and concentrated, yielding 0.35 g (>100%) of intermediate 27, used in the next step without further purification.

Example 1.10 a) Preparation of Intermediate 28

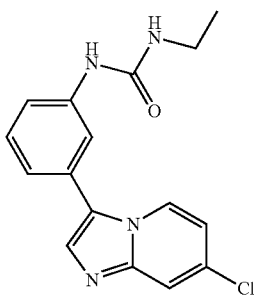 [SMILES: CCNC(=O)Nc1cccc(-c2cnc3cc(Cl)ccn23)c1]

A mixture of 7-chloro-imidazo[1,2-a]pyridine (1.5 g, 8.06 mmol), N-(3-bromophenyl)-N'-ethyl-urea (2.25 g, 9.27 mmol) and Cs₂CO₃ (5.25 g, 16.12 mmol) in DMSO (20 ml) was deoxygenated by evacuation/refill with N₂ (×3). Triphenylphosphine (422.88 mg, 1.61 mmol) and palladium (II) acetate 47% Pd (180.98 mg, 0.81 mmol) were added and the mixture was deoxygenated again (×3) then stirred and heated at 100° C. for 4 hours. The RM was cooled to RT and poured onto ice water. The RM was stirred for 1 hour and the precipitate was filtered off. The residue was dissolved in DCM/MeOH. The organic layer was dried over MgSO₄, filtered and evaporated to dryness. The residue was purified by silica gel chromatography (90 g SiO₂ 15/40 μm, eluent: DCM/MeOH/NH₄OH 100/0/0 to 95/5/0.5). The pure fractions were collected and evaporated to dryness yielding 1.8 g (71%) of intermediate 28.

b) Preparation of Intermediate 29

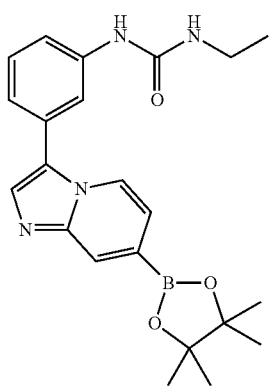 [SMILES: CCNC(=O)Nc1cccc(-c2cnc3cc(B4OC(C)(C)C(C)(C)O4)ccn23)c1]

A mixture of intermediate 28 (1.9 g, 6.04 mmol), 4,4,4',4',5,5,5',5'-octamethyl-2,2'-bi-1,3,2-dioxaborolane (4.6 g, 18.11 mmol), potassium acetate (2.37 g, 24.14 mmol) in dioxane (20 ml) was stirred at RT and degassed for 15 minutes under a N₂ flow. Tricyclohexylphosphine (677 mg, 2.41 mmol) then tris(dibenzylideneacetone)dipalladium (829 mg, 0.90 mmol) were added at RT. The RM was heated at 90° C. overnight, cooled to RT and poured onto ice water. EtOAc was added and the mixture was filtered through a pad of celite, which was washed with EtOAc. The organic and the aqueous layers were separated. The aqueous layer was extracted with EtOAc. The organic layers were combined, washed with brine, dried (MgSO₄), filtered and the solvent was evaporated. The residue was triturated with DIPE, filtered and dried, yielding 990 mg (40%) of intermediate 29.

c) Preparation of Intermediate

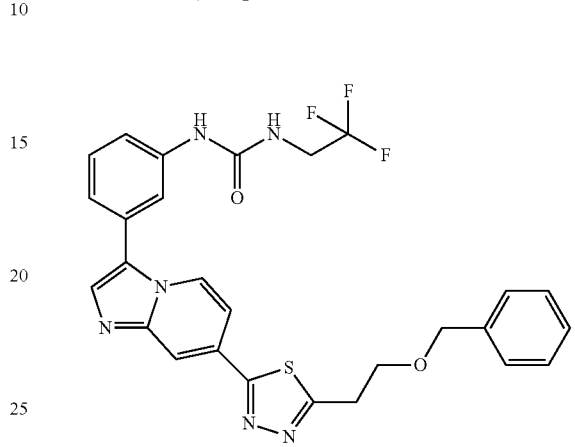

A solution of intermediate 14 (1 g, 2.17 mmol), intermediate 42 (1.3 g, 4.34 mmol), Cs₂CO₃ (2.12 g, 6.52 mmol) in toluene (20 ml), 1-butanol (5 ml) and H₂O (20 ml) were degassed with N₂ for 20 minutes. Tetrakis(triphenylphosphine)palladium (0.75 g, 0.65 mmol) was added and the mixture was heated at 80° C. for 20 hours under N₂. The mixture was poured onto H₂O and extracted with EtOAc. The organic layer was dried over MgSO₄, filtered and evaporated to dryness. The residue was purified by silica gel chromatography Irregular SiOH 20-45 μm 450 g MATREX, Mobile phase (DCM/MeOH/NH₄OH 96/4/0.1). The pure fractions were collected and the solvent was evaporated, yielding 0.645 g (54%) of intermediate 30.

Example 1.11 a) Preparation of Intermediate 31

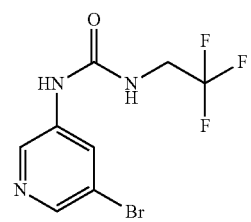 [SMILES: O=C(NCC(F)(F)F)Nc1cncc(Br)c1]

A mixture of 5-bromo-3-pyridinamine (2 g, 0.012 mol) and 4-nitrophenyl chloroformate (3.03 g, 0.015 mol) in THF (20 ml) was heated at 60° C. for 2 hours. The mixture was cooled to RT and 2,2,2-trifluoro-ethanamine (1.02 ml, 0.013 mol) then N-ethyl-N-(1-methylethyl)-2-propanamine (5.73 ml, 0.035 mol) were added. The mixture was stirred at RT for 1 hour. The mixture was poured onto 2N NaO and extracted with DCM. The organic layer was washed with water and brine, dried over MgSO₄, filtered and evaporated till dryness.

The residue was crystallized from Et$_2$O, yielding 2.64 g (76%) of intermediate 31. MP 188° C. (Kofler).

b) Preparation of Intermediate 32

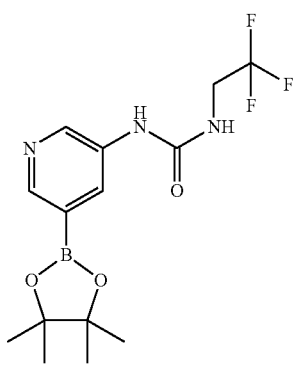 [SMILES: CC1(C)OB(c2cncc(NC(=O)NCC(F)(F)F)c2)OC1(C)C]

A mixture of intermediate 31 (1.58 g, 5.3 mmol), 4,4,4',4',5,5,5',5'-octamethyl-2,2'-bi-1,3,2-dioxaborolane (2.69 g, 10.6 mmol), potassium acetate (1.56 g, 15.9 mmol) in DMSO (13.6 ml) was stirred at RT under a N$_2$ flow (bubbling). After 30 minutes, Pddppf (388 mg, 0.53 mmol) was added and the mixture was heated at 80° C. for 16 hours. The RM was cooled to RT, diluted with EtOAc (200 ml) and poured onto water (150 ml). The mixture was filtered through a pad of celite (the celite was washed with EtOAc). After decantation and separation, the organic layer was washed with a saturated NaCl solution (2×150 ml) and water 1×150 ml). The organic layer was dried over MgSO$_4$, filtered and concentrated. This residue was triturated with a 50/50 mixture of Et$_2$O/petroleum ether, yielding 1.4 g (77%) of intermediate 32.

c) Preparation of Intermediate 33

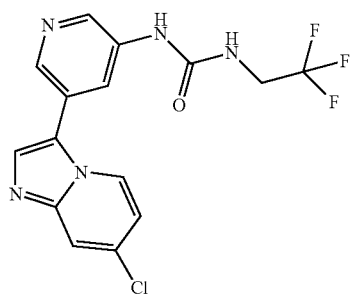 [SMILES: O=C(NCC(F)(F)F)Nc1cncc(-c2cnc3cc(Cl)ccn23)c1]

K$_3$PO$_4$ (1.06 g, 4.98 mmol) was dissolved in H$_2$O (3.9 ml). The resulting solution was added to intermediate 32 (1.29 g; 3.74 mmol) and 7-chloro-3-iodo-imidazo[1,2-a]pyridine (0.69 g ; 2.49 mmol) in dioxane (14.2 ml) under N$_2$ flow. The resulting mixture was degassed with N$_2$ for 30 minutes. Then, Pddppf (0.091 g, 0.00012 mol) was added and the RM was heated at 80° C. overnight under N$_2$ flow. The RM was poured onto ice water and extracted with EtOAc. The organic layer was washed twice with a saturated aqueous NaCl solution, then dried over MgSO$_4$, filtered and evaporated till dryness. The residue was purified by flash chromatography over silica gel (15-40 μm, 90 g, DCM/MeOH/NH$_4$OH: 100/0/0 to 85/15/0.5) The pure fractions were collected and evaporated to dryness, yielding 0.82 g (89%) of intermediate 33.

Example 1.12 a) Preparation of Intermediate 34

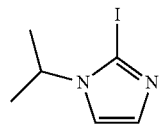

1-(1-methylethyl)-1H-imidazole (330 mg, 3.00 mmol) was dissolved in THF (2,5 ml) at RT and the resulting solution was cooled down to −78° C. Butyllithium 1.6 M in hexane (1.87 ml, 3.00 mmol) was added dropwise. After completion of the addition, the temperature was increased to 0° C. and the RM was stirred at this temperature for 5 minutes. Then, the RM was cooled at −78° C. and a solution of iodine (844.81 mg, 3.30 mmol) in THF (5 ml) was added dropwise. Again, the temperature was increased to 0° C. and the RM was stirred for 20 minutes at this temperature followed by quenching with a 10% solution of Na$_2$S$_2$O$_3$. The RM was extracted with DCM. The organic layer was washed with water, dried over MgSO$_4$, filtered and concentrated, yielding 500 mg (71%) of intermediate 34.

b) Preparation of Intermediate 35

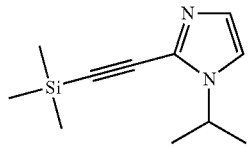

Trimethylsilylacetylene (4.46 ml, 31.35 mmol) was added to a mixture of intermediate 34 (1.48 g, 6.27 mmol), N,N-diethylethanamine (17.45 ml, 125.40 mmol), dichlorobis (triphenylphosphine)palladium (440.08 mg, 0.63 mmol) and CuI (119.41 mg, 0.63 mmol) in THF (11 ml) previously degassed under vacuum and refilled with N$_2$. The mixture was stirred at RT overnight. The RM was filtered and the salts were washed with Et$_2$O. The filtrate was evaporated to dryness. The residue was taken up with Et$_2$O, the salts were filtered again, and the filtrate evaporated, yielding 2 g of intermediate 35, which was used in the next step without further purification.

Example 1.13 a) Preparation of Intermediate 36

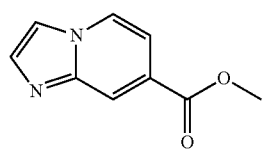

Methyl 2-amino-4-pyridinecarboxylic acid, ester (20 g, 131.5 mmol), 2-chloroacetaldehyde 50% wt solution in water (22.5 ml, 197.2 mmol), $NaH_2CO_3$ (22.1 g, 262.9 mmol) in EtOH (200 ml) were stirred at 80° C. for 4 hours under nitrogen. After cooling down to RT, water was added and EtOH was evaporated. The residue was extracted twice from DCM. The organic layer was dried over $MgSO_4$, filtered and evaporated, yielding 20.9 g of intermediate 36. The crude product was used in the next step without further purification.

b) Preparation of Intermediate 37

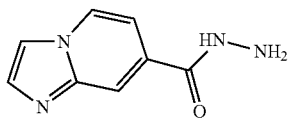 [SMILES: NNC(=O)c1ccn2ccnc2c1]

Hydrazine monohydrate (20.3 ml, 65.3 mmol) was added to a solution of intermediate 36 (11.5 g, 65.28 mmol) in MeOH (300 ml). The mixture was refluxed for 3 hours then hydrazine monohydrate (10 ml, 454 mmol) was added and the mixture was stirred at reflux overnight. After cooling down to RT, the precipitate was filtered off, washed with a few EtOH and dried, yielding 7.2 g (63%) of intermediate 37, used in the next step without further purification.

c) Preparation of Intermediate 38

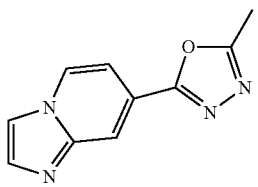

Intermediate 37 (7,2 g; 40.87 mmol) and $H_2SO_4$ (0.23 ml) in 1,1,1-triethoxyethane (202 ml) were heated at 80° C. overnight. After cooling down to RT, the precipitate was filtered off, washed with EtOH and dried to afford solid 1. Water and DCM were added to the filtrate and the organic layer was washed with water, dried over $MgSO_4$, filtered and concentrated to afford solid 2. Solids 1 and 2 were mixed, taken up in EtOH (the minimum) and filtered to afford 7.2 g (88%) of intermediate 38. Concentration of the filtrate followed by another filtration gave an additional amount of 0.92 g (11%) of intermediate 38.

d) Preparation of Intermediate 39

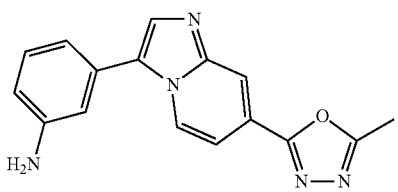 [SMILES: Cc1nnc(-c2ccn3c(-c4cccc(N)c4)cnc3c2)o1]

A mixture of intermediate 38 (3.5 g, 14.34 mmol), 3-iodobenzenamine (1.7 ml, 14.34 mmol) and $Cs_2CO_3$ (9.34 g, 28.67 mmol) in DMSO (20 ml) was desoxygenated by evacuation/refill with $N_2$ (×3). Triphenylphoshpine (0.75 g, 2.87 mmol) and palladium (II) acetate 47% Pd (0.3 g, 1.43 mmol) were added and the mixture was desoxygenated again (×3) then stirred and heated at 100° C. for 4 hours. Water and EtOAc were added and the mixture was filtered over a pad of celite which was washed with DCM. The organic layer was washed with water, dried over $MgSO_4$, filtered and evaporated, yielding 540 mg (13%) of intermediate 39, directly used in the next step without further purification.

Example 1.14 a) Preparation of Intermediate 40

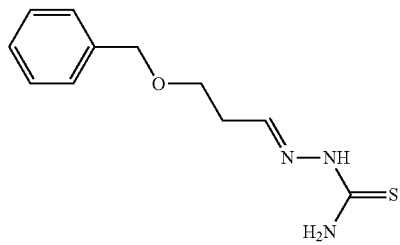 [SMILES: NC(=S)N/N=C/CCOCc1ccccc1]

A mixture of 3-(phenylmethoxy)propanal (4.5 g, 27.40 mmol) and thiosemicarbazide (2.48 g, 27.40 mmol) in EtOH (50 ml) was refluxed for 2 hours. The mixture was evaporated until dryness. The residue was crystallized from DIPE. The precipitate was filtered off and dried, yielding 5.4 g (83%) of intermediate 40.

b) Preparation of Intermediate 41

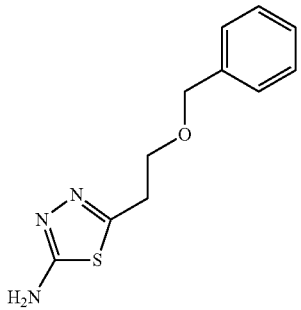 [SMILES: Nc1nnc(CCOCc2ccccc2)s1]

$FeCl_3$ (18.62 ml, 68.26 mmol) was added dropwise to a solution of intermediate 40 (5.4 g, 22.75 mmol) in $H_2O$ (60 ml). The mixture was heated at 90° C. for 2 hours. The mixture was evaporated until dryness and the residue was treated with an aqueous solution of $NH_4OH$. The mixture was extracted with DCM. An insoluble was filtered off. The organic layer was separated, dried over $MgSO_4$, filtered, and the solvent was evaporated, yielding 3.9 g (73%) of intermediate 41.

c) Preparation of Intermediate 42

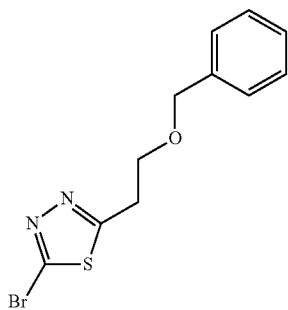 [SMILES: Brc1nnc(CCOCc2ccccc2)s1]

HBr (34 ml) was added to a solution of intermediate 41 (3.4 g, 14.45 mmol) in H₂O (34 ml). The mixture was cooled to 0° C. and CuHBr (0.21 g, 1.44 mmol) was added. A solution of NaNO₂ (1.0 g 14.45 mmol) in H₂O (34 ml) was added dropwise. The mixture was stirred for 10 minutes at 5° C. and was allowed to reach RT. The mixture was stirred at RT for 2 hours. The solution was poured onto H₂O, basified with K₂CO₃ (until the pH of the mixture reached 8) and extracted with DCM. The organic layer was separated, dried over MgSO₄, filtered and evaporated to dryness. The residue (5.4 g) was purified by silica gel chromatography (SiO₂ 15-40 μm DCM 100%). The pure fractions were collected and the solvent was evaporated, yielding 2.9 g (67%) of intermediate 42.

Example 1.15

Preparation of Intermediate 44

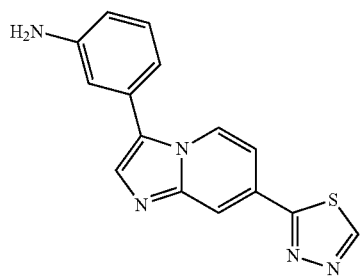 [SMILES: Nc1cccc(-c2cnc3cc(-c4nncs4)ccn23)c1]

HCl (50 ml) was added dropwise to a solution of intermediate 43

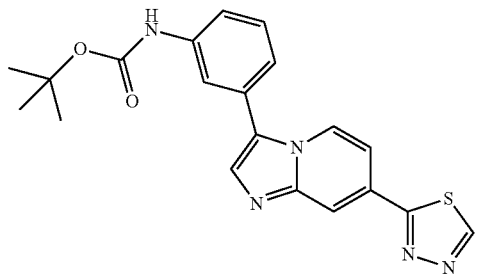 [SMILES: CC(C)(C)OC(=O)Nc1cccc(-c2cnc3cc(-c4nncs4)ccn23)c1]

(1.96 g, 4.98 mmol) (was prepared according to a reaction procedure similar to Example B1a) in MeOH (50 ml). The mixture was stirred at 50° C. for 2 hours. The solution was cooled to RT, poured onto H₂O, basified with 10% aqueous solution of K₂CO₃ and extracted with DCM. The organic layer was separated, dried over MgSO₄, filtered and evaporated to dryness. The residue was taken up with DIPE/EtOAc, filtered and dried under vacuum yielding 1.1 g (75%) of intermediate 44.

Example 1.16 a) Preparation of Intermediate 45

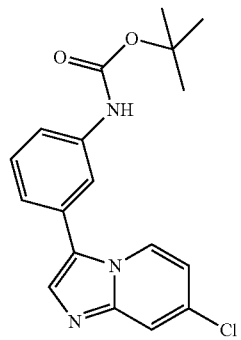 [SMILES: CC(C)(C)OC(=O)Nc1cccc(-c2cnc3cc(Cl)ccn23)c1]

A mixture of 7-chloro-imidazo[1,2-a]pyridine (200 mg, 1.08 mmol), 1,1-dimethylethyl N-(3-iodophenyl)carbamic acid, ester (0.40 g, 1.24 mmol) and Cs₂CO₃ (0.7 g, 2.15 mmol) in DMSO (2.5 ml) was deoxygenated by evacuation /refill with N₂ (×3). Triphenylphosphine (56.38 mg, 0.22 mmol) and palladium (II) acetate 47% Pd were added and the mixture was deoxygenated again (×3), then stirred and heated at 100° C. in a sealed tube for 4 hours. The RM was cooled to RT and poured onto water. The precipitate was filtered and washed several times with water, then dissolved in EtOAc. The organic layer was dried over MgSO₄, filtered and evaporated to dryness. The residue (480 mg) was purified by silica gel chromatography (30 g SiO₂ 15/40 μm—eluent: DCM/MeOH/NH₄OH 97/3/0.3). The pure fractions were collected and evaporated to dryness, yielding 255 mg (69%) of intermediate 45.

b) Preparation of Intermediate 46

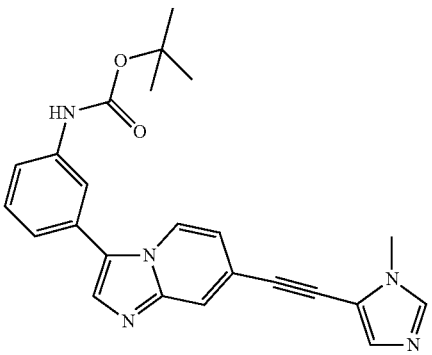 [SMILES: Cn1cncc1C#Cc1ccn2c(-c3cccc(NC(=O)OC(C)(C)C)c3)cnc2c1]

Intermediate 45 (3.2 g, 9.3 mmol), 5-ethynyl-1-methyl-1H-imidazole (4.94 g, 46.5 mmol), Cs₂CO₃ (6.06 g, 2.90 mmol), palladium(11)cloride (0.17 mg, 0.93 mmol), tricylcohexylphosphine (0.52 mg, 1.86 mmol) and DMSO (29 ml)

were mixed together and the mixture was degassed 5 times under vacuum. Then, the mixture was heated for 2 hours at 100° C. The RM was partitioned between water (150 ml) and EtOAc (150 ml) and the resulting suspension was filtered over a pad of celite. The organic layer was washed with aqueous saturated NaCl solution (150 ml), dried over MgSO$_4$, filtered and concentrated. The residue was purified by silica gel chromatography (200 g SiO$_2$ 15/40) (DCM/MeOH/NH$_4$OH: 100/0/0 to 98/2/0.2 in 10 minutes then 98/2/0.2 for 5 minutes then 97/3/0.3 in 5 minutes and 7/3/0.3 for 20 minutes). The desired fraction was collected and the solvent was evaporated, yielding 1.1 g (29%) of intermediate 46.

c) Preparation of Intermediate 47

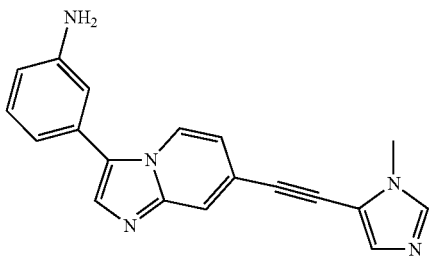 [SMILES: Cn1cncc1C#Cc1ccn2c(-c3cccc(N)c3)cnc2c1]

HCl (1.1 g, 2.66 mmol) was added dropwise to a solution of intermediate 46 (3 ml) in MeOH (11 ml), and the RM was stirred at 50° C. for 2 hours. The RM was cooled to RT, diluted with DCM and quenched with a 10% solution of K$_2$CO$_3$ at 0° C. The organic layer was decanted, dried over MgSO$_4$, filtered and evaporated to dryness, yielding 0.78 g (93%) of intermediate 47.

d) Preparation of Intermediate 48

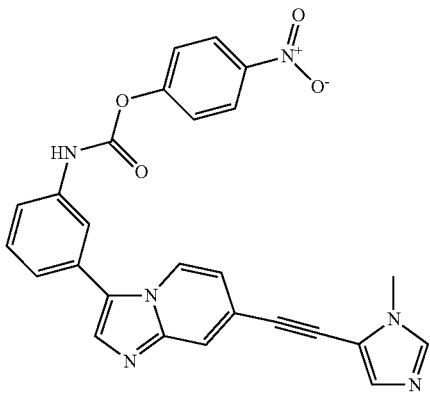 [SMILES: Cn1cncc1C#Cc1ccn2c(-c3cccc(NC(=O)Oc4ccc([N+](=O)[O-])cc4)c3)cnc2c1]

A mixture of intermediate 47 (0.75 g, 2.39 mmol) and 4-nitrophenylchloroformate (0.48 g, 2.39 mmol) in THF (37.5 ml) was heated at 60° C. for 2 hours and allowed to cool to RT for 5 hours. The precipitate was filtered, washed with THF then Et$_2$O and dried under vacuum, yielding 1.1 g (99%) of intermediate 48.

Preparation of the Final Compounds

Example 2.1 a 1) Preparation of compound 250

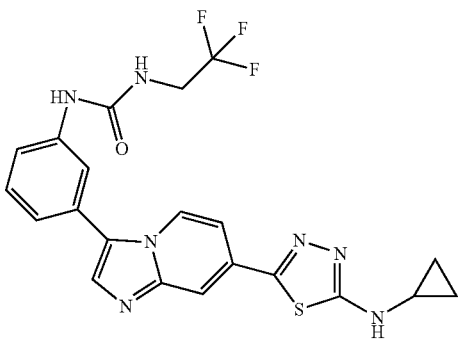 [SMILES: O=C(NCC(F)(F)F)Nc1cccc(-c2cnc3cc(-c4nnc(NC5CC5)s4)ccn23)c1]

A solution of intermediate 2 (1.1 g, 2.87 mmol), intermediate 4 (1.18 g, 3.44 mmol), K$_3$PO$_4$ (1.22 g, 5.74 mmol) in dioxane (75 ml) and H$_2$O (20 ml) was degassed for a few minutes with nitrogen. Then Pddppf (0.12 g, 0.14 mmol) was added. The RM was heated to 80° C. for 4 hours. The RM was concentrated under vacuum. The precipitate was taken up with a 10% aqueous solution of K$_2$CO$_3$, then washed with MeOH and air dried. The residue was purified by silica gel chromatography (Irregular SiOH 15-40 µm 300 g MERCK, Mobile phase (DCM/MeOH/NH$_4$OH 93/7/0.5). The pure fractions were collected and the solvent was evaporated to dryness. The residue was taken up with ACN, then the precipitate was filtered off and dried, yielding 177 mg (13%) of compound 250. MP>280° C. (kofler).

a 2) Preparation of Compound 251

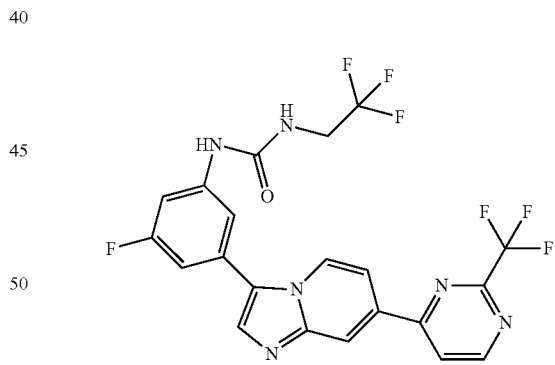

A solution of intermediate 9 (400 mg, 1.02 mmol), intermediate 6 (412 mg, 1.14 mmol) and K$_3$PO$_4$ (484 mg, 2.28 mmol) in dioxane (25 ml) and H$_2$O (5 ml) was degassed for 15 minutes with nitrogen. Then Pddppf (93 mg, 0.11 mmol) was added. The RM was heated to 80° C. for 2 hours. The mixture was cooled to RT, water and EtOAc were added. It was then filtered throught a pad of celite. The filtrate was extracted with EtOAc, washed with brine, dried over MgSO$_4$, filtered and evaporated to dryness. The residue was purified by achiral super critical fluid chromatography on AMINO 6 µm 150× 21.2 mm, Mobile phase (0.3% isopropylamine, 60% CO$_2$, 40% MeOH). The pure fractions were collected and the solvent was evaporated. The residue was crystallized from DIPE and the yellow precipitate was filtered, dried under vacuum, yielding 111 mg (19%) of compound 251. MP=263° C. (DSC).

1:21 Preparation of Compound 252

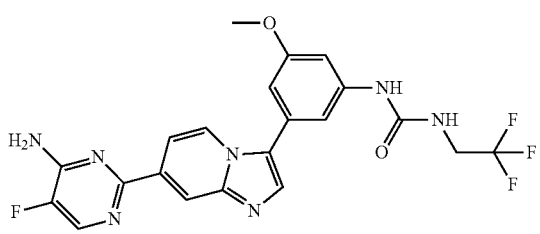 [SMILES: COc1cc(NC(=O)NCC(F)(F)F)cc(-c2cnc3cc(-c4ncc(F)c(N)n4)ccn23)c1]

A solution of intermediate 12 (400 mg; 1.13 mmol), intermediate 7 (548 mg; 1.46 mmol) in dioxane (15 ml) was degassed by bubbling $N_2$ through. $K_3PO_4$ (478 mg; 2.25 mmol), Pddppf (19 mg, 0.022 mmol), $H_2O$ (5 ml) and EtOH (2 ml) were added under $N_2$ flow. The mixture was heated at 80° C. for 5 hours. The solution was poured onto ice-water and filtered over a pad of celite. The product was extracted with EtOAc. The organic layer was dried over $MgSO_4$ and evaporated to dryness. The crude product was crystallized from DCM to give a crude product 1. The filtrate was evaporated to give a crude product 2. Both product 1 and 2 were purified by Normal phase on Irregular SiOH 15-40 µm 300 g MERCK, Mobile phase (0.5% $NH_4OH$, 97% DCM, 3% MeOH). The pure fraction was collected and the solvent was evaporated, yielding 35 mg (7%) of compound 252. MP=154° C. (DSC).

Example 2.2 a) Preparation of Compound 253

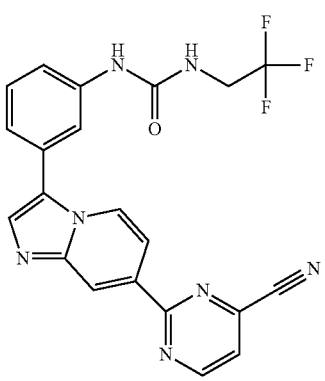 [SMILES: N#Cc1ccnc(-c2ccn3c(-c4cccc(NC(=O)NCC(F)(F)F)c4)cnc3c2)n1]

A mixture of intermediate 14 (0.8 g, 1.74 mmol), 2-chloro-4-pyrimidinecarbonitrile (0.48 g, 3.48 mmol), $Na_2CO_3$ (4 ml) in 1,2-dimethoxyethane (15 ml) was stirred at RT and degassed with $N_2$ for 30 minutes. Tetrakis(triphenylphosphine)palladium (0.15 g, 0.13 mmol) was added and the mixture was heated at 130° C. for 30 minutes. The reaction was performed in a microwave device (Biotage 60). The mixture was poured onto water and filtered through a pad of celite. The organic layer was extracted with DCM, separated, dried, filtered, concentrated to dryness and purified by Normal phase on (Cartridge 15-40 µm 30 g). Mobile phase (0.5% $NH_4OH$, 96% DCM, 4% MeOH). The desired fraction was collected and the solvent was evaporated. The residue was crystallized from DIPE, the precipitate was filtered, dried under vacuum, yielding 0.149 g (20%) of compound 253. MP=210° C. (kofler).

b) Preparation of Compound 165B

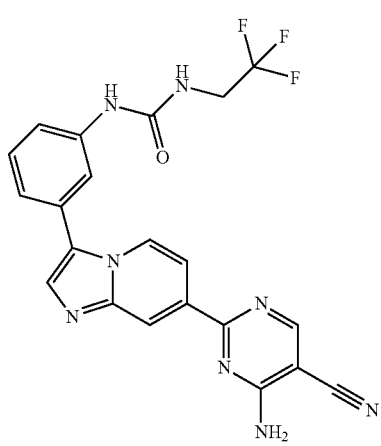 [SMILES: N#Cc1cnc(-c2ccn3c(-c4cccc(NC(=O)NCC(F)(F)F)c4)cnc3c2)nc1N]

Intermediate 14 (1 g, 2.17 mmol), 4-amino-2-chloro-5-pyridinecarbonitrile (0.5 g, 3.26 mmol) and sodium carbonate (2.3 g, 21.7 mmol) were diluted in DME (20 ml) and water (10 ml). The resulting mixture was degassed under a $N_2$ flow for 10 minutes. Then, tetrakis(triphenylphosphine)palladium (0.25 g, 0.22 mmol) was added and the RM was heated at 80° C. for 4 hours. Then, it was cooled to RT. Water was added and DME was concentrated. The insoluble was filtered, washed with water and poured onto DCM. The precipitate was then stirred for 3 hours, filtered and the filtrate was evaporated to dryness. The resulting residue was poured onto DCM/MeOH (8/2), stirred for 2 hours. The precipitate was filtered, dried and purified by Reverse phase on X-Terra-C18 10 µm 19×150 mm, Mobile phase (Gradient from 20% $NH_4HCO_3$ 0.5% (pH 10), 80% ACN to 0% $NH_4HCO_3$ 0.5% (pH 10), 100% ACN). The desired fraction was collected and the solvent was evaporated. The residue was crystallized from $Et_2O$, the precipitate was filtered and dried under vacuum, yielding 0.052 g of compound 165B. MP=161° C. (DSC).

Example 2.3 a) Preparation of Compound 255

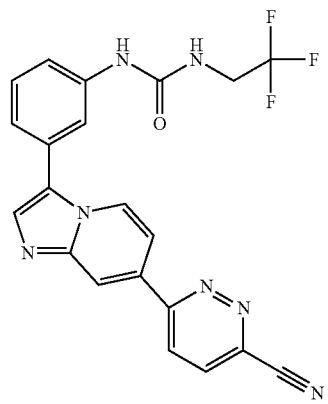 [SMILES: N#Cc1ccc(-c2ccn3c(-c4cccc(NC(=O)NCC(F)(F)F)c4)cnc3c2)nn1]

A mixture of 6-chloro-3-pyridazinecarbonitrile (211 mg, 1.43 mmol), intermediate 14 (858 mg, 1.86 mmol), K$_3$PO$_4$ (455 mg, 2.15 mmol), dicyclohexyl(2',6'-dimethoxy-[1,1'-biphenyl]-2-yl)phosphine (294 mg, 0.72 mmol) in toluene (10 ml) and EtOH (3 ml) was stirred at RT under a N$_2$ flow. After 10 minutes, palladium(II) acetate 47% Pd (97 mg, 0.43 mmol) was added portionwise. Then the mixture was heated at 80° C. for 5 hours. The solution was poured onto ice water and DCM was added. The mixture was filtered through a pad of celite. The filtrate was extracted with DCM, the organic layer was dried over MgSO$_4$, filtered and evaporated to dryness. The residue was purified by Normal phase on Irregular SiOH 15-40 μm 300 g MERCK, Mobile phase (0.5% NH$_4$OH, 93% DCM, 7% MeOH). The pure fractions were collected and the solvent was evaporated. The residue was further purified by achiral super critical fluid chromatography on 2 ethylpyridine 6 μm 150×21.2 mm, Mobile phase (0.3% isopropylamine, 80% CO$_2$, 20% EtOH). The desired fraction was collected and the solvent was evaporated. The residue was crystallized from Et$_2$O, yielding 33 mg (5%) of compound 255. MP=267° C.

b) Preparation of compound 256

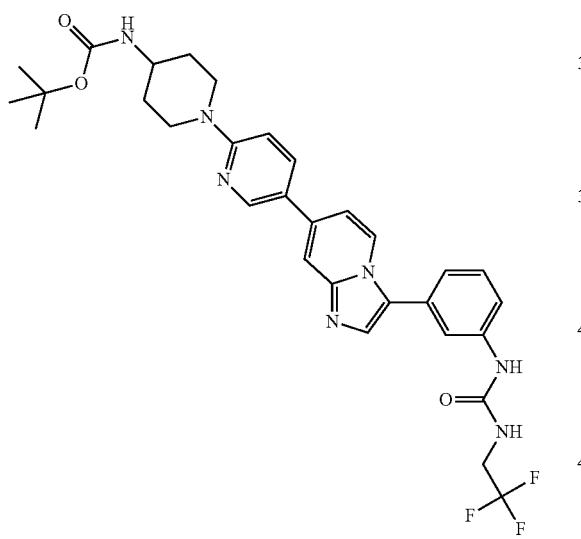

A mixture of 1,1-dimethylethyl N-[1-(5-bromo-2-pyridinyl)-4-piperidinyl]carbamic acid, ester [(480 mg; 1.35 mmol), intermediate 14 (930 mg; 2.02 mmol), K$_3$PO$_4$ (428 mg; 2.02 mmol), dicyclohexyl(2',6'-dimethoxy[1,1'-biphenyl]-2-yl)phosphine (277 mg; 0.67 mmol) in toluene (20 ml) and EtOH (6 ml) was stirred at RT under a N$_2$ flow. After 10 minutes, palladium(II) acetate 47% Pd (90.75 mg; 0.40 mmol) was added portionwise. Then the mixture was heated at 80° C. overnight. The solution was poured onto ice water, DCM was added and the mixture was filtered through a pad of celite. The filtrate was extracted with DCM, the organic layer was dried over MgSO$_4$, filtered and evaporated. The residue was purified by Normal phase on Irregular SiOH 20-45 μm 450 g MATREX, Mobile phase (0.5% NH$_4$OH, 92% DCM, 8% MeOH). The desired fraction was collected and the solvent was evaporated, yielding 587 mg (71%) of compound 256. MP=250/255° C. (kofler).

Example 2.4

Preparation of Compound 257

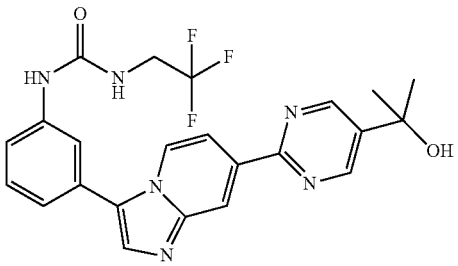 [SMILES: CC(C)(O)c1cnc(-c2ccn3c(-c4cccc(NC(=O)NCC(F)(F)F)c4)cnc3c2)nc1]

A solution of intermediate 14 (0.60 g, 1.31 mmol), 2-chloro-☐,☐-dimethyl-5-pyrimidinemethanol (0.34 g, 1.97 mmol), Cs$_2$CO$_3$ (1.25 g, 3.94 mmol) in toluene (13 ml), 1-butanol (13 ml) and H$_2$O (4 ml) was degassed with N$_2$ for 20 minutes. Tetrakis(triphenylphosphine)palladium (0.46 g, 0.39 mmol) was added and the mixture was heated at 80° C. (bath at 85° C.) for 6 hours under N$_2$. The mixture was poured onto H$_2$O and extracted with EtOAc. The organic layer was dried over MgSO$_4$, filtered and evaporated till dryness. The residue was purified by Normal phase on Irregular SiOH 15-40 μm 300 g Merck, Mobile phase (1% NH$_4$OH, 90% DCM, 10% MeOH). The pure fractions were collected and the solvent was evaporated. The residue was further purified by achiral super critical fluid chromatography on 2-ethylpyridine 6 μm 150×21.2 mm, Mobile phase (0.3% Isopropylamine, 75% CO$_2$, 25% EtOH). The pure fractions were collected and the solvent was evaporated, yielding 0.13 (21%) of compound 257. MP=146° C. (kofler).

Example 2.5

Preparation of Compound 258

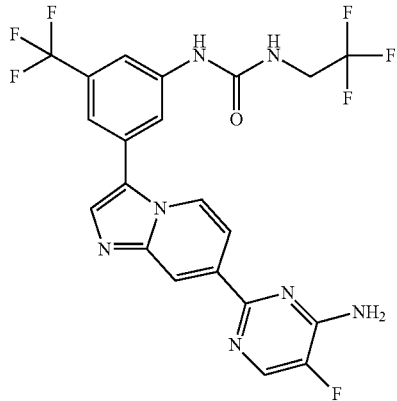 [SMILES: Nc1nc(-c2ccn3c(-c4cc(NC(=O)NCC(F)(F)F)cc(C(F)(F)F)c4)cnc3c2)ncc1F]

A mixture of intermediate 15 (520 mg, 1.17 mmol) and 2-chloro-5-fluoro-4-pyrimidinamine (258 mg, 1.75 mmol) in a saturated aqueous solution of Na$_2$CO$_3$ (3 ml) and DME (15 ml) was degassed by bubbling nitrogen through for 15 minutes. Tetrakis(triphenylphosphine)palladium [(67 mg, 0.058 mmol) was added and the mixture was heated at 80° C. for 5 hours. The solution was cooled, poured onto ice water and DCM. The mixture was filtered through a pad of celite and the filtrate was extracted with DCM. The organic layer was dried over MgSO$_4$, filtered and evaporated. The residue was purified by Normal phase on Spherical SiOH 10 μm 60 g Pharm-Prep MERCK, Mobile phase (0.5% NH₄OH, 95% DCM, 5% MeOH). The pure fractions were collected and the solvent was evaporated. The residue was crystallized from DIPE. The product was filtered off, yielding 71 mg (12%) of compound 258. MP=185° C. (kofler).

Example 2.6

Preparation of Compound 259

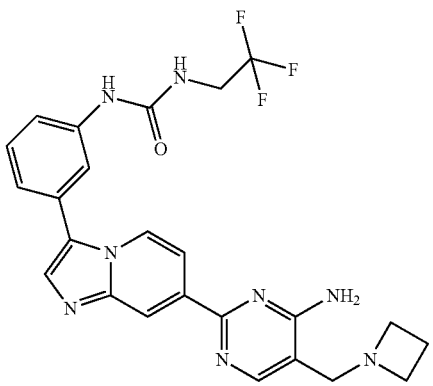 [SMILES: Nc1nc(-c2ccn3c(-c4cccc(NC(=O)NCC(F)(F)F)c4)cnc3c2)ncc1CN1CCC1]

Azetidine (720 μl, 10.71 mmol.) was added to a 50/50 mixture of a suspension of intermediate 18 (573.66 mg, 1.07 mmol) in THF/DCM (20 ml) and the RM was stirred at 50° C. overnight. The RM was cooled to RT, poured onto water and extracted with EtOAc. The organic layer was decanted, dried over MgSO₄, filtered and evaporated to dryness. The residue (800 mg) was purified by Normal phase on Stability Silica 5 μm 150×30.0 mm, Mobile phase (Gradient from 0.3% NH₄OH, 97% DCM, 3% MeOH to 1.4% NH₄OH, 86% DCM, 14% MeOH). The pure fractions were collected and the solvent was evaporated to dryness. The residue was crystallized from ACN. The precipitate was filtered off and dried, yielding 60 mg (11%) of compound 259. MP=195° C. (kofler).;

Example 2.7

Preparation of Compound 260

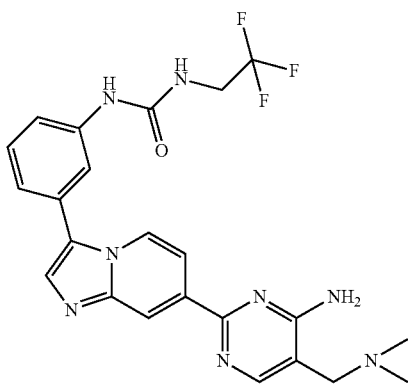 [SMILES: CN(C)Cc1cnc(-c2ccn3c(-c4cccc(NC(=O)NCC(F)(F)F)c4)cnc3c2)nc1N]

A mixture of intermediate 18 (175.65 mg, 0.33 mmol), a solution of N-methylmethanamine in THF 2.0 M (0.25 ml, 0.49 mmol) and Cs₂CO₃ (320.61 mg, 0.98 mmol) in DMF (3 ml) was stirred at RT overnight. The RM was cooled to RT, poured onto water and extracted with EtOAc. The organic layer was decanted, dried over MgSO₄, filtered and evaporated to dryness. The residue was purified by Normal phase on Stability Silica 5 μm 150×30.0 mm, Mobile phase (Gradient from 0.2% NH₄OH, 98% DCM, 2% MeOH to 1.3% NH₄OH, 87% DCM, 13% MeOH). The pure fractions were collected and the solvent was evaporated to dryness, yielding 23 mg (14%) of compound 260. MP=130° C. (kofler).

Example 2.8

Preparation of Compound 261

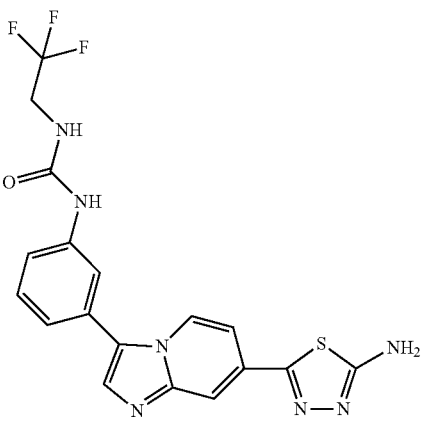 [SMILES: Nc1nnc(-c2ccn3c(-c4cccc(NC(=O)NCC(F)(F)F)c4)cnc3c2)s1]

Intermediate 21 (0.6 g, 1.33 mmol) was dissolved in H₂SO₄ (5 ml) at 0° C. and the RM was stirred for 1 hour at RT. The RM was neutralized with NaOH (3N) at 0° C. Then, the precipitate was filtered and was taken up into a 9/1 mixture of DCM/MeOH. The precipitate was filtered, yielding fraction 1 (15 mg). The filtrate was concentrated and taken up into a 1/1 mixture of DCM/Acetone (5 ml). The precipitate was filtered, yielding a fraction 2 (70 mg). Both fraction 1 and 2 were mixed, washed again with 5 ml of a 1/1 mixture of DCM/Acetone. The precipitate was filtered off and dried, yielding 80 mg (14%) of compound 261. MP>260° C. (kofler).

Example 2.9

Preparation of Compound 262

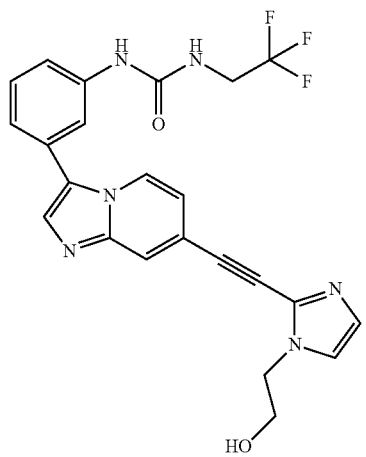 [SMILES: O=C(NCC(F)(F)F)Nc1cccc(-c2cnc3cc(C#Cc4nccn4CCO)ccn23)c1]

Intermediate 27 (250 mg, 0.43 mmol) was dissolved in THF (5 ml). Then, tetrabutylammoniumfluoride (192 µl, 0.64 mmol) was added and the RM was stirred at RT for 16 hours. Additional tetrabutylammoniumfluoride (100 µl, 0.34 mmol) was added and the RM was stirred for 5 additional hours. Then, it was partitioned between EtOAc (100 ml) and water (50 ml). The organic layer was dried over MgSO₄, filtered, concentrated and purified by Normal phase on Stability Silica 5 µm 150×30.0 m, Mobile phase (Gradient from 0.3% NH₄OH, 97% DCM, 3% MeOH to 1.4% NH₄OH, 86% DCM, 14% MeOH). The pure fractions were collected and the solvent was evaporated. The residue was precipated from CH₃CN/MeOH, yielding 0.055 g (27%) of compound 262. MP=228° C. (kofler).

Example 2.10

Preparation of Compound 263

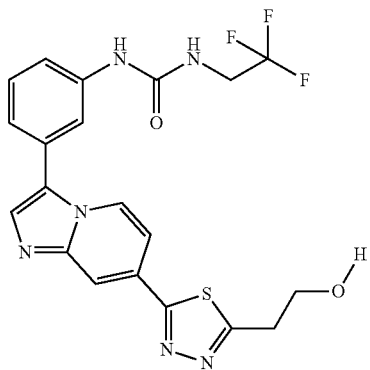 [SMILES: O=C(NCC(F)(F)F)Nc1cccc(-c2cnc3cc(-c4nnc(CCO)s4)ccn23)c1]

A solution of tribromoborane (2.17 ml, 2.17 mmol) was added to a solution of intermediate 30 (2.17 ml, 2.17 mmol) in DCM (20 ml) at −10° C. The mixture was stirred for 30 minutes. A saturated aqueous solution of NaHCO₃ was added at −10° C. The organic layer was separated, washed with brine, dried (MgSO₄), filtered and the solvent was evaporated. The residue was purified by Normal phase on Cartridge 15-40 µm 30 g, Mobile phase (97% DCM, 3% MeOH). The pure fractions were collected and the solvent was evaporated. The residue was crystallized in Et₂O, yielding 118 mg (23%) of compound 263. MP=230° C. (kofler).

Example 2.11 a) Preparation of Compound 264

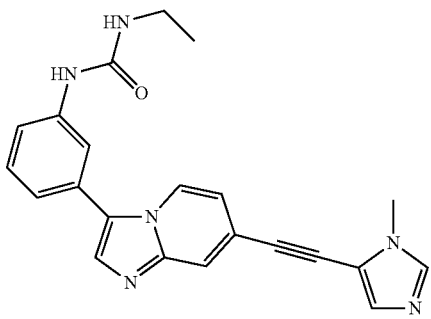 [SMILES: CCNC(=O)Nc1cccc(-c2cnc3cc(C#Cc4cncn4C)ccn23)c1]

A mixture of intermediate 28 (1.8 g, 5.72 mmol), 5-ethynyl-1-methyl-1H-imidazole (2.90 ml, 28.59 mmol) and Cs₂CO₃ (3.73 g, 11.44 mmol) in dry DMSO (30 ml) was deoxygenated by evacuation/refill with N₂ (×3). Tricyclohexylphosphine (320.73 mg, 1.14 mmol) and palladium (II) chloride (102.55 mg, 0.57 mmol) were added and the mixture was deoxygenated again (×3), then stirred and heated at 100° C. under N₂ for 2 hours. The RM was cooled to RT, poured onto ice water and extracted with EtOAc. The mixture was filtered over a pad of celite. The filtrate was decanted and the aqueous layer was extracted 3 times more with EtOAc. The pad of celite was then washed with DCM/MeOH 90/10. The combined organic layers were washed with a saturated aqueous solution of NaCl, dried over MgSO₄, filtered and evaporated to dryness. The residue (6 g) was filtered over a pad of SiO₂ 63/200 µm (Eluent: DCM/MeOH 90/10). The fractions were collected and the solvent was evaporated to dryness. The residue was purified by Normal phase on Irregular SiOH 20-45 µm 450 g MATREX, Mobile phase (0.5% NH₄OH, 93% DCM, 7% MeOH). The desired fraction was collected, evaporated and taken up in 2 ml of MeOH at RT. Then, ACN was added until precipitation of the compound, yielding 0.42 mg (19%) of compound 264. MP=163° C. (kofler).

b) Preparation of Compound 265

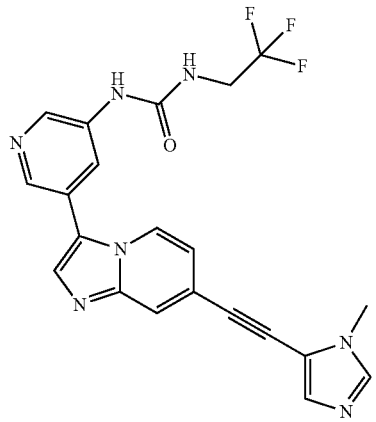 [SMILES: Cn1cncc1C#Cc1ccn2c(-c3cncc(NC(=O)NCC(F)(F)F)c3)cnc2c1]

A mixture of intermediate 33 (0.71 g, 1.92 mmol), 5-ethynyl-1-methyl-1H-imidazole (0.97 ml, 9.6 mmol) and Cs₂CO₃ (1.25 g, 3.84 mmol) in DMSO (7 ml) was deoxygenated by evacuation/refill with N₂ (×3). Dichlorobis(tricyclohexylphosphine)palladium (85 mg, 0.12 mmol) was added and the mixture was deoxygenated again (×3), then stirred and heated at 100° C. under N₂ for 2 hours. The RM was cooled to RT, quenched with water and extracted with EtOAc. The organic layer was decanted, dried over MgSO₄, filtered and evaporated to dryness. The crude was taken up into DOM/MeOH (9/1). The insoluble material removed by filtration was washed with DOM/MeOH (9/1). Then, the filtrate was washed with water and the organic layers were mixed, dried over MgSO₄, filtered and evaporated. The residue was purified by Normal phase on Irregular SiOH 15-40 µm 300 g MERCK, Mobile phase (0.8% NH₄OH, 92% DCM, 8% MeOH). The pure fractions were collected and the solvent was evaporated. The residue was crystallized from MeOH and Et₂O, yielding 0.182 g (22%) of compound 265. MP>250° C. (kofler).

c) Preparation of Compound 266

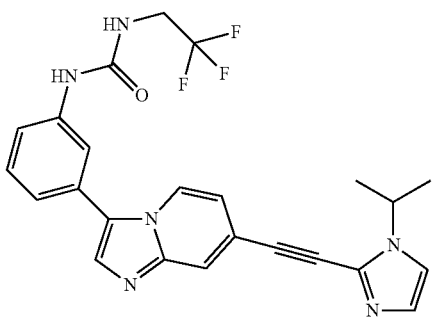 [SMILES: CC(C)n1ccnc1C#Cc1ccn2c(-c3cccc(NC(=O)NCC(F)(F)F)c3)cnc2c1]

A mixture of intermediate 35 (1.29 g, 6.27 mmol) in DMSO (15 ml) was deoxygenated by evacuation/refill with $N_2$ (×3). $Cs_2CO_3$ (2.04, 6.27 mmol) was added and the RM was stirred at RT for 15 minutes. Intermediate 28 (950 mg, 2.58 mmol), tricyclohexylphosphine (175.83 mg, 0.63 mmol) and palladium(II) chloride (56.22 mg, 0.31 mmol) were added and the mixture was deoxygenated again (×3), then stirred and heated at 100° C. under $N_2$ for 1 hour. The RM was cooled to RT, poured onto ice water and extracted with EtOAc. The mixture was filtered over a büchner. The filtrate was decanted and the aqueous layer was extracted 3 times more with EtOAc. The combined organic layers were washed with a saturated aqueous solution of NaCl, dried over $MgSO_4$, filtered and evaporated to dryness. The residue was purified by Normal phase on Stability Silica 5 μm 150×30.0 mm, Mobile phase (Gradient from 0% $NH_4OH$, 100% DCM, 0% MeOH to 0.8% $NH_4OH$, 92% DCM, 8% MeOH). The pure fractions were collected and the solvent was evaporated to dryness, yielding 18 mg (1.5%) of compound 266.

Example 2.12

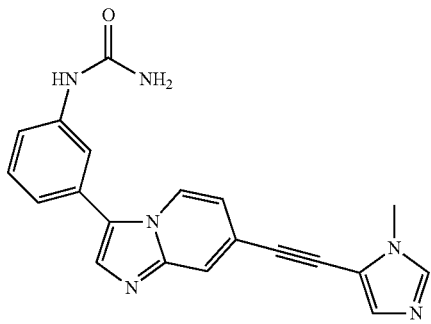 [SMILES: Cn1cncc1C#Cc1ccn2c(-c3cccc(NC(N)=O)c3)cnc2c1]

a) Preparation of Compound 267

To a solution of intermediate 48 (0.48 g, 1.0 mmol) in THF (16 ml) was added N, N-diethylethanamine (168 μl, 1.2 mmol) and a 0.5N solution of $NH_3$ in dioxane (8 ml, 4 mmol). The resulting mixture was stirred at 0° C. for 2 hours. Then, additional 0.5N solution of $NH_3$ in dioxane (4 ml, 2 mmol) was added and the mixture was stirred for 2 more hours. Additional 0.5N solution of $NH_3$ in dioxane (4 ml, 2 mmol) was added again to complete the conversion. The yellow suspension was filtered, yielding fraction 1. The filtrate was diluted with DCM (100 ml) and washed with water (50 ml). The organic layer was dried over $MgSO_4$, filtered and concentrated, yielding fraction 2. Fraction 1 was purified by Reverse phase on X-Bridge-C18 5 μm 30×150 mm, Mobile phase (Gradient from 20% $NH_4HCO_3$ 0.5%, 80% ACN to 0% $NH_4HCO_3$ 0.5%, 100% ACN). Fraction 2 was purified by Reverse phase on X-Bridge-C18 5 μm 30×150 mm, Mobile phase (Gradient from 80% $NH_4HCO_3$ 0.5%, 20% ACN to 0% $NH_4HCO_3$ 0.5%, 100% ACN). The pure fractions of both purifications were collected, yielding 0.235 g (65%) of compound 267. MP=162° C. (kofler).

Example 2.13

Preparation of Compound 268

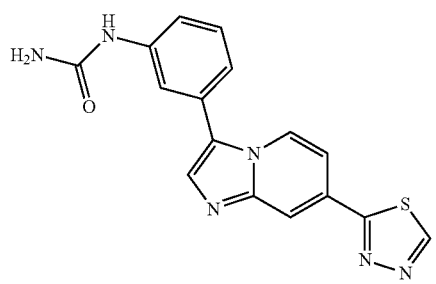 [SMILES: NC(=O)Nc1cccc(-c2cnc3cc(-c4nncs4)ccn23)c1]

To a solution of intermediate 44 (0.28 g, 0.95 mmol) in acetic acid (15 ml), potassium cyanate (0.12 g, 1.43 mmol) was added. The mixture was stirred at RT for 1 hour. The solvent was evaporated and the residue was taken up in DCM/ 10% aqueous $K_2CO_3$. The organic layer was separated, washed with brine, dried ($MgSO_4$), filtered and the solvent was evaporated. The residue was purified by Normal phase on Irregular SiOH 15-40 μm 300 g MERCK, Mobile phase (0.5% $NH_4OH$, 97% DCM, 3% MeOH). The pure fractions were collected and the solvent was evaporated. The residue (0.170 g) was crystallized from DIPE/ACN (90/10), the precipitate was filtered and dried under vacuum, yielding 0.142 g (44%) of compound 268. MP=259° C. (kofler).

Example 2.14 a) Preparation of Compound 269

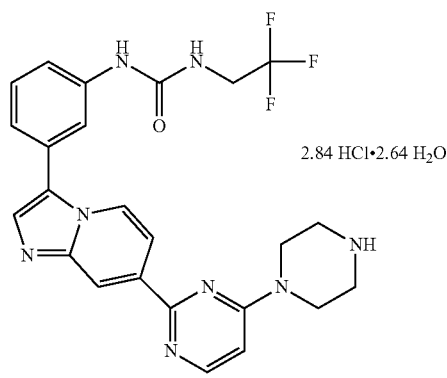 [SMILES: O=C(NCC(F)(F)F)Nc1cccc(-c2cnc3cc(-c4nccc(N5CCNCC5)n4)ccn23)c1]

2.84 HCl•2.64 $H_2O$

HCl (2.65 ml, 13.2 mmol) was added to a solution of compound 317 (263 mg; 0.44 mmol) in 2-propanol (10.5 ml) at RT. The RM was heated to 50° C. for the time necessary to complete the deprotection and cooled to RT. The precipitate was filtered off, washed with 2-propanol and dried, yielding 110 mg (38%) of compound 269. MP=200° C. (kofler).

b) Preparation of Compound 270

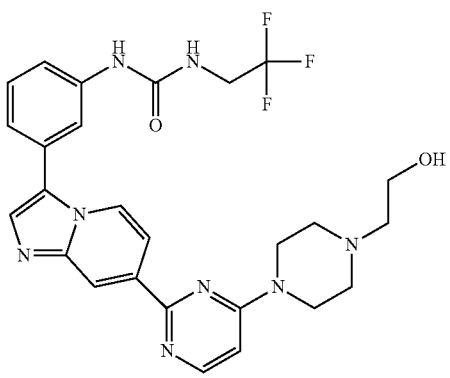 [SMILES: O=C(NCC(F)(F)F)Nc1cccc(-c2cnc3cc(-c4nccc(N5CCN(CCO)CC5)n4)ccn23)c1]

A mixture of compound 269 (223 mg, 0.42 mmol), 2-bromoethanol (105 mg, 0.84 mmol), NaHCO₃ (105 mg, 1.26 mmol) in EtOH (7 ml) was stirred at RT overnight, then at 70° C. for 12 hours. H₂O and DCM were added. The precipitate was filtered off and dried, yielding fraction 1. The organic layer was washed with a saturated aqueous NaCl solution, dried over MgSO₄, filtered and evaporated, yielding fraction 2. The aqueous layer was extracted with DCM using a continuous method to obtain fraction 3 after evaporation.

Fractions 1, 2 and 3 were mixed and purified by Normal phase on Stability Silica 5 µm 150×30.0 mm, Mobile phase (Gradient from 0.3% NH₄OH, 97% DCM, 3% MeOH to 1.4% NH₄OH, 86% DCM, 14% MeOH). The pure fractions were collected and the solvent was evaporated, yielding 18 mg (8%) of compound 270. MP=179.8° C. (DSC).

c) Preparation of Compound 271

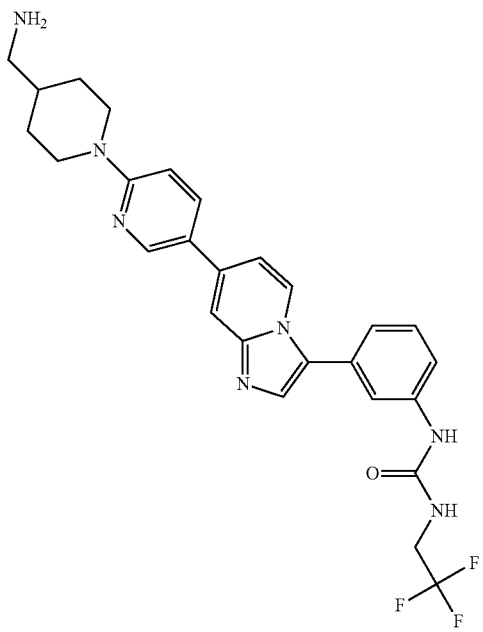 [SMILES: NCC1CCN(c2ccc(-c3ccn4c(-c5cccc(NC(=O)NCC(F)(F)F)c5)cnc4c3)cn2)CC1]

TFA (0.3 ml) was added to a solution of compound 318 (0.11 g, 0.17 mmol) in DCM (3 ml). The solution was stirred at RT for 4 hours, H₂O was added and the solution was basified with K₂CO₃. The aqueous layer was extracted with DCM. The organic layer was dried over MgSO₄ and evaporated to dryness. The residue was purified by Reverse phase on E5420 X-Bridge-C18 5 µm 30×150 mm, Mobile phase (Gradient from 80% NH₄HCO₃ 0.5%, 20% ACN to 0% NH₄HCO₃ 0.5%, 100% ACN). The pure fractions were collected and the solvent was evaporated to dryness, yielding 53.2 mg (60%) of compound 271. MP=80° C. (kofler).

d) Preparation of Compound 272

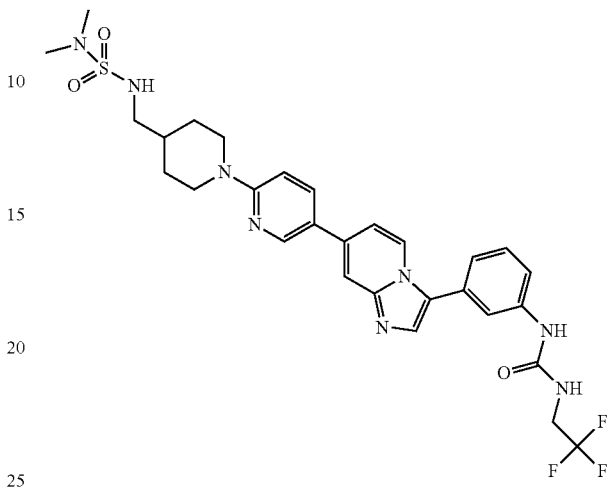

Compound 271 (0.155 g, 0.3 mmol), N,N-dimethyl sulfamoyl chloride (42 µl, 0.4 mmol), N-ethyl-N-(1-methylethyl)-2-propanamine (0.155 ml, 0.9 mmol) in THF (12 ml) were heated at reflux for 24 hours. The solution was cooled and evaporated to dryness. The residue was purified by silica gel chromatography (SiO₂: 15-40 µm/30 g, mobile phase: DCM/MeOH/NH₄OH: 95/5/0.5. The pure fractions were collected and the solvent was evaporated. The residue was purified again by Reverse phase on E5462 X-Bridge-C18 5 µm 30×150 mm, Mobile phase (Gradient from 60% NH₄HCO₃ 0.5%, 40% ACN to 0% NH₄HCO₃ 0.5%, 100% ACN). The pure fractions were collected and the solvent was evaporated, yielding 31.5 mg (17%) of compound 272. MP=145° C. (kofler).

Example 2.15

Preparation of Compound 273

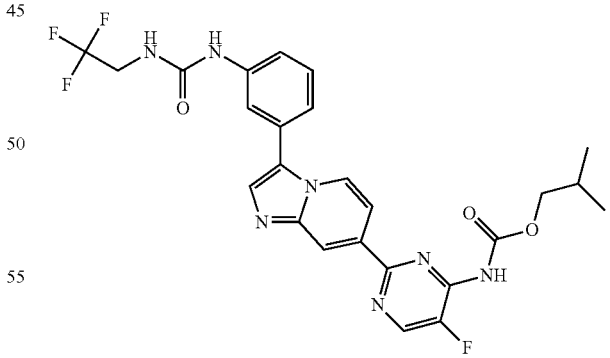

Compound of Example 102 (210 mg, 0.47 mmol), N,N-dimethyl-4-pyridinamine (12 mg, 0.094 mmol), 2-methylpropyl chloroformate (190 µl, 1.46 mmol) and N,N-diethylethamine (230 µl, 1.65 mmol) in THF (5 ml) were stirred at 70° C. for 24 hours. EtOAc and H₂O were added. The organic layer was dried over MgSO₄, filtered and evaporated. The residue was purified by Normal phase on Irregular SiOH 15-40 µm 300 g MERCK, Mobile phase (Gradient from 0.2%

NH₄OH, 98% DCM, 2% MeOH to 1.1% NH₄OH, 89% DCM, 11% MeOH). The pure fractions were collected and the solvent was evaporated. The residue was purified again by Reverse phase on X-Bridge-C18 5 μm 30×150 mm, Mobile phase (Gradient from 60% NH₄HCO₃ 0.5%, 40% ACN to 0% NH₄HCO₃ 0.5%, 100% ACN). The desired fraction was collected and the solvent was evaporated, yielding 54 mg (21%) of compound 273. MP=215.2° C. (DSC).

Example 2.16

Preparation of Compound 274

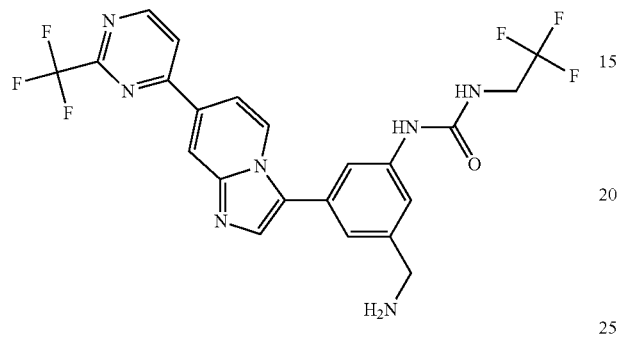

Compound 299 (330 mg, 0.65 mmol) and Ni (396 mg, 6.75 mmol) in NH₃ 7N in MeOH (50 ml) were hydrogenated under 4 bars pressure at RT in a bomb apparatus overnight. It was then filtered through a pad of celite and evaporated.

The residue was purified by Normal phase on Cartridge 15-40 μm 30 g, Mobile phase (1.2% NH₄OH, 88% DCM, 12% MeOH). The pure fractions were collected and the solvent was evaporated, yielding 290 mg (87%) of compound 274. MP=190° C. (DSC)

Example 2.17

Preparation of Compound 275

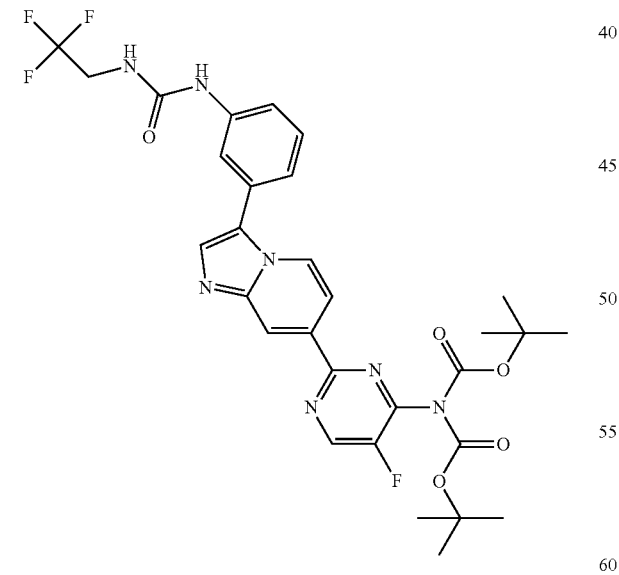

Compound of Example 102 (0.5 g, 1.12 mmol), di-tert-butyldicarbonate (0.73 g, 3.37 mmol) and pyridine (0.32 ml, 3.93 mmol) in THF (6 ml) were stirred at RT for 3 days. Water and HCl 3N were added. The mixture was extracted with DCM. The organic layer was dried over MgSO₄, filtered and evaporated. The residue was purified by Normal phase on Stability Silica 5 μm 150×30.0 mm, Mobile phase (Gradient from 0% NH₄OH, 100% DCM, 0% MeOH to 0.6% NH₄OH, 94% DCM, 6% MeOH). The desired fraction was collected and further purified by Reverse phase on X-Terra-C18 10 μm 19×150 mm, Mobile phase (Gradient from 40% NH₄HCO₃ 0.5%, 60% MeOH to 0% NH₄HCO₃ 0.5%, 100% MeOH). The desired fraction was collected and the solvent was evaporated, yielding 24 mg (3.3%) of compound 275. MP=157.7° C. (DSC)

Example 2.18

Preparation of Compound 276

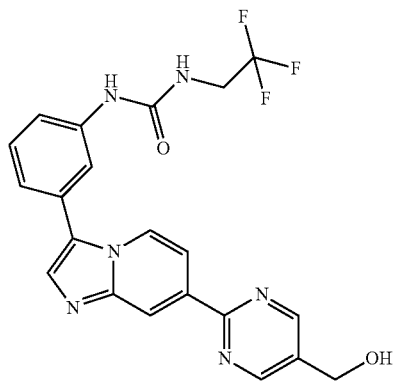 [SMILES: O=C(NCC(F)(F)F)Nc1cccc(-c2cnc3cc(-c4ncc(CO)cn4)ccn23)c1]

Lithium aluminium hydride 1 M in THF (3.04 mmol) was added dropwise at RT to a suspension of compound 290 (476 mg, 1.01 mmol) in THF (57 ml). The RM was stirred at RT for 5 hours. Ice water (0.20 ml) was added with caution, followed by NaOH 3N (0.20 ml) and water (0.60 ml). The RM was partitioned between DCM/MeOH (90/10) and water.

The aqueous layer was extracted once with DCM/MeOH (90/10). The organic layers were mixed, dried over MgSO₄, concentrated and filtered. The residue was purified by Normal phase on Cartridge 15-40 μm 30 g, Mobile phase (0.5% NH₄OH, 95% DCM, 5% MeOH). The pure fractions were collected and the solvent was evaporated. The residue (120 mg, yellow solid) was not pure enough and was purified again by reverse phase HPLC. The pure fractions were collected and the solvent was evaporated, yielding 65 mg (14%) of compound 276. MP=222° C. (kofler, degradation not melting).

Example 2.19

Preparation of Compound 277

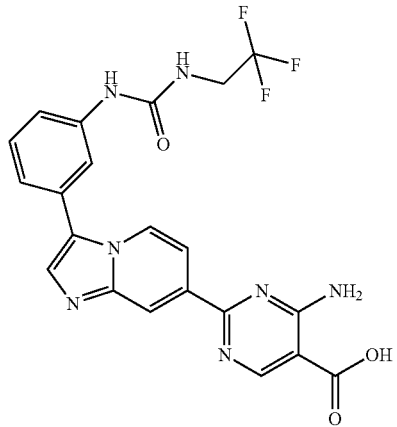

1.16 HCl·3.31 H₂O

A mixture of compound 312 (90 mg, 0.18 mmol) and lithium hydroxide monohydrate (23 mg, 0.54 mmol) in THF/H$_2$O (10/1, 6 ml) was stirred at RT for 60 hours. The RM was acidified with HCl 3N and the solution was evaporated to dryness. The solid residue was taken up with ACN/water. The precipitate was filtered off and taken up again with ACN. After stirring for 1 hour, filtration afforded 42 mg of compound 277. MP>260° C.

Example 2.20

Preparation of Compound 278

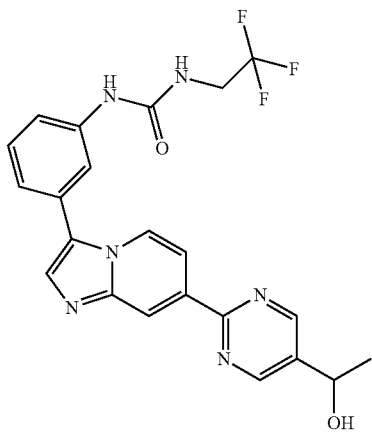 [SMILES: CC(O)c1cnc(-c2ccn3c(-c4cccc(NC(=O)NCC(F)(F)F)c4)cnc3c2)nc1]

NaBH$_4$ (24.98 mg, 0.66 mmol) was added portionwise at RT to a suspension of compound 292 (250 mg, 0.55 mmol) in MeOH (6 ml). The RM was stirred at RT for 15 minutes. The RM was quenched with water and the precipitate was filtered off. The solid was dissolved in DCM/MeOH and the organic layer was dried over MgSO$_4$, filtered and evaporated to dryness. The residue was purified by Normal phase on Cartridge 15-40 μm 30 g, Mobile phase (1% NH$_4$OH, 90% DCM, 10% MeOH). The pure fractions were collected and evaporated to dryness. The residue (100 mg) was crystallized from ACN/MeOH. The precipitate was filtered off and further purified by Reverse phase on (X-Bridge-C18 5 μm 30×150 mm, Mobile phase (Gradient from 40% NH$_4$HCO$_3$ 0.5%, 60% MeOH to 0% NH$_4$HCO$_3$ 0.5%, 100% MeOH). The pure fractions were collected and evaporated to dryness, yielding 60 mg (24%) of compound 278. MP=224° C. (kofler)

Example 2.21

Preparation of Compound 279

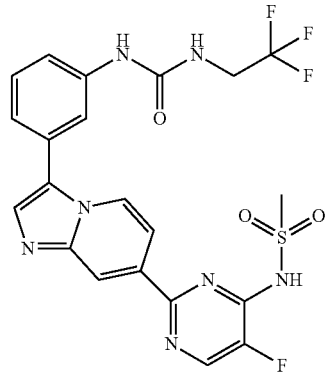 [SMILES: CS(=O)(=O)Nc1nc(-c2ccn3c(-c4cccc(NC(=O)NCC(F)(F)F)c4)cnc3c2)ncc1F]

Under N$_2$, sodium hydride (67.4 mg, 1.68 mmol) was added portionwise to a solution of compound of Example 102 (500 mg, 1.13 mmol) in N,N-dimethylacetamide (20 ml). The mixture was stirred for 3 hours at RT. Methanesulfonyl chloride (0.105 ml, 1.35 mmol) was added dropwise, and the mixture was stirred at RT for 48 hours. The mixture was poured onto water and the product was extracted with EtOAc. The organic layer was washed with water (twice), brine, dried over MgSO$_4$, filtered and evaporated till dryness. The residue was purified by silica gel chromatography (15-40 μm, 30 g, DCM/MeOH/NH$_4$OH 85/15/1) The pure fractions were collected and evaporated to dryness. The resulting residue was purified by Normal phase on Cartridge 15-40 μm 30 g, Mobile phase (80% DCM, 20% MeOH) to give 54 mg (9%) of compound 279. MP>350° C. (DSC)

Analytical Part in Relation to Compounds 250 to 337

LCMS-Method

General Procedure 1

The LC measurement was performed using a HPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 1

In addition to the general procedure 1: Reversed phase HPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

General Procedure 2

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters. Nitrogen was used as the nebulizer gas. Data acquisition was performed with a Waters-Micromass MassLynx-Openlynx data system.

Method 2

In addition to the general procedure 2: Reversed phase HPLC was carried out on a Waters Xterra-RP C18 column (3.5 μm, 4.6×100 mm) with a flow rate of 0.8 ml/min. Two mobile phases (mobile phase A: 100% 7 mM ammonium acetate; mobile phase B: 100% acetonitrile) were employed to run a gradient condition from 80% A and 20% B (hold for 0.5 minute) to 90% B in 4.5 minutes, 90% B for 4 minutes and reequilibrated with initial conditions for 3 minutes. An injection volume of 5 μl was used. Cone voltage was 20 V for positive and negative ionization mode. Mass spectra were acquired by scanning from 100 to 1000 in 0.4 seconds using an interscan delay of 0.3 seconds.

The below Table lists compounds prepared by, or in a manner similar to, the above described examples (Ex: according example; Melting point (MP) was determined either by K=Koffler (° C.) or DSC=differential scanning calorimetry (° C.); LCMS data: Rt=retention time in minutes, MH⁺ is the protonated mass and method reflects the method according to which LCMS data were generated).

| Comp. No. | Ex. | Compound structure | LCMS Data | MP ° C. |
|---|---|---|---|---|
| 250 | 2.1a1 | 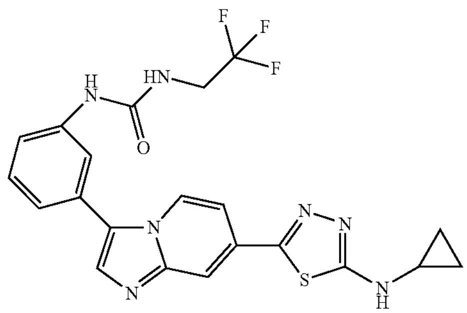 [SMILES: O=C(NCC(F)(F)F)Nc1cccc(-c2cnc3cc(-c4nnc(NC5CC5)s4)ccn23)c1] | Rt: 3.09<br>MH⁺: 474<br>Method: 1 | >280<br>(K) |
| 251 | 2.1a2 | 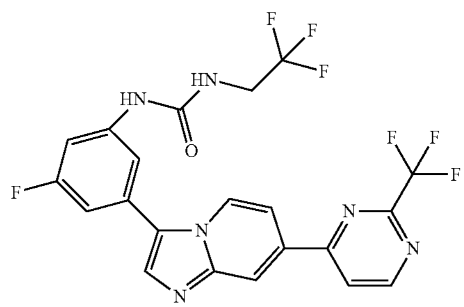 [SMILES: O=C(NCC(F)(F)F)Nc1cc(F)cc(-c2cnc3cc(-c4ccnc(C(F)(F)F)n4)ccn23)c1] | Rt: 3.77<br>MH⁺: 499<br>Method: 1 | 263.18<br>(DSC) |
| 252 | 2.1b | 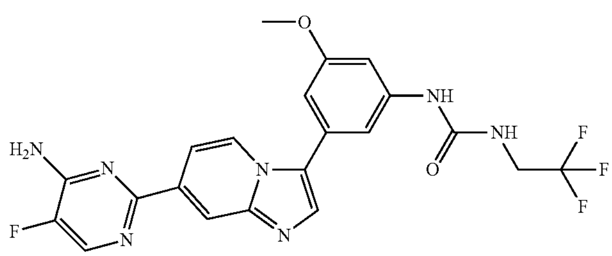 [SMILES: COc1cc(NC(=O)NCC(F)(F)F)cc(-c2cnc3cc(-c4ncc(F)c(N)n4)ccn23)c1] | Rt: 3.11<br>MH⁺: 476<br>Method: 1 | 154.10<br>(DSC) |
| 253 | 2.2a | 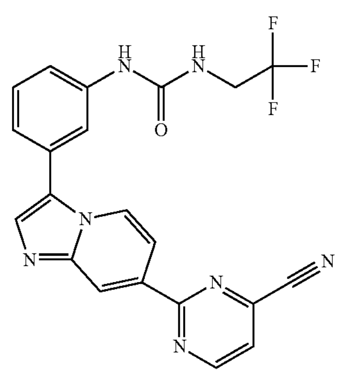 [SMILES: N#Cc1ccnc(-c2ccn3c(-c4cccc(NC(=O)NCC(F)(F)F)c4)cnc3c2)n1] | Rt: 3.37<br>MH⁺: 438<br>Method: 1 | 210<br>(K) |

-continued

| Comp. No. | Ex. | Compound structure | LCMS Data | MP ° C. |
|---|---|---|---|---|
| 165B | 2.2b | 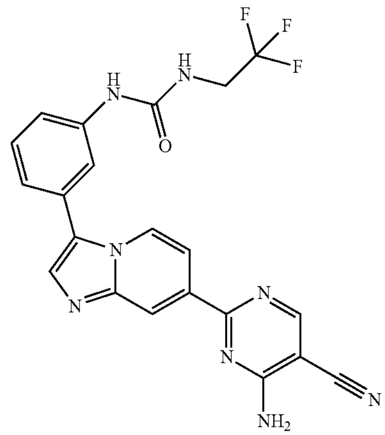 [SMILES: N#Cc1cnc(-c2ccn3c(-c4cccc(NC(=O)NCC(F)(F)F)c4)cnc3c2)nc1N] | Rt: 3.09<br>MH+: 453<br>Method: 1 | 161<br>(DSC) |
| 255 | 2.3a | 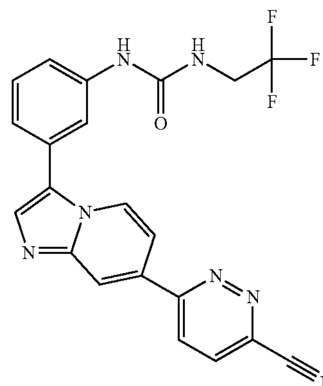 | Rt: 3.18<br>MH+: 438<br>Method: 1 | 267<br>(K)<br>260.3<br>(DSC) |
| 256 | 2.3b | 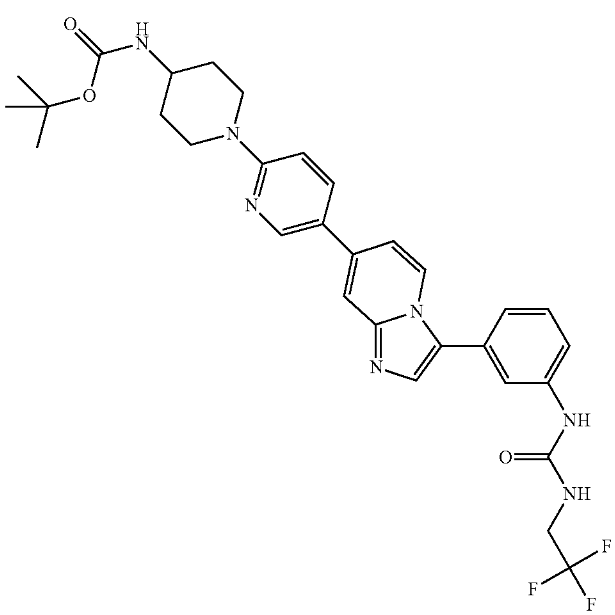 [SMILES: CC(C)(C)OC(=O)NC1CCN(c2ccc(-c3ccn4c(-c5cccc(NC(=O)NCC(F)(F)F)c5)cnc4c3)cn2)CC1] | — | 250-255<br>(K) |

-continued

| Comp. No. | Ex. | Compound structure | LCMS Data | MP °C. |
|---|---|---|---|---|
| 257 | 2.4 | 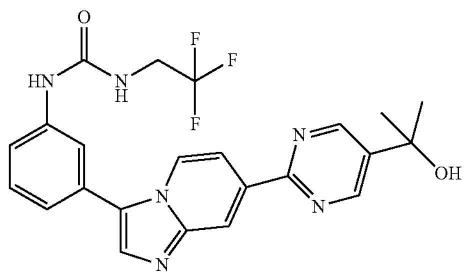 [SMILES: CC(C)(O)c1cnc(-c2ccn3c(-c4cccc(NC(=O)NCC(F)(F)F)c4)cnc3c2)nc1] | Rt: 3.04<br>MH⁺: 471<br>Method: 1 | 146<br>(K) |
| 258 | 2.5 | 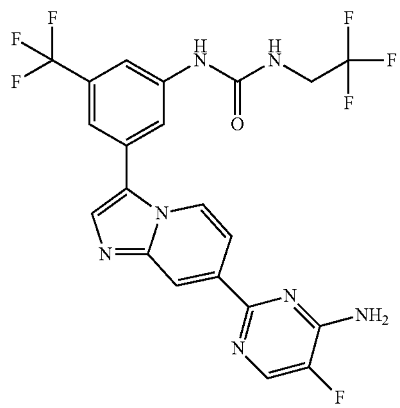 [SMILES: Nc1nc(-c2ccn3c(-c4cc(NC(=O)NCC(F)(F)F)cc(C(F)(F)F)c4)cnc3c2)ncc1F] | Rt: 3.49<br>MH⁺: 514<br>Method: 1 | 185<br>(K) |
| 259 | 2.6 | 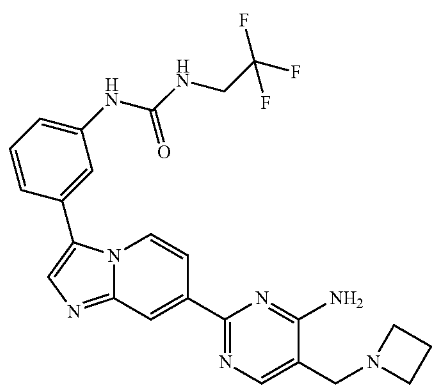 [SMILES: Nc1nc(-c2ccn3c(-c4cccc(NC(=O)NCC(F)(F)F)c4)cnc3c2)ncc1CN1CCC1] | Rt: 2.86<br>MH⁺: 497<br>Method: 1 | 195<br>(K)<br>185.4<br>(DSC) |
| 260 | 2.7 | 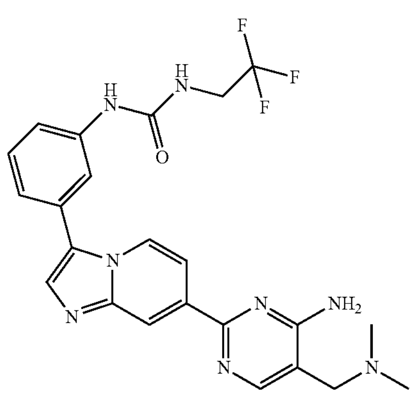 [SMILES: CN(C)Cc1cnc(-c2ccn3c(-c4cccc(NC(=O)NCC(F)(F)F)c4)cnc3c2)nc1N] | Rt: 3.15<br>MH⁺: 485<br>Method: 1 | 130<br>(K) |

-continued

| Comp. No. | Ex. | Compound structure | LCMS Data | MP °C. |
|---|---|---|---|---|
| 261 | 2.8 | 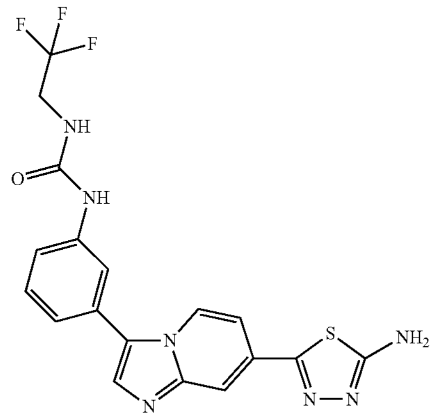 [SMILES: Nc1nnc(-c2ccn3c(-c4cccc(NC(=O)NCC(F)(F)F)c4)cnc3c2)s1] | Rt: 2.71<br>MH⁺: 434<br>Method: 1 | >260 (K) |
| 262 | 2.9 | 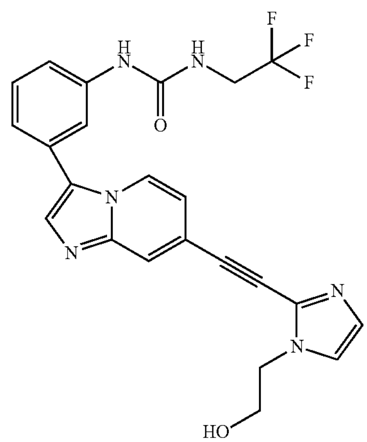 [SMILES: O=C(NCC(F)(F)F)Nc1cccc(-c2cnc3cc(C#Cc4nccn4CCO)ccn23)c1] | Rt: 2.78<br>MH⁺: 469<br>Method: 1 | 228 (K) |
| 263 | 2.10 | 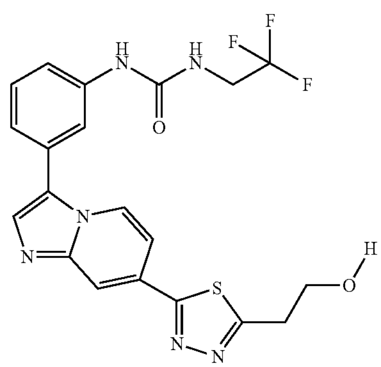 [SMILES: O=C(NCC(F)(F)F)Nc1cccc(-c2cnc3cc(-c4nnc(CCO)s4)ccn23)c1] | Rt: 4.85<br>MH⁺: 463<br>Method: 2 | 230 (K) |
| 264 | 2.11a | 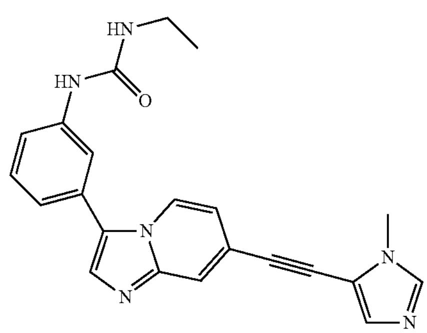 [SMILES: CCNC(=O)Nc1cccc(-c2cnc3cc(C#Cc4cncn4C)ccn23)c1] | Rt: 2.66<br>MH⁺: 385<br>Method: 1 | 163 (K) |

-continued

| Comp. No. | Ex. | Compound structure | LCMS Data | MP ° C. |
|---|---|---|---|---|
| 265 | 2.11b | 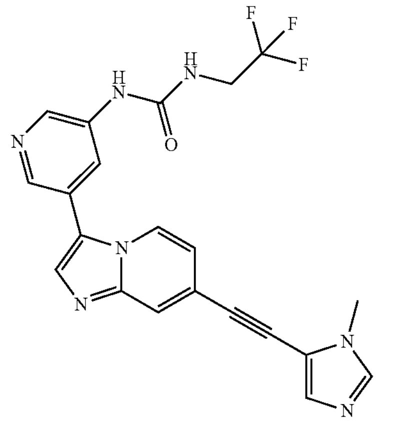 [SMILES: Cn1cncc1C#Cc1ccn2c(-c3cncc(NC(=O)NCC(F)(F)F)c3)cnc2c1] | Rt: 2.55<br>MH+: 440<br>Method: 1 | >250<br>(K) |
| 266 | 2.11c | 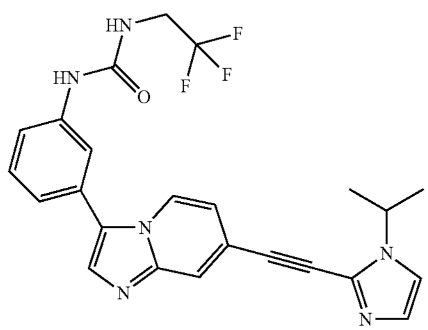 [SMILES: CC(C)n1ccnc1C#Cc1ccn2c(-c3cccc(NC(=O)NCC(F)(F)F)c3)cnc2c1] | Rt: 3.34<br>MH+: 467<br>Method: 1 | |
| 157B | 157B | 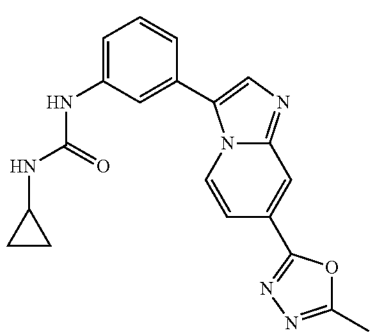 [SMILES: Cc1nnc(-c2ccn3c(-c4cccc(NC(=O)NC5CC5)c4)cnc3c2)o1] | Rt: 2.58<br>MH+: 375<br>Method: 1 | 229<br>(DSC) |
| 158B | 158B | 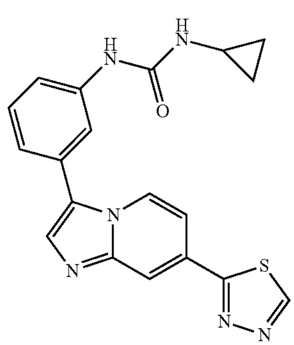 [SMILES: O=C(Nc1cccc(-c2cnc3cc(-c4nncs4)ccn23)c1)NC1CC1] | Rt: 2.52<br>MH+: 377<br>Method: 1 | 205<br>(K) |

| Comp. No. | Ex. | Compound structure | LCMS Data | MP °C |
|---|---|---|---|---|
| 267 | 2.12c | 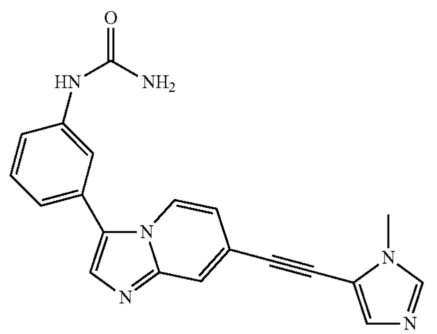 [SMILES: Cn1cncc1C#Cc1ccn2c(-c3cccc(NC(N)=O)c3)cnc2c1] | Rt: 2.36<br>MH+: 357<br>Method: 1 | 162 (K) |
| 268 | 2.13 | 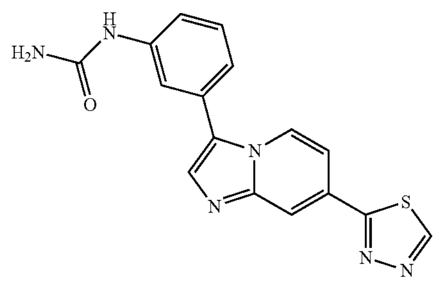 [SMILES: NC(=O)Nc1cccc(-c2cnc3cc(-c4nncs4)ccn23)c1] | Rt: 2.16<br>MH+: 337<br>Method: 1 | 259 (K) |
| 269 | 2.14a | .2.84 HCl .2.64 H₂O | Rt: 2.65<br>MH+: 497<br>Method: 1 | 200 (K) |
| 270 | 2.14b | 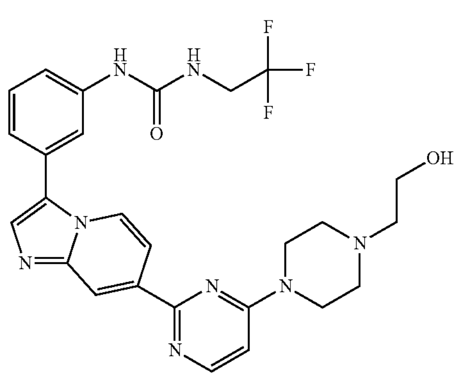 [SMILES: O=C(NCC(F)(F)F)Nc1cccc(-c2cnc3cc(-c4nccc(N5CCN(CCO)CC5)n4)ccn23)c1] | Rt: 2.84<br>MH+: 541<br>Method: 1 | 204 (K)<br>179.8 (DSC) |

| Comp. No. | Ex. | Compound structure | LCMS Data | MP °C |
|---|---|---|---|---|
| 271 | 2.14c | 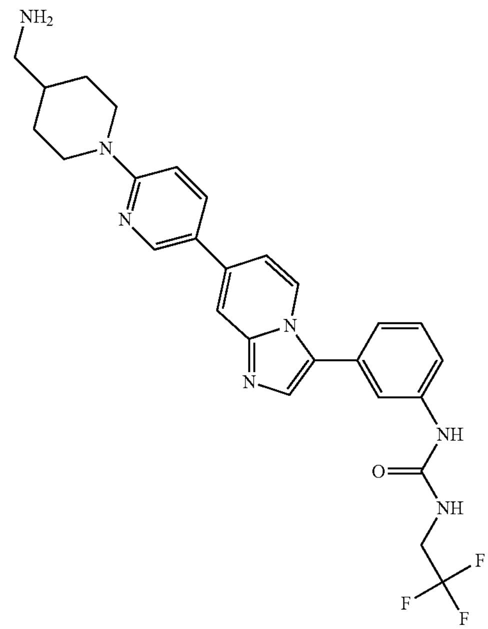 [SMILES: NCC1CCN(c2ccc(-c3ccn4c(-c5cccc(NC(=O)NCC(F)(F)F)c5)cnc4c3)cn2)CC1] | Rt: 2.74<br>MH+: 524<br>Method: 1 | 80<br>(K) |
| 272 | 2.14d | 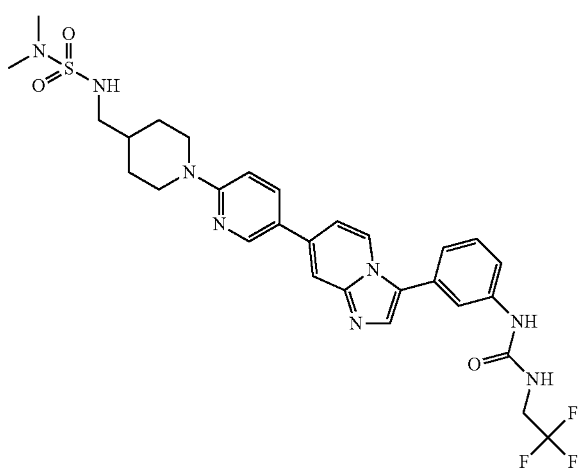 [SMILES: CN(C)S(=O)(=O)NCC1CCN(c2ccc(-c3ccn4c(-c5cccc(NC(=O)NCC(F)(F)F)c5)cnc4c3)cn2)CC1] | Rt: 3.45<br>MH+: 631<br>Method: 1 | 145<br>(K) |
| 273 | 2.15 | 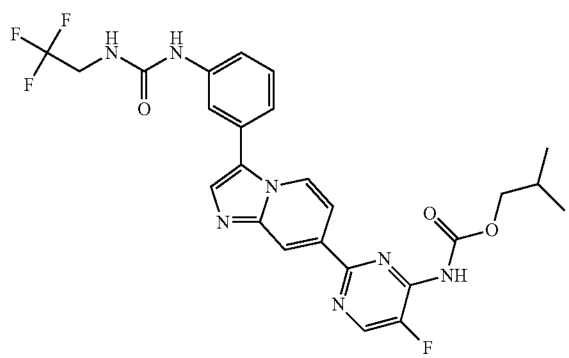 [SMILES: CC(C)COC(=O)Nc1nc(-c2ccn3c(-c4cccc(NC(=O)NCC(F)(F)F)c4)cnc3c2)ncc1F] | Rt: 3.71<br>MH+: 546<br>Method: 1 | 232<br>(K)<br>215.2<br>(DSC) |

-continued

| Comp. No. | Ex. | Compound structure | LCMS Data | MP ° C. |
|---|---|---|---|---|
| 274 | 2.16 | 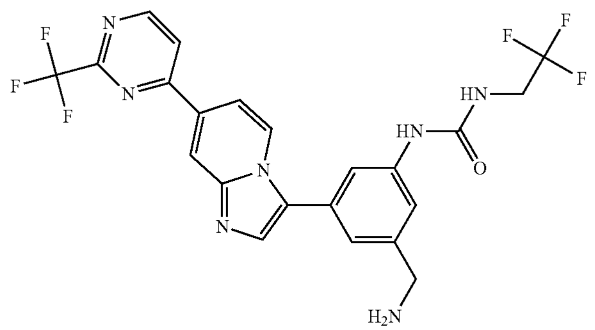 [SMILES: NCc1cc(NC(=O)NCC(F)(F)F)cc(-c2cnc3cc(-c4ccnc(C(F)(F)F)n4)ccn23)c1] | Rt: 2.91<br>MH+: 510<br>Method: 1 | 190.14<br>(DSC) |
| 275 | 2.17 | 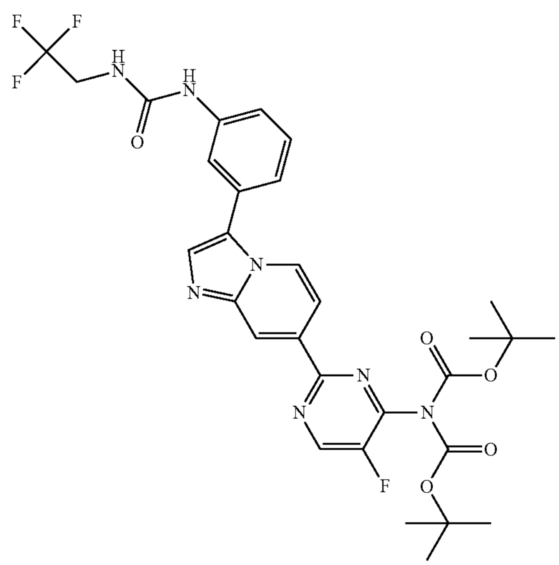 | Rt: 3.09<br>MH+: 474<br>Method: 1 | 157.79<br>(DSC) |
| 276 | 2.18 | 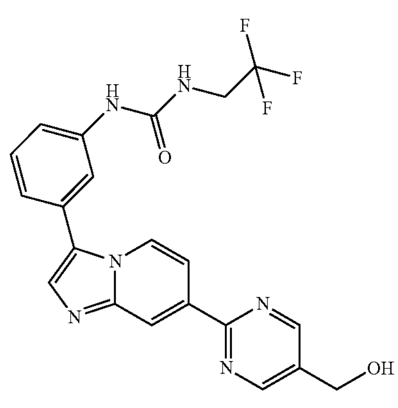 [SMILES: O=C(NCC(F)(F)F)Nc1cccc(-c2cnc3cc(-c4ncc(CO)cn4)ccn23)c1] | Rt: 2088<br>MH+: 443<br>Method: 1 | 222<br>(K) |

| Comp. No. | Ex. | Compound structure | LCMS Data | MP °C. |
|---|---|---|---|---|
| 277 | 2.19 | (structure) .1.16 HCl .3.31 H₂O | Rt: 2.35 MH⁺: 472 Method: 1 | >260 (K) |
| 278 | 2.20 | (structure) | Rt: 2.93 MH⁺: 457 Method: 1 | 224 (K) |
| 279 | 2.21 | (structure) | Rt: 2.49 MH⁺: 524 Method: 1 | >350 (K) |

| Comp. No. | Ex. | Compound structure | LCMS Data | MP ° C. |
|---|---|---|---|---|
| 280 | 2.1a | 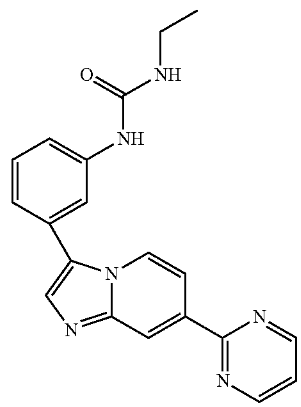 [SMILES: CCNC(=O)Nc1cccc(-c2cnc3cc(-c4ncccn4)ccn23)c1] | Rt: 2.73<br>MH+: 359<br>Method: 1 | 145 (K) |
| 281 | 2.1a | 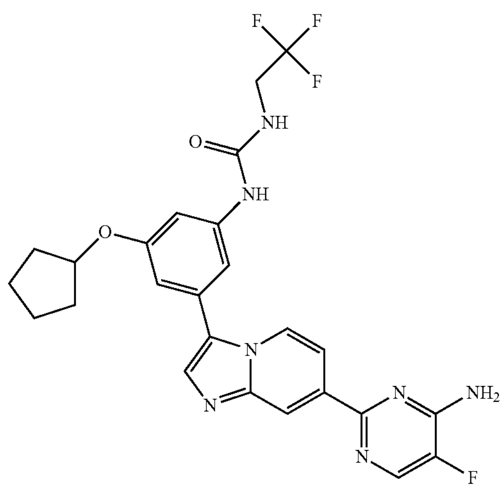 [SMILES: Nc1nc(-c2ccn3c(-c4cc(NC(=O)NCC(F)(F)F)cc(OC5CCCC5)c4)cnc3c2)ncc1F] | Rt: 3.73<br>MH+: 530<br>Method: 1 | 190.6 (K) |
| 282 | 2.1a | 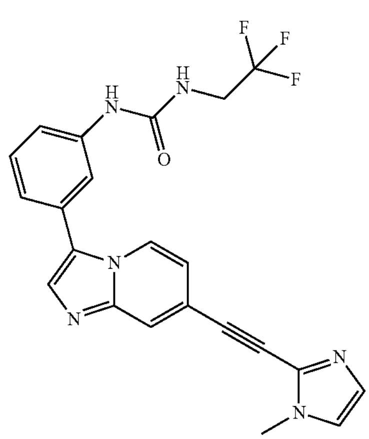 [SMILES: Cn1ccnc1C#Cc1ccn2c(-c3cccc(NC(=O)NCC(F)(F)F)c3)cnc2c1] | | 222 (K) |

-continued

| Comp. No. | Ex. | Compound structure | LCMS Data | MP ° C. |
|---|---|---|---|---|
| 283 | 2.1a | 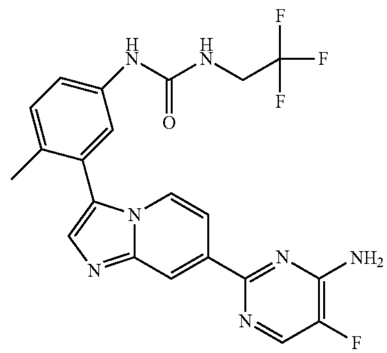 [SMILES: Cc1ccc(NC(=O)NCC(F)(F)F)cc1-c1cnc2cc(-c3ncc(F)c(N)n3)ccn12] | Rt: 3.15<br>MH+: 460<br>Method: 1 | >260 (K) |
| 284 | 2.1a | 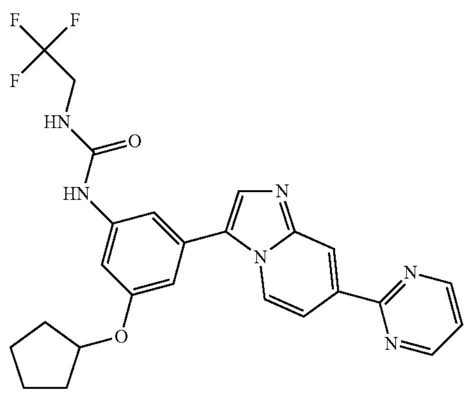 [SMILES: O=C(NCC(F)(F)F)Nc1cc(OC2CCCC2)cc(-c2cnc3cc(-c4ncccn4)ccn23)c1] | Rt: 3.86<br>MH+: 497<br>Method: 1 | 215.47 (K) |
| 285 | 2.1a | 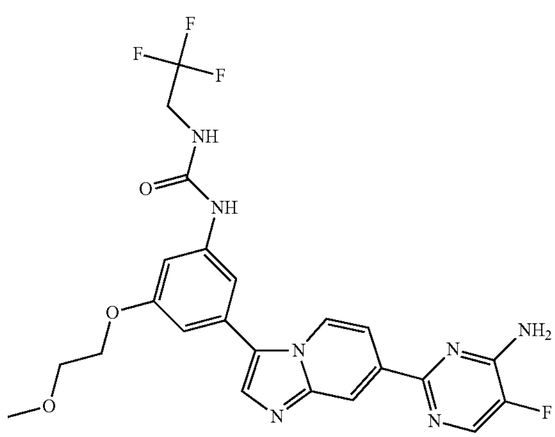 [SMILES: COCCOc1cc(NC(=O)NCC(F)(F)F)cc(-c2cnc3cc(-c4ncc(F)c(N)n4)ccn23)c1] | Rt: 3.08<br>MH+: 520<br>Method: 1 | 226.2 (K) |
| 286 | 2.1a | 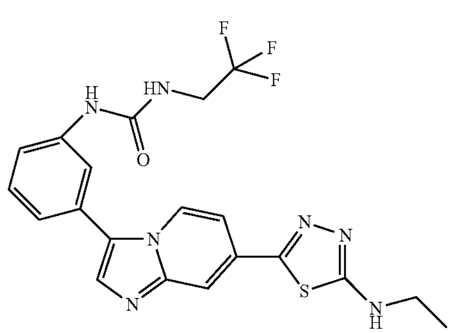 [SMILES: CCNc1nnc(-c2ccn3c(-c4cccc(NC(=O)NCC(F)(F)F)c4)cnc3c2)s1] | Rt: 3.02<br>MH+: 462<br>Method: 1 | >260 (K) |

-continued

| Comp. No. | Ex. | Compound structure | LCMS Data | MP ° C. |
|---|---|---|---|---|
| 287 | 2.1a | 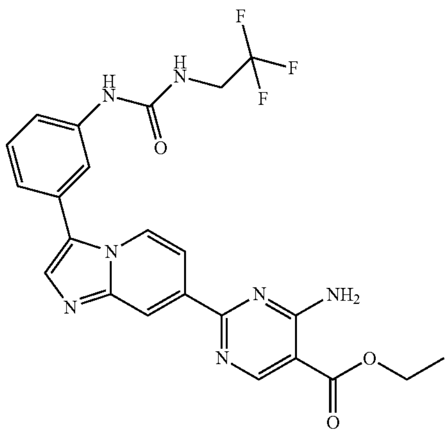 | Rt: 3.52<br>MH+: 500<br>Method: 1 | >260 (K) |
| 288 | 2.1a | 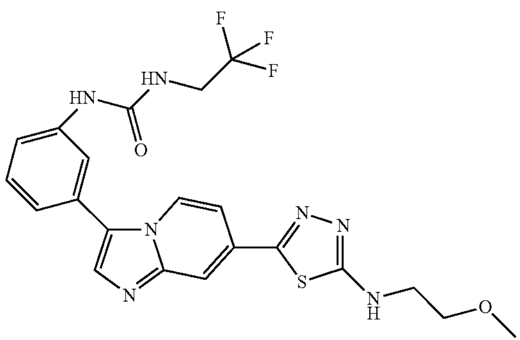 [SMILES: COCCNc1nnc(-c2ccn3c(-c4cccc(NC(=O)NCC(F)(F)F)c4)cnc3c2)s1] | Rt: 2.94<br>MH+: 492<br>Method: 1 | >260 (K) |
| 289 | 2.1a | 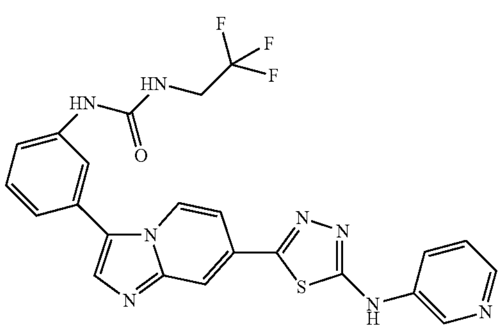 [SMILES: O=C(NCC(F)(F)F)Nc1cccc(-c2cnc3cc(-c4nnc(Nc5cccnc5)s4)ccn23)c1] | Rt: 3.03<br>MH+: 471<br>Method: 1 | >260 (K) |
| 290 | 2.1a | 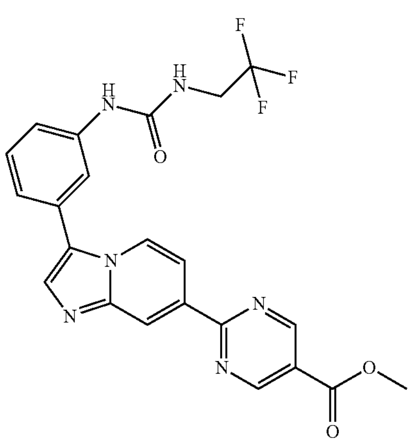 [SMILES: COC(=O)c1cnc(-c2ccn3c(-c4cccc(NC(=O)NCC(F)(F)F)c4)cnc3c2)nc1] | Rt: 3.43<br>MH+: 471<br>Method: 1 | >260 (K) |

-continued

| Comp. No. | Ex. | Compound structure | LCMS Data | MP ° C. |
|---|---|---|---|---|
| 291 | 2.1a | 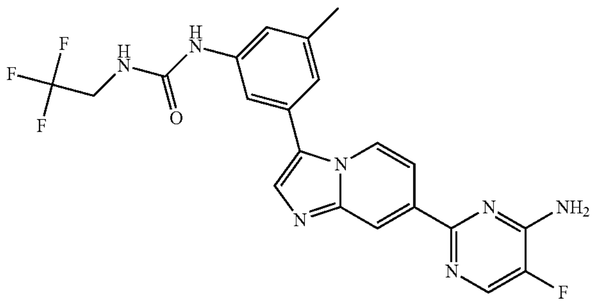 [SMILES: Cc1cc(NC(=O)NCC(F)(F)F)cc(-c2cnc3cc(-c4ncc(F)c(N)n4)ccn23)c1] | Rt: 3.22<br>MH+: 460<br>Method: 1 | 188<br>(K) |
| 292 | 2.1a | 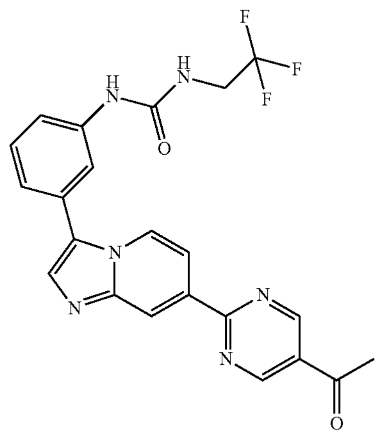 [SMILES: CC(=O)c1cnc(-c2ccn3c(-c4cccc(NC(=O)NCC(F)(F)F)c4)cnc3c2)nc1] | Rt: 3.23<br>MH+: 455<br>Method: 1 | >260<br>(K) |
| 293 | 2.1a | 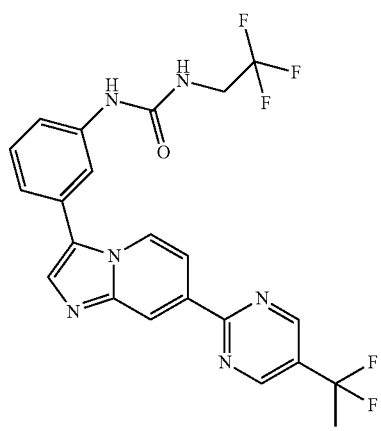 [SMILES: CC(F)(F)c1cnc(-c2ccn3c(-c4cccc(NC(=O)NCC(F)(F)F)c4)cnc3c2)nc1] | Rt: 3.61<br>MH+: 477<br>Method: 1 | 258<br>(K)<br>235.40<br>(DSC) |
| 294 | 2.1a | 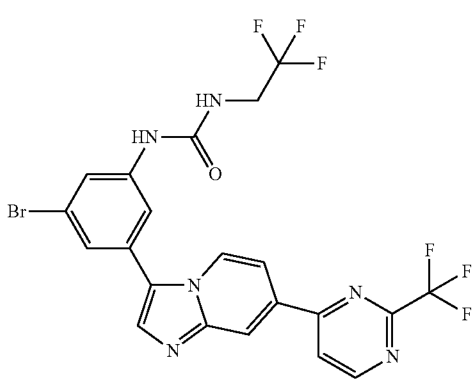 [SMILES: O=C(NCC(F)(F)F)Nc1cc(Br)cc(-c2cnc3cc(-c4ccnc(C(F)(F)F)n4)ccn23)c1] | Rt: 3.97<br>MH+: 559<br>Method: 1 | 210<br>(K) |

-continued

| Comp. No. | Ex. | Compound structure | LCMS Data | MP °C |
|---|---|---|---|---|
| 295 | 2.1a | 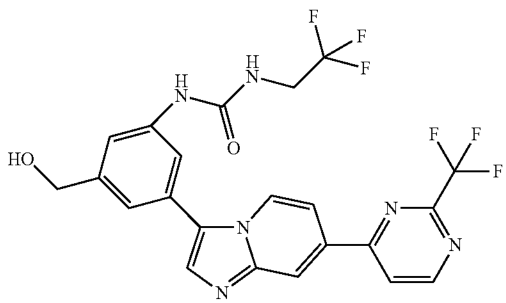 [SMILES: O=C(NCC(F)(F)F)Nc1cc(CO)cc(-c2cnc3cc(-c4ccnc(C(F)(F)F)n4)ccn23)c1] | Rt: 3.23<br>MH⁺: 511<br>Method: 1 | 240<br>(K) |
| 296 | 2.1a | 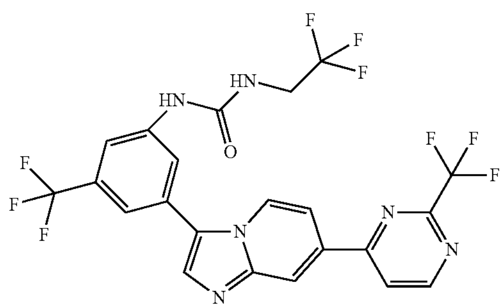 [SMILES: O=C(NCC(F)(F)F)Nc1cc(-c2cnc3cc(-c4ccnc(C(F)(F)F)n4)ccn23)cc(C(F)(F)F)c1] | Rt: 3.98<br>MH⁺: 549<br>Method: 1 | 219.27<br>(DSC) |
| 297 | 2.1a | 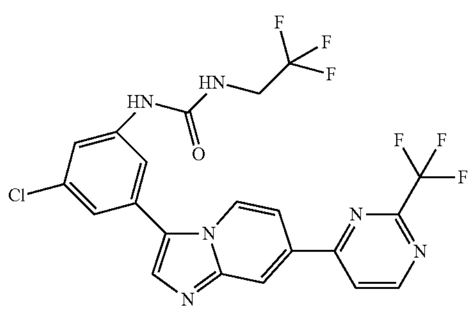 [SMILES: O=C(NCC(F)(F)F)Nc1cc(Cl)cc(-c2cnc3cc(-c4ccnc(C(F)(F)F)n4)ccn23)c1] | Rt: 3.92<br>MH⁺: 515<br>Method: 1 | 252<br>(K) |
| 298 | 2.1a | 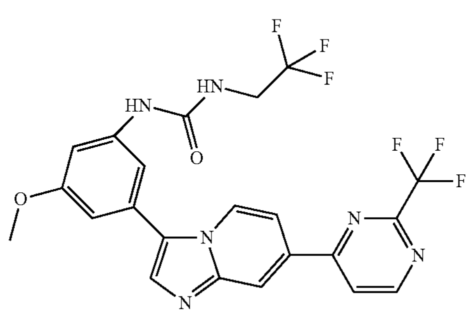 [SMILES: COc1cc(NC(=O)NCC(F)(F)F)cc(-c2cnc3cc(-c4ccnc(C(F)(F)F)n4)ccn23)c1] | Rt: 4.21<br>MH⁺: 511<br>Method: 1 | 250<br>(K) |

-continued

| Comp. No. | Ex. | Compound structure | LCMS Data | MP °C. |
|---|---|---|---|---|
| 299 | 2.1a | 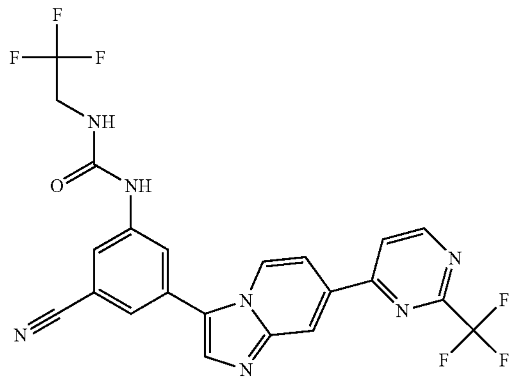 [SMILES: N#Cc1cc(NC(=O)NCC(F)(F)F)cc(-c2cnc3cc(-c4ccnc(C(F)(F)F)n4)ccn23)c1] | Rt: 3.65<br>MH+: 506<br>Method: 1 | >250 (K)<br>267.18 (DSC) |
| 300 | B1a | 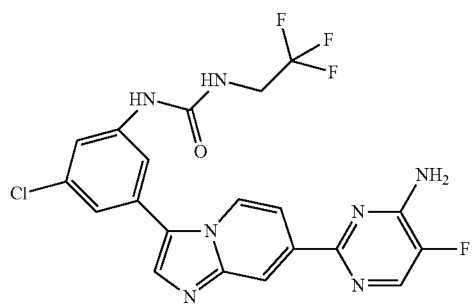 [SMILES: Nc1nc(-c2ccn3c(-c4cc(Cl)cc(NC(=O)NCC(F)(F)F)c4)cnc3c2)ncc1F] | Rt: 3.41<br>MH+: 480<br>Method: 1 | 116 (K) |
| 301 | 2.1a | 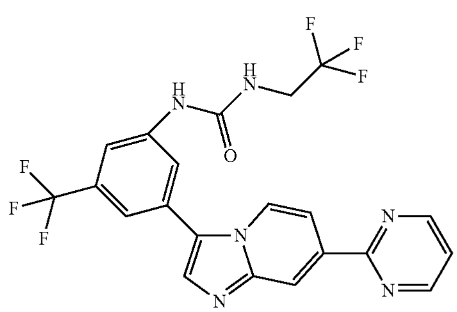 [SMILES: O=C(NCC(F)(F)F)Nc1cc(-c2cnc3cc(-c4ncccn4)ccn23)cc(C(F)(F)F)c1] | Rt: 3.62<br>MH+: 481<br>Method: 1 | 212.60 (DSC) |
| 302 | 2.1a | 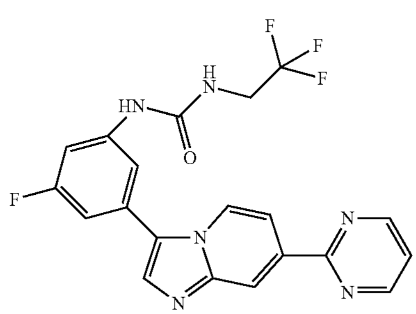 [SMILES: O=C(NCC(F)(F)F)Nc1cc(F)cc(-c2cnc3cc(-c4ncccn4)ccn23)c1] | Rt: 3.33<br>MH+: 431<br>Method: 1 | 238.63 (DSC) |

| Comp. No. | Ex. | Compound structure | LCMS Data | MP ° C. |
|---|---|---|---|---|
| 303 | 2.1a | 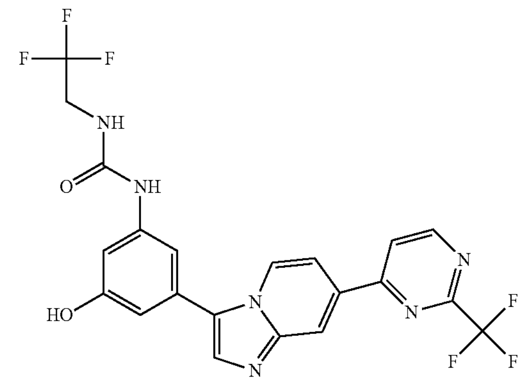 [SMILES: O=C(NCC(F)(F)F)Nc1cc(O)cc(-c2cnc3cc(-c4ccnc(C(F)(F)F)n4)ccn23)c1] | Rt: 3.31<br>MH+: 497<br>Method: 1 | 258.89<br>(DSC) |
| 304 | 2.1a | 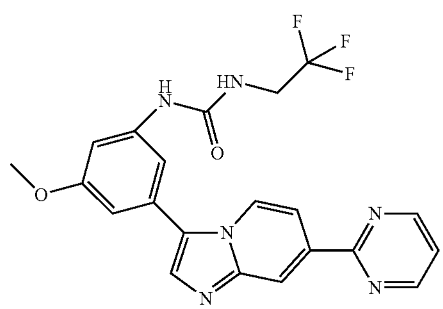 [SMILES: COc1cc(NC(=O)NCC(F)(F)F)cc(-c2cnc3cc(-c4ncccn4)ccn23)c1] | Rt: 3.2<br>MH+: 443<br>Method: 1 | 224<br>(DSC) |
| 305 | 2.1a | 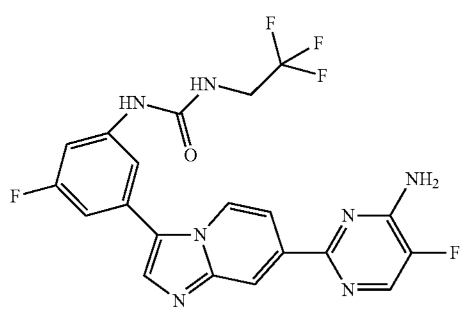 [SMILES: Nc1nc(-c2ccn3c(-c4cc(F)cc(NC(=O)NCC(F)(F)F)c4)cnc3c2)ncc1F] | Rt: 3.25<br>MH+: 464<br>Method: 1 | 256.73<br>(DSC) |
| 306 | 2.1a | 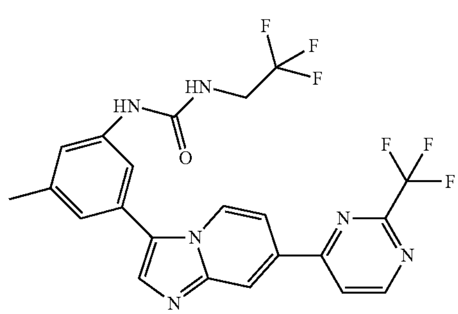 [SMILES: Cc1cc(NC(=O)NCC(F)(F)F)cc(-c2cnc3cc(-c4ccnc(C(F)(F)F)n4)ccn23)c1] | Rt: 3.77<br>MH+: 495<br>Method: 1 | 254.03<br>(DSC) |

-continued

| Comp. No. | Ex. | Compound structure | LCMS Data | MP °C. |
|---|---|---|---|---|
| 307 | 2.1a | 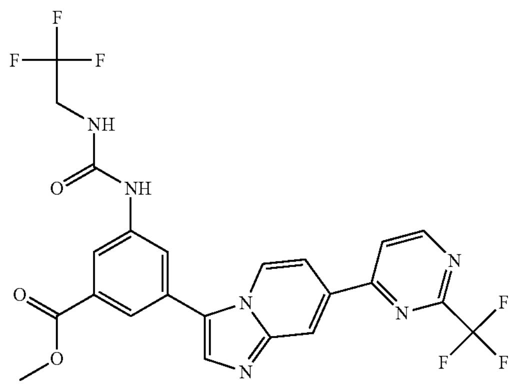 [SMILES: COC(=O)c1cc(NC(=O)NCC(F)(F)F)cc(-c2cnc3cc(-c4ccnc(C(F)(F)F)n4)ccn23)c1] | Rt: 3.69 MH+: 539 Method: 1 | >250 (K) 248.89 (DSC) |
| 308 | 2.1a | 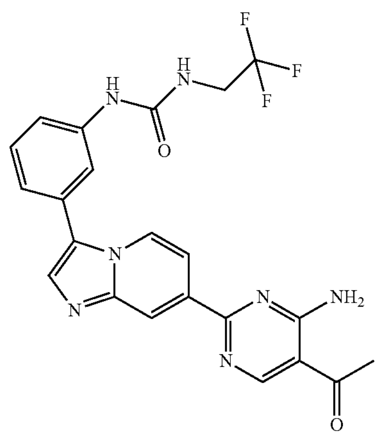 [SMILES: CC(=O)c1cnc(-c2ccn3c(-c4cccc(NC(=O)NCC(F)(F)F)c4)cnc3c2)nc1N] | Rt: 3.15 MH+: 470 Method: 1 | 219 (K) |
| 309 | 2.1a | 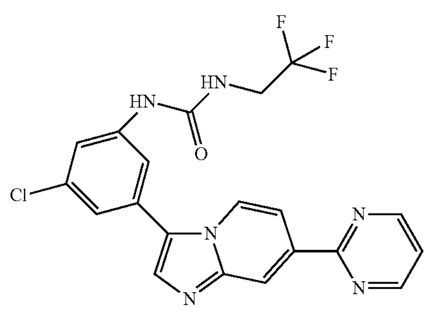 [SMILES: O=C(NCC(F)(F)F)Nc1cc(Cl)cc(-c2cnc3cc(-c4ncccn4)ccn23)c1] | Rt: 3.51 MH+: 447 Method: 1 | 210 (DSC) |
| 310 | 2.1a | 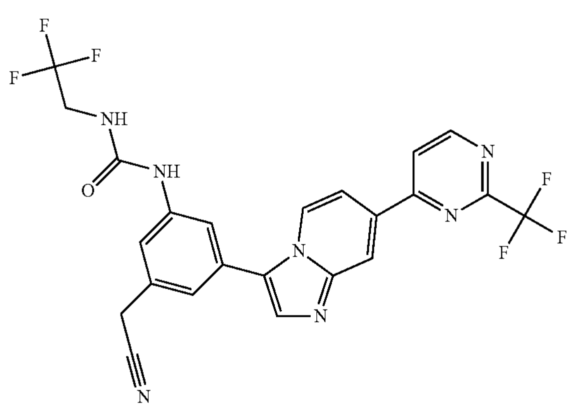 [SMILES: N#CCc1cc(NC(=O)NCC(F)(F)F)cc(-c2cnc3cc(-c4ccnc(C(F)(F)F)n4)ccn23)c1] | -Rt: 3.53 MH+: 520 Method: 1 | 249.94 (DSC) |

-continued

| Comp. No. | Ex. | Compound structure | LCMS Data | MP °C. |
|---|---|---|---|---|
| 311 | 2.2a | 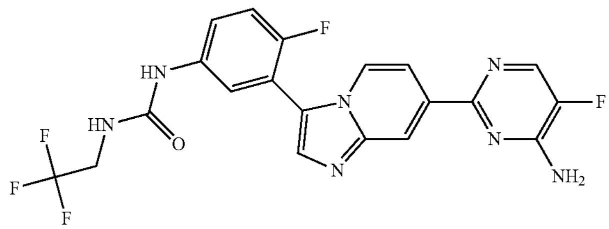 [SMILES: Nc1nc(-c2ccn3c(-c4cc(NC(=O)NCC(F)(F)F)ccc4F)cnc3c2)ncc1F] | Rt: 3.25 MH+: 464 Method: 1 | 235.4 (K) |
| 312 | 2.2a | 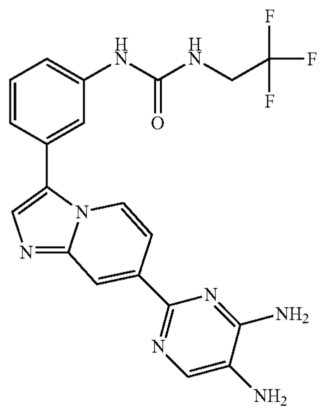 [SMILES: Nc1cnc(-c2ccn3c(-c4cccc(NC(=O)NCC(F)(F)F)c4)cnc3c2)nc1N] | Rt: 2.68 MH+: 443 Method: 1 | — |
| 313 | 2.2a | 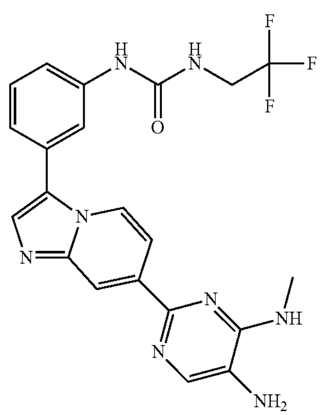 [SMILES: CNc1nc(-c2ccn3c(-c4cccc(NC(=O)NCC(F)(F)F)c4)cnc3c2)ncc1N] | Rt: 2.9 MH+: 457 Method: 1 | 171.6 (DSC) |
| 314 | 2.2a | 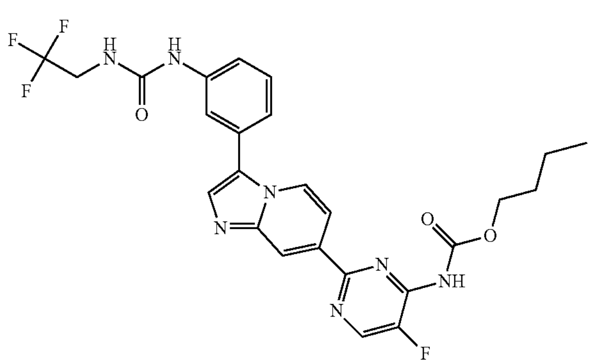 [SMILES: CCCCOC(=O)Nc1nc(-c2ccn3c(-c4cccc(NC(=O)NCC(F)(F)F)c4)cnc3c2)ncc1F] | Rt: 3.72 MH+: 546 Method: 1 | 192 (K) |

-continued

| Comp. No. | Ex. | Compound structure | LCMS Data | MP ° C. |
|---|---|---|---|---|
| 315 | 2.2a | 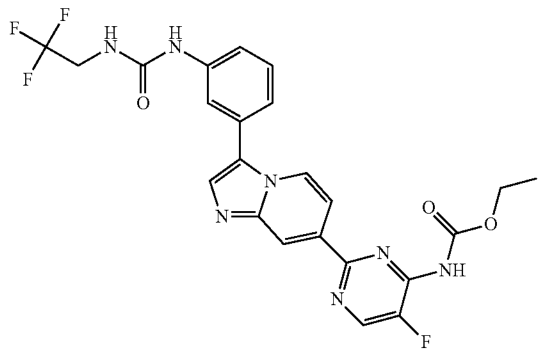 [SMILES: CCOC(=O)Nc1nc(-c2ccn3c(-c4cccc(NC(=O)NCC(F)(F)F)c4)cnc3c2)ncc1F] | Rt: 3.33<br>MH+: 518<br>Method: 1 | 201<br>(K) |
| 316 | 2.2a | 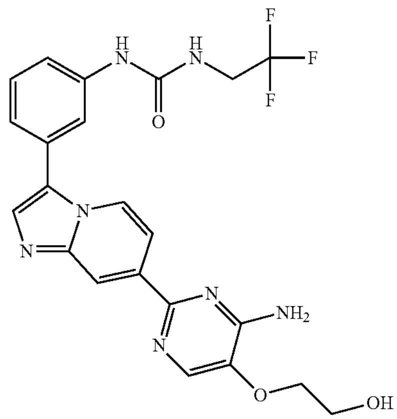 [SMILES: Nc1nc(-c2ccn3c(-c4cccc(NC(=O)NCC(F)(F)F)c4)cnc3c2)ncc1OCCO] | Rt: 2.74<br>MH+: 488<br>Method: 1 | — |
| 317 | 2.2a | | Rt: 3.13<br>MH+: 524<br>Method: 1 | 290<br>(DSC) |
| 317 | 2.2a | | — | — |

-continued

| Comp. No. | Ex. | Compound structure | LCMS Data | MP ° C. |
|---|---|---|---|---|
| 318 | 2.3a | 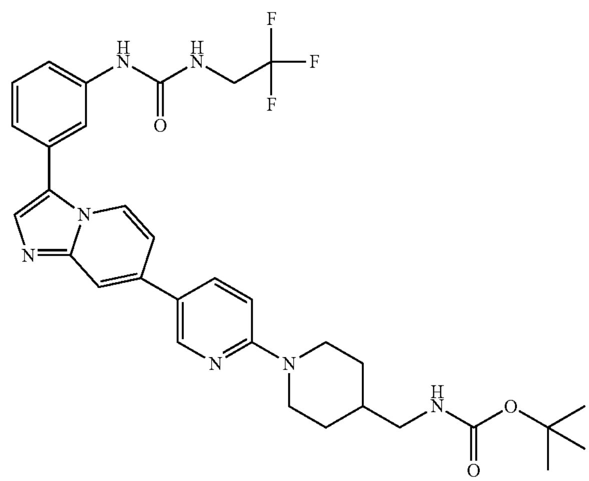 [SMILES: CC(C)(C)OC(=O)NCC1CCN(c2ccc(-c3ccn4c(-c5cccc(NC(=O)NCC(F)(F)F)c5)cnc4c3)cn2)CC1] | — | 213 (K) |
| 319 | 2.4 | 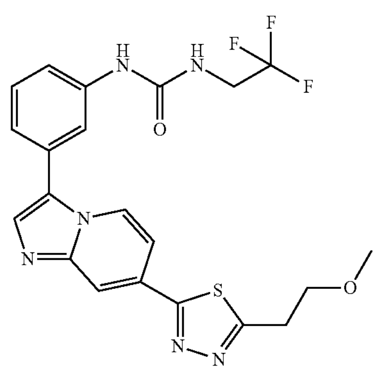 [SMILES: COCCc1nnc(-c2ccn3c(-c4cccc(NC(=O)NCC(F)(F)F)c4)cnc3c2)s1] | Rt: 3.01<br>MH+: 477<br>Method: 1 | 198 (K) |
| 320 | 2.4 | 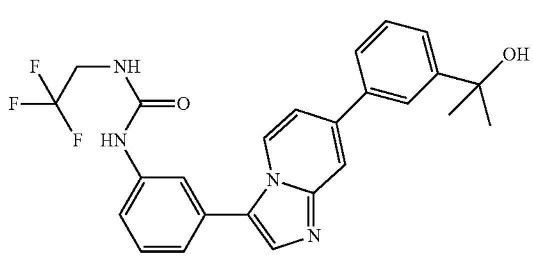 [SMILES: CC(C)(O)c1cccc(-c2ccn3c(-c4cccc(NC(=O)NCC(F)(F)F)c4)cnc3c2)c1] | Rt: 3.37<br>MH+: 469<br>Method: 1 | 207 (K) |
| 321 | 2.4 | 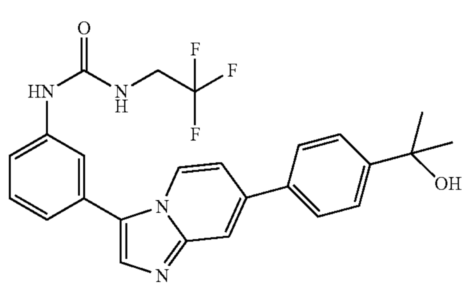 [SMILES: CC(C)(O)c1ccc(-c2ccn3c(-c4cccc(NC(=O)NCC(F)(F)F)c4)cnc3c2)cc1] | Rt: 3.34<br>MH+: 469<br>Method: 1 | 230 (K) |

-continued

| Comp. No. | Ex. | Compound structure | LCMS Data | MP °C. |
|---|---|---|---|---|
| 322 | 2.4 | 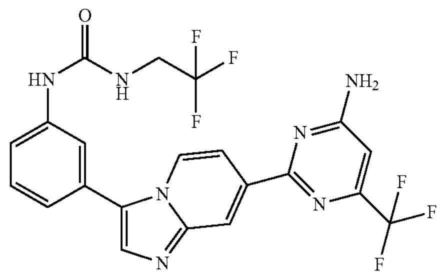 [SMILES: Nc1cc(C(F)(F)F)nc(-c2ccn3c(-c4cccc(NC(=O)NCC(F)(F)F)c4)cnc3c2)n1] | Rt: 3.51<br>MH+: 496<br>Method: 1 | 193 (K) |
| 323 | 2.4 | 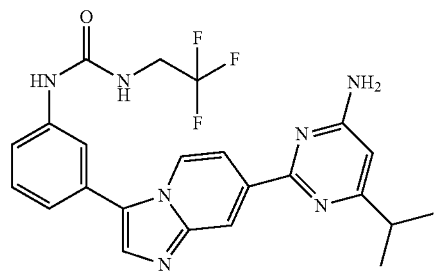 [SMILES: CC(C)c1cc(N)nc(-c2ccn3c(-c4cccc(NC(=O)NCC(F)(F)F)c4)cnc3c2)n1] | Rt: 3.52<br>MH+: 470<br>Method: 1 | 162 (K) |
| 324 | 2.4 | 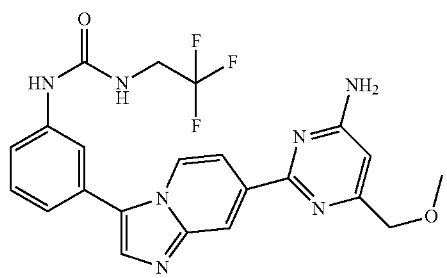 [SMILES: COCc1cc(N)nc(-c2ccn3c(-c4cccc(NC(=O)NCC(F)(F)F)c4)cnc3c2)n1] | Rt: 3.04<br>MH+: 472<br>Method: 1 | >250 (K) |
| 325 | 2.9 | 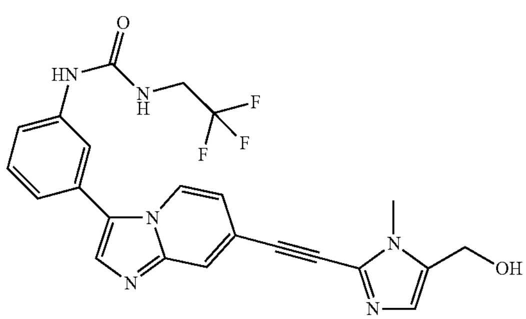 [SMILES: Cn1c(CO)cnc1C#Cc1ccn2c(-c3cccc(NC(=O)NCC(F)(F)F)c3)cnc2c1] | Rt: 2.79<br>MH+: 469<br>Method: 1 | >260 (K) |
| 326 | 2.11a | 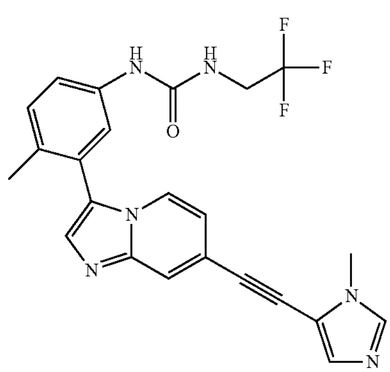 [SMILES: Cc1ccc(NC(=O)NCC(F)(F)F)cc1-c1cnc2cc(C#Cc3cncn3C)ccn12] | Rt: 3.02<br>MH+: 453<br>Method: 1 | 228-230 (K) |

-continued

| Comp. No. | Ex. | Compound structure | LCMS Data | MP ° C. |
|---|---|---|---|---|
| 327 | 2.11a | 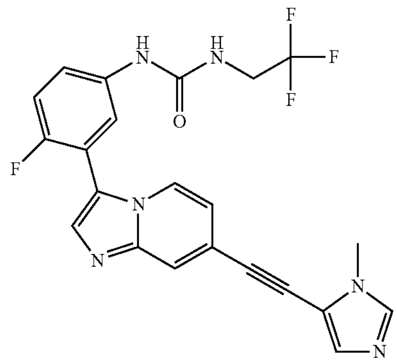 [SMILES: Cn1cncc1C#Cc1ccn2c(-c3cc(NC(=O)NCC(F)(F)F)ccc3F)cnc2c1] | Rt: 3.06<br>MH+: 457<br>Method: 1 | 214<br>(DSC) |
| 328 | 2.12b | 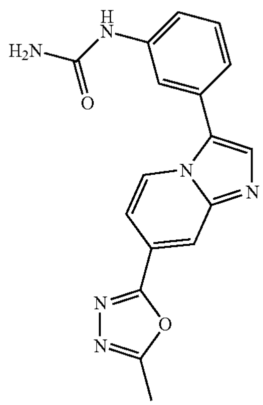 [SMILES: Cc1nnc(-c2ccn3c(-c4cccc(NC(N)=O)c4)cnc3c2)o1] | Rt: 2.16<br>MH+: 335<br>Method: 1 | 237<br>(DSC) |
| 329 | 2.12c | 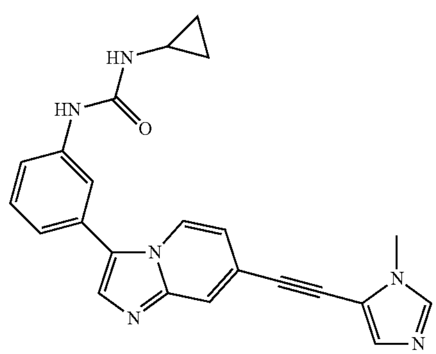 [SMILES: Cn1cncc1C#Cc1ccn2c(-c3cccc(NC(=O)NC4CC4)c3)cnc2c1] | Rt: 2.69<br>MH+: 397<br>Method: 1 | 222<br>(K) |
| 330 | 2.14c | 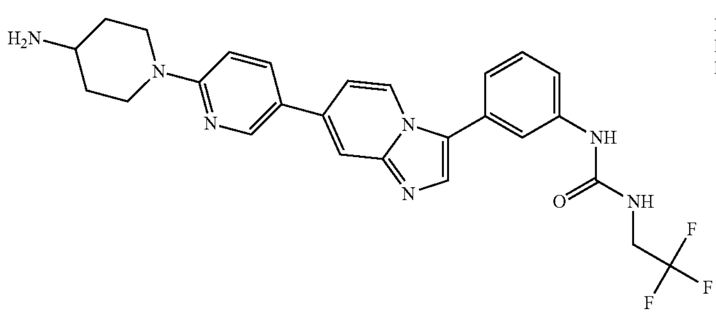 [SMILES: NC1CCN(c2ccc(-c3ccn4c(-c5cccc(NC(=O)NCC(F)(F)F)c5)cnc4c3)cn2)CC1] | Rt: 2.71<br>MH+: 510<br>Method: 1 | 164<br>(K) |

-continued

| Comp. No. | Ex. | Compound structure | LCMS Data | MP ° C. |
|---|---|---|---|---|
| 331 | 1.15 | 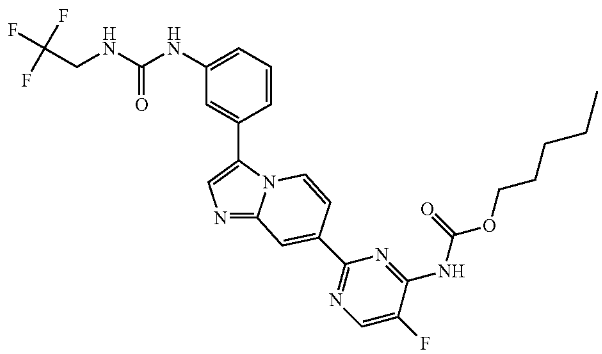 [SMILES: CCCCCOC(=O)Nc1nc(-c2ccn3c(-c4cccc(NC(=O)NCC(F)(F)F)c4)cnc3c2)ncc1F] | Rt: 3.91 MH+: 560 Method: 1 | 200 (K) 188.14 (DSC) |
| 332 | 2.18 | 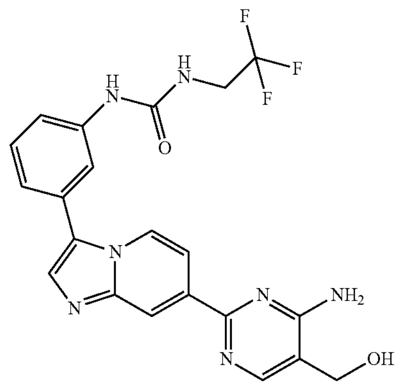 [SMILES: Nc1nc(-c2ccn3c(-c4cccc(NC(=O)NCC(F)(F)F)c4)cnc3c2)ncc1CO] | Rt: 2.71 MH+: 458 Method: 1 | 235 (K) |
| 333 | 2.19 | 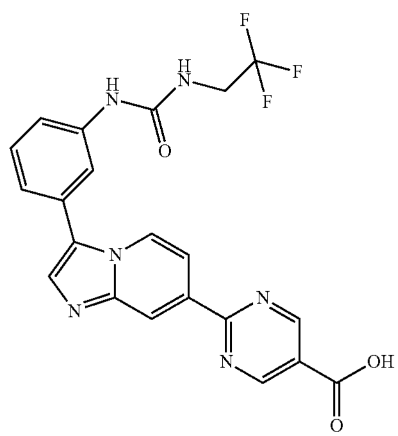 [SMILES: O=C(NCC(F)(F)F)Nc1cccc(-c2cnc3cc(-c4ncc(C(=O)O)cn4)ccn23)c1] | Rt: 2.35 MH+: 457 Method: 1 | 222 (K) |
| 334 | 2.21 | 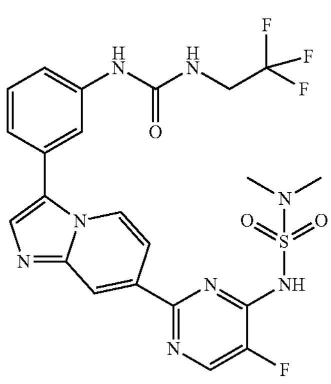 [SMILES: CN(C)S(=O)(=O)Nc1nc(-c2ccn3c(-c4cccc(NC(=O)NCC(F)(F)F)c4)cnc3c2)ncc1F] | Rt: 2.63 MH+: 553 Method: 1 | 179 (K) |

-continued

| Comp. No. | Ex. | Compound structure | LCMS Data | MP ° C. |
|---|---|---|---|---|
| 335 | 2.4 | 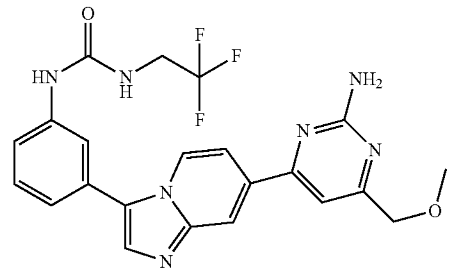 [SMILES: COCc1cc(-c2ccn3c(-c4cccc(NC(=O)NCC(F)(F)F)c4)cnc3c2)nc(N)n1] | Rt: 2.94<br>MH+: 472<br>Method: 1 | >250<br>(K) |
| 336 | 2.2b | 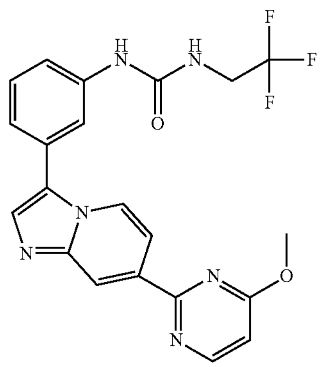 [SMILES: COc1ccnc(-c2ccn3c(-c4cccc(NC(=O)NCC(F)(F)F)c4)cnc3c2)n1] | | 226-228<br>(K) |
| 337 | 159B | 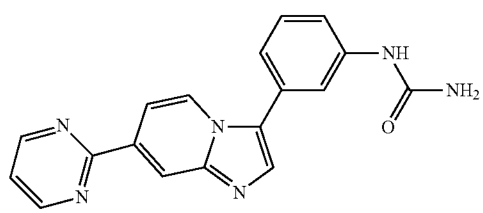 [SMILES: NC(=O)Nc1cccc(-c2cnc3cc(-c4ncccn4)ccn23)c1] | | |

Biological Assays

FGFR3 and PDGFR In Vitro Kinase Inhibitory Activity Assays

Enzymes (from Upstate) were prepared at 2× final concentration in 1× kinase assay buffer (Table 1). Enzymes were then incubated with test compounds, biotinylated Flt3 substrate (biotin –DNEYFYV) (Cell Signalling Technology Inc.) and ATP. The reaction was allowed to proceed for 3 hours (FGFR3) or 2.5 hrs (PDGFR-beta) at room temperature on a plate shaker at 900 rpm before being stopped with 20 µl of 35 mM EDTA, pH 8 (FGFR3) or 55 mM EDTA, pH 8 (PDGFR-beta). Twenty pl of 5× detection mix (50 mM HEPES pH 7.5, 0.1% BSA, 2 nM Eu-anti-pY (PY20) (PerkinElmer) 15 nM SA-XL665 (Cisbio) for FGFR3 and 50 mM HEPES, pH 7.5, 0.5 M KF, 0.1% BSA, 11.34 nM Eu-anti-pY (PT66) (PerkinElmer), 94 nM SA-XL665 (Cisbio) for PDGFR-beta) was then added to each well and the plate sealed and incubated at room temperature for one hour on a plate shaker at 900 rpm. The plate was then read on a Packard Fusion plate reader in TRF mode.

TABLE 1

Final assay conditions for FGFR3 and PDGFR assay

| Enzyme | 1 × Assay Buffer | Flt3 substrate concentration | ATP concentration |
|---|---|---|---|
| FGFR3 | A | 0.125 µM | 8 µM |
| PDGFR-beta | B | 0.15 µM | 30 µM |

Kinase Assay buffers were:

A: 50 mM HEPES pH 7.5, 6 mM MnCl$_2$, 1 mM DTT, 0.1% TritonX-100

B: 20 mM MOPS pH 7.0, 10 mM MnCl$_2$, 0.01% Triton X-100, 1 mM DTT, 0.1 mM Sodium orthovanadate Examples 1-125 have IC50 values less than 10 µM against FGFR3 or provide at least 50% inhibition of the FGFR3 activity at a concentration of 10 µM. Examples 1-116 and 118-125 have IC$_{50}$ values less than 1 µM against FGFR3 or provide at least 50% inhibition of the FGFR3 activity at a concentration of 1 µM.

Preferred compounds of the invention (for example Examples 1-24, 26-76, 78-83, 85-114, 118 and 120-125) have IC50 values of less than 0.1 µM against FGFR3 or provide at least 50% inhibition of the FGFR3 activity at a concentration of 0.1 µM in the FGFR3 assay.

FGFR3Data for the compounds of the invention in the above assays are provided in Table A3.

VEGFR2 In Vitro Kinase Inhibitory Activity Assay

Assay reactions containing VEGFR2 enzyme (purchased from Upstate), and 250 µM Poly (Glu,Tyr) 4:1 substrate (Cis-Bio) in 50 mM HEPES, pH 7.5, 6 mM $MnCl_2$, 1 mM DTT, 0.01% TritonX-100, 5 µM ATP (2.8 Ci/mmol) were set up in the presence of compound. Reactions were stopped after 15 minutes by adding an excess of phosphoric acid. The reaction mixture was then transferred to a Millipore MAPH filter plate where the peptide binds and the unused ATP is washed away. After washing, scintillant was added and the incorporated activity measured by scintillation counting on a Packard Topcount.

VEGFR2 in vitro Kinase Inhibitory Activity Assays

VEGFR2 (from Upstate), prepared at 2× final concentration, was incubated with test compounds, biotinylated Flt3 substrate (biotin-VASSDNEYFYVDF) (Cell Signalling Technology Inc.) and ATP in the appropriate assay buffer (Table 1). The reaction was allowed to proceed for 1 hour at room temperature on a plate shaker at 700 rpm before being stopped with 35 mM EDTA, pH 8 (VEGFR2). 5× detection mix (50 mM HEPES, pH 7.5, 0.1% BSA, 11.34 nM Eu-anti-pY (PY20), 187.5 nM SA-XL665) was then added to each well and the plate sealed and incubated at room temperature for one hour on a plate shaker at 700 rpm. The plate was then read on a Packard Fusion plate reader or a BMG Pherastar both in TRF mode.

TABLE 2

Final assay conditions for VEGFR2 assay

| Enzyme | 1 × Assay Buffer | Flt3 substrate concentration | ATP concentration |
|---|---|---|---|
| VEGFR2 | B | 0.5 µM | 0.5 µM |

Kinase Assay buffers were:

B: 50 mM HEPES pH 7.5, 6 mM $MnCl_2$, 1 mM DTT, 0.01% TritonX-100, 0.1 mM Sodium orthovanadate VEGFR2Data for the compounds of the invention in the above assay are provided in Table A3.

FGFR1, FGFR2, FGFR4, VEGFR1 and VEGFR3 In Vitro Kinase Inhibitory Activity Assays The inhibitory activity against FGFR1, FGFR2, FGFR4, VEGFR1 and VEGFR3 can be determined at Upstate Discovery Ltd. Enzymes were prepared at 10× final concentration in enzyme buffer (20 mM MOPS, pH 7.0, 1 mM EDTA, 0.1% B-mercaptoethanol, 0.01% Brij-35, 5% glycerol, 1 mg/ml BSA). Enzymes were then incubated in assay buffer with various substrates and $^{33}$P-ATP (~500 cpm/µmol) as described in the table. The reaction was initiated by the addition of Mg/ATP. The reaction was allowed to proceed for 40 minutes at room temperature before being stopped with 5 µl of a 3% phosphoric acid solution. Ten µl of the reaction mix was transferred to either a filtermatA or P30 filtermat and washed three times in 75 mM phosphoric acid and once in methanol before being dried for scintillation counting.

Compounds were tested at the concentrations of the assay reagents as detailed below in duplicate against all kinases and the percent activity compared to control was calculated. Where inhibition was high an $IC_{50}$ was determined.

| Enzyme | Assay Buffer | Substrate | ATP Concentration (µM) |
|---|---|---|---|
| FGFR1 | A | 250 µM KKKSPGEYVNIEFG | 200 µM |
| FGFR2 | B | 0.1 mg/ml poly(Glu, Tyr) 4:1 | 90 µM |
| FGFR4 | C | 0.1 mg/ml poly(Glu, Tyr) 4:1 | 155 µM |
| VEGFR1 | A | 250 µM KKKSPGEYVNIEFG | 200 µM |
| VEGFR3 | A | 500 µM GGEEEEYFELVKKKK | 200 µM |

Enzyme buffer A: 8 mM MOPS, pH 7.0, 0.2 mM EDTA, 10 mM MgAcetate

Enzyme buffer B: 8 mM MOPS, pH 7.0, 0.2 mM EDTA, 2.5 mM MnCl2, 10 mM MgAcetate

Enzyme buffer C: 8 mM Mops, pH 7.0, 0.2 mM EDTA, 10 mM $MnCl_2$, 10 mM MgAcetate.

Cell-Based PERK ELISA Method

LP-1 or JIM-1 multiple myeloma cells were seeded in 96 well plates at 1×10$^6$ cells/ml in 200u1 per well in serum free media. HUVEC cells were seeded at 2.5×10$^5$ cells /ml and allowed to recover for 24 h prior to transfer to serum free media. Cells were incubated for 16 h at 37° C. prior to the addition of a test compound for 30 minutes. Test compounds were administered at a 0.1% final DMSO concentration. Following this 30 minute incubation a FGF-1/Heparin (FGF-1 at 100 ng/mlfinal and Heparin at 100 ug/ml) mixture or VEGF$^{165}$ (100 ug/ml) was added to each of the wells for a further 5 minutes. The media was removed and 50u1 ERK ELISA lysis buffer (R and D Systems DuoSet ELISA for pERK and Total ERK #DYC-1940E, DYC-1018E) added. ELISA plates and standards were prepared according to the standard DuoSet protocols and the relative amounts of pERK to total ERK in each sample calculated according to the standard curve.

Data for the compounds of the invention in the above assay are provided in Table A3.

In particular, compounds of the invention were tested against the LP-1 cell line (DSMZ no.: ACC 41) derived from human multiple myeloma. Many compounds of the invention (eg. Examples 1-24, 26-38, 40-53, 56, 58-70, 72-76, 78-83, 85-87, 89-102, 114 and 116) were found to have IC50 values of less than 20 µM in this assay and some compounds (for example Examples 1-19, 21-24, 26-38, 40-53, 56, 58-64, 66-70, 72-76, 78-83, 85-87, 89-94, 96-102 and 114) have IC50 values of less than 1 µM or provide at least 50% inhibition at a concentration of 1 µM.

HUVEC Cell Based Selectivity Assays

HUVEC cells were seeded in 6 well plates at 1×10$^6$ cells/well and allowed to recover for 24 h. They were transferred to serum free media for 16 hours prior to treatment with test compound for 30 minutes in 0.1% DMSO final. Following compound incubation FGF-1 (100 ng/ml) and Heparin (100 ug/ml) or VEGF$^{165}$ (100 ng/ml) were added for 5 minutes. Media was removed, cells washed with ice-cold PBS and lysed in 100 ul TG lysis buffer (20 mM Tris, 130 nM NaCl, 1% Triton-X-100, 10% Glycerol, protease and phosphatase inhibitors, pH 7.5). Samples containing equivalent amounts of protein were made up with LDS sample buffer and run on SDS PAGE followed by western blotting for a number of downstream VEGFR and FGFR pathway targets including phospho-FGFR3, phospho-VEGFR2 and phospho-ERK1/2. The western blot can then be analysed by visual inspection or densitometry.

In vivo Models of Hypertension

A number of animal models exist to measure the potential hypertensive effects of small molecule inhibitors. They can be classified into two main types; indirect and direct measurements. The most common indirect method is the cuff technique. Such methods have the advantages of being non-invasive and as such can be applied to a larger group of experimental animals however the process allows only intermittent sampling of blood pressure and requires the animal to be restrained in some way. Application of restraint can stress the animal and means that changes in blood pressure attributable to a specific drug effect can be hard to pick up.

Direct methodologies include those that make use of radio telemetry technology or via indwelling catheters connected to externally mounted transducers. Such methods require a high level of technical expertise for the initial surgery involved in implantation and costs involved are high. However a key advantage is that they allow continuous monitoring of blood pressure without restraint over the time period of the experiment. These methods are reviewed in Kurz et al (2005), Hypertension. 45, 299-310.

hERG Activity

The activity of compound of formula (I) against the hERG K+ion channel can be determined using the assay described in the article by M. H. Bridgland-Taylor et al., *Journal of Pharmacological and Toxicological Methods*, 54 (2006), 189-199. This IonWorks™ HT hERG screening assay is performed commercially by Upstate (Millipore) using the PrecisION™ hERG-CHO cell line.

Determination of Potency against Cytochrome P450

The potency of the compound of formula (I) against cytochrome P450 (CYP450) enzymes 1A2, 2C9, 2C19, 3A4 and 2D6 can be determined using the Pan Vera Vivid CYP450 screening kits available from Invitrogen (Paisley, UK). The CYP450s are supplied in the form of baculosomes containing the CYP450 and NADPH reductase and the substrates used are the fluorescent Vivid substrates. The final reaction mixtures are as follows:

1A2
100 mM potassium phosphate, pH 8, 1% acetonitrile, 2 µM 1A2 Blue vivid substrate, 100 µM NADP+, 4 nM CYP450 1A2, 2.66 mM glucose-6-phosphate, 0.32 U/ml glucose-6-phosphate dehydrogenase.

2C9
50 mM potassium phosphate, pH 8, 1% acetonitrile, 2 µM Green vivid substrate, 100 µM NADP+, 8 nM CYP450 2C9, 2.66 mM glucose-6-phosphate, 0.32 U/ml glucose-6-phosphate dehydrogenase.

2C19
50 mM potassium phosphate, pH 8, 1% acetonitrile, 8 µM Blue vivid substrate, 100 µM NADP+, 4 nM CYP450 2C19, 2.66 mM glucose-6-phosphate, 0.32 U/ml glucose-6-phosphate dehydrogenase.

3A4
100 mM potassium phosphate, pH 8, 1% acetonitrile, 10 µM 3A4 Blue vivid substrate, 100 µM NADP+, 2.5 nM CYP450 3A4, 2.66 mM glucose-6-phosphate, 0.32 U/ml glucose-6-phosphate dehydrogenase.

2D6
100 mM potassium phosphate, pH 8, 1% acetonitrile, 5 µM 2D6 Blue vivid substrate, 100 µM NADP+, 16 nM CYP450 2D6, 2.66 mM glucose-6-phosphate, 0.32 U/ml glucose-6-phosphate dehydrogenase.

Fluorescence is monitored for 20 minutes at 30 second intervals on a Molecular Devices Gemini fluorescence plate reader. The excitation and emission wavelengths are 390 nm and 460 nm for 1A2, 2C19 and 3A4, 390 nm and 485 nm for 2D6 and 485 nm and 530 nm for 2C9. Initial rates are determined from progress curves.

The test compound is made up in methanol or acetonitirile and tested against the CYP450s at a concentration of 10 µM.

The preferred compounds of formula (I) have an $IC_{50}$ greater than 10 µM against 1A2, 2C9, 2C19, 3A4 and 2D6.

Ba/F3-TEL-FGFR3 & Ba/F3 (WT) cell proliferation assays Stably transfected Ba/F3-TEL-FGFR3 cells were plated out into black 96-well tissue culture plates with clear bottoms in RPMI medium containing 10% FBS and 0.25 mg/ml G418 at a density of $5 \times 10^3$ cells/well (200 µl per well). The parental wild-type Ba/F3 cells (DSMZ no.: ACC 300) were plated out into black 96-well tissue culture plates with clear bottoms in RPMI medium containing 10% FBS and 2 ng/ml mouse IL-3 (R&D Systems) at a density of $2.5 \times 10^3$ cells/well (200 µl per well). Plates were placed in an incubator overnight before adding the compounds the following day. Dilutions of compounds were made in DMSO starting at 10 mM and were diluted into the wells to give a final DMSO concentration of 0.1% in assay. Compounds were left on the cells for 72 hours before the plates were removed from the incubator and 20 µl of Alamar Blue™ (Biosource) was added to each well. Plates were placed in the incubator for 4-6 hours before reading plates at 535 nm (excitation)/590 nm (emission) on a Fusion plate reader (Packard). Where inhibition is high an $IC_{50}$ can be determined.

Data for the compounds of the invention in the above assay are provided in Table A3.

In particular, compounds of the invention were tested against the Ba/F3-TEL-FGFR3 cell line. Many compounds of the invention (eg. Examples 1-4, 6-10, 12-19, 21-24, 26, 28-38, 40-47, 49-53, 56, 58-80, 84-87, 89-94, 96-104, 106-108, 110-111, 113-114, 118-120, 122 and 124-125) were found to have IC50 values of less than 20 µM in this assay and some compounds (for example Examples 1-4, 6-10, 12-19, 21-24, 26, 28-30, 32-34, 36-38, 40-42, 44-45, 47, 49-53, 56, 58-67, 69-76, 78-80, 85-87, 89-93, 96-104, 106-108, 110-111, 113-114, 118-120, 122 and 124) have IC50 values of less than 1 µM or provide at least 50% inhibition at a concentration of 1 µM. Many compounds are more active against Ba/F3-TEL-FGFR3 cell line than the parental wild-type Ba/F3 cell line, for example over 5-fold, in particular 10 fold more active against Ba/F3-TEL-FGFR3 cell line than the parental wild-type Ba/F3 cell line.

TABLE A3

| Eg | FGFR3 IC50(µM)* or % I | VEGFR2 IC50(µM)* or % I | BaF3 WT prolif (µM) | BaF3-TEL-FGFR3 prolif (µM) | LP-1 pERK ELISA (µM) |
|---|---|---|---|---|---|
| 114 | 0.0135 | 0.427 | 0.65 | 0.5 | 0.047 |
| 115 | 0.295 | 8.45 | | | 0% at 10 µM |
| 1 | 0.000830 | 0.0451 | 0.92 | 0.087 | 0.0074 |
| 2 | 0.000850 | 0.0410 | 12% at 10 µM | 0.23 | 62% at 0.003 µM |
| 3 | 0.00120 | 0.0370 | 0.16 | 0.095 | 0.0088 |
| 4 | 0.000570 | 0.0106 | 51% at 10 µM | 0.8 | 0.077 |
| 5 | 0.00115 | 0.0669 | 0% at 10 µM | 0% at 10 µM | 45% at 1 µM |
| 6 | 0.000545 | 0.0134 | 0.87 | 0.062 | 0.0092 |

TABLE A3-continued

| Eg | FGFR3 IC50(μM)* or % I | VEGFR2 IC50(μM)* or % I | BaF3 WT prolif (μM) | BaF3-TEL-FGFR3 prolif (μM) | LP-1 pERK ELISA (μM) |
|---|---|---|---|---|---|
| 7 | 0.000550 | 0.0200 | 0.86 | 0.095 | 0.0063 |
| 8 | 0.00110 | 0.0249 | 0.45 | 0.24 | 0.012 |
| 116 | 0.225 | 1.34 | | | 1.9 |
| 9 | 0.00400 | 0.0812 | 6.40 | 0.797 | 0.14 |
| 10 | 50% at 0.001 μM | 0.0390 | 2.3 | 0.3 | 0.047 |
| 11 | 0.0104 | 0.220 | | | 0.032 |
| 12 | 0.00110 | 0.0133 | 3.7 | 0.24 | 0.041 |
| 13B | 0.00446 | 0.113 | 44% at 10 μM | 0.48 | 0.031 |
| 14 | 0.0110 | 0.195 | 1.4 | 0.29 | 0.1 |
| 15 | 0.000640 | 0.0115 | 2.6 | 0.25 | 0.011 |
| 16 | 0.0242 | 0.950 | 0.83 | 0.23 | 0.11 |
| 17 | 0.00396 | 0.0650 | 0.056 | 0.047 | 0.044 |
| 18 | 0.0133 | 0.198 | 1.4 | 0.19 | 0.095 |
| 19 | 0.0247 | 0.349 | 0.55 | 0.57 | 0.13 |
| 20 | 0.00736 | 0.110 | | | 1.1 |
| 21 | 0.00629 | 0.0804 | 0% at 10 μM | 38% at 10 μM | 0.41 |
| 22 | 0.000704 | 0.00785 | 1.1 | 0.048 | 0.0044 |
| 23 | 58% at 0.001 μM | 0.00945 | 0% at 10 μM | 0.42 | 0.63 |
| 24 | 0.00800 | 0.0893 | 2.20% at 10 μM | 0.63 | 0.57 |
| 25 | 0.545 | 5.09 | | | |
| 26 | 0.0169 | 0.480 | 0.77 | 0.31 | 0.27 |
| 27 | 0.0130 | 0.270 | | | 0.52 |
| 28 | 0.0218 | 0.139 | 35% at 10 μM | 0.92 | 0.17 |
| 29 | 0.0167 | 0.269 | 3.1 | 0.77 | 0.12 |
| 30 | 0.00926 | 0.145 | 0.13 | 0.062 | 0.045 |
| 31 | 0.0800 | 2.60 | 0% at 10 μM | 2.6 | 0.82 |
| 32 | 0.000613 | 0.0112 | 0.67 | 0.012 | 0.014 |
| 33 | 0.00350 | 0.0510 | 0.32 | 0.14 | 0.057 |
| 34 | 0.00305 | 0.0599 | 0% at 10 μM | 0.12 | 0.013 |
| 35 | 0.0375 | 0.757 | 0% at 10 μM | 1.4 | 0.33 |
| 36 | 0.000820 | 0.00906 | 0% at 10 μM | 0.38 | 0.065 |
| 37 | 0.000807 | 0.0126 | 3.3% at 10 μM | 0.73 | 0.29 |
| 38 | 0.000610 | 0.0130 | 0.44 | 0.022 | 0.0086 |
| 39 | 0.00130 | 0.0475 | | | |
| 40 | 0.000612 | 0.0106 | 4 | 0.24 | 0.046 |
| 41 | 0.00105 | 0.0160 | 2.8 | 0.072 | 0.025 |
| 42 | 0.0270 | 0.593 | 1.1 | 0.41 | 0.27 |
| 43 | 0.0103 | 0.285 | 0% at 10 μM | 2.7 | 0.35 |
| 44 | 0.000582 | 0.0110 | 0.9 | 0.045 | 0.022 |
| 45 | 0.000603 | 0.0103 | 0% at 10 μM | 0.58 | 0.35 |
| 46 | 0.0384 | 1.20 | 27% at 10 μM | 1.2 | 0.18 |
| 47 | 0.000542 | 0.0155 | 0.68 | 0.021 | 0.0098 |
| 48 | 0.0220 | >30.0 | 0% at 10 μM | 0% at 10 μM | 0.13 |
| 49 | 0.00225 | 0.0944 | 0.29 | 0.085 | 0.017 |
| 50 | 39% at 0.0003 μM | | 0.71 | 0.029 | 0.021 |
| 51 | 0.00174 | 0.0315 | 10% at 10 μM | 0.04 | 0.015 |
| 52 | 0.00245 | 0.0370 | 51% at 10 μM | 0.91 | 0.33 |
| 53 | 0.000675 | 0.00785 | 4.1 | 0.028 | 0.023 |
| 54 | 0.00125 | 0.0182 | | | |
| 55 | 38% at 0.0003 μM | 0.0180 | | | |
| 56 | 0.00460 | 0.230 | 4.6 | 0.16 | 0.021 |
| 57 | 0.0341 | 0.351 | | | 40% at 3 μM |
| 58 | 0.0150 | 0.420 | 0.7 | 0.25 | 0.077 |
| 59 | 0.0235 | 0.628 | 5.1 | 0.41 | 0.1 |
| 60 | 0.0145 | 0.350 | 0% at 10 μM | 0.27 | 0.087 |
| 61 | 0.00412 | 0.0775 | 15% at 10 μM | 0.053 | 0.064 |
| 62 | 0.00370 | 0.0339 | 1.1 | 0.089 | 0.11 |
| 63 | 50.5% at 0.0003 μM | 0.00800 | 1.4 | 0.092 | 0.05 |
| 64 | 0.00495 | 0.125 | 2.5 | 0.13 | 0.049 |
| 65 | 0.00774 | 0.110 | 8.3% at 10 μM | 0.83 | 1.3 |
| 66 | 43% at 0.0003 μM | 0.0130 | 1.9 | 0.046 | 0.069 |
| 67 | 0.000569 | 0.0143 | 2.1 | 0.69 | 0.84 |
| 68 | 0.00280 | 0.0390 | 36% at 10 μM | 1.5 | 0.53 |
| 69 | 0.00125 | 0.0508 | 4.6 | 0.26 | 0.096 |
| 70 | 0.000740 | 0.0208 | 2.7 | 0.15 | 0.027 |
| 71 | 0.00110 | 0.0550 | 1.5 | 0.16 | |
| 72 | 0.00145 | 0.0475 | 32% at 10 μM | 0.76 | 0.3 |
| 73 | 60% at 0.001 μM | 0.0270 | 3.7 | 0.13 | 0.12 |
| 74 | 51.5% at 0.0003 μM | 0.0130 | 0.82 | 0.096 | 0.018 |
| 75 | 0.000535 | 0.00890 | 32% at 10 μM | 0.03 | 0.63 |
| 117 | 1.15 | 1.50 | | | |
| 76 | 0.000730 | 0.0130 | 26% at 10 μM | 0.49 | 0.51 |
| 77 | 0.100 | 2.70 | 53% at 10 μM | 4.3 | |
| 78 | 0.00279 | 0.0589 | 0.15 | 0.11 | 0.017 |
| 79 | 0.00375 | 0.0734 | 0.4 | 0.16 | 0.035 |
| 80 | 0.000890 | 0.0177 | 0% at 10 μM | 0.08 | 0.039 |

TABLE A3-continued

| Eg | FGFR3 IC50(μM)* or % I | VEGFR2 IC50(μM)* or % I | BaF3 WT prolif (μM) | BaF3-TEL-FGFR3 prolif (μM) | LP-1 pERK ELISA (μM) |
|---|---|---|---|---|---|
| 81 | 0.000447 | 0.0149 | 20% at 3 μM | 0.14 | 0.028 |
| 82 | 0.000715 | 0.0125 | | | 0.0067 |
| 83 | 0.00154 | 0.0325 | | | 0.012 |
| 84 | 0.0789 | 1.64 | 1.4 | 1 | |
| 85 | 0.00489 | 0.118 | 0.17 | 0.16 | 0.065 |
| 86 | 0.00628 | 0.150 | 1.9 | 0.32 | 0.04 |
| 87 | 0.0130 | 0.230 | 0.41 | 0.26 | 0.072 |
| 88 | 0.00787 | 0.130 | 0% at 10 μM | 0.4% at 10 μM | 16% at 10 μM |
| 89 | 0.00830 | 0.190 | 0.097 | 0.085 | 0.073 |
| 90 | 0.0124 | 0.235 | 0.76 | 0.44 | 0.092 |
| 91 | 0.000840 | 0.0269 | 0.1 | 0.072 | 0.0079 |
| 92 | 0.000940 | 0.0290 | 0.53 | 0.26 | 0.11 |
| 93 | 0.00904 | 0.240 | 0.043 | 0.033 | 0.065 |
| 94 | 0.00475 | 0.0834 | 5.8 | 3.1 | 0.95 |
| 95 | 0.000530 | 0.0120 | 0% at 10 μM | 21% at 10 μM | 3.4 |
| 96 | 0.00175 | 0.0504) | 1.7 | 0.19 | 0.0063 |
| 97 | 0.00130 | 0.0869 | 0.44 | 0.11 | 0.0081 |
| 98 | 0.00255 | 0.0583 | 0.7 | 0.22 | 0.02 |
| 99 | 0.00419 | 0.180 | 0.32 | 0.24 | 0.063 |
| 100 | 0.0140 | 0.329 | 0.97 | 0.47 | 0.09 |
| 101 | 0.00280 | 0.0790 | 0.16 | 0.064 | 0.055 |
| 102 | 0.00482 | 0.268 | 2.3 | 0.0283 | 0.0939 |
| 103 | 0.00370 | 0.130 | 0.078 | 0.057 | |
| 104 | 0.0228 | 0.270 | 0.4 | 0.21 | |
| 118 | 0.0135 | 0.330 | 0.88 | 0.19 | |
| 105 | 0.00620 | 0.180 | 16% at 10 μM | 2.7% at 10 μM | |
| 106 | 0.00139 | 0.0214 | 0.41 | 0.033 | |
| 107 | 0.00268 | 0.0324 | 0.89 | 0.1 | |
| 108 | 0.00130 | 0.0490 | 46% at 10 μM | 0.095 | 1.2 |
| 109 | 0.0185 | 0.398 | 32 | 0.67 | |
| 110 | 0.00635 | 0.313 | 43% at 10 μM | 0.25 | 0.0917 |
| 111 | 0.000890 | 0.0315 | 0.180 | 0.027 | 0.016 |
| 112 | 49% at 0.3 μM | | | | |
| 113 | 0.000610 | 0.00779 | 1.4 | 0.01 | 0.016 |
| 119 | 0.0927 | 1.38 | 23% at 3 μM | 0.55 | |
| 120 | 0.0130 | 0.383 | 1.1 | 0.3 | |
| 121 | 0.0862 | 0.847 | | | |
| 122 | 0.000704 | 0.0185 | 2.4 | 0.041 | |
| 123 | 0.00120 | 0.0134 | 8.90 | 1.61 | |
| 124 | 0.000789 | 0.0191 | 0.27 | 0.047 | 0.024 |
| 125 | 0.0657 | 1.01 | 2.1 | 1.3 | |
| 146 | 0.0917 | 51% at 1 μM | 1.2% at 10 μM | 0% at 10 μM | |
| 142 | 0.0171 | 0.455 | 1.1 | 0.25 | |
| 126 | 0.00268 | 0.0384 | 3.7% at 10 μM | 1 | 0.98 |
| 152 | 0.000930 | 0.0153 | 10% at 10 μM | 0.54 | 3.3 |
| 130 | 0.00230 | 0.0394 | 26% at 10 μM | 1.5 | |
| 150 | 0.0440 | 0.581 | 1.7 | 0.77 | |
| 136 | 0.0600 | 0.465 | 0.44 | 0.47 | |
| 135 | 0.00355 | 0.189 | 0.51 | 0.21 | |
| 139 | 0.0349 | 0.980 | 3.6 | 1.9 | |
| 145 | 0.000560 | 0.0135 | 0.82 | 0.077 | |
| 144 | 0.00240 | 0.0353 | 3.6 | 0.19 | 0.13 |
| 131 | 0.00166 | 0.0247 | 2.9% at 10 μM | 0.78 | |
| 160 | 0.0503 | 49.5% at 1 μM | | | |
| 132 | 0.000710 | 0.0159 | 22.9% at 10 μM | 0.0936 | 0.172 |
| 140 | 0.0345 | 0.455 | 7.1% at 10 μM | 0% at 10 μM | |
| 133 | 0.000484 | 0.00973 | 34% at 3 μM; 31% at 10 μM | 0.099 | 0.0714 |
| 149 | 0.00288 | 0.157 | | | |
| 141 | 0.0179 | 0.448 | 0.042 | 0.043 | 0.11 |
| 161 | 0.00248 | 0.0973 | 0.15 | 0.077 | 0.01 |
| 162 | 0.0228 | 59% at 1 μM | 37% at 3 μM | 0.403 | 0.091 |
| 264 | 0.0288 | 0.319 | 25% at 10 μM | 0.63 | 0.31 |
| 336 | 0.00944 | 0.453 | 0.46 | 0.13 | 0.074 |
| 280 | 0.0973 | 1.38 | 74% at 3 μM | 0.62 | 0.35 |
| 163 | 0.0294 | 0.680 | 38% at 3 μM; 11% at 10 μM | 1.45 | 0.22 |
| 164 | 0.0190 | 0.588 | 4.2 | 0.95 | 0.26 |
| 329 | 0.0480 | 0.298 | 31% at 10 μM | 11% at 10 μM | 0.23 |
| 165A/B | 0.00305 | 56.5% at 0.3 μM | 8% at 10 μM | 0.17 | 0.042 |
| 166 | 0.0349 | 0.574 | 0% at 10 μM | 3.7 | 0.29 |
| 167 | 0.00576 | 0.235 | 0% at 10 μM | 56% at 3 μM | 60% at 10 μM |
| 137 | 0.00420 | 0.114 | 23% at 10 μM | 0.12 | 0.034 |
| 168 | 0.00697 | 0.332 | 0% at 10 μM | 0.39 | 0.43 |
| 328 | 0.0265 | 0.686 | 34% at 3 μM | 3 | |
| 159 | 0.210 | 2.18 | | | |

TABLE A3-continued

| Eg | FGFR3 IC50(μM)* or % I | VEGFR2 IC50(μM)* or % I | BaF3 WT prolif (μM) | BaF3-TEL-FGFR3 prolif (μM) | LP-1 pERK ELISA (μM) |
|---|---|---|---|---|---|
| 337 | 0.0353 | 0.706 | 23% at 10 μM | 1 | 1.5 |
| 268 | 0.00489 | 0.0740 | 23.5% at 3 μM | 0.278 | 1.83 |
| 319 | 0.000643 | 0.0239 | 0.15 | 0.019 | 0.012 |
| 265 | 4.10 | >30.0 | | | |
| 327 | 0.00820 | 0.199 | 30% at 10 μM | 0.25 | 0.31 |
| 169 | 0.0151 | 0.520 | | | |
| 170 | 0.0598 | 1.11 | 14% at 3 μM | 0.82 | |
| 148 | 0.00345 | 0.131 | | | |
| 171 | 0.00920 | 0.340 | 16% at 1.0 μM | 0.26 | |
| 172 | 0.00375 | 0.0630 | 3.4 | 0.068 | |
| 173 | 0.00393 | 0.354 | 29.5% at 3 μM; 22% at 10 μM | 0.249 | 0.052 |
| 250 | 0.00460 | 38.7% at 0.3 μM | 1.73 | 0.27 | 0.075 |
| 174 | 0.0133 | 0.449 | 1.5 | 0.79 | 0.49 |
| 138 | 0.00786 | 0.260 | 36% at 3 μM | 0.17 | 0.038 |
| 175 | 0.00583 | 0.419 | 10 | 0.45 | 0.077 |
| 176 | 0.0230 | 0.391 | 59% at 10 μM | 0.6 | 0.33 |
| 154 | 0.00228 | 0.0431 | 5.6 | 0.38 | 0.086 |
| 177 | 0.0440 | >1.00 | 16% at 10 μM | 46% at 10 μM | 47% at 10 μM |
| 267 | 0.00965 | 0.0954 | 55% at 10 μM | 0.35 | |
| 158 | 0.0430 | 0.173 | 2.9 | 0.31 | |
| 178 | 0.00391 | 0.480 | 4.52 | 0.036 | 0.018 |
| 179 | 0.0920 | >10.0 | 22% at 1 μM | 15% at 1 μM | |
| 180 | 0.0260 | 1.20 | 42% at 10 μM | 0.67 | |
| 181 | 0.0115 | 0.351 | 0.49 | 0.14 | 0.046 |
| 182 | 0.0555 | 0.647 | 10 | 0.46 | 2.5 |
| 183 | 0.00420 | 0.150 | 0.29 | 0.075 | 0.028 |
| 184 | 0.00950 | 0.240 | 22% at 10 μM | 44% at 10 μM | |
| 263 | 0.00100 | 0.0190 | 21% at 1 μM | 0.074 | |
| 311 | 0.0340 | 20% at 0.978 μM | 2% at 3 μM; 32% at 10 μM | 1.2 | |
| 157 | 0.230 | 0.700 | 38% at 10 μM | 1.6 | |
| 185 | 0.00756 | 0.171 | 0% at 3 μM | 0.55 | 0.14 |
| 269 | 0.0120 | 0.260 | 0% at 3 μM | 2.6 | |
| 326 | 0.0420 | 45% at 0.978 μM | 18% at 10 μM | 2.1 | |
| 281 | 42% at 0.1 μM | >100 > 10.0 | 1.4 | | |
| 186 | 0.00218 | 0.0954 | 0.32 | 0.073 | 0.019 |
| 187 | 0.00670 | 0.200 | 1.8 | 0.16 | |
| 188 | 0.00590 | 0.180 | 0.43 | 0.16 | 0.09 |
| 189 | 0.0110 | 0.260 | 3.4 | 0.63 | |
| 190 | 0.0820 | 3.80 | 35% at 3 μM | 0% at 3 μM | |
| 282 | 0.00480 | 0.133 | 2.8 | 0.15 | |
| 266 | 0.00866 | 0.403 | 1.4 | 0.3 | |
| 191 | 0.520 | >30.0 | 18% at 1 μM | 4.3 | |
| 192 | 0.380 > 0.300 | >3.00 | 49% at 3 μM | 2.4 | |
| 320 | 0.00180 | 0.0450 | 0.71 | 0.086 | |
| 193 | 0.0161 | 36% at 0.89 μM; 48% at 3.11 μM | 1.5 | 0.68 | |
| 194 | 0.00650 | 0.640 | 26% at 3 μM | 1.4 | |
| 195 | 66% at 0.00097 μM | 0.0370 | 5 | 0.076 | |
| 282 | 0.00720 | 0.120 | 23% at 10 μM | 0.24 | |
| 283 | >1.00 | >10.0 | | | |
| 155 | 0.00460 | 0.0550 | 28% at 3 μM | 0.41 | |
| 197 | 0.0240 | 0.240 | 2.6 | 44% at 1 μM | |
| 198 | | 0.270 | 39% at 3 μM | 0.27 | |
| 199 | 0.00928 | 0.170 | 62% at 10 μM | 0.23 | |
| 200 | 0.0180 | 0.570 | | | |
| 201 | 0.0240 | 0.820 | | | |
| 325 | 0.00370 | 0.130 | | | |
| 262 | 0.00440 | 0.150 | 20% at 10 μM | 50% at 3 μM | |
| 284 | 0.200 | 62% at 10 μM | 14% at 3 μM 3.40 | 2.9 | |
| 285 | 0.150 | 51% at 3 μM | 12% at 1 μM 10% at 10 μM | 2.6 | |
| 318 | 0.00420 | 0.170 | 0.42 | 0.084 | |
| 202 | 46% at 0.001 μM | 0.0250 | 21% at 1 μM | 0.26 | |
| 203 | 0.0240 | 0.520 | 30% at 10 μM | 0.89 | |
| 253 | 0.0120 | 0.830 | 1.8 | 0.41 | |
| 204 | 0.000990 | 0.0270 | 0.82 | 0.025 | |
| 205 | 0.00130 | 0.0590 | 9.8 | 0.087 | |
| 206 | 0.00770 | 0.170 | 2.9 | 0.25 | |
| 313 | 0.0240 | 0.820 | 18% at 10 μM | 36% at 10 μM | |
| 312 | 0.00520 | 0.340 | 3% at 10 μM | 1.3 | |
| 255 | 0.00165 | 0.0500 | 0% at 10 μM | 0.062 | |
| 207 | 0.00110 | 0.0320 | 14% at 10 μM | 0.25 | |
| 208 | 0.00150 | 0.0420 | 21% at 10 μM | 0.11 | |

TABLE A3-continued

| Eg | FGFR3 IC50(μM)* or % I | VEGFR2 IC50(μM)* or % I | BaF3 WT prolif (μM) | BaF3-TEL-FGFR3 prolif (μM) | LP-1 pERK ELISA (μM) |
|---|---|---|---|---|---|
| 209 | 0.0110 | 0.300 | 0% at 10 μM | 15% at 10 μM | |
| 210 | 0.00350 | 42% at 0.1 μM | 13% at 3 μM | 77% at 3 μM | |
| 212 | 0.0130 | >0.300 | 10% at 3 μM | 25% at 3 μM | |
| 213 | 0.000460 | 0.0120 | 22% at 10 μM | 0.16 | |
| 214 | 0.0170 | 0.280 | 2.6 | 0.46 | |
| 215 | 39% at 0.1 μM | >10.0 | 10 | 8.8 | |
| 314 | 0.0300 | 62% at 3 μM | 21% at 10 μM | 0.42 | |
| 315 | 0.0170 | 0.640 | 35% at 10 μM | 0.42 | |
| 216 | 0.00320 | 0.0280 | 28% at 10 μM | 0.1 | |
| 217 | 0.0180 | 1.00 | 37% at 3 μM | 0.39 | |
| 218 | 0.00100 | 0.0220 | 30% at 10 μM | 0.38 | |
| 219 | 0.00210 | 0.110 | 3.5 | 0.095 | |
| 271 | 59% at 0.001 μM | 0.0100 | 0.12 | 0.063 | |
| 273 | 0.0260 | 40% at 1 μM | 43% at 10 μM | 0.69 | |
| 331 | 42% at 0.03 μM | 43% at 3 μM | 60% at 10 μM | 1.6 | |
| 220 | 0.00300 | 0.150 | 1.5 | 0.2 | |
| 270 | 0.00910 | 0.670 | 16% at 3 μM | 0.92 | |
| 261 | 0.000540 | 0.0140 | 0% at 10 μM | 0.16 | |
| 221 | 0.0130 | 0.310 | 21% at 3 μM | 0.33 | |
| 222 | 0.0190 | 0.560 | 2.3 | 0.81 | |
| 223 | 0.0110 | 39% at 0.3 μM | 45% at 3 μM | 0.35 | |
| 224 | 61% at 0.001 μM | 0.0150 | 16% at 3 μM | 0.033 | |
| 225 | 0.00120 | 0.0140 | 0% at 10 μM | 0.27 | |
| 226 | 0.00280 | 0.0830 | 40% at 10 μM | 0.2 | |
| 316 | 0.00420 | 0.330 | 0% at 10 μM | 1.7 | |
| 286 | 57% at 0.0003 μM | 0.00850 | 0% at 10 μM | 55% at 3 μM | |
| 321 | 36% at 0.0003 μM | 0.0170 | 0.46 | 0.021 | |
| 287 | 0.00460 | 0.610 | 0.99 | 0.18 | |
| 227 | 0.00340 | 0.240 | 3.6 | 0.085 | |
| 228 | 0.0170 | 0.110 | 5.1 | 0.27 | |
| 229 | 67% at 0.03 μM | 59% at 0.3 μM | 5.5 | 0.32 | |
| 230 | 49% at 0.003 μM | 0.140 | 0.16 | 0.09 | |
| 288 | 54% at 0.0003 μM | 0.00930 | 7.80% at 10 μM | 0.035 | |
| 322 | 0.0190 | 0.930 | 1.2 | 0.29 | |
| 277 | 0.00260 | 0.340 | 0% at 10 μM | 0% at 10 μM | |
| 231 | 0.0440 | 0.790 | 23% at 10 μM | 0.61 | |
| 232 | 45% at 0.001 μM | 0.0630 | 0.6 | 0.045 | |
| 272 | 51% at 0.00097 μM | 0.0350 | 0.2 | 0.051 | |
| 330 | 66% at 0.00097 μM | 0.00500 | 0.56 | 0.027 | |
| 332 | 0.00540 | 0.400 | 0% at 10 μM | 1.6 | |
| 233 | 0.0750 | 62% at 3.1 μM | 0.0149 | 0.0108 | |
| 234 | 0.00250 | 0.0930 | 6.4 | 0.11 | |
| 235 | 0.000880 | 0.140 | 1.2 | 0.071 | |
| 236 | 46% at 0.31 μM | 6.40 | | | |
| 237 | 0.0110 | 0.160 | 0.12 | 0.079 | |
| 238 | 0.0130 | 40% at 0.31 μM | 41% at 10 μM | 0.2 | |
| 279 | 0.0140 | 2.10 | 7% at 10 μM | 15% at 10 μM | |
| 291 | 0.0160 | 57% at 0.98 μM | 24% at 1 μM | 0.24 | |
| 289 | 0.000990 | 48% at 0.03 μM | 30% at 1 μM | 1.2 | |
| 250 | 0.000500 | 0.0140 | 25% at 3 μM | 0.028 | |
| 290 | 0.00850 | 0.260 | 16% at 1 μM | 0.61 | |
| 239 | 0.0230 | 49% at 1 μM | 26% at 3 μM | 0.57 | |
| 240 | 0.0480 | 0.340 | 17% at 10 μM | 0.56 | |
| 241 | 0.00610 | 0.220 | 4.20% at 10 μM | 0.15 | |
| 242 | 0.000830 | 0.0140 | 1.7 | 0.0097 | |
| 243 | 0.410 | 5.64 | | | |
| 244 | 0.0166 | 0.683 | 17% at 3 μM | 0.95 | |
| 245 | 0.00740 | 43% at 0.3 μM | 2.2 | 0.3 | |
| 246 | 0.00430 | 45% at 0.3 μM | 1 | 0.084 | |
| 335 | 0.0830 | 5.50 | 20% at 10 μM | 24% at 10 μM | |
| 323 | 0.0110 | 0.590 | 0% at 1 μM | 29% at 1 μM | |
| 260 | 0.00200 | 0.140 | 0% at 1 μM | 0.049 | |
| 333 | 0.00810 | 0.360 | 0% at 1 μM | 0% at 1 μM | |
| 247 | 0.000960 | 0.0120 | 36% at 1 μM | 0.015 | |
| 252 | 0.0360 | >1.00 | 0% at 1 μM | 54% at 1 μM | |
| 275 | | | | | |
| 276 | 0.00940 | 0.240 | 0% at 1 μM | 74% at 1 μM | |
| 278 | 0.00380 | 0.130 | 0% at 1 μM | 0.18 | |
| 258 | 0.0583 | 37% at 1 μM | 36% at 3 μM | 0.95 | |
| 335 | 0.000990 | 0.0620 | 0.74 | 0.039 | |
| 257 | 0.00280 | 0.100 | 3.9 | 0.11 | |
| 292 | 0.00520 | 0.150 | 38% at 10 μM | 0.13 | |
| 293 | 0.00370 | 0.180 | 36% at 3 μM | 0.13 | |
| 259 | 0.00224 | 0.140 | 2.6 | 0.034 | |
| 296 | 0.270 | 1.30 | | | |
| 295 | 0.0780 | 0.440 | 30% at 10 μM | 36% at 3 μM | |

TABLE A3-continued

| Eg | FGFR3 IC50(μM)* or % I | VEGFR2 IC50(μM)* or % I | BaF3 WT prolif (μM) | BaF3-TEL-FGFR3 prolif (μM) | LP-1 pERK ELISA (μM) |
|---|---|---|---|---|---|
| 298 | 0.0930 | 0.956 | 3 | 0.86 | |
| 297 | 0.0210 | 0.270 | 5.5 | 0.19 | |
| 299 | 0.0170 | 0.0920 | 17% at 1 μM | 0.15 | |
| 324 | 0.00560 | 0.340 | 9.40% at 10 μM | 0.099 | |
| 300 | 0.00550 | 0.280 | 0% at 10 μM | 0.13 | |
| 301 | 0.110 | 1.30 | 2.81 | 1.24 | |
| 251 | 0.00510 | 0.140 | 0% at 10 μM | 0.089 | |
| 302 | 0.00440 | 0.150 | 0% at 10 μM | 0.095 | |
| 303 | 0.0550 | 0.600 | 0% at 10 μM | 0% at 10 μM | |
| 294 | 0.0390 | 0.500 | 22% at 3 μM | 0.9 | |
| 304 | 55% at 0.1 μM | 59% at 3 μM | | | |
| 305 | 0.00130 | 0.170 | 6% at 10 μM | 0.14 | |
| 307 | 39% at 0.03 μM | 58% at 1 μM | 0% at 10 μM | 25% at 10 μM | |
| 306 | 0.0390 | 60% at 1 μM | 0% at 10 μM | 0.37 | |
| 317 | 53% at 3 μM | 56% at 10 μM | | | |
| 308 | 0.00220 | 0.120 | 0% at 10 μM | 0.14 | |
| 309 | 0.00820 | 0.210 | 2.3 | 0.32 | |
| 310 | 36% at 0.3 μM | >3.00 | | | |
| 274 | 0.150 | 55% at 1 μM | | | |
| 249 | 57.3% at 1 μM | >30.0 | | | |

*where compounds have been tested multiple times, values quoted in the table represent the geometric mean of the values obtained

The invention claimed is:

1. A compound of formula (I):

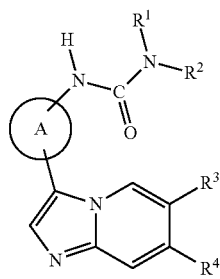

(I)

wherein
R$^2$ represents C$_{1-6}$ alkyl or halo C$_{1-6}$ alkyl;
A is a group A$^d$ which represents a phenyl group which may be optionally substituted by one or more (e.g. 1, 2 or 3) R$^a$ groups;
R$^3$ represents hydrogen or C$_{1-6}$ alkyl;
R$^4$ is a group R$^{4c}$;
R$^{4c}$ is selected from any one of (a)-(f), which represent:
(a) pyridazinyl optionally substituted by one or more (e.g. 1, 2 or 3) R$^e$ groups, or two or more (e.g. 2, 3 or 4) R$^b$ groups;
(b) pyrazinyl optionally substituted by one or more (e.g. 1, 2 or 3) R$^b$ groups;
(c) triazinyl optionally substituted by one or two R$^b$ groups;
(d) pyrimidin-2-yl optionally substituted by one or more (e.g. 1, 2 or 3) R$^b$ groups;
(e) pyrimidin-4-yl optionally substituted by one or more (e.g. 1, 2 or 3) R$^g$ groups or two or more (e.g. 2, 3 or 4) R$^b$ groups;
(f) pyrimidin-5-yl optionally substituted by one or more (e.g. 1, 2 or 3) R$^P$ groups or two or more (e.g. 2, 3 or 4) R$^b$ groups;

R$^w$, R$^x$, R$^y$ and R$^z$ independently represent hydrogen, C$_{1-6}$ alkyl, C$_{2-6}$ alkenyl, C$_{2-6}$ alkynyl, C$_{1-6}$ alkanol, —COOC$_{1-6}$ alkyl, hydroxy, C$_{1-6}$ alkoxy, haloC$_{1-6}$ alkyl, —(CH$_2$)$_n$—O—C$_{1-6}$ alkyl, —CO—(CH$_2$)$_n$—C$_{1-6}$ alkoxy, C$_{1-6}$ alkylamino, —C$_{1-6}$ alkyl-N(C$_{1-6}$ alkyl)$_2$, —C$_{1-6}$ alkyl-NH(C$_{1-6}$ alkyl), C$_{3-8}$ cycloalkyl or C$_{3-8}$ cycloalkenyl or when attached to a nitrogen atom, R$^w$, R$^x$, R$^y$ and R$^z$ may form a ring;

R$^a$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^x$, —(CH$_2$)$_n$—O—C$_{1-6}$ alkyl, —O—(CH$_2$)$_n$—OR$^x$, haloC$_{1-6}$ alkyl, haloC$_{1-6}$ alkoxy, C$_{1-6}$ alkanol, =O, =S, nitro, Si(R$^x$)$_4$, —(CH$_2$)$_s$—CN, —S—R$^x$, —SO—R$^x$, —SO$_2$—R$^x$, —COR$^x$, —(CR$^x$R$^y$)$_s$—COOR$^z$, —(CR$^x$R$^y$)$_s$—CONR$^w$R$^z$, —(CH$_2$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$SO$_2$—R$^y$, —(CH$_2$)$_s$—NH—SO$_2$—NR$^x$R$^y$, —OCONR$^x$R$^y$, —(CH$_2$)$_s$—NR$^x$CO$_2$R$^y$, —O—(CH$_2$)$_2$—NR$^x$R$^y$, —O—(CH$_2$)$_s$—CR$^x$R$^y$—(CH$_2$)$_t$—OR$^z$ or —(CH$_2$)$_s$—SO$_2$NR$^x$R$^y$groups;

R$^b$ represents an R$^a$ group or a -Y-heterocyclyl group wherein said heterocyclyl group may be optionally substituted by one or more (e.g. 1, 2 or 3) R$^a$ groups;

Y represents a bond, —CO—(CH$_2$)$_s$—, —(CR$^x$R$^y$)$_s$—CO—, —COO—, —(CH$_2$)$_n$—(CR$^x$R$^y$)$_s$—, —NR$^x$—(CH$_2$)$_s$—, —(CH$_2$)$_s$—NR$^x$—, —CONR$^x$—, —NR$^x$CO—, —SO$_2$NR$^x$—, —NR$^x$SO$_2$—, —NR$^x$-CONR$^y$—, —NR$^x$CSNR$^y$—, —O—(CH$_2$)$_s$—, —(CH$_2$)$_s$—O—, —S—, —SO— or —(CH$_2$)$_s$—SO$_2$—;

R$^e$ represents halogen, C$_{2-6}$ alkyl, C$_{2-6}$ alkenyl, C$_{2-6}$ alkynyl, C$_{3-8}$ cycloalkyl, C$_{3-8}$ cycloalkenyl, —OR$^x$, —(CH$_2$)$_n$—O—C$_{1-6}$ alkyl, —O—(CH$_2$)$_n$—OR$^x$, haloC$_{1-6}$ alkyl, haloC$_{1-6}$ alkoxy, C$_{1-6}$ alkanol, =O, =S, nitro, Si(R$^x$)$_4$, —(CH$_2$)$_s$—CN, —S—R$^x$, —SO—R$^x$, —SO$_2$—R$^x$, —COR$^x$, —(CR$^x$R$^y$)$_s$—COOR$^z$, —(CR$^x$R$^y$)$_s$—CONR$^w$R$^z$, —(CH$_2$)$_s$—CONR$^x$R$^y$, —(CH$_2$)$_s$—NR$^x$R$^y$, —(CH$_2$)$_s$—NR$^x$COR$^y$, —(CH$_2$)$_s$—

NR$^x$SO$_2$—R$^y$, —(CH$_2$)$_s$—NH—SO$_2$—NR$^x$R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups, or a —Y-heterocyclyl group wherein said heterocyclyl group may be optionally substituted by one or more (e.g. 1, 2 or 3) R$^a$ groups;

R$^g$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^x$, —(CH$_2$)$_n$—O—C$_{1-6}$ alkyl, —O—(CH$_2$)$_n$—OR$^x$, haloC$_{1-6}$alkyl, haloC$_{1-6}$alkoxy, C$_{1-6}$ alkanol, =O, =S, nitro, Si(R$^x$)$_4$, —(CH$_2$)$_s$—CN, —S—R$^x$, —SO—R$^x$, —SO$_2$—R$^x$, —COR$^x$, —(CR$^x$R$^y$)$_s$—COOR$^z$, —(CR$^x$R$^y$)$_s$—CONR$^w$R$^z$, —(CH$_2$)$_s$—CONR$^x$R$^y$, —(CH$_2$)$_s$—NHC$_{1-6}$ alkyl, —(CH$_2$)$_s$—N(C$_{1-6}$ alkyl)$_2$, —(CH$_2$)$_n$—NR$^x$R$^y$, —(CH$_2$)$_s$—NR$^x$COR$^y$, —(CH$_2$)$_s$—NR$^x$SO$_2$—R$^y$, —(CH$_2$)$_s$—NH-SO$_2$—NR$^x$R$^y$, —OCONR$^x$R$^y$,—(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups, or a —Y-heterocyclyl group wherein said heterocyclyl group may be optionally substituted by one or more (e.g. 1, 2 or 3) R$^a$ groups;

R$^p$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^x$, —(CH$_2$)$_n$—O—C$_{1-6}$ alkyl, —O—(CH$_2$)$_n$—OR$^x$, haloC$_{1-6}$alkyl, haloC$_{1-6}$alkoxy, C$_{1-6}$ alkanol, =O, =S, nitro, Si(R$^x$)$_4$, —(CH$_2$)$_s$—CN, —S—R$^x$, —SO—R$^x$, —SO$_2$—R$^x$, —COR$^x$, —(CR$^x$R$^y$)$_s$—COOR$^z$, —(CR$^x$R$^y$)$_s$—CONR$^w$R$^z$, —(CH$_2$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$SO$_2$—R$^y$, —(CH$_2$)$_s$—NH—SO$_2$—NR$^x$R$^y$, —OCONR$^x$R$^y$,—(CH$_2$)$_s$—NR$^x$CO$_2$R$^y$, —O—(CH$_2$)$_s$—CR$^x$R$^y$—(CH$_2$)$_t$—OR$^z$ or —(CH$_2$)$_s$—SO$_2$NR$^x$R$^y$ groups; a —Y-(4-membered heterocyclyl group) wherein said 4-membered heterocyclyl group is substituted by one or more (e.g. 1, 2 or 3) R$^a$ groups; or a —Y-(5-10 membered heterocyclyl group) wherein said 5-10 membered heterocyclyl group may be optionally substituted by one or more (e.g. 1, 2 or 3) R$^a$ groups;

n represents an integer from 1-4;

s and t independently represent an integer from 0-4;

including a pharmaceutically acceptable salt, solvate or tautomer thereof.

2. A compound as defined in claim 1 wherein A$^d$ represents unsubstituted phenyl.

3. A compound as defined in claim 1 wherein R$^2$ represents haloC$_{1-6}$ alkyl.

4. A compound as defined in claim 1 wherein R$^2$ represents ethyl or —CH$_2$—CF$_3$.

5. A compound as defined in claim 4 wherein R$^2$ represents —CH$_2$—CF$_3$.

6. A compound as defined in claim 1 wherein R$^3$ represents hydrogen or methyl.

7. A compound as defined in claim 6 wherein R$^3$ represents hydrogen.

8. A compound as defined in claim 1 wherein R$^4$ is a group R$^{4c}$ and R$^{4c}$ is selected from (d) and (e).

9. A compound as defined in claim 1 which is a compound of formula (Ia)

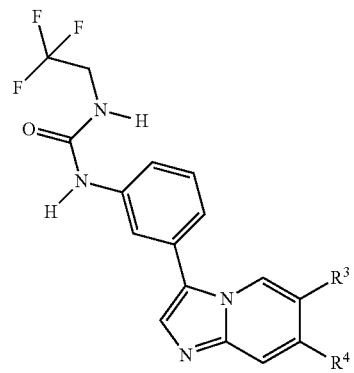

(Ia)

wherein R$^3$ and R$^4$ are as defined in claim 1.

10. A process for the preparation of a compound of formula (I) as defined in claim 1, which process comprises:

(i) the reaction of a compound of the formula (XX):

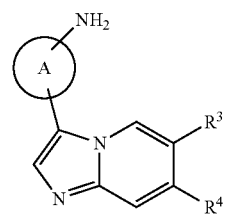

(XX)

or a protected form thereof, wherein A, R$^3$ and R$^4$ are as defined in claim 1, with an appropriately substituted isocyanate or an appropriately substituted amine in the presence of carbonyl diimidazole (CDI) and thereafter removing any protecting group present; or (ii) the reaction of a compound of the formula (XX):

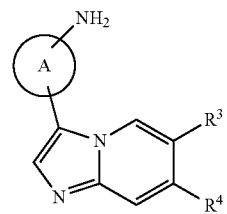

(XX)

or a protected form thereof, wherein A, R$^3$ and R$^4$ are as defined in claim 1, with p-nitrophenyl chloroformate and an appropriately substituted amine and thereafter removing any protecting group present; or (iii) reacting a compound of formula (V) and (VI):

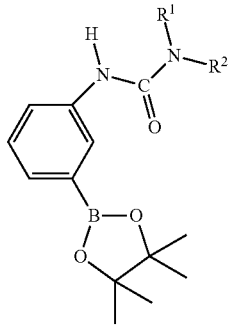

(V)

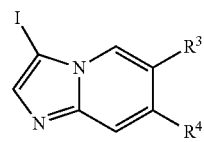

(VI)

wherein R1 is hydrogen, and R², R³ and R⁴ are as defined in claim 1;

and optionally thereafter converting one compound of the formula (I) into another compound of the formula (I).

11. A pharmaceutical composition comprising a compound of formula (I) as defined in claim 1.

12. A method of inhibiting FGFR kinase, which method comprises contacting the kinase with a compound of the formula (I) as defined in claim 1.

13. A method for the treatment of a disease or condition selected from multiple myeloma, bladder carcinoma hepatocellular carcinoma oral squamous cell carcinoma, cervical carcinoma, and urothelial carcinoma, which method comprises administering to a subject in need thereof a compound of the formula (I) as defined in claim 1.

14. A compound as defined in claim 1 wherein the compound is selected from:

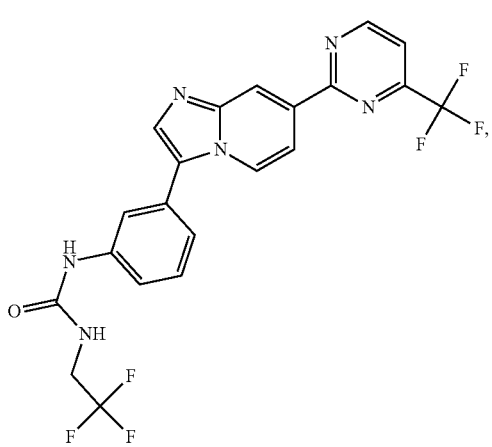

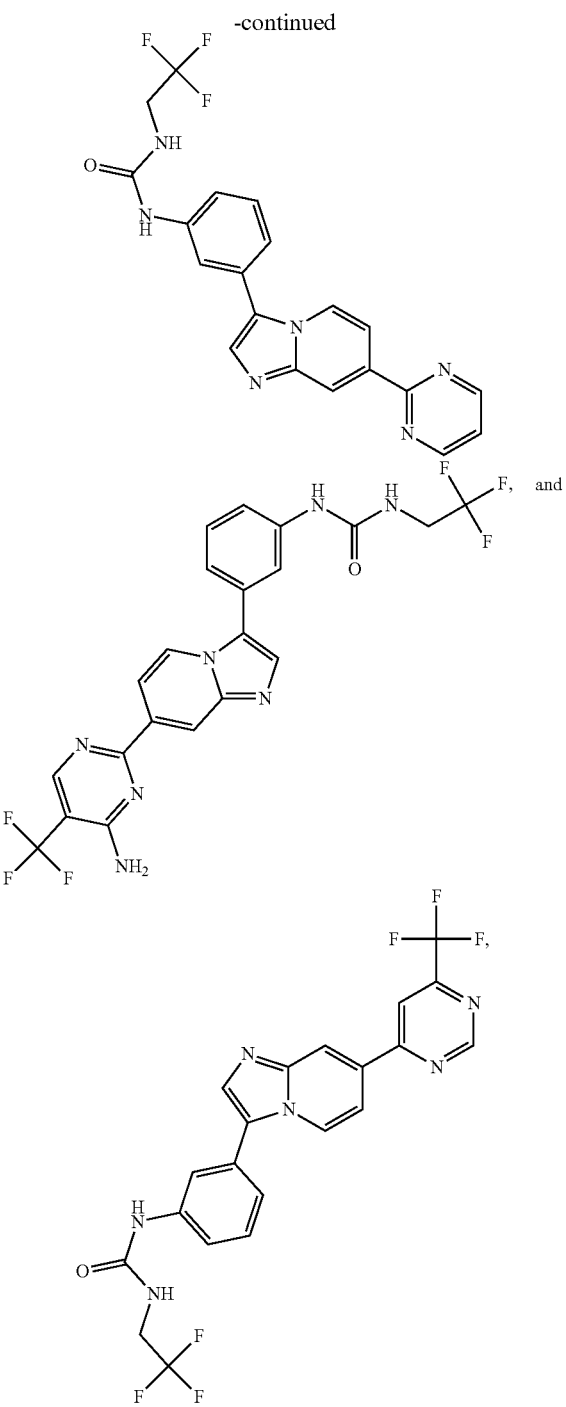

including a pharmaceutically acceptable salt, solvate or tautomer thereof.

15. A compound according to claim 14, wherein the compound is 1-(2,2,2-Trifluoro-ethyl)-3-{3-[7-(4-trifluoromethyl-pyrimidin-2-yl)-imidazo [1,2-a]pyridin-3-yl]-phenyl}-urea hydrochloride.

16. A compound according to claim 14, wherein the compound is 1-{3-[7-(Pyrimidin-2-yl)-imidazo [1,2-a]pyridin-3-yl]-phenyl}-3-(2,2,2-trifluoro-ethyl)-urea hydrochloride.

17. A compound according to claim 14, wherein the compound is 1-{3-[7-(4-Amino-5-trifluoromethyl-pyrimidin-2-yl)-imidazo-[1,2-a]pyridin-3 -yl]-phenyl}1 -3-(2,2,2-trifluoroethyl)-urea hydrochloride.

18. A compound according to claim 14, wherein the compound is 1-(2,2,2-Trifluoro-ethyl)-3-{3-[7-(6-trifluoromethyl-pyrimidin-4-yl)-imidazo[1,2-a]pyridin-3-yl]-phenyl}-urea hydrochloride.

19. A pharmaceutical composition according to claim 11 wherein the compound of formula (I) is selected from:

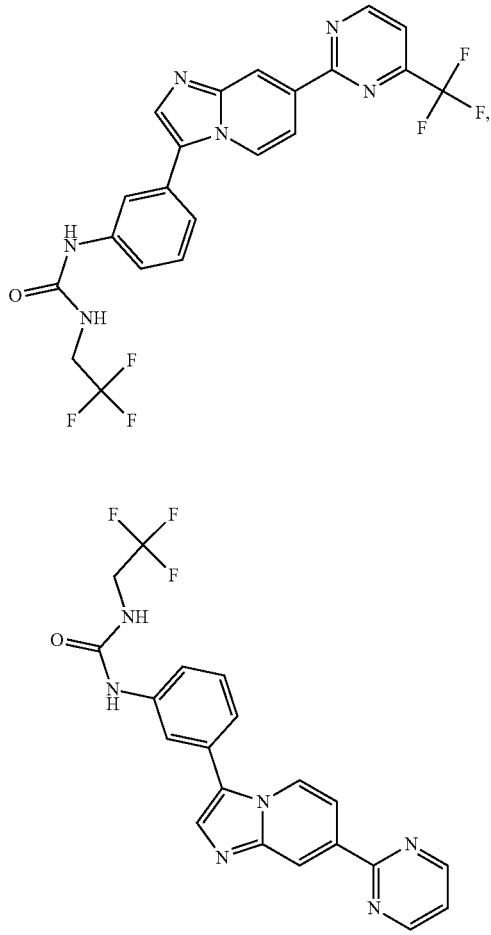

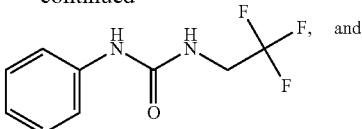

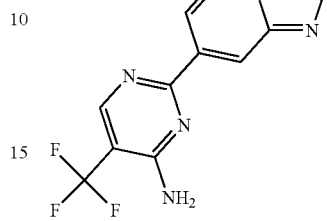

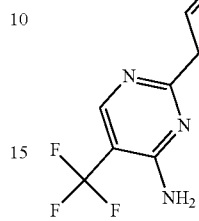

including a pharmaceutically acceptable salt, solvate or tautomer thereof.

20. A compound according to claim 1, wherein the compound is in the form of a free base or salt.

21. A compound according to claim 14, wherein the compound is in the form of a free base or salt.

* * * * *